US007105644B2

(12) United States Patent
Rosen et al.

(10) Patent No.: US 7,105,644 B2

(45) Date of Patent: Sep. 12, 2006

(54) SECRETED PROTEIN HHTLF25 ANTIBODIES

(75) Inventors: Craig A. Rosen, Laytonsville, MD (US); Steven M. Ruben, Olney, MD (US); David W. LaFleur, Washington, DC (US)

(73) Assignee: Human Genome Sciences, Inc., Rockville, MD (US)

( * ) Notice: Subject to any disclaimer, the term of this patent is extended or adjusted under 35 U.S.C. 154(b) by 231 days.

(21) Appl. No.: 09/983,802

(22) Filed: Oct. 25, 2001

(65) Prior Publication Data

US 2003/0022185 A1 Jan. 30, 2003

Related U.S. Application Data

(63) Continuation of application No. 09/227,357, filed on Jan. 8, 1999, now Pat. No. 6,342,581, which is a continuation-in-part of application No. PCT/US98/13684, filed on Jul. 7, 1998.

(60) Provisional application No. 60/058,661, filed on Sep. 12, 1997, provisional application No. 60/058,660, filed on Sep. 12, 1997, provisional application No. 60/058,664, filed on Sep. 12, 1997, provisional application No. 60/058,785, filed on Sep. 12, 1997, provisional application No. 60/055,954, filed on Aug. 18, 1997, provisional application No. 60/055,984, filed on Aug. 18, 1997, provisional application No. 60/055,684, filed on Aug. 18, 1997, provisional application No. 60/056,360, filed on Aug. 18, 1997, provisional application No. 60/055,964, filed on Aug. 18, 1997, provisional application No. 60/055,947, filed on Aug. 18, 1997, provisional application No. 60/055,950, filed on Aug. 18, 1997, provisional application No. 60/055,953, filed on Aug. 18, 1997, provisional application No. 60/055,949, filed on Aug. 18, 1997, provisional application No. 60/055,948, filed on Aug. 18, 1997, provisional application No. 60/055,723, filed on Aug. 18, 1997, provisional application No. 60/055,722, filed on Aug. 18, 1997, provisional application No. 60/051,928, filed on Jul. 8, 1997, provisional application No. 60/051,919, filed on Jul. 8, 1997, provisional application No. 60/052,795, filed on Jul. 8, 1997, provisional application No. 60/052,733, filed on Jul. 8, 1997, provisional application No. 60/051,920, filed on Jul. 8, 1997, provisional application No. 60/051,918, filed on Jul. 8, 1997, provisional application No. 60/051,930, filed on Jul. 8, 1997, provisional application No. 60/051,916, filed on Jul. 8, 1997, provisional application No. 60/051,932, filed on Jul. 8, 1997, provisional application No. 60/051,931, filed on Jul. 8, 1997, provisional application No. 60/052,732, filed on Jul. 8, 1997, provisional application No. 60/052,803, filed on Jul. 8, 1997, provisional application No. 60/051,929, filed on Jul. 8, 1997, provisional application No. 60/051,925, filed on Jul. 8, 1997, provisional application No. 60/052,793, filed on Jul. 8, 1997, and provisional application No. 60/051,926, filed on Jul. 8, 1997.

(51) Int. Cl.

| | |
|---|---|
| ***C07K 16/24*** | (2006.01) |
| ***C12N 5/12*** | (2006.01) |
| ***G01N 33/53*** | (2006.01) |

(52) U.S. Cl. ............................ 530/389.2; 530/388.23; 530/387.1; 530/387.9; 530/388.1; 530/389.1; 530/387.3; 435/7.1; 435/7.2; 435/325; 435/326; 435/1.49

(58) Field of Classification Search .................. 435/7.1, 435/7.2, 325, 326, 1.49; 530/388.23, 387.1, 530/387.9, 388.1, 389.1, 387.3, 389.2, 388.24; 424/1.49

See application file for complete search history.

(56) References Cited

U.S. PATENT DOCUMENTS

| | | | |
|---|---|---|---|
| 6,416,973 | B1 | 7/2002 | Bakker et al. |
| 2004/0132085 | A1 | 7/2004 | Bakker et al. |
| 2004/0177391 | A1 | 9/2004 | Bakker et al. |
| 2005/0084900 | A1 | 4/2005 | Bakker et al. |

FOREIGN PATENT DOCUMENTS

| | | |
|---|---|---|
| WO | WO 99/02546 | 1/1999 |
| WO | WO-99/06548 | 2/1999 |
| WO | WO-99/06577 | 2/1999 |
| WO | WO 00/17356 | 3/2000 |
| WO | WO02/102994 A2 | 12/2002 |

OTHER PUBLICATIONS

Skolmick et al. Nature Biotechnology Mar. 2000, vol. 18, pp. 283–287.*

Lanier et al., "Immunoreceptor DAP12 bearing a tyrosine–based activation motif is involved in activating NK cells," Nature 39:703–707, 1998.

Lucas et al., "Massive inflammatory syndrome and lymphocytic immunodeficiency in KARAP/DAP12–transgenic mice," Eur. J. Immunol 32:2653–2663, 2002.

Bakker et al., "DAP12–Deficient Mice Fail to Develop Autoimmunity Due to Impaired Antigen Priming," Immunity 13:345–353, 2000.

Geneseq Acession No. AAV83519, Moretta et al., "Human killer cell activatory receptor–associated protein," Jan. 28, 1998.

Genbank Accession No. AF141377 (Jan. 15, 1999).

Genbank Accession No. AF169202 (Dec. 12, 1999).

Wilson, et al., "Assessing Annotation Transfer for Genomics: Quantifying . . . ", J. Mol. Biol., 297:233–249 (2000).

Pawlowski, et al., "Sensitive Sequence Comparison as Protein Function Predictor", 2000 Pacific Symposium on Bio Computing.

(Continued)

*Primary Examiner*—Prema Mertz

(74) *Attorney, Agent, or Firm*—Human Genome Sciences, Inc.

(57) ABSTRACT

The present invention relates to novel human secreted proteins and isolated nucleic acids containing the coding regions genes encoding such proteins. Also provided are vectors, host cells, antibodies, and recombinant methods for producing human secreted proteins. The invention further relates to diagnostic and therapeutic methods useful for diagnosing and treating disorders related to these novel human secreted proteins. Disclosed embodiments of the invention also include antibodies that bind to secreted protein HHTLF25 and methods for making and using such antibodies.

70 Claims, No Drawings

OTHER PUBLICATIONS

Genbank Accession No. AA044254 (Sep. 4, 1996).
Genbank Accession No. G15147 (Jan. 4, 1996)).
Genbank Accession No. H46196 (Jul. 31, 1995).
Genbank Accession No. H19490 (Jul. 3, 1995).
Genbank Accession No. AI421986 (Mar. 30, 1999).
Genbank Accession No. H19572 (Jul. 3, 1995).
Genbank Accession No. H46195 (Jul. 31, 1995).
EMBL Database, Accession No. AA481924, Hillier, et al., "zv41f05.r1 Soares ovary tumor NbHOT Homo sapiens cDNA clone IMAGE:756255 5' similar to TR:G498729 G498729 Zinc Finger Protein;, mRNA sequence" (Jun. 24, 1997).
Partial European Search Report for European Patent Application EP 04 00 7560.8 (Jun. 2, 2005).
Brakenhoff et al., "The Human E48 Antigen, Highly Homologous . . . ", I. of Cell Bio., 129(6) 1677–1689 (Jun. 1995).
Hall, Z.W., "Alpha Neurotoxins and Their Relatives: Foes and Friends?", Neuron., 23(1):4–5 (May 1999).
MIWA, et al., "lynx 1, an Endogenous Toxin–like Modulator of Nicotinic Acetylcholine Receptors in the Mammalian CNS", Neuron, 23:105–114 (May 1999).
Geneseq Accession No. Y36014 (Jun. 24, 1999).
Geneseq Accession No. Y12343 (Feb. 11, 1999).
Geneseq Accession No. X41176 (Feb. 11, 1999).
Geneseq Accession No. X97698 (Jun. 24, 1998).
Geneseq Accession No. AA398986 (May 16, 1997).
Geneseq Accession No. X97592 (Jun. 24, 1999).

* cited by examiner

SECRETED PROTEIN HHTLF25 ANTIBODIES

This application is a continuation of, and claims benefit under 35 U.S.C. § 120 of U.S. patent application Ser. No. 09/227,357, filed Jan. 8, 1999, (now U.S. Pat. No. 6,342,581 issued on Jan. 29, 2002), which is hereby incorporated by reference, which is a continuation-in-part of, and claims benefit under 35 U.S.C. § 120 of copending International Application No: PCT/US98/13684, filed Jul. 7, 1998, which is hereby incorporated by reference, which claims benefit under 35 U.S.C. § 119(e) based on U.S. Provisional Applications, each of which is hereby incorporated by reference:

| | Filing Date | Appln No. |
|---|---|---|
| 1. | Jul. 08, 1997 | 60/051,926 |
| 2. | Jul. 08, 1997 | 60/052,793 |
| 3. | Jul. 08, 1997 | 60/051,925 |
| 4. | Jul. 08, 1997 | 60/051,929 |
| 5. | Jul. 08, 1997 | 60/052,803 |
| 6. | Jul. 08, 1997 | 60/052,732 |
| 7. | Jul. 08, 1997 | 60/051,931 |
| 8. | Jul. 08, 1997 | 60/051,932 |
| 9. | Jul. 08, 1997 | 60/051,916 |
| 10. | Jul. 08, 1997 | 60/051,930 |
| 11. | Jul. 08, 1997 | 60/051,918 |
| 12. | Jul. 08, 1997 | 60/051,920 |
| 13. | Jul. 08, 1997 | 60/052,733 |
| 14. | Jul. 08, 1997 | 60/052,795 |
| 15. | Jul. 08, 1997 | 60/051,919 |
| 16. | Jul. 08, 1997 | 60/051,928 |
| 17. | Aug. 18, 1997 | 60/055,722 |
| 18. | Aug. 18, 1997 | 60/055,723 |
| 19. | Aug. 18, 1997 | 60/055,948 |
| 20. | Aug. 18, 1997 | 60/055,949 |
| 21. | Aug. 18, 1997 | 60/055,953 |
| 22. | Aug. 18, 1997 | 60/055,950 |
| 23. | Aug. 18, 1997 | 60/055,947 |
| 24. | Aug. 18, 1997 | 60/055,964 |
| 25. | Aug. 18, 1997 | 60/056,360 |
| 26. | Aug. 18, 1997 | 60/055,684 |
| 27. | Aug. 18, 1997 | 60/055,984 |
| 28. | Aug. 18, 1997 | 60/055,954 |
| 29. | Sep. 12, 1997 | 60/058,785 |
| 30. | Sep. 12, 1997 | 60/058,664 |
| 31. | Sep. 12, 1997 | 60/058,660 |
| 32. | Sep. 12, 1997 | 60/058,661 |

FIELD OF THE INVENTION

This invention relates to newly identified polynucleotides and the polypeptides encoded by these polynucleotides, uses of such polynucleotides and polypeptides, and their production.

BACKGROUND OF THE INVENTION

Unlike bacterium, which exist as a single compartment surrounded by a membrane, human cells and other eucaryotes are subdivided by membranes into many functionally distinct compartments. Each membrane-bounded compartment, or organelle, contains different proteins essential for the function of the organelle. The cell uses "sorting signals," which are amino acid motifs located within the protein, to target proteins to particular cellular organelles.

One type of sorting signal, called a signal sequence, a signal peptide, or a leader sequence, directs a class of proteins to an organelle called the endoplasmic reticulum (ER). The ER separates the membrane-bounded proteins from all other types of proteins. Once localized to the ER, both groups of proteins can be further directed to another organelle called the Golgi apparatus. Here, the Golgi distributes the proteins to vesicles, including secretory vesicles, the cell membrane, lysosomes, and the other organelles.

Proteins targeted to the ER by a signal sequence can be released into the extracellular space as a secreted protein. For example, vesicles containing secreted proteins can fuse with the cell membrane and release their contents into the extracellular space—a process called exocytosis. Exocytosis can occur constitutively or after receipt of a triggering signal. In the latter case, the proteins are stored in secretory vesicles (or secretory granules) until exocytosis is triggered. Similarly, proteins residing on the cell membrane can also be secreted into the extracellular space by proteolytic cleavage of a "linker" holding the protein to the membrane.

Despite the great progress made in recent years, only a small number of genes encoding human secreted proteins have been identified. These secreted proteins include the commercially valuable human insulin, interferon, Factor VIII, human growth hormone, tissue plasminogen activator, and erythropoeitin. Thus, in light of the pervasive role of secreted proteins in human physiology, a need exists for identifying and characterizing novel human secreted proteins and the genes that encode them. This knowledge will allow one to detect, to treat, and to prevent medical disorders by using secreted proteins or the genes that encode them.

SUMMARY OF THE INVENTION

The present invention relates to novel polynucleotides and the encoded polypeptides. Moreover, the present invention relates to vectors, host cells, antibodies, and recombinant methods for producing the polypeptides and polynucleotides. Also provided are diagnostic methods for detecting disorders related to the polypeptides, and therapeutic methods for treating such disorders. The invention further relates to screening methods for identifying binding partners of the polypeptides.

DETAILED DESCRIPTION

Definitions

The following definitions are provided to facilitate understanding of certain terms used throughout this specification.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide.

In the present invention, a "secreted" protein refers to those proteins capable of being directed to the ER, secretory vesicles, or the extracellular space as a result of a signal sequence, as well as those proteins released into the extracellular space without necessarily containing a signal sequence. If the secreted protein is released into the extracellular space, the secreted protein can undergo extracellular processing to produce a "mature" protein. Release into the extracellular space can occur by many mechanisms, including exocytosis and proteolytic cleavage.

As used herein, a "polynucleotide" refers to a molecule having a nucleic acid sequence contained in SEQ ID NO:X or the cDNA contained within the clone deposited with the ATCC®. For example, the polynucleotide can contain the nucleotide sequence of the full length cDNA sequence, including the 5' and 3' untranslated sequences, the coding region, with or without the signal sequence, the secreted protein coding region, as well as fragments, epitopes, domains, and variants of the nucleic acid sequence. Moreover, as used herein, a "polypeptide" refers to a molecule having the translated amino acid sequence generated from the polynucleotide as broadly defined.

In the present invention, the full length sequence identified as SEQ ID NO:X was often generated by overlapping sequences contained in multiple clones (contig analysis). A representative clone containing all or most of the sequence for SEQ ID NO:X was deposited with the American Type Culture Collection ("ATCC®"). As shown in Table 1, each clone is identified by a cDNA Clone ID (Identifier) and the ATCC® Deposit Number. The ATCC® is located at 10801 University Boulevard, Manassas, Va. 20110-2209, USA. The ATCC® deposit was made pursuant to the terms of the Budapest Treaty on the international recognition of the deposit of microorganisms for purposes of patent procedure.

A "polynucleotide" of the present invention also includes those polynucleotides capable of hybridizing, under stringent hybridization conditions, to sequences contained in SEQ ID NO:X, the complement thereof, or the cDNA within the clone deposited with the ATCC®. "Stringent hybridization conditions" refers to an overnight incubation at 42° C. in a solution comprising 50% formamide, 5×SSC (750 mM NaCl, 75 mM sodium citrate), 50 mM sodium phosphate (pH 7.6), 5× Denhardt's solution, 10% dextran sulfate, and 20 μg/ml denatured, sheared salmon sperm DNA, followed by washing the filters in 0.1×SSC at about 65° C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M $NaH_2PO_4$; 0.02M EDTA, pH 7.4), 0.5% SDS, 30% formamide, 100 ug/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone).

The polynucleotide of the present invention can be composed of any polyribonucleotide or polydeoxribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., Meth Enzymol 182:626–646 (1990); Rattan et al., Ann NY Acad Sci 663:48–62 (1992).)

"SEQ ID NO:X" refers to a polynucleotide sequence while "SEQ ID NO:Y" refers to a polypeptide sequence, both sequences identified by an integer specified in Table 1.

"A polypeptide having biological activity" refers to polypeptides exhibiting activity similar, but not necessarily identical to, an activity of a polypeptide of the present invention, including mature forms, as measured in a particular biological assay, with or without dose dependency. In the case where dose dependency does exist, it need not be identical to that of the polypeptide but rather substantially similar to the dose-dependence in a given activity as compared to the polypeptide of the present invention (i.e., the candidate polypeptide will exhibit greater activity or not more than about 25-fold less and, preferably, not more than about tenfold less activity, and most preferably, not more than about three-fold less activity relative to the polypeptide of the present invention.)

Polynucleotides and Polypeptides of the Invention

Features of Protein Encoded by Gene No: 1

This gene is expressed primarily in cerebellum.

Therefore, polynucleotides and polypeptides of the invention are useful as reagents for differential identification of the tissue(s) or cell type(s) present in a biological sample and for diagnosis of diseases and conditions which include, but are not limited to, neural disorders, particularly damage to the cerebellum or additional CNS tissues caused by injuries, which include, but are not limited to, trauma or ischemia. Similarly, polypeptides and antibodies directed to these polypeptides are useful in providing immunological probes for differential identification of the tissue(s) or cell type(s). For a number of disorders of the above tissues or cells, particularly of the central nervous system (CNS), expression of this gene at significantly higher or lower levels may be routinely detected in certain tissues or cell types (e.g., neural, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 150 as residues: Pro-7 to Cys-21, Leu-25 to Ser-30.

The tissue distribution in cerebellum indicates that polynucleotides and polypeptides corresponding to this gene are useful for the detection, treatment, and/or prevention of neurodegenerative disease states, behavioral disorders, or inflammatory conditions which include, but are not limited to Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception.

In addition, elevated expression of this gene product in regions of the brain indicates it plays a role in normal neural function. Potentially, this gene product is involved in synapse formation, neurotransmission, learning, cognition, homeostasis, or neuronal differentiation or survival. Protein, as well as, antibodies directed against the protein may show utility as a tumor marker and/or immunotherapy targets for the above listed tissues. Protein, as well as, antibodies directed against the protein may show utility as a tumor marker and/or immunotherapy targets for the above listed tumors and tissues.

Many polynucleotide sequences, such as EST sequences, are publicly available and accessible through sequence databases. Some of these sequences are related to SEQ ID NO:11 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1868 of SEQ ID NO:11, b is an integer of 15 to 1882, where both a and b correspond to the positions of nucleotide residues shown in SEQ ID NO:11, and where b is greater than or equal to a+14.

Features of Protein Encoded by Gene No: 2

The translation product of this gene was found to have homology to the human env endogenous retrovirus protein (See Genbank Accession No. gi|757872), which is thought to play a contributing role in the events leading up to the onset of cancer or of proliferative disorders in teratocarcinoma cell lines. In specific embodiments, polypeptides of the invention comprise the following amino acid sequence: VDPRVRRFWEDPEYPPVAVMSRLMLRRIPTVMSNTHRTQPSTWEQIKKLSQM VGENLRKAGQPVT (SEQ ID NO: 289), VRRFWEDPEYPPVAVMSRLMLRRIP (SEQ ID NO: 290), SNTHRTQPSTWEQIKKLSQMVGENLRK (SEQ ID NO: 291), SACHSHTVFNWSEQNGQMVQMVRRMARVPIIWNHGSIGAPQPQMIWPIVGA KHKDLWQLLIALNKIKIWERIKKHLEGHSANLSLDIAKYIYIFKASQAHLT LMPELECSKELQTD (SEQ ID NO: 292), MARVPIIWNHGSIGAPQPQMIWPIV (SEQ ID NO: 293), RIKKHLEGHSANLSL DLAKYIYIFKASQAHLT (SEQ ID NO: 294), VFLQQGLTQRSVILIGHICQFWLAIMPGYNHFMTQLHMLSGLNIYHNKSAPIIEAYHP QKSICKQN (SEQ ID NO: 295), IGHICQFWLAIMPGYN HFMTQLHMLSGL (SEQ ID NO: 296), SIPGTPDLNARTGVLEGAADRLAASNPL KWIKTLRSSVISMMIVLLICVVCLYIVCRC (SEQ ID NO: 297), VLEGAADRLAA SNPLKWIKTLRSSVIS (SEQ ID NO: 298), LTVTKLPWLFIALQNKRMGTSWEQA PKSGHKLAPKLVIKISAALSHACDSLTPTLEGCRFTGMRARNNWPTQGG (SEQ ID NO: 299), and/or MGTSWEQAPKSGHKLAPKLVINKISAALS (SEQ ID NO: 300). Polynucleotides encoding these polypeptides are also encompassed by the invention.

This gene is expressed primarily in PHA stimulated T-cells.

Therefore, polynucleotides and polypeptides of the invention are useful as reagents for differential identification of the tissue(s) or cell type(s) present in a biological sample and for diagnosis of the following diseases and conditions which include, but are not limited to, immune disorders, particularly autoimmune, inflammatory, or immunodeficiency diseases, in addition to, proliferative conditions such as cancers. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, teratocarcinoma, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in T-cells indicates that polynucleotides and polypeptides corresponding to this gene are useful for the diagnosis, treatment, and/or prevention of a variety of immune system disorders. The expression of this gene product indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer e.g. by boosting immune responses. Since the gene is expressed in cells of lymphoid origin, the natural gene product may be involved in immune functions. Therefore it may be also used as an agent for immunological disorders including arthritis, asthma, immune deficiency diseases such as AIDS, and leukemia.

In addition, this gene product may have commercial utility in the expansion of stem cells and committed progenitors of various blood lineages, and in the differentiation and/or proliferation of various cell types. The protein may also show utility in the development of novel inhibitors to viral infections, or the protein may be useful in the development of novel vectors, such as those used in gene therapy, and/or immuno-therapy which could lead to the amelioration of disease of disease states. Protein, as well as, antibodies directed against the protein may show utility as a tumor marker and/or immunotherapy targets for the above listed tumors and tissues.

Many polynucleotide sequences, such as EST sequences, are publicly available and accessible through sequence databases. Some of these sequences are related to SEQ ID NO:12 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1576 of SEQ ID NO:12, b is an integer of 15 to 1590, where both a and b correspond to the positions of nucleotide residues shown in SEQ ID NO:12, and where b is greater than or equal to a+14.

Features of Protein Encoded by Gene No: 3

The translation product of this gene was shown to have homology to the human retrovirus-related reverse transcriptase pseudogene (See Genbank Accession No. pir|A25313|GNHUL1). In specific embodiments, polypeptides of the invention comprise the following amino acid sequence: STHASVQKKDLTKFSAHSWLKKK KTFRKMIMEEIFLNLIKNIYKSPYSQCNT (SEQ ID NO: 301), VRSEKGFDKIQC PFMVK (SEQ ID NO: 302), FSKPSSYKTYIPKINLHFYILLMNIWETIKIVPLNNC FTKMNYLGI (SEQ ID NO: 303), KKETKLSLFANDMI (SEQ ID NO: 304), and/or SPLLFNILLEVLSSAVRKEKELK (SEQ ID NO: 305). Polynucleotides encoding these polypeptides are also encompassed by the invention.

This gene is expressed primarily in PHA activated T cells.

Therefore, polynucleotides and polypeptides of the invention are useful as reagents for differential identification of the tissue(s) or cell type(s) present in a biological sample and for diagnosis of diseases and conditions: immune or hematopoietic disorders, particularly inflammation, immunodeficiencies, and autoimmune diseases. Similarly, polypeptides and antibodies directed to these polypeptides are useful in providing immunological probes for differential identification of the tissue(s) or cell type(s). For a number of disorders of the above tissues or cells, particularly of the immune, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 152 as residues: Ile-14 to Thr-24.

The tissue distribution in T-cells indicates that polynucleotides and polypeptides corresponding to this gene are useful for the diagnosis, treatment, and/or prevention of a variety of immune system disorders. The expression of this gene product indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer e.g. by boosting immune responses. Since the gene is expressed in cells of lymphoid origin, the natural gene product may be involved in immune functions. Therefore it may be also used as an agent for immunological disorders including arthritis, asthma, immune deficiency diseases such as AIDS, and leukemia.

In addition, this gene product may have commercial utility in the expansion of stem cells and committed progenitors of various blood lineages, and in the differentiation and/or proliferation of various cell types. Alternatively, the homology to a reverse transcriptase human gene may implicate this gene as providing utility in the understanding of host-viral interactions, particularly those involving retroviruses and other integration-dependent viruses. Moreover, the protein may show utility in the development of novel inhibitors to viral infection, and thus to the amelioration of human diseases and conditions. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:13 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1359 of SEQ ID NO:13, b is an integer of 15 to 1373, where both a and b correspond to the positions of nucleotide residues shown in SEQ ID NO:13, and where b is greater than or equal to a+14.

Features of Protein Encoded by Gene No: 4

The translation product of this gene shares sequence homology with npdcf-1 which is thought to be important in promoting the survival of bi-potential glial progenitor cells (See Genbank Accession No. gi|456107). One embodiment of this gene comprises polypeptides of the following amino acid sequence: LRRPSTPLRRPWLHLQLPRISLGDQRLAQSAEMYHYQHQRQQMLSLERHKEP PKELDTALRMRRMRTETSRCTSARAWPRPGKWRCATICSTTPHCPRPCRPP AHRLHCHDLEADRRPLAPR (SEQ ID NO: 306), RATQGAGHGSSDEENEDG DFTVYECPGMAPTGEMEVRNHLFD HAALSAPLPAPSSPLALP (SEQ ID NO: 307), KAEYATAKALATPAATPDLAWGPAPGTERGDVPLPAPTATDVVPGAA (SEQ ID NO: 308), SAEMYHYQHQRQQML (SEQ ID NO: 309), LERHKEPPKEL (SEQ ID NO: 310), AKCPP- GAHACGP (SEQ ID NO: 31 1), PVHMSPLEP (SEQ ID NO: 312), WCRLQREIRLTQ (SEQ ID NO: 313), SSDEENEDGDFTVYECPG (SEQ ID NO: 314), APTGEMEVRN (SEQ ID NO: 315), CPGSLDCALK (SEQ ID NO: 316), RATQGAGHGSSDEENEDGDFTVYECPGMAPTGEMEVRNHLFDHAALS APLPAPSSPLALP (SEQ ID NO: 317), NEDGDFTVYECPGMAPTGEMEV (SEQ ID NO: 318), RPTRPSSSCVLPRCLRCSRRGARSPRRAPGLAVPCCPGGGAEGWR RRCLRPPRGTCGCCGCCSPASSSAPPCVEPPPATRNVAACPGSLDCALKKRA SVLLVHMPVGLPSALPXGTAKACFAXMRRASXGGRAQPXLEMRLIPGPR ELARKGIWTSIPP (SEQ ID NO: 319), RCLRCSRRGARSPRRAPGLAVPCCP (SEQ ID NO: 320), and/or GSLDCALKKRASVLLVHMPVGLPSALPXGTAKAC (SEQ ID NO: 321). Additional embodiments is the polynucleotides encoding these polypeptides.

This gene is expressed primarily in cerebellum, synovial sarcoma, and to a lesser extent, in several other cancer cell lines.

Therefore, polynucleotides and polypeptides of the invention are useful as reagents for differential identification of the tissue(s) or cell type(s) present in a biological sample and for diagnosis of diseases and conditions which include, but are not limited to, neural or skeletal disorders, particularly tumors characterized by cells of a relatively undifferentiated state, including neural tumors. Similarly, polypeptides and antibodies directed to those polypeptides are useful n providing immunological probes for differential identification of the tissue(s) or cell type(s). For a number of disorders of the above tissues or cells, particularly of the; synovial fluid, prostate, breast and uterus, expression of this gene at significantly higher or lower levels may be routinely detected in certain tissues or cell types (e.g., neural, skeletal, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 153 as residues: Pro-6 to Arg-11, Glu-52 to Gly-59.

The tissue distribution in the cerebellum, combined with the homology to the human npdcf-1 protein indicates that polynucleotides and polypeptides corresponding to this gene are useful for diagnosing and treating tumors that contain relatively high numbers of undifferentiated cells. Moreover, this gene is useful for the detection, treatment, and/or prevention of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception.

In addition, the gene or gene product may also play a role in the treatment and/or detection of developmental disorders associated with the developing embryo, sexually-linked disorders, or disorders of the cardiovascular system. Alternatively, the expression of this gene product in synovium would suggest a role in the detection and treatment of disorders and conditions affecting the skeletal system, in particular osteoporosis, bone cancer, as well as, disorders afflicting connective tissues (e.g., arthritis, trauma, tendonitis, chrondomalacia and inflammation), such as in the diagnosis or treatment of various autoimmune disorders such as rheumatoid arthritis, lupus, scleroderma, and dermatomyositis as well as dwarfism, spinal deformation, and specific joint abnormalities as well as chondrodysplasias (i.e. spondyloepiphyseal dysplasia congenita, familial osteoarthritis, Atelosteogenesis type II, metaphyseal chondrodysplasia type Schmid).

Moreover, the protein may be useful for inducing astroglial proliferation and promoting neuronal survival, in addition to other highly vascular tissues. The protein can also be used to regulate cellular metabolism (e.g., through the modulation of protein expression). Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:14 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1128 of SEQ ID NO:14, b is an integer of 15 to 1142, where both a and b correspond to the positions of nucleotide residues shown in SEQ ID NO:14, and where b is greater than or equal to a+14.

Features of Protein Encoded by Gene No: 5

The translation product of this gene was found to have homology to the RoBo-1 protein from *Rattus norvegicus* (See Genbank Accession No.gi|2895563 (AF041083)) which is thought to be important as a mediator in bone remodeling. In specific embodiments, polypeptides of the invention comprise the following amino acid sequence: DSHQARSRRLEALWSPSLGEVSSST (SEQ ID NO:).

Polynucleotides encoding these polypeptides are also encompassed by the invention.

This gene is expressed primarily in colon, pituitary, and to a lesser extent in fetal lung and fibrosarcoma.

Therefore, polynucleotides and polypeptides of the invention are useful as reagents for differential identification of the tissue(s) or cell type(s) present in a biological sample and for diagnosis of diseases and conditions which include, but are not limited to, endocrine, gastrointestinal, pulmonary, skeletal, or developmental and proliferative disorders, particularly those effecting the Gut/pituitary/hypothalamic axis. Similarly, polypeptides and antibodies directed to these polypeptides are useful in providing immunological probes for differential identification of the tissue(s) or cell type(s). For a number of disorders of the above tissues or cells, particularly of the digestive system and regulation of feeding, expression of this gene at significantly higher or lower levels may be routinely detected in certain tissues or cell types (e.g., gastrointesinal, endocrine, developmental, skeletal, pulmonary, and cancerous and wounded tissues) or bodily fluids (e.g., lymph, serum, plasma, amniotic fluid, pulmonary surfactant or sputum, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 154 as residues: Asn-26 to Cys-32, Cys-100 to Leu-112, Cys-128 to Ser-135.

The tissue distribution in colon and pituitary indicates that polynucleotides and polypeptides corresponding to this gene are useful for creating disorders related to the intake and utilization of food since this gene is expressed in the digestive tract and a CNS site involved in regulation of weight homeostasis the secreted protein can also be used to determine biological activity, to raise antibodies, as tissue markers, to isolate cognate ligands or receptors, to identify agents that modulate their interactions, and as nutritional supplements. It may also have a very wide range of biological activities. Typical of these are cytokine, cell proliferation/differentiation modulating activity or induction of other cytokines; immunostimulating/immunosuppressant activities (e.g., for treating human immunodeficiency virus infection, cancer, autoimmune diseases and allergy); regulation of hematopoiesis (e.g., for treating anemia or as adjunct to chemotherapy); stimulation or growth of bone, cartilage, tendons, ligaments and/or nerves (e.g., for treating wounds, stimulation of follicle stimulating hormone (for control of fertility); chemotactic and chemokinetic activities (e.g., for treating infections, tumors); hemostatic or thrombolytic activity (e.g., for treating hemophilia, cardiac infarction etc.); anti-inflammatory activity (e.g., for treating septic shock, Crohn's disease); as antimicrobials; for treating psoriasis or other hyperproliferative diseases; for regulation of metabolism, and behavior. Also contemplated is the use of the corresponding nucleic acid in gene therapy procedures. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:15 and may have been publicly may ailable prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1020 of SEQ ID NO:15, b is an integer of 15 to 1034, where both a and b correspond to the positions of nucleotide residues shown in SEQ ID NO:15, and where b is greater than or equal to a+14.

Features of Protein Encoded by Gene No: 6

The translation product of this gene shares sequence homology with Cortical granule lectin which is thought to be important in blocking polyspermy (See Genbank Accession No. gnl|PID|e1181610). In specific embodiments, polypeptides of the invention comprise the following amino acid sequence: RSCKEIKD (SEQ ID NO: 323), GGGWTLVASVHEN (SEQ ID NO: 324), ADYPEGDGNWANYNTFGSA (SEQ ID NO: 325), ATSDDYKNPGYYDI (SEQ ID NO: 326), CIGGGGYFPEA (SEQ ID NO: 327), DSDKIT (SEQ ID NO: 329), YQTFCDMT (SEQ ID NO: 330), and/or EITEAAVLLFY (SEQ ID NO: 328). Polynucleotides encoding these polypeptides are also encompassed by the invention.

This gene is expressed primarily in benign and metastatic colon, and to a lesser extent in HEL cells.

Therefore, polynucleotides and polypeptides of the invention are useful as reagents for differential identification of the tissue(s) or cell type(s) present in a biological sample and for diagnosis of diseases and conditions which include, but are not limited to, gastrointestinal, reproductive, or developmental disorders, particularly cancer, or inflammatory conditions. Similarly, polypeptides and antibodies directed to these polypeptides are useful in providing immunological probes for differential identification of the tissue(s) or cell type(s). For a number of disorders of the above tissues or cells, particularly of the digestive system, expression of this gene at significantly higher or lower levels may be detected in certain tissues or cell types (e.g., gastrointestinal, reproductive, proliferating, and cancerous and wounded tissues) or bodily fluids (e.g., lymph, serum, plasma, seminal fluid, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 155 as residues: Arg-15 to Ser-33, Pro-35 to Cys-41.

The tissue distribution in colon, combined with the homology to cortical granule lectins indicates that polynucleotides and polypeptides corresponding to this gene are useful for treating disorders of the colon. These may include diseases related to damage or chronic inflammation as well as tumors of the colon. The product may also be useful for the identification of colon cancer metastasis and, as a secreted protein, may have diagnostic and prognostic applications. Moreover, the protein is useful in the treatment, detection, and/or prevention of reproductive disorders, particularly normal testicular function, in addition having utility in the development of contraceptives, or in the treatment of polyspermy. Protein, as well as, antibodies directed against the protein may show utility as a tumor marker and/or immunotherapy targets for the above listed tumors and tissues.

Many polynucleotide sequences, such as EST sequences, are publicly available and accessible through sequence databases. Some of these sequences are related to SEQ ID NO:16 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1184 of SEQ ID NO:16, b is an integer of 15 to 1198, where both a and b correspond to the positions of nucleotide residues shown in SEQ ID NO:16, and where b is greater than or equal to a+14.

Features of Protein Encoded by Gene No: 7

This gene is expressed primarily in eight week human embryos.

Therefore, polynucleotides and polypeptides of the invention are useful as reagents for differential identification of the tissue(s) or cell type(s) present in a biological sample and for diagnosis of diseases and conditions which include, but are not limited to, fetal and/or developmental abnormalities. Similarly, polypeptides and antibodies directed to these polypeptides are useful in providing immunological probes for differential identification of the tissue(s) or cell type(s). For a number of disorders of the above tissues or cells, particularly of the developing fetus, expression of this gene at significantly higher or lower levels may be routinely detected in certain tissues or cell types (e.g., developing, differentiating, and cancerous and wounded tissues) or bodily fluids (e.g., amniotic fluid, serum, plasma, lymph, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in eight week old tissue indicates that polynucleotides and polypeptides corresponding to this gene are useful for detecting embryonic abnormalities, in particular congenital abnormalities, which include, but are not limited to Tay-Sachs disease, phenylkenonuria, galactosemia, hyperlipidemias, porphyrias, and Hurler's syndrome. Expression within embryonic tissue and other cellular sources marked by proliferating cells indicates that this protein may play a role in the regulation of cellular division, and may show utility in the diagnosis, treatment, and/or prevention of cancer and other proliferative disorders. Similarly, developmental tissues rely on decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:17 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1433 of SEQ ID NO:17, b is an integer of 15 to 1447, where both a and b correspond to the positions of nucleotide residues shown in SEQ ID NO:17, and where b is greater than or equal to a+14.

Features of Protein Encoded by Gene No: 8

In specific embodiments, polypeptides of the invention comprise the following amino acid sequence: MGKRAHEVRRPPHSRPLHGTPAGWVLDPSGYKDVTQDA EVMEVLQNLYRTKSFLFVGCGETLRDQIFQALFLYSVPNKVDLEHYMLVLKE NEDHFFKHQADMLLHGIKVVSYGDCFDHFPGYVQDLATQICKQQSPGHLYS NSWSATPDGRGGP (SEQ ID NO: 331), VLDPSGYKDVTQDAEVMEVLQNLYRT (SEQ ID NO: 332), YSVPNKVDLEHY MLVLKENEDHFFKH (SEQ ID NO: 333), DLATQICKQQSPGHLYSNSWSATPD (SEQ ID NO: 334), RRMKTISLSIRQICFC TESKLYPTGTVLTTFQDMCKTLPLRSANSKAQDICTRIHGVPLLMGEEAHDSD SHASDRGHHTMLPLPAGSFSESSHQAWEVEMLIAWTAPHYWVMHARTVQR GS (SEQ ID NO: 335), TESKLYPTGTVLTTFQDMCKTLPLRSA (SEQ ID NO: 336), and/or LMGEEAH DSDSHASDRGHHTMLPLPAG (SEQ ID NO: 337). Polynucleotides encoding these polypeptides are also encompassed by the invention.

This gene is expressed primarily in endothelial cells, and to a lesser extent in lymph node, tonsils, heart and spinal cord.

Therefore, polynucleotides and polypeptides of the invention are useful as reagents for differential identification of the tissue(s) or cell type(s) present in a biological sample and for diagnosis of diseases and conditions which include, but are not limited to, vascular diseases, such as restenosis, including disorders of the integumentary system. Similarly, polypeptides and antibodies directed to these polypeptides are useful in providing immunological probes for differential identification of the tissue(s) or cell type(s). For a number of disorders of the above tissues or cells, particularly of the vascular system, expression of this gene at significantly higher or lower levels may be routinely detected in certain tissues or cell types (e.g., vascular, integumentary, immune, hematopoietic, neural, cardiovascular, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in endothelial cells indicates that polynucleotides and polypeptides corresponding to this gene are useful for treating diseases of the vasculature including problems associated with diabetes and restenosis following angioplasty. Moreover, the protein is useful in the detection, treatment, and/or prevention of a variety of other vascular conditions, which include, but are not limited to, stroke, microvascular disease, aneurysm, vascular leak syndrome, or embolism. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:18 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1408 of SEQ ID NO:18, b is an integer of 15 to 1422, where both a and b correspond to the positions of nucleotide residues shown in SEQ ID NO:18, and where b is greater than or equal to a+14.

Features of Protein Encoded by Gene No: 9

The translation product of this gene was shown to have homology to the Gcap1 gene product of *Mus musculus*, which is specifically expressed in cerebellum and appears to be developmentally regulated (See Genbank Accession No. gi|862343). In specific embodiments, polypeptides of the invention comprise the following amino acid sequence: LCAVEKTRTFTRGDCGPNRHHKHVLKAKDNNHIQRHQFSSTLEFS SNSTDGLKYICVYLYVCTHPCIYIYLSAHTLHMYTHYLCKI (SEQ ID NO:338), SST LEFSSNSTDGLKYICVYLYVCTHPCIY (SEQ ID NO:339), STSVCICTCAH THVYI FIYLHTHYICIHTIYVKYNICIMHINSNKCICVIFKIEQLYLEVVNAENWF YC (SEQ ID NO:340), IHTIYVKYNICIMHIN SNKCICVIFKIEQLY (SEQ ID NO:341), and/or NSAVTVQMA (SEQ ID NO:342). Polynucleotides encoding these polypeptides are also encompassed by the invention.

This gene is expressed primarily in fetal lung, endothelial cells and to a lesser extent, in astrocytes and fetal brain.

Therefore, polynucleotides and polypeptides of the invention are useful as reagents for differential identification of the tissue(s) or cell type(s) present in a biological sample and for diagnosis of diseases and conditions which include, but are not limited to, vasdcular, developmental, neural, or proliferative conditions, particularly endothelial cell proliferation, such as occurs, in restenosis. Similarly, polypeptides and antibodies directed to these polypeptides are useful in providing immunological probes for differential identification of the tissue(s) or cell type(s). For a number of disorders of the above tissues or cells, particularly of the vascular system, expression of this gene at significantly higher or lower levels may be routinely detected in certain tissues or cell types (e.g., developmental, neural, vascular, and cancerous and wounded tissues) or bodily fluids (e.g., amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in fetal brain, in addition to the homology to a brain-specific regulatory protein indicates that polynucleotides and polypeptides corresponding to this gene are useful for the detection, treatment, or prevention of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of evelopmental disorders associated with the developing embryo, sexually-linked isorders, or disorders of the cardiovascular system.

Alternatively, the tissue distribution indicates that polynucleotides and polypeptides corresponding to this gene are useful for treating abnormal proliferation of endothelial cells such as occurs upon injury to the lung or arteries. Moreover, this protein may play a role in the regulation of cellular division, and may show utility in the diagnosis and treatment of cancer and other proliferative disorders. Similarly, developmental tissues rely on decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:19 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1093 of SEQ ID NO:19, b is an integer of 15 to 1107, where both a and b correspond to the positions of nucleotide residues shown in SEQ ID NO:19, and where b is greater than or equal to a+14.

Features of Protein Encoded by Gene No: 10

In specific embodiments, polypeptides of the invention comprise the following amino acid sequence: TKTSTPLR (SEQ ID NO: 343). Polynucleotides encoding these polypeptides are also encompassed by the invention. The gene encoding the disclosed cDNA is believed to reside on □chromosome 12. Accordingly, polynucleotides related to this invention are useful as a marker in linkage analysis for chromosome 12.

This gene is expressed primarily in infant brain and fetal tissues.

Therefore, polynucleotides and polypeptides of the invention are useful as reagents for differential identification of the tissue(s) or cell type(s) present in a biological sample and for diagnosis of diseases and conditions which include, but are not limited to, developmental abnormalities or neural disorders, particularly gestational conditions, such as spina bifida. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., developing, neural, differentiating, and cancerous and wounded tissues) or bodily fluids (e.g., amniotic fluid, serum, lymph, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in infant brain and fetal tissues suggests that the protein product of this clone is useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system. Alternatively, the tissue distribution suggests that the protein product of this clone is useful for the diagnosis, treatment, and/or prevention of cancer and other proliferative disorders. Moreover, the expression within fetal tissue and other cellular sources marked by proliferating cells suggests that this protein may play a role in the regulation of cellular division. Similarly, embryonic development also involves decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:20 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1169 of SEQ ID NO:20, b is an integer of 15 to 1183, where both a and b correspond to the positions of nucleotide residues shown in SEQ ID NO:20, and where b is greater than or equal to a+14.

Features of Protein Encoded by Gene No: 11

In specific embodiments, polypeptides of the invention comprise the following amino acid sequence: VCIPGAAGLSVLLG (SEQ ID NO: 344). Polynucleotides encoding these polypeptides are also encompassed by the invention.

This gene is expressed primarily in fetal kidney.

Therefore, polynucleotides and polypeptides of the invention are useful as reagents for differential identification of the tissue(s) or cell type(s) present in a biological sample and for diagnosis of diseases and conditions which include, but are not limited to, urogenital, renal, or developmental disorders, particularly renal failure, tumors of the kidney, and/or developmental abnormalities associated with the kidney. Similarly, polypeptides and antibodies directed to these polypeptides are useful in providing immunological probes for differential identification of the tissue(s) or cell type(s). For a number of disorders of the above tissues or cells, particularly of the renal system, expression of this gene at significantly higher or lower levels may be routinely detected in certain tissues or cell types (e.g., urological, renal, developmental, and cancerous and wounded tissues) or bodily fluids (e.g., amniotic fluid, lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 160 as residues: Gln-26 to Gln-34.

The tissue distribution in fetal kidney indicates that polynucleotides and polypeptides corresponding to this gene are useful for the diagnosis, treatment, and/or prevention of cancer and other proliferative disorders, particularly renal disorders. Expression within embryonic tissue and other cellular sources marked by proliferating cells indicates that this protein may play a role in the regulation of cellular division. Similarly, embryonic development also involves decisions involving cell differentiation and/or apoptosis in pattern formation. Thus this protein may also be involved in apoptosis or tissue differentiation and could again be useful in cancer therapy.

Moreover, the protein product of this gene could be used in the treatment and/or detection of kidney diseases including nephritus, renal tubular acidosis, proteinuria, pyuria, edema, pyelonephritis, hydronephritis, nephrotic syndrome, crush syndrome, glomerulonephritis, hematuria, renal colic and kidney stones, in addition to Wilm's Tumor Disease, and congenital kidney abnormalities such as horseshoe kidney, polycystic kidney, and Falconi's syndrome. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:21 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to: 1406 of SEQ ID NO:21, b is an integer of 15 to 1420, where both a and b correspond to the positions of nucleotide residues shown in SEQ ID NO:21, and where b is greater than or equal to a+14.

Features of Protein Encoded by Gene No: 12

The gene encoding the disclosed cDNA is believed to reside on □chromosome 17. Accordingly, polynucleotides related to this invention are useful as a marker in linkage analysis for chromosome 17.

This gene is expressed primarily in breast, fetal kidney, and T-cells.

Therefore, polynucleotides and polypeptides of the invention are useful as reagents for differential identification of the tissue(s) or cell type(s) present in a biological sample and for diagnosis of diseases and conditions which include, but are not limited to, reproductive, immune, developmental, or renal disorders, particularly autoimmune diseases, chronic inflammatory conditions, or urogenital disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, reproductive, cancerous and wounded tissues) or bodily fluids (e.g., breast milk, lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 161 as residues: His-2 to Lys-7, Ser-28 to Glu-35.

The tissue distribution in breast and T-cells indicates that polynucleotides and polypeptides corresponding to this gene are useful for the diagnosis, treatment, and/or prevention of a variety of immune system disorders. Moreover, the expression of this gene product indicates a role in regulating the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer e.g. by boosting immune responses.

Since the gene is expressed in cells of lymphoid origin, the natural gene product may be involved in immune functions. Therefore it may be also used as an agent for immunological disorders including arthritis, asthma, immune deficiency diseases such as AIDS, and leukemia. Protein, as well as, antibodies directed against the protein may show utility as a tumor marker and/or immunotherapy targets for the above listed tumors and tissues. In addition, this gene product may have commercial utility in the expansion of stem cells and committed progenitors of various blood lineages, and in the differentiation and/or proliferation of various cell types.

Alternatively, the expression within fetal tissue indicates this protein may play a role in the regulation of cellular division, and may show utility in the diagnosis and treatment of cancer and other proliferative disorders. Similarly, developmental tissues rely on decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:22 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1561 of SEQ ID NO:22, b is an integer of 15 to 1575, where both a and b correspond to the positions of nucleotide residues shown in SEQ ID NO:22, and where b is greater than or equal to a+14.

Features of Protein Encoded by Gene No: 13

In specific embodiments, polypeptides of the invention comprise the following amino acid sequence: SILPVEMAAAVAGMLRGGLLPQAGRLPTLQTVRYGSKAVTRHRRV (SEQ ID NO: 345), and/or AGMLRGGLLPQAGRLPTLQTVRYGSK (SEQ ID NO: 346). Polynucleotides encoding these polypeptides are also encompassed by the invention.

This gene is expressed primarily in the frontal cortex of the brain.

Therefore, polynucleotides and polypeptides of the invention are useful as reagents for differential identification of the tissue(s) or cell type(s) present in a biological sample and for diagnosis of diseases and conditions which include, but are not limited to, neural disorders, particularly neurodegenerative disorders, ischemia, Alzheimer's, or Parkinson's. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., neural, and cancerous and wounded tissues) or bodily fluids (e.g., serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 162 as residues: Glu-31 to Gly-37.

The tissue distribution in frontal cortex indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo. Protein, as well as, antibodies directed against the protein may show utility as a tumor marker and/or immunotherapy targets for the above listed tumors and tissues.

Many polynucleotide sequences, such as EST sequences, are publicly available and accessible through sequence databases. Some of these sequences are related to SEQ ID NO:23 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 527 of SEQ ID NO:23, b is an integer of 15 to 541, where both a and b correspond to the positions of nucleotide residues shown in SEQ ID NO:23, and where b is greater than or equal to a+14.

Features of Protein Encoded by Gene No: 14

The gene encoding the disclosed cDNA is believed to reside on □chromosome 1. Accordingly, polynucleotides related to this invention are useful as a marker in linkage analysis for chromosome 1.

This gene is expressed primarily in ovary, and to a lesser extent, in infant brain.

Therefore, polynucleotides and polypeptides of the invention are useful as reagents for differential identification of the tissue(s) or cell type(s) present in a biological sample and for diagnosis of diseases and conditions which include, but are not limited to, reproductive, neural, or developmental disorders, particularly cancers and other diseases of the reproductive system including ovarian cysts and hormonal disorders. Similarly, polypeptides and antibodies directed to these polypeptides are useful in providing immunological probes for differential identification of the tissue(s) or cell type(s). For a number of disorders of the above tissues or cells, particularly of the female reproductive system, expression of this gene at significantly higher or lower levels may be routinely detected in certain tissues or cell types (e.g., reproductive, neural, developmental, and cancerous and wounded tissues) or bodily fluids (e.g., amniotic fluid, lymph, seminal fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 163 as residues: Ser-32 to Glu-37.

The tissue distribution in ovarian tissue indicates that polynucleotides and polypeptides corresponding to this gene are useful for diagnosis and intervention of ovarian tumors, in addition to other tumors where expression has been indicated. Alternatively, expression within the fetal brain indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo.

Moreover, the expression within fetal tissue indicates this protein may play a role in the regulation of cellular division, and may show utility in the diagnosis and treatment of cancer and other proliferative disorders. Similarly, developmental tissues rely on decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:24 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 819 of SEQ ID NO:24, b is an integer of 15 to 833, where both a and b correspond to the positions of nucleotide residues shown in SEQ ID NO:24, and where b is greater than or equal to a+14.

Features of Protein Encoded by Gene No: 15

The translation product of this gene was shown to have homology to the highly conserved ras gene which is known to be important in the regulation of cell growth, and thus has been shown to serve as an inducible oncogene in eukaryotic tissues (See Genbank Accession No. gb|Z11804DDRASX).

When tested against PC12 (rat pheochromocytoma cells) and NIH3T3 cell lines, supernatants removed from cells containing this gene activated the EGR1 (early growth response gene 1) promoter element. Thus, it is likely that this gene activates sensory neuron cells and fibroblasts, in addition to other tissues or cell types, through the EGR1 signal transduction pathway. The EGR1 (early growth response gene 1) is a separate signal transduction pathway from Jaks-STAT, genes containing the EGR1 promoter are induced in various tissues and cell types upon activation, leading the cells to undergo differentiation and proliferation.

Moreover, contact of cells with supernatant expressing the product of this gene has been shown to increase the permeability of the plasma membrane of monocytes to calcium. Thus it is likely that the product of this gene is involved in a signal transduction pathway that is initiated when the product binds a receptor on the surface of the plasma membrane of monocytes, in addition to other cell-lines or tissue cell types, such as immune or hematopoietic cells. Thus, polynucleotides and polypeptides have uses which include, but are not limited to, activating monocytes.

In specific embodiments, polypeptides of the invention comprise the following amino acid sequence: ARAGQMQNLESARAGRSVSTQTGS (SEQ ID NO: 347). Polynucleotides encoding these polypeptides are also encompassed by the invention. The gene encoding the disclosed cDNA is believed to reside on chromosome 13. Accordingly, polynucleotides related to this invention are useful as a marker in linkage analysis for chromosome 13.

This gene is expressed primarily in T-cells.

Therefore, polynucleotides and polypeptides of the invention are useful as reagents for differential identification of the tissue(s) or cell type(s) present in a biological sample and for diagnosis of diseases and conditions which include, but are not limited to, diseases involving immune regulation, which include, but are not limited to autoimmune diseases such as rheumatoid arthritis, lupus, and leukemia. Similarly, polypeptides and antibodies directed to these polypeptides are useful in providing immunological probes for differential identification of the tissue(s) or cell type(s). For a number of disorders of the above tissues or cells, particularly of the immune, expression of this gene at significantly higher or lower levels may be routinely detected in certain tissues or cell types (e.g., hematopoietic, immune, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 164 as residues: Ala-28 to His-41, Pro-43 to Gln-64.

The tissue distribution in T-cells, combined with the detected EGR1 and calcium flux activities, indicates polynucleotides and polypeptides corresponding to this gene are useful for the diagnosis, treatment, and/or prevention of a variety of immune system disorders, particularly those dependent upon signalling aberrations. Expression of this gene product in T-cells indicates a role in regulating the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer—particularly considering the homology to a conserved ras gene, and the detected EGR1 biological activity.

Since the gene is expressed in cells of lymphoid origin, the natural gene product may be involved in immune functions. Therefore it may be also used as an agent for immunological disorders including arthritis, asthma, immune deficiency diseases such as AIDS, and leukemia. Protein, as well as, antibodies directed against the protein may show utility as a tumor marker and/or immunotherapy targets for the above listed tumors and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:25 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1541 of SEQ ID NO:25, b is an integer of 15 to 1555, where both a and b correspond to the positions of nucleotide residues shown in SEQ ID NO:25, and where b is greater than or equal to a+14.

Features of Protein Encoded by Gene No: 16

This gene is expressed primarily in kidney cortex.

Therefore, polynucleotides and polypeptides of the invention are useful as reagents for differential identification of the tissue(s) or cell type(s) present in a biological sample and for diagnosis of diseases and conditions which include, but are not limited to, diseases of the kidney including cancer and renal dysfunction, in addition to, endocrine disorders, particularly of the adrenal glands. Similarly, polypeptides and antibodies directed to these polypeptides are useful in providing immunological probes for differential identification of the tissue(s) or cell type(s). For a number of disorders of the above tissues or cells, particularly of the renal system, expression of this gene at significantly higher or lower levels may be routinely detected in certain tissues or cell types (e.g., urogenital, renal, endocrine, and cancerous and wounded tissues) or bodily fluids (e.g., urine, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in kidney cortex indicates that polynucleotides and polypeptides corresponding to this gene are useful for the treatment, diagnosis, and/or prevention of diseases of the kidney including renal failure, nephritus, renal tubular acidosis, proteinuria, pyuria, edema, pyelonephritis, hydronephritis, nephrotic syndrome, crush syndrome, glomerulonephritis, hematuria, renal colic and kidney stones, in addition to Wilm's Tumor Disease, and congenital kidney abnormalities such as horseshoe kidney, polycystic kidney, and Falconi's syndrome. Protein, as well as, antibodies directed against the protein may show utility as a tumor marker and/or immunotherapy targets for the above listed tissues. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:26 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1529 of SEQ ID NO:26, b is an integer of 15 to 1543, where both a and b correspond to the positions of nucleotide residues shown in SEQ ID NO:26, and where b is greater than or equal to a+14.

Features of Protein Encoded by Gene No: 17

This gene is expressed primarily in T-cell lymphoma, and to a lesser extent, in bone marrow stromal cells.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic disorders, particularly cancers, such as lymphomas and leukemias. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in bone marrow stromal cells and T-cell lymphoma indicates that polynucleotides and polypeptides corresponding to this gene are useful for the diagnosis, treatment, and/or prevention of a variety of immune or hematopoietic disorders. Expression of this gene product in T-cells indicates a role in regulating the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, and leukemia. Protein, as well as, antibodies directed against the protein may show utility as a tumor marker and/or immunotherapy targets for the above listed tumors and tissues. In addition, this gene product may have commercial utility in the expansion of stem cells and committed progenitors of various blood lineages, and in the differentiation and/or proliferation of various cell types.

Expression in bone marrow cells suggest that polynucleotides and polypeptides corresponding to this gene are useful for the treatment and diagnosis of hematopoetic related disorders such as anemia, pancytopenia, leukopenia, thrombocytopenia or leukemia since stromal cells are important in the production of cells of hematopoietic lineages. The uses include bone marrow cell ex vivo culture, bone marrow transplantation, bone marrow reconstitution, radiotherapy or chemotherapy of neoplasia The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tumors and tissues.

Many polynucleotide sequences, such as EST sequences, are publicly available and accessible through sequence databases. Some of these sequences are related to SEQ ID NO:27 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1248 of SEQ ID NO:27, b is an integer of 15 to 1262, where both a and b correspond to the positions of nucleotide residues shown in SEQ ID NO:27, and where b is greater than or equal to a+14.

Features of Protein Encoded by Gene No: 18

This gene is expressed primarily in medulloblastoma.

Therefore, polynucleotides and polypeptides of the invention are useful as reagents for differential identification of the tissue(s) or cell type(s) present in a biological sample and for diagnosis of diseases and conditions which include, but are not limited to, disorders of the central nervous system, including cancers. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., neural, cancerous and wounded tissues) or bodily fluids (e.g., serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 167 as residues: Phe-22 to Leu-28.

The tissue distribution indicates that polynucleotides and polypeptides corresponding to this gene are useful for the detection, treatment, and/or prevention of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, AIDS, psychoses, autism, and altered behaviors, including disorders in feeding, sleep patterns, balance, and perception. In addition, the gene or gene product may also play a role in the treatment and/or detection of developmental disorders associated with the developing embryo. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:28 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 739 of SEQ ID NO:28, b is an integer of 15 to 753, where both a and b correspond to the positions of nucleotide residues shown in SEQ ID NO:28, and where b is greater than or equal to a+14.

Features of Protein Encoded by Gene No: 19

The translation product of this gene was shown to have homology to the mammalian notch I protein which has been shown to be important in the regulation of cell-fate during pattern formation and development (See Genbank Accession No. gi|57635). One embodiment of this gene comprises polypeptides of the following amino acid sequence: KHEXHQVSDGALRCFASLADRFTRRGVDPAPLAKHGLTEE LLSRMAAAGGTVSGPSSACKPXRSTTGAPSTTADSKLSNQVSTIVSLLSTLCR GSPVVTHDLLRSELPDSIESALQGDERCVLDTMRLVDFLLVLLFEGRKALPKS SA GSTGRIPGLRRLDSSGERSHRQLIDCIRSKDTDALIDAIDTGAFEVNFMDDVG QTLLNWASAFGTQEMVEFLCERGADVNRGQRSSSLHYAACFGRPQVAKT LLRHGANPDLRDEDGKTPLDKARERGHSEVVAILQSPGDWMCPVNKGDDK (SEQ ID NO: 348), PLDKARERGHSEVVAIL (SEQ ID NO: 349), AKTLLRHG ANPDLRD (SEQ ID NO: 350), GRGRAWLCRRPVGSWIGAVWNDKPDKET FKKPWQMWTQIHCWNGYRWDXXDXKD (SEQ ID NO: 351), SWIGAVWND KPDKETFKKPWQMW (SEQ ID NO: 352), KTMADVDPDTLLEWLQMGXGRXK GHATN TP (SEQ ID NO: 353), RGVDPAPLAKHGLTEELLSRMAAAGGTVSG PSSA (SEQ ID NO: 354), RSTTGAPSTTADSKLSNQVSTIVSLLSTLCR (SEQ: ID NO: 355), FEVNFMDDVGQTLLNWASAFGTQEMVEFLCERGA (SEQ ID NO: 356), and/or EDGKTPLDKARERGHSEVVAILQSPGDW (SEQ ID NO: 357). An additional embodiment is the polynucleotides encoding these polypeptides.

This gene is expressed primarily in endothelial cells.

Therefore, polynucleotides and polypeptides of the invention are useful as reagents for differential identification of the tissue(s) or cell type(s) present in a biological sample and for diagnosis of diseases and conditions which include, but are not limited to, vascular disorders, particularly diseases involving angiogenic abnormalities including diabetic retinopathy, macular degeneration, and other diseases including arteriosclerosis, stroke, aneurysm, embolism, and cancer. Similarly, polypeptides and antibodies directed to these polypeptides are useful in providing immunological probes for differential identification of the tissue(s) or cell type(s). For a number of disorders of the above tissues or cells, particularly of the vascular system, expression of this gene at significantly higher or lower levels may be routinely detected in certain tissues or cell types (e.g., endothelial, vascular, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue from an individual not having the disorder.

Preferred epitopes include those comprising a sequence shown in SEQ ID NO. 168 as residues: Asp-17 to Phe-23.

The tissue distribution in endothelial cells indicates that polynucleotides and polypeptides corresponding to this gene are useful for treating diseases where an increase or decrease in angiogenesis is indicated and as a factor in the wound healing process. The protein is useful in the treatment of cancer cells and tissues, particularly in inhibiting angiogenesis of the invading tumor. Protein, as well as, antibodies directed against the protein may show utility as a tumor marker and/or immunotherapy targets for the above listed tissues.

Alternatively, considering the homology to the Notch I protein, this gene may show utility in the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:29 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1607 of SEQ ID NO:29, b is an integer of 15 to 1621, where both a and b correspond to the positions of nucleotide residues shown in SEQ ID NO:29, and where b is greater than or equal to a+14.

Features of Protein Encoded by Gene No: 20

In specific embodiments, polypeptides of the invention comprise the following amino acid sequence: TRPTMPNFLWFPKCA (SEQ ID NO: 358). Polynucleotides encoding these polypeptides are also encompassed by the invention.

This gene is expressed primarily in meningioma tissues.

Therefore, polynucleotides and polypeptides of the invention are useful as reagents for differential identification of the tissue(s) or cell type(s) present in a biological sample and for diagnosis of diseases and conditions which include, but are not limited to, neural or central nervous system disorders, particularly cancers of the central nervous system and endbthelium. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., neural, endothelial, CNS, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in meningioma tissue indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system.

Moreover, the protein is useful in inhibiting or ameliorating infections of the meninges, particular viral infections. In addition, the protein may show utility in the treatment, detection, and/or prevention of such infections and disorders, in addition to degenerative conditions or congenital defects of the meninges. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:30 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 907 of SEQ ID NO:30, b is an integer of 15 to 921, where both a and b correspond to the positions of nucleotide residues shown in SEQ ID NO:30, and where b is greater than or equal to a+14.

Features of Protein Encoded by Gene No: 21

The translation product of this gene was shown to have homology to the retinoic acid receptor gamma-2 which is thought to be important in the development of, and may be a key determinant for, human breast cancer during aberrant activation (See Genbank Accession No. AA176435). In specific embodiments, polypeptides of the invention comprise the following amino acid sequence: LPPCLAQIFPFFSSGTNLTFCFFVFV FVFVFAELDYRNSYEIEY (SEQ ID NO: 359). Polynucleotides encoding these polypeptides are also encompassed by the invention.

This gene is expressed primarily in ovary, and to a lesser extent, in meningioma.

Therefore, polynucleotides and polypeptides of the invention are useful as reagents for differential identification of the tissue(s) or cell type(s) present in a biological sample and for diagnosis of diseases and conditions which include, but are not limited to, reproductive or neural disorders, particularly ovarian cancer, as well as, other cancers of the reproductive system, meninges, and endothelial tissue in general. Similarly, polypeptides and antibodies directed to these polypeptides are useful in providing immunological probes for differential identification of the tissue(s) or cell type(s). For a number of disorders of the above tissues or cells, particularly of the female reproductive system, expression of this gene at significantly higher or lower levels may be routinely detected in certain tissues or cell types (e.g., ovarian, reproductive, neural, endothelial, endocrine, and cancerous and wounded tissues) or bodily fluids (e.g., amniotic fluid, lymph, serum, plasma, urine, synovial fluid and spinal fluid) or another tissue or cell sample taken from an individual having such a is order, relative to the standard gene expression level, i.e., the expression level in healthy tissue or bodily fluid from an individual not having the disorder.

Preferred epitopes include those comprising a sequence shown in SEQ ID NO. 170 as residues: Leu-8 to Gln-18, Thr-26 to Lys-33, Met-39 to Cys-46, Ala-62 to Pro-69, Pro-83 to Glu-90.

The tissue distribution in ovarian tissues indicates that polynucleotides and polypeptides corresponding to this gene are useful for diagnosis and intervention of tumors within these tissues, in addition to other tumors where expression has been indicated. The protein may also show utility in the treatment, detection, prevention, and/or amelioration of degenerative conditions or congenital disorders of the meninges, and the brain and spinal cord, in general. Protein, as well as, antibodies directed against the protein may show utility as a tissue-specific marker and/or immunotherapy target for the above listed tumors and tissues.

Many polynucleotide sequences, such as EST sequences, are publicly available and accessible through sequence databases. Some of these sequences are related to SEQ ID NO:31 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 2081 of SEQ ID NO:3 1, b is an integer of 15 to 2095, where both a and b correspond to the positions of nucleotide residues shown in SEQ ID NO:3 1, and where b is greater than or equal to a+14.

Features of Protein Encoded by Gene No: 22

This gene is expressed primarily in the spongy tissue from Alzheimer's brain.

Therefore, polynucleotides and polypeptides of the invention are useful as reagents for differential identification of the tissue(s) or cell type(s) present in a biological sample and for diagnosis of diseases and conditions which include, but are not limited to, neural disorders, which include, but are not limited to Alzheimer's disease and other neurodegenerative diseases. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., neural, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 171 as residues: Ser-31 to Ala-37, Ala-50 to Tyr-55, Phe-63 to Arg-68, His-83 to Pro-89.

The tissue distribution in spongy tissue from Alzheimer's patient indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:32 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1824 of SEQ ID NO:32, b is an integer of 15 to 1838, where both a and b correspond to the positions of nucleotide residues shown in SEQ ID NO:32, and where b is greater than or equal to a+14.

Features of Protein Encoded by Gene No: 23

This gene is expressed primarily in bone marrow cells.

Therefore, polynucleotides and polypeptides of the invention are useful as reagents for differential identification of the tissue(s) or cell type(s) present in a biological sample and for diagnosis of diseases and conditions which include, but are not limited to, immune or hematological disorders. Similarly, polypeptides and antibodies directed to these polypeptides are useful in providing immunological probes for differential identification of the tissue(s) or cell type(s). For a number of disorders of the above tissues or cells, particularly of the hematological and immune systems, expression of this gene at significantly higher or lower levels may be routinely detected in certain tissues or cell types (e.g., immune, haematopoeitic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 172 as residues: Glu-22 to Ser-33, Leu-47 to Ser-55, Thr-87 to Arg-104.

The tissue distribution in bone marrow cells indicates that polynucleotides and polypeptides corresponding to this gene are useful for the treatment and diagnosis of hematopoetic related disorders, which include, but are not limited to anemia, pancytopenia, leukopenia, thrombocytopenia or leukemia since stromal cells are important in the production of cells of hematopoietic lineages. The uses include bone marrow cell ex vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:33 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 768 of SEQ ID NO:33, b is an integer of 15 to 782, where both a and b correspond to the positions of nucleotide residues shown in SEQ ID NO:33, and where b is greater than or equal to a+14.

Features of Protein Encoded by Gene No: 24

In specific embodiments, polypeptides of the invention comprise the following amino acid sequence: LKCTIYGGA (SEQ ID NO: 360). Polynucleotides encoding these polypeptides are also encompassed by the invention.

This gene is expressed primarily in neutrophils.

Therefore, polynucleotides and polypeptides of the invention are useful as reagents for differential identification of the tissue(s) or cell type(s) present in a biological sample and for diagnosis of diseases and conditions which include, but are not limited to, diseases of the immune system, including inflammatory diseases and allergies. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, haematopoeitic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 173 as residues: Gln-36 to Lys-41.

The tissue distribution in neutrophils indicates that polynucleotides and polypeptides corresponding to this gene are useful for the diagnosis, treatment, and/or prevention of a variety of immune system disorders. Expression of this gene product indicates a role in regulating the proliferation; survival; differentiation; and/or activation of hematopoietic cell lineages, including blood stem cells. This gene product may be involved in the regulation of cytokine production, antigen presentation, or other processes that may also suggest a usefulness in the treatment of cancer (e.g. by boosting immune responses). Since the gene is expressed in cells of lymphoid origin, the natural gene product may be involved in immune functions.

Therefore it may be also used as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, scleroderma and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:34 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1546 of SEQ ID NO:34, b is an integer of 15 to 1560, where both a and b correspond to the positions of nucleotide residues shown in SEQ ID NO:34, and where b is greater than or equal to a+14.

Features of Protein Encoded by Gene No: 25

In specific embodiments, polypeptides of the invention comprise the following amino acid sequence: HVLWSLLSACWTQFLVYFCCLMILQRTFPPRALRTSPWLSNPMGVKGKKKK GTFME (SEQ ID NO: 361), and/or FLVYFCCLMILQRTFPPRALRTSPWLSNPM (SEQ ID NO: 362). Polynucleotides encoding these polypeptides are also encompassed by the invention.

This gene is expressed primarily in neutrophils.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic disorders, including inflammatory diseases and allergies. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, haematopoeitic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in neutrophils indicates that polynucleotides and polypeptides corresponding to this gene are useful for the diagnosis, treatment, and/or prevention of a variety of immune system disorders. Expression of this gene product indicates a role in regulating the proliferation; survival; differentiation; and/or activation of hematopoietic cell lineages, including blood stem cells. This gene product may be involved in the regulation of cytokine production, antigen presentation, or other processes that may also suggest a usefulness in the treatment of cancer (e.g. by boosting immune responses).

Since the gene is expressed in cells of lymphoid origin, the natural gene product may be involved in immune functions. Therefore it may be also used as an agent for immunological disorders including arthritis, asthma, immunodeficiency diseases such as AIDS, leukemia, rheumatoid arthritis, granulomatous disease, inflammatory bowel disease, sepsis, acne, neutropcnia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, scleroderma and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:35 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1078 of SEQ ID NO:35, b is an integer of 15 to 1092, where both a and b correspond to the positions of nucleotide residues shown in SEQ ID NO:35, and where b is greater than or equal to a+14.

Features of Protein Encoded by Gene No: 26

This gene is expressed primarily in neutrophils.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic disorders, including inflammatory conditions and allergies. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 175 as residues: Lys-9 to Leu-16, Ser-33 to Met-43.

The tissue distribution in neutrophils indicates that polynucleotides and polypeptides corresponding to this gene are useful for the diagnosis, treatment, and/or prevention of a variety of immune system disorders. Expression of this gene product indicates a role in regulating the proliferation; survival; differentiation; and/or activation of hematopoietic cell lineages, including blood stem cells. This gene product may be involved in the regulation of cytokine production, antigen presentation, or other processes that may also suggest a usefulness in the treatment of cancer (e.g. by boosting immune responses).

Since the gene is expressed in cells of lymphoid origin, the natural gene product may be involved in immune functions. Therefore it may be also used as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, scleroderma and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:36 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1139 of SEQ ID NO:36, b is an integer of 15 to 1153, where both a and b correspond to the positions of nucleotide residues shown in SEQ ID NO:36, and where b is greater than or equal to a+14.

Features of Protein Encoded by Gene No: 27

The translation product of this gene was shown to have homology to the intrinsic factor-B12 receptor precursor of *Rattus norvegicus* which is thought to be important in development (See Genbank Accession No. gi|2961490 (AF022247)). One embodiment of this gene comprises polypeptides of the following amino acid sequence: DCNRDYHKAFGNLRSPGWPDNYDNDXDCX-VTLTAPQNHHSGIVENAETISW R (SEQ ID NO: 363), FGNLRSPGWPDNYDN (SEQ ID NO: 364), ASFYRTS (SEQ ID NO: 366), and/or APQNHXLKCRNDFLEV (SEQ ID NO: 365). An additional embodiment is the polynucleotides encoding these polypeptides.

This gene is expressed primarily in neutrophils.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic disorders, including inflammatory disorders, and allergies. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, haematopoetic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in neutrophils indicates that polynucleotides and polypeptides corresponding to this gene are useful for the diagnosis, treatment, and/or prevention of a variety of immune system disorders. Expression of this gene product indicates a role in regulating the proliferation; survival; differentiation; and/or activation of hematopoietic cell lineages, including blood stem cells. This gene product may be involved in the regulation of cytokine production, antigen presentation, or other processes that may also suggest a usefulness in the treatment of cancer (e.g. by boosting immune responses).

Since the gene is expressed in cells of lymphoid origin, the natural gene product may be involved in immune functions. Therefore it may be also used as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, scleroderma and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:37 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 971 of SEQ ID NO:37, b is an integer of 15 to 985, where both a and b correspond to the positions of nucleotide residues shown in SEQ ID NO:37, and where b is greater than or equal to a+14.

Features of Protein Encoded by Gene No: 28

In specific embodiments, polypeptides of the invention comprise the following amino acid sequence: KADVKWHMCLQSPLCGLFCSIEGVLK (SEQ ID NO: 367), ACMNPAMCFVCACPHTGSTPEKAILQGRLIS-LGTSLSPASNGSGQQSFSICMI NPSLPXSTSSHHLFSVLTGDLD-SYSQRKLKPTSRKSFLLPKTQTYXVXHPSSP PLV-LVQHRSPLSTYPKPVPSCCALDLISVIA-LETFLVYIHLFPSIDLSYWILSML QPLLLIKQQSTKTLSLNCMLYSSYYLIS-FLSFKAKVLRRGGNILHHFFTSYSFF NTY (SEQ ID NO: 368), CPHTGSTPEKAILQGRLISLGTSLSPAS (SEQ ID NO: 369), QHRSPLSTYPKPVPSCCALDLISV (SEQ ID NO: 370), and/or IKQQSTKT LSLNCMLYSSYYLIS-FLSFKA (SEQ ID NO: 371). Polynucleotides encoding these polypeptides are also encompassed by the invention.

This gene is expressed primarily in neutrophils.

Therefore, polynucleotides and polypeptides of the invention are useful as reagents for differential identification of the tissue(s) or cell type(s) present in a biological sample and for diagnosis of diseases and conditions which include, but are not limited to, immune and/or haematological disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 177 as residues: Pro-55 to Ser-66.

The tissue distribution in neutrophils indicates that polynucleotides and polypeptides corresponding to this gene are useful for the diagnosis, treatment, and/or prevention of a variety of immune system disorders. Expression of this gene product indicates a role in regulating the proliferation; survival; differentiation; and/or activation of hematopoietic cell lineages, including blood stem cells. This gene product may be involved in the regulation of cytokine production, antigen presentation, or other processes that may also suggest a usefulness in the treatment of cancer (e.g. by boosting immune responses).

Since the gene is expressed in cells of lymphoid origin, the natural gene product may be involved in immune functions. Therefore it may be also used as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, scleroderma and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:38 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1108 of SEQ ID NO:38, b is an integer of 15 to 1122, where both a and b correspond to the positions of nucleotide residues shown in SEQ ID NO:38, and where b is greater than or equal to a+14.

Features of Protein Encoded by Gene No: 29

This gene is expressed primarily in neutrophils.

Therefore, polynucleotides and polypeptides of the invention are useful as reagents for differential identification of the tissue(s) or cell type(s) present in a biological sample and for diagnosis of diseases and conditions which include, but are not limited to, immune and haematological disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in neutrophils indicates that polynucleotides and polypeptides corresponding to this gene are useful for the diagnosis, treatment, and/or prevention of a variety of immune system disorders. Expression of this gene product indicates a role in regulating the proliferation; survival; differentiation; and/or activation of hematopoietic cell lineages, including blood stem cells. This gene product may be involved in the regulation of cytokine production, antigen presentation, or other processes that may also suggest a usefulness in the treatment of cancer (e.g. by boosting immune responses).

Since the gene is expressed in cells of lymphoid origin, the natural gene product may be involved in immune functions. Therefore it may be also used as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, scleroderma and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:39 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 584 of SEQ ID NO:39, b is an integer of 15 to 598, where both a and b correspond to the positions of nucleotide residues shown in SEQ ID NO:39, and where b is greater than or equal to a+14.

Features of Protein Encoded by Gene No: 30

In specific embodiments, polypeptides of the invention comprise the following amino acid sequence: KYLVSSVLPTISMARSLISALRSG (SEQ ID NO: 372). Polynucleotides encoding these polypeptides are also encompassed by the invention. The gene encoding the disclosed cDNA is believed to reside on □chromosome 7. Accordingly, polynucleotides related to this invention are useful as a marker in linkage analysis for chromosome 7.

This gene is expressed primarily in ovarian cancer.

Therefore, polynucleotides and polypeptides of the invention are useful as reagents for differential identification of the tissue(s) or cell type(s) present in a biological sample and for diagnosis of diseases and conditions which include, but are not limited to, reproductive disorders, particularly ovarian cancer. Similarly, polypeptides and antibodies directed to these polypeptides are useful in providing immunological probes for differential identification of the tissue(s) or cell type(s). For a number of disorders of the above tissues or cells, particularly of the reproductive system, expression of this gene at significantly higher or lower levels may be routinely detected in certain tissues or cell types (e.g., reproductive, ovarian, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in ovarian tissues indicates that polynucleotides and polypeptides corresponding to this gene are useful for diagnosis and treatment of ovarian cancer. Moreover, the protein is useful for the treatment, detection, and/or prevention of endocrine disorders, particularly those related to the reproductive system. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:40 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1115 of SEQ ID NO:40, b is an integer of 15 to 1129, where both a and b correspond to the positions of nucleotide residues shown in SEQ ID NO:40, and where b is greater than or equal to a+14.

Features of Protein Encoded by Gene No: 31

In specific embodiments, polypeptides of the invention comprise the following amino acid sequence: MRTLFGAVRAPFSSLTLLLITPSPSPL (SEQ ID NO: 373), AYAFHRTST (SEQ ID NO: 374), LKSTYTLLSILWFLVLIPVEGN (SEQ ID NO: 375), and/or GPLLASHATLCFSLGSKF (SEQ ID NO: 376). Polynucleotides encoding these polypeptides are also encompassed by the invention.

This gene is expressed primarily in ovarian cancer.

Therefore, polynucleotides and polypeptides of the invention are useful as reagents for differential identification of the tissue(s) or cell type(s) present in a biological sample and for diagnosis of diseases and conditions which include, but are not limited to, reproductive, or endocrine disorders, particularly proliferative conditions such as ovarian cancer. Similarly, polypeptides and antibodies directed to these polypeptides are useful in providing immunological probes for differential identification of the tissue(s) or cell type(s). For a number of disorders of the above tissues or cells, particularly of the reproductive system, expression of this gene at significantly higher or lower levels may be routinely detected in certain tissues or cell types (e.g., reproductive, endocrine, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in ovarian tumor tissue indicates that polynucleotides and polypeptides corresponding to this gene are useful for diagnosis and treatment of ovarian cancer. Moreover, the protein is useful for the detection, treatment, and/or prevention of a variety of reproductive disorders such as infertility. In addition, the protein may also be useful in the development of novel or improved contraceptives. The expression within cellular sources marked by proliferating cells indicates this protein may play a role in the regulation of cellular division, and may show utility in the diagnosis and treatment of cancer and other proliferative disorders. Similarly, developmental tissues rely on decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:41 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1144 of SEQ ID NO:41, b is an integer of 15 to 1158, where both a and b correspond to the positions of nucleotide residues shown in SEQ ID NO:41, and where b is greater than or equal to a+14.

Features of Protein Encoded by Gene No: 32

In specific embodiments, polypeptides of the invention comprise the following amino acid sequence: TVWGILPRKR (SEQ ID NO: 377). Polynucleotides encoding these polypeptides are also encompassed by the invention.

This gene is expressed primarily in ovarian tumor.

Therefore, polynucleotides and polypeptides of the invention are useful as reagents for differential identification of the tissue(s) or cell type(s) present in a biological sample and for diagnosis of diseases and conditions which include, but are not limited to, reproductive or endocrine disorders, particularly proliferative conditions such as ovarian cancer. Similarly, polypeptides and antibodies directed to these polypeptides are useful in providing immunological probes for differential identification of the tissue(s) or cell type(s). For a number of disorders of the above tissues or cells, particularly of the reproductive system, expression of this gene at significantly higher or lower levels may be routinely detected in certain tissues or cell types (e.g., reproductive, endocrine, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in ovarian tumor tissue indicates that polynucleotides and polypeptides corresponding to this gene are useful for diagnosis and treatment of ovarian cancer. Moreover, the protein is useful for the detection, treatment, and/or prevention of a variety of reproductive disorders such as infertility. In addition, the protein may also be useful in the development of novel or improved contraceptives.

The expression within cellular sources marked by proliferating cells indicates this protein may play a role in the regulation of cellular division, and may show utility in the diagnosis and treatment of cancer and other proliferative disorders. Similarly, developmental tissues rely on decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:42 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1753 of SEQ ID NO:42, b is an integer of 15 to 1767, where both a and b correspond to the positions of nucleotide residues shown in SEQ ID NO:42, and where b is greater than or equal to a+14.

Features of Protein Encoded by Gene No: 33

The translation product of this gene shares sequence homology with uroplakin III which is thought to be important in urothelial differentiation (See Accession No. d10226610). In specific embodiments, polypeptides of the invention comprise the following amino acid sequence: ASIDTWPGRRSGGMIVTSI (SEQ ID NO: 378) and/or GSPQAETRWSDPIALHQGKSPASIDTW-PGRRSGGMIVITSI (SEQ ID NO: 379). Polynucleotides encoding these polypeptides are also encompassed by the invention.

This gene is expressed primarily in ovarian tumor.

Therefore, polynucleotides and polypeptides of the invention are useful as reagents for differential identification of the tissue(s) or cell type(s) present in a biological sample and for diagnosis of diseases and conditions which include, but are not limited to, reproductive or endocrine disorders, particularly proliferative conditions such as ovarian cancer. Similarly, polypeptides and antibodies directed to these polypeptides are useful in providing immunological probes for differential identification of the tissue(s) or cell type(s). For a number of disorders of the above tissues or cells, particularly of the reproductive system, expression of this gene at significantly higher or lower levels may be routinely detected in certain tissues or cell types (e.g., reproductive, endocrine, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in ovarian tumor tissue, combined with the homology to uroplakin III indicates that polynucleotides and polypeptides corresponding to this gene are useful for the diagnosis and treatment of reproductive disorders, urogential conditions, or endocrine disorders. Moreover, the protein is useful for the detection, treatment, and/or prevention of a variety of reproductive disorders such as infertility. In addition, the protein may also be useful in the development of novel or improved contraceptives. The expression within cellular sources marked by proliferating cells indicates this protein may play a role in the regulation of cellular division, and may show utility in the diagnosis and treatment of cancer and other proliferative disorders. Similarly, developmental tissues rely on decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:43 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 903 of SEQ ID NO:43, b is an integer of 15 to 917, where both a and b correspond to the positions of nucleotide residues shown in SEQ ID NO:43, and where b is greater than or equal to a+14.

Features of Protein Encoded by Gene No: 34

The translation product of this gene shares sequence homology with estrogen-responsive finger protein which is thought to be important in uterine implantation. (See Accession No. 1088467; and J. Biol. Chem. 270 (41), 24406–24413 (1995), herein incorporated by reference in its entirety.) Moreover, the protein product of this gene was also shown to homology to the human rfp transforming protein (See Genbank Accession No. gi|337372) which is thought to play a role in male germ cell development. Preferred polypeptide fragments comprise the amino acid sequence: VXDITFDPDTAHKYLRLQEENRKVTNT-TPWEHPYPDLPSRFLH (SEQ ID NO: 380); LYLHRYY-FEVEIFGAGTYV (SEQ ID NO: 381); SCISGNNFSWS-LQW NGKEFTAW (SEQ ID NO: 382); TPLKAGPFWSSGSILTS (SEQ ID NO: 383); SVSEVKA-VAEMQFGELLAAVRKAQANVMLFLXEKEQAAL (SEQ ID NO: 384); EKSKQELETMAAISNTVQFLEEY-CKFKNTEDITFPSVYIGLKD (SEQ ID NO: 385); LENYKKKLQEFSKEEEYDIRTQVSAXVQR (SEQ ID NO: 386); GTVSR ERRAG (SEQ ID NO: 388), HGDPTQSWPFLELGVYIDFPGGILSFYGVEYDSM TLVHKFACKFSEPVYAAFWL-SKKENAIRIVDLGEEPEKPAP SLVGTAP (SEQ ID NO: 389), SFYGVEYDSMTLVHKFACKFSEPVYAAFWL (SEQ ID NO: 390), AEL QCTQLDLERKLKLNENAISR-LQANQKSVLVSVSEVKAVAEMQFGELLAAV RKAQANVMLFLXEKEQAALSQANGIKAH-LEYKSAEMEKSKQELETMAAISN TVQFLEEYCK-FKNTEDITFPSVYIGLKDKLSGIRKVIT-ESTVHLIXXLENYKKK LQEFSKEEEYDIRTQVSAXVQRKY-WTSKPEPSTREQFLQYVXDITFDPDTAHK YL RLQEENRKVTNTTPWEHPYPDLPSRFLH-WRQVLSQQSLYLHRYYFEVEIFGA GTYVGLTCK-GIDXKGEERXSCISGNNFSWS-LQWNGKEFTAWYSDMETPL KAGPFWSSGSILTSQEGSFPSMA (SEQ ID NO: 391), RTAPYGAKESSWR MFSFRDPIGFQKPATISSYFCP-QITLKCKSHHCSWQRSGIWLLESREQSPPRT VLAS-RVPLPDLQSGWRFPSWKARRQHRLVLKT-CRQTCEPESWNHTLRHRR KGSLLGSQYRPRAPERASFEWGLH-VTVPGRELLPVPLEAPGEVVSGNATXAL LPFXVDAF-AGQANI-GACPEDLHLKIVPVQVQTLLGQHLPPVQEPAGEVRVG MLPGRGVGDLAVLLLQPEILVCCVRVER-DVXHILEELFPGAGLRFGSPIFALN NGRHLSSD-VILLFLGKLLELFLIVLQXXD (SEQ ID NO: 392), and/or GVYIDFP GGILSFYGVEYDSMTLVHKFACKF-SEPVYAA (SEQ ID NO: 387). Also preferred are polynucleotide fragments encoding these polypeptide fragments.

This gene is expressed primarily in ovarian cancer.

Therefore, polynucleotides and polypeptides of the invention are useful as reagents for differential identification of the tissue(s) or cell type(s) present in a biological sample and for diagnosis of diseases and conditions which include, but are not limited to, ovarian cancer and other disorders of the reproductive system. Similarly, polypeptides and antibodies directed to these polypeptides are useful in providing immunological probes for differential identification of the tissue(s) or cell type(s). For a number of disorders of the above tissues or cells, particularly of the reproductive system, expression of this gene at significantly higher or lower levels may be routinely detected in certain tissues or cell types (e.g., reproductive, developmental, ovarian, testicular, and cancerous and wounded tissues) or bodily fluids (e.g., lymph, seminal fluid, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in ovarian tumors, combined with the homology to estrogen-responsive finger protein, in addition, to the conserved rfp transforming protein indicates that polynucleotides and polypeptides corresponding to this gene are useful for diagnosis and treatment of ovarian cancer and other disorders of the reproductive system. Moreover, the expression within cellular sources marked by proliferating cells indicates this protein may play a role in the regulation of cellular division, and may show utility in the diagnosis and treatment of cancer and other proliferative disorders. Similarly, developmental tissues rely on decisions involving cell differentiation and/or apoptosis in pattern formation. Thus this protein may also be involved in apoptosis or tissue differentiation and could again be useful in cancer therapy. The protein may also show utility in the development of novel contraceptives. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:44 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1973 of SEQ ID NO:44, b is an integer of 15 to 1987, where both a and b correspond to the positions of nucleotide residues shown in SEQ ID NO:44, and where b is greater than or equal to a+14.

Features of Protein Encoded by Gene No: 35

This gene shows sequence homology to a *Caenorhabditis elegans* gene, called D1054.3, in addition, to the Sgt1p protein of *Saccharomyces cerevisiae* which are thought to play a role in the regulation of cellular division and developmental precesses (See Accession Nos. gnl|PID|e348554 and gi|1870791, respectively). Preferred polypeptide fragments comprise the amino acid sequence: SKIKYDWYQTESQVVITLMIKNVQKNDVNVEFSEKELSALVKLPSGEDYNLK LELLHPIIPEQSTFKVLSTKIEIKLKKPEAVRWEKLEGQGDVPTPKQFVADVKN LYPSSSPYTRNWDKLVGEIKEEEKNEKLEGDAALNRLFQQIYSDGSDEVKRA MN KSFMESGGTVLSTNWSDVGKRKVEINPPDDMEWKKY (SEQ ID NO: 393); GDAALNRLFQQIYSDGSDEVKRAMNKSFMESGGTVLSTN (SEQ ID NO: 394); MAAAAAGTXXSQRFFQSFSDALIDEDPQAALEELTKALEQKPDDAQYYCQ RAYCHILLGNYCVAVADAKKS LELNPNNSTAMLRKGICEYHEKNYAAALET FTEGQKLDSADAN FSVWIKRCQEAQNGSESEVVSPKFSFFMFLLF (SEQ ID NO: 396), LEELTKALEQKPDD AQYYCQRAYCHILLGNYCVAVADA (SEQ ID NO: 397), AMLRKGICEYHEKNYAAALETFTEGQKLDSA (SEQ ID NO: 398), LRLWN RNQMM HSIIVKELRVTFFLGITVLLLLMQRSL (SEQ ID NO: 399), NSIQIIPLLC (SEQ ID NO: 400), YMHFNNTVAKLTCKNLSLSTYQNQSASQWTHQSKIKYDW YQTESQVVITLMIKNVQKNDVNVEFSEKELSALVKLPSGEDYNLKLELLHPI IPEQSTFKVLSTKIEIKLKKPEAVRWEKLEGQGDVPTPKQFVADVKNLYPSSS PYTRNWDKLVGEIKEEEKNEKLEGDAALNRLFQQIYSDGSDEVKRAMNKSF MESGGTVLSTNWSDVGKRKVEINPPDDMEWKKY (SEQ ID NO: 401), TCKN LSLSTYQNQSASQWTHQSKIKYDWY (SEQ ID NO: 402), EKELSALVKLPSGED YNLKLELLH (SEQ ID NO: 403), LHPIIPEQSTFKVLSTKIEIKLKKPEAVR (SEQ ID NO: 404), KQFVADVKNLYPSSSPYTRNWDKL (SEQ ID NO: 405), and/or DWYQTESQVVITLMIKNVQKNDV (SEQ ID NO: 395). Also preferred are polynucleotide fragments encoding these polypeptide fragments.

This gene is expressed primarily in osteoclastoma.

Therefore, polynucleotides and polypeptides of the invention are useful as reagents for differential identification of the tissue(s) or cell type(s) present in a biological sample and for diagnosis of diseases and conditions which include, but are not limited to, skeletal or developmental disorders, particularly osteoclastoma and other forms of cancer. Similarly, polypeptides and antibodies directed to these polypeptides are useful in providing immunological probes for differential identification of the tissue(s) or cell type(s). For a number of disorders of the above tissues or cells, particularly of the skeletal system, expression of this gene at significantly higher or lower levels may be routinely detected in certain tissues or cell types (e.g., skeletal, developmental, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in osteoclastoma, combined with the homology to the D1054.3 and Sgt1p proteins indicates that polynucleotides and polypeptides corresponding to this gene are usefull for diagnosis and treatment of osteoclastoma and other forms of cancers. Moreover, the expression within embryonic tissue and other cellular sources marked by proliferating cells indicates this protein may play a role in the regulation of cellular division, and may show utility in the diagnosis and treatment of cancer and other proliferative disorders. Similarly, developmental tissues rely on decisions involving cell differentiation and/or apoptosis in pattern formation. Thus this protein may also be involved in apoptosis or tissue differentiation and could again be useful in cancer therapy. Protein may also play a role as a tumor supressor, or in the development of tumor progression inhibitors. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:45 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 2039 of SEQ ID NO:45, b is an integer of 15 to 2053, where both a and b correspond to the positions of nucleotide residues shown in SEQ ID NO:45, and where b is greater than or equal to a+14.

Features of Protein Encoded by Gene No: 36

In specific embodiments, polypeptides of the invention comprise the following amino acid sequence: GSKGQERKWRVRMGYLN (SEQ ID NO: 406), QRYRLL PLFCYVCSRKIKLNENLFVFSAYSLATLPHTYLFSIVEC SSFCLSGTRN (SEQ ID NO: 407), and/or FSAYSLATLPHTYLFSIVEC SSFCLSG (SEQ ID NO: 408). Polynucleotides encoding these polypeptides are also encompassed by the invention. The gene encoding the disclosed cDNA is believed to reside on □chromosome 7. Accordingly, polynucleotides related to this invention are useful as a marker in linkage analysis for chromosome 7.

This gene is expressed primarily in human placenta.

Therefore, polynucleotides and polypeptides of the invention are useful as reagents for differential identification of the tissue(s) or cell type(s) present in a biological sample and for diagnosis of diseases and conditions which include, but are not limited to, developmental, vascular, and/or reproductive disorders. Similarly, polypeptides and antibodies directed to these polypeptides are useful in providing immunological probes for differential identification of the tissue(s) or cell type(s). For a number of disorders of the above tissues or cells, particularly of the embryonic and reproductive systems, expression of this gene at significantly higher or lower levels may be routinely detected in certain tissues or cell types (e.g., developmental, vascular, reproductive, and cancerous and wounded tissues) or bodily fluids (e.g., lymph, serum, plasma, amniotic fluid, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in human placenta tissue indicates that polynucleotides and polypeptides corresponding to this gene are useful for the treatment and diagnosis of the disorders of embryonic and reproductive systems. Moreover, the protein is useful for the detection, treatment, and/or prevention of a variety of vascular disorders, which include, but are not limited to, microvascular disease, aneurysm, arteriosclerosis, atherosclerosis, stroke, or embolism. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:46 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1258 of SEQ ID NO:46, b is an integer of 15 to 1272, where both a and b correspond to the positions of nucleotide residues shown in SEQ ID NO:46, and where b is greater than or equal to a+14.

Features of Protein Encoded by Gene No: 37

This gene is expressed primarily in anergic T-cells.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic disorders, particularly inflammatory conditions and immunodeficiencies such as AIDS. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in anergic T-cells indicates that polynucleotides and polypeptides corresponding to this gene are useful for the treatment and diagnosis of T cell related disorders. Moreover, the expression of this gene product indicates a role in regulating the proliferation; survival; differentiation; and/or activation of hematopoietic cell lineages, including blood stem cells. This gene product may be involved in the regulation of cytokine production, antigen presentation, or other processes that may also suggest a usefulness in the treatment of cancer (e.g. by boosting immune responses).

Since the gene is expressed in cells of lymphoid origin, the natural gene product may be involved in immune functions. Therefore it may be also used as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, scleroderma and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:47 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 759 of SEQ ID NO:47, b is an integer of 15 to 773, where both a and b correspond to the positions of nucleotide residues shown in SEQ ID NO:47, and where b is greater than or equal to a+14.

Features of Protein Encoded by Gene No: 38

The translation product of this gene shares sequence homology with a murine bone-related sulphatase (See Genbank Accession No. 3046314, and Genseq Accession No. R51355) which is thought to be involved in proteoglycan metabolism. In specific embodiments, polypeptides of the invention comprise the following amino acid sequence: ASFGSCSLSLPCSARERTPEGGGWPGGRLSEPLPA (SEQ ID NO: 409), APNVVLV (SEQ ID NO: 410), DGRLTF (SEQ ID NO: 411), PGSQVVKLPFINFM (SEQ ID NO: 412), FLNAYTNSP (SEQ ID NO: 413), ICCPSRAAMWSGLFTHLTE SWNNFKGLDPNYTTWMD (SEQ ID NO: 414), TQKFGK (SEQ ID NO: 415), DYTSGHHSI (SEQ ID NO: 416), SNRVEAWTRDVAFLLRQEGRP (SEQ ID NO: 417), DWQNTIKA (SEQ ID NO: 418), YLGLNLPHPYPSPSSGENFGSSTFHT SLYWLEKV (SEQ ID NO: 419), DAIKIPKW (SEQ ID NO: 420), YTKNCTG (SEQ ID NO: 421), NIRAFYYAMCAETDAMLGEIILALH (SEQ ID NO: 422), LDLLQK TIVIY (SEQ ID NO: 423), MEHRQFYKMSMYEAS (SEQ ID NO: 424), HVPLLM MGPGIKA (SEQ ID NO: 425), VVSLVDIYPTMLDIAGI (SEQ ID NO: 426), DPD ELTN (SEQ ID NO: 427), WKYIAY (SEQ ID NO: 428), NFPEITYSLDQKLHSIINY PKVSASVHQYNKEQFIKWKQSIGQNYSNVIANFRWHQDWQKEPRKYENAID QWLKTHMNPRAV (SEQ ID NO: 429), FPEITYSLDQKL (SEQ ID NO: 430), NYP KVSASVHQYNKEQFI (SEQ ID NO: 431), GQNYSNVIA (SEQ ID NO: 432), RWH QDWQ (SEQ ID NO: 433), and/or PRKYENAI (SEQ ID NO: 434). Polynucleotides encoding these polypeptides are also encompassed by the invention.

This gene is expressed primarily in retina.

Therefore, polynucleotides and polypeptides of the invention are useful as reagents for differential identification of the tissue(s) or cell type(s) present in a biological sample and for diagnosis of diseases and conditions which include, but are not limited to, visual, skeletal, or metabolic disorders, particularly eye dieases and bone metabolic disorders. Similarly, polypeptides and antibodies directed to these polypeptides are useful in providing immunological probes for differential identification of the tissue(s) or cell type(s). For a number of disorders of the above tissues or cells, particularly of the eye, expression of this gene at significantly higher or lower levels may be routinely detected in certain tissues or cell types (e.g., visual, skeletal, metabolic, and cancerous and wounded tissues) or bodily fluids (e.g., lymph, serum, plasma, urine, vitreous humor, aqueous humor, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 187 as residues: Ala-21 to Arg-27, Asp-40 to Arg-45, Glu-97 to Thr-110, Glu-117 to Lys-128, Arg-175 to Lys-182, Pro-207 to Gly-220, Val-253 to Ile-272.

The tissue distribution in retina, combined with the homology to sulphatases indicates that polynucleotides and polypeptides corresponding to this gene are useful for diagnosis and treatment of eye disorders. Moreover, this gene may be useful in the detection, treatment, and/or prevention of bone-related disorders, osteoporosis, Paget's disease, osteomalacia, in addition to bone metabolic disorders, particularly those involving proteoglycans. The protein is also useful in the disorders involving aberrant proteoglycan metabolism or related conditions, which may include arthritis, immune cell migration, cellular proliferation, vascular disorders, hematopoietic disorders, in addition to showing utility in the detection, treatment, and/or prevention of the disorders mentioned above. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:48 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 2105 of SEQ ID NO:48, b is an integer of 15 to 2119, where both a and b correspond to the positions of nucleotide residues shown in SEQ ID NO:48, and where b is greater than or equal to a+14.

Features of Protein Encoded by Gene No: 39

This gene is expressed primarily in human stomach cancers.

Therefore, polynucleotides and polypeptides of the invention are useful as reagents for differential identification of the tissue(s) or cell type(s) present in a biological sample and for diagnosis of diseases and conditions which include, but are not limited to, gastointestinal disorders, particularly cancer. Similarly, polypeptides and antibodies directed to these polypeptides are useful in providing immunological probes for differential identification of the tissue(s) or cell type(s). For a number of disorders of the above tissues or cells, particularly of the cancer, expression of this gene at significantly higher or lower levels may be routinely detected in certain tissues or cell types (e.g., endothelial, gastrointestinal, and cancerous and wounded tissues) or bodily fluids (e.g., lymph, serum, plasma, urine, chyme, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in tumors of the stomach indicates that polynucleotides and polypeptides corresponding to this gene are useful for the diagnosis, treatment, and/or prevention of these tumors, in addition to other tumors in other tissues. The protein may also be useful for the treatment and/or prevention of ulcers, in addition to additional gastrointestinal or metabolic conditions. Protein as well as, antibodies directed against the protein may show utility as a tissue-specific marker and/or immunotherapy target for the above listed tissues.

Many polynucleotide sequences, such as EST sequences, are publicly available and accessible through sequence databases. Some of these sequences are related to SEQ ID NO:49 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1174 of SEQ ID NO:49, b is an integer of 15 to 1188, where both a and b correspond to the positions of nucleotide residues shown in SEQ ID NO:49, and where b is greater than or equal to a+14.

Features of Protein Encoded by Gene No: 40

In specific embodiments, polypeptides of the invention comprise the following amino acid sequence: RNSLHCYN-EQPPNASGLIQWSSD LIPISLQCGCSW (SEQ ID NO: 435). Polynucleotides encoding these polypeptides are also encompassed by the invention.

This gene is expressed primarily in human synovial membrane.

Therefore, polynucleotides and polypeptides of the invention are useful as reagents for differential identification of the tissue(s) or cell type(s) present in a biological sample and for diagnosis of diseases and conditions which include, but are not limited to, diseases of synovial membrane, skeletal and/or musculoskeletal disorders. Similarly, polypeptides and antibodies directed to these polypeptides are useful in providing immunological probes for differential identification of the tissue(s) or cell type(s). For a number of disorders of the above tissues or cells, particularly of the synovial membrane system, expression of this gene at significantly higher or lower levels may be routinely detected in certain tissues or cell types (e.g., skeletal, muscular, rheumatiod, synovial, and cancerous an d wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 189 as residues: Pro-10 to Ser-20.

The tissue distribution in synovial tissue indicates the product of this gene may play a role in the detection, treatment, and/or prevention of disorders and conditions affecting the skeletal system skeletal system, in particular osteoporosis, bone cancer, as well as, disorders afflicting connective tissues (e.g. arthritis, trauma, tendonitis, chrondomalacia and inflammation), such as in the diagnosis or treatment of various autoimmune disorders such as rheumatoid arthritis, lupus, scleroderma, and dennatomyositis as well as dwarfism, spinal deformation, and specific joint abnormalities as well as chondrodysplasias (i.e. spondyloepiphyseal dysplasia congenita, familial osteoarthritis, Atelosteogenesis type II, metaphyseal chondrodysplasia type Schmid). Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:50 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 464 of SEQ ID NO:50, b is an integer of 15 to 478, where both a and b correspond to the positions of nucleotide residues shown in SEQ ID NO:50, and where b is greater than or equal to a+14.

Features of Protein Encoded by Gene No: 41

The translation product of this gene shares sequence homology with adipose specific collagen-like factor as well as the human adipocyte complement related protein Acrp30, the latter of which is known to be important in energy balance and homeostasis involving food intake, particularly in carbohydrate and lipid catabolism/anabolism (See Genbank Accession Nos.gnl|PID|d1008822 and W09108, respectively). One embodiment of this gene comprises polypeptides of the following amino acid sequence: XLWD-PGLPGVCRCGSIVLKSAFSVG-ITTSYPEXRLPIIFNKVLLPRGXALQPC HRGSSSV-LSQGIYYFSYDITLANKHLAIGLVHNGQYRIKTFD ANTGNHDVASG STVIYLQPEDEVWLEIFFT-DQNGLFSDPGWADSLFSGFLLYVDTDYLDSISED DEL (SEQ ID NO: 436), GSIVLKSAFSVGITT (SEQ ID NO: 437), GIYYFSYDIT LANK (SEQ ID NO: 438), DSLFSGFLLYVDT (SEQ ID NO: 439), and/or NHDV ASGSTVIYL (SEQ ID NO: 440). An additional embodiment is the polynucleotides encoding these polypeptides.

This gene is expressed primarily in human schwanoma.

Therefore, polynucleotides and polypeptides of the invention are useful as reagents for differential identification of the tissue(s) or cell type(s) present in a biological sample and for diagnosis of diseases and conditions which include, but are not limited to, neural or integumentary disorders, particularly neurofibroma. Similarly, polypeptides and antibodies directed to these polypeptides are useful in providing immunological probes for differential identification of the tissue(s) or cell type(s). For a number of disorders of the above tissues or cells, particularly of the diseases relating to peripheral or sympathetic nervous system, expression of this gene at significantly higher or lower levels may be routinely detected in certain tissues or cell types (e.g., neural, integumentary, extracellular matrix, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 190 as residues: Gly-16 to Pro-30, Pro-42 to Gly-56, Gly-62 to Gly-77, Glu-93 to Gly-104, Glu-109 to Glu-114, Pro-121 to Asp-126.

The tissue distribution in schwanoma cells combined with the homology to a conserved human adipose specific collagen-like factor as well as to the human adipocyte complement related protein Acrp30, indicates that polynucleotides and polypeptides corresponding to this gene are useful for the detection/treatment of neurodegenerative disease states and behavioural disorders particularly neuroschwannoma, and including Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system.

Moreover, polynucleotides and polypeptides corresponding to this gene are useful for the treatment, diagnosis, and/or prevention of various skin disorders including congenital disorders (i.e. nevi, moles, freckles, Mongolian spots, hemangiomas, port-wine syndrome), integumentary tumors (i.e. keratoses, Bowen's disease, basal cell carcinoma, squamous cell carcinoma, malignant melanoma, Paget's disease, mycosis fungoides, and Kaposi's sarcoma), injuries and inflammation of the skin (i.e. wounds, rashes, prickly beat disorder, psoriasis, dermatitis), atherosclerosis, uticaria, eczema, photosensitivity, autoimmune disorders (i.e. lupus erythematosus, vitiligo, dermatomyositis, morphea, scleroderma, pemphigoid, and pemphigus), keloids, striae, erythema, petechiae, purpura, and xanthelasma. In addition, such disorders may predispose increased susceptibility to viral and bacterial infections of the skin (i.e. cold sores, warts, chickenpox, molluscum contagiosum, herpes zoster, boils, cellulitis, erysipelas, impetigo, tinea, althletes foot, and ringworm). Moreover, the protein product of this gene may also be useful for the treatment or diagnosis of various connective tissue disorders such as arthritis, trauma, tendonitis, chrondomalacia and inflammation, autoimmune disorders such as rheumatoid arthritis, lupus, scleroderma, and dermatomyositis as well as dwarfism, spinal deformation, and specific joint abnormalities as well as chondrodysplasias (i.e. spondyloepiphyseal dysplasia congenita, familial osteoarthritis, Atelosteogenesis type II, metaphyseal chondrodysplasia type Schmid).

Alternatively, considering the homology to a conserved adipose specific collagen-like factor, would suggest that this protein may also be important in the diagnosis or treatment of various autoimmune disorders such as rheumatoid arthritis, lupus, scleroderma, and dermatomyositis as well as dwarfism, spinal deformation, and specific joint abnormalities as well as chondrodysplasias i.e. spondyloepiphyseal dysplasia congenita, familial osteoarthritis, Atelosteogenesis type II, metaphyseal chondrodysplasia type Schmid. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:51 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1319 of SEQ ID NO:51, b is an integer of 15 to 1333, where both a and b correspond to the positions of nucleotide residues shown in SEQ ID NO:51, and where b is greater than or equal to a+14.

Features of Protein Encoded by Gene No: 42

In specific embodiments, polypeptides of the invention comprise the following amino acid sequence: SNSHTHTHVKSFLR (SEQ ID NO: 441). Polynucleotides encoding these polypeptides are also encompassed by the invention.

This gene is expressed primarily in human activated T-Cells.

Therefore, polynucleotides and polypeptides of the invention are useful as reagents for differential identification of the tissue(s) or cell type(s) present in a biological sample and for diagnosis of diseases and conditions which include, but are not limited to, immunodeficiencies, inflammatory conditions, and other immune or hematopoietic disorders. Similarly, polypeptides and antibodies directed to these polypeptides are useful in providing immunological probes for differential identification of the tissue(s) or cell type(s). For a number of disorders of the above tissues or cells, particularly of the disorders of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in T-cells indicates that polynucleotides and polypeptides corresponding to this gene are useful for the diagnosis, treatment, and/or prevention of a variety of immune system disorders. Expression of this gene product in T-cells indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Since the gene is expressed in cells of lymphoid origin, the natural gene product may be involved in immune functions. Therefore it may be also used as an agent for immunological disorders including arthritis, asthma, immune deficiency diseases such as AIDS, and leukemia. Protein, as well as, antibodies directed against the protein may show utility as a tumor marker and/or immunotherapy targets for the above listed tumors and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:52 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1241 of SEQ ID NO:52, b is an integer of 15 to 1255, where both a and b correspond to the positions of nucleotide residues shown in SEQ ID NO:52, and where b is greater than or equal to a+14.

Features of Protein Encoded by Gene No: 43

The protein product of this gene was found to have homology to the human CD84 protein which, as a novel member of the Ig superfamily, is thought to play an important role in the modulation of the immune response. The present invention appears to encode a novel full-length CD84 homolog and is highly enriched, if not specific, for activated T cells. In specific embodiments, polypeptides of the invention comprise the following amino acid sequence: ITPLGLGAAD (SEQ ID NO: 442), TLRVLGKVPA VCPWCALWRKAGMDMTYSWLSRGDSTYTFHEGPVLSTSWRPGDSALSYTC R ANNPISNVSSCPIPDGPFYADPNYASEKPSTAFCLLAKGLLIFLLLVILAMGLW VIRVQKRHKMPRMKKLMRNRMKAKPGSSPA (SEQ ID NO: 443), AVCP WCALWRKAGMDMTYSWL (SEQ ID NO: 444), PGDSALSYTCRANNPISNVSS CPI (SEQ ID NO: 445), YASEKPSTAFCLLAKGLLIFLLLV (SEQ ID NO: 446), and/or QKRHKMPRMKKLMRNRRKEAKPG (SEQ ID NO: 447). Polynucleotides encoding these polypeptides are also encompassed by the invention.

This gene is expressed primarily in human activated T-Cells.

Therefore, polynucleotides and polypeptides of the invention are useful as reagents for differential identification of the tissue(s) or cell type(s) present in a biological sample and for diagnosis of diseases and conditions which include, but are not limited to, immunodeficiencies, inflammatory conditions, infections, and other immune or hematopoietic disorders. Similarly, polypeptides and antibodies directed to these polypeptides are useful in providing immunological probes for differential identification of the tissue(s) or cell type(s). For a number of disorders of the above tissues or cells, particularly of the disorders of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 192 as residues: Glu-15 to Arg-23, Asn-79 to Gly-84.

The tissue distribution in activated T-cells indicates that polynucleotides and polypeptides corresponding to this gene are useful for the diagnosis, treatment, and/or prevention of a variety of immune system disorders. Expression of this gene product in T-cells indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, and leukemia. Protein, as well as, antibodies directed against the protein may show utility as a tumor marker and/or immunotherapy targets for the above listed tumors and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:53 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1126 of SEQ ID NO:53, b is an integer of 15 to 1140, where both a and b correspond to the positions of nucleotide residues shown in SEQ ID NO:53, and where b is greater than or equal to a+14.

Features of Protein Encoded by Gene No: 44

In specific embodiments, polypeptides of the invention comprise the following amino acid sequence: IAWSGNIPSLLCLFEHDMSFQDE (SEQ ID NO: 448). Polynucleotides encoding these polypeptides are also encompassed by the invention.

This gene is expressed primarily in human tonsil.

Therefore, polynucleotides and polypeptides of the invention are useful as reagents for differential identification of the tissue(s) or cell type(s) present in a biological sample and for diagnosis of diseases and conditions which include, but are not limited to, inflammatory conditions, infections, or immunodeficiencies, and immune or hematopoietic diseases and/or disorders. Similarly, polypeptides and antibodies directed to these polypeptides are useful in providing immunological probes for differential identification of the tissue(s) or cell type(s). For a number of disorders of the above tissues or cells, particularly of the immune diseases, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 193 as residues: Ile-2 to Lys-9, Gln-43 to Phe-49, Asn-59 to His-69, Gly-87 to Asp-93.

The tissue distribution in tonsils indicates that polynucleotides and polypeptides corresponding to this gene are useful for the diagnosis, treatment, and/or prevention of a variety of immune system disorders. Expression of this gene product indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Since the gene is expressed in cells of lymphoid origin, the natural gene product may be involved in immune functions. Therefore it may be also used as an agent for immunological disorders including arthritis, asthma, immune deficiency diseases such as AIDS, and leukemia. Protein, as well as, antibodies directed against the protein may show utility as a tumor marker and/or, immunotherapy targets for the above listed tumors and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:54 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1206 of SEQ ID NO:54, b is an integer of 15 to 1220, where both a and b correspond to the positions of nucleotide residues shown in SEQ ID NO:54, and where b is greater than or equal to a+14.

Features of Protein Encoded by Gene No: 45

The translation product of this gene shares sequence homology with a novel human G52-24 secreted protein as well as the early lymphocyte activation antigen CD69, the latter of which has been shown to be important in lymphocyte proliferation and functions as a signal transmitting receptor in lymphocytes, natural killer cells, and platelets (See Genseq and Genbank Accession Nos. W27288 and gi|558352, respectively). Preferred polypeptides comprise the following amino acid sequence: ENFLLRYKGPSDHWIGLSREQGQPWK-WINGTEWTRQLVMKEDGANLYVAK VSQVPRMNPXLS WVLLCYPGWSAVXTIVAHCSLDFPGSK (SEQ ID NO: 449), ELTAIKSHQYVLQAACPESWIGFQRKC-FYFSDDTKNWTSSQRFCDSQDADLA QVESFQELVRK (SEQ ID NO: 450), WIGLSREQGQPWKWING (SEQ ID NO: 451), CPESWIGFQRKC (SEQ ID NO: 452), NFLL-RYKGPSDHWIGL (SEQ ID NO: 453), ASHLRLLSS-WDYRFPILGAGECAYLNDKGASSARHYTERKWI CSKSDIHV (SEQ ID NO: 454), ENFLLRYKGPSDH-WIGLSREQGQPWKWINGTEWTRQLV MKEDGANLY-VAKVSQVPRMNPXLS WVLLCYPGWSAVXTIVAHC-SLDFPGSK (SEQ ID NO: 455), EQLEELELKKKDFIKILESVQGN-WRQNEDSGKGPQRSCL (SEQ ID NO: 457), FWPESKIQPYKDMFSCEII (SEQ ID NO: 458), SWTSS-LLNX CLHSKEHSIKATIWRLFFXILTIILCGM-VAALSAIRANCHQ EPSVCSSSCMP RKLDWFSKKV-FLFF (SEQ ID NO: 456), EQLEELELKKKDFIKILESVQGNWRQ NEDSGKG-PQRSCLHSKEHSIKATLIWRLFFLI (SEQ ID NO: 459), and/or ENFL LRYKGPSDHWIGLXXEQGQPWK-WINGTEWTRQ (SEQ ID NO: 460). Also preferred are the polynucleotides encoding these polypeptides.

This gene is expressed primarily in human testes.

Therefore, polynucleotides and polypeptides of the invention are useful as reagents for differential identification of the tissue(s) or cell type(s) present in a biological sample and for diagnosis of diseases and conditions which include, but are not limited to, reproductive, endocrine, and/or immune or hematopoietic disorders. Similarly, polypeptides and antibodies directed to these polypeptides are useful in providing immunological probes for differential identification of the tissue(s) or cell type(s). For a number of disorders of the above tissues or cells, particularly of the disorders of reproductive system, expression of this gene at significantly higher or lower levels may be routinely detected in certain tissues or cell types (e.g., immune, reproductive, endocrine, cancerous and wounded tissues) or bodily fluids (e.g., lymph, seminal fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 194 as residues: Asn-20 to Pro-25, Ser-48 to Asp-65.

The tissue distribution in human testes indicates that polynucleotides and polypeptides corresponding to this gene are useful for the diagnosis, treatment, and/or prevention of a variety of reproductive disorders, particularly autoimmune disorders, infertility, or the protein may even be useful as a novel contraceptive. Homology of this gene product to the early lymphocyte activation antigen CD69 indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Since the gene is expressed in cells of lymphoid origin, the natural gene product may be involved in immune functions. Therefore it may be also used as an agent for immunological disorders including arthritis, asthma, immune deficiency diseases such as AIDS, and leukemia. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:55 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 680 of SEQ ID NO:55, b is an integer of 15 to 694, where both a and b correspond to the positions of nucleotide residues shown in SEQ ID NO:55, and where b is greater than or equal to a+14.

Features of Protein Encoded by Gene No: 46

In specific embodiments, polypeptides of the invention comprise the following amino acid sequence: RHEPDPM (SEQ ID NO: 461). Polynucleotides encoding these polypeptides are also encompassed by the invention.

This gene is expressed primarily in human testes.

Therefore, polynucleotides and polypeptides of the invention are useful as reagents for differential identification of the tissue(s) or cell type(s) present in a biological sample and for diagnosis of diseases and conditions which include, but are not limited to, male reproductive or endocrine disorders. Similarly, polypeptides and antibodies directed to these polypeptides are useful in providing immunological probes for differential identification of the tissue(s) or cell type(s). For a number of disorders of the above tissues or cells, particularly of the reproductive system, expression of this gene at significantly higher or lower levels may be routinely detected in certain tissues or cell types (e.g., endocrine, reproductive, and cancerous and wounded tissues) or bodily fluids (e.g., lymph, seminal fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 195 as residues: Pro-20 to Trp-25, Arg-33 to Thr-38, Asn-51 to Ile-56, Gly-82 to Ser-91, Lys-151 to Arg-156.

The tissue distribution in human testicular tissues and cells indicates that polynucleotides and polypeptides corresponding to this gene are useful for the detection, treatment, and/or prevention of various endocrine disorders and cancers, particularly Addison's disease, Cushing's Syndrome, and disorders and/or cancers of the pancrease (e.g., diabetes mellitus), adrenal cortex, ovaries, pituitary (e.g., hyper-, hypopituitarism), thyroid (e.g., hyper-, hypothyroidism), parathyroid (e.g., hyper-, hypoparathyroidism), hypothallamus, and testes.

Alternatively, expression within the human testis may be indicative for a role in normal testicular function, and may implicate this gene product in male fertility, and could even suggest its use as a novel contraceptive. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:56 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 974 of SEQ ID NO:56, b is an integer of 15 to 988, where both a and b correspond to the positions of nucleotide residues shown in SEQ ID NO:56, and where b is greater than or equal to a+14.

Features of Protein Encoded by Gene No: 47

One embodiment of this gene comprises polypeptides of the following amino acid sequence: LKGREAGAGPGTAGAPGREDANGXXRGRGGXHQLYLWVDNIPLSRPKRNLS RDFSDGVLVAEVIKFYFPKMVEMHNYVGTSSLQQKLSNWGHLNRKVLKRL NFSVPDDV (SEQ ID NO: 462), WVDNPLSRPKRNLSRDFSDGVLVA (SEQ ID NO: 463), YVGTSSLQQKLSNWGHLNRKVLKRL (SEQ ID NO: 464), GSAWRRG RGAGSRAPAPYRSWLPRMAVATWMWVYPRRPEVKVSRTPREGVSSAGTG RRRLGLQRITGRCRATPASSSRSLK RSRSCWPLKRPCRSCR (SEQ ID NO: 465), WLPRMAVATWMWVYPRRPEVK (SEQ ID NO: 466), CRATPASSSRSLKRSRS CWPLKR (SEQ ID NO: 467), EHNTDFNGAALSRNLQTFRLSTPCARREGRLLRAHRRCPPYSWRSHASPLPLQLLRSPSPRWVPGKLPGGAGEPLSGPGQIPPWLRAWGTSLDGDAAVLGAGRGPDSGGVDRAKGPPPKAQRREMQGRAQGVGHCFG GQARSLHVASGLWKAVHSPDPDLRSGRRRLSPGPALLEFLSHLLHAHPSQGR RALGPQQARESSGLRPPNGLSIGGWVRRGVGALAGTRASPRGPGRRSPLLTX R XLEPPGEVFDPHILELEQVLQAPYLHLQDLHGLLRGQQLLLLFSDLEDEAGVA LQRPVIRWRPRRRRPVPAELTPSLGVRDTFTSGLLGYTHIHVATAILGS QLL (SEQ ID NO: 468), TDFNGAALSRNLQTFRLSTPCARREG (SEQ ID NO: 469), RCPPYSWRSHASPLPLQLLRSPSPR (SEQ ID NO: 470), GAGEPLSGPGQIPPWL RAWGTSLD (SEQ ID NO: 471), LGAGRGPDSGGVDRAKGPPPKAQRREMQGR (SEQ ID NO: 472), QARSLHVASGLWKAVHSPDPDLR (SEQ ID NO: 473), HPSQ GRRALGPQQARESSGL (SEQ ID NO: 474), IGGWVRRGVGALAGTRASPRG PGRRSP (SEQ ID NO: 475), EPPGEVFDPHILELEQVLQAPYLHL (SEQ ID NO: 476), and/or VPAELTPSLGVRDTFTSGLLGYTHIHVA (SEQ ID NO: 477). An additional embodiment is the polynucleotides encoding these polypeptides.

This gene is expressed primarily in human adult testis.

Therefore, polynucleotides and polypeptides of the invention are useful as reagents for differential identification of the tissue(s) or cell type(s) present in a biological sample and for diagnosis of diseases and conditions which include, but are not limited to, reproductive and/or endocrine disorders. Similarly, polypeptides and antibodies directed to these polypeptides are useful in providing immunological probes for differential identification of the tissue(s) or cell type(s). For a number of disorders of the above tissues or cells, particularly of the disorders of the reproductive system, expression of this gene at significantly higher or lower levels may be routinely detected in certain tissues or cell types (e.g., reproductive, endocrine, cancerous and wounded tissues) or bodily fluids (e.g., lymph, seminal fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 196 as residues: Gln-21 to Gly-33, Gln-55 to Glu-60.

The tissue distribution in testicular tissue indicates that polynucleotides and polypeptides corresponding to this gene are useful for the detection, treatment, and/or prevention of reproductive system disorders, and may be indicative of a role for this gene product in normal testicular function, male fertility, and/or as a male contraceptive. Protein, as well as, antibodies directed against the protein may show utility as a tissue-specific marker and/or immunotherapy target for the above listed tissues.

Many polynucleotide sequences, such as EST sequences, are publicly available and accessible through sequence databases. Some of these sequences are related to SEQ ID NO:57 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1486 of SEQ ID NO:57, b is an integer of 15 to 1500, where both a and b correspond to the positions of nucleotide residues shown in SEQ ID NO:57, and where b is greater than or equal to a+14.

Features of Protein Encoded by Gene No: 48

The translation product of this gene shares sequence homology with the human M phase phosphoprotein 10 as well as ORF YJR002w of *Saccharomyces cerevisiae* (See Genbank Accession No.gnl|PED|e266673) which are thought to play important roles in the regulation of cellular division. Preferred polypeptides comprise the following amino acid sequence: AKNSQKEENPEHVEIQKMMDSLFLKLDALSNFHFIPKPPVPEIKVVSNLPAI TMEEVAPVSVSDAALLAPEEIKEKNKAGDIKTAAEKTATDKKRERRKKKYQ KRMKIKEKEKRRKLLEKSSVDQAGKYSKTVASEKLKQLTKTGKASFIKVRTR ERKLLKGTFVGEVDSKCWVTGMSEPADSPPVG (SEQ ID NO: 478), LQDEGK DKALKSSQAFFSKLQDQVKMQINDAKKTEKK KKRQDISVHKLKL (SEQ ID NO: 479), DEGKDKALKSSQAFFSKLQDQVKMQINDA (SEQ ID NO: 480), EENP EHVEIQKMMDSLFLKLDALSNFHF (SEQ ID NO: 481), SSVDQAGKYSKTVASE KLKQLTKTGKASFIK (SEQ ID NO: 483), VSVSDAALLAPEEIKEKNKAGDI (SEQ ID NO: 484), VLEVMVTVAPK (SEQ ID NO: 485), LQDEGKDKALKSSQAFF SKLQDQVKMQINDAKKTE (SEQ ID NO: 486), and/or SNLPAITMEEVAP (SEQ ID NO: 482). Also preferred are the polynucleotides encoding these polypeptides.

This gene is expressed primarily in human thyroid.

Therefore, polynucleotides and polypeptides of the invention are useful as reagents for differential identification of the tissue(s) or cell type(s) present in a biological sample and for diagnosis of diseases and conditions which include, but are not limited to, endocrine, proliferative, or developmental disorders, particularly diseases relating to the thyroid gland, particularly hyper- and hypothyroidism. Similarly, polypeptides and antibodies directed to these polypeptides are useful in providing immunological probes for differential identification of the tissue(s) or cell type(s). For a number of disorders of the above tissues or cells, particularly of the disorders of the endocrine system, expression of this gene at significantly higher or lower levels may be routinely detected in certain tissues or cell types (e.g., endocrine, developmental, metabolic, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in human thyroid indicates that polynucleotides and polypeptides corresponding to this gene are useful for metabolic disorders, particularly hyper-, hypothyroidism, Graves' disease, Hashimoto's thyroiditis, and/or cancer or neoplasias of the thyroid, and/or other endocrine organs and immune system. Moreover, the protein may show utility in the diagnosis, prevention, and/or treatment of developmental disorders. In addition, the homology to an M phase phosphoprotein indicates it may be a key player in the proliferation, maintenance, and/or differentiation of various cell types during development. It may also act as a morphogen to control cell and tissue type specification. Because of potential roles in proliferation and differentiation, this gene product may have applications in the adult for tissue regeneration and the treatment of cancers. Protein, as well as, antibodies directed against the protein may show utility as a tissue-specific marker and/or immunotherapy target for the above listed tissues.

Many polynucleotide sequences, such as EST sequences, are publicly available and accessible through sequence databases. Some of these sequences are related to SEQ ID NO:58 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1377 of SEQ ID NO:58, b is an integer of 15 to 1391, where both a and b correspond to the positions of nucleotide residues shown in SEQ ID NO:58, and where b is greater than or equal to a+14.

Features of Protein Encoded by Gene No: 49

The translation product of this gene was found to have homology to the cell division control protein 48 (cdc48) of *Methanococcus jannaschii* (See Genbank Accession No.gi|1591785) which is thought to play a key role in the regulation of cellular division. In specific embodiments, polypeptides of the invention comprise the following amino acid sequence: HEAAQGAVCRGQGAPATNPQAPVAAAARVARRVN (SEQ ID NO: 487), KIPS ANRRATRCLGCDHQNFVKVRNKHKGKPTFMEEVLEHLPGKTQDEVQQHEK WYQKFLALEERKKESIQIWKTKKQQKREEIFKLKEKADNTPVLFHNKQEDNQ KQKEEQRKKQKLAVEAWKKQKSIEMSMKCASQLKKKKKKKKNQKERQR QFKLKLLLESYTQQKKEQEEFLRLEKEIREKAEKAEKRKNAADEISRFQERDL HKLELKILDRQAKEDEKSQKQRRLAKLKEKVENNVSRDPSRLYKPTK (SEQ ID NO: 488), VKVRNKHKGKPTFMEEVLEHLPGK (SEQ ID NO: 489), QHEKWYQKFLA LEERKKESIQIW (SEQ ID NO: 490), FKLKEKADNTPVLFHNKQEDNQKQKEEQ. RKK (SEQ ID NO: 491), FLRLEKEIREKAEKAEKRKNAADEISRFQERDLHKL (SEQ ID NO: 492), and/or KQRRLAKLKEKVENNVSRDPSRLY (SEQ ID NO: 493). Polynucleotides encoding these polypeptides are also encompassed by the invention.

This gene is expressed primarily in pancreas, and to a lesser extent in kidney and bone marrow.

Therefore, polynucleotides and polypeptides of the invention are useful as reagents for differential identification of the tissue(s) or cell type(s) present in a biological sample and for diagnosis of diseases and conditions which include, but are not limited to, pancreas, urogenital, developmental, metabolic, immune, and/or hematopoietic disorders. Similarly, polypeptides and antibodies directed to these polypeptides are useful in providing immunological probes for differential identification of the tissue(s) or cell type(s). For a number of disorders of the above tissues or cells, particularly of the pancreas, expression of this gene at significantly higher or lower levels may be routinely detected in certain tissues or cell types (e.g., endocrine, developmental, metabolic, immune, hematopoietic, gastrointestinal, and cancerous and wounded tissues) or bodily fluids (e.g., lymph, serum, plasma, bile, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:198 as residues: Pro-35 to Cys-43, Gln-56 to Lys-67, Thr-73 to Lys-78, Tyr-93 to Asp-98, Ser-16 to Gln-125, Leu-142 to Phe-151, Phe-169 to Arg-174, Ile-181 to Glu-190, Thr-243 to Gly-248.

The tissue distribution in pancreas indicates that polynucleotides and polypeptides corresponding to this gene are useful for the detection, treatment, and/or prevention of various endocrine disorders and cancers, particularly Addison's disease, Cushing's Syndrome, and disorders and/or cancers of the pancrease (e.g., diabetes mellitus), adrenal cortex, ovaries, pituitary (e.g., hyper-, hypopituitarism), thyroid (e.g., hyper-, hypothyroidism), parathyroid (e.g., hyper-, hypoparathyroidism), hypothallamus, and testes. Alternatively, the expression within bone marrow indicates that polynucleotides and polypeptides corresponding to this gene are useful for the treatment and diagnosis of hematopoetic related disorders such as anemia, pancytopenia, leukopenia, thrombocytopenia or leukemia since stromal cells are important in the production of cells of heatopoietic lineages. The uses include bone marrow cell ex vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types.

Moreover, the protein product of this gene could be used in the treatment and/or detection of kidney diseases including renal failure, nephritus, renal tubular acidosis, proteinuria, pyuria, edema, pyelonephritis, hydronephritis, nephrotic syndrome, crush syndrome, glomerulonephritis, hematuria, renal colic and kidney stones, in addition to Wilm's Tumor Disease, and congenital kidney abnormalities such as horseshoe kidney, polycystic kidney, and Falconi's syndrome. Considering the homology to a conserved cell division control protein indicates that the protein may show utility in the diagnosis, prevention, and/or treatment of developmental disorders, and may even serve as a suppressor in tumorigenesis. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:59 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1565 of SEQ ID NO:59, b is an integer of 15 to 1579, where both a and b correspond to the positions of nucleotide residues shown in SEQ ID NO:59, and where b is greater than or equal to a+14.

Features of Protein Encoded by Gene No: 50

The translation product of this gene was shown to have homology to the chicken LRP/alpha-2-macroglobulin receptor which is thought to play a pivitol role on the metabolism of alpha-2-macroglubulins, as well as, complexes between plasminogen activators and their endogenous inhibitors (See Genbank Accession No.gb|74904IGGLRPA2MR).

This gene is expressed primarily in neuronal tissues, and to a lesser extent in uterine cancer.

Therefore, polynucleotides and polypeptides of the invention are useful as reagents for differential identification of the tissue(s) or cell type(s) present in a biological sample and for diagnosis of diseases and conditions which include, but are not limited to, neuronal disorders and uterine cancer. Similarly, polypeptides and antibodies directed to these polypeptides are useful in providing immunological probes for differential identification of the tissue(s) or cell type(s). For a number of disorders of the above tissues or cells, particularly of the central neuron system, expression of this gene at significantly higher or lower levels may be routinely detected in certain tissues or cell types (e.g., neural, reproductive, cancerous and wounded tissues) or bodily fluids (e.g., amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in neuronal tissues indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:60 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1227 of SEQ ID NO:60, b is an integer of 15 to 1241, where both a and b correspond to the positions of nucleotide residues shown in SEQ ID NO:60, and where b is greater than or equal to a+14.

Features of Protein Encoded by Gene No: 51

This gene is expressed primarily in uterine cancer.

Therefore, polynucleotides and polypeptides of the invention are useful as reagents for differential identification of the tissue(s) or cell type(s) present in a biological sample and for diagnosis of diseases and conditions which include, but are not limited to, uterine cancer, and other reproductive disorders. Similarly, polypeptides and antibodies directed to these polypeptides are useful in providing immunological probes for differential identification of the tissue(s) or cell type(s). For a number of disorders of the above tissues or cells, particularly of the uterine cancer, expression of this gene at significantly higher or lower levels may be routinely detected in certain tissues or cell types (e.g., reproductive, cancerous and wounded tissues) or bodily fluids (e.g., amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in tumors of the uterus indicates that polynucleotides and polypeptides corresponding to this gene are useful for diagnosis and intervention of these tumors or proliferative conditions, in addition to other tumors or cell types. Protein, as well as, antibodies directed against the protein may show utility as a tissue-specific marker and/or immunotherapy target for the above listed tissues.

Many polynucleotide sequences, such as EST sequences, are publicly available and accessible through sequence databases. Some of these sequences are related to SEQ ID NO:61 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 916 of SEQ ID NO:61, b is an integer of 15 to 930, where both a and b correspond to the positions of nucleotide residues shown in SEQ ID NO:61, and where b is greater than or equal to a+14.

Features of Protein Encoded by Gene No: 52

In specific embodiments, polypeptides of the invention comprise the following amino acid sequence: VKPPDQSCNHWRDEQCLV (SEQ ID NO: 494). Polynucleotides encoding these polypeptides are also encompassed by the invention.

This gene is expressed primarily in wilm's tumor.

Therefore, polynucleotides and polypeptides of the invention are useful as reagents for differential identification of the tissue(s) or cell type(s) present in a biological sample and for diagnosis of diseases and conditions which include, but are not limited to, Wilm's tumor, and other urogenital disorders; Similarly, polypeptides and antibodies directed to these polypeptides are useful in providing immunological probes for differential identification of the tissue(s) or cell type(s). For a number of disorders of the above tissues or cells, particularly of the Wilm's tumor, expression of this gene at significantly higher or lower levels may be routinely detected in certain tissues or cell types (e.g., urogenital, cancerous and wounded tissues) or bodily fluids (e.g., serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in Wilm's tumor indicates that polynucleotides and polypeptides corresponding to this gene are useful for the diagnosis and treatment of Wilm's tumor. Protein, as well as, antibodies directed against the protein may show utility as a tissue-specific marker and/or immunotherapy target for the above listed tissues. Furthermore, this gene or gene product is useful in the treatment and/or detection of kidney diseases including renal failure, nephritus, renal tubular acidosis, proteinuria, pyuria, edema, pyelonephritis, hydronephritis, nephrotic syndrome, crush syndrome, glomerulonephritis, hematuria, renal colic and kidney stones, in addition to congenital kidney abnormalities such as horseshoe kidney, polycystic kidney, and Falconi's syndrome. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:62 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 984 of SEQ ID NO:62, b is an integer of 15 to 998, where both a and b correspond to the positions of nucleotide residues shown in SEQ ID NO:62, and where b is greater than or equal to a+14.

Features of Protein Encoded by Gene No: 53

The translation product of this gene was shown to have homology to the MEK kinase 3 of *Mus musculus*, mutations of which and/or aberrant regulation of, may provide a predisposition to cancer. The gene encoding the disclosed cDNA is thought to reside on chromosome 17. Accordingly, polynucleotides related to this invention are useful as a marker in linkage analysis for chromosome 17.

This gene is expressed primarily in pituitary, and to a lesser extent in ulcerative colitis and hematopoietic cells.

Therefore, polynucleotides and polypeptides of the invention are useful as reagents for differential identification of the tissue(s) or cell type(s) present in a biological sample and for diagnosis of diseases and conditions which include, but are not limited to, immune, gastrointestinal, hematopoietic diseases. Similarly, polypeptides and antibodies directed to these polypeptides are useful in providing immunological probes for differential identification of the tissue(s) or cell type(s). For a number of disorders of the above tissues or cells, particularly of the neuronal and immune tissues, expression of this gene at significantly higher or lower levels may be routinely detected in certain tissues or cell types (e.g., neuronal, immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in hematopoietic tissues indicates that polynucleotides and polypeptides corresponding to this gene are useful for the diagnosis, treatment, and/or prevention of a variety of immune system disorders. Expression of this gene product in ulcerative colitis indicates a role in the regulation of the proliferation;

survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, and leukemia. Protein, as well as, antibodies directed against the protein may show utility as a tumor marker and/or immunotherapy targets for the above listed tumors and tissues. In addition, this gene product may have commercial utility in the expansion of stem cells and committed progenitors of various blood lineages, and in the differentiation and/or proliferation of various cell types.

Many polynucleotide sequences, such as EST sequences, are publicly available and accessible through sequence databases. Some of these sequences are related to SEQ ID NO: 63 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1179 of SEQ ID NO:63, b is an integer of 15 to 1193, where both a and b correspond to the positions of nucleotide residues shown in SEQ ID NO:63, and where b is greater than or equal to a+14.

Features of Protein Encoded by Gene No: 54

When tested against Jurkat T-cell cell lines, supernatants removed from cells containing this gene activated the GAS (gamma activation site) pathway. Thus, it is likely that this gene activates T-cells through the Jaks-STAT signal transduction pathway. GAS (gamma activation site) is a promoter element found upstream in many genes which are involved in the Jaks-STAT pathway. The Jaks-STAT pathway is a large, signal transduction pathway involved in the differentiation and proliferation of cells. Therefore, activation of the Jaks-STATs pathway, reflected by the binding of the GAS element, can be used to indicate proteins involved in the proliferation and differentiation of cells.

This gene is expressed primarily in fetal spleen and adipose tissues.

Therefore, polynucleotides and polypeptides of the invention are useful as reagents for differential identification of the tissue(s) or cell type(s) present in a biological sample and for diagnosis of diseases and conditions which include, but are not limited to, immune, metabolic, and developmental disorders. Similarly, polypeptides and antibodies directed to these polypeptides are useful in providing immunological probes for differential identification of the tissue(s) or cell type(s). For a number of disorders of the above tissues or cells, particularly of the fetal spleen and adipose tissues, expression of this gene at significantly higher or lower levels may be routinely detected in certain tissues or cell types (e.g., immune, developing, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 203 as residues: Tyr-41 to Phe-47.

The tissue distribution in fetal liver/spleen, combined with the detection of GAS promoter activation activity, indicates that polynucleotides and polypeptides corresponding to this gene are useful for the diagnosis, treatment, and/or prevention of a variety of immune system disorders. Expression of this gene product in fetal spleen indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Since the gene is expressed in cells of lymphoid origin, the natural gene product may be involved in immune functions. Therefore it may be also used as an agent for immunological disorders including arthritis, asthma, immune deficiency diseases such as AIDS, and leukemia. Protein, as well as, antibodies directed against the protein may show utility as a tumor marker and/or immunotherapy targets for the above listed tumors and tissues. In addition, this gene product may have commercial utility in the expansion of stem cells and committed, progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases., Some of these sequences are related to SEQ ID NO:64 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between.1 to 816 of SEQ ID NO:64, b is an integer of 15 to 830, where both a and b correspond to the positions of nucleotide residues shown in SEQ ID NO:64, and where b is greater than or equal to a+14.

Features of Protein Encoded by Gene No: 55

This gene is expressed primarily in IL-1/TNF stimulated synovial and human adipose tissues.

Therefore, polynucleotides and polypeptides of the invention are useful as reagents for differential identification of the tissue(s) or cell type(s) present in a biological sample and for diagnosis of diseases and conditions which include, but are not limited to, rheumatoid arthritis or obessity, and disorders of the musculo-skeletal system. Similarly, polypeptides and antibodies directed to these polypeptides are useful in providing immunological probes for differential identification of the tissue(s) or cell type(s). For a number of disorders of the above tissues or cells, particularly of the immune and musculo-skeletal systems, expression of this gene at significantly higher or lower levels may be routinely detected in certain tissues or cell types and cell types (e.g., synovial and adipose cells and tissues, musculo-skeletal, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 204 as residues: Leu-37 to Arg-45, Ser-60 to Ser-65.

The tissue distribution in synovial tissue and adipose tissue indicates that polynucleotides and polypeptides corresponding to this gene are useful for the diagnosis or treatment of rheumatoid arthritis or other immune diseases. In addition, the expression of this gene product in synovium indicates a role in the detection and treatment of disorders and conditions affecting the skeletal system, in particular osteoporosis as well as disorders afflicting connective tissues (e.g. arthritis, trauma, tendonitis, chrondomalacia and inflammation), such as in the diagnosis or treatment of various autoimmune disorders such as rheumatoid arthritis, lupus, scleroderma, and dermatomyositis as well as dwarfism, spinal deformation, and specific joint abnormalities as well as chondrodysplasias (i.e. spondyloepiphyseal dysplasia congenita, familial osteoarthritis, Atelosteogenesis type II, metaphyseal chondrodysplasia type Schmid).

The tissue distribution in adipose tissue indicates that polynucleotides and polypeptides corresponding to this gene are useful for the treatment of obesity and other metabolic and endocrine conditions or disorders. Furthermore, the protein product of this gene may show utility in ameliorating conditions which occur secondary to aberrant fatty-acid metabolism (e.g. aberrant myelin sheath development), either directly or indirectly. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:65 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 853 of SEQ ID NO:65, b is an integer of 15 to 867, where both a and b correspond to the positions of nucleotide residues shown in SEQ ID NO:65, and where b is greater than or equal to a+14.

Features of Protein Encoded by Gene No: 56

When tested against K562 leukemia cell lines, supernatants removed from cells containing this gene activated the ISRE assay. Thus, it is likely that this gene activates leukemia cells through the Jak-STAT signal transduction pathway. The interferon-sensitive response element is a promoter element found upstream of many genes which are involved in the Jak-STAT pathway. The Jak-STAT pathway is a large, signal transduction pathway involved in the differentiation and proliferation of cells. Therefore, activation of the Jak-STAT pathway, reflected by the binding of the ISRE element, can be used to indicate proteins involved in the proliferation and differentiation of cells.

This gene is expressed primarily in aortic endothelium, and to a lesser extent in melanocyte.

Therefore, polynucleotides and polypeptides of the invention are useful as reagents for differential identification of the tissue(s) or cell type(s) present in a biological sample and for diagnosis of diseases and conditions which include, but are not limited to, cardiovascular diseases. Similarly, polypeptides and antibodies directed to these polypeptides are useful in providing immunological probes for differential identification of the tissue(s) or cell type(s). For a number of disorders of the above tissues or cells, particularly of the cardiovascular system, expression of this gene at significantly higher or lower levels may be routinely detected in certain tissues or cell types (e.g., vascular, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 205 as residues: Met-1 to Trp-12, Arg-33 to Ser-53.

The tissue distribution in human aortic endothelial cells indicates that polynucleotides and polypeptides corresponding to this gene are useful for the detection or intervention of cardiovascular diseases, such as hypertension, cadiovascular injuries, congenital heart diseases, ischemic heart diseases, rheumatic and other hypersensitivity diseases, cardiomyopathy, restenosis, atherosclerosis, stoke, angina, thrombosis, and wound healing. Protein, as well as, antibodies directed against the protein may show utility as a tissue-specific marker and/or immunotherapy target for the above listed tissues.

Many polynucleotide sequences, such as EST sequences, are publicly available and accessible through sequence databases. Some of these sequences are related to SEQ ID NO:66 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 671 of SEQ ID NO:66, b is an integer of 15 to 685, where both a and b correspond to the positions of nucleotide residues shown in SEQ ID NO:66, and where b is greater than or equal to a+14.

Features of Protein Encoded by Gene No: 57

The translation product of this gene shares sequence homology with prostaglandin EP3-9 receptor, which is thought to be important in prostaglandin hormonal reaction. In specific embodiments, polypeptides of the invention comprise the following amino acid sequence: MAIPAFSSCQQISSAAALQI (SEQ ID NO: 495), and/or CNGPFKHFSFTVST (SEQ ID NO: 496). Polynucleotides encoding these polypeptides are also encompassed by the invention.

This gene is expressed primarily in human retina.

Therefore, polynucleotides and polypeptides of the invention are useful as reagents for differential identification of the tissue(s) or cell type(s) present in a biological sample and for diagnosis of diseases and conditions which include, but are not limited to, glaucoma or other ocular diseases. Similarly, polypeptides and antibodies directed to these polypeptides are useful in providing immunological probes for differential identification of the tissue(s) or cell type(s). For a number of disorders of the above tissues or cells, particularly of the ocular system, expression of this gene at significantly higher or lower levels may be routinely detected in certain tissues or cell types (e.g., retinal and other optic tissue, tissue of the nervous system, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in retinal tissues and the homology to prostaglandin receptor indicates that polynucleotides and polypeptides corresponding to this gene are useful for the detection and intervention of ocular diseases like glaucoma. Specifically, the receptor can be used for the identification of agonists or antagonists, anti-inflammatories for the eyes, and vasoconstrictive agents, etc. Furthermore, the tissue distribution in retina indicates that polynucleotides and polypeptides corresponding to this gene are useful for the treatment and/or detection of eye disorders including blindness, color blindness, impaired vision, short and long sightedness, retinitis pigmentosa, retinitis proliferans, and retinoblastoma.

Many polynucleotide sequences, such as EST sequences, are publicly available and accessible through sequence databases. Some of these sequences are related to SEQ ID NO:67 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 787 of SEQ ID NO:67, b is an integer of 15 to 801, where both a and b correspond to the positions of nucleotide residues shown in SEQ ID NO:67, and where b is greater than or equal to a+14.

Features of Protein Encoded by Gene No: 58

The translation product of this gene shares weak sequence homology with *Haemophilus influenzae* outmembrane protein P6 which is thought to be important in host cell interaction.

This gene is expressed primarily in human adrenal gland tumor.

Therefore, polynucleotides and polypeptides of the invention are useful as reagents for differential identification of the tissue(s) or cell type(s) present in a biological sample and for diagnosis of diseases and conditions which include, but are not limited to, adrenal insufficiency or hyperfunction, adrenal gland tumors. Similarly, polypeptides and antibodies directed to these polypeptides are useful in providing immunological probes for differential identification of the tissue(s) or cell type(s). For a number of disorders of the above tissues or cells, particularly of the endocrine systems and cancers thereof, expression of this gene at significantly higher or lower levels may be routinely detected in certain tissues or cell types (e.g., adrenal gland, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in adrenal gland tumor and homology to *Haemophilus influenzae* outer membrane protein suggest that polynucleotides and polypeptides corresponding to this gene are useful for adrenal insufficiencies or hyperfunction, because a secretory protein from an endocrine organ may function as a hormone. The protein product of this gene is also useful as a diagnostic and/or treatment for adrenal gland tumors, as well as tumors of other tissues where expression has been observed. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:68 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 894 of SEQ ID NO:68, b is an integer of 15 to 908, where both a and b correspond to the positions of nucleotide residues shown in SEQ ID NO:68, and where b is greater than or equal to a+14.

Features of Protein Encoded by Gene No: 59

When tested against a Jurkat T-cell line, supernatants removed from cells containing this gene activated the GAS (gamma activation site) pathway. Thus, it is likely that this gene activates T-cells through the Jaks-STAT signal transduction pathway. The GAS is a promoter element found upstream in many genes which are involved in the Jaks-STAT pathway. The Jaks-STAT pathway is a complex, signal transduction pathway involved in the differentiation and proliferation of cells. Therefore, activation of the Jaks-STATs pathway, reflected by the binding of the GAS element, can be used to indicate proteins involved in the proliferation and differentiation of cells.

This gene is expressed primarily in human kidney pyramid, and to a lesser extent in human brain.

Therefore, polynucleotides and polypeptides of the invention are useful as reagents for differential identification of the tissue(s) or cell type(s) present in a biological sample and for diagnosis of diseases and conditions which include, but are not limited to, nephrotic, nephritic syndromes, renal failure, hypertensive nephrosclerosis. Similarly, polypeptides and antibodies directed to these polypeptides are useful in providing immunological probes for differential identification of the tissue(s) or cell type(s). For a number of disorders of the above tissues or cells, particularly of the renal system, expression of this gene at significantly higher or lower levels may be routinely detected in certain tissues or cell types (e.g., renal, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in kidney indicates that polynucleotides and polypeptides corresponding to this gene are useful for renal diseases, including renal failure, nephritus, renal tubular acidosis, proteinuria, pyuria, edema, pyelonephritis, hydronephritis, nephrotic syndrome, crush syndrome, glomerulonephritis, hematuria, renal colic and kidney stones, in addition to Wiln's Tumor Disease, and congenital kidney abnormalities such as horseshoe kidney, polycystic kidney, and Falconi's syndrome. Additionally, the gene product may have endocrine functions related to renal function, metabolism and homeostasis. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:69 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 682 of SEQ ID NO:69, b is an integer of 15 to 696, where both a and b correspond to the positions of nucleotide residues shown in SEQ ID NO:69, and where b is greater than or equal to a+14.

Features of Protein Encoded by Gene No: 60

This gene is expressed primarily in both normal or cancerous human breast tissue.

Therefore, polynucleotides and polypeptides of the invention are useful as reagents for differential identification of the tissue(s) or cell type(s) present in a biological sample and for diagnosis of diseases and conditions which include, but are not limited to, Non-neoplastic breast diseases or breast cancers. Similarly, polypeptides and antibodies directed to these polypeptides are useful in providing immunological probes for differential identification of the tissue(s) or cell type(s). For a number of disorders of the above tissues or cells, particularly of the breast, expression of this gene at significantly higher or lower levels may be routinely detected in certain tissues or cell types (e.g., mammary tissue, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 209 as residues: Pro-20 to Ser-28.

The tissue distribution in breast indicates that polynucleotides and polypeptides corresponding to this gene are useful for either non-neoplastic breast diseases, such as congentital anomalities, gynecomastia, mastitis and abscess, duct ectasia and fat necrosis, or neoplasia in the breast. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:70 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 441 of SEQ ID NO:70, b is an integer of 15 to 455, where both a and b correspond to the positions of nucleotide residues shown in SEQ ID NO:70, and where b is greater than or equal to a+14.

Features of Protein Encoded by Gene No: 61

When tested against a K562 cell line, supernatants removed from cells containing this gene activated the ISRE (interferon-sensitive responsive element) pathway. Thus, it is likely that this gene activates leukemia cells, or more generally, immune or hematopoietic cells, or other cells or cell-types, through the Jaks-STAT signal transduction pathway. The ISRE is a promoter element found upstream in many genes which are involved in the Jaks-STAT pathway. The Jaks-STAT pathway is a complex, signal transduction pathway involved in the differentiation and proliferation of cells. Therefore, activation of the Jaks-STATs pathway, reflected by the binding of the ISRE element, can be used to indicate proteins involved in the proliferation and differentiation of cells. In specific embodiments, polypeptides of the invention comprise the following amino acid sequence: IRHERLWAELALLTGRNE (SEQ ID NO: 497). Polynucleotides encoding these polypeptides are also encompassed by the invention. The gene encoding the disclosed cDNA is thought to reside on chromosome 3. Accordingly, polynucleotides related to this invention are useful as a marker in linkage analysis for chromosome 3.

This gene is expressed primarily in activated T-cells and osteoarthritis, and to a lesser extent in aortic endothelium and placenta.

Therefore, polynucleotides and polypeptides of the invention are useful as reagents for differential identification of the tissue(s) or cell type(s) present in a biological sample and for diagnosis of diseases and conditions which include, but are not limited to, inflammatory conditions, vascular disorders. Similarly, polypeptides and antibodies directed to these polypeptides are useful in providing immunological probes for differential identification of the tissue(s) or cell type(s). For a number of disorders of the above tissues or cells, particularly of the immune system and vascular tissues, expression of this gene at significantly higher or lower levels may be routinely detected in certain tissues or cell types and cell types (e.g., T-cells and other cells and tissue of the immune system, bone tissue, endothelium and placenta, vascular tissue, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 210 as residues: Gln-36 to Glu-49, Glu-51 to Leu-66, Asp-68 to Ser-73.

The tissue distribution in activated T-cells and under inflammatory conditions like osteoarthritis suggest that the protein product of this gene is involved in the inflammatory reactions. Therefore it may be useful in the diagnosis or intervention in the inflammatory diseases with the involvement of T-cells, including osteoarthritis. Furthermore, the tissue distribution indicates that polynucleotides and polypeptides corresponding to this gene are useful for the diagnosis and/or treatment of disorders of the placenta. Specific expression within the placenta indicates that this gene product may play a role in the proper establishment and maintenance of placental function.

Alternately, this gene product may be produced by the placenta and then transported to the embryo, where it may play a crucial role in the development and/or survival of the developing embryo or fetus. Expression of this gene product in a vascular-rich tissue such as the placenta also indicates that this gene product may be produced more generally in endothelial cells or within the circulation. In such instances, it may play more generalized roles in vascular function, such as in angiogenesis. It may also be produced in the vasculature and have effects on other cells within the circulation, such as hematopoietic cells. It may serve to promote the proliferation, survival, activation, and/or differentiation of hematopoietic cells, as well as other cells throughout the body.

Many polynucleotide sequences, such as EST sequences, are publicly available and accessible through sequence databases. Some of these sequences are related to SEQ ID NO:71 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 399 of SEQ ID NO:71, b is an integer of 15 to 413, where both a and b correspond to the positions of nucleotide residues shown in SEQ ID NO:71, and where b is greater than or equal to a+14.

Features of Protein Encoded by Gene No: 62

In specific embodiments, polypeptides of the invention comprise the following amino acid sequence: GTESPMVMCCREVSQSENCLFLDTIFRFIFGKTFTNHDYISIHFYFLKAFLFSFF YSNV (SEQ ID NO: 498). Polynucleotides encoding these polypeptides are also encompassed by the invention.

This gene is expressed primarily in breast lymph nodes, B-cell lymphoma, and to a lesser extent in neutrophils and bone marrow cells.

Therefore, polynucleotides and polypeptides of the invention are useful as reagents for differential identification of the tissue(s) or cell type(s) present in a biological sample and for diagnosis of diseases and conditions which include, but are not limited to, inflammation, immunodeficiency, allergy. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types and cell types (e.g., blood cells, hematopoietic cells, and cells and tissue of the immune system, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in the cells of immunological functions indicates that polynucleotides and polypeptides corresponding to this gene are useful for the diagnosis or intervention of immunologically mediated disorders, such as allergy, immunodeficiency, immune surveillance, etc. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:72 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 835 of SEQ ID NO:72, b is an integer of 15 to 849, where both a and b correspond to the positions of nucleotide residues shown in SEQ ID NO:72, and where b is greater than or equal to a+14.

Features of Protein Encoded by Gene No: 63

The translation product of this gene shares weak sequence homology with Interferon induced 1-8 gene encoded polypeptide, which is thought to be important in retroviral REV responsive element binding and thus viral replication.

This gene is expressed primarily in B-cell lymphoma.

Therefore, polynucleotides and polypeptides of the invention are useful as reagents for differential identification of the tissue(s) or cell type(s) present in a biological sample and for diagnosis of diseases and conditions which include, but are not limited to, immune response to viral infections and other immunologically related disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types and cell types (e.g., T-cells and other cells and tissue of the immune system, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 212 as residues: Pro-47 to Asn-53.

The tissue distribution in B-cell lymphoma and homology to interferon induced 1-8 gene indicates that polynucleotides and polypeptides corresponding to this gene are useful for the intervention of viral infection and other immunologically related disorders. The homology with interferon induced 1-8 REV response element binding gene indicates the gene product may bind to viral components to interfere with the entry, packaging, replication, or induce the host cell anti-viral response by intereferon mediated pathways. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:73 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 491 of SEQ ID NO:73, b is an integer of 15 to 505, where both a and b correspond to the positions of nucleotide residues shown in SEQ ID NO:73, and where b is greater than or equal to a+14.

Features of Protein Encoded by Gene No: 64

In specific embodiments, polypeptides of the invention comprise the following amino acid sequence: IRHEEKG-GKAQRWAE (SEQ ID NO: 499). Polynucleotides encoding these polypeptides are also encompassed by the invention.

This gene is expressed primarily in bone marrow.

Therefore, polynucleotides and polypeptides of the invention are useful as reagents for differential identification of the tissue(s) or cell type(s) present in a biological sample and for diagnosis of diseases and conditions which include, but are not limited to, hemapoiesis disorders. Similarly, polypeptides and antibodies directed to these polypeptides are useful in providing immunological probes for differential identification of the tissue(s) or cell type(s). For a number of disorders of the above tissues or cells, particularly of the hemapoietic system, expression of this gene at significantly higher or lower levels may be routinely detected in certain tissues or cell types (e.g., bone marrow, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 213 as residues: Thr-45 to Tyr-50.

The tissue distribution in bone marrow indicates that polynucleotides and polypeptides corresponding to this gene are useful for hemapoiesis disorders. The gene product may function as a growth factor or mobilization agent for the cells of myeloid or lymphoid lineages. Furthermore, the polypeptides or polynucleotides are also useful to enhance or protect proliferation, differentiation, and functional activation of hematopoietic progenitor cells (e.g., bone marrow cells), useful in treating cancer patients undergoing chemotherapy or patients undergoing bone marrow transplantation. Protein, as well as, antibodies directed against the protein may show utility as a tissue-specific marker and/or immunotherapy target for the above listed tissues.

Many polynucleotide sequences, such as EST sequences, are publicly available and accessible through sequence databases. Some of these sequences are related to SEQ ID NO:74 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 705 of SEQ ID NO:74, b is an integer of 15 to 719, where both a and b correspond to the positions of nucleotide residues shown in SEQ ID NO:74, and where b is greater than or equal to a+14.

Features of Protein Encoded by Gene No: 65

The translation product of this gene shares sequence homology familial adenomatous polyposis gene which is thought to be important in the tumorigenesis of colon cancer (see, e.g., Fulton, Nature 368, 32–38 (1994); accession no. U28412; Joslyn et al., Cell 66 (3), 601–613 (1991); accession no. M73547; and Spirio et al., Nucleic Acids Res. 19 (22), 6348 (1991)). In specific embodiments, polypeptides of the invention comprise the following amino acid sequence: CRWRPESAAPC (SEQ ID NO: 500), TRPGR-GAQAPVK (SEQ ID NO: 501), MVSWMISRAVVLVFG-MLYPAY (SEQ ID NO: 502), GMLYPAYYSYKAVKTKN (SEQ ID NO: 503), EYVRWMMYW IVFALYTV (SEQ ID NO: 504), YPAYYSYKAVKTKNVKE (SEQ ID NO: 505), VA WFPLYYELKIA (SEQ ID NO: 506), and/or MVSWMISRAVVLVFGMLYPAYYSYK AVKTKN-VKEYVRWMMYWIVFALYTVIET-VADQTVAWFPLYYELKIAFVIWL LSPYTKGASL RKFLHPLLSSKEREIDDYIVQAKERGY-ETMVNFGRQGLNLA ATAAVTAAVKSQGAITERLRSF-SMHDLTTIQGDEPVGQRPYQPLPEAKKKSX QPPVN QXVMEFHXKTXMXKQXKKQRGHIQIMRC (SEQ ID NO: 507). Polynucleotides encoding these polypeptides are also encompassed by the invention.

This gene is expressed primarily in osteoclastoma, prostate, bone marrow and to a lesser extent in testes and dendritic cells. Northern data has demonstrated that an abundant 1.3 kb band is seen in testes tissues.

Therefore, polynucleotides and polypeptides of the invention are useful as reagents for differential identification of the tissue(s) or cell type(s) present in a biological sample and for diagnosis of diseases and conditions which include, but are not limited to, colon cancer and cancers of various origin, including osteoclastoma and prostate cancer, as well as reproductive disorders. Similarly, polypeptides and antibodies directed to these polypeptides are useful in providing immunological probes for differential identification of the tissue(s) or cell type(s). For a number of disorders of the above tissues or cells, particularly of the tumorigenesis and reproductive disorders, expression of this gene at significantly higher or lower levels may be routinely detected in certain tissues or cell types and cell types (e.g., bone, prostate, reproductive, bone marrow, colon and other gastrointestinal tissue, tissue of the nervous system, and testis and other reproductive tissue, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 214 as residues: Ser-59 to Ile-64, Ala-71 to Tyr-76, Pro-125 to Ser-141.

The tissue distribution in osteoclastoma, prostate, bone marrow and homology to familial adenomatous polyposis gene indicates that polynucleotides and polypeptides corresponding to this gene are useful for diagnosis and intervention of tumors of various origins, including colon cancer, osteoclastoma and prostate cancer. Alternatively, the Northern data demonstrating expression in testes tissues indicates that the translation product of this gene is useful for the diagnosis and/or treatment of reproductive disorders and conditions concerning proper testicular function (e.g., endocrine function, sperm maturation), as well as cancer. Therefore, this gene product is useful in the treatment of male infertility and/or impotence.

This gene product is also useful in assays designed to identify binding agents, as such agents (antagonists) are useful as male contraceptive agents. Similarly, the protein is believed to be useful in the treatment and/or diagnosis of testicular cancer.

The testes are also a site of active gene expression of transcripts that may be expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications.

Many polynucleotide sequences, such as EST sequences, are publicly available and accessible through sequence databases. Some of these sequences are related to SEQ ID NO:75 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1260 of SEQ ID NO:75, b is an integer of 15 to 1274, where both a and b correspond to the positions of nucleotide residues shown in SEQ ID NO:75, and where the b is greater than or equal to a+14.

Features of Protein Encoded by Gene No: 66

The translation product of this gene shares regional and weak sequence homology with neu differentiation factor and a serine protease N-terminal fragment which contains a EGF-like domain and is thought to be important in the growth and differentiation of several cell types, including colon epithelial cells and Schwann cells.

This gene is expressed primarily in fetal lung, bone marrow, fetal liver, and to a lesser extent in brain.

Therefore, polynucleotides and polypeptides of the invention are useful as reagents for differential identification of the tissue(s) or cell type(s) present in a biological sample and for diagnosis of diseases and conditions which include, but are not limited to, tissue injuries or diseases in lung, bone marrow, or liver. Similarly, polypeptides and antibodies directed to these polypeptides are useful in providing immunological probes for differential identification of the tissue(s) or cell type(s). For a number of disorders of the above tissues or cells, particularly of the liver and lung, expression of this gene at significantly higher or lower levels may be routinely detected in certain tissues or cell types and cell types (e.g., lung and pulmonary tissue, bone marrow, hepatic tissue, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in fetal liver, combined with the homology to neu differentiation factor indicates that polynucleotides and polypeptides corresponding to this gene are useful for the diagnosis or intervention of liver or lung injuries, including hepatic failure, recovery from hepatitis, cirrhosis, hepatoblastoma, jaundice, liver metabolic diseases and conditions that are attributable to the differentiation of hepatocyte progenitor cells, and complications from liver transplantation. Moreover, the protein product of this clone is useful for the treatment and diagnosis of hematopoietic related disorders such as anemia, pancytopenia, leukopenia, thrombocytopenia or leukemia since stromal cells are important in the production of cells of hematopoietic lineages. The uses include bone marrow cell ex-vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:76 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 505 of SEQ ID NO:76, b is an integer of 15 to 519, where both a and b correspond to the positions of nucleotide residues shown in SEQ ID NO:76, and where b is greater than or equal to a+14.

Features of Protein Encoded by Gene No: 67

This gene is expressed primarily in activated T-cells.

Therefore, polynucleotides and polypeptides of the invention are useful as reagents for differential identification of the tissue(s) or cell type(s) present in a biological sample and for diagnosis of diseases and conditions which include, but are not limited to, arthritis, asthma, auto-immune and immunodeficiency diseases. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types and cell types (e.g., T-cells and other cells and tissue of the immune system, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The expression of this gene in T-cells indicates a potential role in the treatment/detection of immune disorders such as arthritis, asthma, hypersensitivity reactions and transplant rejection, and also in immune deficiency diseases such as AIDS, and leukemia. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:77 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 375 of SEQ ID NO:77, b is an integer of 15 to 389, where both a and b correspond to the positions of nucleotide residues shown in SEQ ID NO:77, and where b is greater than or equal to a+14.

Features of Protein Encoded by Gene No: 68

The gene encoding the disclosed cDNA is thought to reside on chromosome 7. Accordingly, polynucleotides related to this invention are useful as a marker in linkage analysis for chromosome 7.

This gene is expressed primarily in brain, and to a lesser extent in breast.

Therefore, polynucleotides and polypeptides of the invention are useful as reagents for differential identification of the tissue(s) or cell type(s) present in a biological sample and for diagnosis of diseases and conditions which include, but are not limited to, neurodegenerative conditions and behavioural disorders. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., brain and other tissue of the nervous system, mammary tissue, and cancerous and wounded tissues) or bodily fluids (e.g., lymph, serum, plasma, urine, synovial fluid and spinal fluid) or another tissue or cell-sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 217 as residues: Leu-40 to His-46.

The tissue distribution in brain indicates that polynucleotides and polypeptides corresponding to this gene are useful for the detection/treatment of neurodegenerative disease states and behavioural disorders such as Alzheimers Disease, Parkinsons Disease, Huntingtons Disease, schizophrenia, mania, dementia, paranoia, obsessive compulsive disorder and panic disorder. In addition, the gene or gene product may also play a role in the treatment and/or detection of developmental disorders associated with the developing embryo, or sexually-linked disorders. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:78 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 809 of SEQ ID NO:78, b is an integer of 15 to 823, where both a and b correspond to the positions of nucleotide residues shown in SEQ ID NO:78, and where b is greater than or equal to a+14.

Features of Protein Encoded by Gene No: 69

The translation product of this gene shares sequence homology with a rat secretory carrier membrane protein which is believed to play a role in cell surface recycling. See e.g., Brand et al., EMBO J 1993 October; 12(10):3753–3761. Secretory carrier membrane proteins (SCAMPs) are widely distributed as components of post-Golgi membranes that function as recycling carriers to the cell surface. In fibroblasts, SCAMPs are concentrated in compartments involved in the endocytosis and recycling of cell surface receptors while in neurons and other cell types having regulated transport pathways, SCAMPs are also components of regulated carriers (synaptic vesicles, secretion granules and transporter vesicles). Their presence in multiple pathways distinguishes them from proteins (e.g., recycling cell surface receptors and synaptic vesicle proteins) which are concentrated in selected pathways. The SCAMPs also do not appear to reside beyond the boundaries of these pathways. This distribution indicates that SCAMPs are general markers of membranes that function in cell surface recycling. Accordingly, polpeptides of the invention and antibodies thereto, may be used to identify membranes that function in cell surface recycling. The gene encoding the disclosed cDNA is thought to reside on chromosome 15. Accordingly, polynucleotides related to this invention are useful as a marker in linkage analysis for chromosome 15.

This gene is expressed primarily in hematopoietic cell types.

Therefore, polynucleotides and polypeptides of the invention are useful as reagents for differential identification of the tissue(s) or cell type(s) present in a biological sample and for diagnosis of diseases and conditions which include, but are not limited to, immune and hematopoetic disorders.

Similarly, polypeptides and antibodies directed to these polypeptides are useful in providing immunological probes for differential identification of the tissue(s) or cell type(s). For a number of disorders of the above tissues or cells, particularly of the immune and hematopoetic systems, expression of this gene at significantly higher or lower levels may be routinely detected in certain tissues or cell types and cell types (e.g., hematopoietic cells, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 218 as residues: Ser-25 to Gly-31, Gln-149 to Ser-155.

The hematopoetic tissue distribution and homology to a cell surface molecule indicates that polynucleotides and polypeptides corresponding to this gene are useful for the detection and/or treatment of immune or hematopoietic disorders including arthritis, asthma and immunodeficiency diseases. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:79 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 2441 of SEQ ID NO:79, b is an integer of 15 to 2455, where both a and b correspond to the positions of nucleotide residues shown in SEQ ID NO:79, and where b is greater than or equal to a+14.

Features of Protein Encoded by Gene No: 70

The gene encoding the disclosed cDNA is thought to reside on chromosome 4. Accordingly, polynucleotides related to this invention are useful as a marker in linkage analysis for chromosome 4. When tested against a Jurkat T-cell line, supernatants removed from cells containing this gene activated the GAS (gamma activation site) pathway. Thus, it is likely that this gene activates T-cells through the Jaks-STAT signal transduction pathway. The GAS is a promoter element found upstream in many genes which are involved in the Jaks-STAT pathway. The Jaks-STAT pathway is a complex, signal transduction pathway involved in the differentiation and proliferation of cells. Therefore, activation of the Jaks-STATs pathway, reflected by the binding of the GAS element, can be used to indicate proteins involved in the proliferation and differentiation of cells.

This gene is expressed primarily in brain.

Therefore, polynucleotides and polypeptides of the invention are useful as reagents for differential identification of the tissue(s) or cell type(s) present in a biological sample and for diagnosis of diseases and conditions which include, but are not limited to, neurodegenerative conditions and behavioural disorders. Similarly, polypeptides and antibodies directed to these polypeptides are useful in providing immunological probes for differential identification of the tissue(s) or cell type(s). For a number of disorders of the above tissues or cells, particularly of the brain and central nervous system, expression of this gene at significantly higher or lower levels may be routinely detected in certain tissues or cell types (e.g., brain and other tissues of the nervous system, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 219 as residues: Asp-57 to Gly-64.

The tissue distribution of this gene primarily in brain indicates that polynucleotides and polypeptides corresponding to this gene are useful for the treatment and/or detection of neurodegenerative disease states and behavioural disorders such as Alzheimers Disease, Parkinsons Disease, Huntingtons Disease, schizophrenia, mania, dementia, paranoia, obsessive compulsive disorder and panic disorder. In addition, the gene or gene product may also play a role in the treatment and/or detection of developmental disorders associated with the developing embryo, or sexually-linked disorders. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:80 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 907 of SEQ ID NO:80, b is an integer of 15 to 921, where both a and b correspond to the positions of nucleotide residues shown in SEQ ID NO:80, and where b is greater than or equal to a+14.

Features of Protein Encoded by Gene No: 71

This gene is expressed primarily in hematopoietic progenitor cells (CD34+ cells).

Therefore, polynucleotides and polypeptides: of the invention are useful as reagents for differential identification of the tissue(s) or cell type(s) present in a biological sample and for diagnosis of diseases and conditions which include, but are not limited to, autoimmune and immunodeficiency disease states. Similarly, polypeptides and antibodies directed to these polypeptides are useful in providing immunological probes for differential identification of the tissue(s) or cell type(s). For a number of disorders of the above tissues or cells, particularly of the hematopoietic system, expression of this gene at significantly higher or lower levels may be routinely detected in certain tissues or cell types and cell types (e.g., hematopoietic cells, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution of this gene predominantly in hematopoietic progenitor cell types indicates that the gene could be important for the treatment or detection of immune or hematopoietic disorders including arthritis, asthma, immunodeficiency diseases, leukemia, hypersensitivity and transplant rejection. Additionally, expression of this gene product in CD34+ cells indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:81 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 664 of SEQ ID) NO:81, b is an integer of 15 to 678, where both a and b correspond to the positions of nucleotide residues shown in SEQ ID NO:81, and where b is greater than or equal to a+14.

Features of Protein Encoded by Gene No: 72

This gene is expressed primarily in hematopoietic progenitor cells (CD34+cells).

Therefore, polynucleotides and polypeptides of the invention are useful as reagents for differential identification of the tissue(s) or cell type(s) present in a biological sample and for diagnosis of diseases and conditions which include, but arc not limited to, auto-immune and immunodeficiency disease states. Similarly, polypeptides and antibodies directed to these polypeptides are useful in providing immunological probes for differential identification of the tissue(s) or cell type(s). For a number of disorders of the above tissues or cells, particularly of the hematopoietic system, expression of this gene at significantly higher or lower levels may be routinely detected in certain tissues or cell types and cell types (e.g., hematopoietic cells, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution of this gene predominantly in hematopoietic progenitor cell types indicates that the gene is important for the treatment or detection of immune or hematopoietic disorders including arthritis, asthma, immunodeficiency diseases, leukemia, and transplant rejection. Expression of this gene product in CD34+ cells indicates a role in the regulation of the proliferation; survival; differentiation; and/or activation of potentially all hematopoietic cell lineages, including blood stem cells.

This gene product may be involved in the regulation of cytokine production, antigen presentation, or other processes that may also suggest a usefulness in the treatment of cancer (e.g. by boosting immune responses).

Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:82 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 843 of SEQ ID NO:82, b is an integer of 15 to 857, where both a and b correspond to the positions of nucleotide residues shown in SEQ ID NO:82, and where b is greater than or equal to a+14.

Features of Protein Encoded by Gene No: 73

The translation product of this gene shares sequence homology with rat synaptogyrin which is thought to be important in membrane trafficking (see e.g., Stenius et al., J. Cell Biol. 131 (6 Pt 2), 1801–1809 (1995)). In specific embodiments, polypeptides of the invention comprise the following amino acid sequences: QPYQVLPSRQVFALI (SEQ ID NO: 508), VFSCIYGEGYSNAHESKQ MYCVFN (SEQ ID NO: 509), RNEDACRYGSAIGV-LAFL (SEQ ID NO: 510), LVVDAYFPQISNATDRK (SEQ ID NO: 511), and/or SALWTFLWFVGFCFLTNQW AVT-NPK (SEQ ID NO: 512). Polynucleotides encoding these polypeptides are also encompassed by the invention.

This gene is expressed primarily in breast and ovary, and to a lesser extent in most hematopoietic tissue types.

Therefore, polynucleotides and polypeptides of the invention are useful as reagents for differential identification of the tissue(s) or cell type(s) present in a biological sample and for diagnosis of diseases and conditions which include, but are not limited to, female infertility and female reproductive abnormalities. Similarly, polypeptides and antibodies directed to these polypeptides are useful in providing immunological probes for differential identification of the tissue(s) or cell type(s). For a number of disorders of the above tissues or cells, particularly of the reproductive system, expression of this gene at significantly higher or lower levels may be routinely detected in certain tissues or cell types (e.g., mammary tissue, and ovary and other reproductive tissue, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 222 as residues: Pro-9 to Trp-18, Thr-20 to Ala-27.

The tissue distribution in ovary and breast and homology to a protein involved in membrane trafficking indicates that this protein may play a role in the detection/treatment of female fertility disorders, endocrine disorders, ovarian failure, amenorrhea, ovarian cancer, and also potentially in both non-neoplastic breast diseases such as congenital abnormalities and neoplasia in the breast. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:83 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1963 of SEQ ID NO:83, b is an integer of 15 to 1977, where both a and b correspond to the positions of nucleotide residues shown in SEQ ID NO:83, and where b is greater than or equal to a+14.

Features of Protein Encoded by Gene No: 74

The gene encoding the disclosed cDNA is thought to reside on chromosome 12. Accordingly, polynucleotides related to this invention are useful as a marker in linkage analysis for chromosome 12. In specific embodiments, polypeptides of the invention comprise the following amino acid sequence: LNIDSFDYGKFESLLAKQHYKFSFLLPLAAGTERCKWWLKIEEASSDQCGCW FLVKCVPKPPSPCRQPPTQVSKIGHAPFFL (SEQ ID NO: 513). Polynucleotides encoding these polypeptides are also encompassed by the invention.

This gene is expressed primarily in brain, and to a lesser extent in placenta and spleen.

Therefore, polynucleotides and polypeptides of the invention are useful as reagents for differential identification of the tissue(s) or cell type(s) present in a biological sample and for diagnosis of diseases and conditions which include, but are not limited to, behavioural disorders and neurodegenerative disease states. Similarly, polypeptides and antibodies directed to these polypeptides are useful in providing immunological probes for differential identification of the tissue(s) or cell type(s). For a number of disorders of the above tissues or cells, particularly of the brain and central nervous system, expression of this gene at significantly higher or lower levels may be routinely detected in certain tissues or cell types (e.g., brain and other tissue of the nervous system, spleen and other cells and tissue of the immune system, placenta, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in brain indicates that polynucleotides and polypeptides corresponding to this gene are useful for the detection/treatment of neurodegenerative disease states and behavioural disorders such as Alzheimers Disease, Parkinsons Disease, Huntingtons Disease, schizophrenia, mania, dementia, paranoia, obsessive compulsive disorder and panic disorder. In addition, the gene or gene product may also play a role in the treatment and/or detection of developmental disorders associated with the developing embryo, or sexually-linked disorders. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:84 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1135 of SEQ ID NO:84, b is an integer of 15 to 1149, where both a and b correspond to the positions of nucleotide residues shown in SEQ ID NO:84, and where b is greater than or equal to a+14.

Features of Protein Encoded by Gene No: 75

When tested against a K562 cell line, supernatants removed from cells containing this gene activated the ISRE (interferon-sensitive responsive element) pathway. Thus, it is likely that this gene activates leukemia cells, or more generally, in immune or hematopoietic cells, or other cells or cell-types, through the Jaks-STAT signal transduction pathway. The ISRE is a promoter, element found upstream in many genes which are involved in the Jaks-STAT pathway. The Jaks-STAT pathway is a complex, signal transduction pathway involved in the differentiation and proliferation of cells. Therefore, activation of the Jaks-STATs pathway, reflected by the binding of the GAS element, can be used to indicate proteins involved in the proliferation and differentiation of cells.

This gene is expressed primarily in bone marrow and spleen.

Therefore, polynucleotides and polypeptides of the invention are useful as reagents for differential identification of the tissue(s) or cell type(s) present in a biological sample and for diagnosis of diseases and conditions which include, but are not limited to, autoimmune diseases, transplant rejection and immunodeficiency disease states. Similarly, polypeptides and antibodies directed to these polypeptides are useful in providing immunological probes for differential identification of the tissue(s) or cell type(s). For a number of disorders of the above tissues or cells, particularly of the hematopoietic and immune systems, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 224 as residues: Pro-22 to His-33, Ser-42 to Trp-48.

The tissue distribution of this gene predominantly in hematopoietic cell types indicates that the gene is important for the treatment or detection of immune or hematopoietic disorders including arthritis, asthma, immunodeficiency diseases, leukemia, and transplant rejection. Furthermore, the polypeptides or polynucleotides are also useful to enhance or protect the proliferation, differentiation, and functional activation of hematopoietic progenitor cells (e.g., bone marrow cells), useful in treating cancer patients undergoing chemotherapy or patients undergoing bone marrow transplantation. The polypeptides or polynucleotides are also useful to increase the proliferation of peripheral blood leukocytes, which can be used in the combat of a range of hematopoietic disorders, including immunodeficiency diseases, leukemia, and septicemia.

Many polynucleotide sequences, such as EST sequences, are publicly available and accessible through sequence databases. Some of these sequences are related to SEQ ID NO:85 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 753 of SEQ ID NO:85, b is an integer of 15 to 767, where both a and b correspond to the positions of nucleotide residues shown in SEQ ID NO:85, and where b is greater than or equal to a+14.

Features of Protein Encoded by Gene No: 76

In specific embodiments, polypeptides of the invention comprise the sequence: SLQYR GRPT (SEQ ID NO: 514), DLVTYTSSLQY IGRPTRP (SEQ ID NO: 515), VKTAECYSIPLGSCPVNIQRVR (SEQ ID NO: 517), and/or LGNKKYIN IRCLEMQVTLKILCEIEKKERRGTHCLV (SEQ ID NO: 516). Polynucleotides encoding these polypeptides are also encompassed by the invention. Contact of cells with supernatant expressing the product of this gene increases the permeability of U937 monocyte cells to calcium. Thus, it is likely that the product of this gene is involved in a signal transduction pathway that is initiated when the product of this gene binds a receptor on the surface of the monocyte cell. Thus, polynucleotides and polypeptides have uses which include, but are not limited to, activating monocyte cells.

This gene is expressed in primary dendritic cells.

Therefore, polynucleotides and polypeptides of the invention are useful as reagents for differential identification of the tissue(s) or cell type(s) present in a biological sample and for diagnosis of diseases and conditions which include, but are not limited to, auto-immune disorders such as asthma and arthritis, in transplant rejection, leukemia and immunodeficiency disease states. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types and cell types (e.g., primary dendritic cells and other cells and tissue of the immune system, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 225 as residues: Gly-2 to Glu-7, Arg-27 to Gly-34.

The tissue distribution of this gene predominantly in hematopoietic cell types indicates that the gene is important for the treatment or detection of immune or hematopoietic disorders including arthritis, asthma, immunodeficiency diseases, leukemia, hypersensitivity and graft rejection. Expression of this gene product in primary dendritic cells also strongly indicates a role for this protein in immune function and immune surveillance. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:86 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 714 of SEQ ID NO:86, b is an integer of 15 to 728, where both a and b correspond to the positions of nucleotide residues shown in SEQ ID NO:86, and where b is greater than or equal to a+14.

Features of Protein Encoded by Gene No: 77

This gene is expressed primarily in 12 week old early stage human.

Therefore, polynucleotides and polypeptides of the invention are useful as reagents for differential identification of the tissue(s) or cell type(s) present in a biological sample and for diagnosis of diseases and conditions which include, but are not limited to, developmental abnormalities. Similarly, polypeptides and antibodies directed to these polypeptides are useful in providing immunological probes for differential identification of the tissue(s) or cell type(s). For a number of disorders of the above tissues or cells, particularly of the developmental system, expression of this gene at significantly higher or lower levels may be routinely detected in certain tissues or cell types (e.g., developing and differentiating tissue, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 226 as residues: Thr-14 to Thr-19.

The expression of this gene primarily in the embryo indicates a key role in embryonic development, and could be used in the treatment and or detection of developmental disorders. Expression within embryonic tissue and other cellular sources marked by proliferating cells indicates that this protein may play a role in the regulation of cellular division, and may show utility in the diagnosis and treatment of cancer and other proliferative disorders. Similarly, embryonic development also involves decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:87 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 721 of SEQ ID NO:87, b is an integer of 15 to 735, where both a and b correspond to the positions of nucleotide residues shown in SEQ ID NO:81, and where b is greater than or equal to a+14.

Features of Protein Encoded by Gene No: 78

This gene is expressed primarily in T-cells, and to a lesser extent in cord blood and osteosarcoma.

Therefore, polynucleotides and polypeptides of the invention are useful as reagents for differential identification of the tissue(s) or cell type(s) present in a biological sample and for diagnosis of diseases and conditions which include, but are not limited to, auto-immune diseases, immunodeficiency diseases and host-graft rejection. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., cells and tissues of the immune system, bone, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 227 as residues: Pro-36 to Ala-41.

The expression of this gene in T-cells indicates a potential role in the treatment/detection of immune disorders such as arthritis, asthma, immune deficiency diseases such as AIDS, leukemia and transplant rejection. Expression of this gene product in T cells also strongly indicates a role for this protein in immune function and immune surveillance. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:88 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 875 of SEQ ID NO:88, b is an integer of 15 to 889, where both a and b correspond to the positions of nucleotide residues shown in SEQ ID NO:88, and where b is greater than or equal to a+14.

Features of Protein Encoded by Gene No: 79

In specific embodiments, polypeptides of the invention comprise the following amino acid sequence: LFYLLTCSCAPGHLAFVCSQCLPFDMGKELWPKSPSSCTSTSVAQGWGGRGR PSPYICVV (SEQ ID NO: 518), IQGSRLPPLPAPLHPLPLIYLLLGSPAQSWLLVPS WGHPSTLTLTMAAEHQAWPSGFHGDH (SEQ ID NO: 519). Polynucleotides encoding these polypeptides are also encompassed by the invention.

This gene is expressed primarily in placenta and 9 week old embryo, and to a lesser extent in fetal spleen.

Therefore, polynucleotides and polypeptides of the invention are useful as reagents for differential identification of the tissue(s) or cell type(s) present in a biological sample and for diagnosis of diseases and conditions which include, but are not limited to, developmental disorders. Similarly, polypeptides and antibodies directed to these polypeptides are useful in providing immunological probes for differential identification of the tissue(s) or cell type(s). For a number of disorders of the above tissues or cells, particularly of the developmental system, expression of this gene at significantly higher or lower levels may be routinely detected in certain tissues or cell types (e.g., developing and differentiating tissues, and spleen and other cells and tissue of the immune system, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The expression of this gene primarily in the embryo indicates a key role in embryonic development, and could be used in the treatment and or detection of developmental disorders. The tissue distribution in placenta also indicates that polynucleotides and polypeptides corresponding to this gene are useful for the diagnosis and/or treatment of disorders of the placenta. Specific expression within the placenta indicates that this gene product may play a role in the proper establishment and maintenance of placental function. Alternately, this gene product may be produced by the placenta and then transported to the embryo, where it may play a crucial role in the development and/or survival of the developing embryo or fetus. Expression within embryonic tissue and other cellular sources marked by proliferating cells indicates that this protein may play a role in the regulation of cellular division. Similarly, embryonic development also involves decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:89 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 555 of SEQ ID NO:89, b is an integer of 15 to 569, where both a and b correspond to the positions of nucleotide residues shown in SEQ ID NO:89, and where b is greater than or equal to a+14.

Features of Protein Encoded by Gene No: 80

This gene is expressed primarily in early stage brain.

Therefore, polynucleotides and polypeptides of the invention are useful as reagents for differential identification of the tissue(s) or cell type(s) present in a biological sample and for diagnosis of diseases and conditions which include, but are not limited to, developmental and neurodegenerative diseases of the brain and nervous system. Similarly, polypeptides and antibodies directed to these polypeptides are useful in providing immunological probes for differential identification of the tissue(s) or cell type(s). For a number of disorders of the above tissues or cells, particularly of the brain, expression of this gene at significantly higher or lower levels may be routinely detected in certain tissues or cell types (e.g., brain and other tissue of the nervous system, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in brain indicates that polynucleotides and polypeptides corresponding to this gene are useful for the treatment and detection of developmental and neurodegenerative diseases, as well as behavioral or nervous system disorders. Examples of such conditions would include: depression, schizophrenia, mania, dementia, paranoia, addictive behavior and sleep disorders. In addition a brain-specific gene product may be useful in the diagnosis of specific brain tumors. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:90 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 320 of SEQ ID NO:90, b is an integer of 15 to 334, where both a and b correspond to the positions of nucleotide residues shown in SEQ ID NO:90, and where b is greater than or equal to a+14.

Features of Protein Encoded by Gene No: 81

This gene is expressed primarily in synovial tissue.

Therefore, polynucleotides and polypeptides of the invention are useful as reagents for differential identification of the tissue(s) or cell type(s) present in a biological sample and for diagnosis of diseases and conditions which include, but are not limited to, arthritis, tendonitis and chrondomalacia. Similarly, polypeptides and antibodies directed to these polypeptides are useful in providing immunological probes for differential identification of the tissue(s) or cell type(s). For a number of disorders of the above tissues or cells, particularly of the synovium, expression of this gene at significantly higher or lower levels may be routinely detected in certain tissues or cell types (e.g., synovial tissue, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in synovial tissues indicates that polynucleotides and polypeptides corresponding to this gene are useful for the treatment and diagnosis of connective tissue disorders such as arthritis, tendonitis, chrondomalacia, inflammation and trauma. In addition, the expression of this gene product in synovium indicates a role in the detection and treatment of disorders and conditions affecting the skeletal system, in particular osteoporosis as well as disorders afflicting connective tissues (e.g. arthritis, trauma, tendonitis, chrondomalacia and inflammation), such as in the diagnosis or treatment of various autoimmune disorders such as rheumatoid arthritis, lupus, scleroderma, and dermatomyositis as well as dwarfism, spinal deformation, and specific joint abnormalities as well as chondrodysplasias (i.e. spondyloepiphyseal dysplasia congenita, familial osteoarthritis, Atelosteogenesis type II, metaphyseal chondrodysplasia type Schmid). Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:91 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 781 of SEQ ID NO:91, b is an integer of 15 to 795, where both a and b correspond to the positions of nucleotide residues shown in SEQ ID NO:91, and where b is greater than or equal to a+14.

Features of Protein Encoded by Gene No: 82

In specific embodiments, polypeptides of the invention comprise the following amino acid sequence: VDPPGCRNSARGCTRLLRGSSKI (SEQ ID NO: 520). Polynucleotides encoding these polypeptides are also encompassed by the invention.

This gene is expressed primarily in the frontal cortex of the brain.

Therefore, polynucleotides and polypeptides of the invention are useful as reagents for differential identification of the tissue(s) or cell type(s) present in a biological sample and for diagnosis of diseases and conditions which include, but are not limited to, developmental and neurodegenerative diseases of the brain. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., brain and other tissue of the nervous system, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 231 as residues: Ser-4 to Tyr-13.

The tissue distribution in brain indicates that polynucleotides and polypeptides corresponding to this gene are useful for the detection and treatment of developmental and neurodegenerative diseases of the brain and nervous system, including malignancies as well as behavioral disorders. Examples of such conditions might include: depression, schizophrenia, Alzheimer's disease, Parkinson's disease, Huntington's disease, mania, dementia, paranoia, addictive behavior and sleep disorders. Furthermore, elevated expression of this gene product within the frontal cortex of the brain indicates that it may be involved in neuronal survival; synapse formation; conductance; neural differentiation, etc. Such involvement may impact many processes, such as learning and cognition. It may also be useful in the treatment of such neurodegenerative disorders as schizophrenia; ALS; or Alzheimer's.

Many polynucleotide sequences, such as EST sequences, are publicly available and accessible through sequence databases. Some of these sequences are related to SEQ ID NO:92 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 563 of SEQ ID NO:92, b is an integer of 15 to 577, where both a and b correspond to the positions of nucleotide residues shown in SEQ ID NO:92, and where b is greater than or equal to a+14.

Features of Protein Encoded by Gene No: 83

The translation product of this gene shares sequence homology with the L6 cell surface antigen, which is highly expressed in lung, breast, colon, and ovarian carcinomas. See e.g., Marken et al., Proc Natl Acad Sci USA 1992 Apr. 15; 89(8):3503–3507. In specific embodiments, polypeptides of the invention comprise the sequence: ITLCLVCIVANA (SEQ ID NO: 521). Polynucleotides encoding these polypeptides are also encompassed by the invention. This gene was recently cloned and sequenced by another group, which identified the gene as a putative tetraspan transmembrane (TM4) protein L6H from humans. The transmembrane 4 superfamily (TM4SF) or tetraspan superfamily has at least 16 members (including CD9, CD20, CD37, CD53, CD63, CD81, CD82, A15, CO-029, Sm23, RDS, Uro B, Uro A, SAS, Rom-1, PETA3, and YKK8), is the second biggest subfamily among CD antigen superfamilies, and are activation antigens of T-cells. All TM4SF members contain four putative transmembrane domains, two extracellular loops, and two short cytoplasmic tails. They are variously expressed on immature, early, mature, activated lymphocytes, monocytes, macrophages, granulocytes, platelets, eosinophils, basophils, certain leukemic and lymphoma cells, and a variety of other cells and tissues.

This gene is expressed primarily in fetal liver/spleen tissues.

Therefore, polynucleotides and polypeptides of the invention are useful as reagents for differential identification of the tissue(s) or cell type(s) present in a biological sample and for diagnosis of diseases and conditions which include, but are not limited to, cancers of the liver, immune system disorders. Similarly, polypeptides and antibodies directed to these polypeptides are useful in providing immunological probes for differential identification of the tissue(s) or cell type(s). For a number of disorders of the above tissues or cells, particularly of the hepatic and immune system, expression of this gene at significantly higher or lower levels may be routinely detected in certain tissues or cell types (e.g., lung and pulmonary tissue, colon and other gastrointestinal tissue, mammary tissue, ovarian tissue and other tissue of the reproductive system, hepatic tissue, immune system tissues, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 232 as residues: Asn-32 to Asn-41, Thr-140 to Ala-147, Asp-188 to His-197.

The murine monoclonal antibody (mAb) L6 recognizes an integral membrane glycoprotein that is highly expressed in lung, breast, colon, and ovarian carcinomas and is referred to as the L6 antigen. This antigen is an attractive target for therapeutic intervention due to its high level expression on malignant cells. The tissue distribution and homology to L6 antigen indicates that polynucleotides and polypeptides corresponding to this gene are useful for detection and treatment of neoplastic tissues—particularly of the liver. The translation product of this gene is a member of the tetraspan transmembrane superfamily, and therefore, antigenic regions of members of this family could be valuable immunogens or targets to implement active and passive immunotherapy in patients with cancer. Moreover, the protein product of this clone is useful for the treatment and diagnosis of hematopoietic related disorders such as anemia, pancytopenia, leukopenia, thrombocytopenia or leukemia since stromal cells are important in the production of cells of hematopoietic lineages. The uses include bone marrow cell ex-vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:93 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 954 of SEQ ID NO:93, b is an integer of 15 to 968, where both a and b correspond to the positions of nucleotide residues shown in SEQ ID NO:93, and where b is greater than or equal to a+14.

Features of Protein Encoded by Gene No: 84

This gene is expressed primarily in glioblastoma.

Therefore, polynucleotides and polypeptides of the invention are useful as reagents for differential identification of the tissue(s) or cell type(s) present in a biological sample and for diagnosis of diseases and conditions which include, but are not limited to, glioblastoma. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., tissue of the nervous system, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in glioblastoma indicates that polynucleotides and polypeptides corresponding to this gene are useful for the detection and treatment of malignancies, as well as developmental and neurodegenerative diseases of the brain and nervous system. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:94 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 539 of SEQ ID NO:94, b is an integer of 15 to 553, where both a and b correspond to the positions of nucleotide residues shown in SEQ ID NO:94, and where b is greater than or equal to a+14.

Features of Protein Encoded by Gene No: 85

The translation product of this gene shares sequence homology with Tbx, which is thought to be important in developmental regulation (see e.g., Knezevic et al., Development 124, 411–419 (1997); and accession U80951). In specific embodiments, polypeptides of the invention comprise the sequence: VTAYQNQQITRLKIDRNPFA KGFR (SEQ ID NO: 522), GTATVTAYQNQQITRL (SEQ ID NO: 523), KIDRNPFA KGFRDSGRNRMGLEAL (SEQ ID NO: 524), STLLQVLGMAFLPLTLTFCLA (SEQ ID NO: 525), and/or VESYAFWRPSLRT LTFEDIPGIPKQGNASS (SEQ ID NO: 526). Polynucleotides encoding these polypeptides are also encompassed by the invention.

This gene is expressed primarily in synovial carcoma and to a lesser extent in osteoclastoma, osteoblastoma, and hemangiopericytoma.

Therefore, polynucleotides and polypeptides of the invention are useful as reagents for differential identification of the tissue(s) or cell type(s) present in a biological sample and for diagnosis of diseases and conditions which include, but are not limited to, osteosarcoma, osteoclastoma, and chondrosarcoma, and diseases of the skeletal system, such as osteoporosis. Similarly, polypeptides and antibodies directed to these polypeptides are useful in providing immunological probes for differential identification of the tissue(s) or cell type(s). For a number of disorders of the above tissues or cells, particularly of the skeletal system, expression of this gene at significantly higher or lower levels may be routinely detected in certain tissues or cell types and cell types (e.g., bone cells and tissue, synovial cells and tissue, cartilage, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 234 as residues: Ala-45 to Asp-50, Arg-57 to Pro-63.

The tissue distribution in skeletal tissues indicates that polynucleotides and polypeptides corresponding to this gene are useful for the treatment and diagnosis of osteoperosis, fracture, osteosarcoma, osteoclastoma, chondrosarcoma, ossification and osteonecrosis, arthritis, tendonitis, chrondomalacia, and inflammation. Elevated levels of expression of this gene product in osteoclastoma and osteoblastoma indicates that it may play a role in the survival, proliferation, and/or growth of these cells. Therefore, it may be useful in influencing bone mass in such conditions as osteoporosis. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:95 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 954 of SEQ ID NO:95, b is an integer of 15 to 968, where both a and b correspond to the positions of nucleotide residues shown in SEQ ID NO:95, and where b is greater than or equal to a+14.

Features of Protein Encoded by Gene No: 86

The gene encoding the disclosed cDNA is thought to reside on chromosome 19. Accordingly, polynucleotides related to this invention are useful as a marker in linkage analysis for chromosome 19. The translation product of this gene is a transmembrane protein that forms disulfide-bonded homodimers and contains a motif in its cytoplasmic domain (located at the carboxy terminus of the protein relative to the transmembrane domain) that functions as an adaptor for associating protein complexes involved in triggering cellular activation. The transmembrane domain is predicted to consist of the amino acid sequence: VLAGIVMGDLVLTVLIALAVYFLG (SEQ ID NO: 528). In specific embodiments, polypeptides of the invention comprise the following amino acid sequences: QAQSDCSCSTVSPG (SEQ ID NO: 527), VLAGIVMGDLVLTVLIAL AVYFLG (SEQ ID NO: 528), VPRGRGAAEATRKQRITETESPYQELQGQRSDVY SDL (SEQ ID NO: 529), and/or ETESPYQELQGQRSDVYSDLNT (SEQ ID NO: 530). Polynucleotides encoding these polypeptides are also encompassed by the invention.

This gene is expressed primarily in macrophage, and to a lesser extent in primary dendritic cells and neutrophils.

Therefore, polynucleotides and polypeptides of the invention are useful as reagents for differential identification of the tissue(s) or cell type(s) present in a biological sample and for diagnosis of diseases and conditions which include, but are not limited to, immunologically mediated disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types and cell types (e.g., blood cells, and cells and tissue of the immune system, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 235 as residues: Ala-28 to Ser-33, Ala-76 to Lys-111.

The tissue distribution in immune tissues indicates that polynucleotides and polypeptides corresponding to this gene are useful for the diagnosis, treatment, and/or prevention of immune disorders including: leukemias, lymphomas, autoimmunities, immunodeficiencies (e.g., AIDS), immunosupressive conditions (transplantation) and hematopoietic disorders. Furthermore, expression of this gene product in macrophage and primary dendritic cells also strongly indicates a role for this protein in immune function and immune surveillance. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:96 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 683 of SEQ ID NO:96, b is an integer of 15 to 697, where both a and b correspond to the positions of nucleotide residues shown in SEQ ID NO:96, and where b is greater than or equal to a+14.

Features of Protein Encoded by Gene No: 87

This gene is expressed primarily in prostate cancer.

Therefore, polynucleotides and polypeptides of the invention are useful as reagents for differential identification of the tissue(s) or cell type(s) present in a biological sample and for diagnosis of diseases and conditions which include, but are not limited to, prostate cancer. Similarly, polypeptides and antibodies directed to these polypeptides are useful in providing immunological probes for differential identification of the tissue(s) or cell type(s). For a number of disorders of the above tissues or cells, particularly of the prostate, expression of this gene at significantly higher or lower levels may be routinely detected in certain tissues or cell types (e.g., prostate, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in prostate cancerous tissue indicates that polynucleotides and polypeptides corresponding to this gene are useful for the detection and treatment of prostate cancer and other prostate disorders, as well as cancers in other tissues where expression has been indicated. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:97 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 852 of SEQ ID NO:97, b is an integer of 15 to 866, where both a and b correspond to the positions of nucleotide residues shown in SEQ ID NO:97, and where b is greater than or equal to a+14.

Features of Protein Encoded by Gene No: 88

The translation product of this gene shares sequence homology with retinal epithelial membrane protein (REMP), which is thought to be important in development and maintenance of normal retinal function (See e.g., Philp et al., Exp. Cell Res. 219 (1), 64–73 (1995); and Genbank Accesion No. U15685). The translation product of this gene also shares homology with monocarboxylate transporter protein (Genbank Accesion no. U87627). Another group recently cloned and sequenced this gene, describing it as a monocarboxylate transporter protein (Genbank Accession No. gi|2463634). In quantitative terms, lactic acid is one of the most important metabolites in the body, substantial amounts being used and/or produced by almost all mammalian cells. As such it must be rapidly transported into and out of cells. Lactic acid transport across the plasma membrane is catalysed by proton-linked monocarboxylate transporters (MCTs), which are also responsible for the transport of pyruvate and the ketone bodies acetoacetate, -hydroxybutyrate and acetate. In specific embodiments, polypeptides of the invention comprise the following amino acid sequence: FLCALSPLGQLLQDRYGWRGGFLILGGL (SEQ ID NO: 531), LLNCCVCAAL MRPLVVTAQPGXGPPRP (SEQ ID NO: 532), and/or SRRLXDLSVFRDRGFVLY AVAASVM (SEQ ID NO: 533). Polynucleotides encoding these polypeptides are also encompassed by the invention. The gene encoding the disclosed cDNA is thought to reside on chromosome 17. Accordingly, polynucleotides related to this invention are useful as a marker in linkage analysis for chromosome 17.

This gene is expressed primarily in neutrophils, and to a lesser extent in a variety of other tissues and cell types, including retina.

Therefore, polynucleotides and polypeptides of the invention are useful as reagents for differential identification of the tissue(s) or cell type(s) present in a biological sample and for diagnosis of diseases and conditions which include, but are not limited to, eye, and metabolic and cellular transport disorders. Similarly, polypeptides and antibodies directed to these polypeptides are useful in providing immunological probes for differential identification: of the tissue(s) or cell type(s). For a number of disorders of the above tissues or cells, particularly of the eye and immune system, expression of this gene at significantly higher or lower levels may be routinely detected in certain tissues or cell types and cell types (e.g., retinal cells, neutrophils and other blood cells, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in retinal tissue and the homology to REMP indicates that polynucleotides and polypeptides corresponding to this gene are useful for the diagnosis, treatment, and/or prevention of eye disorders, including neoplasms, visual impairments and blindness. Alternatively, the homology to monocarboxylate transporter protein indicates that the translation product of this gene is useful for the diagnosis and/or treatment of disorders involving the cellular transport of lactic acid into and out of the cell.

Many polynucleotide sequences, such as EST sequences, are publicly available and accessible through sequence databases. Some of these sequences are related to SEQ ID NO:98 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1354 of SEQ ID NO:98, b is an integer of 15 to 1368, where both a and b correspond to the positions of nucleotide residues shown in SEQ ID NO:98, and where b is greater than or equal to a+14.

Features of Protein Encoded by Gene No: 89

The translation product of this gene shares sequence homology with human squamous cell E48 antigen which is thought to be important in self-recognition and immune function. In specific embodiments, polypeptides of the invention comprise the following amino acid sequences: MMATPSTRPPPPAASTTSATAPALPPRP-PWPWPPSSWPPSGVSSKAPEADPLK NKAL (SEQ ID NO: 534); LLLTSPLPRCPPACSHDAPAHPDPGGPH-GLTSGPGL GLPRVCLQRRQLLQPHALPGYGCLLH-DHAHLLHPHQDEGQ (SEQ ID NO: 535); and/or WLLQARVHHLLLPVRPLQRHRPCHPGH-PGPGPHPPGHPLGSPLKPP RQTHSRTKLS (SEQ ID NO: 536). Polynucleotides encoding these polypeptides are also encompassed by the invention. When tested against K562 leukemia cell lines, supernatants removed from cells containing this gene activated the ISRE assay. Thus, it is likely that this gene activates leukemia cells through the Jak-STAT signal transduction pathway. The interferon-sensitive response element is a promoter element found upstream of many genes which are involved in the Jak-STAT pathway. The Jak-STAT pathway is a large, signal transduction pathway involved in the differentiation and proliferation of cells. Therefore, activation of the Jak-STAT pathway, reflected by the binding of the ISRE element, can be used to indicate proteins involved in the proliferation and differentiation of cells.

This gene is expressed primarily in adult brain, and to a lesser extent in fetal lung.

Therefore, polynucleotides and polypeptides of the invention are useful as reagents for differential identification of the tissue(s) or cell type(s) present in a biological sample and for diagnosis of diseases and conditions which include, but are not limited to, autoimmune disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 238 as residues: Tyr-28 to Phe-34, Thr-54 to Val-60, Tyr-73 to Thr-82.

The tissue distribution and homology to human squamous cell E48 antigen indicates that polynucleotides and polypeptides corresponding to this gene are useful for study, diagnosis and treatment of autoimmune diseases and disorders, such as lupus, transplant rejection, allergic reactions, and arthritis. Protein, as well as, antibodies directed against the protein may show utility as a tissue-specific marker and/or immunotherapy target for the above listed tissues.

Many polynucleotide sequences, such as EST sequences, are publicly available and accessible through sequence databases. Some of these sequences are related to SEQ ID NO:99 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 599 of SEQ ID NO:99, b is an integer of 15 to 613, where both a and b correspond to the positions of nucleotide residues shown in SEQ ID NO:99, and where b is greater than or equal to a+14.

Features of Protein Encoded by Gene No: 90

In specific embodiments, polypeptides of the invention comprise the following amino acid sequence: QEFQT-GLGNMVKPCLYEKYRNISWLWWHTPV-VPATWEAEVGGSLEPGRLRL Q (SEQ ID NO: 537), and/or ILGGESILILSWVFSYIFFRIALEITIYILNVSPFCLGR WLMPVIPALWEAEVGGLPELRSSRPA (SEQ ID NO: 538). Polynucleotides encoding these polypeptides are also encompassed by the invention.

This gene is expressed primarily in human adult lymph node tissue.

Therefore, polynucleotides and polypeptides of the invention are useful as reagents for differential identification of the tissue(s) or cell type(s) present in a biological sample and for diagnosis of diseases and conditions which include, but are not limited to, immune disorders and lymphomas. Similarly, polypeptides and antibodies directed to these polypeptides are useful in providing immunological probes for differential identification of the tissue(s) or cell type(s). For a number of disorders of the above tissues or cells, particularly of the immune and metabolic systems, expression of this gene at significantly higher or lower levels may be routinely detected in certain tissues or cell types (e.g., immune, metabolic, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in lymph nodes indicates that polynucleotides and polypeptides corresponding to this gene are useful for the study, diagnosis and treatment of immune and lymph diseases and disorders such as lymphomas. This gene product may be involved in the regulation of cytokine production, antigen presentation, or other processes that may also suggest a usefulness in the treatment of cancer (e.g. by boosting immune responses). Since the gene is expressed in cells of lymphoid origin, the natural gene product may be involved in immune functions. Therefore it may be also used as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, scleroderma and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:100 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 671 of SEQ ID NO:100, b is an integer of 15 to 685, where both a and b correspond to the positions of nucleotide residues shown in SEQ ID NO:100, and where b is greater than or equal to a+14.

Features of Protein Encoded by Gene No: 91

In specific embodiments, polypeptides of the invention comprise the following amino acid sequence: MPKQLAQLLYRLPRG (SEQ ID NO: 539), LFQAISVSGSHR QGSRTWNTLTEGNAEAACTVALQTSKRLILASRW (SEQ ID NO: 540), TLSFM NSHCVPIKALFFLSVVSYIFIHHIFFTVKILKSCFQVGQLMKL (SEQ ID NO: 541), and/or RPTRPITFSSNISEWVPSTGFQDLEHFCRSSLHSCFTDFQEA DSGFKMEPWSWFFFFFFFPQRTCGCALCVLFLFSIWGPHGKELLNSFLYELPL CSYKGPFLS (SEQ ID NO: 542). Polynucleotides encoding these polypeptides are also encompassed by the invention.

This gene is expressed primarily in placenta and synovium.

Therefore, polynucleotides and polypeptides of the invention are useful as reagents for differential identification of the tissue(s) or cell type(s) present in a biological sample and for diagnosis of diseases of the synovium and placenta. Similarly, polypeptides and antibodies directed to these polypeptides are useful in providing immunological probes for differential identification of the tissue(s) or cell type(s). For a number of disorders of the above tissues or cells, particularly of the placenta and synovium, expression of this gene at significantly higher or lower levels may be routinely detected in certain tissues or cell types (e.g., placenta, synovium, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in placenta and synovium indicates that polynucleotides and polypeptides corresponding to this gene are useful for the study, diagnosis and treatment of growth and developmental disorders and arthritic and inflammatory conditions. Expression within embryonic tissue and other cellular sources marked by proliferating cells indicates that this protein may play a role in the regulation of cellular division, and may show utility in the diagnosis and treatment of cancer and other proliferative disorders. Similarly, embryonic development also involves decisions involving cell differentiation and/or apoptosis in pattern formation. Thus this protein may also be involved in apoptosis or tissue differentiation and could again be useful in cancer therapy. Specific expression within the placenta indicates that this gene product may play a role in the proper establishment and maintenance of placental function. Alternately, this gene product may be produced by the placenta and then transported to the embryo, where it may play a crucial role in the development and/or survival of the developing embryo or fetus. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:101 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 632 of SEQ ID NO: 101, b is an integer of 15 to 646, where both a and b correspond to the positions of nucleotide residues shown in SEQ ID NO: 101, and where b is greater than or equal to a+14.

Features of Protein Encoded by Gene No: 92

In specific embodiments, polypeptides of the invention comprise the following amino acid sequence: VDPRVRLPLFWWQPSCAVYLFPRVYNNMCTRVLGTLPHCWDLATLLQPSSRI WGNVSEAPGM (SEQ ID NO: 543), VPYHIAGTLPHCCSLPVGYGGMSVRLQGCRYVGNVGPQGNMQSGRSWALKMVLLCNSCLGLGVGSVGPSMSSLFGAV LSETPGSSVY (SEQ ID NO: 544), and/or MLDPRATCNLVGVGLSKWCCCVTAA WVLG (SEQ ID NO: 545). Polynucleotides encoding these polypeptides are also encompassed by the invention.

This gene is expressed primarily in chronic lymphocytic leukemia.

Therefore, polynucleotides and polypeptides of the invention are useful as reagents for differential identification of the tissue(s) or cell type(s) present in a biological sample and for diagnosis of diseases of immune system including cancer. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in chronic lymphocytic leukemia indicates that polynucleotides and polypeptides corresponding to this gene are useful for the study, diagnosis and treatment of disorders of the immune system including cancers. Therefore it may be also used as an agent for immunological disorders including arthritis, asthma, immune deficiency diseases such as AIDS, leukemia, rheumatoid arthritis, inflammatory bowel disease, sepsis, acne, and psoriasis. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:102 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 812 of SEQ ID NO:102, b is an integer of 15 to 826, where both a and b correspond to the positions of nucleotide residues shown in SEQ ID NO:102, and where b is greater than or equal to a+14.

Features of Protein Encoded by Gene No: 93

In specific embodiments, polypeptides of the invention comprise the following amino acid sequence: HGDWIYVHIVEQLNQANNKSVTSHTYFVVKTCKIHSLSNFQASNTLLXTVVT MLYNRSLELILPV (SEQ ID NO: 546), TYSSCLTKILYSLINIYPIPHCSPAXITTILL SASMNLTFFFFRFHICEIAQYLSFCAWLISLNIKSL (SEQ ID NO: 547), and/or MNLTFFFFRFHICEIAQYLSFCAWLISLNIKSL (SEQ ID NO: 548). Polynucleotides encoding these polypeptides are also encompassed by the invention.

This gene is expressed primarily in brain medulloblastoma.

Therefore, polynucleotides and polypeptides of the invention are useful as reagents for differential identification of the tissue(s) or cell type(s) present in a biological sample and for diagnosis of cancer and disorders of the CNS. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., brain, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in brain indicates that polynucleotides and polypeptides corresponding to this gene are useful for the diagnosis, treatment, and/or prevention of cancers and other disorders and diseases of the CNS. The tissue distribution further indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered bahaviors, including disorders in feeding, sleep patterns, balance, and perception. In addition, the gene or gene product may also play a role in the treatment and/or detection of developmental disorders associated with the developing embryo, or sexually-linked disorders. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:103 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 572 of SEQ ID NO:103, b is an integer of 15 to 586, where both a and b correspond to the positions of nucleotide residues shown in SEQ ID NO:103, and where b is greater than or equal to a+14.

Features of Protein Encoded by Gene No: 94

In specific embodiments, polypeptides of the invention comprise the following amino acid sequence: LVCYCSTKKEKKLHEIAIQQGQNWRWLLFYKEISVPGFQSVWCSYKCLCVV WKAGEGG (SEQ ID NO: 549), RRSCSGPPLVNTAGKILSSSPAKLACKRTDFHIP SI (SEQ ID NO: 550), RASILGIDNERGCHFRHFNPLKEYKRKKKENKSFRIV (SEQ ID NO: 551), SKNKTRGGDWCVTVLRKRRKSFMKSPFSKDRTGDGF SFTKKSLSQAFSLFGVHTSVCVLCGRRGKAGEGGPVQ GPLW (SEQ ID NO: 552), and/or MKSPFSKDRTGDGFSFTKKSLSQAFSLFGVHTSVCVLCGR RGKAGEGGPVQGPLW (SEQ ID NO: 553). Polynucleotides encoding these polypeptides are also encompassed by the invention.

This gene is expressed primarily in meningima and neutrophils and to a lesser extent in anergic T cells and CD34 depleted buffy coat.

Therefore, polynucleotides and polypeptides of the invention are useful as reagents for differential identification of the tissue(s) or cell type(s) present in a biological sample and for diagnosis of diseases and conditions which include, but are not limited to, inflammatory, immune and hemopoietic disorders. Similarly, polypeptides and antibodies directed to these polypeptides are useful in providing immunological probes for differential identification of the tissue(s) or cell type(s). For a number of disorders of the above tissues or cells, particularly of the hemopoietic, immune and inflammatory systems, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 243 as residues: Glu-45 to Asn-50.

The tissue distribution in immune tissues indicates that polynucleotides and polypeptides corresponding to this gene are useful for the study, diagnosis and treatment of various disorders and diseases of the immune, inflammatory, and hemopoietic systems. Furthermore, the tissue distribution indicates that polynucleotides and polypeptides corresponding to this gene are useful for the diagnosis and/or treatment of hematopoietic disorders. This gene product is primarily expressed in hematopoietic cells and tissues, suggesting that it plays a role in the survival, proliferation, and/or differentiation of hematopoieitic lineages. Expression of this gene product in T cells and neutrophils also strongly indicates a role for this protein in immune function and immune surveillance. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:104 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 614 of SEQ ID NO:104, b is an integer of 15 to 628, where both a and b correspond to the positions of nucleotide residues shown in SEQ ID NO:104, and where b is greater than or equal to a+14.

Features of Protein Encoded by Gene No: 95

In specific embodiments, polypeptides of the invention comprise the following amino acid sequence: MGESECYR-RLSGASCTWTVHVDFA (SEQ ID NO: 554); MHCGTRVWKTMKHDYFLLACLSMTSTGGILCTL 9SEQ ID NO: 555); STLSLI PTSSSLSFWPWCTAIIG-SIFTYCVCVCVCFVVMNRTCYLPNSIIYSKLATIID KSMTLS (SEQ ID NO: 556); and/or MWILPKVSLI-CIVELGYGKP (SEQ ID NO: 557). Polynucleotides encoding these polypeptides are also encompassed by the invention.

This gene is expressed primarily in human meningima.

Therefore, polynucleotides and polypeptides of the invention are useful as reagents for differential identification of the tissue(s) or cell type(s) present in a biological sample and for diagnosis of diseases and conditions which include, but are not limited to, meningitis and other inflammatory conditions. Similarly, polypeptides and antibodies directed to these polypeptides are useful in providing immunological probes for differential identification of the tissue(s) or cell type(s). For a number of disorders of the above tissues or cells, particularly of the cerebrospinal membranes, expression of this gene at significantly higher or lower levels may be routinely detected in certain tissues or cell types (e.g., cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 244 as residues: Ser-35 to Phe-41.

The tissue distribution indicates that polynucleotides and polypeptides corresponding to this gene are useful for study, treatment, and diagnosis of disorders of the meningima. The protein is also useful in the development of inhibitors of infections, particularly, though not limited to, the meninges or other neural-associated or neural tissue. In addition, the protein is useful for the treatment of injuries to the meninges, potentially in regeneration, or in congenital disorders, birth defects, etc. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:105 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 544 of SEQ ID NO:105, b is an integer of 15 to 558, where both a and b correspond to the positions of nucleotide residues shown in SEQ ID NO:105, and where b is greater than or equal to a+14.

Features of Protein Encoded by Gene No: 96

In specific embodiments, polypeptides of the invention comprise the following amino acid sequence: MST-GDGRDAEKGWPVSEEENQRSVYPGYP-ECDERQAVPQHCAIASPSSLQSH HPASACVPRR (SEQ ID NO: 558), QQMTLGTKIKWGQLQRGQEIPTGD-FTVRNFM RFSIIYC (SEQ ID NO: 559), and/or PFLF-CASRIRXQGIGIHGQVACSAVRMYN NR (SEQ ID NO: 560). Polynucleotides encoding these polypeptides are also encompassed by the invention. The gene encoding the disclosed cDNA is thought to reside on chromosome 10. Accordingly, polynucleotides related to this invention are useful as a marker in linkage analysis for chromosome 10.

This gene is expressed primarily in neutrophils and activated monocytes.

Therefore, polynucleotides and polypeptides of the invention are useful as reagents for differential identification of the tissue(s) or cell type(s) present in a biological sample and for diagnosis of diseases and conditions which include, but are not limited to, immune and hematopoietic disorders. Similarly, polypeptides and antibodies directed to these polypeptides are useful in providing immunological probes for differential identification of the tissue(s) or cell type(s). For a number of disorders of the above tissues or cells, particularly of the immune and hematopoietic systems, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 245 as residues: Met-1 to Ser-6, Pro-29 to Ser-34.

The tissue distribution in monocytes and neutrophils indicates that polynucleotides and polypeptides corresponding to this gene are useful for the study, diagnosis and treatment of diseases of the immune and hematopoietic systems. Expression of this gene product in monocytes and neutrophils also strongly indicates a role for this protein in immune function and immune surveillance. This gene product may be involved in the regulation of cytokine production, antigen presentation, or other processes that may also suggest a usefulness in the treatment of cancer (e.g. by boosting immune responses). Since the gene is expressed in cells of lymphoid origin, the gene or protein, as well as, antibodies directed against the protein may show utility as a tumor marker and/or immunotherapy targets for the above listed tissues. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:106 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 742 of SEQ ID NO:106, b is an integer of 15 to 756, where both a and b correspond to the positions of nucleotide residues shown in SEQ ID NO:106, and where b is greater than or equal to a+14.

Features of Protein Encoded by Gene No: 97

In specific embodiments, polypeptides of the invention comprise the following amino acid sequence: VLCEE-AGQKVPSTPSWSSWTLQKRLRGSPAE-ANCSPSFPAPPGKE (SEQ ID NO: 561), MSLSALACD-FTPIQPWEWEEYEQITLGLTAPSNLLESNYLGQASE CFVRKLVRRFPQLLPGPPGHCRKDLGD-PQQRPIALLPSLPHQERNNVHRLEAD SEVDL (SEQ ID NO: 562), CVDFDEYFSSWEPLLKMMFKGVVGGK-MKAW RRKKRRKPLPYKIHAD (SEQ ID NO: 563), and/or MMFKGVVGGKMKAWRR KKRRKPLPYKIHAD (SEQ ID NO: 564). Polynucleotides encoding these polypeptides are also encompassed by the invention.

This gene is expressed primarily in bone marrow, and to a lesser extent in testes.

Therefore, polynucleotides and polypeptides of the invention are useful as reagents for differential identification of the tissue(s) or cell type(s) present in a biological sample and for diagnosis of diseases and conditions which include, but are not limited to, hematopoietic and reproductive disorders. Similarly, polypeptides and antibodies directed to these polypeptides are useful in providing immunological probes for differential identification of the tissue(s) or cell type(s). For a number of disorders of the above tissues or cells, particularly of the hematopoietic and reproductive systems, expression of this gene at significantly higher or lower levels may be routinely detected in certain tissues or cell types (e.g., reproductive, immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in bone marrow and testes indicates that polynucleotides and polypeptides corresponding to this gene are useful for the study, diagnosis and treatment of various disorders involving the hematopoietic and reproductive systems. The uses include bone marrow cell ex vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. Furthermore, polynucleotides and polypeptides corresponding to this gene are useful for the treatment and diagnosis of conditions concerning proper testicular function (e.g. endocrine function, sperm maturation), as well as cancer. Therefore, this gene product is useful in the treatment of male infertility and/or impotence. This gene product is also useful in assays designed to identify binding agents, as such agents (antagonists) are useful as male contraceptive agents.

Similarly, the protein is believed to be useful in the treatment and/or diagnosis of testicular cancer. The testes are also a site of active gene expression of transcripts that may be expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications. Protein, as well as, antibodies directed against the protein may show utility as a tissue-specific marker and/or immunotherapy target for the above listed tissues.

Many polynucleotide sequences, such as EST sequences, are publicly available and accessible through sequence databases. Some of these sequences are related to SEQ ID NO:107 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1132 of SEQ ID NO:107, b is an integer of 15 to 1146, where both a and b correspond to the positions of nucleotide residues shown in SEQ ID NO:107, and where b is greater than or equal to a+14.

Features of Protein Encoded by Gene No: 98

In specific embodiments, polypeptides of the invention comprise the following amino acid sequence: LISSVNKT-KQKRSDATLSHKHDRLLNHFVFFGNSYNY (SEQ ID NO: 565), SSK FPSDMLLRIQQIIYCHKLTIILTKWRN-TARHKSKKKKEDELILKHELQLKKWKN RLILKRAAAEESNFPERSSSEVFLVDE-TLKCDISLLPEXAILQVCMNSVYIIYYN LPSV-VVHACNPSCLGG (SEQ ID NO: 566), SLESTNAIKSN (SEQ ID NO: 567), IRP NKNDQMRHCLINMIDY (SEQ ID NO: 568) ITLCFLETAITINIYSNLVNFLQICYC GYNRSSIVTS (SEQ ID NO: 569), and/or ISFRYA-IADTTDHLLSQANHYPNKMA EYSKT (SEQ ID NO: 570). Polynucleotides encoding these polypeptides are also encompassed by the invention.

This gene is expressed primarily in T-cells, tonsils, and heart tissue.

Therefore, polynucleotides and polypeptides of the invention are useful as reagents for differential identification of the tissue(s) or cell type(s) present in a biological sample and for diagnosis of immune system and vascular tissue disorders. Similarly, polypeptides and antibodies directed to these polypeptides are useful in providing immunological probes for differential identification of the tissue(s) or cell type(s). For a number of disorders of the above tissues or cells, particularly of the immune system and vascular tissue, expression of this gene at significantly higher or lower levels may be routinely detected in certain tissues or cell types (e.g., immune, vascular, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in T-cells, tonsils and heart indicates that polynucleotides and polypeptides corresponding to this gene are useful for the diagnosis and treatment of disorders of the immune system and vascular tissues. Expression of this gene product in tonsils indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses). Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types.

Expression of this gene product in T cells also strongly indicates a role for this protein in immune function and immune surveillance. The tissue distribution in heart muscle tissue indicates that the protein product of this gene is useful for the diagnosis and treatment of conditions and pathologies of the cardiovascular system, such as heart disease, restenosis, atherosclerosis, stoke, angina, thrombosis, and wound healing. Protein, as well as, antibodies directed against the protein may show utility as a tumor marker and/or immunotherapy targets for the above listed tissues.

Many polynucleotide sequences, such as EST;sequences, are publicly available and accessible through sequence databases. Some of these sequences are related to SEQ ID NO:108 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 761 of SEQ ID NO:108, b is an integer of 15 to 775, where both a and b correspond to the positions of nucleotide residues shown in SEQ ID NO:108, and where b is greater than or equal to a+14.

Features of Protein Encoded by Gene No: 99

An embodiment of the invention is directed to polypeptides comprising those which exhibit sequence homology with honeybee venom sacepin. In specific embodiments, polypeptides of the invention comprise the following amino acid sequence: PQIKLLNSDALGMRTTSXDLVPCNQCFIPLPPSCNRIASRKAVNWKQQRLPAV RGLLNNAPHRRPPTPRTPCVFPSEGPKGYGFHV (SEQ ID NO: 571), EQLAXISCR VINVSFRCLHHVIESLPERQLTGSSRGSQP (SEQ ID NO: 572), EDCSTMPPIAAP PPLAPLVFSPLRGPRVMAFMSRCGDRGGRGRSXAGRGWPWSESGVINAHPK KRPCPGPMLS (SEQ ID NO: 573), and/or EFGTRRQWGTRCFPPLVGRKQSALR RREGKARAGRCCGKRSVKAGFDA (SEQ ID NO: 574). Polynucleotides encoding these polypeptides are also encompassed by the invention.

This gene is expressed primarily in activated and control neutrophils, and to a lesser extent in fetal liver and spleen.

Therefore, polynucleotides and polypeptides of the invention are useful as reagents for differential identification of the tissue(s) or cell type(s) present in a biological sample and for diagnosis of disorders of the immune and endocrine systems. Similarly, polypeptides and antibodies directed to these polypeptides are useful in providing immunological probes for differential identification of the tissue(s) or cell type(s). For a number of disorders of the above tissues or cells, particularly of the immune, inflammatory and hormonal systems, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in neutrophils and fetal liver and spleen indicates that polynucleotides and polypeptides corresponding to this gene are useful for the study, diagnosis and treatment of inflammation and various disorders of the immune and endocrine systems. This gene product may be involved in the regulation of cytokine production, antigen presentation, or other processes that may also suggest a usefulness in the treatment of cancer (e.g. by boosting immune responses). Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis.

In addition, this gene product may have commercial utility in the expansion of stem cells and committed progenitors of various blood lineages, and in the differentiation and/or proliferation of various cell types. Expression of this gene product in neutrophils also strongly indicates a role for this protein in immune function and immune surveillance. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:109 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 897 of SEQ ID NO:109, b is an integer of 15 to 911, where both a and b correspond to the positions of nucleotide residues shown in SEQ ID NO:109, and where b is greater than or equal to a+14.

Features of Protein Encoded by Gene No: 100

In specific embodiments, polypeptides of the invention comprise the following amino acid sequence: AFFLLQALEIQSQLATPASSTARNPAPDLHHPHQPTIERFCRHSSSWERIEY (SEQ ID NO: 575). Polynucleotides encoding these polypeptides are also encompassed by the invention. When tested against Jurkat T-cell lines, supernatants removed from cells containing this gene activated the GAS assay. Thus, it is likely that this gene activates T-cells through the Jak-STAT signal transduction pathway. The gamma activating sequence (GAS) is a promoter element found upstream of many genes which are involved in the Jak-STAT pathway. The Jak-STAT pathway is a large, signal transduction pathway involved in the differentiation and proliferation of cells. Therefore, activation of the Jak-STAT pathway, reflected by the binding of the GAS element, can be used to indicate proteins involved in the proliferation and differentiation of cells. Furthermore, contact of cells with supernatant expressing the product of this gene increases the permeability of Brian microvascular pericyte cells to calcium. Thus, it is likely that the product of this gene is involved in a signal transduction pathway that is initiated when the product of this gene binds a receptor on the surface of the pericyte cell. Thus, polynucleotides and polypeptides have uses which include, but are not limited to, activating pericyte (endothelial) cells.

This gene is expressed primarily in activated neutrophils.

Therefore, polynucleotides and polypeptides of the invention are useful as reagents for differential identification of the tissue(s).or cell type(s) present in a biological sample and for diagnosis of diseases and conditions which include, but are not limited to, immune disorders, inflammation.

Similarly, polypeptides and antibodies directed to these polypeptides are useful in providing immunological probes for differential identification of the tissue(s) or cell type(s). For a number of disorders of the above tissues or cells, particularly of the immune, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in neutrophils and the biological activity data suggest that polynucleotides and polypeptides corresponding to this gene are useful for the study and treatment of inflammatory and immune conditions. This gene product may be involved in the regulation of cytokine production, antigen presentation, or other processes that may also suggest a usefulness in the treatment of cancer (e.g. by boosting immune responses). Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis.

In addition, this gene product may have commercial utility in the expansion of stem cells and committed progenitors of various blood lineages, and in the differentiation and/or proliferation of various cell types. Expression of this gene product in neutrophils also strongly indicates a role for this protein in immune function and immune surveillance. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:110 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 442 Of SEQ ID NO:110, b is an integer of 15 to 456, where both a and b correspond to the positions of nucleotide residues shown in SEQ ID NO:110, and where b is greater than or equal to a+14.

Features of Protein Encoded by Gene No: 101

In specific embodiments, polypeptides of the invention comprise the following amino acid sequence: ATVPGSIYNYFYHYNAGALKPEHASESPRGLCAQTAGPFPSF (SEQ ID NO: 576), IRHEPPPPRFKRFSCLSLLSSWDYRRAPPHVAIFCTLSRDGVLPHWPG WSQTPDLK (SEQ ID NO: 577), STHLGLPRCWDYRHEPLCLAPFTTISIIIMQGLS NLSMPQNPPEGCAHRLLDLSPASDSVPPEWGSKIAFEV (SEQ ID NO: 578), and/or LRVGGTSENCCRGECCGSVCIPPGRL (SEQ ID NO: 579). Polynucleotides encoding these polypeptides are also encompassed by the invention. When tested against Jurkat T-cell lines, supernatants removed from cells containing this gene activated the GAS assay. Thus, it is likely that this gene activates T-cells through the Jak-STAT signal transduction pathway. The gamma activating sequence (GAS) is a promoter element found upstream of many genes which are involved in the Jak-STAT pathway. The Jak-STAT pathway is a large, signal transduction pathway involved in the differentiation and proliferation of cells. Therefore, activation of the Jak-STAT pathway, reflected by the binding of the GAS element, can be used to indicate proteins involved in the proliferation and differentiation of cells.

This gene is expressed primarily in neutrophils.

Therefore, polynucleotides and polypeptides of the invention are useful as reagents for differential identification of the tissue(s) or cell type(s) present in a biological sample and for diagnosis of diseases and conditions which include, but are not limited to, immune disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in neutrophils indicates that polynucleotides and polypeptides corresponding to this gene are useful for the study and treatment of immune disorders. Expression of this gene product in neutrophils also strongly indicates a role for this protein in immune function and immune surveillance. This gene product may be involved in the regulation of cytokine production, antigen presentation, or other processes that may also suggest a usefulness in the treatment of cancer (e.g. by boosting immune responses).

Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:111 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 540 of SEQ ID NO:111, b is an integer of 15 to 554, where both a and b correspond to the positions of nucleotide residues shown in SEQ ID NO:111, and where b is greater than or equal to a+14.

Features of Protein Encoded by Gene No: 102

This gene is expressed primarily in neutrophils.

Therefore, polynucleotides and polypeptides of the invention are useful as reagents for differential identification of the tissue(s) or cell type(s) present in a biological sample and for diagnosis of diseases and conditions which include, but arc not limited to, immune conditions. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 251 as residues: Lys-33 to Lys-41.

The tissue distribution in neutrophils indicates that polynucleotides and polypeptides corresponding to this gene are useful for study and treatment of immune disorders. This gene product may be involved in the regulation of cytokine production, antigen presentation, or other processes that may also suggest a usefulness in the treatment of cancer (e.g. by boosting immune responses). Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:112 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 708 of SEQ ID NO:112, b is an integer of 15 to 722, where both a and b correspond to the positions of nucleotide residues shown in SEQ ID NO:112, and where b is greater than or equal to a+14.

Features of Protein Encoded by Gene No: 103

When tested against K562 leukemia cell lines, supernatants removed from cells containing this gene activated the ISRE assay. Thus, it is likely that this gene activates leukemia cells through the Jak-STAT signal transduction pathway. The interferon-sensitive response element is a promoter element found upstream of many genes which are involved in the Jak-STAT pathway. The Jak-STAT pathway is a large, signal transduction pathway involved in the differentiation and proliferation of cells. Therefore, activation of the Jak-STAT pathway, reflected by the binding of the ISRE element, can be used to indicate proteins involved in the proliferation and differentiation of cells. In specific embodiments, polypeptides of the invention comprise the following amino acid sequence: MCVTRMHVKCPPPSASVTAVKWPLSWSSSSFCISLHAGRH (SEQ ID NO: 580), and/or EERNKNHLSCQGLSTICCSYLSSKGEHLRNLSPYSF (SEQ ID NO: 581). Polynucleotides encoding these polypeptides are also encompassed by the invention.

This gene is expressed primarily in neutrophils.

Therefore, polynucleotides and polypeptides of the invention are useful as reagents for differential identification of the tissue(s) or cell type(s) present in a biological sample and for diagnosis of diseases and conditions which include, but are not limited to, immune conditions. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in neutrophils indicates that polynucleotides and polypeptides corresponding to this gene are useful for the study and treatment of immune disorders. This gene product may be involved in the regulation of cytokine production, antigen presentation, or other processes that may also suggest a usefulness in the treatment of cancer (e.g. by boosting immune responses). Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Expression of this gene product in neutrophils also strongly indicates a role for this protein in immune function and immune surveillance. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:113 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 917 of SEQ ID NO:113, b is an integer of 15 to 931, where both a and b correspond to the positions of nucleotide residues shown in SEQ ID NO:113, and where b is greater than or equal to a+14.

Features of Protein Encoded by Gene No: 104

In specific embodiments, polypeptides of the invention comprise the following amino acid sequence: GLCMVHSLLTSSLGGRCCNYPYIADKDIETEVKPPSQGHTWHLHCS (SEQ ID NO: 582), QLWCITALPSTRHCSKGFAWFTHSLRHPSVAGAVIILILQTRTLRQRSSHLPKGTHGICTAPDRPTERAAVTILK (SEQ ID NO: 583), SFDNNN SYGVSQLYQVPDTVLRALHGSLTPYVIPRWQVL (SEQ ID NO: 584), and/or DRGQATFPRAHMASALLLTDRQRELLSRSSNELCMSKV (SEQ ID NO: 585). Polynucleotides encoding these polypeptides are also encompassed by the invention.

This gene is expressed primarily in neutrophils.

Therefore, polynucleotides and polypeptides of the invention are useful as reagents for differential identification of the tissue(s) or cell type(s) present in a biological sample and for diagnosis of immune diseases and disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in neutrophils indicates that polynucleotides and polypeptides corresponding to this gene are useful for the study and treatment of immune disorders. This gene product may be involved in the regulation of cytokine production, antigen presentation, or other processes that may also suggest a usefulness in the treatment of cancer (e.g. by boosting immune responses). Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Expression of this gene product in neutrophils also strongly indicates a role for this protein in immune function and immune surveillance. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:114 and may have been publicly available prior to conception of the present invention. Preferably, such related polynucleotides are specifically excluded from the scope of the present invention. To ,list every related sequence would be cumbersome. Accordingly, preferably excluded from the present invention are one or more polynucleotides comprising a nucleotide sequence described by the general formula of a–b, where a is any integer between 1 to 574 of SEQ ID NO:114, b is an integer of 15 to 588, where both a and b correspond to the positions of nucleotide residues shown in SEQ ID NO:114, and.,where b is greater than or equal to a+14.

Features of Protein Encoded by Gene No: 105

In specific embodiments, polypeptides of the invention comprise the following amino acid sequence: LLLILRPFLNSQFKLQLPLVLFHSSCTYICLLYNYELFHIVALTGKLMNLGLHL FAHHLILAVAHXGCSIPIY (SEQ ID NO: 586), and/or THNSNYSSLWFSSTAVVL TYVYYIIMNCFILSPLQVN (SEQ ID NO: 587). Polynucleotides encoding these polypeptides are also encompassed by the invention.

This gene is expressed primarily in neutrophils.

Therefore, polynucleotides and polypeptides of the invention are useful as reagents for differential identification of the tissue(s) or cell type(s) present in a biological sample and for diagnosis of immune disorders and diseases. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in neutrophils indicates that polynucleotides and polypeptides corresponding to this gene are useful for the study and treatment of inflammatory and immune disorders. This gene product may be involved in the regulation of cytokine production, antigen presentation, or other processes that may also suggest a usefulness in the treatment of cancer (e.g. by boosting immune responses). Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Expression of this gene product in neutrophils also strongly indicates a role for this protein in immune function and immune surveillance. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:115 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 798 of SEQ ID NO:115, b is an integer of 15 to 812, where both a and b correspond to the positions of nucleotide residues shown in SEQ ID NO:115, and where b is greater than or equal to a+14.

Features of Protein Encoded by Gene No: 106

In specific embodiments, polypeptides of the invention comprise the following amino acid sequence: TLVAGSPCSLSRWIMAGFCHGELVQSDMESQEWERGQVVLSHTSLPWCYVS PR (SEQ ID NO: 588), MAGFCHGELVQSDMESQEWERGQVVLSHTSLPWCYVSP R (SEQ ID NO: 589), MAVWISGSYSSFCSRSNWDVFSPNIVLASLPFSFRSVSK AAKPWWLALPALFPDGLWLDSAMGSLYSQTWKARNGKEVRWF SPTPHCLG AMSHL (SEQ ID NO: 590), and/or GWLYGSVGLIPHSAAEATG (SEQ ID NO: 591). Polynucleotides encoding these polypeptides are also encompassed by the invention.

This gene is expressed primarily in neutrophils.

Therefore, polynucleotides and polypeptides of the invention are useful as reagents for differential identification of the tissue(s) or cell type(s) present in a biological sample and for diagnosis of immune disorders and diseases. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 255 as residues: Pro-54 to Gly-62.

The tissue distribution in neutrophils indicates that polynucleotides and polypeptides corresponding to this gene are useful for the study and treatment of immune disorders. This gene product may be involved in the regulation of cytokine production, antigen presentation, or other processes that may also suggest a usefulness in the treatment of cancer (e.g. by boosting immune responses). Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Expression of this gene product in neutrophils also strongly indicates a role for this protein in immune function and immune surveillance. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:116 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 492 of SEQ ID NO:116, b is an integer of 15 to 506, where both a and b correspond to the positions of nucleotide residues shown in SEQ ID NO:116, and where b is greater than or equal to a+14.

Features of Protein Encoded by Gene No: 107

In specific embodiments, polypeptides of the invention comprise the following amino acid sequence: RSKRQSQGSRCSVPLLAQQSRSPPVPLQAQPAWLLGSETIAWSGGGSGWEGP RDPGTSTAAGNSGPGIGMGHRTPPPSHTGR (SEQ ID NO: 592), RWDPAWGLDIPESSCPVTMGELRSGDGIVL (SEQ ID NO: 593), GALLWDNSMISAPRGSHREA GALFPSWLSNPAVLPSRSRPSQPGCLDPRQ (SEQ ID NO: 594), NSAREPRRWIR PTRGSGETTAPCCFEPLNGGTLVHAAAMARASEAAGTG (SEQ ID NO: 595), MARASEAAGTG (SEQ ID NO: 596), CFTTAFQKALRDPRPTLPDTHGSLRNAP LKSLTLPAAFVVSFFFLSLLQDGIKERSQTQNATFFFHDRSDIEGLSEEPCSGTT P (SEQ ID NO: 597), LALQEAVTGKQVLCSPPGSAIPQSSRPAPGPASLAAWIRDN SLVWRRLRVGGTQGPGHQYSSWEFRPRDRDGAQDTTPISHREMKVGSSMGT GHP (SEQ ID NO: 598), and/or MAGRLFTLLLWQELARRLVPGDASPRLSRKR SVTPGPPFPTLTVPSE (SEQ ID NO: 599). Polynucleotides encoding these polypeptides are also encompassed by the invention. When tested against sensory neuron cell lines, supernatants removed from cells containing this gene activated the EGR1 assay. Thus, it is likely that this gene activates sensory neuron cells through a signal transduction pathway. Early growth response 1 (EGR1) is a promoter associated with certain genes that induces various tissues and cell types upon activation, leading the cells to undergo differentiation and proliferation.

This gene is expressed primarily in neutrophils.

Therefore, polynucleotides and polypeptides of the invention are useful as reagents for differential identification of the tissue(s) or cell type(s) present in a biological sample and for diagnosis of immune disorders and diseases. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 256 as residues: Met-25 to Gly-30.

The tissue distribution in neutrophils indicates that polynucleotides and polypeptides corresponding to this gene are useful for the study and treatment of immune disorders. This gene product may be involved in the regulation of cytokine production, antigen presentation, or other processes that may also suggest a usefulness in the treatment of cancer (e.g. by boosting immune responses). Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Expression of this gene product in neutrophils also strongly indicates a role for this protein in immune function and immune surveillance. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:117 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 737 of SEQ ID NO:117, b is an integer of 15 to 751, where both a and b correspond to the positions of nucleotide residues shown in SEQ ID NO:117, and where b is greater than or equal to a+14.

Features of Protein Encoded by Gene No: 108

In specific embodiments, polypeptides of the invention comprise the following amino acid sequence: MYSKIFYFLLLNSDTSNNVTSKTLVSSISSSNNRLAVSIVF (SEQ ID NO: 600), SRQKNLLKLHSNPNCDNFCFIFNYKPKYICIFKLICLKILLY IFGSG (SEQ ID NO: 601), and/or MLLSLLMVFTSELYVKRHISFKSXDKPHCH KNQDIDVLFRKLLEKHFKVIMICFP (SEQ ID NO: 602). Polynucleotides encoding these polypeptides are also encompassed by the invention.

This gene is expressed primarily in fetal liver, and to a lesser extent in bone and breast cancer cell lines.

Therefore, polynucleotides and polypeptides of the invention are useful as reagents for differential identification of the tissue(s) or cell type(s) present in a biological sample and for diagnosis of diseases and conditions which include, but are not limited to, cancer and metabolic disorders. Similarly, polypeptides and antibodies directed to these polypeptides are useful in providing immunological probes for differential identification of the tissue(s) or cell type(s). For a number of disorders of the above tissues or cells, particularly of the digestive and skeletal system, expression of this gene at significantly higher or lower levels may be routinely detected in certain tissues or cell types (e.g., digestive, skeletal, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in fetal liver/spleen, as well as bone and breast cancer, indicates that polynucleotides and polypeptides corresponding to this gene are useful for study and treatment of growth and metabolic disorders and neoplasias (e.g. hepatoblastoma, jaundice, hepatitis, liver metabolic diseases and conditions that are attributable to the differentiation of hepatocyte progenitor cells). Furthermore, the tissue distribution indicates that polynucleotides and polypeptides corresponding to this gene are useful for the diagnosis and/or treatment of bone and breast cancer, as well as cancers of other tissues where expression has been observed. The expression within fetal tissue and other cellular sources marked by proliferating cells suggests this protein may play a role in the regulation of cellular division, and may show utility in the diagnosis and treatment of cancer and other proliferative disorders. Similarly, developmental tissues rely on decisions involving cell differentiation and/or apoptosis in pattern formation. Thus this protein may also be involved in apoptosis or tissue differentiation and could again be useful in cancer therapy. The protein product of this clone is useful for the treatment and diagnosis of hematopoietic related disorders such as anemia, pancytopenia, leukopenia, thrombocytopenia or leukemia since stromal cells are important in the production of cells of hematopoietic lineages. The uses include bone marrow cell ex-vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:118 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 946 of SEQ ID NO:118, b is an integer of 15 to 960, where both a and b correspond to the positions of nucleotide residues shown in SEQ ID NO:118, and where b is greater than or equal to a+14.

Features of Protein Encoded by Gene No: 109

In specific embodiments, polypeptides of the invention comprise the following amino acid sequence: FREYGFYNLHIFC (SEQ ID NO: 603), LVTTDYYDGCNEDYE YNWSYMFLNSEQLFIKFYPTFFC (SEQ ID NO: 604), and/or NVIAPGLESSCANS LFLLFVCLPVAHHRHNFLFIKHSLYNHLRDYESDFDKI (SEQ ID NO: 605). Polynucleotides encoding these polypeptides are also encompassed by the invention.

This gene is expressed primarily in T cells, fetal heart and infant brain, and to a lesser extent in some transformed cell lines.

Therefore, polynucleotides and polypeptides of the invention are useful as reagents for differential identification of the tissue(s) or cell type(s) present in a biological sample and for diagnosis of growth and immune disorders and diseases. Similarly, polypeptides and antibodies directed to these polypeptides are useful in providing immunological probes for differential identification of the tissue(s) or cell type(s). For a number of disorders of the above tissues or cells, particularly of the immune and cardiovascular systems, expression of this gene at significantly higher or lower levels may be routinely detected in certain tissues or cell types (e.g., immune, cardiovascular, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in immune cells, heart tissue, and brain tissue indicates that polynucleotides and polypeptides corresponding to this gene are useful for the study and treatment of developmental and immune disorders. This gene product may be involved in the regulation of cytokine production, antigen presentation, or other processes that may also suggest a usefulness in the treatment of cancer (e.g. by boosting immune responses). Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Expression of this gene product in T cells also strongly indicates a role for this protein in immune function and immune surveillance.

The tissue distribution in heart muscle tissue indicates that the protein product of this gene is useful for the diagnosis and treatment of conditions and pathologies of the cardiovascular system, such as heart disease, restenosis, atherosclerosis, stoke, angina, thrombosis, and wound healing. The tissue distribution in brain tissue indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered bahaviors, including disorders in feeding, sleep patterns, balance, and perception. In addition, the gene or gene product may also play a role in the treatment and/or detection of developmental disorders associated with the developing embryo, or sexually-linked disorders. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:119 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1428 of SEQ ID NO:119, b is an integer of 15 to 1442, where both a and b correspond to the positions of nucleotide residues shown in SEQ ID NO:119, and where b is greater than or equal to a+14.

Features of Protein Encoded by Gene No: 110

In specific embodiments, polypeptides of the invention comprise the following amino acid sequence: PKVLAVLKKKNHVALSIFELLSNDICSFISFFMS (SEQ ID NO: 606), EGPDINSNLKFLLCLKKKIMWPFQYLNC (SEQ ID NO: 607), and/or LLSLILLRIWYDFSKQTVFWFFLNVFNFFSSCNNDGACSYKYRKVQI (SEQ ID NO: 608). Polynucleotides encoding these polypeptides are also encompassed by the invention.

This gene is expressed primarily in osteoblasts, and to a lesser extent in bone marrow and bladder.

Therefore, polynucleotides and polypeptides of the invention are useful as reagents for differential identification of the tissue(s) or cell type(s) present in a biological sample and for diagnosis of diseases and conditions which include, but are not limited to, skeletal and hematopoietic diseases and disorders. Similarly, polypeptides and antibodies directed to these polypeptides are useful in providing immunological probes for differential identification of the tissue(s) or cell type(s). For a number of disorders of the above tissues or cells, particularly of the skeletal and vascular systems, expression of this gene at significantly higher or lower levels may be routinely detected in certain tissues or cell types (e.g., skeletal, vascular, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 259 as residues: Gly-33 to Lys-38.

The tissue distribution in bone marrow and osteoblasts indicates that polynucleotides and polypeptides corresponding to this gene are useful for the study, diagnosis, and treatment of bone and hematopoietic: disorders. Elevated levels of expression of this gene product in osteoblasts indicates that it may play a role in the survival, proliferation, and/or growth of osteoblasts. Therefore, it may be useful in influencing bone mass in such conditions as osteoporosis. More generally, as evidenced by expression in bone marrow, this gene may play a role in the survival, proliferation, and/or differentiation of hematopoietic cells in general, and may be of use in augmentation of the numbers of stem cells and committed progenitors. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:120 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 831 of SEQ ID NO:120, b is an integer of 15 to 845, where both a and b correspond to the positions of nucleotide residues shown in SEQ ID NO:120, and where b is greater than or equal to a+14.

Features of Protein Encoded by Gene No: 111

In specific embodiments, polypeptides of the invention comprise the following amino acid sequence: HTLFISFLWAEG (SEQ ID NO: 609), MLPVFVLFFCFTY SARKQSVFKKGNVFE (SEQ ID NO: 610), and/or SPCSAAECHNLSLLSSCSL VSSNILFSFPFFGQKARCCLFLFYFSASHIAHESRVYSKKEMCL (SEQ ID NO: 611). Polynucleotides encoding these polypeptides are also encompassed by the invention.

This gene is expressed primarily in prostate cancer.

Therefore, polynucleotides and polypeptides of the invention are useful as reagents for differential identification of the tissue(s) or cell type(s) present in a biological sample and for diagnosis of diseases and conditions which include, but are not limited to, prostate and other cancers. Similarly, polypeptides and antibodies directed to these polypeptides are useful in providing immunological probes for differential identification of the tissue(s) or cell type(s). For a number of disorders of the above tissues or cells, particularly of the endocrine system, expression of this gene at significantly higher or lower levels may be routinely detected in certain tissues or cell types (e.g., endocrine, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in prostate cancer indicates that polynucleotides and polypeptides corresponding to this gene are useful for the study and treatment of prostate cancer, as well as cancers of other tissues where expression has been observed. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:121 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 346 of SEQ ID NO:121, b is an integer of 15 to 360, where both a and b correspond to the positions of nucleotide residues shown in SEQ ID NO:121, and where b is greater than or equal to a+14.

Features of Protein Encoded by Gene No: 112

In specific embodiments, polypeptides of the invention comprise the following amino acid sequence: HKCFQCFILANGFLKVIKPFQRNWSDKTFFLVCLNKAISEALLSKMTFLSFFKT NLLLLETFCTI (SEQ ID NO: 612), LLGVLKPLYFSVEPVLGERSVAFEEVREKNH GTSGFLSLYSLAAIVCGHLMFFHTLLGRGGNDHPGQSPLPGMRPLRGGLAGQ APSGHPWMQPLDTCLL (SEQ ID NO: 613), RPTRPPTRPDRPSLELAPGLCADF LGSSNHCIFLLSLYLGRDQ (SEQ ID NO: 614), and/or EKRIMVPQGFFPFTRWQP LSVGTSCFSTLYWAVEVTITQASLLCLGCAL (SEQ ID NO: 615). Polynucleotides encoding these polypeptides are also encompassed by the invention.

This gene is expressed primarily in haemopoietic and neural tissues, and to a lesser extent in a number of cancers and other tissues.

Therefore, polynucleotides and polypeptides of the invention are useful as reagents for differential identification of the tissue(s) or cell type(s) present in a biological sample and for diagnosis of diseases and conditions which include, but are not limited to, diseases of the haemopoietic and neural systems. Similarly, polypeptides and antibodies directed to these polypeptides are useful in providing immunological probes for differential identification of the tissue(s) or cell type(s). For a number of disorders of the above tissues or cells, particularly of the immune and neural system, expression of this gene at significantly higher or lower levels may be routinely detected in certain tissues or cell types (e.g., immune, neural, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in immune and neural tissues indicates that polynucleotides and polypeptides corresponding to this gene are useful for the diagnosis and treatment of diseases of the haemopoietic and neural systems, including several cancers. This gene product may be involved in the regulation of cytokine production, antigen presentation, or other processes that may also suggest a usefulness in the treatment of cancer (e.g. by boosting immune responses). Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis.

In addition, this gene product may have commercial utility in the expansion of stem cells and committed progenitors of various blood lineages, and in the differentiation and/or proliferation of various cell types. Furthermore, the tissue distribution indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered bahaviors, including disorders in feeding, sleep patterns, balance, and perception. In addition, the gene or gene product may also play a role in the treatment and/or detection of developmental disorders associated with the developing embryo, or sexually-linked disorders. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:122 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 930 of SEQ ID NO:122, b is an integer of 15 to 944, where both a and b correspond to the positions of nucleotide residues shown in SEQ ID NO:122, and where b is greater than or equal to a+14.

Features of Protein Encoded by Gene No: 113

The translation product of this gene shares sequence homology with intestinal epithelium proliferating cell-associated mRNA sequence, which is thought to be important in the growth and development of epithelial cells. In specific embodiments, polypeptides of the invention comprise the following amino acid sequence: MTLDEWKNLQEQTRPKPEFNIRKPESTVPSKAVVIRESKYRDDMVKDDYEDDSHVFRKPANDITSQLEINFGNLPRPGRGARGGTRGGRGRAENYGPRAEVV MQDVAPNPDDPEDFPALS (SEQ ID NO: 616), CKMLPPTQMTRKISLRCLERALFPSTAELHCTPVGRLFQLGQGSQTLRTIDVAFPVSCKFVALFWAELLEGLLQR LESRPFPKKMKNGDCVFIEGISNEE (SEQ ID NO: 617), PPSSWAWSQRRHPG RPGKDQEGRELWTQSRSGDARCCPQPR (SEQ ID NO: 618), and/or CLKCVY RDSIDSSAEAWRERRL (SEQ ID NO: 619). Polynucleotides encoding these polypeptides are also encompassed by the invention.

This gene is expressed primarily in brain and central nervous system tissues, such as the frontal cortex, amygdala, and hypothalmus, and to a lesser extent in testis.

Therefore, polynucleotides and polypeptides of the invention are useful as reagents for differential identification of the tissue(s) or cell type(s) present in a biological sample and for diagnosis of diseases and conditions which include, but are not limited to, diseases of the neural system. Similarly, polypeptides and antibodies directed to these polypeptides are useful in providing immunological probes for differential identification of the tissue(s) or cell type(s). For a number of disorders of the above tissues or cells, particularly of the neural and reproductive system, expression of this gene at significantly higher or lower levels may be routinely detected in certain tissues or cell types (e.g., neural, reproductive, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 262 as residues: Glu-20 to Glu-27, Glu-30 to Trp-44.

The tissue distribution and homology to intestinal epithelium proliferating cell-associated mRNA sequence indicates that polynucleotides and polypeptides corresponding to this gene are useful for growth and developmental diseases of the brain, central nervous system and reproductive system. The tissue distribution in neural tissues indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered bahaviors, including disorders in feeding, sleep patterns, balance, and perception.

In addition, the gene or gene product may also play a role in the treatment and/or detection of developmental disorders associated with the developing embryo, or sexually-linked disorders. Elevated expression of this gene product within the frontal cortex of the brain indicates that it may be involved in neuronal survival; synapse formation; conductance; neural differentiation, etc. Such involvement may impact many processes, such as learning and cognition. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:123 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 900 of SEQ ID NO:123, b is an integer of 15 to 914, where both a and b correspond to the positions of nucleotide residues shown in SEQ ID NO:123, and where b is greater than or equal to a+14.

Features of Protein Encoded by Gene No: 114

In specific embodiments, polypeptides of the invention comprise the following amino acid sequence: LSYSVLLILPLFHSLPTLKDTHTHNKWVE (SEQ ID NO: 620), EVNGVGYKHSCFSDISSVLENKDSRMRAPHYASFQHFFSVLLKL SPQACLTESQCIPLTFY (SEQ ID NO: 621), KTHTHTISGWSKKSTELDISIPAFL TSPVSWRTRILE (SEQ ID NO: 622), and/or IRHELGSSDPPAEASQIAGTAAVS HHAQP (SEQ ID NO: 623). Polynucleotides encoding these polypeptides are also encompassed by the invention.

This gene is expressed primarily in spinal cord.

Therefore, polynucleotides and polypeptides of the invention are useful as reagents for differential identification of the tissue(s) or cell type(s) present in a biological sample and for diagnosis of diseases and conditions which include, but are not limited to, spinal cord injuries and diseases of the neural system. Similarly, polypeptides and antibodies directed to these polypeptides are useful in providing immunological probes for differential identification of the tissue(s) or cell type(s). For a number of disorders of the above tissues or cells, particularly of the neural system, expression of this gene at significantly higher or lower levels may be routinely detected in certain tissues or cell types (e.g., neural, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 263 as residues: Pro-45 to Gln-52.

The tissue distribution in spinal cord indicates that polynucleotides and polypeptides corresponding to this gene are useful for the diagnosis and treatment of spinal cord injuries and diseases of the neural system, such as spinal deformation, spinocerebullar ataxia types I and III, dentatorubropallidoluysian and spinal bulbar muscular atrophy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:124 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 448 of SEQ ID NO:124, b is an integer of 15 to 462, where both a and b correspond to the positions of nucleotide residues shown in SEQ ID NO:124, and where b is greater than or equal to a+14.

Features of Protein Encoded by Gene No: 115

In specific embodiments, polypeptides of the invention comprise the following amino acid sequence: MLYLIL-ISLSSLSFSFSLPPFSIII (SEQ ID NO: 624), SSYFL RHFRIYHTCPKYFSMNIN (SEQ ID NO: 625), KLTLT-KGNKSWSSTAVAAA LELVDPPGCRNSARDSLPNSTM MFYYACFILYSSLSPLSLSLSPSLLSLL (SEQ ID NO: 626), and/or QFHTGNSYDHDYAK (SEQ ID NO: 627). Polynucleotides encoding these polypeptides are also encompassed by the invention. When tested against U937 Myeloid cell lines, supernatants removed from cells containing this gene activated the GAS assay. Thus, it is likely that this gene activates myeloid cells through the Jak-STAT signal transduction pathway. The gamma activating sequence (GAS) is a promoter element found upstream of many genes which are involved in the Jak-STAT pathway. The Jak-STAT pathway is a large, signal transduction pathway involved in the differentiation and proliferation of cells. Therefore, activation of the Jak-STAT pathway, reflected by the binding of the GAS element, can be used to indicate proteins involved in the proliferation and differentiation of cells.

This gene is expressed primarily in striatum.

Therefore, polynucleotides and polypeptides of the invention are useful as reagents for differential identification of the tissue(s) or cell type(s) present in a biological sample and for diagnosis of a number of diseases of the neural system. Similarly, polypeptides and antibodies directed to these polypeptides are useful in providing immunological probes for differential identification of the tissue(s) or cell type(s). For a number of disorders of the above tissues or cells, particularly of the neural diseases, expression of this gene at significantly higher or lower levels may be routinely detected in certain tissues or cell types (e.g., striatum, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in striatum indicates that polynucleotides and polypeptides corresponding to this gene are useful for the diagnosis and treatment of diseases of the neural system. Furthermore, the tissue distribution indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered bahaviors, including disorders in feeding, sleep patterns, balance, and perception. In addition, the gene or gene product may also play a role in the treatment and/or detection of developmental disorders associated with the developing embryo, or sexually-linked disorders. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:125 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 531 of SEQ ID NO:125, b is an integer of 15 to 545, where both a and b correspond to the positions of nucleotide residues shown in SEQ ID NO:125, and where b is greater than or equal to a+14.

Features of Protein Encoded by Gene No: 116

In specific embodiments, polypeptides of the invention comprise the following amino acid sequence: AVCTGGY-CESCRCEHCVCVCVDLCVLFSGKELRVR (SEQ ID NO: 628), VSFFFVFKWSFAEIKSREEHWASLTP-KPTLLSALLTCDVLKS SIIFKCCESTEDKGFDS-FFQASKDGSSSRI (SEQ ID NO: 629), RSWGSQRSLCLL FIPFAAESYSVVWMGHLFVVCLLSSWWT-FRPFALAVTVNHVAVNIVCVSAW TCVSCSLGRSCG-LEGSFLFPLETLWFPHMVVLCLTF (SEQ ID NO: 630), MGHLFV VCLLSSWWTFRPFALAVTVNH-VAVNIVCVSAWTCVSCSLGRSCGLEGSFLFP LETLW-FPHMVVLCLTF (SEQ ID NO: 63 1), HDVLGAR-NAACVCCSFLLQQNRILL FGWATCLLSVYSPAGGHLGRLHWRLL (SEQ ID NO: 632), MLDFKTSQVSKAL KRVGFGVRLAQCSSLD-LISAKLHLKTKKKETYITSTVMTAASLFLSYVTSEFT RSIMATFYCFVLKL-HIGEMGTLQTAGGSKMTWPLQKAIWQ-FLKRLSIKLPYV ETRESPGETKNY (SEQ ID NO: 633), and/or LTRNSFPENRTHKSTQTHTQCSQRHD SQ (SEQ ID NO: 634). Polynucleotides encoding these polypeptides are also encompassed by the invention.

This gene is expressed primarily in intestine and cancer cells.

Therefore, polynucleotides and polypeptides of the invention are useful as reagents for differential identification of the tissue(s) or cell type(s) present in a biological sample and for diagnosis of diseases and conditions which include, but are not limited to, diseases of the gastrointestinal tract and cancer. Similarly, polypeptides and antibodies directed to these polypeptides are useful in providing immunological probes for differential identification of the tissue(s) or cell type(s). For a number of disorders of the above tissues or cells, particularly of the digestive system, expression of this gene at significantly higher or lower levels may be routinely detected in certain tissues or cell types (e.g., digestive, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in gastrointestinal tissues and cancerous tissues indicates that polynucleotides and polypeptides corresponding to this gene are useful for the treatment and diagnosis of diseases of the digestive system and cancer. Furthermore, the tissue distribution in gastrointestinal tissues indicates that polynucleotides and polypeptides corresponding to this gene are useful for the diagnosis, prevention, and/or treatment of various metabolic disorders such as Tay-Sachs disease, phenylkenonuria, galactosemia, porphyrias, and Hurler's syndrome. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:126 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 898 of SEQ ID NO:126, b is an integer of 15 to 912, where both a and b correspond to the positions of nucleotide residues shown in SEQ ID NO:126, and where b is greater than or equal to a+14.

Features of Protein Encoded by Gene No: 117

The translation product of this gene shares sequence homology with a human apoptosis regulating protein which is thought to be important in regulating cell death. In specific embodiments, polypeptides of the invention comprise the following amino acid sequence: IRHEGQSSSRGSSHCDSPSPQEDGQIMFDVEMHTSRDHSSQSEEEVVEGEKEV EALKKSADWVSDWSSRPENIPPKEFHFRHPKRSVSLS (SEQ ID NO: 635), GILLTLYPFWPEDILEFPNRVYCCLEICKGFFSANATSRL (SEQ ID NO: 636), EFGTRDRVVPEAVLTVTALRHKKMGRSCLMWKCTPAGTIALSQKKKL (SEQ ID NO: 637), AHPLPAPTEGKEKPLEMRVTCEVVYCHSSLFELETIVSMTQPT TLFLHIQFQ (SEQ ID NO: 638), TFCVFKHEEKWSHEERGYFLRRISEGVHSISLP FSCFGFGARHLYWKATEHTLCQHLLRERKSPWKCV (SEQ ID NO: 639), and/or QSLLLFRNLQGLLFRKCHQQIIILSAMLLSLISATRLDLYHSWYKFYSCNITTIS LLKRDQVSK (SEQ ID NO: 640). Polynucleotides encoding these polypeptides are also encompassed by the invention. When tested against Jurkat cell lines, supernatants removed from cells containing this gene activated the NF-kB transcription factor. Thus, it is likely that this gene activates Jurkat cells by activating a transcriptional factor found within these cells. Nuclear factor kB is a transcription factor activated by a wide variety of agents, leading to cell activation, differentiation, or apoptosis. Reporter constructs utilizing the NF-kB promoter element are used to screen supernatants for such activity.

This gene is expressed primarily in muscle, fibroblast cells, haemopoietic cells, and fetal lung.

Therefore, polynucleotides and polypeptides of the invention are useful as reagents for differential identification of the tissue(s) or cell type(s) present in a biological sample and for diagnosis of diseases and conditions which include, but are not limited to, diseases of the haemopoietic, muscular and developing systems. Similarly, polypeptides and antibodies directed to these polypeptides are useful in providing immunological probes for differential identification of the tissue(s) or cell type(s). For a number of disorders of the above tissues or cells, particularly of the immune and muscular system, expression of this gene at significantly higher or lower levels may be routinely detected in certain tissues or cell types (e.g., immune, muscular, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 266 as residues: Met-1 to Ala-6.

The tissue distribution in muscle and homology to apoptosis regulating protein indicates that polynucleotides and polypeptides corresponding to this gene are useful for diagnosis and treatment of diseases of the haemopoietic, muscular and developing systems. Expression within embryonic tissue and other cellular sources marked by proliferating cells indicates that this protein may play a role in the regulation of cellular division. Additionally, the expression in hematopoietic cells and tissues indicates that this protein may play a role in the proliferation, differentiation, and/or survival of hematopoietic cell lineages. In such an event, this gene may be useful in the treatment of lymphoproliferative disorders, and in the maintenance and differentiation of various hematopoietic lineages from early hematopoietic stem and committed progenitor cells. Similarly, embryonic development also involves decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:127 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1034 of SEQ ID NO:127, b is an integer of 15 to 1048, where both a and b correspond to the positions of nucleotide residues shown in SEQ ID NO:127, and where b is greater than or equal to a+14.

Features of Protein Encoded by Gene No: 118

In specific embodiments, polypeptides of the invention comprise the following amino acid sequence: IRHESFNPLTCGFSLFFSLFS (SEQ ID NO: 641), METLLLL LFFLSLLIFRFRILVSQCIN (SEQ ID NO: 642), FLLTTVLLFSSKVRDPRANFD QSLRVLKHAKKVQPDVISKTSIMLGLGENDEQVYATMKGKEIEK (SEQ ID NO: 643), and/or QQSCCFPVRFVILGPILISPYVY (SEQ ID NO: 644). Polynucleotides encoding these polypeptides are also encompassed by the invention.

This gene is expressed primarily in synovium.

Therefore, polynucleotides and polypeptides of the invention are useful as reagents for differential identification of the tissue(s) or cell type(s) present in a biological sample and for diagnosis of diseases and conditions which include, but are not limited to, arthritis and other diseases of the musculo-skeletal system. Similarly, polypeptides and antibodies directed to these polypeptides are useful in providing immunological probes for differential identification of the tissue(s) or cell type(s). For a number of disorders of the above tissues or cells, particularly of the musculo-skeletal system, expression of this gene at significantly higher or lower levels may be routinely detected in certain tissues or cell types (e.g., musculo-skeletal, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in synovium indicates that polynucleotides and polypeptides corresponding to this gene are useful for the treatment and diagnosis of diseases of the muscular-skeletal system. Furthermore, the expression of this gene product in synovium indicates a role in the detection and treatment of disorders and conditions affecting the skeletal system, in particular osteoporosis as well as disorders afflicting connective tissues (e.g. arthritis, trauma, tendonitis, chrondomalacia and inflammation), such as in the diagnosis or treatment of various autoimmune disorders such as rheumatoid arthritis, lupus, scleroderma, and dermatomyositis as well as dwarfism, spinal deformation, and specific joint abnormalities as well as chondrodysplasias (i.e. spondyloepiphyseal dysplasia congenita, familial osteoarthritis, Atelosteogenesis type II, metaphyseal chondrodysplasia type Schmid). Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:128 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 708 of SEQ ID NO:128, b is an integer of 15 to 722, where both a and b correspond to the positions of nucleotide residues shown in SEQ ID NO:128, and where b is greater than or equal to a+14.

Features of Protein Encoded by Gene No: 119

In specific embodiments, polypeptides of the invention comprise the following amino acid sequence: VWLLSSILLRVLWNRYTLQELSFWLPWFASRATSLVLQHGDNYLLFLFCFVC FVLAMPF (SEQ ID NO: 645), IRHEVSMAFVFHLAQGTLEPLYIAGA (SEQ ID NO: 646), NSARGEYGFCLPSCSGYFGTAIHCRSLASGYHGLLPEQQA (SEQ ID NO: 647), and/or HELTVPSRMGSKGKPYPCGFYSSLIP (SEQ ID NO: 648). Polynucleotides encoding these polypeptides are also encompassed by the invention. When tested against U937 Myeloid cell lines, supernatants removed from cells containing this gene activated the GAS assay. Thus, it is likely that this gene activates myeloid cells through the Jak-STAT signal transduction pathway. The gamma activating sequence (GAS) is a promoter element found upstream of many genes which are involved in the Jak-STAT pathway. The Jak-STAT pathway is a large, signal transduction pathway involved in the differentiation and proliferation of cells. Therefore, activation of the Jak-STAT pathway, reflected by the binding of the GAS element, can be used to indicate proteins involved in the proliferation and differentiation of cells.

This gene is expressed primarily in rejected kidney, stromal cells, and infant brain.

Therefore, polynucleotides and polypeptides of the invention are useful as reagents for differential identification of the tissue(s) or cell type(s) present in a biological sample and for diagnosis of diseases and conditions which include, but are not limited to, diseases of the renal, central nervous and immune systems. Similarly, polypeptides and antibodies directed to these polypeptides are useful in providing immunological probes for differential identification of the tissue(s) or cell type(s). For a number of disorders of the above tissues or cells, particularly of the immune, renal and central nervous system, expression of this gene at significantly higher or lower levels may be routinely detected in certain tissues or cell types (e.g., immune, renal, nervous, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 268 as residues: Ser-6 to Arg-15.

The tissue distribution rejected kidney, stromal cells, and infant brain indicates that polynucleotides and polypeptides corresponding to this gene are useful for the diagnosis and treatment of diseases of the renal, central nervous, and immune systems. The tissue distribution in infant brain indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered bahaviors, including disorders in feeding, sleep patterns, balance, and perception. In addition, the gene or gene product may also play a role in the treatment and/or detection of developmental disorders associated with the developing embryo, or sexually-linked disorders.

Alternatively, this gene product may be involved in the regulation of cytokine production, antigen presentation, or other processes that may also suggest a usefulness in the treatment of cancer (e.g. by boosting immune responses). Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types.

The tissue distribution in kidney indicates that this gene or gene product is useful in the treatment and/or detection of kidney diseases including renal failure, nephritus, renal tubular acidosis, proteinuria, pyuria, edema, pyelonephritis, hydronephritis, nephrotic syndrome, crush syndrome, glomerulonephritis, hematuria, renal colic and kidney stones, in addition to Wilm's Tumor Disease, and congenital kidney abnormalities such as horseshoe kidney, polycystic kidney, and Falconi's syndrome. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:129 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 463 of SEQ ID NO:129, b is an integer of 15 to 477, where both a and b correspond to the positions of nucleotide residues shown in SEQ ID NO:129, and where b is greater than or equal to a+14.

Features of Protein Encoded by Gene No: 120

The protein of the invention has sequence identity to the *Saccharomyces cerevisiae* ankyrin repeat-containing protein (gi|466522). The translation product of this gene also shares homology with *C. elegans* protein C43H6.7 gene product (Genbank Accession No. gi|1255324). In specific embodiments, polypeptides of the invention comprise the following amino acid sequence: KCIYPKPARTHHCSICN-RCVLKMDHHCPWLNNCVGHYNHRYFFSFCFFMTLG CVYCSYGSWDLFREAYAAIEKMKQLD-KNKLQAVANQTYHQTPPPTFSFRER (SEQ ID NO: 649), ARGHWNLILIVFHYYQAITTPPGYP-PQGRNDIATVSIC (SEQ ID NO: 650), WQCELD-CVSHDSSTHSAPYVISRASKGSFSQNP (SEQ ID NO: 651), SKRASGPALGYHAGQFKDQPFIYHCRRK-TQCGEILGLTSLYSGKQK FQPQTRGQAASYLPCPVL-TRTSSRIQHWSWPPPLLLAV (SEQ ID NO: 652), ESL QLRLLGQLEGIPGCGYRKALAYSGALTF (SEQ ID NO: 653), and/or SLAPWEW NELGAPSLGDCSLSLCDGS-VSWTVSATTRALILLPMLFQGPPRAAFLRILDQK EPVGLP (SEQ ID NO: 654). Polynucleotides encoding these polypeptides are also encompassed by the invention.

This gene is expressed primarily in endometrial tumor, colon tumor, prostate cancer, and ovarian cancer.

Therefore, polynucleotides and polypeptides of the invention are useful as reagents for differential identification of the tissue(s) or cell type(s) present in a biological sample and for diagnosis of a number of types of cancers, particularly endometrial, prostate, ovarian, and colon cancers. Similarly, polypeptides and antibodies directed to these polypeptides are useful in providing immunological probes for differential identification of the tissue(s) or cell type(s). For a number of disorders of the above tissues or cells, particularly of the endometrium, prostate, colon, and ovary, expression of this gene at significantly higher or lower levels may be routinely detected in certain tissues or cell types (e.g., prostate, colon, ovary, endometrium, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 269 as residues: Asn-43 to Arg-49, Phe-57 to Cys-65, Pro-93 to Ser-99.

The tissue distribution in prostate cancer, ovarian cancer, colon cancer, and endometrial cancer tissues indicates that polynucleotides and polypeptides corresponding to this gene are useful for the diagnosis and treatment of diseases and cancers of the prostate, ovaries, colon, and endometrium, as well as cancers of other tissues where expression has been observed. Expression within cellular sources marked by proliferating cells suggests this protein may play a role in the regulation of cellular division, and may show utility in the diagnosis and treatment of cancer and other proliferative disorders. Similarly, developmental tissues rely on decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:130 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1282 of SEQ ID NO:130, b is an integer of 15 to 1296, where both a and b correspond to the positions of nucleotide residues shown in SEQ ID NO:130, and where b is greater than or equal to a+14.

Features of Protein Encoded by Gene No: 121

The translation product of this gene shares sequence homology with adrenalin receptor (Patent serial No. J08126491-A.) In specific embodiments, polypeptides of the invention comprise the following amino acid sequence: TATLNSFFGGWGLALLLRLECSDTIM-DHCSLDLLGSSNPPASASQVVGTTGAR HHAQLIFCFFVQTRSHSVA (SEQ ID NO: 655), MDHC-SLDLLGSSNPPASASQVV GTTGAR-HHAQLIFCFFVQTRSHSVA (SEQ ID NO: 656), GVLKQSSHLVLSKG (SEQ ID NO: 657), DYS-CESLCPALLSIAPDIVLN (SEQ ID NO: 658), TTIHK-TQLG SYKILWEPKEGYHNSTWI (SEQ ID NO: 659), IREIFLRRP (SEQ ID NO: 660), and/or LKFQKPGKIQM-RGGGRVFWYKNCK (SEQ ID NO: 661). Polynucleotides encoding these polypeptides are also encompassed by the invention.

This gene is expressed primarily in synovial sarcoma.

Therefore, polynucleotides and polypeptides of the invention are useful as reagents for differential identification of the tissue(s) or cell type(s) present in a biological sample and for diagnosis of diseases and conditions which include, but are not limited to, arthritis and other diseases of the synovium including cancers. Similarly, polypeptides and antibodies directed to these polypeptides are useful in providing immunological probes for differential identification of the tissue(s) or cell type(s). For a number of disorders of the above tissues or cells, particularly of the immune and muscular-skeletal system, expression of this gene at significantly higher or lower levels may be routinely detected in certain tissues or cell types (e.g., immune, musculo-skeletal, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in synovial sarcoma-tissue and the homology to adrenalin receptor indicates that polynucleotides and polypeptides corresponding to this gene are useful for the diagnosis and treatment of diseases of the synovium, immune system and musculo-skeletal system including cancers of these tissues and systems. It may also be useful for identifying and therapeutically using antagonists and agonists for this receptor family. In addition, the expression of this gene product in synovium indicates a role in the detection and treatment of disorders and conditions affecting the skeletal system, in particular osteoporosis as well as disorders afflicting connective tissues (e.g. arthritis, trauma, tendonitis, chrondomalacia and inflammation), such as in the diagnosis or treatment of various autoimmune disorders such as rheumatoid arthritis, lupus, scleroderma, and dermatomyositis as well as dwarfism, spinal deformation, and specific joint abnormalities as well as chondrodysplasias (i.e. spondyloepiphyseal dysplasia-congenita, familial osteoarthritis, Atelosteogenesis type II, metaphyseal chondrodysplasia type Schmid). Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:131 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 724 of SEQ ID NO:131, b is an integer of 15 to 738, where both a and b correspond to the positions of nucleotide residues shown in SEQ ID NO:13 1, and where b is greater than or equal to a+14.

Features of Protein Encoded by Gene No: 122

In specific embodiments, polypeptides of the invention comprise the following amino acid sequence: NSARVTQKGESVGSVGCMRAIAGFDNYPLF (SEQ ID NO: 662), GTIGIFWPLPVAILSSGDYLQTQIIR-PLLHRGT (SEQ ID NO: 663), LPLPL SSLLHIATCNPF-PKT (SEQ ID NO: 664), SYFFVYNLILKIIQGDHASIIL-LATIP IFGDIYVKGQLASFGPYL (SEQ ID NO: 665), LFYHLEIISRHKSIAHCSIEA (SEQ ID NO: 666), CSCHCPSRAFST (SEQ ID NO: 667), and/or PHAIH-SQKPSS IFLITDVFPDPPVGIYLL (SEQ ID NO: 668). Polynucleotides encoding these polypeptides are also encompassed by the invention.

This gene is expressed primarily in chronic synovitis.

Therefore, polynucleotides and polypeptides of the invention are useful as reagents for differential identification of the tissue(s) or cell type(s) present in a biological sample and for diagnosis of diseases and conditions which include, but are not limited to, inflammatory diseases and disorders of the musculo-skeletal system. Similarly, polypeptides and antibodies directed to these polypeptides are useful in providing immunological probes for differential identification of the tissue(s) or cell type(s). For a number of disorders of the above tissues or cells, particularly of the inflammatory and musculo-skeletal system, expression of this gene at significantly higher or lower levels may be routinely detected in certain tissues or cell types (e.g., musculo-skeletal, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 271 as residues: Ser-39 to Pro-44.

The tissue distribution in chronic synovitis tissue indicates that polynucleotides and polypeptides corresponding to this gene are useful for the treatment and diagnosis of disorders and diseases of the inflammatory and musculo-skeletal system. In addition, the expression of this gene product in synovium indicates a role in the detection and treatment of disorders and conditions affecting the skeletal system, in particular osteoporosis as well as disorders afflicting connective tissues (e.g. arthritis, trauma, tendonitis, chrondomalacia and inflammation), such as in the diagnosis or treatment of various autoimmune disorders such as rheumatoid arthritis, lupus, scleroderma, and dermatomyositis as well as dwarfism, spinal deformation, and specific joint abnormalities as well as chondrodysplasias (i.e. spondyloepiphyseal dysplasia congenita, familial osteoarthritis, Atelosteogenesis type 11, metaphyseal chondrodysplasia type Schmid). Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:132 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 428 of SEQ ID NO:132, b is an integer of 15 to 442, where both a and b correspond to the positions of nucleotide residues shown in SEQ ID NO:132, and where b is greater than or equal to a+14.

Features of Protein Encoded by Gene No: 123

In specific embodiments, polypeptides of the invention comprise the following amino acid sequence: RKLFHKIN-SKSFHLSGMHILISVWIVRSRI-IKVKYELLLCFFDVIFYV (SEQ ID NO: 669), NSARD-VFFTQKILYSQTCIFFPCLVPFSFLFSFFFFLSFVG (SEQ ID NO: 670), MFSSLKKFYILKHVYSFPVLFHFLFF-FLFSFSFLSWAEKGAG KMKLATENCKMVKS (SEQ ID NO: 671), and/or IQLLYLKGAAMKYLSYVARLL FLKA-LDLFAPKMVQIDSF (SEQ ID NO: 672). Polynucleotides encoding these polypeptides are also encompassed by the invention.

This gene is expressed primarily in kidney and infant brain.

Therefore, polynucleotides and polypeptides of the invention are useful as reagents for differential identification of the tissue(s) or cell type(s) present in a biological sample and for diagnosis of diseases and conditions which include, but are not limited to, diseases of the renal and central nervous systems. Similarly, polypeptides and antibodies directed to these polypeptides are useful in providing immunological probes for differential identification of the tissue(s) or cell type(s). For a number of disorders of the above tissues or cells, particularly of the neural and renal system, expression of this gene at significantly higher or lower levels may be routinely detected in certain tissues or cell types (e.g., neural, renal, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 272 as residues: Gly-24 to Lys-31.

The tissue distribution in kidney and infant brain tissues indicates that polynucleotides and polypeptides corresponding to this gene are useful for the diagnosis and treatment of diseases of the neural and renal systems. The tissue distribution in infant brain indicates that polynucleotides and polypeptides corresponding to this gene are useful for the detection/treatment of neurodegenerative disease states and behavioural disorders such as Aliheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered bahaviors, including disorders in feeding, sleep patterns, balance, and perception. In addition, the gene or gene product may also play a role in the treatment and/or detection of developmental disorders associated with the developing embryo, or sexually-linked disorders.

The tissue distribution in kidney indicates that this gene or gene product is useful in the treatment and/or detection of kidney diseases including renal failure, nephritus, renal tubular acidosis, proteinuria, pyuria, edema, pyelonephritis, hydronephritis, nephrotic syndrome, crush syndrome, glomerulonephritis, hematuria, renal colic and kidney stones, in addition to Wilm's Tumor Disease, and congenital kidney abnormalities such as horseshoe kidney, polycystic kidney, and Falconi's syndrome. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:133 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 868 of SEQ ID NO:133, b is an integer of 15 to 882, where both a and b correspond to the positions of nucleotide residues shown in SEQ ID NO:133, and where b is greater than or equal to a+14.

TABLE 1

| Gene No. | cDNA Clone ID | ATCC ® Deposit Nr and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 1 | HCEIA77 | 209119 Jun. 12, 1997 | Uni-ZAP XR | 11 | 1882 | 676 | 1882 | 785 | 785 | 150 | 1 | 37 | 38 | 53 |
| 2 | HCFCE10 | 209119 Jun. 12, 1997 | pSport1 | 12 | 1590 | 18 | 1590 | 198 | 198 | 151 | 1 | 19 | 20 | 45 |
| 3 | HCFNC26 | 209119 Jun. 12, 1997 | pSport1 | 13 | 1373 | 6 | 1373 | 85 | 85 | 152 | 1 | 18 | 19 | 24 |
| 4 | HCHAA63 | 209119 Jun. 12, 1997 | pSport1 | 14 | 1142 | 1 | 1142 | 130 | 130 | 153 | 1 | 37 | 38 | 264 |
| 5 | HCNSP40 | 209119 Jun. 12, 1997 | pBluescript | 15 | 1034 | 1 | 1034 | 106 | 106 | 154 | 1 | 19 | 20 | 237 |
| 5 | HCNSP40 | 209119 Jun. 12, 1997 | pBluescript | 134 | 1032 | 1 | 1032 | | 111 | 273 | 1 | | | 14 |
| 6 | HDAAC10 | 209119 Jun. 12, 1997 | pSport1 | 16 | 1198 | 1 | 1198 | 117 | 117 | 155 | 1 | 21 | 22 | 313 |
| 7 | HE8CV18 | 209119 Jun. 12, 1997 | Uni-ZAP XR | 17 | 1447 | 1 | 1447 | 176 | 176 | 156 | 1 | 29 | 30 | 98 |
| 8 | HELDY05 | 209119 Jun. 12, 1997 | Uni-ZAP XR | 18 | 1422 | 1 | 1375 | 79 | 79 | 157 | 1 | 34 | 35 | 36 |
| 9 | HELDZ32 | 209119 Jun. 12, 1997 | Uni-ZAP XR | 19 | 1107 | 12 | 1107 | 148 | 148 | 158 | 1 | 15 | 16 | 22 |
| 10 | HFGAL10 | 209119 Jun. 12, 1997 | Uni-ZAP XR | 20 | 1183 | 1 | 1183 | 179 | 179 | 159 | 1 | 20 | 21 | 96 |
| 10 | HFGAL10 | 209119 Jun. 12, 1997 | Uni-ZAP XR | 135 | 1766 | 3 | 1765 | 179 | 179 | 274 | 1 | 17 | 18 | 36 |
| 11 | HFKEB72 | 209119 Jun. 12, 1997 | Uni-ZAP XR | 21 | 1420 | 1 | 1420 | 43 | 43 | 160 | 1 | 29 | 30 | 65 |
| 12 | HFTCU19 | 209119 Jun. 12, 1997 | Uni-ZAP XR | 22 | 1575 | 1266 | 1575 | 137 | 137 | 161 | 1 | 30 | 31 | 222 |
| 12 | HFTCU19 | 209119 Jun. 12, 1997 | Uni-ZAP XR | 136 | 470 | 1 | 470 | 157 | 157 | 275 | 1 | 24 | 25 | 56 |
| 13 | HFXHN31 | 209119 Jun. 12, 1997 | Lambda ZAP II | 23 | 541 | 1 | 541 | 172 | 172 | 162 | 1 | 30 | 31 | 91 |
| 13 | HFXHN31 | 209119 Jun. 12, 1997 | Lambda ZAP II | 137 | 1168 | 1 | 1168 | 293 | 293 | 276 | 1 | 22 | 23 | 26 |
| 14 | HGLAM53 | 209119 Jun. 12, 1997 | Uni-ZAP XR | 24 | 833 | 219 | 833 | 359 | 359 | 163 | 1 | 27 | 28 | 74 |
| 14 | HGLAM53 | 209119 Jun. 12, 1997 | Uni-ZAP XR | 138 | 1294 | 226 | 1288 | | 369 | 277 | 1 | 26 | 27 | 67 |
| 15 | HJABB94 | 209119 Jun. 12, 1997 | pBluescript SK- | 25 | 1555 | 1 | 1555 | 74 | 74 | 164 | 1 | 28 | 29 | 77 |
| 16 | HKIYO61 | 209119 Jun. 12, 1997 | pBluescript | 26 | 1543 | 1 | 1543 | 181 | 181 | 165 | 1 | 19 | 20 | 37 |
| 17 | HLTAI94 | 209119 Jun. 12, 1997 | Uni-ZAP XR | 27 | 1262 | 1 | 1262 | 47 | 47 | 166 | 1 | 18 | 19 | 44 |
| 18 | HMDAI51 | 209119 Jun. 12, 1997 | Uni-ZAP XR | 28 | 753 | 1 | 753 | 12 | 12 | 167 | 1 | 21 | 22 | 38 |
| 19 | HMELR03 | 209119 Jun. 12, 1997 | Lambda ZAP II | 29 | 1621 | 8 | 1535 | 200 | 200 | 168 | 1 | 25 | 26 | 173 |

TABLE 1-continued

| Gene No. | cDNA Clone ID | ATCC ® Deposit Nr and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 20 | HMKAH10 | 209119 Jun. 12, 1997 | pSport1 | 30 | 921 | 1 | 921 | 48 | 48 | 169 | 1 | 43 | 44 | 54 |
| 21 | HMKCW19 | 209119 Jun. 12, 1997 | pSport1 | 31 | 2095 | 473 | 1934 | 529 | 529 | 170 | 1 | 30 | 31 | 344 |
| 21 | HMKCW19 | 209119 Jun. 12, 1997 | pSport1 | 139 | 1720 | 103 | 1692 | 188 | 188 | 278 | 1 | 27 | 28 | 45 |
| 22 | HMSJW18 | 209119 Jun. 12, 1997 | Uni-ZAP XR | 32 | 1838 | 1 | 1838 | 28 | 28 | 171 | 1 | 23 | 24 | 89 |
| 23 | HMWGY01 | 209119 Jun. 12, 1997 | Uni-Zap XR | 33 | 782 | 1 | 782 | 423 | 423 | 172 | 1 | 30 | 31 | 104 |
| 23 | HMWGY01 | 209119 Jun. 12, 1997 | Uni-Zap XR | 140 | 774 | 1 | 774 | 17 | 17 | 279 | 1 | 31 | 32 | 39 |
| 24 | HNFID82 | 209119 Jun. 12, 1997 | pBluescript | 34 | 1560 | 1 | 1560 | 161 | 161 | 173 | 1 | 17 | 18 | 41 |
| 25 | HNFIG36 | 209119 Jun. 12, 1997 | pBluescript | 35 | 1092 | 1 | 1082 | 171 | 171 | 174 | 1 | 18 | 19 | 46 |
| 26 | HNGEV29 | 209119 Jun. 12, 1997 | Uni-ZAP XR | 36 | 1153 | 1 | 1153 | 173 | 173 | 175 | 1 | 30 | 31 | 73 |
| 26 | HNGEV29 | 209119 Jun. 12, 1997 | Uni-ZAP XR | 141 | 1566 | 1 | 1566 | 79 | 79 | 280 | 1 | | | 10 |
| 27 | HNGIK21 | 209119 Jun. 12, 1997 | Uni-ZAP XR | 37 | 985 | 1 | 985 | 152 | 152 | 176 | 1 | 25 | 26 | 28 |
| 28 | HNGJJ65 | 209124 Jun. 19, 1997 | Uni-ZAP XR | 38 | 1122 | 1 | 1122 | 84 | 84 | 177 | 1 | 22 | 23 | 67 |
| 29 | HNGJU42 | 209124 Jun. 19, 1997 | Uni-ZAP XR | 39 | 598 | 6 | 598 | 273 | 273 | 178 | 1 | 17 | 18 | 23 |
| 30 | HODAZ26 | 209124 Jun. 19, 1997 | Uni-ZAP XR | 40 | 1129 | 8 | 1129 | 133 | 133 | 179 | 1 | | | 30 |
| 31 | HODDB05 | 209124 Jun. 19, 1997 | Uni-ZAP XR | 41 | 1158 | 22 | 1158 | 244 | 244 | 180 | 1 | | | 10 |
| 32 | HOFAF39 | 209124 Jun. 19, 1997 | pSport1 | 42 | 1767 | 1 | 1767 | 57 | 57 | 181 | 1 | 22 | 23 | 31 |
| 33 | HOFNY71 | 209124 Jun. 19, 1997 | pCMVSport 2.0 | 43 | 917 | 1 | 917 | 114 | 114 | 182 | 1 | 31 | 32 | 35 |
| 34 | HORBI81 | 209124 Jun. 19, 1997 | Uni-ZAP XR | 44 | 1987 | 8 | 1965 | 31 | 31 | 183 | 1 | 34 | 35 | 34 |
| 35 | HOSCY73 | 209124 Jun. 19, 1997 | Uni-ZAP XR | 45 | 2053 | 196 | 2048 | 209 | 209 | 184 | 1 | | | 28 |
| 36 | HPMBR15 | 209124 Jun. 19, 1997 | Uni-ZAP XR | 46 | 1272 | 25 | 1272 | 262 | 262 | 185 | 1 | | | 5 |
| 37 | HSAVD46 | 209124 Jun. 19, 1997 | Uni-ZAP XR | 47 | 773 | 2 | 767 | 155 | 155 | 186 | 1 | 20 | 21 | 58 |
| 38 | HSLBF69 | 209124 Jun. 19, 1997 | Uni-ZAP XR | 48 | 2119 | 1 | 2119 | 107 | 107 | 187 | 1 | 19 | 20 | 405 |
| 39 | HSOAH66 | 209124 Jun. 19, 1997 | Uni-ZAP XR | 49 | 1188 | 7 | 1188 | 196 | 196 | 188 | 1 | 27 | 28 | 36 |
| 39 | HSOAH66 | 209124 Jun. 19, 1997 | Uni-ZAP XR | 143 | 537 | 1 | 537 | 136 | 136 | 282 | 1 | 21 | 22 | 47 |
| 40 | HSVBH58 | 209124 Jun. 19, 1997 | Uni-ZAP XR | 50 | 478 | 24 | 155 | 249 | 249 | 189 | 1 | 40 | 41 | 57 |
| 40 | HSVBH58 | 209124 Jun. 19, 1997 | Uni-ZAP XR | 144 | 680 | 1 | 680 | 168 | 168 | 283 | 1 | 20 | 21 | 22 |
| 41 | HSZAF47 | 209124 Jun. 19, 1997 | Uni-ZAP XR | 51 | 1333 | 2 | 1333 | 107 | 107 | 190 | 1 | 18 | 19 | 126 |
| 42 | HTADV27 | 209124 Jun. 19, 1997 | Uni-ZAP XR | 52 | 1255 | 14 | 1255 | 69 | 69 | 191 | 1 | 20 | 21 | 20 |
| 43 | HTADX17 | 209124 Jun. 19, 1997 | Uni-ZAP XR | 53 | 1140 | 22 | 1140 | 84 | 84 | 192 | 1 | 24 | 25 | 142 |
| 44 | HTDAD22 | 209124 Jun. 19, 1997 | pSport1 | 54 | 1220 | 1 | 1220 | 193 | 193 | 193 | 1 | 37 | 38 | 109 |
| 45 | HTEDS39 | 209124 Jun. 19, 1997 | Uni-ZAP XR | 55 | 694 | 198 | 694 | 205 | 205 | 194 | 1 | 21 | 22 | 80 |
| 45 | HTEDS39 | 209124 Jun. 19, 1997 | Uni-ZAP XR | 145 | 1048 | 1 | 1048 | | 227 | 284 | 1 | | | 20 |
| 46 | HTEHH53 | 209124 Jun. 19, 1997 | Uni-ZAP XR | 56 | 988 | 1 | 980 | 22 | 22 | 195 | 1 | 24 | 25 | 209 |
| 47 | HTLDP69 | 209124 Jun. 19, 1997 | Uni-ZAP XR | 57 | 1500 | 237 | 1500 | 330 | 330 | 196 | 1 | 29 | 30 | 148 |
| 48 | HTNBR95 | 209124 Jun. 19, 1997 | pBluescript SK- | 58 | 1391 | 1 | 1386 | 70 | 70 | 197 | 1 | 28 | 29 | 35 |
| 49 | HTPCS60 | 209124 Jun. 19, 1997 | Uni-ZAP XR | 59 | 1579 | 7 | 1259 | 105 | 105 | 198 | 1 | 19 | 20 | 257 |

TABLE 1-continued

| Gene No. | cDNA Clone ID | ATCC ® Deposit Nr and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 50 | HUKBH05 | 209124 Jun. 19, 1997 | Lambda ZAP II | 60 | 1241 | 1 | 1215 | 151 | 151 | 199 | 1 | 18 | 19 | 58 |
| 51 | HUKEX85 | 209124 Jun. 19, 1997 | Lambda ZAP II | 61 | 930 | 7 | 925 | 35 | 35 | 200 | 1 | 18 | 19 | 33 |
| 51 | HUKEX85 | 209124 Jun. 19, 1997 | Lambda ZAP II | 146 | 930 | 6 | 917 | 83 | 83 | 285 | 1 | 30 | 31 | 122 |
| 52 | HWTBM45 | 209124 Jun. 19, 1997 | Uni-ZAP XR | 62 | 998 | 1 | 998 | 69 | 69 | 201 | 1 | 19 | 20 | 25 |
| 53 | HADFF38 | 209124 Jun. 19, 1997 | pSport1 | 63 | 1193 | 1 | 1034 | 64 | 64 | 202 | 1 | 19 | 20 | 33 |
| 54 | HADFK68 | 209124 Jun. 19, 1997 | pSport1 | 64 | 830 | 1 | 830 | 91 | 91 | 203 | 1 | 24 | 25 | 58 |
| 54 | HADFK68 | 209124 Jun. 19, 1997 | pSport1 | 147 | 830 | 1 | 830 | 45 | 45 | 286 | 1 | 26 | 27 | 26 |
| 55 | HADGG19 | 209125 Jun. 19, 1997 | pSport1 | 65 | 867 | 1 | 867 | 262 | 262 | 204 | 1 | 30 | 31 | 75 |
| 55 | HADGG19 | 209125 Jun. 19, 1997 | pSport1 | 148 | 865 | 1 | 865 | 281 | 281 | 287 | 1 | | | 7 |
| 56 | HAEAV45 | 209125 Jun. 19, 1997 | pBluescript SK- | 66 | 685 | 46 | 647 | 487 | 487 | 205 | 1 | 34 | 35 | 66 |
| 56 | HAEAV45 | 209125 Jun. 19, 1997 | pBluescript SK- | 149 | 545 | 1 | 545 | 24 | 24 | 288 | 1 | 25 | 26 | 28 |
| 57 | HARAA15 | 209125 Jun. 19, 1997 | pBluescript SK- | 67 | 801 | 1 | 801 | 185 | 185 | 206 | 1 | 34 | 35 | 43 |
| 58 | HATDL27 | 209125 Jun. 19, 1997 | Uni-ZAP XR | 68 | 908 | 1 | 908 | 82 | 82 | 207 | 1 | 28 | 29 | 31 |
| 59 | HBAFQ54 | 209125 Jun. 19, 1997 | pSport1 | 69 | 696 | 209 | 696 | 229 | 229 | 208 | 1 | 20 | 21 | 47 |
| 60 | HBGBA14 | 209125 Jun. 19, 1997 | Uni-ZAP XR | 70 | 455 | 1 | 452 | 32 | 32 | 209 | 1 | 24 | 25 | 36 |
| 61 | HBIAS26 | 209125 Jun. 19, 1997 | Uni-ZAP XR | 71 | 413 | 1 | 372 | 57 | 57 | 210 | 1 | 27 | 28 | 73 |
| 62 | HBJFU48 | 209125 Jun. 19, 1997 | Uni-ZAP XR | 72 | 849 | 1 | 849 | 20 | 20 | 211 | 1 | 39 | 40 | 40 |
| 63 | HBJFV28 | 209125 Jun. 19, 1997 | Uni-ZAP XR | 73 | 505 | 1 | 505 | 306 | 306 | 212 | 1 | 21 | 22 | 53 |
| 64 | HBMWB01 | 209125 Jun. 19, 1997 | Uni-ZAP XR | 74 | 719 | 1 | 719 | 48 | 48 | 213 | 1 | 17 | 18 | 62 |
| 65 | HBMXN79 | 209125 Jun. 19, 1997 | Uni-ZAP XR | 75 | 1274 | 141 | 974 | 192 | 192 | 214 | 1 | 44 | 45 | 175 |
| 66 | HBMXP84 | 209125 Jun. 19, 1997 | Uni-ZAP XR | 76 | 519 | 1 | 519 | 161 | 161 | 215 | 1 | 31 | 32 | 39 |
| 67 | HCFMM26 | 209125 Jun. 19, 1997 | pSport1 | 77 | 389 | 1 | 389 | 178 | 178 | 216 | 1 | 27 | 28 | 54 |
| 68 | HCNAV36 | 209125 Jun. 19, 1997 | Lambda ZAP II | 78 | 823 | 411 | 823 | 505 | 505 | 217 | 1 | 15 | 16 | 46 |
| 69 | HCNSB01 | 209125 Jun. 19, 1997 | pBluescript | 79 | 2455 | 533 | 1308 | 552 | 552 | 218 | 1 | 22 | 23 | 179 |
| 70 | HCRBR74 | 209125 Jun. 19, 1997 | Uni-ZAP XR | 80 | 921 | 365 | 911 | 415 | 415 | 219 | 1 | 20 | 21 | 98 |
| 71 | HCUBN59 | 209125 Jun. 19, 1997 | ZAP Express | 81 | 678 | 1 | 678 | 96 | 96 | 220 | 1 | 39 | 40 | 43 |
| 72 | HCUDB38 | 209125 Jun. 19, 1997 | ZAP Express | 82 | 857 | 1 | 857 | 221 | 221 | 221 | 1 | 17 | 18 | 41 |
| 73 | HCUFZ62 | 209125 Jun. 19, 1997 | ZAP Express | 83 | 1977 | 28 | 661 | 233 | 233 | 222 | 1 | 28 | 29 | 51 |
| 74 | HDHMB42 | 209125 Jun. 19, 1997 | pCMVSport 2.0 | 84 | 1149 | 427 | 1149 | 592 | 592 | 223 | 1 | 26 | 27 | 31 |
| 75 | HDPCO25 | 209125 Jun. 19, 1997 | pCMVSport 3.0 | 85 | 767 | 76 | 767 | 182 | 182 | 224 | 1 | 20 | 21 | 53 |
| 76 | HDPHI51 | 209125 Jun. 19, 1997 | pCMVSport 3.0 | 86 | 728 | 1 | 728 | 245 | 245 | 225 | 1 | 30 | 31 | 40 |
| 77 | HE2EC79 | 209125 Jun. 19, 1997 | Uni-ZAP XR | 87 | 735 | 1 | 735 | 151 | 151 | 226 | 1 | 21 | 22 | 30 |
| 78 | HE9FE83 | 209125 Jun. 19, 1997 | Uni-ZAP XR | 88 | 889 | 332 | 889 | 351 | 351 | 227 | 1 | 21 | 22 | 59 |
| 79 | HE9HW52 | 209125 Jun. 19, 1997 | Uni-ZAP XR | 89 | 569 | 73 | 569 | 122 | 122 | 228 | 1 | 25 | 26 | 34 |
| 80 | HEBFL88 | 209125 Jun. 19, 1997 | Uni-ZAP XR | 90 | 334 | 2 | 334 | 76 | 76 | 229 | 1 | 22 | 23 | 38 |
| 81 | HFIVB57 | 209125 Jun. 19, 1997 | pSport1 | 91 | 795 | 92 | 795 | 286 | 286 | 230 | 1 | 35 | 36 | 38 |

TABLE 1-continued

| Gene No. | cDNA Clone ID | ATCC ® Deposit Nr and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 82 | HFPDE69 | 209125 Jun. 19, 1997 | Uni-ZAP XR | 92 | 577 | 1 | 577 | 72 | 72 | 231 | 1 | 33 | 34 | 61 |
| 83 | HGBGV89 | 209125 Jun. 19, 1997 | Uni-ZAP XR | 93 | 968 | 1 | 968 | 55 | 55 | 232 | 1 | 26 | 27 | 197 |
| 84 | HGLDE38 | 209125 Jun. 19, 1997 | Uni-ZAP XR | 94 | 553 | 1 | 553 | 31 | 31 | 233 | 1 | 19 | 20 | 61 |
| 85 | HHGDU58 | 209125 Jun. 19, 1997 | Lambda ZAP II | 95 | 968 | 70 | 898 | 235 | 235 | 234 | 1 | 46 | 47 | 80 |
| 86 | HHTLF25 | 209125 Jun. 19, 1997 | ZAP Express | 96 | 697 | 1 | 661 | 142 | 142 | 235 | 1 | 26 | 27 | 111 |
| 87 | HJMAV91 | 209125 Jun. 19, 1997 | pCMVSport 3.0 | 97 | 866 | 74 | 866 | 251 | 251 | 236 | 1 | 16 | 17 | 32 |
| 88 | HKAFB88 | 209125 Jun. 19, 1997 | pCMVSport 2.0 | 98 | 1368 | 219 | 795 | 238 | 238 | 237 | 1 | 45 | 46 | 228 |
| 89 | HLHFP03 | 209126 Jun. 19, 1997 | Uni-ZAP XR | 99 | 613 | 1 | 613 | 224 | 224 | 238 | 1 | 20 | 21 | 116 |
| 90 | HLNAB07 | 209126 Jun. 19, 1997 | Lambda ZAP II | 100 | 685 | 1 | 685 | 187 | 187 | 239 | 1 | 32 | 33 | 36 |
| 91 | HLWCF05 | 209126 Jun. 19, 1997 | pCMVSport 3.0 | 101 | 646 | 1 | 646 | 155 | 155 | 240 | 1 | 36 | 37 | 58 |
| 92 | HLYAF80 | 209126 Jun. 19, 1997 | pSport1 | 102 | 826 | 1 | 826 | 222 | 222 | 241 | 1 | 24 | 25 | 47 |
| 93 | HMDAA66 | 209126 Jun. 19, 1997 | Uni-ZAP XR | 103 | 586 | 1 | 586 | 106 | 106 | 242 | 1 | 23 | 24 | 31 |
| 94 | HMKDD07 | 209126 Jun. 19, 1997 | pSport1 | 104 | 628 | 43 | 628 | 267 | 267 | 243 | 1 | 29 | 30 | 63 |
| 95 | HMKDS08 | 209126 Jun. 19, 1997 | pSport1 | 105 | 558 | 1 | 558 | 230 | 230 | 244 | 1 | 30 | 31 | 67 |
| 96 | HMSHM14 | 209126 Jun. 19, 1997 | Uni-ZAP XR | 106 | 756 | 1 | 756 | 103 | 103 | 245 | 1 | 29 | 30 | 45 |
| 97 | HMWDC28 | 209126 Jun. 19, 1997 | Uni-Zap XR | 107 | 1146 | 105 | 754 | 124 | 124 | 246 | 1 | 30 | 31 | 42 |
| 98 | HNDAH54 | 209126 Jun. 19, 1997 | pCMVSport 2.0 | 108 | 775 | 1 | 775 | 26 | 26 | 247 | 1 | 20 | 21 | 31 |
| 99 | HNFDS53 | 209126 Jun. 19, 1997 | Uni-ZAP XR | 109 | 911 | 1 | 911 | 200 | 200 | 248 | 1 | 22 | 23 | 23 |
| 100 | HNFIU96 | 209126 Jun. 19, 1997 | pBluescript | 110 | 456 | 1 | 456 | 170 | 170 | 249 | 1 | 33 | 34 | 79 |
| 101 | HNGAC63 | 209126 Jun. 19, 1997 | Uni-ZAP XR | 111 | 554 | 1 | 554 | 214 | 214 | 250 | 1 | | | 15 |
| 102 | HNGAX58 | 209126 Jun. 19, 1997 | Uni-ZAP XR | 112 | 722 | 1 | 722 | 100 | 100 | 251 | 1 | 16 | 17 | 46 |
| 103 | HNGEM24 | 209126 Jun. 19, 1997 | Uni-ZAP XR | 113 | 931 | 1 | 931 | 239 | 239 | 252 | 1 | 30 | 31 | 31 |
| 104 | HNGFT78 | 209126 Jun. 19, 1997 | Uni-ZAP XR | 114 | 588 | 1 | 588 | 20 | 20 | 253 | 1 | 29 | 30 | 35 |
| 105 | HNHDL85 | 209126 Jun. 19, 1997 | Uni-ZAP XR | 115 | 812 | 1 | 812 | 194 | 194 | 254 | 1 | 22 | 23 | 50 |
| 106 | HNHFU59 | 209126 Jun. 19, 1997 | Uni-ZAP XR | 116 | 506 | 1 | 506 | 278 | 278 | 255 | 1 | 16 | 17 | 76 |
| 107 | HNHFW22 | 209126 Jun. 19, 1997 | Uni-ZAP XR | 117 | 751 | 1 | 751 | 228 | 228 | 256 | 1 | 26 | 27 | 60 |
| 108 | HOAAF80 | 209126 Jun. 19, 1997 | Uni-ZAP XR | 118 | 960 | 131 | 960 | 303 | 303 | 257 | 1 | 33 | 34 | 36 |
| 109 | HODCJ90 | 209126 Jun. 19, 1997 | Uni-ZAP XR | 119 | 1442 | 326 | 1133 | 344 | 344 | 258 | 1 | 18 | 19 | 42 |
| 110 | HOECO90 | 209126 Jun. 19, 1997 | Uni-ZAP XR | 120 | 845 | 215 | 845 | 299 | 299 | 259 | 1 | 24 | 25 | 38 |
| 111 | HPEBT80 | 209126 Jun. 19, 1997 | Uni-ZAP XR | 121 | 360 | 1 | 360 | 21 | 21 | 260 | 1 | 40 | 41 | 50 |
| 112 | HSDAG05 | 209126 Jun. 19, 1997 | Uni-ZAP XR | 122 | 944 | 231 | 848 | 419 | 419 | 261 | 1 | 37 | 38 | 75 |
| 113 | HSDGR57 | 209126 Jun. 19, 1997 | Uni-ZAP XR | 123 | 914 | 115 | 914 | 195 | 195 | 262 | 1 | 21 | 22 | 44 |
| 114 | HSDJJ82 | 209126 Jun. 19, 1997 | Uni-ZAP XR | 124 | 462 | 1 | 462 | 79 | 79 | 263 | 1 | 32 | 33 | 52 |
| 115 | HSDZM95 | 209126 Jun. 19, 1997 | pBluescript | 125 | 545 | 1 | 545 | 223 | 223 | 264 | 1 | 23 | 24 | 42 |
| 116 | HSIDI15 | 209126 Jun. 19, 1997 | Uni-ZAP XR | 126 | 912 | 1 | 873 | 273 | 273 | 265 | 1 | 22 | 23 | 74 |
| 117 | HSKYU29 | 209126 Jun. 19, 1997 | pBluescript | 127 | 1048 | 1 | 1047 | 290 | 290 | 266 | 1 | 36 | 37 | 51 |

TABLE 1-continued

| Gene No. | cDNA Clone ID | ATCC ® Deposit Nr and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 118 | HSNAA55 | 209126 Jun. 19, 1997 | Uni-ZAP XR | 128 | 722 | 1 | 722 | 35 | 35 | 267 | 1 | 15 | 16 | 40 |
| 119 | HSQFP66 | 209126 Jun. 19, 1997 | Uni-ZAP XR | 129 | 477 | 1 | 477 | 96 | 96 | 268 | 1 | 32 | 33 | 78 |
| 120 | HSRDE35 | 209126 Jun. 19, 1997 | Uni-ZAP XR | 130 | 1296 | 232 | 804 | 428 | 428 | 269 | 1 | 21 | 22 | 116 |
| 121 | HSSJN64 | 209126 Jun. 19, 1997 | Uni-ZAP XR | 131 | 738 | 1 | 738 | 70 | 70 | 270 | 1 | 33 | 34 | 61 |
| 122 | HSVAQ28 | 209126 Jun. 19, 1997 | Uni-ZAP XR | 132 | 442 | 1 | 442 | 149 | 149 | 271 | 1 | 24 | 25 | 98 |
| 123 | HSVAY16 | 209126 Jun. 19, 1997 | Uni-ZAP XR | 133 | 882 | 1 | 790 | 52 | 52 | 272 | 1 | 30 | 31 | 31 |

Table 1 summarizes the information corresponding to each "Gene No." described above. The nucleotide sequence identified as "NT SEQ ID NO:X" was assembled from partially homologous ("overlapping") sequences obtained from the "cDNA clone ID" identified in Table 1 and, in some cases, from additional related DNA clones. The overlapping sequences were assembled into a single contiguous sequence of high redundancy (usually three to five overlapping sequences at each nucleotide position), resulting in a final sequence identified as SEQ ID NO:X.

The cDNA Clone ID was deposited on the date and given the corresponding deposit number listed in "ATCC® Deposit No:Z and Date." Some of the deposits contain multiple different clones corresponding to the same gene. "Vector" refers to the type of vector contained in the cDNA Clone ID.

"Total NT Seq." refers to the total number of nucleotides in the contig identified by "Gene No." The deposited clone may contain all or most of these sequences, reflected by the nucleotide position indicated as "5' NT of Clone Seq." and the "3' NT of Clone Seq." of SEQ ID NO:X. The nucleotide position of SEQ ID NO:X of the putative start codon (methionine) is identified as "5' NT of Start Codon." Similarly, the nucleotide position of SEQ ID NO:X of the predicted signal sequence is identified as "5' NT of First AA of Signal Pep."

The translated amino acid sequence, beginning with the methionine, is identified as "AA SEQ ID NO:Y," although other reading frames can also be easily translated using known molecular biology techniques. The polypeptides produced by these alternative open reading frames are specifically contemplated by the present invention.

The first and last amino acid position of SEQ ID NO:Y of the predicted signal peptide is identified as "First AA of Sig Pep" and "Last AA of Sig Pep." The predicted first amino acid position of SEQ ID NO:Y of the secreted portion is identified as "Predicted First AA of Secreted Portion." Finally, the amino acid position of SEQ ID NO:Y of the last amino acid in the open reading frame is identified as "Last AA of ORF."

SEQ ID NO:X and the translated SEQ ID NO:Y are sufficiently accurate and otherwise suitable for a variety of uses well known in the art and described further below. For instance, SEQ ID NO:X is useful for designing nucleic acid hybridization probes that will detect nucleic acid sequences contained in SEQ ID NO:X or the cDNA contained in the deposited clone. These probes will also hybridize to nucleic acid molecules in biological samples, thereby enabling a variety of forensic and diagnostic methods of the invention. Similarly, polypeptides identified from SEQ ID NO:Y may be used to generate antibodies which bind specifically to the secreted proteins encoded by the cDNA clones identified in Table 1.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring-precision in the nucleotide sequence or the amino acid sequence, the present invention provides not only the generated nucleotide sequence identified as SEQ ID NO:X and the predicted translated amino acid sequence identified as SEQ ID NO:Y, but also a sample of plasmid DNA containing a human cDNA of the invention deposited with the ATCC®, as set forth in Table 1. The nucleotide sequence of each deposited clone can readily be determined by sequencing the deposited clone in accordance with known methods. The predicted amino acid sequence can then be verified from such deposits. Moreover, the amino acid sequence of the protein encoded by a particular clone can also be directly determined by peptide sequencing or by expressing the protein in a suitable host cell containing the deposited human cDNA, collecting the protein, and determining its sequence.

The present invention also relates to the genes corresponding to SEQ ID NO:X, SEQ ID NO:Y, or the deposited clone. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are species homologs. Species homologs may be isolated and identified by making suitable probes or primers from the sequences provided herein and screening a suitable nucleic acid source for the desired homologue.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the secreted protein, including the mature form, or may be a part of a larger protein, such as a fusion protein (see below). It is often advantageous to include an additional amino acid sequence which contains secretory or leader sequences, prosequences, sequences which aid in purification, such as multiple histidine residues, or an additional sequence for stability during recombinant production.

The polypeptides of the present invention are preferably provided in an isolated form, and preferably are substantially purified. A recombinantly produced version of a polypeptide, including the secreted polypeptide, can be substantially purified by the one-step method described in Smith and Johnson, Gene 67:31–40 (1988). Polypeptides of the invention also can be purified from natural or recombinant sources using antibodies of the invention raised against the secreted protein in methods which are well known in the art.

Signal Sequences

Methods for predicting whether a protein has a signal sequence, as well as the cleavage point for that sequence, are available. For instance, the method of McGeoch, Virus Res. 3:271–286 (1985), uses the information from a short N-terminal charged region and a subsequent uncharged region of the complete (uncleaved) protein. The method of von Heinje, Nucleic Acids Res. 14:4683–4690 (1986) uses the information from the residues surrounding the cleavage site, typically residues −13 to +2, where +1 indicates the amino terminus of the secreted protein. The accuracy of predicting the cleavage points of known mammalian secretory proteins for each of these methods is in the range of 75–80%. (von Heinje, supra.) However, the two methods do not always produce the same predicted cleavage point(s) for a given protein.

In the present case, the deduced amino acid sequence of the secreted polypeptide was analyzed by a computer program called SignalP (Henrik Nielsen et al., Protein Engineering 10:1–6 (1997)), which predicts the cellular location of a protein based on the amino acid sequence. As part of this computational prediction of localization, the methods of McGeoch and von Heinje are incorporated. The analysis of the amino acid sequences of the secreted proteins described herein by this program provided the results shown in Table 1.

As one of ordinary skill would appreciate, however, cleavage sites sometimes vary from organism to organism and cannot be predicted with absolute certainty. Accordingly, the present invention provides secreted polypeptides having a sequence shown in SEQ ID NO:Y which have an N-terminus beginning within 5 residues (i.e., + or −5 residues) of the predicted cleavage point. Similarly, it is also recognized that in some cases, cleavage of the signal sequence from a secreted protein is not entirely uniform, resulting in more than one secreted species. These polypeptides, and the polynucleotides encoding such polypeptides, are contemplated by the present invention.

Moreover, the signal sequence identified by the above analysis may not necessarily predict the naturally occurring signal sequence. For example, the naturally occurring signal sequence may be further upstream from the predicted signal sequence. However, it is likely that the predicted signal sequence will be capable of directing the secreted protein to the ER. These polypeptides, and the polynucleotides encoding such polypeptides, are contemplated by the present invention.

Polynucleotide and Polypeptide Variants

"Variant" refers to a polynucleotide or polypeptide differing from the polynucleotide or polypeptide of the present invention, but retaining essential properties thereof Generally, variants are overall closely similar, and, in many regions, identical to the polynucleotide or polypeptide of the present invention.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown in Table 1, the ORF (open reading frame), or any fragement specified as described herein.

As a practical matter, whether any particular nucleic acid molecule or polypeptide is at least 90%, 95%, 96%, 97%, 98% or 99% identical to a nucleotide sequence of the presence invention can be determined conventionally using known computer programs. A preferred method for determing the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence arid therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequences shown in Table 1 or to the amino acid sequence encoded by deposited DNA clone can be determined conventionally using known computer programs. A preferred method for determing the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. Polynucleotide variants can be produced for a variety of reasons, e.g., to optimize codon expression for a particular host (change codons in the human mRNA to those preferred by a bacterial host such as *E. coli*).

Naturally occurring variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level. Alternatively, non-naturally occurring variants maybe produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the secreted protein without substantial loss of biological function. The authors of Ron et al., J. Biol. Chem. 268: 2984–2988 (1993), reported variant KGF proteins having heparin binding activity even after deleting 3, 8, or 27 amino-terminal amino acid residues. Similarly, Interferon gamma exhibited up to ten times higher activity after deleting 8–10 amino acid residues from the carboxy terminus of this protein. (Dobeli et al., J. Biotechnology 7:199–216 (1988).)

Moreover, ample evidence demonstrates that variants often retain a biological activity similar to that of the naturally occurring protein. For example, Gayle and coworkers (J. Biol. Chem 268:22105–22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See, Abstract.) In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the secreted form will likely be retained when less than the-majority of the residues of the secreted form are removed from the N-terminus or C-terminus. Whether a particular polypeptide lacking N- or C-terminal residues of a protein retains such immunogenic activities can readily be determined by routine methods described herein and otherwise known in the art.

Thus, the invention further includes polypeptide variants which show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie, J. U. et al., Science 247:1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gin, replacement of the basic residues Lys, Arg, and His; replacement of the aromatic residues Phe, Tyr, and Tip, and replacement of the small-sized amino acids Ala, Ser, Thr, Met, and Gly.

Besides conservative amino acid substitution, variants of the pre sent invention include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).)

Polynucleotide and Polypeptide Fragments

In the present invent ion, a "polynucleotide fragment" refers to a short polynucleotide having a nucleic acid sequence contained in the deposited clone or shown in SEQ ID NO:X. The short nucleotide fragments are preferably at least about 15 nt, and more preferably at least about 20 nt, still more preferably at least about 30 nt, and even more preferably, at least about 40 nt in length. A fragment "at least 20 nt in length," for example, is intended to include 20 or more contiguous bases from the cDNA sequence contained in the deposited clone or the nucleotide sequence shown in SEQ ID NO:X. These nucleotide fragments are useful as diagnostic probes and primers as discussed herein. Of course, larger fragments (e.g., 50, 150, 500, 600, 2000 nucleotides) are preferred.

Moreover, representative examples of polynucleotide fragments of the invention, include, for example, fragments having a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, 951–1000, 1001–1050, 1051–1100, 1101–1150, 1151–1200, 1201–1250, 1251–1300, 1301–1350, 1351–1400, 1401–1450, 1451–1500, 1501–1550, 1551–1600, 1601–1650, 1651–1700, 1701–1750, 1751–1800, 1801–1850, 1851–1900, 1901–1950, 1951–2000, or 2001 to the end of SEQ ID NO:X or the cDNA contained in the deposited clone. In this context "about" includes the particularly recited ranges, larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein.

In the present invention, a "polypeptide fragment" refers to a short amino acid sequence contained in SEQ ID NO:Y or encoded by the cDNA contained in the deposited clone. Protein fragments may be "free-standing," or comprised within a larger polypeptide of which the fragment forms a part or region, most preferably as a single continuous region. Representative examples of polypeptide fragments of the invention, include, for example, fragments from about amino acid number 1–20, 21–40, 41–60, 61–80, 81–100, 102–120, 121–140, 141–160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges, larger or smaller by several (5, 4, 3, 2, or 1) amino acids, at either extreme or at both extremes.

Preferred polypeptide fragments include the secreted protein as well as the mature form. Further preferred polypeptide fragments include the secreted protein or the mature form having a continuous series of deleted residues from the amino or the carboxy terminus, or both. For example, any number of amino acids, ranging from 1–60, can be deleted from the amino terminus of either the secreted polypeptide or the mature form. Similarly, any number of amino acids, ranging from 1–30, can be deleted from the carboxy terminus of the secreted protein or mature form. Furthermore, any combination of the above amino and carboxy terminus deletions are preferred. Similarly, polynucleotide fragments encoding these polypeptide fragments are also preferred.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:Y falling within conserved domains are specifically contemplated by the present invention. Moreover, polynucleotide fragments encoding these domains are also contemplated.

Other preferred fragments are biologically active fragments. Biologically active fragments are those exhibiting activity similar, but not necessarily identical, to an activity of the polypeptide of the present invention. The biological activity of the fragments may include an improved desired activity, or a decreased undesirable activity.

Epitopes & Antibodies

In the present invention, "epitopes" refer to polypeptide fragments having antigenic or immunogenic activity in an animal, especially in a human. A preferred embodiment of the present invention relates to a polypeptide fragment comprising an epitope, as well as the polynucleotide encoding this fragment. A region of a protein molecule to which an antibody can bind is defined as an "antigenic epitope." In contrast, an "immunogenic epitope" is defined as a part of a protein that elicits an antibody response. (See, for instance, Geysen et al., Proc. Natl. Acad. Sci. USA 81:3998–4002 (1983).)

Fragments which function as epitopes may be produced by any conventional means. (See, e.g., Houghten, R. A., Proc. Natl. Acad. Sci. USA 82:5131–5135 (1985) further described in U.S. Pat. No. 4,631,211.)

In the present invention, antigenic epitopes preferably contain a sequence of at least seven, more preferably at least nine, and most preferably between about 15 to about 30 amino acids. Antigenic epitopes are useful to raise antibodies, including monoclonal antibodies, that specifically bind the epitope. (See, for instance,-Wilson et al., Cell 37:767–778 (1984); Sutcliffe, J. G. et al., Science 219:660–666 (1983).)

Similarly, immunogenic epitopes can be used to induce antibodies according to methods well known in the art. (See, for instance, Sutcliffe et al., supra; Wilson et al., supra; Chow, M. et al., Proc. Natl. Acad. Sci. USA 82:910–914; and Bittle, F. J. et al., J. Gen. Virol. 66:2347–2354 (1985).) A preferred immunogenic epitope includes the secreted protein. The immunogenic epitopes may be presented together with a carrier protein, such as an albumin, to an animal system (such as rabbit or mouse) or, if it is long enough (at least about 25 amino acids), without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting.)

As used herein, the term "antibody" (Ab) or "monoclonal antibody" (Mab) is meant to include intact molecules as well as antibody fragments (such as, for example, Fab and F(ab')2 fragments) which are capable of specifically binding to protein. Fab and F(ab')2 fragments lack the Fc fragment of intact antibody, clear more rapidly from the circulation, and may have less non-specific tissue binding than an intact antibody. (Wahl et al., J. Nucl. Med. 24:316–325 (1983).) Thus, these fragments are preferred, as well as the products of a FAB or other immunoglobulin expression library. Moreover, antibodies of the present invention include chimeric, single chain, and humanized antibodies.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because secreted proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Also, peptide moieties may be added to the polypeptide to facilitate purification. Such regions may be removed prior to final preparation of the polypeptide. The addition of peptide moieties to facilitate handling of polypeptides are familiar and routine techniques in the art.

Moreover, polypeptides of the present invention, including fragments, and specifically epitopes, can be combined with parts of the constant domain of immunoglobulins (IgG), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331:84–86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958–3964 (1995).)

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem. 270:9459–9471 (1995).)

Moreover, the polypeptides of the present invention can be fused to marker sequences, such as a peptide which facilitates purification of the fused polypeptide. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984).)

Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector: containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli*, *Streptomyces* and *Salmonella typhimurium* cells; fungal cells, such as yeast cells; insect cells such as *Drosophila* S2 and *Spodoptera* Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can be used as a chromosome marker.

Briefly, sequences can be mapped to chromosomes by preparing PCR primers (preferably 15–25 bp) from the sequences shown in SEQ ID NO:X. Primers can be selected using computer analysis so that primers do not span more than one predicted exon in the genomic DNA. These primers are then used for PCR screening of somatic cell hybrids containing individual human chromosomes. Only those hybrids containing the human gene corresponding to the SEQ ID NO:X will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000–4,000 bp are preferred. For a review of this technique, see Verma et al., "Human Chromosomes: a Manual of Basic Techniques," Pergamon Press, New York (1988).

For chromosome mapping, the polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. (Disease mapping data are found, for example, in V. McKusick, Mendelian Inheritance in Man (available on line through Johns Hopkins University Welch Medical Library).) Assuming 1 megabase mapping resolution and one gene per 20 kb, a cDNA precisely localized to a chromosomal region associated with the disease could be one of 50–500 potential causative genes.

Thus, once coinheritance is established, differences in the polynucleotide and the corresponding gene between affected and unaffected individuals can be examined. First, visible structural alterations in the chromosomes, such as deletions or translocations, are examined in chromosome spreads or by PCR. If no structural alterations exist, the presence of point mutations are ascertained. Mutations observed in some or all affected individuals, but not in normal individuals, indicates that the mutation may cause the disease. However, complete sequencing of the polypeptide and the corresponding gene from several normal individuals is required to distinguish the mutation from a polymorphism. If a new polymorphism is identified, this polymorphic polypeptide can be used for further linkage analysis.

Furthermore, increased or decreased expression of the gene in affected individuals as compared to unaffected individuals can be assessed using polynucleotides of the present invention. Any of these alterations (altered expression, chromosomal rearrangement, or mutation) can be used as a diagnostic or prognostic marker.

In addition to the foregoing, a polynucleotide can be used to control gene expression through triple helix formation or antisense DNA or RNA. Both methods rely on binding of the polynucleotide to DNA or RNA. For these techniques, preferred polynucleotides are usually 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat disease.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell.

The polynucleotides are also useful for identifying individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult.

The polynucleotides of the present invention can be used as additional DNA markers for RFLP.

The polynucleotides of the present invention can also be used as an alternative to RFLP, by determining the actual base-by-base DNA sequence of selected portions of an individual's genome. These sequences can be used to prepare PCR primers for amplifying and isolating such selected DNA, which can then be sequenced. Using this technique, individuals can be identified because each individual will have a unique set of DNA sequences. Once an unique ID database is established for an individual, positive identification of that individual, living or dead, can be made from extremely small tissue samples.

Forensic biology also benefits from using DNA-based identification techniques as disclosed herein. DNA sequences taken from very small biological samples such as tissues, e.g., hair or skin, or body fluids, e.g., blood, saliva, semen, etc., can be amplified using PCR. In one prior art technique, gene sequences amplified from polymorphic loci, such as DQa class II HLA gene, are used in forensic biology to identify individuals. (Erlich, H., PCR Technology, Freeman and Co. (1992).) Once these specific polymorphic loci are amplified, they are digested with one or more restriction enzymes, yielding an identifying set of bands on a Southern blot probed with DNA corresponding to the DQa class II HLA gene. Similarly, polynucleotides of the present invention can be used as polymorphic markers for forensic purposes.

There is also a need for reagents capable of identifying the source of a particular tissue. Such need arises, for example, in forensics when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination.

In the very least, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of the Polypeptides

Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods. (Jalkanen, M., et al., J. Cell. Biol. 101:976–985 (1985); Jalkanen, M., et al., J. Cell. Biol. 105:3087–3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (1251, 1211), carbon (14C), sulfur (35S), tritium (3H), indium (112In), and technetium (99mTc), and fluorescent labels, such as fluorescein and rhodamine, and biotin.

In addition to assaying secreted protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of a polypeptide of the present invention in cells or body fluid of an individual; (b) comparing the level of gene expression with a standard gene expression level, whereby an increase or decrease in the assayed polypeptide gene expression level compared to the standard expression level is indicative of a disorder.

Moreover, polypeptides of the present invention can be used to treat disease. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B), to inhibit the activity of a polypeptide (e.g., an oncogene), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth).

Similarly, antibodies directed to a polypeptide of the present invention can also be used to treat disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to .measure protein expression from a recombinant cell, as a way of assessing transformation of the host cell. Moreover, the polypeptides of the present invention can be used to test the following biological activities.

Biological Activities

The polynucleotides and polypeptides of the present invention can be used in assays to test for one or more biological activities. If these polynucleotides and polypeptides do exhibit activity in a particular assay, it is likely that these molecules may be involved in the diseases associated with the biological activity. Thus, the polynucleotides and polypeptides could be used to treat the associated disease.

Immune Activity

A polypeptide or polynucleotide of the present invention may be useful in treating deficiencies or disorders of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, a polynucleotide or polypeptide of the present invention can be used as a marker or detector of a particular immune system disease or disorder.

A polynucleotide or polypeptide of the present invention may be useful in treating or detecting deficiencies or disorders of hematopoietic cells. A polypeptide or polynucleotide of the present invention could be used to increase differentiation and proliferation of hematopoietic cells, including the pluripotent stem cells, in an effort to treat those disorders associated with a decrease in certain (or many) types hematopoietic cells. Examples of immunologic deficiency syndromes include, but are not limited to: blood protein disorders (e.g. agarunaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, a polypeptide or polynucleotide of the present invention could also be used to modulate hemostatic (the stopping of bleeding) or thrombolytic activity (clot formation). For example, by increasing hemostatic or thrombolytic activity, a polynucleotide or polypeptide of the present invention could be used to treat blood coagulation disorders (e.g., afibrinogenemia, factor deficiencies), blood platelet disorders (e.g. thrombocytopenia), or wounds resulting from trauma, surgery, or other causes. Alternatively, a polynucleotide or polypeptide of the present invention that can decrease hemostatic or thrombolytic activity could be used to inhibit or dissolve clotting. These molecules could be important in the treatment of heart attacks (infarction), strokes, or scarring.

A polynucleotide or polypeptide of the present invention may also be useful in treating or detecting autoimmune disorders. Many autoimmune disorders result from inappropriate recognition of self as foreign material by immune cells. This inappropriate recognition results in an immune response leading to the destruction of the host tissue. Therefore, the administration of a polypeptide or polynucleotide of the present invention that inhibits an immune response, particularly the proliferation, differentiation, or chemotaxis of T-cells, may be an effective therapy in preventing autoimmune disorders.

Examples of autoimmune disorders that can be treated or detected by the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalnia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated by a polypeptide or polynucleotide of the present invention. Moreover, these molecules can be used to treat anaphylaxis, hypersensitivity to an antigenic molecule, or blood group incompatibility.

A polynucleotide or polypeptide of the present invention may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of a polypeptide or polynucleotide of the present invention that inhibits an immune response, particularly the proliferation, differentiation, or chemotaxis of T-cells, may be an effective therapy in preventing organ rejection or GVHD.

Similarly, a polypeptide or polynucleotide of the present invention may also be used to modulate inflammation. For example, the polypeptide or polynucleotide may inhibit the proliferation and differentiation of cells involved in an inflammatory response. These molecules can be used to treat inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

A polypeptide or polynucleotide can be used to treat or detect hyperproliferative disorders, including neoplasms. A polypeptide or polynucleotide of the present invention may inhibit the proliferation of the disorder through direct or indirect interactions. Alternatively, a polypeptide or polynucleotide of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

Examples of hyperproliferative disorders that can be treated or detected by a polynucleotide or polypeptide of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated or detected by a polynucleotide or polypeptide of the present invention. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

Infectious Disease

A polypeptide or polynucleotide of the present invention can be used to treat or detect infectious agents. For example, by increasing the immune response, particularly increasing the proliferation and differentiation of B and/or T cells, infectious diseases may be treated. The immune response may be increased by either enhancing an existing immune response, or by initiating a new immune response. Alternatively, the polypeptide or polynucleotide of the present invention may also directly inhibit the infectious agent, without necessarily eliciting an immune response.

Viruses are one example of an infectious agent that can cause disease or symptoms that can be treated or detected by a polynucleotide or polypeptide of the present invention. Examples of viruses, include, but are not limited to the following DNA and RNA viral families: Arbovirus, Adenoviridae, Arenaviridae, Arterivirus, Bimaviridae, Bunyaviridae, Caliciviridae, Circoviridae, Coronaviridae, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza), Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox , hemorrhagic fever, Measles, Mumps, Parainfluenza, Rabies, the common cold, Polio, leukemia, Rubella, sexually transmitted diseases, skin diseases (e.g., Kaposi's, warts), and viremia. A polypeptide or polynucleotide of the present invention can be used to treat or detect any of these symptoms or diseases.

Similarly, bacterial or fungal agents that can cause disease or symptoms and that can be treated or detected by a polynucleotide or polypeptide of the present invention include, but not limited to, the following Gram-Negative and Gram-positive bacterial families and fungi: Actinomycetales (e.g., *Corynebacterium, Mycobacterium, Norcardia*), *Aspergillosis*, Bacillaceae (e.g., Anthrax, *Clostridium*), Bacteroidaceae, Blastomycosis, *Bordetella, Borrelia*, Brucellosis, Candidiasis, *Campylobacter*, Coccidioidomycosis, Cryptococcosis; Dermatocycoses, Enterobacteriaceae (*Klebsiella, Salmonella, Serratia, Yersinia*), *Erysipelothrix, Helicobacter*, Legionellosis, Leptospirosis, *Listeria*, Mycoplasmatales, Neisseriaceae (e.g., *Acinetobacter*, Gonorrhea, Menigococcal), Pasteurellacea Infections (e.g., *Actinobacillus, Heamophilus, Pasteurella*), *Pseudomonas*, Rickettsiaceae, Chlamydiaceae, Syphilis, and Staphylococcal. These bacterial or fungal families can cause the following diseases or symptoms, including, but not limited to: bacteremia, endocarditis, eye infections (conjunctivitis, *tuberculosis*, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, *Tuberculosis*, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. A polypeptide or polynucleotide of the present invention can be used to treat or detect any of these symptoms or diseases.

Moreover, parasitic agents causing disease or symptoms that can be treated or detected by a polynucleotide or polypeptide of the present invention include, but not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), Malaria, pregnancy complications, and toxoplasmosis. A polypeptide or polynucleotide of the present invention can be used to treat or detect any of these symptoms or diseases.

Preferably, treatment using a polypeptide or polynucleotide of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

A polynucleotide or polypeptide of the present invention can be used to differentiate, proliferate, and attract cells, leading to the regeneration of tissues. (See, Science 276:59–87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vascular (including vascular endothelium), nervous, hematopoietic, and skeletal (bone, cartilage, tendon, and ligament) tissue. Preferably, regeneration occurs without or decreased scarring. Regeneration also may include angiogenesis.

Moreover, a polynucleotide or polypeptide of the present invention may increase regeneration of tissues difficult to heal. For example, increased tendon/ligament regeneration would quicken recovery time after damage. A polynucleotide or polypeptide of the present invention could also be used prophylactically in an effort to avoid damage. Specific diseases that could be treated include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using a polynucleotide or polypeptide of the present invention to proliferate and differentiate nerve cells. Diseases that could be treated using this method include central and peripheral nervous system diseases, neuropathies, or mechanical and traumatic disorders (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the polynucleotide or polypeptide of the present invention.

Chemotaxis

A polynucleotide or polypeptide of the present invention may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

A polynucleotide or polypeptide of the present invention may increase cbemotaxic activity of particular cells. These chemotactic molecules can then be used to treat inflammation, infection, hyperproliferative disorders, or any immune system disorder by increasing the number of cells targeted to a particular location in the body. For example, chemotaxic molecules can be used to treat wounds and other trauma to tissues by attracting immune cells to the injured location. Chemotactic molecules of the present invention can also attract fibroblasts, which can be used to treat wounds.

It is also contemplated that a polynucleotide or polypeptide of the present invention may inhibit chemotactic activity. These molecules could also be used to treat disorders. Thus, a polynucleotide or polypeptide of the present invention could be used as an inhibitor of chemotaxis.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors), or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2): Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide, either as a secreted protein or on the cell membrane. Preferred cells include cells from mammals, yeast, *Drosophila*, or *E. coli*. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

All of these above assays can be used as diagnostic or prognostic markers. The molecules discovered using these assays can be used to treat disease or to bring about a particular result in a patient (e.g., blood vessel growth) by activating or inhibiting the polypeptide/molecule. Moreover, the assays can discover agents which may inhibit or enhance the production of the polypeptide from suitably manipulated cells or tissues.

Therefore, the invention includes a method of identifying compounds which bind to a polypeptide of the invention comprising the steps of: (a) incubating a candidate binding compound with a polypeptide of the invention; and (b) determining if binding has occurred. Moreover, the invention includes a method of identifying agonists/antagonists comprising the steps of: (a) incubating a candidate compound with a polypeptide of the invention, (b) assaying a biological activity, and (b) determining if a biological activity of the polypeptide has been altered.

Other Activities

A polypeptide or polynucleotide of the present invention may also increase or decrease the differentiation or proliferation of embryonic stem cells, besides, as discussed above, hematopoietic lineage.

A polypeptide or polynucleotide of the present invention may also be used to modulate mammalian characteristics, such as body height, weight, hair color, eye color, skin, percentage of adipose tissue, pigmentation, size, and shape (e.g., cosmetic surgery). Similarly, a polypeptide or polynucleotide of the present invention may be used to modulate mammalian metabolism affecting catabolism, anabolism, processing, utilization, and storage of energy.

A polypeptide or polynucleotide of the present invention may be used to change a mammal's mental state or physical state by influencing biorhythms, caricadic rhythms, depression (including depressive disorders), tendency for violence, tolerance for pain, reproductive capabilities (preferably by Activin or Inhibin-like activity), hormonal or endocrine levels, appetite, libido, memory, stress, or other cognitive qualities.

A polypeptide or polynucleotide of the present invention may also be used as a food additive or preservative, such as to increase or decrease storage capabilities, fat content, lipid, protein, carbohydrate, vitamins, minerals, cofactors or other nutritional components.

Other Preferred Embodiments

Other preferred embodiments of the claimed invention include an isolated nucleic acid molecule comprising a nucleotide sequence which is at least 95% identical to a sequence of at least about 50 contiguous nucleotides in the nucleotide sequence of SEQ ID NO:X wherein X is any integer as defined in Table 1.

Also preferred is a nucleic acid molecule wherein said sequence of contiguous nucleotides is included in the nucleotide sequence of: SEQ ID NO:X in the range of positions beginning with the nucleotide at about the position of the 5' Nucleotide of the Clone Sequence and ending with the nucleotide at about the position of the 3' Nucleotide of the Clone Sequence as defined for SEQ ID NO:X in Table 1.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Start Codon and ending with the nucleotide at about the position of the 3' Nucleotide of the Clone Sequence as defined for SEQ ID NO:X in Table 1.

Similarly preferred is a nucleic acid molecule wherein said sequence of contiguous nucleotides is included in the nucleotide sequence of SEQ ID NO:X in the range of positions beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table 1.

Also preferred is an isolated nucleic acid molecule comprising a nucleotide sequence which is at least 95% identical to a sequence of at least about 150 contiguous nucleotides in the nucleotide sequence of SEQ ID NO:X.

Further preferred is an isolated nucleic acid molecule comprising a nucleotide sequence which is at least 95% identical to a sequence of at least about 500 contiguous nucleotides in the nucleotide sequence of SEQ ID NO:X.

A further preferred embodiment is a nucleic acid molecule comprising a nucleotide sequence which is at least 95% identical to: the nucleotide sequence of SEQ ID NO:X beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table 1.

A further preferred embodiment is an isolated nucleic acid molecule comprising a nucleotide sequence which is at least 95% identical to the complete nucleotide sequence of SEQ ID NO:X.

Also preferred is an isolated nucleic acid molecule which hybridizes under stringent hybridization conditions to a nucleic acid molecule, wherein said nucleic acid molecule which hybridizes does not hybridize under stringent hybridization conditions to a nucleic acid molecule having a nucleotide sequence consisting of only A residues or of only T residues.

Also preferred is a composition of matter comprising a DNA molecule which comprises a human cDNA clone identified by a cDNA Clone Identifier in Table 1, which DNA molecule is contained in the material deposited with the American Type Culture Collection and given the ATCC® Deposit Number shown in Table 1 for said cDNA Clone Identifier.

Also preferred is an isolated nucleic acid molecule comprising a nucleotide sequence which is at least 95% identical to a sequence of at least 50 contiguous nucleotides in the nucleotide sequence of a human cDNA clone identified by a cDNA Clone Identifier in Table 1, which DNA molecule is contained in the deposit given the ATCC® Deposit Number shown in Table 1.

Also preferred is an isolated nucleic acid molecule, wherein said sequence of at least 50 contiguous nucleotides is included in the nucleotide sequence of the complete open reading frame sequence encoded by said human cDNA clone.

Also preferred is an isolated nucleic acid molecule comprising a nucleotide sequence which is at least 95% identical to sequence of at least 150 contiguous nucleotides in the nucleotide sequence encoded by said human cDNA clone.

A further preferred embodiment is an isolated nucleic acid molecule comprising a nucleotide sequence which is at least 95% identical to sequence of at least 500 contiguous nucleotides in the nucleotide sequence encoded by said human cDNA clone.

A further preferred embodiment is an isolated nucleic acid molecule comprising a nucleotide sequence which is at least 95% identical to the complete nucleotide sequence encoded by said human cDNA clone.

A further preferred embodiment is a method for detecting in a biological sample a nucleic acid molecule comprising a nucleotide sequence which is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC® Deposit Number shown for said cDNA clone in Table 1; which method comprises a step of comparing a nucleotide sequence of at least one nucleic acid molecule in said sample with a sequence selected from said group and determining whether the sequence of said nucleic acid molecule in said sample is at least 95% identical to said selected sequence.

Also preferred is the above method wherein said step of comparing sequences comprises determining the extent of nucleic acid hybridization between nucleic acid molecules in said sample and a nucleic acid molecule comprising said sequence selected from said group. Similarly, also preferred is the above method wherein said step of comparing sequences is performed by comparing the nucleotide sequence determined from a nucleic acid molecule in said sample with said sequence selected from said group. The nucleic acid molecules can comprise DNA molecules or RNA molecules.

A further preferred embodiment is a method for identifying the species, tissue or cell type of a biological sample which method comprises a step of detecting nucleic acid molecules in said sample, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC® Deposit Number shown for said cDNA clone in Table 1.

The method for identifying the species, tissue or cell type of a biological sample can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a method for diagnosing in a subject a pathological condition associated with abnormal structure or expression of a gene encoding a secreted protein identified in Table 1, which method comprises a step of detecting in a biological sample obtained from said subject nucleic acid molecules, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC® Deposit Number shown for said cDNA clone in Table 1.

The method for diagnosing a pathological condition can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a composition of matter comprising isolated nucleic acid molecules wherein the nucleotide sequences of said nucleic acid molecules comprise a panel of at least two nucleotide sequences, wherein at least one sequence in said panel is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC® Deposit Number shown for said cDNA clone in Table 1. The nucleic acid molecules can comprise DNA molecules or RNA molecules.

Also preferred is an isolated polypeptide comprising an amino acid sequence at least 90% identical to a sequence of at least about 10 contiguous amino acids in the amino acid sequence of SEQ ID NO:Y wherein Y is any integer as defined in Table 1.

Also preferred is a polypeptide, wherein said sequence of contiguous amino acids is included in the amino acid sequence of SEQ ID NO:Y in the range of positions beginning with the residue at about the position of the First Amino Acid of the Secreted Portion and ending with the residue at about the Last Amino Acid of the Open Reading Frame as set forth for SEQ ID NO:Y in Table 1.

Also preferred is an isolated polypeptide comprising an amino acid sequence at least 95% identical to a sequence of at least about 30 contiguous amino acids in the amino acid sequence of SEQ ID NO:Y.

Further preferred is an isolated polypeptide comprising an amino acid sequence at least 95% identical to a sequence of at least about 100 contiguous amino acids in the amino acid sequence of SEQ ID NO:Y.

Further preferred is an isolated polypeptide comprising an amino acid sequence at least 95% identical to the complete amino acid sequence of SEQ ID NO:Y.

Further preferred is an isolated polypeptide comprising an amino acid sequence at least 90% identical to a sequence of at least about 10 contiguous amino acids in the complete amino acid sequence of a secreted protein encoded by a human cDNA clone identified by a cDNA Clone Identifier in Table 1 and contained in the deposit with the ATCC® Deposit Number shown for said cDNA clone in Table 1.

Also preferred is a polypeptide wherein said sequence of contiguous amino acids is included in the amino acid sequence of a secreted portion of the secreted protein encoded by a human cDNA clone identified by a cDNA Clone Identifier in Table 1 and contained in the deposit with the ATCC® Deposit Number shown for said cDNA clone in Table 1.

Also preferred is an isolated polypeptide comprising an amino acid sequence at least 95% identical to a sequence of at least about 30 contiguous amino acids in the amino acid sequence of the secreted portion of the protein encoded by a human cDNA clone identified by a cDNA Clone Identifier in Table 1 and contained in the deposit with the ATCC® Deposit Number shown for said cDNA clone in Table 1.

Also preferred is an isolated polypeptide comprising an amino acid sequence at least 95% identical to a sequence of at least about 100 contiguous amino acids in the amino acid sequence of the secreted portion of the protein encoded by a human cDNA clone identified by a cDNA Clone Identifier in Table 1 and contained in the deposit with the ATCC® Deposit Number shown for said cDNA clone in Table 1.

Also preferred is an isolated polypeptide comprising an amino acid sequence at least 95% identical to the amino acid sequence of the secreted portion of the protein encoded by a human cDNA clone identified by a cDNA Clone Identifier in Table 1 and contained in the deposit with the ATCC® Deposit Number shown for said cDNA clone in Table 1.

Further preferred is an isolated antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC® Deposit Number shown for said cDNA clone in Table 1.

Further preferred is a method for detecting in a biological sample a polypeptide comprising an amino acid sequence which is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC® Deposit Number shown for said cDNA clone in Table 1; which method comprises a step of comparing an amino acid sequence of at least one polypeptide molecule in said sample with a sequence selected from said group and determining whether the sequence of said polypeptide molecule in said sample is at least 90% identical to said sequence of at least 10 contiguous amino acids.

Also preferred is the above method wherein said step of comparing an amino acid sequence of at least one polypeptide molecule in said sample with a sequence selected from said group comprises determining the extent of specific binding of polypeptides in said sample to an antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC® Deposit Number shown for said cDNA clone in Table 1.

Also preferred is the above method wherein said step of comparing sequences is performed by comparing the amino acid sequence determined from a polypeptide molecule in said sample with said sequence selected from said group.

Also preferred is a method for identifying the species, tissue or cell type of a biological sample which method comprises a step of detecting polypeptide molecules in said sample, if any, comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC® Deposit Number shown for said cDNA clone in Table 1.

Also preferred is the above method for identifying the species, tissue or cell type of a biological sample, which method comprises a step of detecting polypeptide molecules comprising an amino acid sequence in a panel of at least two amino acid sequences, wherein at least one sequence in said panel is at least 90% identical to a sequence of at least 10 contiguous amino acids in a sequence selected from the above group.

Also preferred is a method for diagnosing in a subject a pathological condition associated with abnormal structure or expression of a gene encoding a secreted protein identified in Table 1, which method comprises a step of detecting in a biological sample obtained from said subject polypeptide molecules comprising an amino acid sequence in a panel of at least two amino acid sequences, wherein at least one sequence in said panel is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC® Deposit Number shown for said cDNA clone in Table 1.

In any of these methods, the step of detecting: said polypeptide molecules includes using an antibody.

Also preferred is an isolated nucleic acid molecule comprising a nucleotide sequence which is at least 95% identical to a nucleotide sequence encoding a polypeptide wherein said polypeptide comprises an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC® Deposit Number shown for said cDNA clone in Table 1.

Also preferred is an isolated nucleic acid molecule, wherein said nucleotide sequence encoding a polypeptide has been optimized for expression of said polypeptide in a prokaryotic host.

Also preferred is an isolated nucleic acid molecule, wherein said polypeptide comprises an amino acid sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC® Deposit Number shown for said cDNA clone in Table 1.

Further preferred is a method of making a recombinant vector comprising inserting any of the above isolated nucleic acid molecule into a vector. Also preferred is the recombinant vector produced by this method. Also preferred is a method of making a recombinant host cell comprising introducing the vector into a host cell, as well as the recombinant host cell produced by this method.

Also preferred is a method of making an isolated polypeptide comprising culturing this recombinant host cell under conditions such that said polypeptide is expressed and recovering said polypeptide. Also preferred is this method of making an isolated polypeptide, wherein said recombinant host cell is a eukaryotic cell and said polypeptide is a secreted portion of a human secreted protein comprising an amino acid sequence selected from the group consisting of: an amino acid sequence of SEQ ID NO:Y beginning with the residue at the position of the First Amino Acid of the Secreted Portion of SEQ ID NO:Y wherein Y is an integer set forth in Table 1 and said position of the First Amino Acid of the Secreted Portion of SEQ ID NO:Y is defined in Table 1; and an amino acid sequence of a secreted portion of a protein encoded by a human cDNA clone identified by a cDNA Clone Identifier in Table 1 and contained in the deposit with the ATCC® Deposit Number shown for said cDNA clone in Table 1. The isolated polypeptide produced by this method is also preferred.

Also preferred is a method of treatment of an individual in need of an increased level of a secreted protein activity, which method comprises administering to such an individual a pharmaceutical composition comprising an amount of an isolated polypeptide, polynucleotide, or antibody of the claimed invention effective to increase the level of said protein activity in said individual.

Having generally described the invention, the same will be more readily understood by reference to the following examples, which are provided by way of illustration and are not intended as limiting.

EXAMPLES

Example 1

Isolation of a Selected cDNA Clone from the Deposited Sample

Each cDNA clone in a cited ATCC® deposit is contained in a plasmid vector. Table 1 identifies the vectors used to construct the cDNA library from which each clone was isolated. In many cases, the vector used to construct the library is a phage vector from which a plasmid has been excised. The table immediately below correlates the related plasmid for each phage vector used in constructing the cDNA library. For example, where a particular clone is identified in Table 1 as being isolated in the vector "Lambda Zap," the corresponding deposited clone is in "pBluescript."

| Vector Used to Construct Library | Corresponding Deposited Plasmid |
|---|---|
| Lambda Zap | pBluescript (pBS) |
| Uni-Zap XR | pBluescript (pBS) |
| Zap Express | pBK |
| lafmid BA | plafmid BA |
| pSport1 | pSport1 |
| pCMVSport 2.0 | pCMVSport 2.0 |
| pCMVSport 3.0 | pCMVSport 3.0 |
| pCR ®2.1 | pCR ®2.1 |

Vectors Lambda Zap (U.S. Pat. Nos. 5,128,256 and 5,286, 636), Uni-Zap XR (U.S. Pat. Nos. 5,128, 256 and 5,286, 636), Zap Express (U.S. Pat. Nos. 5,128,256 and 5,286,636), pBluescript (pBS) (Short, J. M. et al., Nucleic Acids Res. 16:7583–7600 (1988); Alting-Mees, M. A. and Short, J. M., Nucleic Acids Res. 17:9494 (1989)) and pBK (Alting-Mees, M. A. et al., Strategies 5:58–61 (1992)) are commercially available from Stratagene Cloning Systems, Inc., 11011 N. Torrey Pines Road, La Jolla, Calif., 92037. pBS contains an ampicillin resistance gene and pBK contains a neomycin resistance gene. Both can be transformed into *E. coli* strain XL-1 Blue, also available from Stratagene. pBS comes in 4 forms SK+, SK−, KS+ and KS. The S and K refers to the orientation of the polylinker to the T7 and T3 primer sequences which flank the polylinker region ("S" is for SacI and "K" is for KpnI which are the first sites on each respective end of the linker). "+" or "−" refer to the orientation of the f1 origin of replication ("ori"), such that in one orientation, single stranded rescue initiated from the f1 ori generates sense strand DNA and in the other, antisense.

Vectors pSport1, pCMVSport 2.0 and pCMVSport 3.0, were obtained from Life Technologies, Inc., P. O. Box 6009, Gaithersburg, Md. 20897. All Sport vectors contain an ampicillin resistance gene and may be transformed into *E. coli* strain DH10B, also available from Life Technologies. (See, for instance, Gruber, C. E., et al., Focus 15:59 (1993).) Vector lafmid BA (Bento Scares, Columbia University, NY) contains an ampicillin resistance gene and can be transformed into *E. coli* strain XL-1 Blue. Vector pCR12.1, which is available from Invitrogen, 1600 Faraday Avenue, Carlsbad, Calif. 92008, contains an ampicillin resistance gene and may be transformed into *E. coli* strain DH10B, available from Life Technologies. (See, for instance, Clark, J. M., Nuc. Acids Res. 16:9677–9686 (1988) and Mead, D. et al., Biotechnology 9: (1991).) Preferably, a polynucleotide of the present invention does not comprise the phage vector sequences identified for the particular clone in Table 1, as well as the corresponding plasmid vector sequences designated above.

The deposited material in the sample assigned the ATCC® Deposit Number cited in Table 1 for any given cDNA clone also may contain one or more additional plasmids, each comprising a cDNA clone different from that given clone. Thus, deposits sharing the same ATCC® Deposit Number contain at least a plasmid for each cDNA clone identified in Table 1. Typically, each ATCC® deposit sample cited in Table 1 comprises a mixture of approximately equal amounts (by weight) of about 50 plasmid DNAs, each containing a different cDNA clone; but such a deposit sample may include plasmids for more or less than 50 cDNA clones, up to about 500 cDNA clones.

Two approaches can be used to isolate a particular clone from the deposited sample of plasmid DNAs cited for that clone in Table 1. First, a plasmid is directly isolated by screening the clones using a polynucleotide probe corresponding to SEQ ID NO:X.

Particularly, a specific polynucleotide with 30–40 nucleotides is synthesized using an Applied Biosystems DNA synthesizer according to the sequence reported. The oligonucleotide is labeled, for instance, with $^{32}P$-γ-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host, as indicated above (such as XL-1 Blue (Stratagene)) using techniques known to those of skill in the art, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17–20 nucleotides derived from both ends of the SEQ ID NO:X (i.e., within the region of SEQ ID NO:X bounded by the 5' NT and the 3' NT of the clone defined in Table 1) are synthesized and used to amplify the desired cDNA using the deposited cDNA plasmid as a template. The polymerase chain reaction is carried out under routine conditions, for instance, in 25 μl of reaction mixture with 0.5 ug of the above cDNA template. A convenient reaction mixture is 1.5–5 mM $MgCl_2$, 0.01% (w/v) gelatin, 20 μM each of dATP, dCTP, dGTP, dTTP, 25 pmol of each primer and 0.25 Unit of Taq polymerase. Thirty five cycles of PCR (denaturation at 94° C. for 1 min; annealing at 55° C. for 1 min; elongation at 72° C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-coding portions of a gene which may not be present in the deposited clone. These methods include but are not limited to, filter probing, clone enrichment using specific probes, and protocols similar or identical to 5' and 3' "RACE" protocols which are well known in the art. For instance, a method similar to 5' RACE is available for generating the missing 5' end of a desired full-length transcript. (Fromont-Racine et al., Nucleic Acids Res. 21(7) :1683–1684 (1993).)

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full length gene.

This above method starts with total RNA isolated from the desired source, although poly-A+ RNA can be used. The RNA preparation can then be treated with phosphatase if necessary to eliminate 5' phosphate groups on degraded or damaged RNA which may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligate.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene.

Example 2

Isolation of Genomic Clones Corresponding to a Polynucleotide

A human genomic P1 library (Genomic Systems, Inc.) is screened by PCR using primers selected for the cDNA sequence corresponding to SEQ ID NO:X., according to the method described in Example 1. (See also, Sambrook.)

Example 3

Tissue Distribution of Polypeptide

Tissue distribution of mRNA expression of polynucleotides of the present invention is determined using protocols for Northern blot analysis, described by, among others, Sambrook et al. For example, a cDNA probe produced by the method described in Example 1 is labeled with $P^{32}$ using the rediprime™ DNA labeling system (Amersham Life Science), according to manufacturer's instructions. After labeling, the probe is purified using CHROMA SPIN-100™ column (Clontech Laboratories, Inc.), according to manufacturer's protocol number PT1200-1. The purified labeled probe is then used to examine various human tissues for mRNA expression.

Multiple Tissue Northern (MTN) blots containing various human tissues (H) or human immune system tissues (IM) (Clontech) are examined with the labeled probe using ExpressHyb™ hybridization solution (Clontech) according to manufacturer's protocol number PT1190-1. Following hybridization and washing, the blots are mounted and exposed to film at −70° C. overnight, and the films developed according to standard procedures.

Example 4

Chromosomal Mapping of the Polynucleotides

An oligonucleotide primer set is designed according to the sequence at the 5' end of SEQ ID NO:X. This primer preferably spans about 100 nucleotides. This primer set is then used in a polymerase chain reaction under the following set of conditions: 30 seconds, 95° C.; 1 minute, 56° C.; 1 minute, 70° C. This cycle is repeated 32 times followed by one 5 minute cycle at 70° C. Human, mouse, and hamster DNA is used as template in addition to a somatic cell hybrid panel containing individual chromosomes or chromosome fragments (Bios, Inc). The reactions is analyzed on either 8% polyacrylamide gels or 3.5% agarose gels. Chromosome mapping is determined by the presence of an approximately 100 bp PCR fragment in the particular somatic cell hybrid.

Example 5

Bacterial Expression of a Polypeptide

A polynucleotide encoding a polypeptide of the present invention is amplified using PCR oligonucleotide primers corresponding to the 5' and 3' ends of the DNA sequence, as outlined in Example 1, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance ($Amp^r$), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the *E. coli* strain M15/rep4 (Qiagen, Inc.) which contains multiple copies of the plasmid pREP4, which expresses the lacI repressor and also confers kanamycin resistance ($Kan^r$). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 ($O.D.^{600}$) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000×g). The cell pellet is solubilized in the chaotropic agent 6 Molar Guanidine HCl by stirring for 3–4 hours at 4° C. The cell debris is removed by centrifugation, and the supernatant containing the polypeptide is loaded onto a nickel-nitrilo-tri-acetic acid ("Ni-NTA") affinity resin column (available from QIAGEN, Inc., supra). Proteins with a 6× His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immunobilized on the Ni-NTA column. The recommended conditions are as follows: renature using a linear 6M–1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80° C.

In addition to the above expression vector, the present invention further includes an expression vector comprising phage operator and promoter elements operatively linked to a polynucleotide of the present invention, called pHE4a. (ATCC® Accession Number 209645, deposited on Feb. 25, 1998.) This vector contains: 1) a neomycinphosphotransferase gene as a selection marker, 2) an *E. coli* origin of replication, 3) a T5 phage promoter sequence, 4) two lac operator sequences, 5) a Shine-Delgarno sequence, and 6) the lactose operon repressor gene (lacIq). The origin of replication (oriC) is derived from pUC19 (LTI, Gaithersburg, Md.). The promoter sequence and operator sequences are made synthetically.

DNA can be inserted into the pHEa by restricting the vector with NdeI and XbaI, BamHI, XhoI, or Asp718, running the restricted product on a gel, and isolating the larger fragment (the stuffer fragment should be about 310 base pairs). The DNA insert is generated according to the PCR protocol described in Example 1, using PCR primers having restriction sites for NdeI (5' primer) and XbaI, BamHI, XhoI, or Asp718 (3' primer). The PCR insert is gel purified and restricted with compatible enzymes. The insert and vector are ligated according to standard protocols.

The engineered vector could easily be substituted in the above protocol to express protein in a bacterial system.

Example 6

Purification of a Polypeptide from an Inclusion Body

The following alternative method can be used to purify a polypeptide expressed in *E coli* when it is present in the form of inclusion bodies. Unless otherwise specified, all of the following steps are conducted at 4–10° C.

Upon completion of the production phase of the *E. coli* fermentation, the cell culture is cooled to 4–10° C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfluidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the polypeptide containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Commassie blue stained 16% SDS-PAGE gel when 5 μg of purified protein is loaded. The purified protein can also be tested for endotoxin/LPS contamination, and typically the LPS content is less than 0.1 ng/ml according to LAL assays.

Example 7

Cloning and Expression of a Polypeptide in a Baculovirus Expression System

In this example, the plasmid shuttle vector pA2 is used to insert a polynucleotide into a baculovirus to express a polypeptide. This expression vector contains the strong polyhedrin promoter of the *Autographa californica* nuclear polyhedrosis virus (AcMNPV) followed by convenient restriction sites such as BamHI, XbaI and Asp718. The polyadenylation site of the simian virus 40 ("SV40") is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pAc373, pVL941, and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39 (1989).

Specifically, the cDNA sequence contained in the deposited clone, including the AUG initiation codon and the naturally associated leader sequence identified in Table 1, is amplified using the PCR protocol described in Example 1. If the naturally occurring signal sequence is used to produce the secreted protein, the pA2 vector does not need a second signal peptide. Alternatively, the vector can be modified (pA2 GP) to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified fragment is isolated from a 1% agarose gel using a commercially available kit ("Geneclean," BIO 101 Inc., La Jolla, Ca.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Ca.).

The fragment and the dephosphorylated plasmid are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five µg of a plasmid containing the polynucleotide is co-transfected with 1.0 µg of a commercially available linearized baculovirus DNA ("BaculoGold™ baculovirus DNA", Pharmingen, San Diego, Calif.), using the lipofection method described by Felgner et al., Proc. Natl. Acad. Sci. USA 84:7413–7417 (1987). One µg of BaculoGold™ virus DNA and 5 µg of the plasmid are mixed in a sterile well of a microtiter plate containing 50 µl of serum-free Grace's medium (Life Technologies Inc., Gaithersburg, Md.). Afterwards, 10 µl Lipofectin plus 90 µl Grace's medium are added, mixed and incubated for 15 minutes at room temperature. Then the transfection mixture is added drop-wise to Sf9 insect cells (ATCC® CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10.) After appropriate incubation, blue stained plaques are picked with the tip of a micropipettor (e.g., Eppendorf). The agar containing the recombinant viruses is then resuspended in a microcentrifuge tube containing 200 µl of Grace's medium and the suspension containing the recombinant baculovirus is used to infect Sf9 cells seeded in 35 mm dishes. Four days later the supernatants of these culture dishes are harvested and then they are stored at 4° C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 µCi of $^{35}$S-methionine and 5 µCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 8

Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC® 37152), pSV2dhfr (ATCC® 37146), pBC12MI (ATCC® 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QCI-3 cells, mouse L cells and Chinese hamster ovary (CHO) cells.

Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. 253:1357–1370 (1978); Hamlin, J. L. and Ma, C., Biochem. et Biophys. Acta, 1097:107–143 (1990); Page, M. J. and Sydenham, M. A., Biotechnology 9:64–68 (1991).) Another useful selection marker is the enzyme glutamine synthase (GS) (Murphy et al., Biochem J. 227:277–279 (1991); Bebbington et al., Bio/Technology 10:169–175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

Derivatives of the plasmid pSV2-dhfr (ATCC® Accession No. 37146), the expression vectors pC4 (ATCC® Accession No. 209646) and pC6 (ATCC® Accession No.209647) contain the strong promoter (LTR) of the Rous Sarcoma Virus (Cullen et al., Molecular and Cellular Biology, 438447 (March, 1985)) plus a fragment of the CMV-enhancer (Boshart et al., Cell 41:521–530 (1985).)

Multiple cloning sites, e.g., with the restriction enzyme cleavage sites BamHI, XbaI and Asp718, facilitate the cloning of the gene of interest. The vectors also contain the 3' intron, the polyadenylation and termination signal of the rat preproinsulin gene, and the mouse DHFR gene under control of the SV40 early promoter.

Specifically, the plasmid pC6, for example, is digested with appropriate restriction enzymes and then dephosphorylated using calf intestinal phosphates by procedures known in the art. The vector is then isolated from a 1% agarose gel.

A polynucleotide of the present invention is amplified according to the protocol outlined in Example 1. If the naturally occurring signal sequence is used to produce the secreted protein, the vector does not need a second signal peptide. Alternatively, if the naturally occurring signal sequence is not used, the vector can be modified to include a heterologous signal sequence. (See, e.g., WO 96/34891.)

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transfection. Five μg of the expression plasmid pC6 is cotransfected with 0.5 μg of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 mM, 20 mM). The same procedure is repeated until clones are obtained which grow at a concentration of 100–200 μM. Expression of the desired gene product is analyzed, for instance, by SDS-PAGE and Western blot or by reversed phase HPLC analysis.

Example 9

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example 5; see also EP A 394,827; Traunecker, et al., Nature 331:84–86 (1988).) Similarly, fusion to IgG-1, IgG-3, and albumin increases the halflife time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described -above can be made by modifying the following protocol, which outlines the fusion of a polypeptide to an IgG molecule, or the protocol described in Example 5.

Briefly, the human Fc portion of the IgG molecule can be PCR amplified using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and a polynucleotide of the present invention, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

Human IgG Fc Region:

GGGATCCGGAGCCCAAATCTTCTGA-
CAAAACTCACACATGCCCACCGTGC CCAGCAC-
CTGAATrCGAGGGTGCACCGTCAGTCT-
TCCTCTTCCCCCCAAAA
CCCAAGGACACCCTCATGATCTCCCG-
GACTCCTGAGGTCACATGCGTGGT GGTGGACG-
TAAGCCACGAAGACCCTGAGGTCAAGT-
TCAACTGGTACGTGG
ACGGCGTGGAGGTGCATAATGCCAAGA-
CAAAGCCGCGGGAGGAGCAGTA CAACAGCACG-
TACCGTGTGGTCAGCGTCCTCACCGTC-
CTGCACCAGGACT
GGCTGAATGGCAAGGAGTACAAGTG-
CAAGGTCTCCAACAAAGCCCTCCCA
ACCCCCATCGAGAAAACCATCTC-
CAAAGCCAAAGGGCAGCCCCGAGAAC CACAG-
GTGTACACCCTGCCCCCATCCCGGGAT-
GAGCTGACCAAGAACCAG
GTCAGCCTGACCTGCCTGGTCAAAGGCT-
TCTATCCAAGCGACATCGCCGT GGAGTGG-
GAGAGCAATGGGCAGCCGGAGAACAAC-
TACAAGACCACGCCT
CCCGTGCTGGACTCCGACGGCTCCTTCT-
TCCTCTACAGCAAGCTCACCGTG GACAAGAG-
CAGGTGGCAGCAGGGGAACGTCTTCT-
CATGCTCCGTGATGCA
TGAGGCTCTGCACAACCACTACACGCA-
GAAGAGCCTCTCCCTGTCTCCGG GTAAATGAGT-
GCGACGGCCGCGACTCTAGAGGAT (SEQ ID NO:1)

Example 10

Production of an Antibody from a Polypeptide

The antibodies of the present invention can be prepared by a variety of methods. (See, Current Protocols, Chapter 2.)

For example, cells expressing a polypeptide of the present invention is administered to an animal to induce the production of sera containing polyclonal antibodies. In a preferred method, a preparation of the secreted protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Köhler et al., Nature 256:495 (1975); Köhler et al., Eur. J. Immunol. 6:511 (1976); Köhler et al., Eur. J. Immunol. 6:292 (1976); Hammerling et al., in: Monoclonal Antibodies and T-Cell Hybridomas, Elsevier, N.Y., pp. 563–681 (1981).) In general, such procedures involve immunizing an animal (preferably a mouse) with polypeptide or, more preferably, with a secreted polypeptide-expressing cell. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 μg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC®. After fusion, the resulting hybridoma cells are selectively maintained in HAT medium, and then cloned by limiting dilution as described by Wands et al. (Gastroenterology 80:225–232 (1981).) The hybridoma cells obtained through such a selection are then assayed to identify clones which secrete antibodies capable of binding the polypeptide.

Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, secreted protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Example 11

Production of Secreted Protein for High-throughput Screening Assays

The following protocol produces a supernatant containing a polypeptide to be tested. This supernatant can then be used in the Screening Assays described in Examples 13–20.

First, dilute Poly-D-Lysine (644 587 Boehringer-Mannheim) stock solution (1 mg/ml in PBS) 1:20 in PBS (w/o calcium or magnesium 17-516F Biowhittaker) for a working solution of 50 ug/ml. Add 200 ul of this solution to each well (24 well plates) and incubate at RT for 20 minutes. Be sure to distribute the solution over each well (note: a 12-channel pipetter may be used with tips on every other channel). Aspirate off the Poly-D-Lysine solution and rinse with 1 ml PBS (Phosphate Buffered Saline). The PBS should remain in the well until just prior to plating the cells and plates may be poly-lysine coated in advance for up to two weeks.

Plate 293T cells (do not carry cells past P+20) at $2\times10^5$ cells/well in 0.5 ml DMEM (Dulbecco's Modified Eagle Medium) (with 4.5 G/L glucose and L-glutamine (12-604F Biowhittaker))/10% heat inactivated FBS (14-503F Biowhittaker)/1× Penstrep (17-602E Biowhittaker). Let the cells grow overnight.

The next day, mix together in a sterile solution basin: 300 ul Lipofectamine (18324-012 Gibco/BRL) and 5 ml Optimem I (31985070 Gibco/BRL)/96-well plate. With a small volume multi-channel pipetter, aliquot approximately 2 ug of an expression vector containing a polynucleotide insert, produced by the methods described in Examples 8 or 9, into an appropriately labeled 96-well round bottom plate. With a multi-channel pipetter, add 50 ul of the Lipofectamine/Optimem I mixture to each well. Pipette up and down gently to mix. Incubate at RT 15-45 minutes. After about 20 minutes, use a multi-channel pipetter to add 150 ul Optimem I to each well. As a control, one plate of vector DNA lacking an insert should be transfected with each set of transfections.

Preferably, the transfection should be performed by tag-teaming the following tasks. By tag-teaming, hands on time is cut in half, and the cells do not spend too much time on PBS. First, person A aspirates off the media from four 24-well plates of cells, and then person B rinses each well with 0.5–1 ml PBS. Person A then aspirates off PBS rinse, and person B, using a 12-channel pipetter with tips on every other channel, adds the 200 ul of DNA/Lipofectamine/Optimem I complex to the odd wells first, then to the even wells, to each row on the 24-well plates. Incubate at 37° C. for 6 hours.

While cells are incubating, prepare appropriate media, either 1% BSA in DMEM with 1× penstrep, or CHO-5 media (116.6 mg/L of CaCl2 (anhyd); 0.00130 mg/L $CuSO_4$-$5H_2O$; 0.050 mg/L of $Fe(NO_3)_3$-$9H_2O$; 0.417 mg/L of $FeSO_4$-$7H_2O$; 311.80 mg/L of Kcl; 28.64 mg/L of $MgCl_2$; 48.84 mg/L of $MgSO_4$; 6995.50 mg/L of NaCl; 2400.0 mg/L of $NaHCO_3$; 62.50 mg/L of $NaH_2PO_4$-$H_2O$; 71.02 mg/L of $Na_2$HPO4; 0.4320 mg/L of $ZnSO_4$-$7H_2O$; 0.002 mg/L of Arachidonic Acid; 1.022 mg/L of Cholesterol; 0.070 mg/L of DL-alpha-Tocopherol-Acetate; 0.0520 mg/L of Linoleic Acid; 0.010 mg/L of Linolenic Acid; 0.010 mg/L of Myristic Acid; 0.010 mg/L of Oleic Acid; 0.010 mg/L of Palmitric Acid; 0.010 mg/L of Palmitic Acid; 100 mg/L of Pluronic F-68; 0.010 mg/L of Stearic Acid; 2.20 mg/L of Tween 80; 4551 mg/L of D-Glucose; 130.85 mg/ml of L-Alanine; 147.50 mg/ml of L-Arginine-HCL; 7.50 mg/ml of L-Asparagine-$H_2O$; 6.65 mg/ml of L-Aspartic Acid; 29.56 mg/ml of L-Cystine-2HCL-$H_2O$; 31.29 mg/ml of L-Cystine-2HCL; 7.35 mg/ml of L-Glutamic Acid; 365.0 mg/ml of L-Glutamine; 18.75 mg/ml of Glycine; 52.48 mg/ml of L-Histidine-HCL-$H_2O$; 106.97 mg/ml of L-Isoleucine; 111.45 mg/ml of L-Leucine; 163.75 mg/ml of L-Lysine HCL; 32.34 mg/ml of L-Methionine; 68.48 mg/ml of L-Phenylalainine; 40.0 mg/ml of L-Proline; 26.25 mg/ml of L-Serine; 101.05 mg/ml of L-Threonine; 19.22 mg/ml of L-Tryptophan; 91.79 mg/ml of L-Tryrosine-2Na-$2H_2O$; 99.65 mg/ml of L-Valine; 0.0035 mg/L of Biotin; 3.24 mg/L of D-Ca Pantothenate; 11.78 mg/L of Choline Chloride; 4.65 mg/L of Folic Acid; 15.60 mg/L of i-Inositol; 3.02 mg/L of Niacinamide; 3.00 mg/L of Pyridoxal HCL; 0.031 mg/L of Pyridoxine HCL; 0.319 mg/L of Riboflavin; 3.17 mg/L of Thiamine HCL; 0.365 mg/L of Thymidine; and 0.680 mg/L of Vitamin $B_{12}$; 25 mM of HEPES Buffer; 2.39 mg/L of Na Hypoxanthine; 0.105 mg/L of Lipoic Acid; 0.081 mg/L of Sodium Putrescine-2HCL; 55.0 mg/L of Sodium Pyruvate; 0.0067 mg/L of Sodium Selenite; 20 uM of Ethanolamine; 0.122 mg/L of Ferric Citrate; 41.70 mg/L of Methyl-B-Cyclodextrin complexed with Linoleic Acid; 33.33 mg/L of Methyl-B-Cyclodextrin complexed with Oleic Acid; and 10 mg/L of Methyl-B-Cyclodextrin complexed with Retinal) with 2 mm glutamine and 1× penstrep. (BSA (81-068-3 Bayer) 100 gm dissolved in 1 L DMEM for a 10% BSA stock solution). Filter the media and collect 50 ul for endotoxin assay in 15 ml polystyrene conical.

The transfection reaction is terminated, preferably by tag-teaming, at the end of the incubation period. Person A aspirates off the transfection media, while person B adds 1.5 ml appropriate media to each well. Incubate at 37° C. for 45 or 72 hours depending on the media used: 1% BSA for 45 hours or CHO-5 for 72 hours.

On day four, using a 300 ul multichannel pipetter, aliquot 600 ul in one 1 ml deep well plate and the remaining supernatant into a 2 ml deep well. The supernatants from each well can then be used in the assays described in Examples 13–20.

It is specifically understood that when activity is obtained in any of the assays described below using a supernatant, the activity originates from either the polypeptide directly (e.g., as a secreted protein) or by the polypeptide inducing expression of other proteins, which are then secreted into the supernatant. Thus, the invention further provides a method of identifying the protein in the supernatant characterized by an activity in a particular assay.

Example 12

Construction of GAS Reporter Construct

One signal transduction pathway involved in the differentiation and proliferation of cells is called the Jaks-STATs pathway. Activated proteins in the Jaks-STATs pathway bind to gamma activation site "GAS" elements or interferon-sensitive responsive element ("ISRE"), located in the promoter of many genes. The binding of a protein to these elements alter the expression of the associated gene.

GAS and ISRE elements are recognized by a class of transcription factors called Signal Transducers and Activators of Transcription, or "STATs." There are six members of the STATs family. Stat1 and Stat3 are present in many cell types, as is Stat2 (as response to IFN-alpha is widespread). Stat4 is more restricted and is not in many cell types though it has been found in T helper class I, cells after treatment with IL-12. Stat5 was originally called mammary growth factor, but has been found at higher concentrations in other cells including myeloid cells. It can be activated in tissue culture cells by many cytokines.

The STATs are activated to translocate from the cytoplasm to the nucleus upon tyrosine phosphorylation by a set of kinases known as the Janus Kinase ("Jaks") family. Jaks represent a distinct family of soluble tyrosine kinases and include Tyk2, Jak1, Jak2, and Jak3. These kinases display significant sequence similarity and are generally catalytically inactive in resting cells.

The Jaks are activated by a wide range of receptors summarized in the Table below. (Adapted from review by Schidler and Darnell, Ann. Rev. Biochem. 64:621–51 (1995).) A cytokine receptor family, capable of activating Jaks, is divided into two groups: (a) Class 1 includes receptors for IL-2, IL-3, IL-4, IL-6, IL-7, IL-9, IL-11, IL-12, IL-15, Epo, PRL, GH, G-CSF, GM-CSF, LIF, CNTF, and thrombopoietin; and (b) Class 2 includes IFN-a, IFN-g, and IL-10. The Class 1 receptors share a conserved cysteine motif (a set of four conserved cysteines and one tryptophan) and a WSXWS motif (a membrane proximal region encoding Trp-Ser-Xxx-Trp-Ser (SEQ ID NO:2)).

Thus, on binding of a ligand to a receptor, Jaks are activated, which in turn activate STATs, which then translocate and bind to GAS elements. This entire process is encompassed in the Jaks-STATs signal transduction pathway.

Therefore, activation of the Jaks-STATs pathway, reflected by the binding of the GAS or the ISRE element, can be used to indicate proteins involved in the proliferation and differentiation of cells. For example, growth factors and cytokines are known to activate the Jaks-STATs pathway. (See Table below.) Thus, by using GAS elements linked to reporter molecules, activators of the Jaks-STATs pathway can be identified.

| | | JAKs | | | | |
|---|---|---|---|---|---|---|
| Ligand | tyk2 | Jak1 | Jak2 | Jak3 | STATS | GAS (elements) or ISRE |
| IFN family | | | | | | |
| IFN-a/B | + | + | − | − | 1,2,3 | ISRE |
| IFN-g | | + | + | − | 1 | GAS (IRF1>Lys6>IFP) |
| Il-10 | + | ? | ? | − | 1,3 | |

-continued

| Ligand | tyk2 | JAKs Jak1 | Jak2 | Jak3 | STATS | GAS (elements) or ISRE |
|---|---|---|---|---|---|---|
| gp130 family | | | | | | |
| IL-6 (Pleiotrophic) | + | + | + | ? | 1,3 | GAS (IRF1>Lys6>IFP) |
| I1-11 (Pleiotrophic) | ? | + | ? | ? | 1,3 | |
| OmM (Pleiotrophic) | ? | + | + | ? | 1,3 | |
| LIF (Pleiotrophic) | ? | + | + | ? | 1,3 | |
| CNTF (Pleiotrophic) | −/+ | + | + | ? | 1,3 | |
| G-CSF (Pleiotrophic) | ? | + | ? | ? | 1,3 | |
| IL-12 (Pleiotrophic) | + | − | + | + | 1,3 | |
| g-C family | | | | | | |
| IL-2 (lymphocytes) | − | + | − | + | 1,3,5 | GAS |
| IL-4 (lymph/myeloid) | − | + | − | + | 6 | GAS (IRF1 = IFP>>Ly6)(IgH) |
| IL-7 (lymphocytes) | − | + | − | + | 5 | GAS |
| IL-9 (lymphocytes) | − | + | − | + | 5 | GAS |
| IL-13 (lymphocyte) | − | + | ? | ? | 6 | GAS |
| IL-15 | ? | + | ? | + | 5 | GAS |
| gp 140 family | | | | | | |
| IL-3 (myeloid) | − | − | + | − | 5 | GAS (IRF1>IFP>>Ly6) |
| IL-5 (myeloid) | − | − | + | − | 5 | GAS |
| GM-CSF (myeloid) | − | − | + | − | 5 | GAS |
| Growth hormone family | | | | | | |
| GH | ? | − | + | − | 5 | GAS(B-CAS>IRF1 = IFP>>Ly6) |
| PRL | ? | +/− | + | − | 1,3,5 | |
| EPO | ? | − | + | − | 5 | |
| Receptor Tyrosine Kinases | | | | | | |
| EGF | ? | + | + | − | 1,3 | GAS (IRF1) |
| PDGF | ? | + | + | − | 1,3 | |
| CSF-1 | ? | + | + | − | 1,3 | GAS (not IRF1) |

To construct a synthetic GAS containing promoter element, which is used in the Biological Assays described in Examples 13–14, a PCR based strategy is employed to generate a GAS-SV40 promoter sequence. The 5' primer contains four tandem copies of the GAS binding site found in the IRF1 promoter and previously demonstrated to bind STATs upon induction with a range of cytokines (Rothman et al., Immunity 1:457–468 (1994).), although other GAS or ISRE elements can be used instead. The 5' primer also contains 18bp of sequence complementary to the SV40 early promoter sequence and is flanked with an XhoI site. The sequence of the 5' primer is:

5':GCGCCTCGAGATTTCCCCGAAATCTAGATTTCCCCGAAATGATTTCCCC GAAATGATTTCCCCGAAATATCTGCCATCTCAATTAG:3' (SEQ ID NO:3)

The downstream primer is complementary to the SV40 promoter and is flanked with a HindIII site:

5':GCGGCAAGCTTTTTGCAAAGCCTAGGC:3' (SEQ ID NO:4)

PCR amplification is performed using the SV40 promoter template present in the B-gal:promoter plasmid obtained from Clontech. The resulting PCR fragment is digested with XhoI/HindIII and subcloned into BLSK2-. (Stratagene.) Sequencing with forward and reverse primers confirms that the insert contains the following sequence:

5':CTCGAGATTTCCCCGAAATCTAGATTTCCCC GAAATGATTTCCCCGAAA TGATTTCCCCGAAATATCTGCCATCTCAATTAGTCAGCAACCATAGTCCCG CCCCTAACTCCGCCCATCCCGCCCCTAACTCCGCCCAGTTCCGCC CATTCT CCGCCCCATGGCTGACTAATTTTTTTTATTTATGCAGAGGCCGAGGCCGCC TCGGCCTCTGAGCTATTCCAGAAGTAGTGAGGAGGCTTTTTTGGAGGCCT AGGCTTTTGCAAAAAGCTT:3' (SEQ ID NO:5)

With this GAS promoter element linked to the SV40 promoter, a GAS:SEAP2 reporter construct is next engineered. Here, the reporter molecule is a secreted alkaline phosphatase, or "SEAP." Clearly, however, any reporter molecule can be instead of SEAP, in this or in any of the other Examples. Well known reporter molecules that can be used instead of SEAP include chloramphenicol acetyltransferase (CAT), luciferase, alkaline phosphatase, B-galactosidase, green fluorescent protein (GFP), or any protein detectable by an antibody.

The above sequence confirmed synthetic GAS-SV40 promoter element is subcloned into the pSEAP-Promoter vector obtained from Clontech using HindIII and XhoI, effectively replacing the SV40 promoter with the amplified GAS:SV40 promoter element, to create the GAS-SEAP vector. However, this vector does not contain a neomycin resistance gene, and therefore, is not preferred for mammalian expression systems.

Thus, in order to generate mammalian stable cell lines expressing the GAS-SEAP reporter, the GAS-SEAP cassette is removed from the GAS-SEAP vector using SalI and NotI, and inserted into a backbone vector containing the neomycin resistance gene, such as pGFP-1 (Clontech), using these restriction sites in the multiple cloning site, to create the GAS-SEAP/Neo vector. Once this vector is transfected into mammalian cells, this vector can then be used as a reporter molecule for GAS binding as described in Examples 13–14.

Other constructs can be made using the above description and replacing GAS with a different promoter sequence. For example, construction of reporter molecules containing NFK-B and EGR promoter sequences are described in Examples 15 and 16. However, many other promoters can be substituted using the protocols described in these Examples. For instance, SRE, IL-2, NFAT, or Osteocalcin promoters can be substituted, alone or in combination (e.g., GAS/NF-KB/EGR, GAS/NF-KB, Il-2/NFAT, or NF-KB/GAS). Similarly, other cell lines can be used to test reporter construct activity, such as HELA (epithelial), HUVEC (endothelial), Reh (B-cell), Saos-2 (osteoblast), HUVAC (aortic), or Cardiomyocyte.

Example 13

High-throughput Screening Assay for T-cell Activity

The following protocol is used to assess T-cell activity by identifying factors, such as growth factors and cytokines, that may proliferate or differentiate T-cells. T-cell activity is assessed using the GAS/SEAP/Neo construct produced in Example 12. Thus, factors that increase SEAP activity indicate the ability to activate the Jaks-STATS signal transduction pathway. The T-cell used in this assay is Jurkat T-cells (ATCC® Accession No. TIB-152), although Molt-3 cells (ATCC® Accession No. CRL-1552) and Molt-4 cells (ATCC® Accession No. CRL-1582) cells can also be used.

Jurkat T-cells are lymphoblastic CD4+ Th1 helper cells. In order to generate stable cell lines, approximately 2 million Jurkat cells are transfected with the GAS-SEAP/neo vector using DMRIE-C (Life Technologies) (transfection procedure described below). The transfected cells are seeded to a density of approximately 20,000 cells per well and transfectants resistant to 1 mg/ml genticin selected. Resistant colonies are expanded and then tested for their response to increasing concentrations of interferon gamma. The dose response of a selected clone is demonstrated.

Specifically, the following protocol will yield sufficient cells for 75 wells containing 200 ul of cells. Thus, it is either scaled up, or performed in multiple to generate sufficient cells for multiple 96 well plates. Jurkat cells are maintained in RPMI+10% serum with 1% Pen-Strep. Combine 2.5 mls of OPTI-MEM (Life Technologies) with 10 ug of plasmid DNA in a T25 flask. Add 2.5 ml OPTI-MEM containing 50 ul of DMRIE-C and incubate at room temperature for 15–45 mins.

During the incubation period, count cell concentration, spin down the required number of cells ($10^7$ per transfection), and resuspend in OPTI-MEM to a final concentration of $10^7$ cells/ml. Then add 1 ml of $1\times10^7$ cells in OPTI-MEM to T25 flask and incubate at 37° C. for 6 hrs. After the incubation, add 10 ml of RPMI+15% serum.

The Jurkat:GAS-SEAP stable reporter lines are maintained in RPMI+10% serum, 1 mg/ml Genticin, and 1% Pen-Strep. These cells are treated with supernatants containing a polypeptide as produced by the protocol described in Example 11.

On the day of treatment with the supernatant, the cells should be washed and resuspended in fresh RPMI+10% serum to a density of 500,000 cells per ml. The exact number of cells required will depend on the number of supernatants being screened. For one 96 well plate, approximately 10 million cells (for 10 plates, 100 million cells) are required.

Transfer the cells to a triangular reservoir boat, in order to dispense the cells into a 96 well dish, using a 12 channel pipette. Using a 12 channel pipette, transfer 200 ul of cells into each well (therefore adding 100,000 cells per well).

After all the plates have been seeded, 50 ul of the supernatants are transferred directly from the 96 well plate containing the supernatants into each well using a 12 channel pipette. In addition, a dose of exogenous interferon gamma (0.1, 1.0, 10 ng) is added to wells H9, H10, and H11 to serve as additional positive controls for the assay.

The 96 well dishes containing Jurkat cells treated with supernatants are placed in an incubator for 48 hrs (note: this time is variable between 48–72 hrs). 35 ul samples from each well are then transferred to an opaque 96 well plate using a 12 channel pipette. The opaque plates should be covered (using sellophene covers) and stored at −20° C. until SEAP assays are performed according to Example 17. The plates containing the remaining treated cells are placed at 4° C. and serve as a source of material for repeating the assay on a specific well if desired.

As a positive control, 100 Unit/ml interferon gamma can be used which is known to activate Jurkat T cells. Over 30 fold induction is typically observed in the positive control wells.

The above protocol may be used in the generation of both transient, as well as, stable transfected cells, which would be apparent to those of skill in the art.

Example 14

High-throughput Screening Assay Identifying Myeloid Activity

The following protocol is used to assess myeloid activity by identifying factors, such as growth factors and cytokines, that may proliferate or differentiate myeloid cells. Myeloid cell activity is assessed using the GAS/SEAP/Neo construct produced in Example 12. Thus, factors that increase SEAP activity indicate the ability to activate the Jaks-STATS signal transduction pathway. The myeloid cell used in this assay is U937, a pre-monocyte cell line, although TF-1, HL60, or KG1 can be used.

To transiently transfect U937 cells with the GAS/SEAP/Neo construct produced in Example 12, a DEAE-Dextran method (Kharbanda et. al., 1994, Cell Growth & Differentiation, 5:259–265) is used. First, harvest $2\times10e^7$ U937 cells and wash with PBS. The U937 cells are usually grown in RPMI 1640 medium containing 10% heat-inactivated fetal bovine serum (FBS) supplemented with 100 units/ml penicillin and 100 mg/ml streptomycin.

Next, suspend the cells in 1 ml of 20 mM Tris-HCl (pH 7.4) buffer containing 0.5 mg/ml DEAE-Dextran, 8 ug GAS-SEAP2 plasmid DNA, 140 mM NaCl, 5 mM KCl, 375 uM $Na_2HPO_4.7H_2O$, 1 mM $MgCl_2$, and 675 uM $CaCl_2$. Incubate at 37° C. for 45 min.

Wash the cells with RPMI 1640 medium containing 10% EBS and then resuspend in 10 ml complete medium and incubate at 37° C. for 36 hr.

The GAS-SEAP/U937 stable cells are obtained by growing the cells in 400 ug/ml G418. The G418-free medium is used for routine growth but every one to two months, the cells should be re-grown in 400 ug/ml G418 for couple of passages.

These cells are tested by harvesting $1\times10^8$ cells (this is enough for ten 96-well plates assay) and wash with PBS. Suspend the cells in 200 ml above described growth medium, with a final density of $5\times10^5$ cells/ml. Plate 200 ul cells per well in the 96-well plate (or $1\times10^5$ cells/well).

Add 50 ul of the supernatant prepared by the protocol described in Example 11. Incubate at 37° C. for 48 to 72 hr. As a positive control, 100 Unit/ml interferon gamma can be used which is known to activate U937 cells. Over 30 fold induction is typically observed in the positive control wells. SEAP assay the supernatant according to the protocol described in Example 17.

Example 15

High-throughout Screening Assay Identifying Neuronal Activity

When cells undergo differentiation and prolife ration, a group of genes are activated through many different signal transduction pathways. One of these genes, EGR1 (early growth response gene 1), is induced in various tissues and cell types upon activation. The promoter of EGR1 is responsible for such induction. Using the EGR1 promoter linked to reporter molecules, activation of cells can be assessed.

Particularly, the following protocol is used to assess neuronal activity in PC12 cell lines. PC12 cells (rat pheochromocytoma cells) are known to proliferate and/or differentiate by activation with a number of mitogens, such as TPA (tetradecanoyl phorbol acetate), NGF (nerve growth factor), and EGF (epidermal growth factor). The EGR1 gene expression is activated during this treatment. Thus, by stably transfecting PC 12 cells with a construct containing an EGR promoter linked to SEAP reporter, activation of PC12 cells can be assessed.

The EGR1SEAP reporter construct can be assembled by the following protocol. The EGR-1 promoter-sequence (−633 to +1) (Sakamoto K et al., Oncogene 6:867–871 (1991)) can be PCR amplified from human genomic DNA using the following primers:

5' GCGCTCGAGGGATGACAGCGATAGAACCCCGG-3' (SEQ ID NO:6)

5' GCGAAGCTTCGCGACTCCCCGGATCCGCCTC-3' (SEQ ID NO:7)

Using the GAS:SEAP/Neo vector produced in Example 12, EGR1 amplified product can then be inserted into this vector. Linearize the GAS:SEAP/Neo vector using restriction enzymes XhoI/HindIII, removing the GAS/SV40 stuffer. Restrict the EGR1 amplified product with these same enzymes. Ligate the vector and the EGR1 promoter.

To prepare 96 well-plates for cell culture, two mls of a coating solution (1:30 dilution of collagen type I (Upstate Biotech Inc. Cat #08-115) in 30% ethanol (filter sterilized)) is added per one 10 cm plate or 50 ml per well of the 96-well plate, and allowed to air dry for 2 hr.

PC12 cells are routinely grown in RPMI-1640 medium (Bio Whittaker) containing 10% horse serum (JRH BIOSCIENCES, Cat. #12449-78P), 5% heat-inactivated fetal bovine serum (FBS) supplemented with 100 units/ml penicillin and 100 ug/ml streptomycin on a precoated 10 cm tissue culture dish. One to four split is done every three to four days. Cells are removed from the plates by scraping and resuspended with pipetting up and down for more than 15 times.

Transfect the EGR/SEAP/Neo construct into PC 12 using the Lipofectamine protocol described in Example 11. EGR-SEAP/PC 12 stable cells are obtained by growing the cells in 300 ug/ml G418. The G418-free medium is used for routine growth but every one to two months, the cells should be re-grown in 300 ug/ml G418 for couple of passages.

To assay for neuronal activity, a 10 cm plate with cells around 70 to 80% confluent is screened by removing the old medium. Wash the cells once with PBS (Phosphate buffered saline). Then starve the cells in low serum medium (RPMI-1640 containing 1% horse serum and 0.5% FBS with antibiotics) overnight.

The next morning, remove the medium and wash the cells with PBS. Scrape off the cells from the plate, suspend the cells well in 2 ml low serum medium. Count the cell number and add more low serum medium to reach final cell density as $5\times10^5$ cells/ml.

Add 200 ul of the cell suspension to each well of 96-well plate (equivalent to $1\times10^5$ cells/well). Add 50 ul supernatant produced by Example 11, 37° C. for 48 to 72 hr. As a positive control, a growth factor known to activate PC12 cells through EGR can be used, such as 50 ng/ul of Neuronal Growth Factor (NGF). Over fifty-fold induction of SEAP is typically seen in the positive control wells. SEAP assay the supernatant according to Example 17.

Example 16

High-throughput Screening Assay for T-cell Activity

NF-κB (Nuclear Factor κB) is a transcription factor activated by a wide variety of agents including the inflammatory cytokines IL-1 and TNF, CD30 and CD40, lymphotoxin-alpha and lymphotoxin-beta, by exposure to LPS or thrombin, and by expression of certain viral gene products. As a transcription factor, NF-κB regulates the expression of genes involved in immune cell activation, control of apoptosis (NF-κB appears to shield cells from apoptosis), B and T-cell development, anti-viral and antimicrobial responses, and multiple stress responses.

In non-stimulated conditions, NF-κB is retained in the cytoplasm with I-κB (Inhibitor κB). However, upon stimulation, I-κB is phosphorylated and degraded, causing NF-κB to shuttle to the nucleus, thereby activating transcription of target genes. Target genes activated by NF-κB include IL-2, IL-6, GM-CSF, ICAM-1 and class 1 MHC.

Due to its central role and ability to respond to a range of stimuli, reporter constructs utilizing the NF-κB promoter element are used to screen the supernatants produced in Example 11. Activators or inhibitors of NF-kB would be useful in treating diseases. For example, inhibitors of NF-κB could be used to treat those diseases related to the acute or chronic activation of NF-kB, such as rheumatoid arthritis.

To construct a vector containing the NF-κB promoter element, a PCR based strategy is employed. The upstream primer contains four tandem copies of the NF-κB binding site (GGGGACTTTCCC) (SEQ ID NO:8), 18 bp of sequence complementary to the 5' end of the SV40 early promoter sequence, and is flanked with an XhoI site:

5':GCGGCCTCGAGGGGACTTTCCCGGGGACTTTCCGGGGACTTTCCGGGAC TTTCCATCCTGCCATCTCAATTAG:3' (SEQ ID NO:9)

The downstream primer is complementary to the 3' end of the SV40 promoter and is flanked with a HindIII site:

5':GCGGCAAGCTTTTTGCAAAGCCTAGGC:3' (SEQ ID NO:4)

PCR amplification is performed using the SV40 promoter template present in the pB-gal:promoter plasmid obtained from Clontech. The resulting PCR fragment is digested with XhoI and HindIII and subcloned into BLSK2-. (Stratagene) Sequencing with the T7 and T3 primers confirms the insert contains the following sequence:

5':CTCGAGGGGACTTTCCCGGGGACTTTCCGGGGACTTTCCGGGACTTTCC ATCTGCCATCTCAATTAGTCAGCAACCATAGTCCCGCCCCTAACTCCGCCC ATCCCGCCCCTAACTCCGCCCAGTTCCGCCCATTCTCCGCCCCATGGCTGA CTAATTTTTTTTATTTATGCAGAGGCCGAGGCCGCCTCGGCCTCTGAGCTA TTCCA-

GAAGTAGTGAGGAGGCTTTTTTGGAGGC-CTAGGCTTTTGCAAAAA GCTT:3' (SEQ ID NO:10)

Next, replace the SV40 minimal promoter element present in the pSEAP2-promoter plasmid (Clontech) with this NF-κB/SV40 fragment using XhoI and HindIII. However, this vector does not contain a neomycin resistance gene, and therefore, is not preferred for mammalian expression systems.

In order to generate stable mammalian cell lines, the NF-κB/SV40/SEAP cassette is removed from the above NF-κB/SEAP vector using restriction enzymes SalI and NotI, and inserted into a vector containing neomycin resistance. Particularly, the NF-κ/BSV40/SEAP cassette was inserted into pGFP-1 (Clontech), replacing the GFP gene, after restricting pGFP-1 with SalI and NotI.

Once NF-κB/SV40/SEAP/Neo vector is created, stable Jurkat T-cells are created and maintained according to the protocol described in Example 13. Similarly, the method for assaying supernatants with these stable Jurkat T-cells is also described in Example 13. As a positive control, exogenous TNF alpha (0.1,1,10 ng) is added to wells H9, H10, and H11, with a 5–10 fold activation typically observed.

Example 17

Assay for SEAP Activity

As a reporter molecule for the assays described in Examples 13–16, SEAP activity is assayed using the Tropix Phospho-light Kit (Cat. BP-400) according to the following general procedure. The Tropix Phospho-light Kit supplies the Dilution, Assay, and Reaction Buffers used below.

Prime a dispenser with the 2.5× Dilution Buffer and dispense 15 μl of 2.5× dilution buffer into Optiplates containing 35 μl of a supernatant. Seal the plates with a plastic sealer and incubate at 65° C. for 30 min. Separate the Optiplates to avoid uneven heating.

Cool the samples to room temperature for 15 minutes. Empty the dispenser and prime with the Assay Buffer. Add 50 μl Assay Buffer and incubate at room temperature 5 min. Empty the dispenser and prime with the Reaction Buffer (see the table below). Add 50 μl Reaction Buffer and incubate at room temperature for 20 minutes. Since the intensity of the chemiluminescent signal is time dependent, and it takes about 10 minutes to read 5 plates on luminometer, one should treat 5 plates at each time and start the second set 10 minutes later.

Read the relative light unit in the luminometer. Set H12 as blank, and print the results. An increase in chemiluminescence indicates reporter activity.

Reaction Buffer Formulation:

| # of plates | Rxn buffer diluent (ml) | CSPD (ml) |
|---|---|---|
| 10 | 60 | 3 |
| 11 | 65 | 3.25 |
| 12 | 70 | 3.5 |
| 13 | 75 | 3.75 |
| 14 | 80 | 4 |
| 15 | 85 | 4.25 |
| 16 | 90 | 4.5 |
| 17 | 95 | 4.75 |
| 18 | 100 | 5 |
| 19 | 105 | 5.25 |
| 20 | 110 | 5.5 |
| 21 | 115 | 5.75 |
| 22 | 120 | 6 |
| 23 | 125 | 6.25 |
| 24 | 130 | 6.5 |
| 25 | 135 | 6.75 |
| 26 | 140 | 7 |
| 27 | 145 | 7.25 |
| 28 | 150 | 7.5 |
| 29 | 155 | 7.75 |
| 30 | 160 | 8 |
| 31 | 165 | 8.25 |
| 32 | 170 | 8.5 |
| 33 | 175 | 8.75 |
| 34 | 180 | 9 |
| 35 | 185 | 9.25 |
| 36 | 190 | 9.5 |
| 37 | 195 | 9.75 |
| 38 | 200 | 10 |
| 39 | 205 | 10.25 |
| 40 | 210 | 10.5 |
| 41 | 215 | 10.75 |
| 42 | 220 | 11 |
| 43 | 225 | 11.25 |
| 44 | 230 | 11.5 |
| 45 | 235 | 11.75 |
| 46 | 240 | 12 |
| 47 | 245 | 12.25 |
| 48 | 250 | 12.5 |
| 49 | 255 | 12.75 |
| 50 | 260 | 13 |

Example 18

High-throughput Screening Assay Identifying Changes in Small Molecule Concentration and Membrane Permeability Binding of a ligand to a receptor is known to alter intracellular levels of small molecules, such as calcium, potassium, sodium, and pH, as well as alter membrane potential. These alterations can be measured in an assay to identify supernatants which bind to receptors of a particular cell. Although the following protocol describes an assay for calcium, this protocol can easily be modified to detect changes in potassium, sodium, pH, membrane potential, or any other small molecule which is detectable by a fluorescent probe.

The following assay uses Fluorometric Imaging Plate Reader ("FLIPR") to measure changes in fluorescent molecules (Molecular Probes) that bind small molecules. Clearly, any fluorescent molecule detecting a small molecule can be used instead of the calcium fluorescent molecule, fluo-4 (Molecular Probes, Inc.; catalog no. F-14202), used here.

For adherent cells, seed the cells at 10,000–20,000 cells/well in a Co-star black 96-well plate with clear bottom. The plate is incubated in a $CO_2$ incubator for hours. The adherent cells are washed two times in Biotek washer with 200 ul of HBSS (Hank's Balanced Salt Solution) leaving 100 ul of buffer after the final wash.

A stock solution of 1 mg/ml fluo-4 is made in 10% pluronic acid DMSO. To load the cells with fluo-4, 50 ul of 12 ug/ml fluo-4 is added to each well. The plate is incubated at 37° C. in a $CO_2$ incubator for 60 min. The plate is washed four times in the Biotek washer with HBSS leaving 100 ul of buffer.

For non-adherent cells, the cells are spun down from culture media. Cells are re-suspended to 2–5×$10^6$ cells/ml with HBSS in a 50-ml conical tube. 4 ul of 1 mg/ml fluo-4 solution in 10% pluronic acid DMSO is added to each ml of cell suspension. The tube is then placed in a 37° C. water bath for 30–60 min. The cells are washed twice with HBSS, resuspended to $1\times10^6$ cells/ml, and dispensed into a microplate, 100 ul/well. The plate is centrifuged at 1000 rpm for 5 min. The plate is then washed once in Denley Cell Wash with 200 ul, followed by an aspiration step to 100 ul final volume.

For a non-cell based assay, each well contains a fluorescent molecule, such as fluo-4. The supernatant is added to the well, and a change in fluorescence is detected.

To measure the fluorescence of intracellular calcium, the FLIPR is set for the following parameters: (1) System gain is 300–800 mW; (2) Exposure time is 0.4 second; (3) Camera F/stop is F/2; (4) Excitation is 488 nm; (5). Emission is 530 nm; and (6) Sample addition is 50 ul. Increased emission at 530 nm indicates an extracellular signaling event which has resulted in an increase in the intracellular $Ca^{++}$ concentration.

Example 19

High-throughput Screening Assay Identifying Tyrosine Kinase Activity

The Protein Tyrosine Kinases (PTK) represent a diverse group of transmembrane and cytoplasmic kinases. Within the Receptor Protein Tyrosine Kinase RPTK) group are receptors for a range of mitogenic and metabolic growth factors including the PDGF, FGF, EGF, NGF, HGF and Insulin receptor subfamilies. In addition there are a large family of RPTKs for which the corresponding ligand is unknown. Ligands for RPTKs include mainly secreted small proteins, but also membrane-bound and extracellular matrix proteins.

Activation of RPTK by ligands involves ligand-mediated receptor dimerization, resulting in transphosphorylation of the receptor subunits and activation of the cytoplasmic tyrosine kinases. The cytoplasmic tyrosine kinases include receptor associated tyrosine kinases of the src-family (e.g., src, yes, lck, lyn, fyn) and non-receptor linked and cytosolic protein tyrosine kinases, such as the Jak family, members of which mediate signal transduction triggered by the cytokine superfamily of receptors (e.g., the Interleukins, Interferons, GM-CSF, and Leptin).

Because of the wide range of known factors capable of stimulating tyrosine kinase activity, the identification of novel human secreted proteins capable of activating tyrosine kinase signal transduction pathways are of interest. Therefore, the following protocol is designed to identify those novel human secreted proteins capable of activating the tyrosine kinase signal transduction pathways.

Seed target cells (e.g., primary keratinocytes) at a density of approximately 25,000 cells per well in a 96 well Loprodyne Silent Screen Plates purchased from Nalge Nunc (Naperville, Ill.). The plates are sterilized with two 30 minute rinses with 100% ethanol, rinsed with water and dried overnight. Some plates are coated for 2 hr with 100 ml of cell culture grade type I collagen (50 mg/ml), gelatin (2%) or polylysine (50 mg/ml), all of which can be purchased from Sigma Chemicals (St. Louis, Mo.) or 10% Matrigel purchased from Becton Dickinson (Bedford, Mass.), or calf serum, rinsed with PBS and stored at 4° C. Cell growth on these plates is assayed by seeding 5,000 cells/well in growth medium and indirect quantitation of cell number through use of alamarBlue as described by the manufacturer Alamar Biosciences, Inc. (Sacramento, Calif.) after 48 hr. Falcon plate covers #3071 from Becton Dickinson (Bedford, Mass.) are used to cover the Loprodyne Silent Screen Plates. Falcon Microtest III cell culture plates can also be used in some proliferation experiments.

To prepare extracts, A431 cells are seeded onto the nylon membranes of Loprodyne plates (20,000/200 ml/well) and cultured overnight in complete medium. Cells are quiesced by incubation in serum-free basal medium for 24 hr. After 5–20 minutes treatment with EGF (60 ng/ml) or 50 ul of the supernatant produced in Example 11, the medium was removed and 100 ml of extraction buffer ((20 mM HEPES pH 7.5, 0.15 M NaCl, 1% Triton X-100, 0.1% SDS, 2 mM Na3VO4, 2 mM Na4P2O7 and a cocktail of protease inhibitors (#1836170) obtained from Boeheringer Mannheim (Indianapolis, Ind.) is added to each well and the plate is shaken on a rotating shaker for 5 minutes at 4° C. The plate is then placed in a vacuum transfer manifold and the extract filtered through the 0.45 mm membrane bottoms of each well using house vacuum. Extracts are collected in a 96-well catch/assay plate in the bottom of the vacuum manifold and immediately placed on ice. To obtain extracts clarified by centrifugation, the content of each well, after detergent solubilization for 5 minutes, is removed and centrifuged for 15 minutes at 4° C. at 16,000×g.

Test the filtered extracts for levels of tyrosine kinase activity. Although many methods of detecting tyrosine kinase activity are known, one method is described here.

Generally, the tyrosine kinase activity of a supernatant is evaluated by determining its ability to phosphorylate a tyrosine residue on a specific substrate (a biotinylated peptide). Biotinylated peptides that can be used for this purpose include PSK1 (corresponding to amino acids 6–20 of the cell division kinase cdc2-p34) and PSK2 (corresponding to amino acids 1–17 of gastrin). Both peptides are substrates for a range of tyrosine kinases and are available from Boehringer Mannheim.

The tyrosine kinase reaction is set up by adding the following components in order. First, add 10 ul of 5 uM Biotinylated Peptide, then 10 ul ATP/$Mg_{2+}$ (5mM ATP/50 mM $MgCl_2$), then 10 ul of 5× Assay Buffer (40 mM imidazole hydrochloride, pH7.3, 40 mM beta-glycerophosphate, 1 mM EGTA, 100 mM $MgCl_2$, 5 mM $MnCl_2$, 0.5 mg/ml BSA), then 5 ul of Sodium Vanadate (1 nM), and then 5 ul of water. Mix the components gently and preincubate the reaction mix at 30° C. for 2 min. Initial the reaction by adding 10 ul of the control enzyme or the filtered supernatant.

The tyrosine kinasc assay reaction is then terminated by adding 10 ul of 120 mm EDTA and place the reactions on ice.

Tyrosine kinase activity is determined by transferring 50 ul aliquot of reaction mixture to a microtiter plate (MTP) module and incubating at 37° C. for 20 min. This allows the streptavadin coated 96 well plate to associate with the biotinylated peptide. Wash the MTP module with 300 ul/well of PBS four times. Next add 75 ul of anti-phospotyrosine antibody conjugated to horse radish peroxidase (anti-P-Tyr-POD (0.5u/ml)) to each well and incubate at 37° C. for one hour. Wash the well as above.

Next add 100 ul of peroxidase substrate solution (Boehringer Mannheim) and incubate at room temperature for at least 5 mins (up to 30 min). Measure the absorbance of the sample at 405 nm by using ELISA reader. The level of bound peroxidase activity is quantitated using an ELISA reader and reflects the level of tyrosine kinase activity.

Example 20

High-throughput Screening Assay Identifying Phosphorylation Activity

As a potential alternative and/or compliment to the assay of protein tyrosine kinase activity described in Example 19, an assay which detects activation (phosphorylation) of major intracellular signal transduction intermediates can also be used. For example, as described below one particular assay can detect tyrosine phosphorylation of the Erk-1 and Erk-2 kinases. However, phosphorylation of other molecules, such as Raf, JNK, p38 MAP, Map kinase kinase (MEK), MEK kinase, Src, Muscle specific kinase (MuSK), IRAK, Tec, and Janus, as well as any other phosphoserine, phosphotyrosine, or phosphothreonine molecule, can be detected by substituting these molecules for Erk-1 or Erk-2 in the following assay.

Specifically, assay plates are made by coating the wells of a 96-well ELISA plate with 0.1 ml of protein G (1 ug/ml) for 2 hr at room temp, (RT). The plates are then rinsed with PBS and blocked with 3% BSA/PBS for 1 hr at RT. The protein G plates are then treated with 2 commercial monoclonal antibodies (10 ng/well) against Erk-1 and Erk-2 (1 hr at RT) (Santa Cruz Biotechnology). (To detect other molecules, this step can easily be modified by substituting a monoclonal antibody detecting any of the above described molecules.) After 3–5 rinses with PBS, the plates are stored at 4° C. until use.

A431 cells are seeded at 20,000/well in a 96-well Loprodyne filterplate and cultured overnight in growth medium. The cells are then starved for 48 hr in basal medium (DMEM) and then treated with EGF (6 ng/well) or 50 ul of the supernatants obtained in Example 11 for 5–20 minutes. The cells are then solubilized and extracts filtered directly into the assay plate.

After incubation with the extract for 1 hr at RT, the wells are again rinsed. As a positive control, a commercial preparation of MAP kinase (10 ng/well) is used in place of A43 1 extract. Plates are then treated with a commercial polyclonal (rabbit) antibody (1 ug/ml) which specifically recognizes the phosphorylated epitope of the Erk-1 and Erk-2 kinases (1 hr at RT). This antibody is biotinylated by standard procedures. The bound polyclonal antibody is then quantitated by successive incubations with Europium-streptavidin and Europium fluorescence enhancing reagent in the Wallac DELFIA instrument (time-resolved fluorescence). An increased fluorescent signal over background indicates a phosphorylation.

Example 21

Method of Determining Alterations in a Gene Corresponding to a Polynucleotide

RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID) NO:X. Suggested PCR conditions consist of 35 cycles at 95° C. for 30 seconds; 60–120 seconds at 52–58° C.; and 60–120 seconds at 70° C., using buffer solutions described in Sidransky, D., et al., Science 252:706 (1991).

PCR products are then sequenced using primers labeled at their 5' end with T4 polynucleotide kinase, employing SequiTherm Polymerase. (Epicentre Technologies). The intron-exon borders of selected exons is also determined and genomic PCR products analyzed to confirm the results. PCR products harboring suspected mutations is then cloned and sequenced to validate the results of the direct sequencing.

PCR products is cloned into T-tailed vectors as described in Holton, T. A. and Graham, M. W., Nucleic Acids Research, 19:1156 (1991) and sequenced with T7 polymerase (United States Biochemical). Affected individuals are identified by mutations not present in unaffected individuals.

Genomic rearrangements are also observed as a method of determining alterations in a gene corresponding to a polynucleotide. Genomic clones isolated according to Example 2 are nick-translated with digoxigenindeoxy-uridine 5'-triphosphate (Boehringer Manheim), and FISH performed as described in Johnson, Cg. et al., Methods Cell Biol. 35:73–99 (1991). Hybridization with the labeled probe is carried out using a vast excess of human cot-1 DNA for specific hybridization to the corresponding genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region hybridized by the probe are identified as insertions, deletions, and translocations. These alterations are used as a diagnostic marker for an associated disease.

Example 22

Method of Detecting Abnormal Levels of a Polypeptide in a Biological Sample

A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at a final concentration of 0.2 to 10 ug/ml. The antibodies are either monoclonal or polyclonal and are produced by the method described in Example 10. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbounded polypeptide.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Example 23

Formulating a Polypeptide

The secreted polypeptide composition will be formulated and dosed in a fashion consistent with good medical practice, taking into account the clinical condition of the individual patient (especially the side effects of treatment with the secreted polypeptide alone), the site of delivery, the method of administration, the scheduling of administration, and other factors known to practitioners. The "effective amount" for purposes herein is thus determined by such considerations.

As a general proposition, the total pharmaceutically effective amount of secreted polypeptide administered parenterally per dose will be in the range of about 1 μg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the secreted polypeptide is typically administered at a dose rate of about 1 μg/kg/hour to about 50 μg/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the secreted protein of the invention are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The secreted polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547–556 (1983)), poly(2-hydroxyethyl methacrylate) (R. Langer et al., J. Biomed. Mater. Res. 15:167–277 (1981), and R. Langer, Chem. Tech. 12:98–105 (1982)), ethylene vinyl acetate (R. Langer et al.) or poly-D-(−)-3-hydroxybutyric acid (EP 133,988). Sustained-release compositions also include liposomally entrapped polypeptides. Liposomes containing the secreted polypeptide are prepared by methods known per se: DE 3,218,121; Epstein et al., Proc. Natl. Acad. Sci. USA 82:3688–3692 (1985); Hwang et al., Proc. Natl. Acad. Sci. USA 77:4030–4034 (1980); EP 52,322; EP 36,676; EP 88,046; EP 143,949; EP 142,641; Japanese Pat. Appl. 83–118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal secreted polypeptide therapy.

For parenteral administration, in one embodiment, the secreted polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The secreted polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Any polypeptide to be used for therapeutic administration can be sterile. Sterility is readily accomplished by filtration through sterile filtration membranes (e.g., 0.2 micron membranes). Therapeutic polypeptide compositions generally are placed into a container having a sterile access port, for example, an intravenous solution bag or vial having a stopper pierceable by a hypodermic injection needle.

Polypeptides ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous polypeptide solution, and the resulting mixture is lyophilized. The infusion solution is prepared by reconstituting the lyophilized polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Example 24

Method of Treating Decreased Levels of the Polypeptide

It will be appreciated that conditions caused by a decrease in the standard or normal expression level of a secreted protein in an individual can be treated by administering the polypeptide of the present invention, preferably in the secreted form. Thus, the invention also provides a method of treatment of an individual in need of an increased level of the polypeptide comprising administering to such an individual a pharmaceutical composition comprising an amount of the polypeptide to increase the activity level of the polypeptide in such an individual.

For example, a patient with decreased levels of a polypeptide receives a daily dose 0.1–100 ug/kg of the polypeptide for six consecutive days. Preferably, the polypeptide is in the secreted form. The exact details of the dosing scheme, based on administration and formulation, are provided in Example 23.

Example 25

Method of Treating Increased Levels of the Polypeptide

Antisense technology is used to inhibit production of a polypeptide of the present invention. This technology is one example of a method of decreasing levels of a polypeptide, preferably a secreted form, due to a variety of etiologies, such as cancer.

For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 23.

Example 26

Method of Treatment Using Gene Therapy

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 1. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector has the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

It will be clear that the invention maybe practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

What is claimed is:

1. An isolated antibody or fragment thereof that specifically binds to a protein selected from the group consisting of:

(a) a protein consisting of amino acid residues 47 to 111 of SEQ ID NO:235;

(b) a protein consisting of a portion of SEQ ID NO:235, wherein said portion comprises at least 30 contiguous amino acid residues from 47 to 111 of SEQ ID NO:235; and (c) a protein consisting of a portion of SEQ ID NO:235, wherein said portion comprises at least 50 contiguous amino acid residues from 47 to 111 of SEQ ID NO:235.

2. The antibody or fragment thereof of claim 1 that specifically binds protein (a).

3. The antibody or fragment thereof of claim 1 that specifically binds protein (b).

4. The antibody or fragment thereof of claim 1 that specifically binds protein (c).

5. The antibody or fragment thereof of claim 3 that specifically binds protein (a).

6. The antibody or fragment thereof of claim 3 wherein said protein bound by said antibody or fragment thereof is glycosylated.

7. The antibody or fragment thereof of claim 3 which is a human antibody.

8. The antibody or fragment thereof of claim 3 which is a polyclonal antibody.

9. The antibody or fragment thereof of claim 3 which is selected from the group consisting of:

(a) a chimerical antibody;

(b) a humanized antibody;

(c) a single chain antibody; and (d) a Fab fragment.

10. The antibody or fragment thereof of claim 3 which is labeled.

11. The antibody or fragment thereof of claim 10 wherein the label is selected from the group consisting of:

(a) an enzyme;

(b) a fluorescent label;

(c) a luminescent label; and (d) a bioluminescent label.

12. The antibody or fragment thereof of claim 3 wherein said antibody or fragment thereof specifically binds to said protein in a Western blot.

13. The antibody or fragment thereof of claim 3 wherein said antibody or fragment thereof specifically binds to said protein in an ELISA.

14. An isolated cell that produces the antibody or fragment thereof of claim 3.

15. A hybridoma that produces the antibody or fragment thereof of claim 3.

16. A method of detecting Secreted Protein HHTLF25 in a biological sample comprising:

(a) contacting the biological sample with the antibody or fragment thereof of claim 3; and (b) detecting Secreted Protein HHTLF25 in the biological sample.

17. The method of claim 16 wherein the antibody or fragment thereof is a polyclonal antibody.

18. An isolated monoclonal antibody or fragment thereof that specifically binds to a protein selected from the group consisting of:

(a) a protein consisting of amino acid residues 47 to 111 of SEQ ID NO:235;

(b) a protein consisting of a portion of SEQ ID NO:235, wherein said portion comprises at least 30 contiguous amino acid residues from 47 to 111 of SEQ ID NO:235; and (c) a protein consisting of a portion of SEQ ID NO:235, wherein said portion comprises at least 50 contiguous amino acid residues from 47 to 111 of SEQ ID NO:235.

19. The antibody or fragment thereof of claim 18 that specifically binds protein (a).

20. The antibody or fragment thereof of claim 18 that specifically binds protein (b).

21. The antibody or fragment thereof of claim 18 that specifically binds protein (c).

22. The antibody or fragment thereof of claim 20 that specifically binds protein (a).

23. The antibody or fragment thereof of claim 20 wherein said protein bound by said antibody or fragment thereof is glycosylated.

24. The antibody or fragment thereof of claim 20 which is a human antibody.

25. The antibody or fragment thereof of claim 20 which is selected from the group consisting of:

(a) a chimerical antibody;

(b) a humanized antibody;

(c) a single chain antibody; and (d) a Fab fragment.

26. The antibody or fragment thereof of claim 20 which is labeled.

27. The antibody or fragment thereof of claim 26 wherein the label is selected from the group consisting of:

(a) an enzyme;

(b) a fluorescent label;

(c) a luminescent label; and (d) a bioluminescent label.

28. The antibody or fragment thereof of claim 20 wherein said antibody or fragment thereof specifically binds to said protein in a Western blot.

29. The antibody or fragment thereof of claim 20 wherein said antibody or fragment thereof specifically binds to said protein in an ELISA.

30. An isolated cell that produces the antibody or fragment thereof of claim 20.

31. A hybridoma that produces the antibody or fragment thereof of claim 20.

32. A method of detecting Secreted Protein HHTLF25 in a biological sample comprising:

(a) contacting the biological sample with the antibody or fragment thereof of claim 26; and (b) detecting Secreted Protein HHTLF25 in the biological sample.

33. An isolated antibody or fragment thereof that specifically binds to a protein selected from the group consisting of:

(a) a protein consisting of the full-length polypeptide encoded by the HHTLF25 cDNA contained in ATCC Deposit No. 209125;

(b) a protein consisting of a portion of the polypeptide encoded by the HHTLF25 cDNA contained in ATCC Deposit No. 209125, wherein said portion comprises at least 30 contiguous amino acids residues of the polypeptide encoded by the HHTLF25 cDNA contained in ATCC Deposit No. 209125; and (c) a protein consisting of a portion of the polypeptide encoded by the HHTLF25 cDNA contained in ATCC Deposit No. 209125, wherein said portion comprises at least 50 contiguous amino acids residues of the polypeptide encoded by the HHTLF25 cDNA contained in ATCC Deposit No. 209125.

34. The antibody or fragment thereof of claim 33 that specifically binds protein (a).

35. The antibody or fragment thereof of claim 33 that specifically binds protein (b).

36. The antibody or fragment thereof of claim 33 that specifically binds protein (c).

37. The antibody or fragment thereof of claim 35 that specifically binds protein (a).

38. The antibody or fragment thereof of claim 35 wherein said protein bound by said antibody or fragment thereof is glycosylated.

39. The antibody or fragment thereof of claim 35 which is a human antibody.

40. The antibody or fragment thereof of claim 35 which is a polyclonal antibody.

41. The antibody or fragment thereof of claim 35 which is selected from the group consisting of:

(a) a chimerical antibody;

(b) a humanized antibody;

(c) a single chain antibody; and (d) a Fab fragment.

42. The antibody or fragment thereof of claim 35 which is labeled.

43. The antibody or fragment thereof of claim 42 wherein the label is selected from the group consisting of:

(a) an enzyme;

(b) a fluorescent label;

(c) a luminescent label; and (d) a bioluminescent label.

44. The antibody or fragment thereof of claim 35 wherein said antibody or fragment thereof specifically binds to said protein in a Western blot.

45. The antibody or fragment thereof of claim 35 wherein said antibody or fragment thereof specifically binds to said protein in an ELISA.

46. An isolated cell that produces the antibody or fragment thereof of claim 35.

47. A hybridoma that produces the antibody or fragment thereof of claim 35.

48. A method of detecting Secreted Protein HHTLF25 in a biological sample comprising:

(a) contacting the biological sample with the antibody or fragment thereof of claim 35; and (b) detecting Secreted Protein HHTLF25 in the biological sample.

49. The method of claim 48 the antibody or fragment thereof is a polyclonal antibody.

50. An isolated monoclonal antibody or fragment thereof that specifically binds to a protein selected from the group consisting of:

(a) a protein consisting of the full-length polypeptide encoded by the HHTLF25 cDNA contained in ATCC Deposit No. 209125;

(b) a protein consisting of a portion of the polypeptide encoded by the HHTLF25 cDNA contained in ATCC Deposit No. 209125, wherein said portion comprises at least 30 contiguous amino acid residues of the polypeptide encoded by the HHTLF25 cDNA contained in ATCC Deposit No. 209125; and (c) a protein consisting of a portion of the polypeptide encoded by the HHTLF25 cDNA contained in ATCC Deposit No. 209125, wherein said portion comprises at least 50 contiguous amino acid residues of the polypeptide encoded by the HHTLF25 cDNA contained in ATCC Deposit No. 209125.

51. The antibody or fragment thereof of claim 50 that specifically binds protein (a).

52. The antibody or fragment thereof of claim 50 that specifically binds protein (b).

53. The antibody or fragment thereof of claim 50 that specifically binds protein (c).

54. The antibody or fragment thereof of claim 52 that specifically binds protein (a).

55. The antibody or fragment thereof of claim 52 wherein said protein bound by said antibody or fragment thereof is glycosylated.

56. The antibody or fragment thereof of claim 52 which is a human antibody.

57. The antibody or fragment thereof of claim 52 which is selected from the group consisting of:

(a) a chimeric antibody;

(b) a humanized antibody;

(c) a single chain antibody; and (d) a Fab fragment.

58. The antibody or fragment thereof of claim 52 which is labeled.

59. The antibody or fragment thereof of claim 58 wherein the label is selected from the group consisting of:

(a) an enzyme;

(b) a fluorescent label;

(c) a luminescent label; and (d) a bioluminescent label.

60. The antibody or fragment thereof of claim 52 wherein said antibody or fragment thereof specifically binds to said protein in a Western blot.

61. The antibody or fragment thereof of claim 52 wherein said antibody or fragment thereof specifically binds to said protein in an ELISA.

62. An isolated cell that produces the antibody or fragment thereof of claim 52.

63. A hybridoma that produces the antibody or fragment thereof of claim 52.

64. A method of detecting Secreted Protein HHTLF25 in a biological sample comprising:

(a) contacting the biological sample with the antibody or fragment thereof of claim 52; and (b) detecting Secreted Protein HHTLF25 in the biological sample.

65. An isolated antibody or fragment thereof that specifically binds Secreted Protein HHTLF25 expressed on the surface of cells in a cell culture wherein the cells in said cell culture comprise a polynucleotide encoding amino acids 47 to 111 of SEQ ID NO:235 operably associated with a regulatory sequence that controls the expression of said polynucleotide.

66. The antibody or fragment thereof of claim 65 which is a monoclonal antibody.

67. The antibody or fragment thereof of claim 65 which is a human antibody.

68. The antibody or fragment thereof of claim 65 which is selected from the group consisting of:

(a) a chimeric antibody;

(b) a polyclonal antibody;

(c) a humanized antibody;

(d) a single chain antibody; and (e) a Fab fragment.

69. The antibody or fragment thereof of claim 65 wherein said antibody or fragment thereof specifically binds to said protein in a Western blot.

70. The antibody or fragment thereof of claim 65 wherein said antibody or fragment thereof specifically binds to said protein in an ELISA.

* * * * *

UNITED STATES PATENT AND TRADEMARK OFFICE

CERTIFICATE OF CORRECTION

PATENT NO. : 7,105,644 B2
APPLICATION NO. : 09/983802
DATED : September 12, 2006
INVENTOR(S) : Rosen et al.

It is certified that error appears in the above-identified patent and that said Letters Patent is hereby corrected as shown below:

On the Title Page

Item (54) Other Publications:

"Skolmick et al." should read --Skolnick et al--.

"Genbank Accession No. AF141377 (Jan. 15, 1999)" should read --Genbank Accession No. AF141377 (Jun. 15, 1999)--.

Item (57) Abstract:

The phrase "the coding regions genes encoding" should read --the coding regions of the genes encoding--.

On Page 2

Item (54) Other Publications:

"Brakenhoff et al., "The Human E48 Antigen, Highly Homologous . . .", I. of Cell Bio., 129(6) 1677-1689 (Jun. 1995)." should read --Brakenhoff et al., "The Human E48 Antigen, Highly Homologous . . .", J. of Cell Biol., 129(6):1677-1689 (Jun. 1995).--

In the Claims

Col. 647, Line 35 In Claim 32(a), line 35, "fragment thereof of claim 26; and" should read --fragment thereof of claim 20; and--.

Col. 647, Line 48 In Claim 33(b), line 48, "amino acids residues" should read --amino acid residues--.

Col. 647, Line 54 In Claim 33(c), line 54, "amino acids residues" should read --amino acid residues--.

UNITED STATES PATENT AND TRADEMARK OFFICE

CERTIFICATE OF CORRECTION

PATENT NO. : 7,105,644 B2 
APPLICATION NO. : 09/983802
DATED : September 12, 2006
INVENTOR(S) : Rosen et al.

It is certified that error appears in the above-identified patent and that said Letters Patent is hereby corrected as shown below:

Col. 648, Line 36 In Claim 49 line 36, “method of claim 48 the antibody”

should read--method of claim 48 wherein the antibody--.

Signed and Sealed this

Twenty-ninth Day of May, 2007

JON W. DUDAS
*Director of the United States Patent and Trademark Office*

SEQUENCE LISTING

<160> NUMBER OF SEQ ID NOS: 672

<210> SEQ ID NO 1
<211> LENGTH: 733
<212> TYPE: DNA
<213> ORGANISM: Homo sapiens

<400> SEQUENCE: 1
gggatccgga gcccaaatct tctgacaaaa ctcacacatg cccaccgtgc ccagcacctg 60
aattcgaggg tgcaccgtca gtcttcctct tccccccaaa acccaaggac accctcatga 120
tctcccggac tcctgaggtc acatgcgtgg tggtggacgt aagccacgaa gaccctgagg 180
tcaagttcaa ctggtacgtg gacggcgtgg aggtgcataa tgccaagaca aagccgcggg 240
aggagcagta caacagcacg taccgtgtgg tcagcgtcct caccgtcctg caccaggact 300
ggctgaatgg caaggagtac aagtgcaagg tctccaacaa agccctccca acccccatcg 360
agaaaaccat ctccaaagcc aaagggcagc cccgagaacc acaggtgtac accctgcccc 420
catcccggga tgagctgacc aagaaccagg tcagcctgac ctgcctggtc aaaggcttct 480
atccaagcga catcgccgtg gagtgggaga gcaatgggca gccggagaac aactacaaga 540
ccacgcctcc cgtgctggac tccgacggct ccttcttcct ctacagcaag ctcaccgtgg 600
acaagagcag gtggcagcag gggaacgtct tctcatgctc cgtgatgcat gaggctctgc 660
acaaccacta cacgcagaag agcctctccc tgtctccggg taaatgagtg cgacggccgc 720
gactctagag gat 733

<210> SEQ ID NO 2
<211> LENGTH: 5
<212> TYPE: PRT
<213> ORGANISM: Homo sapiens
<220> FEATURE:
<221> NAME/KEY: Site
<222> LOCATION: (3)
<223> OTHER INFORMATION: Xaa equals any of the twenty naturally ocurring L-amino acids

<400> SEQUENCE: 2

Trp Ser Xaa Trp Ser
1 5

<210> SEQ ID NO 3
<211> LENGTH: 86
<212> TYPE: DNA
<213> ORGANISM: Homo sapiens

<400> SEQUENCE: 3
gcgcctcgag atttccccga aatctagatt tccccgaaat gatttccccg aaatgatttc 60
cccgaaatat ctgccatctc aattag 86

<210> SEQ ID NO 4
<211> LENGTH: 27
<212> TYPE: DNA
<213> ORGANISM: Homo sapiens

<400> SEQUENCE: 4
gcggcaagct ttttgcaaag cctaggc 27

<210> SEQ ID NO 5
<211> LENGTH: 271

-continued

<212> TYPE: DNA
<213> ORGANISM: Homo sapiens

<400> SEQUENCE: 5
ctcgagattt ccccgaaatc tagatttccc cgaaatgatt tccccgaaat gatttccccg 60
aaatatctgc catctcaatt agtcagcaac catagtcccg cccctaactc cgcccatccc 120
gcccctaact ccgcccagtt ccgcccattc tccgccccat ggctgactaa ttttttttat 180
ttatgcagag gccgaggccg cctcggcctc tgagctattc cagaagtagt gaggaggctt 240
ttttggaggc ctaggctttt gcaaaaagct t 271

<210> SEQ ID NO 6
<211> LENGTH: 32
<212> TYPE: DNA
<213> ORGANISM: Homo sapiens

<400> SEQUENCE: 6
gcgctcgagg gatgacagcg atagaacccc gg 32

<210> SEQ ID NO 7
<211> LENGTH: 31
<212> TYPE: DNA
<213> ORGANISM: Homo sapiens

<400> SEQUENCE: 7
gcgaagcttc gcgactcccc ggatccgcct c 31

<210> SEQ ID NO 8
<211> LENGTH: 12
<212> TYPE: DNA
<213> ORGANISM: Homo sapiens

<400> SEQUENCE: 8
ggggactttc cc 12

<210> SEQ ID NO 9
<211> LENGTH: 73
<212> TYPE: DNA
<213> ORGANISM: Homo sapiens

<400> SEQUENCE: 9
gcggcctcga ggggactttc ccggggactt tccggggact ttccgggact ttccatcctg 60
ccatctcaat tag 73

<210> SEQ ID NO 10
<211> LENGTH: 256
<212> TYPE: DNA
<213> ORGANISM: Homo sapiens

<400> SEQUENCE: 10
ctcgagggga ctttcccggg gactttccgg ggactttccg ggactttcca tctgccatct 60
caattagtca gcaaccatag tcccgcccct aactccgccc atcccgcccc taactccgcc 120
cagttccgcc cattctccgc cccatggctg actaattttt tttatttatg cagaggccga 180
ggccgcctcg gcctctgagc tattccagaa gtagtgagga ggcttttttg gaggcctagg 240
cttttgcaaa aagctt 256

<210> SEQ ID NO 11
<211> LENGTH: 1882
<212> TYPE: DNA

-continued

<213> ORGANISM: Homo sapiens
<220> FEATURE:
<221> NAME/KEY: SITE
<222> LOCATION: (12)
<223> OTHER INFORMATION: n equals a,t,g, or c
<221> NAME/KEY: SITE
<222> LOCATION: (565)
<223> OTHER INFORMATION: n equals a,t,g, or c

<400> SEQUENCE: 11
ttcggcacgg anactggaag gaaagaaaga aaggtcagct ttggcccaga tgtggttacc 60
ccttggtctc ctgtctttat gtctttctcc tcttcctatt ctgtcatctc cctcacttaa 120
gtctcaggcc tgtcagcagc tcctgtggac attgccatcc cctctggtag ccttcagagc 180
aaacaggaca acctatgtta tggatgtttc caccaaccag ggtagtggca tggagcaccg 240
taaccatctg tgcttctgtg atctctatga cagagccact tctccacctc tgaaatgttc 300
cctgctctga aatctggcat gagatggcac aggtgaccac gcagaagcca ccagaatytt 360
gcctgcccta ttcctcctcc caagtctgtt ctcttattgt caacctcagc acaacaggct 420
ggcgccaatg gcattacaga gaaagcaatc tgtgtggcta gtgggcagat taccatgcaa 480
gccccaggag aaatggagga gctttgtagc cacctccctg tcasccagta ttaacatgtc 540
cccttccccc tgccccgccg taganttcag gacattcgcc cctgtgtgcc accaaaccag 600
ggactttccc cttsssttgg gttggcatcc ctgggctctc tcctggtacc cagcaagacg 660
tctgttccag ggcagggcac gagctttcaa gctccgttac tatggcgatg gccatgatgt 720
tacaatccca cttgcctgaa taatcaagtg ggaasgggaa gcasagggaa atggggccat 780
gtgaatgcag ctgctctgtt ctccctaccc tgaggaaaaa ccaaagggaa gcaacaggaa 840
cttctgcaac tggtttttat cggaaagatc atcctgcctg cagatgctgt tgaaggggca 900
caagaaattg gagctggaga agattgatga aagtgcaggt gtgtaaggaa atagaacagt 960
ctgctgggag tcagacctgg aattctgatt ccaaactctt tattactttg ggaagtcact 1020
cagcctcccc gtagccatct ccagggtgac ggaacccagt gtattacctg ctggaaccaa 1080
ggaaactaac aatgtaggtt actagtgaat accccaatgg tttctccaat tatgcccatg 1140
ccaccaaaac aataaaacaa aattctctaa cactgcaaag agtgagccat gcctgttaac 1200
actgtaaaga atgtaacatg tgggggacac acaggggcag atgggatggt ttagtttagg 1260
attttattag tgcatgccct accctctggg cgaacgtccc ctctgaggtt ttcttctcgg 1320 tgggggggatt taacttctgt cctagggaaa acagtgtctg atgaggagtg tttccaacac 1380
aggctacatg aattccccta taccagtgcg aaagcagcca ggagtccccg ttggaaaaga 1440
acaatgccac tctcttttat gtatcttggt tctgcaactc atttgttgta agtagggtta 1500
atcgagtatc aggttcacag tatcctgccc ttattatttt atgattcact gactcaagtt 1560
ccacgaagtc cttagaaatg gacctcttca tgtaaaatat cttgagaata ataaatgtga 1620
gggaataaga aaggcaagct ttggacacag atatgatagg tgcatcagct tcggaagaga 1680
agaatgatgt gcagagtgtt aggaagacat ccgggctgct gagactcggg attagaagaa 1740
agagaggtaa ataaagtggg tcctggaatc ttttaggact tctgctgtag gacaaacagc 1800
tgcctttggt gttttaatgt ctcccaaagt acccttcagc caataaatac catctgttgg 1860
tgcaaaaaaa aaaaaaaaaa aa 1882

<210> SEQ ID NO 12
<211> LENGTH: 1590
<212> TYPE: DNA

-continued

<213> ORGANISM: Homo sapiens
<220> FEATURE:
<221> NAME/KEY: SITE
<222> LOCATION: (1374)
<223> OTHER INFORMATION: n equals a,t,g, or c
<221> NAME/KEY: SITE
<222> LOCATION: (1397)
<223> OTHER INFORMATION: n equals a,t,g, or c
<221> NAME/KEY: SITE
<222> LOCATION: (1516)
<223> OTHER INFORMATION: n equals a,t,g, or c

<400> SEQUENCE: 12
gggtcgaccc acgcgtccgg agattctggg aggatcccga gtacccccca gttgcagtca 60
tgtcaagact gatgctcagg aggatcccaa ctgtcatgag caacacccat cgaacacagc 120
catccacctg ggaacagatc aagaagctgt cacagatggt gggagaaaac ctgaggaaag 180
cgggacaacc agtcacaatg agtaatttaa tggtagctat gatagcagtg atcaccattg 240
ccgtgagtat tccttcaaca agggctgaca cagagatcag ttatacttat tgggcatatt 300
tgtcaatttt ggctggcaat aatgcctgga tataatcact ttatgacaca gttacacatg 360
ctttctggtc tcaatattta ccataataag tctgctccta taattgaggc ataccaccct 420
caaaaatcta tttgtaaaca aaattgaacc tggccagaaa aaatgaatgt actttttag 480 gaaggttgca ttgcagaaca ggcagaggtg ctgcacaacg attcctatgg aatcattatt 540
gattggtccc ctaaggggat gtttagcttg aattgcacct cttagtctgc atgtcacagc 600
cacactgtgt tcaactggtc tgaacagaat ggtcagatgg tacaaatggt aagacgtatg 660
gcaagagttc ctattatctg gaaccatggc agtatagggg cacctcaacc tcaaatgata 720
tggcccattg taggagctaa acataaggat ttgtggcaac tgttaatagc tcttaataag 780
atcaaaattt gggaaagaat aaaaaagcat ctagaaggac actctgcaaa cttgtctttg 840
gatattgcaa aatatatata tatatttaaa gcatcccagg cacacctgac cttaatgcca 900
gaactggagt gctcgaagga gctgcagaca gattagcagc tagtaaccca ttaaaatgga 960
taaaaacact tagaagctct gtgatttcaa tgatgattgt gcttttaatc tgtgttgttt 1020
gtctttatat agtctgcaga tgctgatctt gactcctgtg agaagtagct caccgtgaca 1080
aagctgcctt ggctttttat cgctttgcaa aacaagagaa tggggacaag ttgggaacag 1140
gccccaaaat ctggccataa actggcccct aaactggtca taaacaaaat ctctgcagca 1200
ctgtcacatg cttgtgatag cctgacgccc acgttggaag gctgtcggtt taccggaatg 1260
agggcaagga acaactggcc cactcagggc ggataaccac ttaaggcatt cttaaaccac 1320
aaacaatagc atgagctatc tgtgccttaa ggacatgttc atgctgcaga taantagcca 1380
gagcccatcc ctttacntcg gcccatccct ttatttccca taaggaatac ttatagttaa 1440
tctatagaaa caatgcttat cactggcttg ctgtcaataa atatgtgggt aaatctctgt 1500
tcaaggctct cagctntgaa ggctgtgaga cccctgattt cccactccac aatctaaaaa 1560
aaaaataaaa acaaaaaaaa aaaaaaaaaa 1590

<210> SEQ ID NO 13
<211> LENGTH: 1373
<212> TYPE: DNA
<213> ORGANISM: Homo sapiens

<400> SEQUENCE: 13
tcgacccacg cgtccgttca gaaaaaggat ttgacaaaat tcagtgccca ttcatggtta 60
aaaaaaaaaa aaactttcag aaaaatgata atggaggaga tctttctcaa cttgataaag 120

-continued

```
aacatctaca aaagccccta cagccaatgt aacacataat agtaaaagac taattgcttt    180
tctccaatat cagggatatt agggacagag atgtctgtcc tcaccactct tattcaacat    240
attgctggaa gttctgtcta gtgcagtgag gaaagaaaag gaattaaaaa gcatgcagac    300
aaaaagaagg aaacaaaact gtctctattt gcaaatgaca tgattctcta aataaaaaat    360
cccaaggaat ctacaaaaaa aactagagct aggtggggtg tggtggctca tgcctgtaat    420
cccagcactt tgggaggctg aattaagagg attacctaaa ccaagaagtt caagaccagc    480
ctgcgcaaca tagtaagacc cccatctcta caaaaaattg aaaaattagc tggatgtatt    540
agctactcag ggagctgagc tgggagggat tgtttgagcc agagaggtca gggctctggt    600
gatccatgat cacatcacca tactccagcc tgggcaaccg agtgagacct gtccttaaaa    660
aacaaacaaa aacaaactag atctagtgag agttcagcaa gccctcaagc tacaagacct    720
atataccaaa aatcaacttg catttctata tactattaat gaacatatgg gaaacctaaa    780
tttaaaagat agtaccactt aacaattgtt tcacaaaaat gaattacctg ggcataaatt    840
aaataaacat atacaggatc tgtatgctaa aaattgcaaa atactgataa aagaaatcaa    900
agcaaaccca aagaagtgga gacacatacc gtgttcatgt actggaaggc tcagcagaga    960
cgtgggttcc ctccagactg atgtacaggt ttgatgtact tgctagcaaa aatcccagca   1020
aggtattttt ttgtagatgc gcaagattat tctaaaattt gtatggaagg gcagtgaaac   1080
taaaagtcac gaaaataatc ttgaaaaaga aaaagaaaat gggcagaatc actgtatttg   1140
ataacatacc ttgttatata actgcagtaa tcaagacagt atagtgttgg tgaagggaca   1200
gacacaaggt caatgaaaca gaatagagaa cccagacata gacccacaca agtaccacca   1260
gtggatttgg acaaggtgca aaagcaactc attggaggaa ggcagcctat ttagccaatg   1320
tgactggagc actggatacc cataagccaa aaaaagaaaa aaaaaaaaaa agg          1373
```

```
<210> SEQ ID NO 14
<211> LENGTH: 1142
<212> TYPE: DNA
<213> ORGANISM: Homo sapiens
<220> FEATURE:
<221> NAME/KEY: SITE
<222> LOCATION: (341)
<223> OTHER INFORMATION: n equals a,t,g, or c
<221> NAME/KEY: SITE
<222> LOCATION: (369)
<223> OTHER INFORMATION: n equals a,t,g, or c
<221> NAME/KEY: SITE
<222> LOCATION: (386)
<223> OTHER INFORMATION: n equals a,t,g, or c
<221> NAME/KEY: SITE
<222> LOCATION: (408)
<223> OTHER INFORMATION: n equals a,t,g, or c
<221> NAME/KEY: SITE
<222> LOCATION: (412)
<223> OTHER INFORMATION: n equals a,t,g, or c
<221> NAME/KEY: SITE
<222> LOCATION: (526)
<223> OTHER INFORMATION: n equals a,t,g, or c
<221> NAME/KEY: SITE
<222> LOCATION: (598)
<223> OTHER INFORMATION: n equals a,t,g, or c
<221> NAME/KEY: SITE
<222> LOCATION: (676)
<223> OTHER INFORMATION: n equals a,t,g, or c
<221> NAME/KEY: SITE
<222> LOCATION: (739)
<223> OTHER INFORMATION: n equals a,t,g, or c

<400> SEQUENCE: 14
```

-continued tcgacccacg cgtccgtctt cctcctgcgt cctcccccgc tgcctccgct gctcccgacg 60
cggagcccgg agcccgcgcc gagcccctgg cctcgcggtg ccatgctgcc ccggcggcgg 120
cgctgaagga tggcgacgcc gctgcctccg ccctccccgc ggcacctgcg gctgctgcgg 180
ctgctgctct ccggcctcgt cctcggcgcc gccctgcgtg gagccgccgc cggccacccg 240
gaatgttgcc gcctgtcccg ggagcctgga ctgtgccctg aagaagcggg caagtgtcct 300
cctggtgcac atgcctgtgg gcctgccttc agcccttcca naaggaacag caaaggcttg 360
ttttgccang atgcgccggg cttcangcgg gggccgggcc caacccanac tngaaatgag 420
attgattcct ggcccaaggg agcttgcccg gaaaggaatt tggacatcaa ttccgcccta 480
acccaaggac ggacagcggt tcccggagct tgccaccttg ggattntcgg cacgggggca 540
ggggctggag ctgggcttcc cttccactcc aggaaccccc acgcccacgc cccacacnta 600
ccatgggtta cccctgtgtc atccgacccg gtgcacatgt cgcccctgga gccccgggga 660
gggcaaggcg acggcntcgc ccttgtgctg atcctggcgt tctgtgtggc cggtgcagcc 720
gccctctccg tagcctccnt ctgctggtgc aggctgcagc gtgagatccg cctgactcag 780
aaggccgagt acgccactgc gaaggccctg gctacacctg cagctacccc ggatctcgct 840
tggggaccag cgcctggcac agagcgcgga gatgtaccac taccagcacc aacggcaaca 900
gatgttgtcc ctggagcggc ataaagagcc acccaaggag ctggacacgg ctcttcggat 960
gaggagaatg aggacggaga cttcacggtg tacgagtgcc cgggcatggc cccgaccggg 1020
gaaatggagg tgcgcaacca tctgttcgac cacgccgcac tgtccgcgcc cctgccggcc 1080
cccagctcac cgcttgcact gccatgacct ggaggcagac agacgcccac ttgctccccg 1140
ac 1142

<210> SEQ ID NO 15
<211> LENGTH: 1034
<212> TYPE: DNA
<213> ORGANISM: Homo sapiens

<400> SEQUENCE: 15
gaattcggca cgaggaacca ccttctgtag gacagtcacc aggccagatc cagaaggctt 60
gaggccctgt ggtccccatc cttgggagaa gtcagctcca gcaccatgaa gggcatcctc 120
gttgctggta tcactgcagt gcttgttgca gctgtagaat ctctgagctg cgtgcagtgt 180
aattcatggg aaaaatcctg tgtcaacagc attgcctctg aatgtccctc acatgccaac 240
accagctgta tcagctcctc agccagctcc tctctagaga caccagtcag attataccag 300
aatatgttct gctcagcgga gaactgcagt gaggagacac acattacagc cttcactgtc 360
cacgtgtctg ctgaagaaca ctttcatttt gtaagccagt gctgccaagg aaaggaatgc 420
agcaacacca gcgatgccct ggaccctccc ctgaagaacg tgtccagcaa cgcagagtgc 480
cctgcttgtt atgaatctaa tggaacttcc tgtcrtggga agccctggaa atgctatgaa 540
gaagaacagt gtgtcyttct agttgcagaa cttaagaatg acattgagtc taagagtctc 600
gtgctgaaag gctgttccaa cgtcagtaac gccacctgtc agttcctgtc tggtgaaaac 660
aagactcttg gaggagtcat ctttcgaaag tttgagtgtg caaatgtaaa cagcttaacc 720
cccacgtctg caccaaccac ttcccacaac gtgggctcca aagcttccct ctacctcttg 780
gcccttgcca gcctccttct tcggggactg ctgccctgag gtcctggggc tgcactttgc 840
ccagcacccc atttctgctt ctctgaggtc cagagcatcc cctgcggtgc tgacaccctc 900
tttccctgct ctgccccgtt taactgccca gtaagtggga gtcacaggtc tccaggcaat 960

-continued

```
gccgacagct gccttgttct tcattattaa agcactggtt cattcactga aaaaaaaaaa   1020

aaaaaaaaac tcga                                                     1034


<210> SEQ ID NO 16
<211> LENGTH: 1198
<212> TYPE: DNA
<213> ORGANISM: Homo sapiens

<400> SEQUENCE: 16

cccacgcgtc cgggagaaag ctgcactctg ttgagctcca gggcgcagtg gagggaggga     60

gtgaaggagc tctctgtacc caaggaaagt gcagctgaga ctcagacaag attacaatga    120

accaactcag cttcctgctg tttctcatag cgaccaccag aggatggagt acagatgagg    180

ctaatactta cttcaaggaa tggacctgtt cttcgtctcc atctctgccc agaagctgca    240

aggaaatcaa agacgaatgt cytagtgcat ttgatggcct gtattttctc cgcactgaga    300

atggtgttat ctaccagacc ttctgtgaca tgacctctgg gggtggcggc tggaccctgg    360

tggccagcgt gcatgagaat gacatgcgtg ggaagtgcac ggtgggcgat cgctggtcca    420

gtcagcaggg cagcaaagca gactacccag agggggacgg caactgggcc aactacaaca    480

cctttggatc tgcagaggcg gccacgagcg atgactacaa gaaccctggc tactacgaca    540

tccaggccaa ggacctgggc atctggcacg tgcccaataa gtcccccatg cagcactgga    600

gaaacagctc cctgmtgagg taccgcacgg acactggctt cctccagaca ctgggacata    660

atctgtttgg catctaccag aaatatccag tgaaatatgg agaaggaaag tgttggactg    720

acaacggccc ggtgatccct gtggtctatg attttggcga cgcccagaaa acagcatctt    780

attactcacc ctatggccag cgggaattca ctgcgggatt tgttcagttc agggtattta    840

ataacgagag agcagccaac gccttgtgtg ctggaatgag ggtcaccgga tgtaacactg    900

agcaccactg cattggtgga ggaggatact ttccagaggc cagtccccag cagtgtggag    960

atttttctgg ttttgattgg agtggatatg gaactcatgt tggttacagc agcagccgtg   1020

agataactga ggcagctgtg cttctattct atcgttgaga gttttgtggg agggaaccca   1080

gacctctcct cccaaccatg agatcccaag gatggagaac aacttaccca gtagctagaa   1140

tgttaatggc agaagagaaa acaataaatc atattgactc aaaaaaaaaa aaaaaaa      1198


<210> SEQ ID NO 17
<211> LENGTH: 1447
<212> TYPE: DNA
<213> ORGANISM: Homo sapiens
<220> FEATURE:
<221> NAME/KEY: SITE
<222> LOCATION: (1420)
<223> OTHER INFORMATION: n equals a,t,g, or c
<221> NAME/KEY: SITE
<222> LOCATION: (1432)
<223> OTHER INFORMATION: n equals a,t,g, or c
<221> NAME/KEY: SITE
<222> LOCATION: (1436)
<223> OTHER INFORMATION: n equals a,t,g, or c

<400> SEQUENCE: 17

caagcgcgca agggcgcggg cgagcaggcc tgtgaattcg caggatcatt tcagacccgc     60

acttcggcag ccaactcgaa agcaggcggt tgtgtgcggc agcagttggc gtttgctttg    120

cacttcggaa cctgttgcgt tttgacccac ggaggtggag gagtaacttt ttgacatgtt    180

ggcctttcca gttttgttgg aagtttcatg gtcggttttg tttygtttct cattcttctc    240
```

-continued

```
tccksgcccc tcagcccccc aacccccaac cccctcccgg tccgtgttgc atgcacgctg    300

ttcaaatgtg aggtctgaaa tggctggcac acgggaaaag ctgcttgtgt cattcgtttc    360

tgggagtggg atggctctga gcagcctcgc ctccctgttt gtactatttg aactttgcag    420

atctctgttc tctcaagcag aactcccaac cagatccatt cttgaccagt gaccggctcg    480

gaatctggcc ttttgtgtga gatgatcacg gtttcttttg tttatcacgc catttgcaaa    540

tcagagcaag agctctttct caagggcaag aaacgcaaac aagaaatatt tgtgagatga    600

aagttgtcaa ttggattttc ttcctaaaca aacaacaaca acaaactact agaagtctcc    660

ctgagtccac tcgcttggat ttctgacaca gtttacaaaa aaggaaaaag gcactgctcc    720

tattttccct tatggctgag ttcaccttaa gattgtaaat gtgtatatgt cagtgaaaac    780

attgaggctt ggaaaatgtg ttattttcgt tgccctaagt ttgagtcgac tttagactca    840

aaaacatttt gagcgaatat caaagttaac ttttaaaaat tgcgaaacta tttcagaatc    900

gcaattttat cgaagattaa atcagacttt tttgtctggt aattatatat ttattattta    960

gcaaaactga agaaaaaaag cacagaattg tttcaacaga tgtctctcat tttcagctag   1020

catttctctc ccaagttgag ctggtttaat gtgttttgga tttccctcct caattggctt   1080

attttttaga tcacctgcaa ttcatttgca aattgcaata aaacacattt tagaaaaaag   1140

gaaccttcaa ttattagctt tgtttctttt taaatgtata taaaaagact aatgtttgtg   1200

aatgaagttg gctaacatgt atttagtttc attttggctt tatgtaatat aaagttttta   1260

aaattttaaa tatggtttta acctttatgt gtaaatgatt ttctagtgtg accttctaat   1320

ttaatattag acgtctaagg tatatctgta aattagaatc cgactatcac tctgttcatt   1380

ttttttgaac aaagagttta aataaagcct gaaccagggn acagataaag anaatnaaaa   1440

aaaaaaa                                                              1447
```

```
<210> SEQ ID NO 18
<211> LENGTH: 1422
<212> TYPE: DNA
<213> ORGANISM: Homo sapiens
<220> FEATURE:
<221> NAME/KEY: SITE
<222> LOCATION: (1397)
<223> OTHER INFORMATION: n equals a,t,g, or c

<400> SEQUENCE: 18

gtttctctta ggttttgaag gtataagtgt aaagtgaagc atctctcgat gattctttcc     60

aagataggtt taaaaactat gaatccattt tcagtattty cttctctctg tttgaaacag    120

tttgaggatg tgtytctttt tcttggcttg atgtttggta sgtccttgaa tgggcaagag    180

ggcacatgaa gtacggcgtc ctccacattc acggcctcta cacgggaccc ctgcggggtg    240

ggtgctggac ccatcggggt ataaagacgt cactcaagac gcagaagtca tggaagtcct    300

ccagaactta taccgcacca agtcctttct gtttgtgggc tgtggggaga cccttcgtga    360

tcagatattc caggccctct ttctttactc cgtgccgaat aaggtggatt tggagcacta    420

catgcttgtg ctgaaggaga atgaagacca tttctttaag catcaggcag atatgcttct    480

gcacggaatc aaagttgtat cctacgggga ctgttttgac cactttccag gatatgtgca    540

agaccttgcc actcagatct gcaaacagca aagcccagga catttgtact cgaattcatg    600

gagtgccact cctgatggga gaggaggccc atgacagtga cagtcatgct agtgatcgcg    660

gacaccacac catgctgcct ttgccagctg gctccttcag cgagtcctcg caccaagcct    720

gggaggtaga gatgctgatc gcgtggacag caccacatta ttgggtaatg catgccagga    780
```

-continued

```
ctgtgcaaag aggaagttag aagagaatgg aattgaagtt tcaaaaaaac gcacacaatc    840
agatactggt gtctgtgcca tcctcatgct cgcgggagtt ttggcatggg attctccgtt    900
gtgattcccc cggactccac tgtctgaaga ccaggtttcc tatgaagagg gtctgatggg    960
aacctgttcc cagtgatttg aagatgatgc tggagggtct tgaaatcttt acagtaaaac   1020
ctgcaacttg aaaactagcc tttctgtaac cacagtgccc aaacgaagag gaatgtatgg   1080
agaactccac gtggatctct gattgggaaa ccgtcacata caccaagaga gccacatggg   1140
catgtggccc tcaaggctgg gtgagagggc tcccctgtgt gttgaactat gcaggagggt   1200
gacgcggaca catttcaggt ggactttgca aggactgatg gatagctacc tcagggacca   1260
gaatccgtgg gaagggatgg acctggtgtt cccgttccca tctgacaggc tctcttttgt   1320
ccaaggtggt atttttcgta ataaaagggg aagagtaaar amwrwmmaar maamagtagc   1380
tgccaaagag aaaatangaa atagacactt tttttttttg gg                      1422
```

<210> SEQ ID NO 19
<211> LENGTH: 1107
<212> TYPE: DNA
<213> ORGANISM: Homo sapiens

<400> SEQUENCE: 19

```
ctaaactatt tagttcaaaa gtaacccaac taattaaagt gaaaaaaaat tgttgaatca     60
caatgaacaa acataaaaca atacttaaat gagaattctg tgtctttttt ggttttatct    120
gtgatttatt ttgtccagta ttaaggaatg gttatcttta tcattcttct aacatgtttt    180
ggtttctcta atggttcatt ttcctttagc ttgtgaaaat tagggcagtt tgtccagagc    240
cttactcgca ggagacacca gacccaaccc atgcttagat ttctgttaat aaaagggaga    300
agggtatttg aataggtagt aaaggcaggt acaagtttaa gggagcaggg ctatcatatg    360
tactaggtga gattactata aatgtctgaa aagttacatg catagtcatt ggctcaggta    420
atttctctga atttgaactt atttgattta tttaaccaag ttattataat atgcagttct    480
ctttaatcaa tcttctatta ttcaatcatc tatccattta ttaattcaac aaatatttat    540
taaagtgcct accatgatta tgtgctgtag aaaagacaag gacatttact agggggggatt    600
gtgggcccaa tcggcatcat aagcatgttc tgaaagccaa agacaataat cacatccaac    660
ggcaccagtt cagctcaact ttagaattca gcagtaacag tacagatggc ctaaagtaca    720
tctgtgtgta tctgtacgtg tgcacacacc catgtatata tatttatcta tctgcacaca    780
cactacatat gtatacacac tatctatgta aaatataata tatgtataat gcatataaat    840
tctaacaagt gtatttgtgt tatctttaaa atagaacaat tgtatcttga agtggtaaat    900
gcagagaatt ggttttattg ttgatctgtg gatttaatga tttctaggtg aaaaggacgt    960
ttaagtgtac aatttctttt cttaatttaa tatatttatg taaatgcatg cctgaaattt   1020
ggttagattg gctgtgtttt gtgtctttta acatgatcaa atgattaaac tttatgctta   1080
tgacttgaaa aaaaaaaaaa aaaaaaa                                       1107
```

<210> SEQ ID NO 20
<211> LENGTH: 1183
<212> TYPE: DNA
<213> ORGANISM: Homo sapiens
<220> FEATURE:
<221> NAME/KEY: SITE
<222> LOCATION: (266)
<223> OTHER INFORMATION: n equals a,t,g, or c
<221> NAME/KEY: SITE -continued
<222> LOCATION: (426)
<223> OTHER INFORMATION: n equals a,t,g, or c
<221> NAME/KEY: SITE
<222> LOCATION: (1170)
<223> OTHER INFORMATION: n equals a,t,g, or c
<221> NAME/KEY: SITE
<222> LOCATION: (1178)
<223> OTHER INFORMATION: n equals a,t,g, or c

<400> SEQUENCE: 20
gtgattcaaa gccatcacaa aacactataa gactgaccaa aatttagata acctttgaac 60
cacgattttt ttccacatct gtytgtgaga cacagcgcaa tgctactgcc cttccagaaa 120
ctgtgctaaa aagagaaagt ccaaaagact ctaaacaaaa acctcgacgc cgttgaggat 180
gtgtttcatt ctggtggtct gttttgcaag cttgataaca gaatgtccgt gccattgtaa 240
atgttgtaga gatgtgggcc gtggcncaac cgtcctatat gwgtgtagca tggtacagaa 300
caaactgctt acacaggtct cactagttag aaacctgtgg gccatggagg tcagacatcc 360
atcttgtmcm tctataggca agaagtgttt ccagatcctt tggaaaggtg ggcatggggc 420
aggtsnttgg agagtggcgt ttgagcagag cgaccccatt tccgtgtgaa ccataggcac 480
aacccaggaa gtttccccac ttgtaggagt gtgggtattc cagagcaaga ctgtggccac 540
catcttcccc tcttggtgtt ttccgaaagt gacagtgttg gtcatcccat gaccactgaa 600
gcttagtaac cagcgccaaa aagtagattc atcaaactag agaccccagc tcccc ttctc 660 gccatcttct ttctcaagtt gaccgtggtg ctgtttctgg aaggcatctg caactccaag 720
tccatgcaga actctggaag gccaagttca tcgcagcatg ttcaccatat cccagcctcc 780
aaatctatcc tcctaccttc caacgcatga cctgttgggg agcagagact taaccccaa 840 ctcagaggaa cccttcctcc agcgtctttg gcatggtttc tagggtgaga gttcccaatt 900
tggatagaac ggccaccata ttggttactg aatctctctc ccttgttttt attacgtttc 960
ctttttcaaa ctgtccatgg gaaggctgaa ttgagtgact ccccagaatg aagatgagaa 1020
ggtgaatata atcaatgcca atgtaatgcc agcgggtgar gatggccgat ggraggtttt 1080
caaagatgta gctagcattt tggaaaccat atgggcaaaa cccgggcaac cagagggggg 1140
aacaggttaa gggaccgttt cccaggaaan tccccaantt ttt 1183

<210> SEQ ID NO 21
<211> LENGTH: 1420
<212> TYPE: DNA
<213> ORGANISM: Homo sapiens
<220> FEATURE:
<221> NAME/KEY: SITE
<222> LOCATION: (524)
<223> OTHER INFORMATION: n equals a,t,g, or c
<221> NAME/KEY: SITE
<222> LOCATION: (585)
<223> OTHER INFORMATION: n equals a,t,g, or c
<221> NAME/KEY: SITE
<222> LOCATION: (596)
<223> OTHER INFORMATION: n equals a,t,g, or c
<221> NAME/KEY: SITE
<222> LOCATION: (1042)
<223> OTHER INFORMATION: n equals a,t,g, or c
<221> NAME/KEY: SITE
<222> LOCATION: (1062)
<223> OTHER INFORMATION: n equals a,t,g, or c
<221> NAME/KEY: SITE
<222> LOCATION: (1144)
<223> OTHER INFORMATION: n equals a,t,g, or c
<221> NAME/KEY: SITE
<222> LOCATION: (1171)
<223> OTHER INFORMATION: n equals a,t,g, or c
<221> NAME/KEY: SITE -continued
<222> LOCATION: (1286)
<223> OTHER INFORMATION: n equals a,t,g, or c
<221> NAME/KEY: SITE
<222> LOCATION: (1350)
<223> OTHER INFORMATION: n equals a,t,g, or c

<400> SEQUENCE: 21
gtctgcatcc cgggcgcggc tgggttgagt gttctcttag gaatggtgga gaactgggtc 60
cttgaggagt caccggggag actgctcgca ctgtttgtgg tgcgacgggc actggcccag 120
ggacagaggg aagagaaggg ccagccagcg gcagtggagt cggcaggctg gctgcccact 180
cgctttctct cctcacaaga ctcgcttccc ctgtcttcga ggatctcgaa cggactatag 240
tctggactcg ctgggctgga ggaaacttgg ccgctggcca cccggaggag actgaaaatc 300
ctttggtcaa cagggcgcct ttccttgaac caaaacaaaa ctttccgaag ccggaaagga 360
aacgcccagt gtcgcctgag agccctggag ctgcgcgaga cccaggcact gagtgcggcc 420
tcggcctctg acctctaaca cgccgggaac aaaccatctg ggcggcccg caggcctgcg 480
ggagcggaat gtgacccgaa accgaccgac ttcctgaccc atantccata gttctcttca 540
gcaacttgaa cattttggaa aaagaaacaa tcttaacatg ccacnaccta atgganaaac 600
taaatcccct tcctacacct tgctttccaa aagttaaaaa aaaatagtta aacgctatta 660
gaggtctcaa gttcactgtc accagatcag ctaggtccag aatcttcagt tcttgaagcc 720
aagccctaca aatagattta ttgtagcata tcacacctct tcaggtgact taaaacaatg 780
agaattcatg agaaattatc ttcatcctca agtaaaaatc atgaggtgcc tttcacatgg 840
atgaaattgt aagtgcttgt tgaacaagga ataattggat aatggtattg tggtcatact 900
ttttaagaat atctgttaga aagatatagg atgcagaaca tctaggattt gctgaaagtc 960
atttattatg gatagggggt atgagtaagt tcatagatga aaagggatga aacaagattg 1020
gccatagttg ctctattttt gngtatcttg tttctttatt tngtttcttt aaaaagtcct 1080
catatcactg acatttacac ttagttttag ggaaagtcaa atttagaaat aagctacagc 1140
tctntaagct atcggtctaa ctggattttt ntcgatgctg aagaactttt taaaaaattc 1200
agccatttag gtcacacagc aaatacattt ggcattaaat tcctagtatc actaaagtac 1260
tccctcccac cgccgcgccc cccccnttcc ccccgcaccc ttagacctgg gcaagagaga 1320
cttctatcct ggactccatg ctttaaaggn acttacatat cacacacaca cattaattta 1380
aaaaggaaaa aaaaaaaaaa aaaaaaaaaa aaaaaaaaaa 1420

<210> SEQ ID NO 22
<211> LENGTH: 1575
<212> TYPE: DNA
<213> ORGANISM: Homo sapiens

<400> SEQUENCE: 22
gtccattctt ccggtggaga tggctgcggc cgtggcgggg atgctgcgag gggtctcct 60
gccccaggcg ggccggctgc ctaccctcca gactgtccgc tatggctcca aggctgttac 120
ccgccaccgt cgtgtgatgc actttcagcg gcagaagctg atggctgtga ctgaatatat 180
ccccccgaaa ccagccatcc acccatcatg cctgccatct cctcccagcc ccccacagga 240
ggagataggc ctcatcaggc ttctccgccg ggagatagca gcagttttcc aggacaaccg 300
aatgatagcc gtctgccaga atgtggctct gagtgcagag gacaagcttc ttatgcgaca 360
ccagctgcgg aaacacaaga tcctgatgaa grtcttcccc aaccaggtcc tgaagccctt 420
cctggaggat tccaagtacc aaaatctgct gcccctttt gtggggcaca acatgctgct 480

-continued

```
ggtcagtgaa gagcccaagg tcaaggagat ggtacggatc ttaaggactg tgccattcct    540
gccgctgcta ggtggctgca ttgatgacac catcctcagc aggcagggct ttatcaacta    600
ctccaagctc cccagcctgc ccctggtgca gggggagctt gtaggaggcc tcacctgcct    660
cacagcccag acccactccc tgctccagca ccagcccctc cagctgacca ccctgttgga    720
ccagtacatc agagagcaac gcgagaagga ttctgtcatg tcggccaatg ggaagccaga    780
tcctgacact gttccggact cgtagccagc ctgtttagcc agccctgcgc ataaatacac    840
tctgcgttat tggctgtgct ctcctcaatg ggacatgtgg aagaacttgg ggtcggggag    900
tgtgtttgtc acttggtttt cactagtaat gatattgtca ggtatagggc cacttggaga    960
tgcagaggat tccatttcag atgtcagtca ccggcttcgt ccttagtttt cccaacttgg   1020
gacgtgatag gagcaaagtc tctccattct ccaggtccaa ggcagagatc ctgaaaagat   1080
agggctattg tcccctgcct ccttggtcac tgcctcttgc tgcacgggct cctgagccca   1140
ccccttggg gcacaacctg ccactgccac agtagctcaa ccaagcagtt gtgctgagaa   1200
tggcacctgg tgagagcctg ctgtgtgcca ggctttgtgc tgagtgctgt acatgtatta   1260
gttcctttac tgctgaccac attgtaccca tttcacagag aaggagcaga gaaattaagt   1320
ggcttgctca aggtcatgca gttagtaagt ggcagaacag ggacttgaac caagccctct   1380
gctctgaaga ccgcgtcctg aatttcttca ctagagcttc ctcatcaggt tacccagaag   1440
tgggtcccat ccaccatcca ggtgtgcttg gatgttagtt ctccaccctc gaggtgtacg   1500
ctgtgaaaag tttgggagca ctgctttata ataaaatgaa atatattcta maaaaaaaaa   1560
aaaaaaaaaa ykcga                                                    1575
```

<210> SEQ ID NO 23
<211> LENGTH: 541
<212> TYPE: DNA
<213> ORGANISM: Homo sapiens

<400> SEQUENCE: 23

```
caggagcaag gctttgtgct atatctacat aatcttagac cctgttcctt ccaattccag     60
ggatatgctc ttaaccactg cagtataagc ctcccccgcya cactctgagt ggagcagagg    120
aaggtgtttt tgtctttgag aaaggcaagg atgaagggca agatttgagc catggtggta    180
gatcagaaag aagatctgat aacaggctta gggatcaaaa tggtaaggaa atggcttcag    240
gggagtcagg cctggcccct ggagagggag gagagggaag ggctaggctc tttatgtaca    300
tgctgtccat ggggcctggt aagattcmtg gaatcactaa cccatttcac aggtgaggca    360
attgagcctc tcagagctga agtaactgac ccaaagcatc cgtgctcttg tgtggcagag    420
ccagaagtca aatccaggtc tctgtgamct caaggggcac caaartgagt atcaaaaagg    480
cagaaaggga cttatccctt cactcactca gcaaaagcat agtaagcagg tggcgtgcct    540
t                                                                     541
```

<210> SEQ ID NO 24
<211> LENGTH: 833
<212> TYPE: DNA
<213> ORGANISM: Homo sapiens

<400> SEQUENCE: 24

```
gatcttgtcc aagcagtcgg ggctacttcc aagaatgtca gctcctgtta gcaaccagtg     60
gagtctggcc ttgggctcta agttgacctc tctatagctc caaatcctac caatctcaga    120
```

-continued

```
aaactgtaag aggcacagat gactccacca gctgcagagt gactctgaag agagtcttca    180
cttactgcac aggcaaagaa aggcacagga atatttccta cctctccctc ctgtgagtcc    240
cacctccccc cacccccatc tccaggaggc aggtagagca gttctraccg agaggataga    300
ctgctgttgc tgtctttccc cagctctgaa ctagttttaa ggtagcttag gatgaaaaat    360
ggagaatgat tggggggttcc aaaccacttt yttctccctt ggcttatatc tcttcaccat    420
ttggtggtca actgtgggsc taccctggac ctcatctact cagcgagaat tggacatgaa    480
gctagaggca gctgccttgg aagggaagtm aggctcactt ggacagccca ggccatggca    540
ggaagaatcc cttcctcttg gggtccttga tgggcatgtg tgatggggaa ggagcagtct    600
cccagccctg ggtctgctcc ccacatctct cctaattcca cttcaccttt tgccaccccc    660
tccccaccag aggcctagcc cttttgtcac cgaaggcccc cagagtgttt ctgtgtgaaa    720
ccctctcatt tacactgtgg catcaaaatc cacaaaagat ggattaattg cactctggtt    780
aatagcagca gcacaatgat taaaatctat attcctaaaa aaaaaaaaaa aaa           833
```

<210> SEQ ID NO 25
<211> LENGTH: 1555
<212> TYPE: DNA
<213> ORGANISM: Homo sapiens
<220> FEATURE:
<221> NAME/KEY: SITE
<222> LOCATION: (1248)
<223> OTHER INFORMATION: n equals a,t,g, or c
<221> NAME/KEY: SITE
<222> LOCATION: (1389)
<223> OTHER INFORMATION: n equals a,t,g, or c
<221> NAME/KEY: SITE
<222> LOCATION: (1391)
<223> OTHER INFORMATION: n equals a,t,g, or c
<221> NAME/KEY: SITE
<222> LOCATION: (1393)
<223> OTHER INFORMATION: n equals a,t,g, or c
<221> NAME/KEY: SITE
<222> LOCATION: (1396)
<223> OTHER INFORMATION: n equals a,t,g, or c
<221> NAME/KEY: SITE
<222> LOCATION: (1551)
<223> OTHER INFORMATION: n equals a,t,g, or c

<400> SEQUENCE: 25

```
ggcacgagct gggcagatgc aaaatctgga gagcgcgagg gccgggcggt cagtcagcac     60
ccagactggc agcatgaccg gtcagatacc aaggctttct aaagtcaacc ttttcactct    120
gctcagcctc tggatggagc tctttccagc agaagcccag cggcaaaaat ctcagaaaaa    180
tgaagaggga aagcatggac ccttaggaga taatgaagag aggaccagag tatctactga    240
caaaagacag gattactggg agcagctaag atgcctarat gaaaggttta ccatcactgc    300
tggttaggaa atggattatg agaactcgaa cagagggaag gtgaaatgca accggaggaa    360
acactctgat atgaggtttg aggccttcaa aattgctttg cagcataagc cacagtgagt    420
caggagtacc agggagtgga tagaatgttt atttgtttaa ctgagacttt ttagttcatc    480
aattattttg aagggtagaa cactctgtgg gctctctttc tatttccttc tgggtacaat    540
cacaaaaaaa aaatctctcc tagctgaaat tacatgcagt actagcaaag ggtctctttg    600
ttataaactg ttcattaatt gacgaacatt tgtgtactta actatgtata aggcatctca    660
tcgttcaatt tcaaatacaa attaaaatat tttttcacat ttgttatcct gttatgtttt    720
ctcttttaca aattgtctgt tcgtatcttt ttgtctctct ttaggcctta ttcttgtcaa    780
ttcatatgtg ctctaatgaa ttgaaatatt ttctgtatat taaacattac taacctttcc    840
```

-continued

```
tctgtcacac tgattgaaaa atgatctatt tagtttgttg ttttgtcttt aattttgtaa    900

gctttaaaaa gttaatattg cccttcagac accatcccaa catcacataa gaattttttc    960

atgttataaa ttctttgtgg acatatttga taactgtttt attatgagga ggaccataat   1020

taattcaacc attcccctat tttggtcatt taggtttttg ggtttgggtt ttttgtttgt   1080

ttaacgtctt tgcttgctat tttaaagaat gctgcactaa atgtgaatgc ttgagatttc   1140

ttctctgtat ttagaatatt ttcctagaat ggattctcag aagaattctc agtctgtgga   1200

gaggaacatt tttaatgcat ggaagagctg gagtgaaccg aatttcanac tgccctgctg   1260

atccagaaat aagtttgctt acggaggctt ctagttctga agatgcaaag ttagatgcca   1320

aagcagtgga aagattgaag tcaaacagtc gggcccatgt gtgtgtctta cttcaacctt   1380

tggtgtgtna nanggngcag tttgtagagg agacctctta caaatgtgac tttattcaaa   1440

aaattacaaa aacattgccg gatgctaaca ctgactttta ttatgaatgt aaacaagaaa   1500

gaataaaaga atatgaaatg ttaaaaaaaa aaaaaaaaaa aaaaaaaaaa naaaa        1555
```

<210> SEQ ID NO 26
<211> LENGTH: 1543
<212> TYPE: DNA
<213> ORGANISM: Homo sapiens
<220> FEATURE:
<221> NAME/KEY: SITE
<222> LOCATION: (69)
<223> OTHER INFORMATION: n equals a,t,g, or c
<221> NAME/KEY: SITE
<222> LOCATION: (717)
<223> OTHER INFORMATION: n equals a,t,g, or c
<221> NAME/KEY: SITE
<222> LOCATION: (899)
<223> OTHER INFORMATION: n equals a,t,g, or c

<400> SEQUENCE: 26

```
gagcgggata acaatttcac acagggaaca agctatgacc atggattacg ccaagcttgg     60

aattaaccnt cactaaaggg aacaaaagct gggagctccc accgcggtgg cggccgttct    120

agaactagtg gatcccccgg gctgcaggaa ttcggcacga gccgaacagt aggacatgtc    180

atggcatttt tgctcaccct tgttccactc ctccccagcc gttgtcttgg tttggaggag    240

atggcagttc ctaattccac ctgtattagt ccattctcat gctgctatgg ataaatatct    300

aagactgggt aatttataaa ggaaagaggt ttagttgact cacagttctg catagctgag    360

gagacctcag gaaccttata atcatggcaa aaggcaaagg agaagcagac aggacagagt    420

gaatgccagc aggagaaatg ccagacgctt ataaaaccat caaatcttgt gagaactctt    480

cactatcata agaacggcat ggggaaaact gcccccatga ttcagttacc tccacctggt    540

cccacccttg acatgtggga attattacaa ttcaaggtga gatttgggtg gggacacaca    600

gccaaatcat atcaccatcc cttgaaccaa aacgaacaag gctgacctta tttgcaacat    660

tctaacttgt ctaaaggctg cctgaagaat tgatccctga ttcacctaac tcagatntct    720

gctaggagac aagcatggcc ttaatctcag atgaggagaa gcagtagtca tggctcagaa    780

agctgcagag agaccctaca gattcctggg gcaaaagatt ataggtggag acatatgaca    840

gaccatcaag accccacaaa gatctcttgg gaaatttaag acaattaaaa gcagccatnt    900

atacagagat tcaaaaaacc acaaacaggt ccaggcaagg atgcatgctc agtaaagacc    960

tgagaagacc tttagctttc tctttgatgt gatctcaaaa ttcagaagca aggccaagat   1020

aattaggaaa ggacttccat ggcaaagagc cagtctacag agaatgggag aagtagctgt   1080

ttttcttttt gttttcaaat ccccaacata actattgtga atttaaaatc ccaaaatcac   1140
```

-continued

```
aatgcataaa aagaaacgga aacatggacc attcaataat aataataaat tggcagaaac   1200

tatccctgaa aaaatacagg tatcagactt actagaaaaa gattttcaaa caatgtttta   1260

aatatgttca aacagtaaag aacaacatgg acagagacct aaaggaaatc aggtaaatta   1320

tatgaacaaa ggggaatttc aacagagata gacattatta aaagaaccaa ccagaaattc   1380

tggaaatgaa aaatataatg ggcacactgg ggatagtcaa acttaaaaat tcactagagg   1440

gattcaatag cagacttgga cagaagaaag aataaacaag cttaaagata acttatttga   1500

aattatctag tatgaggtac aaaaaaaaaa aaaaaaaaaa aaa                     1543
```

<210> SEQ ID NO 27
<211> LENGTH: 1262
<212> TYPE: DNA
<213> ORGANISM: Homo sapiens
<220> FEATURE:
<221> NAME/KEY: SITE
<222> LOCATION: (621)
<223> OTHER INFORMATION: n equals a,t,g, or c
<221> NAME/KEY: SITE
<222> LOCATION: (641)
<223> OTHER INFORMATION: n equals a,t,g, or c
<221> NAME/KEY: SITE
<222> LOCATION: (722)
<223> OTHER INFORMATION: n equals a,t,g, or c
<221> NAME/KEY: SITE
<222> LOCATION: (723)
<223> OTHER INFORMATION: n equals a,t,g, or c
<221> NAME/KEY: SITE
<222> LOCATION: (726)
<223> OTHER INFORMATION: n equals a,t,g, or c
<221> NAME/KEY: SITE
<222> LOCATION: (730)
<223> OTHER INFORMATION: n equals a,t,g, or c
<221> NAME/KEY: SITE
<222> LOCATION: (1259)
<223> OTHER INFORMATION: n equals a,t,g, or c
<221> NAME/KEY: SITE
<222> LOCATION: (1261)
<223> OTHER INFORMATION: n equals a,t,g, or c

<400> SEQUENCE: 27

```
ggcaccagaa aaaaaaaaga taatccaaag aatttaaatt gtaatcatgt ttcatgtatt     60

tgttttatta cttactttta tagcacttag tcccagtggt attagactgc tatttggttt    120

catacaaaaa ggattaaatt taaattcatt catgtttaga cttgagttat tacattttta    180

aaactatcat cttgccttta atgtttgtgg tcctacacaa actattagta catttcagta    240

tcctcttacc cctttgtttt taagtttttg attgctaaag caagactttt ttcttctaga    300

atttaagtca accaagtgtt atctatgttg taaaaatgga taatagtaga ttttaggtga    360

taaaacaact tgttagtaag acatttccta gcttaaaaaa aaaaatcaaa aattccatga    420

tagaaatgca gacctgtgag ggaaactcct gaaaagcata agaagcatcc cagagagcca    480

tgggttttct agaccagaga atttagaggg agattgtgga actgaggctt aggtggtcag    540

atcgtttccc ttatcactgt aatattttct gggggaaaaa tgctttctga gttgtttaaa    600

caagcatcct tacatttttt ntttaattaa aacagcctgt ntagggcttg ggattcccta    660

atactacagt agcagtatat gaatatgatt ttgtgattgt gttttttaaa agataagtaa    720

tnngangaan tgttcttttg cagtcagaaa acactcacaa aaagacaaaa aaagttccac    780

agtattatat ttcatgtcag ttcaggccta aaatcctttg caaataagat gtttataggc    840

tggtcacaat taacaatgtt attattggca gcacttcttg gatggatacc ttttgggacc    900

tttcattaga aagagggaaa gaatggggtg gttttgtatg ggctcctgtt tggggtaaaa    960
```

-continued

```
atagcagagt cagttgctga ggaccaatga cctttcctta taaacattta gtttcatacc   1020

catattaggt cttgtcttga ggacccttta tatgtgcttg tttactagtg gccttccagc   1080

catagcattc ttaccttttt ttcctattct aagaattaaa aaaaaaaatt atagagccag   1140

caagggagga ggcaggaaac agaaatcgaa tttcatcatt ccagtatagt tgtccctttt   1200

tttgtatttc tgacttggtt ttataattat atttacttac taaaaaaaaa aaaaagggna   1260

na                                                                  1262
```

<210> SEQ ID NO 28
<211> LENGTH: 753
<212> TYPE: DNA
<213> ORGANISM: Homo sapiens

<400> SEQUENCE: 28

```
ggcacgaggt gatgacttca ctcccaattc tggcatttgg ggctgtctat tggccagacc     60

ttgcttcaca tagtttctca ccctcaagga gtctagccca gactccccat atgtcagtct    120

cagggtagca tttcaagagg gataaggtag acgtttctgg cctgttgtgg tgtaggctgt    180

gaattaccat aacatcactt ctttgagatt ttcttggtca aggcaaatca catgacaagg    240

actcaagagg gtagagaaat aggttctact atttagtgga aaggacagca aagtgacatc    300

acaaagagga atgcatatag agatgggggg aatatgtgac caactttagt aatcactgta    360

attctgaatt gactcacaaa cactatcaag acggatcatt gtcataccct agttcaaaaa    420

gcagtccttg cagcaataca gaacagatag aagtgaagag aatgtgattt tgctaaaaat    480

gacatattta catgaccagt gatgggtgag acctatgaaa aatccccaga gattctcaag    540

aactcataaa gtgcatttcc atatttatgt agaatatcaa tctcctgctg tctttgactt    600

cacctagtat attcctaggt atgtgtatct aagcccaagt tggtctcacg tttttgccta    660

cttccgagtc aatatgtgac atgccatccc accttttttgt gttaccacat tattataaca    720

taaggggtgg ttatgtttcc tggatatctt gag                                753
```

<210> SEQ ID NO 29
<211> LENGTH: 1621
<212> TYPE: DNA
<213> ORGANISM: Homo sapiens
<220> FEATURE:
<221> NAME/KEY: SITE
<222> LOCATION: (527)
<223> OTHER INFORMATION: n equals a,t,g, or c
<221> NAME/KEY: SITE
<222> LOCATION: (542)
<223> OTHER INFORMATION: n equals a,t,g, or c
<221> NAME/KEY: SITE
<222> LOCATION: (553)
<223> OTHER INFORMATION: n equals a,t,g, or c
<221> NAME/KEY: SITE
<222> LOCATION: (701)
<223> OTHER INFORMATION: n equals a,t,g, or c
<221> NAME/KEY: SITE
<222> LOCATION: (731)
<223> OTHER INFORMATION: n equals a,t,g, or c
<221> NAME/KEY: SITE
<222> LOCATION: (906)
<223> OTHER INFORMATION: n equals a,t,g, or c

<400> SEQUENCE: 29

```
ggcacaggcg cggcctgcgg cttcttggga actctagggc cgcggccggg cctggctctg     60

ccggcggcct gttgggagct ggatcggagc ggtttggaac gacaagcccg acaaagagac    120

ttttaaaaaa ccatggcaga tgtggaccca gatacattgc tggaatggct acagatggga    180
```

-continued

```
casggragat saaaaggaca tgcaactaat accccttgaa cagctatgca tgctgctttt    240
gatgtctgac aacgtggatc gttgttttga aacatgtcct cctcgcactt tcttaccagc    300
cctttgcaaa atttttcttg atgaaagtgc tccagacaat gtattagagg tgacagcccg    360
tgccataaca tactacctgg atgtatctgc ggaatgtacc cgaaggattg ttggggtaga    420
tggagctata aaagcacttt gtaatcsttt ggttgtagtt gaacttaaca acaggactag    480
cagagactta gctgaacagt gtgtaaaggt attagaactg atatgtnctc ctgagtccgg    540
ancagtcttt gangctggtg gtttgaatcg tgttgcttac cttccaagcg tgaacagtgg    600
acatctagtt cataaagaca ccttgcactc tgctatggct gtggtatcaa gactctgtgg    660
caaaatggag cctcaagatt cttctttaga aatttgtgta naatctctgt ctagtttatg    720
aaagcatgaa natcatcagg tttcagatgg agctctgcga tgctttgcat cactggctga    780
ccgatttacc cgtcgtggtg ttgacccagc tccattagcc aagcatggat taactgagga    840
gctgttatct cgaatggctg ctgctggtgg tactgtttca ggaccatcat cagcatgcaa    900
accagntcgc agcaccacag gagctccatc caccactgca gattccaaat tgagtaatca    960
ggtgtcaaca attgtaagtc tgctctcaac actttgcaga ggctctccgg tagtaacaca   1020
tgatcttctg aggtcggagc ttccagattc aattgaaagt gcattgcagg gtgatgaaag   1080
atgtgtgctt gatactatgc gtttggttga ctttctcttg gtgctattat ttgaaggacg   1140
aaaagctttg ccaaagtcta gtgctggatc tacaggcaga atcccaggac tccggagatt   1200
agatagttct ggggagcgct cacatcggca gcttatagat tgtattcgaa gtaaagatac   1260
cgatgcactt atagatgcaa ttgacacagg agcctttgaa gtaaatttta tggatgatgt   1320
aggtcagact ctattaaact gggcctctgc ttttggaact caggaaatgg tagaatttct   1380
ttgtgagaga ggtgcagatg ttaatagagg tcaaaggtca tcatcattac attatgctgc   1440
atgttttgga agacctcaag tagcaaagac tctgttacgg catggtgcaa atccagatct   1500
gagagatgaa gatgggaaaa ctccattaga taaagctcga gaaaggggcc atagtgaagt   1560
ggtagctatt cttcagtctc caggtgattg gatgtgtcca gttaataaag gagatgataa   1620
g                                                                   1621
```

<210> SEQ ID NO 30
<211> LENGTH: 921
<212> TYPE: DNA
<213> ORGANISM: Homo sapiens

<400> SEQUENCE: 30

```
ccacgcgtcc gaccatgcca aatttcttgt ggttccctaa atgcgccatg tttgaagata     60
ctctgaggac attgtatata cttttgttct acctgagata catttgctta ctttctccac    120
atattgccct catgacactt atccttattg atggatttct tcaatgctac tattgtgcct    180
tacatgtgcc ttgtattata gcatttttat agcatttctc acccaattgt ggctatttgt    240
ttacatgtct gtctccttgg tggaactgtg aactctgtca taacagatgc cattttatgt    300
cagttagact tctttggttg ccagtaagag aagctgactc taatctaaac caaaaggaat    360
tcattggacg gatgtgggtt ggctcacaaa atcaaaggga caactgcgga ccgatcttgg    420
aatgatgctc tgacaccaga acagctctgt gaattcagat aggggtagtg aattgaccat    480
ttcatcaaat gctgcagcaa gctaggtggt ttccccaaag gaaattgagg agtgttacaa    540
gaagaccatt aggggaacgg ttatctggtg gctgataata acaaatttcc atggcagtct    600
```

-continued

```
ctttgctctc tgttggaaga ggtactccac catgggcctt gagcatctct acacatcctt    660

gctaagcgtg tcaaatttca agtcctaact gtcctctgtc tctggaggag gagacaggtt    720

tggttactgt ttgttgtaaa aattactgag cccttcacca tgggtgcctc agctgtatgc    780

aaagcccctt gtattgctgg gggacagagc aactggtact gccatgctgg tgctctggct    840

gtttgctgtt ggcaataaac tattctgttt tggttcaaaa aaaaaaaaaa aaaaaaaaaa    900

aaaaaaaaaa aaaaaaaaaa a                                              921
```

```
<210> SEQ ID NO 31
<211> LENGTH: 2095
<212> TYPE: DNA
<213> ORGANISM: Homo sapiens
<220> FEATURE:
<221> NAME/KEY: SITE
<222> LOCATION: (14)
<223> OTHER INFORMATION: n equals a,t,g, or c

<400> SEQUENCE: 31

cccacgcggt ccgnatcgtc cttccctcac ttcagagggt ggccagagct gaatacccag     60

agagggacaa gtaagggtcc agttccaaaa catcatgagg atgtatcatc ccacgtgtct    120

cacctgacag ttacagagga aacccgcacc cagaatgcac gtgctgtctt atgggaacac    180

tcagcgcaga gtgctcaggt ccggccacac tcgggctgtg cttggtcgtg ccatggaatt    240

cctcaggact ttctcagcct ccctaatggc agaagcccct ttacagcaag acatttaccg    300

tttgtctgaa aatagccgaa ctgagccttt tcttcaggct atatgagaag tctctagaca    360

gtgggcaccg tcagaaagcc cagagccttg tgatagctcc caccctgcct ggctcagatc    420

ttcccatttt tttcctctgg cactaacctc accttttgtt tttttgtgtt tgtgtttgtt    480

tttgtttttg cagagttgga ttacagaaac tcctatgaaa ttgaatatat ggagaaaatt    540

ggctcctcct tacctcagga cgacgatgcc ccgaagaagc aggccttgta ccttatgttt    600

gacacttctc aggagagccc tgtcaagtca tctcccgtcc gcatgtcaga gtccccgacg    660

ccgtgttcag ggtcaagttt tgaagagact gaagcccttg tgaacactgc tgcgaaaaac    720

cagcatcctg tcccacgagg actggcccct aaccaagagt cacacttgca ggtgccagag    780

aaatcctccc agaaggagct ggaggccatg ggcttgggca ccccttcaga agcgattgaa    840

attagagagg ctgctcaccc aacagacgtc tccatctcca aaacagcctt gtactcccgc    900

atcrggaccr ctgaggtgga gaaacctgca ggccttctgt tccagcagcc cgacctggac    960

tctgccctcc agatcgccag agcagagatc ataaccaagg agagagaggt ctcagaatgg   1020

aaagataaat atgaagaaag caggcgggaa gtgatggaaa tgaggaaaat agtggccgag   1080

tatgagaaga ccatcgctca gatgatagag gacgaacaga gagagaagtc agtctcccac   1140

cagacggtgc agcagctggt tctggagaag gagcaagccc tggccgacct gaactccgtg   1200

gagaagtctc tggccgacct cttcagaaga tatgagaaga tgaaggaggt cctagaaggc   1260

ttccgcaaga atgaagaggt gttgaagaga tgtgcgcagg agtacctgtc ccgggtgaag   1320

aaggaggagc agaggtacca ggccctgaag gtgcacgcgg aggagaaact ggacagggcc   1380

aatgctgaga ttgctcaggt tcgaggcaag gcccagcagg agcaagccgc ccaccaggcc   1440

agcctgcgga aggagcagct gcgagtggac gccctggaaa ggacgctgga gcagaagaat   1500

aaagaaatag aagaactcac caagatttgt gacgaactga ttgccaaaat ggggaaaagc   1560

taactctgaa ccgaatgttt tggacttaac tgttgcgtgc aatatgaccg tcggcacact   1620

gctgttcctc cagttccatg gacaggttct gttttcactt tttygtatgc actactgtat   1680
```

-continued

```
ttcctttcta aataaaattg atttgattgt atgcagtact aaggagacta tcagaatttc   1740

ttgctattgg tttgcatttt cctagtataa ttcatagcaa gttgacctca gagttcctgt   1800

atcagggaga ttgtctgatt ctctaataaa agacacattg ctgaccttgg ccttgccctt   1860

tgtacacaag ttcccagggt gagcagcttt tggatttaat atgaacatgt acagcgtgca   1920

tagggactct tgccttaagg agtgtaaact tgatctgcat ttgctgattt gtttttaaaa   1980

aaacaagaaa tgcatgtttc aaataaaatt ctctattgta aataaaattt tttctttgga   2040

tcttggcaaw aaaaaaaaaa aaaaaaaaaa aaaaaaaaaa aaaaaaaaaa aattc        2095
```

<210> SEQ ID NO 32
<211> LENGTH: 1838
<212> TYPE: DNA
<213> ORGANISM: Homo sapiens
<220> FEATURE:
<221> NAME/KEY: SITE
<222> LOCATION: (1076)
<223> OTHER INFORMATION: n equals a,t,g, or c

<400> SEQUENCE: 32

```
tgttcaccag tagctgggat tacaggcatg tatcactatg cctggctaat tttgtattt     60

ttagtagaaa tggggttttg ccatgttggc caggctggtc tcaaacttct gacctcaagt    120

gatccacctg cctcggcctc ccaaagtgct gggattacag gtgtgagcca ccatgcctgg    180

ggcaaaagat attttcaaaa cattgtmaat aacttctccc ccaaacccag acagggtctc    240

attctgttgc ccaggctgga gtggcagggg caccatcgta gctcactgca gccttgaaca    300

ccggggctca agcaatcctc ccgcctcagc ctgccaaagt gctgggatta cacacgtaag    360

ccagtgcact cagtcctaag taacttttta aataccaaag gtagaaaagg aagaagaggg    420

aaaaaaaaaa taagcccata tatggaaaag gaaaagacag cagataaata taggcaaata    480

gaggtggaaa atataatcac gtagaattta gtatagtaaa ggattatctc tgaaaaacaa    540

aaacagaaaa ctatcagagc caaataaaga aaaatggaaa tgactgggga aaaccactca    600

ctaatgagtt gaatgttcaa gagaaactga gaaagagtac tgcttatata aaaattatgt    660

gaaattaaac aaaaatgtag tttagtaatg aatggtgttt aagcacttat ggaatataaa    720

attatcacct gttaaataag aatgcatagt aaatggaatg gacaaagaat atgagtgaca    780

gataaaatca gtttttaaaa aattttatta aagttgatta agcctattag tgaaagaaag    840

caggccaggc acaatggctt gctcctgtaa tgccaatact ctgggaggtc aaggcaggaa    900

gatcacctga gcccaggagt ttgagataag cctgggtaac acagtgagac tccatctcta    960

aaaaaattaa aaagtaaaaa aaaattagct ggtcatggtg acacacacct gtsgkccyas   1020

skmctwkgga ggctgaggca agaggattac ataagcccag gaagatgaag ctgcantgac   1080

ccatgattgt gccactgcac tccggcttgg gtaacaaagt gagatcctat tttccatccc   1140

caaccagtcc ccccagaaaa ggccaggtgt ggtagctcat gcctgtaatc ccagcacttt   1200

gggaggccga ggtgggagga ttgcttgagc ccaggrgcyy ysagtascag tttaggcaac   1260

aaagtgaaac cctgtcttta caaaaggcaa tacagtgaaa ccttgtcttt acaaaaagtg   1320

caaaaataag ctgggcatgt gtgccacaac acctgtaatt gcagctactc aggaggcaga   1380

gacaggagga ttgcttgagc ccagaggtca agactgtaat gaaccatgat tgtgccattg   1440

cactccagtt taactgacag agtgagactc tgtcttaaaa aaaaaattat tttgatatta   1500

agtgataagt ggctatttgc ctagtagctt cctaaaataa actagcataa aatgaaactt   1560
```

-continued

```
attttccaac ctatccctaa gcccttggaa tttcagttct aataactaga atagttacat   1620

aaaaccagta aaaagttgtt taataagaat gtacacattt cccctactaa aatttattgc   1680

ttgtagtttc aaaataaaat cataaagtta tctcaaagcc aagcaaaaaa attatttggt   1740

acaaagtagc aaactcgctg cattagaaga aaaggccatt tcttcacata tttgaataca   1800

ggcaccaaca catagttcca catgaaatta tatttcgg                           1838
```

<210> SEQ ID NO 33
<211> LENGTH: 782
<212> TYPE: DNA
<213> ORGANISM: Homo sapiens

<400> SEQUENCE: 33

```
tacgagtttt tttttttttt ttttgagaag gagtctcggg ctctgtcacc caggctggag     60

tgcagtggcg agactccgtt tcaaaacaaa aacaaagcat caattcctga tcatgaccca    120

ctgtaacttc aagcaagcta caagaatcta tactagggtt cagacctttg aggctgacag    180

cgagctttga gtttgatgac agtacctaaa atatattaag tgtactcagg aactggccaa    240

gcatggggtg gggcttgtca ggaaactggt atttctttct tctatttgta gtgaataaga    300

tgctcaatag acgactttta ctcctcgtca atggtcgcat aactgtctct ttttagacac    360

ttatgaaatt gtctgaactt cctcctctac ttctccaact cccagaagag tgaaggtaac    420

aaatgttatg tccaaaccac ggtttgttcc cagaccctgg tttccaatgc ccacctcttt    480

tccaagaagt ccaaagagac gcccctcatc gcaaaggaag tgctaccgtg ctgcctcgat    540

gtccccccttg ggtgccatcc ctgaaacatc gaacctccca tacctcttct ccagccgtcc    600

ccctcatcct cgttccccgc ctaccctctc ttcaacttca ttcattcatc caacattcgc    660

tgggggattt ctacattgac acgccccgga cagaagcctg ggtaaagat gatcaggaac    720

acgttccctc ccgctaagcg gcttggcaga gtaagaggca tcccaaaact cgtgccgaat    780

tc                                                                  782
```

<210> SEQ ID NO 34
<211> LENGTH: 1560
<212> TYPE: DNA
<213> ORGANISM: Homo sapiens
<220> FEATURE:
<221> NAME/KEY: SITE
<222> LOCATION: (461)
<223> OTHER INFORMATION: n equals a,t,g, or c
<221> NAME/KEY: SITE
<222> LOCATION: (497)
<223> OTHER INFORMATION: n equals a,t,g, or c
<221> NAME/KEY: SITE
<222> LOCATION: (499)
<223> OTHER INFORMATION: n equals a,t,g, or c
<221> NAME/KEY: SITE
<222> LOCATION: (595)
<223> OTHER INFORMATION: n equals a,t,g, or c
<221> NAME/KEY: SITE
<222> LOCATION: (621)
<223> OTHER INFORMATION: n equals a,t,g, or c
<221> NAME/KEY: SITE
<222> LOCATION: (622)
<223> OTHER INFORMATION: n equals a,t,g, or c

<400> SEQUENCE: 34

```
ggctttttct gacattggtg aaccccctag actacaatta atccctttgc tacagacacc     60

tgtagccctt gctgcctcct ttttgttaag aggtcttata attttatgtt tgatgtccat    120

cttccccact tgattgaaat gcactattta tggaggagct atgtctgtat tgtttgttgc    180
```

-continued

```
tgtatcccta ttgtctagca tagtgcctga catacagtac aggctcaaga catatttgca    240

cattgattta tggaaaactg atactcaggt tctgaagaat aaataaatgc acctgaactg    300

tcaaagtgct aaaagcaggc aatccagaaa tgtctggagg taggaatcac agctgcaaga    360

ggcacttcct ggttaacctc gccctccgac ctctagttgg agccacccct ttggatccta    420

cttcagcctt tctggagtca gtggctcaca ggtttcctga nacaaagaga agaggcttga    480

gactattatt acatatnant cttctttaga agcaaagttg gttcgtggat tgaattttca    540

accttacagt accaattata aatcctgagg cattctatca gttaagacaa cttanaatat    600

ttgatcccat tcagaacttt nncatttgtt ttaaagcagg aaaagtaaar gmagtcaatg    660

twmtaacyct tcttctttaa aatgtggatc atagtcctct tggggatgtt tgttcattta    720

atattaacat tttttaagct tgscatgtwt cgtgggtgta tctgtttggt ttcctttggt    780

aactgcattt tgccatgacc cttgatacca gctctactgc tacagcccta ggctaggcca    840

ccgtcatctg tggcctggac cctttcagtc ctaactggtt gccgtgtctc ctttcttagg    900

ccccccaaca gttcatcttc catatccaca cacagtagcc cttaatgatg tttttaaagg    960

aatgagctat attaggatga tttctttgcc caaaaactcc ttcaatggtt ttccacttac   1020

tccagagacc caaaaatcta aggcattttc cctatgggcc ctggatggcc ccacattccc   1080

cctgaccccc gtctccagtg ctgtcccctc ctgcttgctg tgcttccagc ccacactggc   1140

ttccttcctt accctcaggg ttccaccaat ctggatcttg tctcataaac tttgttcctc   1200

tgacttcttc tttttgaatg ttcttttccc agaccttcac atggctcttt gctctcccct   1260

tctgagtctg aacacaaagg tcactgactt aaagaggctt tttcccacca tccagttgaa   1320

atcagcaccc tctctgtaac tgtgtaccac attgtcttat tctttctcat aggtctgaaa   1380

ttgtcgtatt catttttaat gtattttttg cctttttgtc cctgctaaca tataagcttt   1440

ttgaggtcag agactttctt ttcactgtag tattcccagt tcctaaaaca gggccctaca   1500

catattggat gtttaataaa catttattga ctaatacaaa tgaaaaaaaa aaaaaaaaaa   1560
```

```
<210> SEQ ID NO 35
<211> LENGTH: 1092
<212> TYPE: DNA
<213> ORGANISM: Homo sapiens

<400> SEQUENCE: 35

ggcacgtgtt gtggagtctc ctaagtgctt gctggacaca atttcttgtc tatttttgct     60

gccttatgat tctccaaagg acatttcccc cacgggctct gaggacatct ccgtggcttt    120

ccaaccccat gggggttaaa gggaaaaaaa aaaaaggaac gtttatggaa atgatgctag    180

ggttgttctc tcctctttgc cttgtcactg gaattgctga aggcagggct gaagatgctt    240

ctctacatga catctgcacc acccaacaca cacttacctt cacaccttca taccctgttg    300

gagggtcctg atgactacag ggcagtaaat tcagccccac aggagggcca cagcagcccc    360

cagcctctag cctcctaccc tccttcttag gcaaccttga caggaaattt tccctctgcc    420

ttctccttga tcccaacggt agctgcataa tagctgagct cacataatcc ctgtcgccag    480

tgctagagtg cccttagatg gaggtagccc aggtttgact tcctgaatcc ccagcagcag    540

gccttttctt tctagagctc tttgcaggaa gagaaagctt tggaccagct catgctgggt    600

gtaatccttt gtggaagcct ccctgtttcc cttctctgat ctgccccgga gattcctgtg    660

tgtcccagtc tctagggagg gaggcttagc tggagaggtt caagggcagg agaaagcagg    720

agaatgcaga ggccgcgggg agaggacaga aagtatatca tttataacta acctttagcc    780
```

-continued

```
tttagccact caaaaatatt tcctaatagc ctaagggttc ttggcaggtc tttccccaca    840
tcagcaagaa atcttgggag ttgggaagag tcagaccttg ttccctgaac aagctttctg    900
ctttggccaa gagttgttag gagattaatg cctgtccctg aaaggcacag gttggagtgt    960
ttacttcttc ctctcctttc ctctctcccc ccttagagat cgtgaccctt cctgcttgcc   1020
tccctggtgg gctctttcag gctggacaca gggtttaaaa aaaaaaaaaa aaaaaaaaaa   1080
aaaaaaactc ga                                                       1092
```

<210> SEQ ID NO 36
<211> LENGTH: 1153
<212> TYPE: DNA
<213> ORGANISM: Homo sapiens
<220> FEATURE:
<221> NAME/KEY: SITE
<222> LOCATION: (409)
<223> OTHER INFORMATION: n equals a,t,g, or c
<221> NAME/KEY: SITE
<222> LOCATION: (511)
<223> OTHER INFORMATION: n equals a,t,g, or c
<221> NAME/KEY: SITE
<222> LOCATION: (1001)
<223> OTHER INFORMATION: n equals a,t,g, or c
<221> NAME/KEY: SITE
<222> LOCATION: (1089)
<223> OTHER INFORMATION: n equals a,t,g, or c
<221> NAME/KEY: SITE
<222> LOCATION: (1113)
<223> OTHER INFORMATION: n equals a,t,g, or c

<400> SEQUENCE: 36

```
agactatcct caaggagctt acatatcagt aaataaatta ttaaaggtgg aaaatgtggt     60
aaaagagaca taatgtctcg gagagagaac aaatttctgc tttaggagtg ttcttagtta    120
aggtaacatt agcttctata atacgcacac tcccaaatct cagtatttca acatgagttt    180
ctctcttgct catgtaaaga ctggtcaggg acccaggttg acagaggctc ttcagtacat    240
agcttccaag attgctgtgg gtgtgacatc cagccagaaa tctggtgaag agagagcaat    300
grttacacag gaacttttaa tggaccaggc ctgggacagc gtatgtcact tccaccaaca    360
tcccactcac cagaatttsg tcacagggcc atagctatct gcagagaang ctgggaaatg    420
gaacttagct atgtgctcaa gaggaaaagt aaaacagtta ttgaataatt agtaataatt    480
agcaagtaac tacctagggg tcacagagga nctctcaggt agaatttaga cttaaagatg    540
atgggggagt gtgtggaaga gtggtgcaga atagggaaag gggggattga aggaagaaca    600
agctctagct tcacctgcat gggtagagcc cacagtgttg gtagggacat gttagctttc    620
aacatcagct tcttaacagt attattcttt catcggagga aattagtcta tttctgagga    720
aaaaaaaatc tgcaatacgt agcaatttac ttacttggat attgaatgtt aaagcagaga    780
gagactttgt cctcaaaacc ctcccatttc agaagtgagg agcctgggga ggtcatgctc    840
tctggatgtc acacagtgag tcactgtcaa agccagaata gaacccagac ctctcagttt    900
cccatwccag tgctctttct atgaggaaag tataagtttg agcattttta aaccttaatt    960
atgtagaaat aaccatgata ttttatcgta aattatttca ntcatctcat tttaaatttt   1020
actccaaact aaaggaaaac ggtactgatt taaaacatct atcataattc aatatagccc   1080
atatttctnc tttaggaaaa attttttttt gtnttttatc ctgaagaccc gtgccctctt   1140
cctgtgtctc atg                                                      1153
```

<210> SEQ ID NO 37

-continued

<211> LENGTH: 985
<212> TYPE: DNA
<213> ORGANISM: Homo sapiens
<220> FEATURE:
<221> NAME/KEY: SITE
<222> LOCATION: (633)
<223> OTHER INFORMATION: n equals a,t,g, or c
<221> NAME/KEY: SITE
<222> LOCATION: (642)
<223> OTHER INFORMATION: n equals a,t,g, or c

<400> SEQUENCE: 37
ggcacgagca cacccccctg agaccaggga gcatttattc aaggaaacac ttgtctttag 60
aggatgttga cgatgcccca aacttactgt agctgtcagg aaaattaggt gagctattta 120
gtatcattga gcttcatttt acagaaccag catgttgtcc ttagacttcc ctctgatcct 180
tttaggtctc aacttacata ttgccctctt gagccttcta gttcccagac tgagttagga 240
accccaaccc atgctggact cagttagtcc tttccacatt gtgctgtaat tggctatacc 300
ccatctgtcc ttcctgccag actaggagtc tcctgcgggc cctaacgttc ccaatttccg 360
gtgtttggac tggtgctctg tagatgttta gggaatgaaa gggtaatgaa taaattaatg 420
aaacaaataa gaatcatata gtattagcag cactagataa aaggtgtaaa atcttaagtg 480
atccaccatc ttttaaataa ttcattcaaa cgatatttca aatgcatatc acctccaaga 540
aatcgtttct gcatttcrrs tgasttctac gatgccwwrt gaatgarraa rsrrgracak 600
ggyrtggttc tggggggctg tgagagtaac ggngcaatcc tngtcattgt cgtagttatc 660
tggccatcca gggcttctca ggttgccaaa tgccttgtga tagtctctgt tgcaatctta 720
gaggaaaaat aggcataatt aatgtacgca ttccaatatt tagtgctctt tcaacttaca 780
caggaatcat tcaaaaagat cattgcattt gataaacttt agaaaaaagt aatccagctt 840
cttcgtttac ctttgagata attgagaccc tgagcagtga agtgaattgc tcaagcagca 900
cacacaggtg caacgcaaca gctcgttcac acaaacacgc ctacaggaag catgacacag 960
gaggcttctc ctttaaagac gaata 985

<210> SEQ ID NO 38
<211> LENGTH: 1122
<212> TYPE: DNA
<213> ORGANISM: Homo sapiens
<220> FEATURE:
<221> NAME/KEY: SITE
<222> LOCATION: (380)
<223> OTHER INFORMATION: n equals a,t,g, or c
<221> NAME/KEY: SITE
<222> LOCATION: (381)
<223> OTHER INFORMATION: n equals a,t,g, or c
<221> NAME/KEY: SITE
<222> LOCATION: (402)
<223> OTHER INFORMATION: n equals a,t,g, or c
<221> NAME/KEY: SITE
<222> LOCATION: (499)
<223> OTHER INFORMATION: n equals a,t,g, or c
<221> NAME/KEY: SITE
<222> LOCATION: (505)
<223> OTHER INFORMATION: n equals a,t,g, or c

<400> SEQUENCE: 38
agtgaaaagc agatgttaag tggcatatgt gtcttcagtc acctctgtgt gggttgttct 60
gtagtataga gggtgttcta aaaatgatct ttaggaatgg agtgaggctt gtttttgttt 120
ttgttttgtt ttacacttcc acacaatccc ttttcaattc cttgcaaact gctgagtatg 180
tactattttg ccagcaaagg ctgagcctgt atgaacccag ccatgtgctt tgtctgtgca 240

-continued

```
tgtccccaca caggaagcac accagagaaa gcgatacttc agggtagatt gatttcatta    300

ggaacttcat tatcaccagc ctcaaatggt tctggccagc agtctttttc tatctgtatg    360

attaaccctt ctctgccgcn nagcacctcc tcccaccacc tnttctcagt gttaacaggt    420

gatctagact cctactctca gagaaaattg aagccaacaa gtagaaagtc tttttttgcta   480

ccaaagacac aaacctatnt tgttntgcat ccatcctcac ccccgctggt gcttgttcaa    540

cacaggagtc ctctctccac ctacccaaag cctgtcccct cctgctgtgc cctggatctt    600

atctctgtca ttgccttaga aacctttctt gtatatattc atcttttttcc ttcaatagat   660

ctttcttatt ggattttaag catgttgcag cctcttctgt taataaaaca acaatcaaca    720

aaaacactct cccttaactg catgctttat tccagctact accttatatc attcctttcc    780

ttcaaggcca aagtcctcag aagaggtggc aatatcctcc atcatttctt cacttcatac    840

tcattcttca acacatacta atctagtctc ttaccccata attcattaaa acacttattc    900

ttgggtcatg ggtgacttct gtatagctaa atccagtgga tatttttcag gcctcctctt    960

ccttacattt tagtatttca ccctattggc cattcttttc ttcttgaaat actctctcct   1020

ttagctttta tgacactgta ctcctggttt ttctcccatt tcttgtctgc tcctgcttag   1080

ttccctctgt aaacttggcc tctttcacaa ggccagtaaa ca                      1122
```

<210> SEQ ID NO 39
<211> LENGTH: 598
<212> TYPE: DNA
<213> ORGANISM: Homo sapiens

<400> SEQUENCE: 39

```
gaattcggca cgagctggct gcaaggtctg ttgggggagg gtcctcactt gacccttact     60

ggggtcagtg tgggtcaagg gttaagtgtc accctcggcc cttgggagcc tcattgctga    120

gggtctcagc gcttaccact ggtcctggcg tcacggactg tggagctggg ggcagcccgt    180

ggtgggtttt atagcaagtg gtgagatgtg ggcgctgtgc tccaaaccag accccgttaa    240

gtgccacatg gtcaacagtt tagtgtgcag aaatgaattt ccttctctta atttttcctt    300

atttttccag cctgttgggg gaggtggagg tggtgaaatg ttagcagtga ccagttcatc    360

ctgatctgct tgggaccttc cagttttagc actgaaagcc ccacagccca agaatccctt    420

ggatatcaac cacggttcct ccttccagaa tgtcccaaga gccttagggc ctggagacac    480

acaggtgggg gcctgagccc ctgtccccct cctccagatg gagcaggcag ggccccaggg    540

ccccagggct cacggtgttc tggggtccac agtgtgctgt gcggccaggc tggtcttc      598
```

<210> SEQ ID NO 40
<211> LENGTH: 1129
<212> TYPE: DNA
<213> ORGANISM: Homo sapiens
<220> FEATURE:
<221> NAME/KEY: SITE
<222> LOCATION: (1053)
<223> OTHER INFORMATION: n equals a,t,g, or c

<400> SEQUENCE: 40

```
ggcacgagct tatttatttc tgctgtcctt tttcttatta ttctgcctat attatcctga     60

aaatatttag tcagttctgt tttgcccaca attagcatgg ctaggtcatt gatttcagca    120

ctcaggtcag gtatgtcccc aggaagggtc tcagtggttt ctttgcaggg atcacagcta    180

tgtcttttgg tatctattgc aatcatgggt ttgcttctat tttgaatttg tctgtcttat    240

ctcttggaca tcaaaagtgc ccttcagggt aggcatgcta cttgttttat atctgccacc    300
```

-continued

```
caatttcaac tgtaaaatcc taatcacaag tggcaactag ataggttaaa atgatttctg    360
gaactttcct tctggacatg taagatccta aaatcttacg agaatttcag tgagttgatt    420
ttgtctttaa tattttttct taggaaaaag aagacccatt ttgaatctgt tcaactgaaa    480
acctcaagat ccccaaatat atgaagagac agtgctgtag cccttgagac taatgaacaa    540
agaaacctgc tctagtttta caggaccata ttttagggtc tgtcctcata cctgtcacat    600
tggtgatctc acagaggagg gccatgccgc tgaaaaggga aggagattga aacatttgat    660
tgccttatca catggtcaag taccttgcca aataaaggaa agcaaatgat ttgggtctca    720
actgaagatg aagctcaact caggaagaga tttatctgta tatacacata actgaaaacc    780
aagtttaagc ccaccaatgc actgctgatg catgccatat aattaatggg taactttgat    840
tctttatgac gtctacataa caagtgtgat ttggaaggca catgtgagca tatgcattat    900
gatccaattt atgtttttc tttgtttata ttttggggaa aattaaaatt tttttaaggt    960
atatttttcc cattatttat tttcctgacc ttaaaacagc ttttctacta aaaaatggtg   1020
agcaatgaag acaataaatt tttcattttt ccnaaaaaaa aaaaaaaaaa aaaaaaaaaa   1080
aaaaaaaaaa aaaaaaaaaa aaaaaaaaaa aaaaaaaaaa aaaaaaccc              1129
```

<210> SEQ ID NO 41
<211> LENGTH: 1158
<212> TYPE: DNA
<213> ORGANISM: Homo sapiens

<400> SEQUENCE: 41

```
ttaacccaaa tgggttggga tggcacgagg ggaaatggga ggggaagaga acagctgaca     60
tcttgaggaa agctttgggg tagtggagag gtaaggggt catggtcagt ctgaactcaa    120
caatagggct gaatgaattt accaaaggaa gctgccttat attatatgcc aggctgctgg    180
ggaaagcctc aggtcctggc cagcccctgt tctcacaaga acatgcaggt taccacataa    240
ataatggcat atgccttcca taggacgtca acctgactta aatctaccta taccctactc    300
tctattcttt ggtttttggt tctcatccct gtggaaggaa atgggcctct tctggcatct    360
catgctactc tgtgcttttc cttgggctcc aaattctagc tcataaagat gcaagttttg    420
caatttccta taaatggtta agaaaagagc aagctgtcca gagagtgaga agtttgaaaa    480
gagaggtgca taagagagaa atgatgtcca tttgagcccc accacggagg ttatgtggtc    540
ccaaaaggaa tgatggccaa gcaattaatt tttcctccta gttcttagct tgcttctgca    600
ttgattggct ttacacaact ggcatttagt ctgcattaca caaatagaca ctaatttatt    660
tggaacaagc agcaaaatga gaactttatt tggtgcagtc agggctccat ttagttccct    720
cactctgctt ctaatcaccc cttctcccag ccctcttcta tttgatagag gtctgtccct    780
cagatcagca atgtcttagc cctctcctc tcttccattc cttcctgttg gtactcattt    840
cttctaactt ttaataaaca tttaggtata atacattaca gtaagtgcta tttagataca    900
aacttaaaac atactatata ttttaaggat ctaagaatcc tttagagaag gcacatgact    960
gaagtacctc agctgcgcag cctgtagcca gtttttttaa tgtaaaagta agaatgccag   1020
ccttaaccta gccctgcaga taaaagctaa cttttattaa taccagccct gaataatggc   1080
actaatccac actcttcctt agagtgatgc tggaaaaata aaatcagggg cttcaggatt   1140
aaaaaaaaaa aaaaaaaa                                                 1158
```

<210> SEQ ID NO 42

-continued

<211> LENGTH: 1767
<212> TYPE: DNA
<213> ORGANISM: Homo sapiens
<220> FEATURE:
<221> NAME/KEY: SITE
<222> LOCATION: (765)
<223> OTHER INFORMATION: n equals a,t,g, or c
<221> NAME/KEY: SITE
<222> LOCATION: (1130)
<223> OTHER INFORMATION: n equals a,t,g, or c
<221> NAME/KEY: SITE
<222> LOCATION: (1545)
<223> OTHER INFORMATION: n equals a,t,g, or c
<221> NAME/KEY: SITE
<222> LOCATION: (1658)
<223> OTHER INFORMATION: n equals a,t,g, or c
<221> NAME/KEY: SITE
<222> LOCATION: (1744)
<223> OTHER INFORMATION: n equals a,t,g, or c
<221> NAME/KEY: SITE
<222> LOCATION: (1748)
<223> OTHER INFORMATION: n equals a,t,g, or c

<400> SEQUENCE: 42
ccgggtcgac ccacgcgtcc gattgaacgg tttggggcat ccttcctagg aaaagaatgt 60
cagttaaggt ggggtctctt ctggttttgg tgtattttac cctgggccca gttgttgcag 120
aactggaggt gaccctgcct tctcattcct aacatttttc tctactacca cccggatttt 180
gaggcagacc cccaactcgt catggctcca gctgaagttt gaaatataac gtcccggact 240
tctagcctgt aggagctgca gatgtagtgg ggcagacatg gggagggtca gtggtgagcc 300
tatagaaaca tctctttccg caggaaaaga taaaggatgt gatgtgtgta gctcacctcc 360
aggctgaaat gcagactttc ctcatcttcc acagtaagca ggattccctt ctgataacct 420
tgtcagaaat gttgtttttc aaagggcatg tatggtatct gtcactttca gtgatgattg 480
tgtcgtcagt tgatgtctct tgacctgaac tgagtatgcc tgtggaaggt cctcttagcc 540
ccctcacaga aataggaggg ggtgtcctcg ggctgtagct gtgcttcctc tgaaggtcac 600
tggggaaaag ggataccaag ggccgttgtc cagcttatta tcccagctgc tgcacaaagt 660
gtccaggaac tggtccttag agcttttgag ttttatcaga tcagtttgtt ccttgggttg 720
gccatcaaga tgggtctcaa tataaatgaa ggaatctgaa tagantccag ttttatgtgt 780
ttctagagaa aatgctcaag tgttcttatg caagtcatgt tagatttata tgatgtgtga 840
aatctgctta caaggaaatt ttcatgattt gtgttagatt agcatttaat tgtctgcttt 900
aacagatact taatttattt caaaaataag gaaaaataga ggaatcggtg tgaatgtttt 960
aagactgaga gatgatgatc ctttactttt cctgtaaaga agataatttt taaatctttc 1020
atatcctgta gagaaaacca acttttcctc tgtgatatag tacattatgt ttgcactact 1080
ataatgtcaa gactgaaagt ataaaaaatg tacatataag attaattttn atatcttttt 1140
ttttaaaggg gtttgaggtg cctgcctggc tcattcagta aaacatacaa ctctcgatct 1200
tgggatcatg agttcaagcc ccacgttagg ggtagagttt actttaaaaa taaataaaag 1260
gggttgagtc tattgcacta agctctacat gactaattta aagtggagag atgttgtgct 1320
agatttaaaa aaaataacta gttttcttaa tgtgtctttg tatgatcaac agcatgccat 1380
aagcaataca aaacaccaag ccttatactt acaagaaaaa aggttaacat actggtaaag 1440
ttctaaacat atcaaatgta cataagtgac aaaggtagga ttttaaggaa atgtcagtat 1500
atagagaagc tcagtactgc attaaggaac ttcttcagaa ctagngaagt attcctgtgt 1560
ttgaggagaa aacttagggg tttgagaagt tatatttttc tatttaaaag ggttaaatta 1620

-continued

```
ttgcataatt tggaaaaggt tgctttgaat gtaggacnaa actgtttcaa agatttttgt   1680

ttgaaaagtt tatgtatttt tgtgccttaa tatttgttct gacttttaat aaaatgcttt   1740

ctgnaaanaa aaaaaaaaaa aaaaaaa                                        1767
```

<210> SEQ ID NO 43
<211> LENGTH: 917
<212> TYPE: DNA
<213> ORGANISM: Homo sapiens

<400> SEQUENCE: 43

```
ccacgcgtcc gggctcaccc caggccgaga ccaggtggtc cgaccccatc gctcttcacc     60

aagggaagtc gccagcctcc atcgacacgt ggccagggcg acgcagtggt ggtatgatcg    120

tcatcacctc tatcctctcc tccctggcca gcctcctgct cctggccttc ctggcagcgt    180

ccaccgcacg cttgagccct cagtcacttc cagagacctg ataccggggt tagtcagggc    240

aaccacctgg aggaagtggg ccaggagctg cttctagaag gaaggaaagg gagagactgc    300

aggaggaccg gggacccagt gctgcctcct ctccccatcc agctccagcc tgtggtggcc    360

ggaggaggcc ccggagcagc tgagaattgg ctccttcatg gggaagcgct acatgaccca    420

ccacatccca cccagcgaag ccgccaccct gcccgtgggc tgtgagcctg gcctggaccc    480

cctccccagc ctcagcccct agcctggccc ttgtggctgg ggcgtgtgtg gctgtggcca    540

gtgtgggggc aaggacgtgg tagttattcc cagcccctgc accctcctcc tcacccctgc    600

caaagtccca ctgatgtagg acagatgtca gggttctaga cgtctttggt gcaaaaaggg    660

ggttttattc aagcacaggg acaggaccca tgggcaggga gagcggcacc ggggtggtga    720

ggagtggccc gttatatata ctttcgagtt gggagggctt agagagagcg taagtctcta    780

aggaattttg gaagcaaggt ctccagggtc ctgagggggc tagctgttgt taggaaaagg    840

tcatttatta ctgtttagta aaaactttca ccagaaaaaa aaaaaaaaaa aaaaaaaaaa    900

aaaaaaaaaa aaaaaaa                                                   917
```

<210> SEQ ID NO 44
<211> LENGTH: 1987
<212> TYPE: DNA
<213> ORGANISM: Homo sapiens
<220> FEATURE:
<221> NAME/KEY: SITE
<222> LOCATION: (1554)
<223> OTHER INFORMATION: n equals a,t,g, or c

<400> SEQUENCE: 44

```
ggcacagttt ccagggaaag aagggcgggg atgtcagggc tggagagtgc ccgtgtcctt     60

ctgtgtgcat tgggctcctt cctccttaat tctctgcttt ccacttttag gctgaactcc    120

agtgcaccca gttagacttg gagcggaaac tcaagttgaa tgaaaatgcc atctccaggc    180

tccaggctaa ccaaaagtct gttctggtgt cggtgtcaga ggtcaaagca gtggctgaaa    240

tgcagtttgg ggaactcctt gctgctgtga ggaaggccca ggccaatgtg atgctcttct    300

takakgagaa ggagcaagct gcgctgagcc aggccaacgg tatcaaggcc cacctggagt    360

acaagagtgc cgagatggag aagagtaagc aggagctgga gacgatggcg gccatcagca    420

acactgtcca gttcttggag gagtactgca agtttaagaa cactgaagac atcaccttcc    480

ctagtgttta catagggctg aaggataaac tctcgggcat ccgcaaagtt atcacggaat    540

ccactgtaca cttaatccak ttkytggaga actataagaa aaagctccag gagttttcca    600

aggaagagga gtatgacatc agaactcaag tgtctgccrt tgttcagcgc aaatattgga    660
```

-continued

```
cttccaaacc tgagcccagc accagggaac agttcctcca atatgtgyat gacatcacgt     720
tcgacccgga cacagcacac aagtatctcc ggctgcagga ggagaaccgc aaggtcacca     780
acaccacgcc ctgggagcat ccctacccgg acctccccag caggttcctg cactggcggc     840
aggtgctgtc ccagcagagt ctgtacctgc acaggtacta ttttgaggtg gagatcttcg     900
gggcaggcac ctatgttggc ctgacctgca aaggcatcga ccrgaaaggg gaggagcgca     960
rcagttgcat ttccggaaac aacttctcct ggagcctcca atggaacggg aaggagttca    1020
cggcctggta cagtgacatg gagaccccac tcaaagctgg ccctttctgg agctcggggt    1080
ctatattgac ttcccaggag ggatcctttc cttctatggc gtagagtatg attccatgac    1140
tctggttcac aagtttgcct gcaagttttc agaaccagtc tatgctgcct tctggctttc    1200
caagaaggaa aacgccatcc ggattgtaga tctgggagag gaacccgaga agccagcacc    1260
gtccttggtg gggactgctc cctagactcc aggagccata tcccagacct ttgccagcta    1320
cagtgatggg atttgcattt tagggtgatt tgggggcaaa aataactgct gatggtagct    1380
ggcttttgaa atcctatggg gtctctgaat gaaaacattc tccagctgct ctcttttgct    1440
ccatatggtg ctgttctcta tgtgtttggc agtaattctt tttttttttt tttttttgag    1500
acggagtctc gcactgttgc ccaggctgga gtgcagtggc gcgaatcttg gctncactgc    1560
caagtccgcc tcccgagttc caagccaatt ctcctgcctc agcctcccga gtagctggga    1620
ttacaggtgc ctgccaccac acccagctaa cgttttgtat ttttagtaga gatggggttt    1680
caccatgttg gccaggcaga tctcaaactt ctgacctcgt gatgcactca cctcggcctc    1740
ccaaagtgct gggattacag gcgtgagcca ctgcgccctg cctgtttgta gtaattttta    1800
ggcaccaaat ctccctcatc ttctagtgcc attctcctct ctgttcaggt aaatgtcaca    1860
ctgtgcccag aatggatgac caggaacctt caagagtggc tgaaaagatt gcagagttat    1920
cataataaat tgctaacttg cgtatwaaaa aaaaaaaaaa aaaaaaaaaa aaaaaaaaaa    1980
aaaaaaa                                                              1987
```

<210> SEQ ID NO 45
<211> LENGTH: 2053
<212> TYPE: DNA
<213> ORGANISM: Homo sapiens

<400> SEQUENCE: 45

```
acgctgggac ttgggcggtg gtggaggtgg taaccgtgat agtagcagct ccggcgrcag      60
caacagcgac tacgagggat ggcggcggct gcagcaggaa ctgmarcatc ccagaggttt     120
ttccagagct tctcggatgc cctaatcgac gaggaccccc aggcggcgtt agargagctg     180
actaaggctt tggaacagaa accagatgat gcacagtatt attgtcaaag agcttattgt     240
cacattcttc ttgggaatta ctgtgttgct gttgctgatg caaagaagtc tctagaactc     300
aatccaaata attccactgc tatgctgaga aaaggaatat gtgaatacca tgaaaaaaac     360
tatgctgctg ccctagaaac ttttacagaa ggacaaaaat tagatagtgc agatgctaat     420
ttcagtgtct ggattaaaag gtgtcaagaa gctcagaatg gctcagaatc tgaggtggta     480
agtccaaagt tttcattctt catgttttta ttattttaaa tttcagctac caaatatatt     540
tgagacaaga ctcaggatga gctgtctgat atttaaatat taagcaattc catttaagtg     600
ctggttcctc taggcactga aataaaatca ttttttgata aatatagaag tttccagtca     660
tgaaaattat tggcctattt taatgaattt agtgtgtggt taaagttgat ttcgtgtgtt     720
```

-continued

```
ttaatatggt catgatgatc atttatcttt tccgttacta aaaccttatt gcatttattt    780
aggttcaaca gtttgaatca cttgtagggc tttttatgat aggctaagac aaaagttaaa    840
gaaaattgga aattgacagg gtcttgctct gtcatgcagg ctggagtgca gtggtgccat    900
catagtgcac ttgagcttca aactcctggg ctcaagcaat cttcccacct cagccttcca    960
agtagctggg actacaggtg tacaccacca agcctggcta attactctgt ttctttaaaa   1020
cgatttttaa aacaatgtta ttttagttta ggaagttgct gaatcttaga actggccatt   1080
ttatataagc aacctttttct aatcatgcct ttagaagttt tctgttattt aaagttctgt   1140
tattttagag caaaaatctt ttatgaaatt caatctaaga ttttttaaat gctgagcatt   1200
ctaatttttt tccgaaaact agtggtattt aacaattaca gttactatgt ctttggaagg   1260
aaaattttca tgtagttatt ttatatcaaa ataactgcag tgttgggtaa attaataata   1320
catgcatttt aataatacag ttgctaaact gacttgtaaa aatctttctc tttcaactta   1380
ccaaaatcaa tctgcatccc agtggactca tcagtcaaaa atcaagtatg actggtatca   1440
aacagaatct caagtagtca ttacacttat gatcaagaat gttcagaaga atgatgtaaa   1500
tgtggaattt tcagaaaaag agttgtctgc tttggttaaa cttccttctg gagaggatta   1560
caatttgaaa ctggaacttc ttcatcctat aataccagaa cagagcacgt ttaaagtact   1620
ttcaacaaag attgaaatta aactgaaaaa gccagaggct gtgagatggg aaaagctaga   1680
ggggcaagga gatgtgccta cgccaaaaca attcgtagca gatgtaaaga acctatatcc   1740
atcatcatct ccttatacaa gaaattggga taaattggtt ggtgagatca aagaagaaga   1800
aaagaatgaa aagttggagg gagatgcagc tttaaacaga ttatttcagc agatctattc   1860
agatggttct gatgaagtga aacgtgccat gaacaaatcc tttatggagt cgggtggtac   1920
agttttgagt accaactggt ctgatgtagg taaaaggaaa gttgaaatca atcctcctga   1980
tgatatggaa tggaaaaagt actaaataaa ttaatttgct ctcaaaaaaa aaaaaaaaaa   2040
aaaaaaaact cga                                                      2053
```

<210> SEQ ID NO 46
<211> LENGTH: 1272
<212> TYPE: DNA
<213> ORGANISM: Homo sapiens
<220> FEATURE:
<221> NAME/KEY: SITE
<222> LOCATION: (1264)
<223> OTHER INFORMATION: n equals a,t,g, or c

<400> SEQUENCE: 46

```
aggctgctac actaatagga tgtagcaaag ggcggaggag gagatccaga agcaaacaca     60
agcaatgcaa gaactccaca gagtggagct ggagagagag aaagcgcgga taagagagga    120
gtatgaagag aaaatcagaa agctggaaga taaagtggag caggaaaaga gaaagaagca    180
aatggagaaa gaaactagca gaacaggagg ctcactatgc tgtaaggcag caaagggcaa    240
gaacggaagt ggagagtaag gatgggatac ttgaattaat catgacagcg ttacagattg    300
cttcctttat tttgttacgt ctgttcgcgg aagattaaac ttaatgaaaa tctgtttgta    360
ttttctgcat attctctggc aaccttgccc catacttact tatttagcat agtcgagtgc    420
tctagtttct gtctctcagg cactcgtaac taaggaccac cattggccat tggtagatgt    480
ttgattgact taacaagaga gggacaaatt ttcaatttgt gaaactccaa agcagaaagt    540
attggtgctt gctaccttgt gaattcttcc ttagacatgc agagaaaatg tatgcaagag    600
accaaaaaga tggctccaag ctatgtcatg ttacctgtaa taaaatcttt tcttctagat    660
```

-continued tctttctatg ttggcagata atctcccctt gtagcttcca ctcacttatt cttgcattca 720
gagtcacaat gatcatctta cccatgtggt ttttgagaaa gaaagatcaa ttctttgttt 780
gcagtaggta atcttagaga tggagatgat tgtagaatta ttcctagatg agtgtcaatt 840
tatttaattc cattgtcata taaggagtca aattgtttct tatcatttgt tcattgaaga 900
acagagacct gtctggaaaa tcgatctcta caaattcaat taaataatga tccccaaatg 960
sykmaaaagt gaaatacagc aattcaacag ataatagagc aatgtttagt atattcagct 1020
gtatctgtag aaactctttg acgaacctca atttaaccaa tttgatgaat acccagttct 1080
cttcttttct agagaaagat agttgcaacc tcacctccct cactcaacac tttgaatact 1140
tattgtttgg caggtcatcc acacacttct gcccccactg cattgaattt tttgcttatg 1200
ttgtttataa taaaactttt caattatctc ataaaaaaaa aaaaaaaaaa aggggggg cc 1260 cggnacccaa tt 1272

<210> SEQ ID NO 47
<211> LENGTH: 773
<212> TYPE: DNA
<213> ORGANISM: Homo sapiens
<220> FEATURE:
<221> NAME/KEY: SITE
<222> LOCATION: (459)
<223> OTHER INFORMATION: n equals a,t,g, or c
<221> NAME/KEY: SITE
<222> LOCATION: (503)
<223> OTHER INFORMATION: n equals a,t,g, or c

<400> SEQUENCE: 47
cggcacgagc ttttgcccat aggataagta caaactagat ctggttactg cctgccccac 60
cagcctcagt atctctcaca actaggacta actttttctt ctgacaacta taaaatattt 120
cccttgcctt ctcaagtttg ctcaaggtca agttatgcct tttgcctgga atgacttgac 180
ttctcttttg ttttacttag ctggctgctt ttcatcttgt aggttaggtc aagggactcc 240
aggaagtctt ccctggacaa gtaatgaaga gggcataatc caagggccaa ctcccatgtt 300
ttggaacctg actccatttt caggcacgta atattgtcaa attcctttta aaagcacctg 360
tctgtctgtt aacgttggtg cagatactgc tattcccctc ctccatacca ttgctgatgg 420
ttactgaggg tatgggaagg gccgactagt ccagctgtnc acaaacagcc cttaatgtca 480
aactgaatac tgccaacgta gtnccagttt ctgtatctaa agactcagct tggagtcact 540
tgtctggact aaaaaagtac ccctccttgt ctggtttgtg actttctgta ctctgatgcc 600
cccagctttc tgccttctag aaatttgtca gaatttccaa aattcttggg ccttccttct 660
tgctctatat atggttttgg attcattcct tttaaaaaat atttactgtc atttcagtag 720
aattttgaca caataaatat aagcacatca aaaaaaaaaa aaaaaaactc gga 773

<210> SEQ ID NO 48
<211> LENGTH: 2119
<212> TYPE: DNA
<213> ORGANISM: Homo sapiens
<220> FEATURE:
<221> NAME/KEY: SITE
<222> LOCATION: (1424)
<223> OTHER INFORMATION: n equals a,t,g, or c
<221> NAME/KEY: SITE
<222> LOCATION: (1438)
<223> OTHER INFORMATION: n equals a,t,g, or c

<400> SEQUENCE: 48

-continued

```
wgcaagcttt gggagttgtt cgctgtccct gccctgctct gctagggaga gaacgccaga      60
gggaggcggc tggcccggcg gcaggctctc agaaccgcta ccggcgatgc tactgctgtg     120
ggtgtcggtg gtcgcagcct tggcgctggc ggtactggcc cccggagcag gggagcagag     180
gcggagagca gccaaagcgc ccaatgtggt gctggtcgtg agcgactcct acgatggaag     240
gttaacattt catccaggaa gtcaggtagt gaaacttcct tttatcaact ttatgaagac     300
acgtgggact tcctttctga atgcctacac aaactctcca atttgttgcc catcacgcgc     360
agcaatgtgg agtggcctct tcactcactt aacagaatct tggaataatt ttaagggtct     420
agatccaaat tatacaacat ggatggatgt catggagagg catggctacc gaacacaaaa     480
atttgggaaa ctggactata cttcaggaca tcactccatt agtaatcgtg tggaagcgtg     540
gacaagagat gttgctttct tactcagaca agaaggcagg cccatggtta atcttatccg     600
taacaggact aaagtcagag tgatggaaag ggattggcag aatacagaca aagcagtaaa     660
ctggttaaga aaggaagcaa ttaattacac tgaaccattt gttatttact tgggattaaa     720
tttaccacac ccttaccctt caccatcttc tggagaaaat tttggatctt caacatttca     780
cacatctctt tattggcttg aaaaagtgtc tcatgatgcc atcaaaatcc caaagtggtc     840
acctttgtca gaaatgcacc ctgtagatta ttactcttct tatacaaaaa actgcactgg     900
aagatttacw aaaaaagaaa ttaakaatat tagagcattt tattatgcta tgtgtgctga     960
gacagatgcc atgcttggtg aaattatttt ggcccttcat caattagatc ttcttcagaa    1020
aactattgtc atatactcct cagaccatgg agagctggcc atggaacatc gacagtttta    1080
taaaatgagc atgtacgagg ctagtgcaca tgttccgctt ttgatgatgg gaccaggaat    1140
taaagccggc ctacaagtat caaatgtggt ttctcttgtg gatatttacc ctaccatgct    1200
tgatattgct ggaattcctc tgcctcagaa cctgagtgga tactcttcgt tgccgttatc    1260
atcagaaaca tttaagaatg aacataaagt caaaaacctg catccaccct ggattactga    1320
gtgaattacc atggatgtaa tgtgaatgcc tccacctaca tgcttcgaac taaccacttg    1380
gaaatatata gcctattcgg atgttgcatc aatgttgcct caantctttg atctttcntc    1440
ggatccagat gaattaacaa atgttgctgt aaaatttccc agaaattact tattctttgg    1500
atcagaagct tcattccatt ataaactacc ctaaagtttc tgcttctgtc caccagtata    1560
ataaagagca gtttatcaag tggaaacaaa gtataggaca gaattattca aacgttatag    1620
caaattttag gtggcaccaa gactggcaga aggaaccaag gaagtatgaa aatgcaattg    1680
atcagtggct taaaacccat atgaatccaa gagcagtttg aacaaaaagt ttaaaaatag    1740
tgttctagag atacatataa atatattaca agatcataat tatgtatttt aaatgaaaca    1800
gttttaataa ttaccaagtt ttggccgggc acagtggctc acacctgtaa tcccaggact    1860
ttgggaggct gaggaaagca gatcacaagg tcaagagatt gagaccatcc tggccaacat    1920
ggtgaaaccc tgtctctact aaaaatacaa aaattagctg ggcgcggtgg tgcacaccta    1980
tagtctcagc tactcagagg ctgaggcagg aggatcgctt gaacccggga ggcagcagtt    2040
gcagtgagct gagattgcgc cactgtactc cagcctggca acagagtgag actgtgtcgc    2100
aaaaaaaaaa aaaaaaaaa                                                 2119
```

<210> SEQ ID NO 49
<211> LENGTH: 1188
<212> TYPE: DNA
<213> ORGANISM: Homo sapiens
<220> FEATURE:
<221> NAME/KEY: SITE -continued
<222> LOCATION: (577)
<223> OTHER INFORMATION: n equals a,t,g, or c
<221> NAME/KEY: SITE
<222> LOCATION: (1022)
<223> OTHER INFORMATION: n equals a,t,g, or c
<221> NAME/KEY: SITE
<222> LOCATION: (1052)
<223> OTHER INFORMATION: n equals a,t,g, or c

<400> SEQUENCE: 49
gaattcggca cgagtaattt tgtattttta gtagagacag ggtttctccg tgttggtcag 60
actggtctcg aactcccgac ctcaggtgat ctgcccacct cggcctccca aagtgctggg 120
attacaggcg tgagccaccg agcctagccc tgtttaggct ttttatagcc tatgttctta 180
tgagcagtaa acattatgaa tggtttagtt agacctgttg aattgaattc acttcttctg 240
cctgtggtca ggtatcaggt agcacagcca cagaagttac tgaatgtctt tgttggtgga 300
ctttaggaaa gtggtttaat ttatgtggta ttcctatctg ggaattgcaa cagtattgtt 360
agattgcatt ttgtcacagg gaggaaatta cctggtaact ccctgattag gaacaaaatg 420
aagcttcccc tttttacaaa tcctggctaa cattccattt ggatctcttc tgttgaacac 480
ctctctctct cccctccctc ctcactccat tttctcagtt attttattgt ttactattgg 540
aagtcacctc ccaactcagg atacttgtta gtccatntta ggaaaaatat caccattctt 600
tcactattat tctctgttga agttgaagaa cagaatatta cttttttttct ttccattatt 660
ggttacacca gctagttaga gacttggggt aatactgtgg gcatgggttg gatcctgata 720
tctgtgtcag ttagtgagag ttggttctat gaccctagag ctctttgtgt ccttcaaacg 780
agggtgctga aacaagacga acatagaact gtctatacca agcaaaaaac tcctgaaagc 840
acatgcccac tgcaggtgaa ttggtagcat agtgtggaga taagtgggca gtgcttggtc 900
ctgtttctgc ctcctagaga gtacctctca gcatccaggg atgctttagt aactcttagt 960
taaaacgaaa tgaactataa ttaattacct tttttttggg ggggacacag agagtttcca 1020
cngcatttac catgcttttt tttttttttt gnaaaggaaa tatgatagga tattaagatt 1080
gacagagctg ggatgggtt ggaggctgaa ttatgatgtg tgtatttctt tatgcttgga 1140
ttatttcata attaaaaacc aaacatataa aaaaaaaaaa gaaaaaaa 1188

<210> SEQ ID NO 50
<211> LENGTH: 478
<212> TYPE: DNA
<213> ORGANISM: Homo sapiens

<400> SEQUENCE: 50 tttttagca tttcacgcta tttattcccc aaaaccttct gccatagaag acagccacca 60
tacagattgg aaaatgtgga cgaggagaaa aggggtgtat ggtaagcaaa ataaattgta 120
ttttccatcc ttggggagga taaaggaact ctttgcactg ctataatgaa cagcccccaa 180
atgccagtgg tttaattcag tggagttcag acctcattcc tatatcattg cagtgtggat 240
gctcctggat gaaggctctt gtaggtaact ctcctccagt cggtgattca gggacccagc 300
ctccttctgc cttgcggctt tgccttttaa aggtcctcag ggtgctctcc atgtatcttg 360
ccaatgggga acgagtgtgg aggactcaca agcgggtcyc acatcacgtc ctccggggct 420
aatacacatc ccttctcccc acactctgtt ggtcagaagt cactgcttgg cgccctgc 478

<210> SEQ ID NO 51
<211> LENGTH: 1333
<212> TYPE: DNA

-continued

<213> ORGANISM: Homo sapiens
<220> FEATURE:
<221> NAME/KEY: SITE
<222> LOCATION: (485)
<223> OTHER INFORMATION: n equals a,t,g, or c
<221> NAME/KEY: SITE
<222> LOCATION: (486)
<223> OTHER INFORMATION: n equals a,t,g, or c
<221> NAME/KEY: SITE
<222> LOCATION: (493)
<223> OTHER INFORMATION: n equals a,t,g, or c
<221> NAME/KEY: SITE
<222> LOCATION: (496)
<223> OTHER INFORMATION: n equals a,t,g, or c
<221> NAME/KEY: SITE
<222> LOCATION: (587)
<223> OTHER INFORMATION: n equals a,t,g, or c
<221> NAME/KEY: SITE
<222> LOCATION: (633)
<223> OTHER INFORMATION: n equals a,t,g, or c
<221> NAME/KEY: SITE
<222> LOCATION: (1330)
<223> OTHER INFORMATION: n equals a,t,g, or c

<400> SEQUENCE: 51
agctggtacc aaagcaagtt tttcactgag ctctcatgaa agatcctcag tctcttgtgg 60
atttagaatc ctgcagcagc ccaccatcta agagcaagar ccaaagatgt ttgtcttgct 120
ctatgttaca agttttgcca tttgtgccag tggacaaccc cggggtaatc agttgaaagg 180
agagaactac tcccccaggt atatctgcag cattcctggc ttgcctggac ctccagggcc 240
ccctggagca aatggttccc ctgggcccca tggtcgcatc ggccttccag gaagagatgg 300
tagagacggc aggaaaggag agaaaggtga aaagggaact gcaggtttga gaggtaagac 360
tggaccgcta ggtcttgccg gtgagaaagg ggaccaagga gagactggga agaaaggacc 420
cataggacca gagggagaga aaggagaagt aggtccaatt ggtcctcctg gaccaaaggg 480
agacnnatga tanctntggg acccggggct gcctggagtt tgcagatgtg gaagcatcgt 540
gctcaaatcc gccttttctg ttggcatcac aaccagctac ccagaanaaa gactacctat 600
tatatttaac aaggtcctcc ttccacgagg ganagcacta caaccctgcc acaggggaag 660
ttcatctgtg ctttcccagg ggatctatta cttttcttat gatatcacat tggctaataa 720
gcatctggca atcggactgg tacacaatgg gcaataccgg ataaagacct tcgacgccaa 780
cacaggaaac catgatgtgg cttcggggtc cacagtcatc tatctgcagc cagaagatga 840
agtctggctg gagattttct tcacagacca gaatggcctc ttctcagacc caggttgggc 900
agacagctta ttctccgggt ttctcttata cgttgacaca gattacctag attccatatc 960
agaagatgat gaattgtgat caggaccaag atccctgtgg taaacactct gattgaatct 1020
ggggttccag aaggtggaac aagcaggaat gggatccaaa gagactccca ctcagattct 1080
aaagcattta aagacaattc tagcagaatt tatcaaaaca agatgaaaca cagaaaagtt 1140
gaaaccacaa caaaatgaat tctattaaag aatagcccca gatataaatt ctcttgaaag 1200
caatgttcat aaatatttaa gcaaattaaa gacaatgtta acaaattttc tattaaatgc 1260
cctgagtgat aaaaccagtt ggcaataata ttgccttatt aaatcttcaa aaaataaaaa 1320
aaattaaaan aaa 1333

<210> SEQ ID NO 52
<211> LENGTH: 1255
<212> TYPE: DNA
<213> ORGANISM: Homo sapiens
<220> FEATURE:
<221> NAME/KEY: SITE -continued
<222> LOCATION: (541)
<223> OTHER INFORMATION: n equals a,t,g, or c
<221> NAME/KEY: SITE
<222> LOCATION: (542)
<223> OTHER INFORMATION: n equals a,t,g, or c
<221> NAME/KEY: SITE
<222> LOCATION: (1156)
<223> OTHER INFORMATION: n equals a,t,g, or c
<221> NAME/KEY: SITE
<222> LOCATION: (1162)
<223> OTHER INFORMATION: n equals a,t,g, or c
<221> NAME/KEY: SITE
<222> LOCATION: (1223)
<223> OTHER INFORMATION: n equals a,t,g, or c

<400> SEQUENCE: 52
gaattcggca cgagcacatt taataatcta attcacacac acacacacac gtgaaatcat 60
tcttgagaat gaaatttatc atgcttttac ttcttccttc aatcttccca actactgttg 120
aaatgatctg agattttaga tctacattat tgttactttt taacattatg tatcttctgt 180
ttcaagaagg cttttgatgt ttgagttaag tttcataagc ttttaaacaa gcatttagac 240
atttacacct gcttaactga tttcattgat cacttttatt tcatttgcac tgtatatccc 300
cattatttca actcatttca cagttgtctt tggtacttct tttagtactt ttttaaggaa 360
cagatgggtg atacagtatt atatgttctt gccttcctga agatacttgt gttcaataga 420
gcgtaacatt tttttcccac agtgactttt ccctcagaat actaaagtca cagaaagtta 480
tcacatcaac ttaatgttgc ccaagagaag tccaaactct ttgcgcttct tttgtaggtt 540
nntttgggtt atctccccac aatgatgttt atagattctt tattctttct tcttggaaca 600
aagaaatttc attgggatat gtttttaaaa atagatctct ttttattatt tttgcatggt 660
actagatgag acattttagt gcatagatgc aagtcttttt tcaactctgg gaattttact 720
tctatggaat tttttttttct ttccctaata ttttttcact ctttttctta tcctttagaa 780
atttttatgt tgatccccta gatctgctct ctgttctgac tagtttttgc tcattatatc 840
tttttatcct tttcccttag aatcagtact tcttgaaata aactgcttct atgattctga 900
ggtatagcca aattggggaa gccctcttgt gaagggtcag cagtgtttac ctggaagaag 960
aacccatttc agttgtgctt cttgctgttt ggctgcctga ttcaatcagt ggcagaaaat 1020
catattaaat atatttagag tactcccttt aaaagratta cctctctttg aaattcagta 1080
aatttacatt gagratattt gacaaatttg tatatacatt tgcaggcaat aatttttatg 1140
agctgatctg ccatgnttaa angttttcct ttgtaaacca tttggtgtgg gtattttttta 1200
aatttcctca gtatgatccc agngggcatt aactgtccaa aaaaaaaaaa aaaaa 1255

<210> SEQ ID NO 53
<211> LENGTH: 1140
<212> TYPE: DNA
<213> ORGANISM: Homo sapiens

<400> SEQUENCE: 53
ctaggagcct cctaatgcag tgttctgcac agtcctgggg actgactgac tgaatcacac 60
ctctggggct gggggctgct gacatgtgtg cctttccttg gctgcttctt ctcctgctgc 120
tccaggargg cagccaaagg agactctgga gatggtgtgg atccgaggaa gtggttgcgg 180
tccttcagga gtccatcagc ctccccctgg aaataccacc agatgaagag gttgagaaca 240
tcatctggtc ctctcacaaa agtcttgcca ctgtggtgcc agggaaagag ggacatccag 300
ctaccatcat ggtgaccaat ccacactacc agggccaagt gagcttcctg gaccccarct 360

-continued

```
attccctgca tatcagcaat ctgagctggg aggattcagg gctttaccaa gctcaagtca    420

acctgagaac atcccagatc tctaccatgc agcagtacaa tctatgtgtc taccgatggc    480

tgtcagagdc cccasatcac tgtgaacttt gagagttctg gggaaggtgc ctgcagtatg    540

tccctggtgt gctctgtgga graaggcagg catggatatg acctacagct ggctctcccg    600

gggggatagc acttatacat tccatgaagg ccctgtcctc agcacatcct ggaggccggg    660

ggacagtgcc ctctcctaca cctgcagagc caacaacccc atcagcaacg tcagttcttg    720

ccccatccct gatgggccct tctatgcaga tcctaactat gcttctgaga agccttcaac    780

agccttctgc ctcctggcca agggattgct catcttcttg ctcttggtaa ttctggccat    840

gggactctgg gtcatccgag tccagaaaag acacaaaatg ccaaggatga agaaactcat    900

gagaaacaga atgaaattga ggaaggaggc aaagcctggc tccagccctg cctgactgct    960

ccttgggaac cccagtcctg agcttggttt cttcccagca cccagagaat ccttcctcag   1020

ctctcttctt tccaggggaa ggaggtgctc aggggtgggt atccagagag ccatacttct   1080

gagggaagac tggctggcaa taaagtcaaa ttaagtgacc accaaaaaaa aaaaaaaaaa   1140


<210> SEQ ID NO 54
<211> LENGTH: 1220
<212> TYPE: DNA
<213> ORGANISM: Homo sapiens
<220> FEATURE:
<221> NAME/KEY: SITE
<222> LOCATION: (1197)
<223> OTHER INFORMATION: n equals a,t,g, or c
<221> NAME/KEY: SITE
<222> LOCATION: (1208)
<223> OTHER INFORMATION: n equals a,t,g, or c
<221> NAME/KEY: SITE
<222> LOCATION: (1209)
<223> OTHER INFORMATION: n equals a,t,g, or c

<400> SEQUENCE: 54

ccacgcgtcc gcaaatagqt acctaaggca tgtgatttta tttttaaata acaaaaaata     60

acccaagttt cttgcttctc caaagtattc ttctcatagc ttataaaaga aagtccacat    120

tgaatagcat ggtctgggaa cattccttct ttattgtgtt tatttgaaca tgatatgagt    180

ttccaagatg aaatgatcaa aaaagataag taccacaaga aagttttttt gtttggttgg    240

tttttttgtt tgtttgtttt tttcttgaga ctgagtctct ccctgttgcc caagttggag    300

tgcaatcttg gctcactgca gcctccacct ccccggttcc agcgattctc ctgcctcagc    360

ctcttgaata gctgggatta caggcgcccg ccaccacacc tggctaattt ttgtgttgtt    420

agtagaggcg gggtttcatc atgttggcca ggctggtctc gaactcctga tctcatgatc    480

cgtctgcctc ggcctcccag agtgctggga ttacaggcat gagccactgc gcccggccaa    540

gaaagtatgt ttttagaggt gtgtgtaagt gcatttgtat tacctatgaa caaaattacc    600

tgactcttgt cccaggaaag ctgtttcgca ttttcgcttt ttgattggta ttatccagtt    660

ctatgtagtt catattattg ttctgtctga ctctcagaaa ttacttcttc acgccagtgt    720

cttgttgcat gactttgatg tcacctatag gaatacacct cactgcacgt aagtgggtat    780

cttactgtat aaaaggtcta catggcttta ggttttagga caaatgtgta gatttataga    840

ccatttctgt tggccaggac acagattttg agagctgtgt gtatatatat ataatcatgt    900

ttgtattttt ttcctgaaag ttatcaattg cttttgttta aaacagtttg ttttagaggt    960

ggggtgggga tgtatataac gaggaaaagt tatatgtact ttaaagtatg tcaagttctt   1020

actagtttcc tgtactgaag gttcaatttt ttttatataa gtttactttt cacctgctct   1080
```

-continued

```
attctttgtg gggaaaaaat gcatctagaa aaacatagtt taaatactgt atataagata   1140

atgaaagtta gtaatgtcca ttatttaata aagtttgtaa agtacaaggt aaaaaanaaa   1200

aaaaaaanna aaaaaaaagg                                               1220
```

```
<210> SEQ ID NO 55
<211> LENGTH: 694
<212> TYPE: DNA
<213> ORGANISM: Homo sapiens
<220> FEATURE:
<221> NAME/KEY: SITE
<222> LOCATION: (621)
<223> OTHER INFORMATION: n equals a,t,g, or c
<221> NAME/KEY: SITE
<222> LOCATION: (651)
<223> OTHER INFORMATION: n equals a,t,g, or c

<400> SEQUENCE: 55

ataactggag agacatcaaa ctcatgctga gaacaactag aagagttaga attgaagaaa     60

aaggatttca ttaagatatt agagagtgtt caaggcaact ggaggcagaa cgargattct    120

ggaaaggggc cacagagaag ttgtctgcat tcaaaagagc attctattaa agctacctta    180

atttggcgct tatttttctt aatcatgttt ctgacaatca tagtgtgtgg aatggttgct    240

gctttaagyg caataagagc taactgccat caagagccat cagtatgtct tcaagctgca    300

tgcccagaaa gctggattgg ttttcaaaga aagtgtttct atttttctga tgacaccaag    360

aactggacat caagtcagag gttttgtgac tcacaagatg ctgatcttgc tcaggttgaa    420

agmttccagg aactgktaag aaaatagttc tggccagaat caaagattca gccctacaag    480

gatatgtttt cctgtgaaat tatctaagag aatttcctgt tgagatataa aggcccatct    540

gatcactgga ttgggctgas caragaacaa ggccaaccat ggaaatggat aaatggtact    600

gaatggacaa gacagtaagt nctaaaaatc tggcagtaat atttgtattt naatttactt    660

tgcattaaat ctgaagtgtt ctctagttac atgc                                694
```

```
<210> SEQ ID NO 56
<211> LENGTH: 988
<212> TYPE: DNA
<213> ORGANISM: Homo sapiens

<400> SEQUENCE: 56

cggcacgagc cagaccctat gatgtgtcca ctctggaggc tcctcatctt cctcgggttg     60

ctggccttgc ccttggcacc acacaagcag ccttggcctg gcctggccca agcccacaga    120

gacaacaaat ccaccctggc aagaattatt gctcagggcc tcataaagca caacgcagaa    180

agccgaattc agaacatcca ctttggggac agactgaatg cctcagcaca agtggcccca    240

gggctggtgg gctggctaat cagcggcagg aaacaccagc agcagcaaga gagcagcatc    300

aacatcacca acattcagct ggactgtggt gggatccaga tatcattcca taaggagtgg    360

ttctcggcaa atatctcact tgaatttgac cttgaattga gaccgtcctt cgataacaac    420

atcataaaga tgtgtgcaca tatgagcatc gttgtggagt tctggctgga gaaagacgag    480

tttggccgga gggatctggt gataggcaaa tgcgatgcag agcccagcag tgtccatgtg    540

gccatcctca ctgaggctat cccaccaaag atgaatcagt ttctctacaa cctcaaagag    600

aatctgcaaa aagttctccc acacatggta gaaagtcagc ccctggcctg atccttctct    660

ctgtgctgat ggtccaggta tgtcctctga tcggtgaaat cctcgggcag ctggatgtga    720

aactgttgaa aagcctcata gaacaggagg ctgctcatga accaacccac catgaaacca    780
```

gccaaccctc tgcatgccag gctggagagt cccccagctg acttctgctg atcagaagga 840
aagtccacat cttgcaacct taagtctccc ttagagtggg gcttctgcta ccctaaaaac 900
tttaccccag gctctgtgga cataccatcc tctcctacaa taaactctag ctctgaaggg 960
tgaaaaaaaa aaaaaaaaaa cggcacga 988

<210> SEQ ID NO 57
<211> LENGTH: 1500
<212> TYPE: DNA
<213> ORGANISM: Homo sapiens
<220> FEATURE:
<221> NAME/KEY: SITE
<222> LOCATION: (71)
<223> OTHER INFORMATION: n equals a,t,g, or c
<221> NAME/KEY: SITE
<222> LOCATION: (73)
<223> OTHER INFORMATION: n equals a,t,g, or c
<221> NAME/KEY: SITE
<222> LOCATION: (755)
<223> OTHER INFORMATION: n equals a,t,g, or c

<400> SEQUENCE: 57
gcctgaaggg tcgtgaggct ggggcgggac ccggcaccgc tggggcgcca ggccgtgagg 60
acgccaatgg nangcakcgt ggacgaggag gcrctcacca gctgtacctg tgggtagaca 120
acatccctct gtcccggccc aagcgaaacc tctcccggga ctttagcgat ggagtccttg 180
ttgcagaggt catcaagttt tacttcccca agatggtgga gatgcacaat tatgtcggca 240
cgagctctct ccagcagaag ctcagcaact ggggtcatct gaacaggaag gtactgaaga 300
ggctgaactt ttcagtaccg gatgacgtga tgcgcaagat cgcgcagtgc gccccaggcg 360
tggtggagct ggtgctcatc ccgctgaggc agcgcctgga ggagaggcag aggcgcagga 420
agcagggcgc cggctcctta caggagctgg ctccccagga tggcagtggc tacatggatg 480
tgggtgtatc ccagaaggcc cgaggtgaar gtgtcccgga cccccaggga gggggtcagc 540
tcagctggga ccggccgccg gcgcctcggc ctccagcgta taaccgggcg ttgcagggcg 600
accccagctt cgtcctccag atcgctgaaa aggagcagga gctgttggcc tctcaagaga 660
ccgtgcaggt cctgcagatg aaggtaaggc gcctggagca cctgctccag ctcaagaatg 720
tgcggatcga aaacctctcc cggcggctcc agcangcgga rcgtaagcag cggtgagcgg 780
cggcccgggc cgcgcgggga cgcccgggta cccgccagag ccccgacgcc gcgccggacc 840
cacccaccga tggatagacc attgggaggg cggagcccgc tgctctcacg agcctgctgg 900
ggcccgagtg ccctccttcc ttgggatggg tgagcgtgga ggagatggga caggaactct 960
aggagcgcag gcccgggact gagccgcctc ctaccactcc ggagatccgg gtcaggagaa 1020
tggaccgctt tccagagccc agaagccacg tgcagagacc tagcctgtcc cccaaagcag 1080
tgtccaacac cttgggcccg gccttgcatc tcccggcgct gggccttggg gggcggtccc 1140
ttggctctgt ccacacccccc agaatcaggt ccccgcccag ctccgaggac ggcggcgtct 1200
ccatccaggc tagttcccca tgccctcagc catgggggaa tctgtcccgg gccgctgagg 1260
ggctcccctg cccctcctgg gagcttacct gggacccacc tcggcgacgg agaccgcagc 1320
agctggagag gaaggggtga ggcgtgggat cgccaggagt agggaggaca tcgacgatgt 1380
gcccgtagca gtcgcccctc cctcctcgcg cacggggtac tgaggcggaa ggtttgaagg 1440
ttacggctca gggctgcccc attaaagtca gtgttgtgtt ctaaaaaaaa aaaaaaaaaa 1500

<210> SEQ ID NO 58

-continued

<211> LENGTH: 1391
<212> TYPE: DNA
<213> ORGANISM: Homo sapiens

<400> SEQUENCE: 58
ggtaaatacc aaggtaatta aatttttaag ttctgagtat tagaggtaat ggttactgta 60
gctcctaaaa tgcacatcac atctctggta ggtgctggaa ccctcatggt actgctgctt 120
ttaattttgc ttttggaatg tttctttgta gctgaagctt tagtgatgag aagttagaaa 180
tactctcatt gacctttagt gttttgtcct gttgatatat atcaagttcg cttagtttga 240
cattgtttga acttatttcc ctaagcaaaa aacagccaga aagaagaaaa tccagaacat 300
gtagaaattc agaagatgat ggattccctc ttcttaaaat tggatgccct ctcaaacttc 360
cactttatcc ctaaaccgcc tgtaccagag attaaagttg tgtcaaatct gccagccata 420
accatggagg aagtagcccc agtgagtgtt agtgatgcag ctctcctggc cccagaggag 480
atcaaggaga aaaataaagc tggagatata aaaacagctg ctgaaaaaac agctacagac 540
aagaaacgag agcgaaggaa aaagaaatat caaaagcgta tgaaaataaa agagaaggag 600
aagcggagaa aactgcttga aaagagcagt gtagatcaag cagggaaata cagcaaaaca 660
gtagcttcgg agaagttaaa acagctgacc aaaactggca aagcttcctt cataaaggta 720
aggacaaggg aaagaaaact gctcaagggg acctttgtgg gggaagtgga tagcaagtgc 780
tgggtgactg gaatgtctga gccagctgac agcccacctg tgggatagag atgcatgatg 840
ctgactggct ggaatcgcaa cctttaatgt tctagaattt ttcacgtagg gtcctcacaa 900
taacctgggt cctggcagca gcttgtcttc cactcctttc tctcttagat tataagaaca 960
ttgtagcagt gcagaatacg tctatgctaa ctgattccag ttttctgtaa ttctagtccc 1020
tttttcatat ttatggttgc atacattgtt gtaatggtga tgtactattt ttggcttttt 1080
tcacttataa gtacatttta cagcataagc atgtggtgtt tttaattgca ggatgaaggt 1140
aaagacaagg ccttaaagtc ctctcaagca ttcttttcta aattacaaga tcaagtaaaa 1200
atgcaaatca atgatgcaaa gaaaacagaa aagaaaaaga agaaaagaca ggatatttct 1260
gttcataaat taaagctgta atatattttg aatataatgt aaatattaat gtgtaagctt 1320
atattgtgtc attgttctgt tttataataa aattcttgag aaccttcaaa aaaaaaaaaa 1380
aaaaaactcg a 1391

<210> SEQ ID NO 59
<211> LENGTH: 1579
<212> TYPE: DNA
<213> ORGANISM: Homo sapiens

<400> SEQUENCE: 59
ggcacgaggc agcgcaggga gctgtctgca gaggccaggg tgcgcctgcc acgaatcccc 60
aggcaccggt ggccgccgcg gcccgagtag ctcggcgggt aaacatggcc gcactgacga 120
cggttgtggt agcggctgcg gccaccgcgg tagccggggc tgtggcaggg gcgggcgcgg 180
ccaccgggac cggcgtggga gcgacgccag cgcctcaaca gagtgatggc tgttttagta 240
cttcaggtgg aattcgtcct tttcatcttc agaactggaa gcagaaagtt aatcagacta 300
agaaagcaga atttgtacgc acagcagaaa aatttaaaaa tcaagtaatt aacatggaaa 360
aagataaaca cagtcatttc tacaaccaaa aaagtgactt cagatttgag catagtatgc 420
tagaagaatt ggaaaataaa ttgattcaca gcaggaaaac agaaagagca aaattccagc 480
aacaattggc caaaatacat aataatgtaa agaaacttca gcatcaatta aaagatgtga 540

-continued

```
agcctacacc tgattttgtt gagaagctca gagaaatgat ggaagaaatt gaaaatgcaa    600

ttaacacttt taaagaagag cagaggttga tatatgaaga gctaattaaa gaagagaaga    660

caactaataa tgagttgagt gccatatcaa gaaaaattga cacatgggct ttgggtaatt    720

cagaaacaga gaaagctttc agagcaatct caagcaaagt tcctgtagac aaagtaacac    780

caagtactct tccagaagag gtactagatt ttgaaaaatt ccttcagcaa acaggagggc    840

gacaaggtgc ctgggatgtg atcaccagaa ctttgtaaag gtgagaaaca aacataaagg    900

gaagccaaca tttatggaag aagttctaga acaccttcct ggaaaaacac aagatgaagt    960

tcaacagcat gaaaaatggt atcaaaagtt tctggctcta gaagaaagaa aaaaagagtc   1020

aattcagatt tggaaaacta aaaagcagca aaaaagggag gaaattttca agttaaagga   1080

aaaggcagac aacacacctg tgctttttca taataaacaa gaggataatc aaaagcaaaa   1140

agaggaacaa agaaagaaac agaaattggc agttgaagct tggaagaaac agaaaagtat   1200

agaaatgtca atgaaatgtg cttcccagtt aaaaaaaaaa aaaaaaaaaa aaaaaaaaaa   1260

tcagaaagaa cgccagcgcc agtttaagtt aaaattacta ctagaaagtt atacccagca   1320

gaagaaagaa caggaagaat ttttgaggct tgaaaaggag ataagggaaa aggcagaaaa   1380

ggcagaaaaa aggaaaaatg ctgctgatga aatttccaga tttcaagaaa gagatttaca   1440

taaacttgaa ctgaaaattc tagatagaca ggcaaaggaa gatgaaaagt cacaaaaaca   1500

aagaagactg gcaaaattaa aagaaaaggt tgaaaacaat gttagtagag atccctctag   1560

gctttacaaa cccaccaaa                                                1579


<210> SEQ ID NO 60
<211> LENGTH: 1241
<212> TYPE: DNA
<213> ORGANISM: Homo sapiens
<220> FEATURE:
<221> NAME/KEY: SITE
<222> LOCATION: (8)
<223> OTHER INFORMATION: n equals a,t,g, or c
<221> NAME/KEY: SITE
<222> LOCATION: (59)
<223> OTHER INFORMATION: n equals a,t,g, or c
<221> NAME/KEY: SITE
<222> LOCATION: (78)
<223> OTHER INFORMATION: n equals a,t,g, or c
<221> NAME/KEY: SITE
<222> LOCATION: (84)
<223> OTHER INFORMATION: n equals a,t,g, or c
<221> NAME/KEY: SITE
<222> LOCATION: (86)
<223> OTHER INFORMATION: n equals a,t,g, or c
<221> NAME/KEY: SITE
<222> LOCATION: (104)
<223> OTHER INFORMATION: n equals a,t,g, or c
<221> NAME/KEY: SITE
<222> LOCATION: (128)
<223> OTHER INFORMATION: n equals a,t,g, or c

<400> SEQUENCE: 60

ggcacganct gttatcctac ttcctgctgg ctgcctttaa acatggagct gctacacana     60

caggtcctgg ctctgcanac acananggtc ctgctggaga agangcggaa ggcttcagcc    120

tgggaacnga acctgggcta ccccctggct atgctgtgct tgctggtgct gacsggcctg    180

tytgtgctca ttgtgggcat ccacatcctg gagctgctca tcgatgaggc tgccatgccc    240

cgaggcatgc agggtacctc cttaggccag gtctccttct ccaagctggg ctcctttgcc    300

tcttcagcct ccctttctgc aagatagggg caagggcggc tagatggatg tgtctgctgg    360
```

-continued

```
gcaagtcata taacatttct gatcctcagt ttcatcctac aaaatgggcg taacaatgtc    420
tacctactcc attgtgtgga ccaaaggaga tggttaatgt gaaagccctt tgtgaacctg    480
aagtgagcaa ctgctggatg aatgtcatta cgggcacagg ctctgtgtca tctcctctcc    540
tagtgcttcc acagccagga ccagagacct ccctgatgac tggggaacct ggtgatggtg    600
gcctttctct ttatggggag cctgagtatg ctcagatcgc agctttcctt ccctagacat    660
tgtgtaattg ggggtggggg cacacttgcc ccacwkccta gctccagcct ttcctcctct    720
taggatggct caggatgagt ccccccctcaa caaggcagct acccaagagt aattcccctg    780
gggactttct gtgtgaatct ccccttcccc ctcctctctt ttccctttcc tggacccagc    840
cactgatgta accaacctca cagactagtt gtttattata ttaatagttt gagcatataa    900
agaggaactt gtgatgggag agatctaggg aggagtaaag aagtatagga atgtctggcc    960
tgtattctct tcacctggga ccactgattt ttaagctgcc acattggctg gagaacaggc   1020
tatggagttc ataatgtgtg gtctcctgga gctcctgttc agctctgcct tctttgaggg   1080
ggcagggatg gggcagggag cacatygtaa tactaacggc ctcagagmtg ccccctgatg   1140
tcctcctgcc tgttaccccg tgcctctgtc tcttaacagt gggatgatga agatgccacc   1200
gtcaacaagr ktgcgctcga gctgtgcamc tttaacctgg g                       1241
```

<210> SEQ ID NO 61
<211> LENGTH: 930
<212> TYPE: DNA
<213> ORGANISM: Homo sapiens

<400> SEQUENCE: 61

```
gaattcggca cgagctaagt cctgatatcc catgatgttt tttgttttac tttgtttttg     60
gctatttcct ttttctaaaa atagccctct ctggggaatg ctgagatctt cattctttat    120
tagtatcaat ttataattat ctacatctgt aagcagttat tcgaaagtct ccagatctta    180
ttctatcctg gcacccatgg tgactaaaaa aatcaaagac gttaaatctt tgaaagcagc    240
cttcaaacca catactccaa ccaacttacc ttatatgtcg gggagttatg gagcaaatac    300
attaattaac ttgacagaag ttgcacactt tctgtacttc tgaaccaaaa tttggatgca    360
tgtttttctt tatcatgagt cacacctgat taggatttcc ttagcttttg ttggggtcag    420
acaggattgt gaccaaaggc aagatttctc tgtcatctct tttgacagaa tttccacaat    480
catggatttt gtaatagtcc tggacattca tcagaaagta acctgtagtg ggctgccta    540
cataggattc ttcctttgaa aagccttaaa catttttcta atggttggtc tctcttaact    600
aacaataaaa aacagcaaca atgcasctgg gcacagtggc ttttgcctgt aatcccagca    660
ctttgggagg cccaggcagg tggatcaact gaggtcagga gtttaagacc agcctggcca    720
acatgtgaaa ccctgtctct acgaaaaata caaaaattag ccggatgttg tgttgcacac    780
ccgtagtccc acctactggg gaggctgagg caggagaatt gcttaaaccc aggaggcaga    840
gcttgcattg agctgaaatc gtaccacagc actccagcct gggcaacaga gtgagactcc    900
atatccaaaa aaaaaaaaaa aaaaactcga                                     930
```

<210> SEQ ID NO 62
<211> LENGTH: 998
<212> TYPE: DNA
<213> ORGANISM: Homo sapiens

<400> SEQUENCE: 62

```
ggcacgaggc ttaagtcaag ccacctgatc agtcttgtaa ccactggaga gatgagcagt     60
```

-continued

```
gtttagtcat gtccctaata ctgttattgt cagtcaccct tttacatctg tctttttctg    120

ttggcttctt tctttttagg ttgtagggga gacccattgt ctagagagaa tatacgcttt    180

gacttgatga aatcccagtt taatctagaa aggtccattt tgaggttaag aacatttcgg    240

agatgtggag gtgaagatat aaagtaggtc tcagctttgg ctggccaata tgggatccta    300

cttatctcct caggggactg gacaattcgt gtcaagactc tgtgcttcag gagcctctgc    360

ttcttcctcc ttcatggtcc aactttcctg ccccttcttc atctcattag cttaaccctc    420

agttgcctga cccaagtcaa ggtgtgtgac ctggtcctga tcaccacctc tttttggggg    480

cttctgcaac tgtgctctgt cctggcaacc tgcttctgta atctgtttat ccccaaattt    540

gaatgagtaa taggaattgc ctaaattttg gataaattat cctacaaaat aaaagcattc    600

tcacattgcc ctctcaaatc acatgatctt tgtagaaaat ggccggtccc tatgaagcta    660

attgatcttt ggcatcaata gggaaattca gctgggcgca gtggctcaca cctgtaatcc    720

cagcactttg ggaggccgag gtgggagggt catttgaggt caagcattca agaccagcct    780

ggccaacgtg gtgaaacccc gcctctacta aaaatacaaa aaaattagct gggcgtggtg    840

gtgtgtgcct gtaatcccag ctactcagga ggctgaggca ggagaattgc ttgaaccagg    900

gagatggagc ttgcagtgag ccgggattgc gccactgcac tacagccagg atgacagagt    960

gaggctccat ctcaaaaaaa aaaaaaaaaa aaaaaaaa                             998
```

<210> SEQ ID NO 63
<211> LENGTH: 1193
<212> TYPE: DNA
<213> ORGANISM: Homo sapiens
<220> FEATURE:
<221> NAME/KEY: SITE
<222> LOCATION: (1080)
<223> OTHER INFORMATION: n equals a,t,g, or c
<221> NAME/KEY: SITE
<222> LOCATION: (1186)
<223> OTHER INFORMATION: n equals a,t,g, or c

<400> SEQUENCE: 63

```
ggtcgaccca cgcgtccgca ccgaagccca gagggtctgg gggcacaaga ctgacgccag     60

ggtatgaaga gtgttatttt cattcaaagt gttattttgt ttttccttcc aatgtctgga    120

gaccaccagg gcatctctgg gctggatgag ctcccacaag cctgagggaa aggccagcac    180

tcgctagcag tggcaggcag aggcccaggc tgccgtcccc tagagtccca ggttggctct    240

gccagtgcct gtcctttacc aaagatgaat gaagcaaatg tcatgctgcc ttattcaggg    300

aaggaggagc ctgtcctgcc tgtggccatg accctgcctc tcccaggcag gggcccgcga    360

tgtggaactg ctgccactga gggggggatcc agttttgtca atgcagttgt ctctgtttta    420

caagttggag tcactcttat gctgtaccca gtttctaaac tggagactgt gtgtgccctc    480

tggctctgag taccccctgct ttgggcttgg gcctaggctg cattgaaaag agctgaaggt    540

tgtggccttt gcgctcctgg cccagccttt gttccccact ggagcagaag gggagatgga    600

cgacacggts ggggcatctg gcctggccag tgccctgatc ccagagagcc cgaggaggtg    660

tctcaggctg cctgagtcgt gacctgctag gccagagccc actccatctg gtagaaggga    720

aagcccatat gctaccacca gctgtgtcca aaaccgccag ctctgttctt cctcagccag    780

cctcgcccat ccccttgagg tctcagcccc tttcccttgt agctcctccc ctggaggggg    840

aatggcagca ggggttgggg aaacagcatc tccaagcagc ttagagttgg ccatatttac    900

ctcagcctgg gcgctggtcc tttcttccgg cccctcccct ccaaaatgtg cctattgcta    960
```

gagctcctcc ctctcaacac ccagtttcct tgggagttgt cattaaagga aaaaaaaaaa 1020
aaaaaaaaag ccagtgccca gggatgggca tctccaggga gctggggatt agtgccaggn 1080
agccctgcca gccatgccta catccccatg ggcacagaac aagccaaagc cttcgttgta 1140
tgttgacgat gcacttttat gaaatgtagt ttctatcgct gttttnagcc ttt 1193

<210> SEQ ID NO 64
<211> LENGTH: 830
<212> TYPE: DNA
<213> ORGANISM: Homo sapiens

<400> SEQUENCE: 64
ggtcgaccca cgcgtccgct gaaaggaaaa gcactgtttg gagaatgatc cacctttcaa 60
gattttactt attgttgata atgctcccac atgtcctctt ttttacgggt gatcttcatt 120
cctaatatca aagtgatatt tcttcctcca ggcaccacct ctttgatcca cacaatggat 180
caaggagtta tagcagcttt taagttctac tacctgagaa gggaggactt ttgcccagtc 240
ccatactgca gtggaggaag acactgagaa gactctgatg aaattctgaa cagcatcaag 300
aaccttgttt aggcttggat tatgtcgcta aggactgtag gaatggcacc tggaagaaga 360
cacgcaagag gtttgtcaat aayttcaaag gatttgccaa ggatgasgaa gttgcaaaaa 420
tcaagaargc tgtggttgag atggcaaaca actttaacct gggtgtggat gtggatgaca 480
ttgagtaatt cctagagggg gttcctgagg aattgactaa tgggttgctg ttggaactgg 540
aataggagtg catagctgaa gaagaggtaa agaaaaagaa agtgcaggag aagggaaaaa 600
agaactccca agaatactca cagtgatggg tttagcagaa gcttcttcag actccaacaa 660
gctccttaag aagtctgaaa acatggaccc caaaactgaa aggttttcac taatagagag 720
gaaagttcat ggtgcattat ctgcctacaa gcaaaaccag gattcaaaaa accctttgag 780
ctggagcttc aaagcacaaa aaaaaaaaaa aaaaaaaaaa aagggcggcc 830

<210> SEQ ID NO 65
<211> LENGTH: 867
<212> TYPE: DNA
<213> ORGANISM: Homo sapiens
<220> FEATURE:
<221> NAME/KEY: SITE
<222> LOCATION: (457)
<223> OTHER INFORMATION: n equals a,t,g, or c

<400> SEQUENCE: 65
ggccgccctt tttttttttt tttttttttt ttttttattg gttaaagtgc tgatgccaga 60
tgacccttga gatcccttat tagtgaaatg ttctgataat aaagaagagt ttggctcacc 120
tgctggtctc caccacacag gtttataacc aagagcccta cagctcttgt cccaccctga 180
gggcctgact gacctgtgga gggcccccacc tttcgcctcc attcactcac ccctgttccc 240
aagaaccact gacttcttta catgaagcct actttgagta agtttttagg tacagatgct 300
gaattaccca agctgtatcc accctcactc caggcacccc gaggagagac tcaactgctt 360
ggcccagggt tagagaggcc cacacgggaa ggcagagtgg agcagatgtt atttaaccaa 420
aagtctgtat cctggggctc ccagctacca cagtcangaa acacattttt aaaaaatcma 480
gacccttgaa ctagcagcag tagtcaccca taccgtatac gataaataaa agtaagccaa 540
tgtttattct tctttgcata aaatcaccta taccaacact tatacattac agcatcattc 600
agttaattca agtctgaatc ccagaaactc tcctgaaatc aagccacagt tcagccctat 660

-continued

```
tcttcctagt ttttcctgac atacttttgc ttactctata aatccacgga tattcttctt    720

gcctactccc accaaagccc aaatacacgt gaaaaaagtt aatcatgaag tttttcttat    780

tcccttacat ttagaaaatc agcatctact ctcatagact acttgtaaga agacaaattt    840

ctgctactcc ggacgcgtgg gtcgacc                                        867
```

<210> SEQ ID NO 66
<211> LENGTH: 685
<212> TYPE: DNA
<213> ORGANISM: Homo sapiens
<220> FEATURE:
<221> NAME/KEY: SITE
<222> LOCATION: (7)
<223> OTHER INFORMATION: n equals a,t,g, or c

<400> SEQUENCE: 66

```
gggcccnttt gggggccccc cctttttttt tttttttttt tttttttttt tttttttttt     60

tttttttttt tttggacagg aagtagaatt tattggtgag tattaagagg ggggcagcac    120

attggaagcc ctcatgagtg cagggcccgc cacttgtcca gagggccacg actggggatg    180

tacttgaccc cacagccatc tgggatgagc cgcttttcag ccaccatgtc ttcaaattca    240

tcagcattga acttggtgaa gccccacttc tttgagatgt ggatcttctg gcggccagga    300

aacttgaact tggccctgcg cagggcctca atcacatgct ccttgttctg cagcttggtg    360

cggatggaca tgataacttg gccaatgtga accctggcca cagtgccctg gggctttcca    420

aaggcacctc gcatgcctgt ttggagcctg tcagccccag cacaggacaa catcttgttg    480

atgcggatga cgtggaaggg gtggagccgc acccggatat ggaagccatc tttgccacaa    540

ctttttacca tgtacttatt ggcacaaatt cgggcagcct ccagggcttc agaggacagc    600

tgctcatatt catctgacac catgtggcca caaagcggaa actcatccac ttttgccttt    660

ttccgcccca ggtyaaaaat gcgaa                                          685
```

<210> SEQ ID NO 67
<211> LENGTH: 801
<212> TYPE: DNA
<213> ORGANISM: Homo sapiens

<400> SEQUENCE: 67

```
gaattcggca cgagtggaga tgcactgacc ttccttgcaa gagcctttcc ctgaagttgg     60

gctcctgaga gaagttctga acatggctat ccctgccttt tcatcttgtc agcagatttc    120

ttcagcagct gctctacaaa tatgcaatgg accctttaag catttctcct ttacagtgag    180

cacaatgcta agctttgtca gcagatgcca ctggagcagc attgcagaag aaagcgagtt    240

tctcttcctg attttggtgt gctacttttc ttcttcttgc tccagctgca ttatccatca    300

gtggtactat gtataagacc atcccgctgt gccctgccct accacctgcc cagaggcaca    360

tccctcactg actatttggc ctgattctga gcctgtggcc accttctcac agccctgcaa    420

cacaggcact gtgtgctcca ggcctcacgt ccccagcagt ggcctgactg tgcacttagc    480

cacagcctca gtttgcctgt gctccaagaa attgcatcct atttgcccag cagctatgga    540

ccagctctct ggtcctggaa aacagcaggc ttctctgaca tctagtggac tgcaaacaca    600

ccttctccaa caaggcctga ccccagcctt aaggagagaa ccgtctttcc gagttgtctt    660

tccttgggta ctctccctca atcctcggat acccttgaaa gttctcttta cattgttata    720

gttattcttc tatcactgtc gaataatttt ttatattaaa cttctcttgc tttacattaa    780

aaaaaaaaaa aaaaaactcg a                                              801
```

-continued

<210> SEQ ID NO 68
<211> LENGTH: 908
<212> TYPE: DNA
<213> ORGANISM: Homo sapiens

<400> SEQUENCE: 68
gaattcggca cgagatttta ttaaaaataa gtgcttttct ctgcttacct tttactatga 60
tctaactatg atactttcaa tatgctgcag actctcattc ttatctttct tttgttgtta 120
ccttgttacc tagaactctt atgtttcagc ctaatttctt catctgcaaa gacctaatag 180
gaagaaattt ttactttggt ttagtgtgta taaaatctgg gaacagctaa atttcagttt 240
taatataaaa ttttgacttt tatatattac ccaatattgt taaaaggaga attctatgta 300
tacctatctc ttaaaaatat tgctctatat attacccgct taaaacaaca acagcaacaa 360
caaaaactta gaaggtaaac aaaaagtaat ctcataaaac atagaagggg aatacacctt 420
ggtttcagat atgcacagaa agtatgtaag ctgtacccca gaagcatcct tataaatttt 480
gcagtcagtt tctctgacct ttctttacac aggagggatt tgttgtayca atctttaatc 540
taagtgtgat acaccaactt cctattgaat tgccttagag cagaagaaaa ggtataaaga 600
tgatgcatct tacttagaaa tgaaaatata acaaaacaag tcatgttaaa caaggaaaga 660
tatggatctt taatcacgaa cccaaaccaa gttggtggct gaacagagaa gaactgtggg 720
agccaggcca gttggcatga cagtatgtgt tcagctggtg tggagtaagc ccctggactg 780
agggtgttca gtgtggcttc agccagggga ttcagtggtg aagaaccctc ttgctactgt 840
actctttgtc tttattacaa tactagtcaa gaaaaaattc tttctaaaaa gaaaaaaaaa 900
aaactcga 908

<210> SEQ ID NO 69
<211> LENGTH: 696
<212> TYPE: DNA
<213> ORGANISM: Homo sapiens
<220> FEATURE:
<221> NAME/KEY: SITE
<222> LOCATION: (605)
<223> OTHER INFORMATION: n equals a,t,g, or c
<221> NAME/KEY: SITE
<222> LOCATION: (648)
<223> OTHER INFORMATION: n equals a,t,g, or c
<221> NAME/KEY: SITE
<222> LOCATION: (655)
<223> OTHER INFORMATION: n equals a,t,g, or c

<400> SEQUENCE: 69
ggaaaatttt taaaaaatag attataatga tacatattgg tatcattaag acaacagatt 60
tgagcaaata caattaaggt gtcttatttt ttgcatcaag taattattgc tgtggtcttt 120
ctactccaca aaataatttt ttctttttgc agttgaaaat taactgcatt attaactaat 180
taataaaata aatcaagtgg tataagggat tagtttaccc tcaagccgat gactccatgg 240
ctactgatat tagttagttt wggattttta aaaagcatat cagaccccca gtttcaggaa 300
ttgagtataa atattgcttc ttgtcaccct gggacagtaa tgccttatag tggcactagt 360
caccttaagt agattacaca tggttgaggt gaataaagct gcatgggaat ttgctttcgt 420
gatatatttc atttgcaaac ttctacataa tcaagtttta tgtttaaaac catcggttct 480
atatatctag ctttaggaag ttgcccttac aggtgggacc ttttgtgtta atctgttttc 540
tccccagtca tcttattggc tatgttaaaa aaaaaaaaaa aaaaaagggs ggccgctcta 600

-continued kaggntccaa gcttacgtac gcgtgcatgc gacgtcatag ctcttctnta agggncacct 660
aaattcaatt cactgggcgg ccgtttacaa cgtcgg 696

<210> SEQ ID NO 70
<211> LENGTH: 455
<212> TYPE: DNA
<213> ORGANISM: Homo sapiens
<220> FEATURE:
<221> NAME/KEY: SITE
<222> LOCATION: (431)
<223> OTHER INFORMATION: n equals a,t,g, or c
<221> NAME/KEY: SITE
<222> LOCATION: (432)
<223> OTHER INFORMATION: n equals a,t,g, or c

<400> SEQUENCE: 70
gtgctcaggg agctgaatac acggctgcgg gatgacaggg acgcctgcct gggcccacct 60
gctgctgctg ctgttgctgg gctcggcccc ccagacgcgg ctctggccac cttcccagtg 120
cccggtgacc agccccgagt gactcacgga ccatgagcta gaagctgccc ttgcaggagg 180
cttgtcatgg gtcggggrtg cccactcagg atgcaggctc tccccagggg gccccaggct 240
cgcctgactg aagacatgaa ggacctagcc taggagtggt cagggtcccg ggagtggcca 300
gggtcccgtg tgtkccctct gccagtcttc gctctgtccc cgttcaatca accccatctc 360
agttcagcag aaaacccccct cgtcaaataa aacccactga ctgcaaaaaa aaaaaaaaaa 420
aaaaaaactc nngggggggc ccggtaccca atttg 455

<210> SEQ ID NO 71
<211> LENGTH: 413
<212> TYPE: DNA
<213> ORGANISM: Homo sapiens
<220> FEATURE:
<221> NAME/KEY: SITE
<222> LOCATION: (343)
<223> OTHER INFORMATION: n equals a,t,g, or c
<221> NAME/KEY: SITE
<222> LOCATION: (385)
<223> OTHER INFORMATION: n equals a,t,g, or c
<221> NAME/KEY: SITE
<222> LOCATION: (410)
<223> OTHER INFORMATION: n equals a,t,g, or c

<400> SEQUENCE: 71
gaattcggca cgagcggctt tgggcggaac tggctttgtt gaccgggaga aacgagatgg 60
gggtgaagct ggagatattt cggatgataa tctacctcac tttccctgtg gctatgttct 120
gggtttccaa tcaggccgag tggtttgagg acgatgtcat acagcgcaag agggagctgt 180
ggccacctga gaagcttcaa gagatagagg aattcaaaga gaggttacgg aagcggcggg 240
aggagaagct ccttcgcgac gcccagcaga actcctgagg cctccaagtg ggagtcctag 300
cccctcccct gatgaaatat acatatactc agttccttgt tanaaaaaaa aaaaaaaaaa 360
aaaaaaaaaa aaaaaaaaaa aaaanaaaaa aaaaaaaaaa aaaaaaaaan aaa 413

<210> SEQ ID NO 72
<211> LENGTH: 849
<212> TYPE: DNA
<213> ORGANISM: Homo sapiens

<400> SEQUENCE: 72
gaattcggca cgaggtataa tgccattctc ttcctctgtg aagtgcctgt tcggggtgtt 60
gctacgtttt tgttttgttg tgttttctgt tgtagtgttt acatttttct tgtcgattcc 120

-continued

```
taagaggact ttagggtact gagtcaccca tggtcatgtg ttgcagagaa gtgtcacaga    180

gtgaaaactg tcttttcctt gatactacct ttagattcat atttgggaag accttcacta    240

atcatgacta cataagtatt cacttttact ttcttaaggc ctttttgttt tcattctttt    300

atagtaatgt ctaagccatc tggaattagt ttgttgatta tgcaagaaag ggatcgaagt    360

gctttttctg agtcattatc cacatgccga aacatttatt gaatagccct ttccttattg    420

atctgaaaac accttcttat aaaaccttgc attggttttt ggacttgctg tgctttcagg    480

agtcagaaga acattctttt gattatkgta gctttacatw aataatacat ttkggccggg    540

tgcggtggct cacgtatgta atcctagcat tttgggagac tgaggcaggc ggaacacctg    600

aggtcagggg ttcaagacca gactggccaa catggcaaaa ccccgtctct acaaaaaaaa    660

aaaaaaaaaa aattagctgg gcatggtggt gcctgcctga aatcccagct actttgggag    720

gctgaggcag gagaacctct tgagcctggg aggtagaggc tgcagtgagc cgagcttgca    780

ccactgcact ccaacttggg taacagagtg agactccatc tcaaaaaaaa aaaaaaaaaa    840

aaaactcga                                                            849
```

<210> SEQ ID NO 73
<211> LENGTH: 505
<212> TYPE: DNA
<213> ORGANISM: Homo sapiens
<220> FEATURE:
<221> NAME/KEY: SITE
<222> LOCATION: (12)
<223> OTHER INFORMATION: n equals a,t,g, or c
<221> NAME/KEY: SITE
<222> LOCATION: (501)
<223> OTHER INFORMATION: n equals a,t,g, or c

<400> SEQUENCE: 73

```
gctccaccgc gntggcggcc cctctagaac tagtggatcc cccgggttgc caggaattcg     60

gcacgagttc atctattgaa gggtgtttga gtttttttcac tttttggctt ttgtaagtga    120

tatagtttgg atctgggtcc ccattcaaat ctcatgtcaa gttgcagtcc ctagtgttgg    180

aggtgggcct ggtgggaggt gatgggatgg tagggttggc ttctcatgaa tggttaacac    240

catccccttt ggtactgtct ttggcatagt gagtttgttc tcctgagatc tcatttttta    300

aaagcatgtg gcacctctcc tttcactgtc tcttgctcct gctcccacta tgtgaggtga    360

ctcactcttt gtttgctttc taccataatt ggaagctttt tgaggcctct ctagaaacag    420

aagctgctat gcttcctgta cagcctgcag aaccacgagc caattaaacc tttttctaaa    480

aaaaaaaaaa aaaaactcga ngggg                                          505
```

<210> SEQ ID NO 74
<211> LENGTH: 719
<212> TYPE: DNA
<213> ORGANISM: Homo sapiens

<400> SEQUENCE: 74

```
gaattcggca cgaggagaaa ggagggaagg cacagcgctg ggcagagatg ccagaaaacc     60

tagttctaat cttggccttg ctgctgtcag tgtgtggcct taagcaagtc atttttctct    120

cggcctcaat ttactctaaa atgtgtaccc tcatagctac taagaaagtt gttgcaaaaa    180

ctagaaatga tgcttactgg tatttaatta gtctcaaaca catagtaggc ttttaacaat    240

tagtggctgt cattttcatt attattaggc gcttcaattt ttacatgttg gcaatctcaa    300

acataccatt ttcttttttt taaaaccctt ttttttkttt tttttttga gacagaatct    360
```

-continued ccagcctggg agacagagca agaccgtgtc tcagaaaaaa gtggggccgg gtgcagtggc 420
tcatgcctgt aatcccagca ctttgggagg ccagggcggg cggatcacaa gatcaggaga 480
tcgagaccat cctggctaat gcggtgaaaa catgtctcta ctaaaaatac aaaaaattgg 540
ctgggcttgg tggtgggcgc ctgtagtccc agctactcag gaggctgagg caggagaatg 600
gcgtgagccc gggaggcgga gcttgcagtg agcagaaatt gcgccactgc actccagcct 660
gggcaacaga gcgagactct gtctccaaaa aaaaaaaaaa aaaaaaaaaa aaaactcga 719

<210> SEQ ID NO 75
<211> LENGTH: 1274
<212> TYPE: DNA
<213> ORGANISM: Homo sapiens
<220> FEATURE:
<221> NAME/KEY: SITE
<222> LOCATION: (1243)
<223> OTHER INFORMATION: n equals a,t,g, or c
<221> NAME/KEY: SITE
<222> LOCATION: (1270)
<223> OTHER INFORMATION: n equals a,t,g, or c

<400> SEQUENCE: 75
cctgccgttg gcggcctgag tccgcagcgc cctgckccac ccgccccgga cgtggggccc 60
aagcccccgt gaagatggtg tcctggatga tctccagagc cgtggtgctg gtgtttggaa 120
tgctttatcc tgcatattat tcatacaaag ctgtgaaaac aaaaaacgtg aaggaatatg 180
ttcgatggat gatgtactgg attgtttttg ctctctatac tgtgattgaa acagtagccg 240
atcaaacagt tgcttggttt cccctgtact atgagctgaa gattgctttt gtcatatggc 300
tgctttctcc ctataccaaa ggagcaagtt taatatatag aaaattcctt catccacttc 360
tttcttcaaa ggaaagggag attgatgatt atattgtaca agcaaaggaa cgaggctatg 420
aaaccatggt aaactttgga cggcaaggtt taaaccttgc agckactgct gctgttactg 480
cagcagtaaa gagccaagga gcaataactg aacgtttaag aagcttcagt atgcatgatt 540
taacaactat ccaaggtgat gagcctgtgg gacaaagacc ataccaacct ctaccagaag 600
cmaaaaagaa aagtarccag cccccagtga atcagcmggt tatggaattc cactgraaga 660
cggrgatgwg raaacagatk aagaagcaga ggggccatat tcagataatg agatgttaac 720
acacaaaggg cttcgaagat cgcaaagcat gaaatctgtg aaaaccacca aaggccgcaa 780
agaggtgcgg tacgggtcac taaaatacaa agtgaagaaa cgaccacaag tgtattttta 840
gtcatctaca cgtcaaatat cccaagacag attatgctaa atacatcgac ttcatcttct 900
aacatgatat attcaggatt tacacattaa aatgattatt taaattgtgg cagtgatggg 960
gtttactttc atgaatttaa attgttttta tttcctgtaa caattgcttc caaatattga 1020
ctactaaagg cagttctgca agatgtacta aatatgtata ttagaaatta tagaaaatca 1080
tgttgtccgt tttcaaattc atcaacagcc tagagtgcct gagatataag atgaaacaca 1140
aatccacagt atacttgaaa ggagcctttt tacggttcag gataaatcag cctttgtgat 1200
gtactgtgtt tacctccttt tgtgttgtat ctggtaatta aantagggcc cagattcagc 1260
aagtgacatn acaa 1274

<210> SEQ ID NO 76
<211> LENGTH: 519
<212> TYPE: DNA
<213> ORGANISM: Homo sapiens
<220> FEATURE:
<221> NAME/KEY: SITE
<222> LOCATION: (13)

-continued

<223> OTHER INFORMATION: n equals a,t,g, or c
<221> NAME/KEY: SITE
<222> LOCATION: (24)
<223> OTHER INFORMATION: n equals a,t,g, or c
<221> NAME/KEY: SITE
<222> LOCATION: (35)
<223> OTHER INFORMATION: n equals a,t,g, or c
<221> NAME/KEY: SITE
<222> LOCATION: (44)
<223> OTHER INFORMATION: n equals a,t,g, or c

<400> SEQUENCE: 76
accaaaagct ggnagctccc accncggttg gccgnccgct ctangaacta gtggaatccc 60
cccggggctg caggaattcg gcacgaggtt ttgttttgtt tttttctaat cctgctttca 120
tactagccag tgtggggaaa aggtacaata tgtcaaagag atgagagagt gttatttctt 180
gggcaatttt ctattagtgt ttcttatttt ggccagttct tttatttatg tccttgtgac 240
ccaggtactt ggggggccag ctacccttct ggccttttag cgtctttgaa ggagaccaga 300
catgagtgaa tacctaggag agtgtcagca tgtttctgga aaattggcag agaccaagcc 360
ctgctgcaga ttcgtcaggc caggtgaaag ggccaggcag ttgcagctga tgatgtaaat 420
attttgtaca gtagataaat aaatgtttaa aaaaaaaaaa aaaaaaaaaa aaaaraaaaa 480
aaarwaaaaa aaaactcgag ggggggcccg gtacccaat 519

<210> SEQ ID NO 77
<211> LENGTH: 389
<212> TYPE: DNA
<213> ORGANISM: Homo sapiens

<400> SEQUENCE: 77
ggtcgaccca cgcgtccggt ttgccatata atgagcattt tgtatacata aatttatagt 60
ttaattaaat taggacattt gtaaaaaatt ggatacaatt ttattttcaa atacctttt 120 ttagctacac tcaaacactt attgaattga aattatgcac atgtttgatt tagtgatatg 180
gtattacaaa acaccaatac cctgttaatt gtttctgcct ttcttctttc catgctgttt 240
ttcaaatttt ctattgctat atttctagtc actaatctgt cttttgaaag gtctaatctg 300
ttgttagggc catccagtga tttgttttta aattttaagt aatttatctc tataagttct 360
agatcgcgag cggccgctct agagggatc 389

<210> SEQ ID NO 78
<211> LENGTH: 823
<212> TYPE: DNA
<213> ORGANISM: Homo sapiens

<400> SEQUENCE: 78
cccacgcgtc cgcccacgcg tccggtaact ttatgaatat aaatttacag tttgatacag 60
gaattattag gagtaattct tttctgtttc tgtttataat gtagctacag tgttcttcat 120
tttcagaagt taacatcaag ccatcaaacc tgggtatagt gcagaaaacg tggcacacac 180
tgaccacaca ttaggctgtg tcaccattgt gtggtgtacc tgctggaaga attctagcat 240
gctacttggg gacataattt cagtgggaaa tatgccactg accgattttt ttttttcct 300 ctttgcagtg gggctaggac agttgattca acaaagtatt tttttctttt ttctcagtcc 360
taatttgaac aggtcaaaga tgtgttcagg cattccaggt aacaggtgtg tatgtaaagt 420
taaaaatagg ctttttagga actcactctt tagatattta catccagctt ctcatgttaa 480
atatttgtcc ttaaagggtt tgagatgtac atctttcatt tcgtatttct cataggctat 540

-continued

```
gccatgtgcg gaattcaagt taccaatgta acactggcca gcgggcccag caatctccat    600

gtgtacttat tacagtctta tttaaccagg ggtcctaacc actaacattg tgactttgct    660

ttgagacctt tcctctcctg ggtactgagg tgctatgaag ccaactgaca aagatgcatc    720

acgtgtctta ggctgatgcc actacccgat ttgtttattt gcaatttgag ccatttaaag    780

accaataaac ttccttttt aaaaaaaaaa aaaaaaaact cga                       823
```

<210> SEQ ID NO 79
<211> LENGTH: 2455
<212> TYPE: DNA
<213> ORGANISM: Homo sapiens
<220> FEATURE:
<221> NAME/KEY: SITE
<222> LOCATION: (2277)
<223> OTHER INFORMATION: n equals a,t,g, or c

<400> SEQUENCE: 79

```
ggcctcgctc ccggaagtgg agggtctaca cgaagcgccg ctgggtctgg gtgcccggag     60

gcagcagcgt tcgcggagtt cgcccgctgg cccccgatca ccatgtcggc tttcgacacc    120

aacccccttcg cggacccagt ggatgtaaac cccttccagg atccctctgt gacccagctg    180

accaacgccc cgcagsggcc ctggcggaat tcaacccctt ctcagagaca aatgcagcga    240

caacagttcc tgtcacccaa ctccctgggt cctcacagcc agcggttctc cagccatcag    300

tggaaccaac ccagccgacc ccccaggccg tggtgtctgc agcccaggca ggcctgctcc    360

ggcagcagga agaactggac aggaaagctg ccgagctgga acgcaaggag cgggagctgc    420

agaacactgt agccaacttg catgtgagac agaacaactg gccccctctg ccctcgtggt    480

gccctgtgaa gccctgcttc tatcaggatt tctccacaga gatccctgcc gactaccagc    540

ggatatgcaa gatgctctac tatctgtgga tgttgcattc agtgactctg tttctgaacc    600

tgcttgcctg cctggcctgg ttctcgggca acagctccaa gggagtggac tttggcctct    660

ccatcctgtg gtttctgatc ttcactccct gtgccttcct ttgttggtac cgacccatct    720

ataaggcctt taggtccgac aactctttca gcttctttgt gttcttcttt gtatttttt     780

gtcaaatagg gatctacatc atccagttgg ttggcatccc tggcctgggg gacagcggtt    840

ggattgcagc cctgtctaca ctggataatc attccctggc catatcagtc atcatgatgg    900

tggtggctgg cttcttcacc ctctgtgccg tgctctcagt cttcctcctg cagcgggtgc    960

actccctcta ccgacggaca ggggccagct tccagcaggc ccaggaggag ttttcccagg   1020

gcatcttcag cagcagaacc ttccacagag ctgcttcatc tgctgcccaa ggagccttcc   1080

aggggaatta gtcctcctct cttctctccc cctcagcctt tctctcgcct gccttctgag   1140

ctgcactttc cgtgggtgcc ttatgtggtg gtggttgtgc ccagcacaga cctggcaggg   1200

ttcttgccgt ggctcttcct cctccctcag cgaccagctc tccctggaac gggagggaca   1260

gggaattttt tccccctcta tgtacaaaaa aaaacaaagc tctctttcct tctctggtga   1320

tggtttggta ggattctttt gtctctggaa gcagtgggac tgaagttctc ttcgtcctgt   1380

gcacacacag acaccccccac acagttggga tcacaggctg acctgggccc atcccagctg   1440

gagctttctg ccagggtcct gggccttgac tcccccaccc tgcaggcctg gcctgaatct   1500

ggcttcttag acacagccca gtccttcctg cctgggctgg gaataagcct ctcacaggtt   1560

ctggtggaca gatctgttcc ccaggtcact ccagtggtct ccaggcttcc agagaaggct   1620

ggttgcctca agctcttctc tgcctcataa acggatccag agaaggctgg ttgccttaag   1680

ctcttccctg cctcgtgttc ctgagaaacg gattaatagc cctttatccc cctgcaccct   1740
```

cctgcagggg atggcacttt gagccctctg gagccctccc cttgctgagc cttactctct 1800
tcagactttc tgaatgtaca gtgccgttgg ttgggatttg gggactggaa gggaccaagg 1860
acactgaccc caagctgtcc tgcctagcgt ccagcgtctt ctaggagggt ggggtctgcc 1920
tgtcctggtg tggttggttt ggccctgttt gctgtgacta cccccccccc tccccgaacc 1980
gagggacggc tgcctttgtc tctgcctcag atgccacctg ccccgcccat gctccccatc 2040
agcagcatcc agactttcag gaagggcagg gccagccagt ccagaaccgc atccctcagc 2100
agggactgat aagccatctc tcggagggcc ccctaatacc cagtggagtc tggtttcama 2160
ccctgggggg tgtgtcactg tgatgggaca cgtaggagtc cacccttaaa accagcaccc 2220
tgtccctcga ggctgccgag tgggtgtgtg gactcggggg ccttcccaca aaaactnstc 2280
cggctctggg cccgagacag ccgcaggccc cagccactga atgatactgg cagcggctgg 2340
ggttttatga actcctttct ggtatttttt cccctctatg tacaaatgta tatgttacgt 2400
ctcaattttt gtgcttaagt aaaaataaaa acattttcag acaaaaaaaa aaaaa 2455

<210> SEQ ID NO 80
<211> LENGTH: 921
<212> TYPE: DNA
<213> ORGANISM: Homo sapiens
<220> FEATURE:
<221> NAME/KEY: SITE
<222> LOCATION: (111)
<223> OTHER INFORMATION: n equals a,t,g, or c

<400> SEQUENCE: 80
ttttcttaag ggaaaaatca cgctgtgttc ttttaaaatc cctcaggttt tatgttttat 60
tgctaccaga gtctgcctcc ctgaggttct tgtatagact agttatttcc ntctgtaaag 120
aagctgttct attcgttctc gcctggtttg gaacaaactg aacacttcca aaggaggcag 180
tccttgcagc cttgtctcct tccactcccc tcctccccac agtcctgggc tggagcagcg 240
agtctgtcga tcccagggcc agagacaagg cagacaaagg ttcatttgta aagaagctcc 300
ttccagcacc tcctctcttc tccttttgcc caaactcacc cagtgagtgt gagcatttaa 360
gaagcatcct ctgccaagac caaaaggaaa gaagaaaaag ggccaaaagc caaaatgaaa 420
ctgatggtac ttgttttcac cattgggcta actttgctgc taggagttca agccatgcct 480
gcaaatcgcc tctcttgcta cagaaagata ctaaaagatc acaactgtca caaccttccg 540
gaaggagtag ctgacctgac acagattgat gtcaatgtcc aggatcattt ctgggatggg 600
aagggatgtg agatgatctg ttactgcaac ttcagcgaat tgctctgctg cccaaaagac 660
gttttctttg gaccaaagat ctctttcgtg attccttgca acaatcaatg agaatcttca 720
tgtattctgg agaacaccat tcctgatttc ccacaaactg cactacatca gtataactgc 780
atttctagtt tctatatagt gcaatagagc atagattcta taaattctta cttgtctaag 840
acaagtaaat ctgtgttaaa caagtagtaa taaaagttaa ttcaatctaa tttttctctg 900
tggaaaaaaa aaaaaaaaaa t 921

<210> SEQ ID NO 81
<211> LENGTH: 678
<212> TYPE: DNA
<213> ORGANISM: Homo sapiens

<400> SEQUENCE: 81
gaattcggca cgctcttggg ggtagtggat gcgggttgag gggtttcagg tgccctgggc 60

-continued

```
tgtcactttg taaaggcttg ccaacctaga ttgagatggg tggtaaagga atcaattaca    120

caatgccaca catttgcttg cttctgctga atgccttagt agtttcatgt ttattgctgg    180

aagccattct cttacagcat ctagtgctgt gtaacgagct accttaaaat gtaaaggctt    240

aaaacagcca tctttgatgt ctttgcaggt ctagaagtca ggaagggtaa ttattcagct    300

ccaagtggca ttggctctag ttactacctg atattccagg gtggtagctg gagtggtctc    360

aagggtccaa gctgacctca cttacaagct gggtgccttg gcagggacag ttaggaggct    420

gtgtgtagca gagcctcact cggtctttgt attctccagg cctcttcagt ggtttctttg    480

gcacttctta aatgatgtca gggttccagg agttaatgtt ccaagagaca ggaagtggat    540

gctgcccatc tctttttttt tgtttgtttg tttgtttgtt tttttgagat ggagtcttac    600

tctgtcacca ctgcactcca gcctgggcaa cagagcgaga ctctgtctca aaaaaaaaaa    660

aaaaaaaaaa aaactcga                                                  678
```

<210> SEQ ID NO 82
<211> LENGTH: 857
<212> TYPE: DNA
<213> ORGANISM: Homo sapiens
<220> FEATURE:
<221> NAME/KEY: SITE
<222> LOCATION: (493)
<223> OTHER INFORMATION: n equals a,t,g, or c
<221> NAME/KEY: SITE
<222> LOCATION: (562)
<223> OTHER INFORMATION: n equals a,t,g, or c

<400> SEQUENCE: 82

```
gaattcggca cgaggggaaa taatgtttgt ggaaaattgc ttagaggaaa tggagtatat     60

tactggtata ggtactctaa aatgtctttt gaattaagtc agagttagag ggttgtgtct    120

ctaaaccgca tcttactggt attatgctat cagcctgtat tgagagactt tataggtaaa    180

gtccaattta ggctgtttgg tattatctat taaaattaga atgttcatgc tctgtaacct    240

gctacttcca cttctagaat ttatctttgg aagcacatat ctgtccacag acctatattt    300

acacacatgt atgaagaatg tkttccttca cattcattca ttttaacaaa tgttttgatg    360

tgtagggcct aagctgattt gaatgcagct gaaatgcaca tatctggttg agtcmtggga    420

actgatttgc atgtgtcttt ctcttttatg gcttgaagag gagagaaatt tgtgcttagc    480

acattgaagg gcntacgaga tacaaggagt ctgtccttag ctctgccctt tggactgttg    540

tctgaaggct aaagaagaga gnacaaagaa agcttgcatt gggaggctga ggtgggagga    600

tcacttgagc ttaggagttt gagaccagcc tgggcaacat agggagactg cacctctata    660

agaaatttta aaaattagcc gggttggcag cgtgctcttg tggtcccagc cgcttgaaaa    720

gctgaggtgg gagaatcgcg tgagcctggg aggtcgaggc tgcagtgcac cgtgattatg    780

ccactgcact ccagcttggc aacattgact gtctcaaaaa gattatatat ctctaaaaaa    840

aaaaaaaaaa aactcga                                                   857
```

<210> SEQ ID NO 83
<211> LENGTH: 1977
<212> TYPE: DNA
<213> ORGANISM: Homo sapiens
<220> FEATURE:
<221> NAME/KEY: SITE
<222> LOCATION: (664)
<223> OTHER INFORMATION: n equals a,t,g, or c
<221> NAME/KEY: SITE
<222> LOCATION: (716)
<223> OTHER INFORMATION: n equals a,t,g, or c -continued
<221> NAME/KEY: SITE
<222> LOCATION: (1319)
<223> OTHER INFORMATION: n equals a,t,g, or c

<400> SEQUENCE: 83
gcaaaaaccc aaaaggggac agcagtagtg ggagaggcca gcatctgtac accccatcag 60
ggtccccgct gtgtgtgccc ctcaggcggc caccagccct accaggtcct cccctcccgg 120
caggtcttcg ccttgatcgt gttctcctgc atctatggtg agggctacag caatgcccac 180
gagtctaagc agatgtactg cgtgttcaac cgcaacgagg atgcctgccg ctatggcagt 240
gccatcgggg tgctggcctt cctggcctcg gccttcttct tggtggtcga cgcgtatttc 300
ccccagatca gcaacgccac tgaccgcaag tacctggtca ttggtgacct gctcttctca 360
ggtatctgcc tgtggcacct ccatttgatc ttgggggagg cattaactct agggttccgc 420
agctgggagg gtctcggcct ctctgggagg ggcagggagc agctcactcc tccagggcat 480
ttttaggaaa gggttttcag ctagtgtttt tccgtgcttg aatggcacca gccctgcctg 540
gggtagctag aagctgagtg gacctgcagc acacccgagc agatgggctt tgcctctgcc 600
ccttttgtcc cctaggctgt ctgctgtggc ccaccctgcc aaggcccgag tgtgggggac 660
tttngaggtg gctcccggcc cggcttccaa gtcctcccct ccatagtgtg gaagcntccc 720
ccgggaggtc cctgccctac ctgcccgcgt cccctcccag agtcctggaa agcccctccc 780
tttccatgga actgacgctt cacccgtcct cttctcagct ctctggacct tcctgtggtt 840
tgttggtttc tgcttcctca ccaaccagtg ggcagtcacc aacccgaaga cgtgctggtg 900
ggggccgact ctgtgagggc agccatcacc ttcagcttct tttccatctt ctcctggcgc 960
tacaaggctg gcgtggacga cttcatccag aattacgttg accccactcc ggaccccaac 1020
actgcctacg cctcctaccc aggtgcatct gtggacaact accaacagcc acccttcacc 1080
cagaacgcgg agaccaccga gggctaccag ccgccccctg tgtactgagc ggcggttagc 1140
gtgggaaggg ggacagagag ggccctcccc tctgccctgg actttcccat gagcctcctg 1200
gaactgccag cccctctctt tcacctgttc catcctgtgc agctgacaca cagctaagga 1260
gcctcatagc ctggcggggg ctggcagagc cacaccccaa gtgcctgtgc ccagagggnt 1320
tcagtcagcy gctcactcct ccagggcact tttaggaaag ggtttttagc tagtgttttt 1380
cctcgctttt aatgacctca gccccgcctg cagtggctag aagccagcag gtgcccatgt 1440
gctactgaca agtgcctcag cttccccccg gcccgggtca ggccgtggga gccgctatta 1500
tctgcgttct ctgccaaaga ctcgtggggg ccatcacacc tgccctgtgc agcggagccg 1560
gaccaggctc ttgtgtcctc actcaggttt gcttcccctg tgcccactgc tgtatgatct 1620
gggggccacc accctgtgcc ggtggcctct gggctgcctc ccgtggtgtg agggcggggc 1680
tggtgctcat ggcacttcct ccttgctccc accccctggca gcagggaagg ctttgcctga 1740
caacacccag ctttatgtaa atattctgca gttgttactt aggaagcctg gggagggcag 1800
gggtgcccca tggctcccag actctgtctg tgccgagtgt attataaaat cgtgggggag 1860
atgcccggcc tgggatgctg tttggagacg gaataaatgt tttctcattc aaaaaaaaaa 1920
aaaaaaaaaa aaaaaaaaaa aaaaaaaaaa aaagggcggc cgctcgcgat ctagaac 1977

<210> SEQ ID NO 84
<211> LENGTH: 1149
<212> TYPE: DNA
<213> ORGANISM: Homo sapiens
<220> FEATURE:
<221> NAME/KEY: SITE -continued
<222> LOCATION: (837)
<223> OTHER INFORMATION: n equals a,t,g, or c

<400> SEQUENCE: 84
acccactgac aggcattatg acctaacagg aggttggtag cagtagatcc aagcatgcat 60
gttgcctggc ctgtagattg gccttatcag gtttctgggt gcctctgcct taagatcctg 120
aaggmaaatt ttgtttcaac agtttggaag tcatctgtgg gtccagcttg actttggagg 180
aataagaaga tacttctaga gtatgggaat gattccagat aatttctggg atttgaatct 240
acttgagttt aagggcctgg gacctaattt ggtttagtat agaatttgaa gaattaattt 300
ataggcagct gaatacccaa aacttgggtg gtggtcctgt ggtttggctg agctgtccgg 360
gcataacctg gttctctgtt atgttaaggc tttctgggaa gccagccact ctgcgcagga 420
gtgaaacatg aagttgtttt ctgaggacct gttttggtgg gattgtttgg gcagaggact 480
gtgtttatgc agggcaaatc ccagaaagat aagaggaagc tagagaaact taatgtacct 540
gaattcttca tggtgtattt gcaaactaac ttaacataga ttcttttgac tatggtaagt 600
ttgaatctct ccttgccaaa caacattata agtttagttt tcttcttcct cttgcagccg 660
gtacagaaag gtgtaagtgg tggctgaaaa ttgaggaagc ttcatctgac caatgtgggt 720
gctggtttct tgtgaaatgt gtccctaagc ctccttctcc ttgcaggcag ccacccaccc 780
aggtgtctaa gataggacat gctcctttct ttctctaatc csatcctgag gttgccngca 840
aagccaatat gaccactact gagaaatagt aatgacttct acaaatgcaa gggtcttacc 900
ctcctctttc ccttaaamac cctccctttt ccttagaccc cgtttttgcc atcccccaaa 960
tgtgtggtat ggtgaaacta atcccctgaa tgtgaattgc tatccttatt gccctattaa 1020
agaagagcca gctggtatat tgtcaggaag cactatttaa aatgtgaact gttatagagt 1080
aaataaataa atactctaca ggaaaaaaaa aaaaaaaaaa aaaaaaaaaa aaaaaaaaaa 1140
agggcggcc 1149

<210> SEQ ID NO 85
<211> LENGTH: 767
<212> TYPE: DNA
<213> ORGANISM: Homo sapiens

<400> SEQUENCE: 85
catgaaaaca cattctctta tagtttttaa attcatcatc caagagttcc tgctctttga 60
tgatgagaca tacctggtag actccaaaac agagagcaga cgcctagtat ctttgttctg 120
gggtgtgcat taagagtaca ttgacctgtc tgtctccagt cttgactctt ttggaagaga 180
gatgctagta ctgatgacaa cctgcattct ggctgcggtg tgygtccaca ctgcacagtg 240
tgcaccagac tctcgtatgg acaatgactg tccctcacat caggcgcaga tccattttag 300
agcctcagaa gtcaggagag ggtggacttt caaccacgac tgaaaacact gtctttctta 360
ggacatgctg tgtgtatgac acacttacag atgtctgtgc tcactgatgc ttgttgatgt 420
gtcatcgcac atcagtgaca aacatttgtc atgtttttgc ctttggtgga acttctttat 480
tatactcact ttcctcccaa accatttttc tcaacttcat catgaagcaa atgtcatgtg 540
gtcattctgt gatggggctc agggctaggt taggtgatga tttctgaaag ctcagagacg 600
tgaaggaaaa aggacatcag tgcttggatc ttagctctta taagcctcac gtgcaacaat 660
aaacccgagt tcaagaatca gattcttaga tagattggtt tggtagcaaa tgacaaaaaa 720
ccaacgtaaa tatgcttcgg caaaaaaaaa aaaaaaaaag ggcggcc 767

-continued

<210> SEQ ID NO 86
<211> LENGTH: 728
<212> TYPE: DNA
<213> ORGANISM: Homo sapiens

<400> SEQUENCE: 86
aaatgattta gtgacctata caagtagcct gcagtaccgg atccgaattc ccggtcgacc 60
cacgcgtccg gtgaaaacag cagagtgcta ctccatacca ctgggatctt gtccagtaaa 120
catccagaga gtgaggttag gaaataaaaa gtatataaat attagatgcc tagaaatgca 180
agtcacttta aagattttat gtgaaataga aaaaaaagag aggagaggga ctcattgtct 240
tgtaatgggt ccttcccaga gagaggtgac tgtccagtgg caccgggccc ttttcctcct 300
tcccctttta ctcttatcaa ctaggacaga aactaagaat tttggcttca agtggctaaa 360
agactgatgg gggaaaaaag aaaatagaaa aaaataacag agagactgac gctctaggca 420
gttacaagtc caagaaaaaa gacagaaact tttaagtatt gagccaaaac caggtctagc 480
aamcataatg ctggccctag attatttatt aatttatgaa gaaacttcta gatatggggg 540
tgacaaaagg aaattaaatc cattatatat gcatatattt taatgtaaat atataataga 600
taaattatgt atacataata tataaccaaa ttgaaacagt tttacaattt ggtttgactg 660
gaaattcaaa atccatatat taatttttgt agtaaaagtt tatgtaaaaa aaaaaaaaaa 720
gggcggcc 728

<210> SEQ ID NO 87
<211> LENGTH: 735
<212> TYPE: DNA
<213> ORGANISM: Homo sapiens
<220> FEATURE:
<221> NAME/KEY: SITE
<222> LOCATION: (376)
<223> OTHER INFORMATION: n equals a,t,g, or c

<400> SEQUENCE: 87
gaattcggca cgagtagcag cttgattttc tgttagccta tgaaatgtta ttgtcctata 60
aaaataactt taaactgatt taatatttca tatttacatt atatgaaaat caattacatt 120
ataaaaggaa tccctaatgc agaaacaaag atgcaacttt caaaattctt attattccta 180
tttgtatata cacgagagaa cccaaccagt gcctgtgttt ggggggaaaa gtcaacagtg 240
tagttctaaa ccttatccca aacagaaaat gtggktaatg atgtcacttt ccttgctggk 300
catcattagg cttaaattaa atgctgaagc tgtcatcaaa gagtttacac taaaatcttc 360
agggctttaa ataaanggtt aagtccagct tccaaacaca attttccaca ttagcagctc 420
caatcttctt aaataaagct ctgttttcct atatttttat gactgctgag accccacagg 480
gaccaatatt tgtattcaaa ttacatttca tggtttccca ttgtttcaca atgagttcta 540
ataaatggga tttactataa taatccaagt atgacatagc cggtatgctt tcatgaatgt 600
ttttatgtag attttcctcc catgaacatg agtaaataaa tctgtttcct gaatggattg 660
tggttgcatt taaagctctg taataattct aataaattta ctctatagaa aaaaaaaaaa 720
aaaaaaaaaa ctcga 735

<210> SEQ ID NO 88
<211> LENGTH: 889
<212> TYPE: DNA
<213> ORGANISM: Homo sapiens
<220> FEATURE:
<221> NAME/KEY: SITE -continued
<222> LOCATION: (117)
<223> OTHER INFORMATION: n equals a,t,g, or c
<221> NAME/KEY: SITE
<222> LOCATION: (292)
<223> OTHER INFORMATION: n equals a,t,g, or c
<221> NAME/KEY: SITE
<222> LOCATION: (341)
<223> OTHER INFORMATION: n equals a,t,g, or c

<400> SEQUENCE: 88
tgttaggtta attattgctt cacatgtggt cacggtttga aaacttattt tgggggggagt 60 ataaagtaga atacagagat tccttgctca tagctcctac tgctatcggg gaacaancct 120
tgagggtgag aacgtggatt gattcttgat tgatagtggg gattccatta tctgtatttg 180
gcagttatgg cctgctgcgg tgtatagaag cttctttcca ttcattttcc cgaattttca 240
tactgctcaa ggaacagttg ggggggaatg ggcagaaggt tgggcacttg angtatttga 300
gctatcggta ataactgact ttttagggcg cacagatttg nagtagagcc atggtagtag 360
ttagtaccaa tgggtttttg ctgcttctac tctttcttaa cagaaaaagt ggattgtgtt 420
catataggaa agcagttcac agactgtctt cctgcccctc ccgccaccaa gctggaccta 480
gaatcaagtg tgactttaaa tggggaaagc tgtgttacag ttgtgcttaa gccactgctg 540
tggcttaacc tcacctatgc ataagaattt gctcgtggct ggccgggcgc ggtggctcga 600
gcctgtaatc ccagcacttt gggaggctga ggcgggcgga tcacgaggtc aggagattgg 660
gaccatcgtg gctaacacgg tgaagccccg tctctactaa aaatacaaaa aaaattagcc 720
gggcgtggtg gcgggcgccg ctagtcccac tactgagtcc caggctgaag caggagaatg 780
gtgtgaaccc aggaggcgga sttgcarcga gccgagatcc tgtcactgca ctccagcctg 840
ggcgaagcga gactctgtct caaaaaaaaa aaaaaaaaaa aaaactcga 889

<210> SEQ ID NO 89
<211> LENGTH: 569
<212> TYPE: DNA
<213> ORGANISM: Homo sapiens
<220> FEATURE:
<221> NAME/KEY: SITE
<222> LOCATION: (1)
<223> OTHER INFORMATION: n equals a,t,g, or c

<400> SEQUENCE: 89
ntaaggtgtt gattctggat cacgggatac cattcctgtc macaccccga ccaggggcta 60
gaaaatttgt ttgagatttt tatatcatct tgtcaaattg cttcagttgt aaatgtgaaa 120
aatgggctgg ggaaaggagg tggtgtccct aattgtttta cttgttaact tgttcttgtg 180
cccctgggca cttggccttt gtctgctctc agtgtcttcc ctttgacatg ggaaaggagt 240
tgtggccaaa atccccatct tcttgcacct caacgtctgt ggctcagggc tggggtggca 300
gagggaggcc ttcaccttat atctgtgttg ttatccaggg ctccagactt cctcctctgc 360
ctgccccact gcaccctctc ccccttatct atctccttct cggctcccca gcccagtctt 420
ggcttcttgt cccctcctgg ggtcatccct ccactctgac tctgactatg gcagcagaac 480
accaggcctg gcccagtgga tttcatggtg atcattaaaa aagaaaaatc gcaaccaaaa 540
aaaaaaaaaa aaaaaaaaaa aaaactcga 569

<210> SEQ ID NO 90
<211> LENGTH: 334
<212> TYPE: DNA
<213> ORGANISM: Homo sapiens
<220> FEATURE:

-continued

<221> NAME/KEY: SITE
<222> LOCATION: (321)
<223> OTHER INFORMATION: n equals a,t,g, or c

<400> SEQUENCE: 90
agaaaatgaa caaactagtg agaaacattg taaacatata gtgtagatga taactctgaa 60
cttaagtaca agataatgat gaatattctg ctgcttaagt atatcttaga aatattaatt 120
cttagtgaaa atcttaacct attcaacatc acttatggta agtataactt atttttccta 180
tacaggtatt aaatatataa tttatatgcc agtcacattt cctcacacta aataaggcag 240
cagacacata tatttaatat catgggtatg cattttaggt tctaaaacct aaggtatgtg 300
gatttcttaa agccatatct naaatatttt cacc 334

<210> SEQ ID NO 91
<211> LENGTH: 795
<212> TYPE: DNA
<213> ORGANISM: Homo sapiens
<220> FEATURE:
<221> NAME/KEY: SITE
<222> LOCATION: (3)
<223> OTHER INFORMATION: n equals a,t,g, or c

<400> SEQUENCE: 91
cgnaccattt tttttttttt gaatatcatc agcttacttg actggcaagg gcagaagctg 60
gggttggcct gaactctgcc aaacaaatat caaagtgtat ttaatagtta aatttgtgcc 120
ctttcccttc ttgctgcacc catgttgtca cttaaccccc aggagttatt tattatcttt 180
ttgttaaagt caggctcatt tggggtaatg tgatgactgt ttaggtttac atgaccctcc 240
tctcctttcc ctacccccaa atatgtatat atacatatat aaaatatgta tatattttac 300
ctatataaaa tatatatata tacacatata tgtatctata ttcctttgtt tctttgcctg 360
cttatactgg ccataaaaga gggagctgcc ttcaatgtat aaagtataag aagagtgcca 420
gggaatgcca taatggaggc ttttggatct gaatttggac catttcacta aagagaacat 480
gagtttgctc agccctttcc tcacaagagg gagggccccg gttccccaga cttctccacg 540
cgctggctcc ataaaggcca gctttggccr ggctgccaca ggggcctgag gagctcactc 600
tgggcctacc tggtttcagt tagagggtcc tcctgttatt tttccattta aaaagtatgt 660
cctcagaaaa ctgtactgga aggatgggtg gcaggaactt gtatagttca gcttccaaca 720
ctttggaaca gattaaaaag ggaatctttt aaataaaaac gtataaaaat aaaaaaaaaa 780
aaaaaaaggg cggcc 795

<210> SEQ ID NO 92
<211> LENGTH: 577
<212> TYPE: DNA
<213> ORGANISM: Homo sapiens

<400> SEQUENCE: 92
tagtggatcc cccgggctgc aggaattcgg cacgaggctg cacgaggttg ttgagaggat 60
caagtaagat aatgaatgaa agtgtctatg acgacagtac tagttcttac acaccatccc 120
tccacatttt gggatgtctg ttgctgctct tccttggggt ggaaagagca ctggagccct 180
tctctggtct ttgtgcttct ttacatgatg tgagacctat agtaaacccc ttaacctcct 240
tcagcctcat ttattagaga gagagagaaa aaaaaaggtg attttaaaaa aatctgtttt 300
cggccaggtg cagtggctca tgcctgtaat cccagcactt tgggaggccg aggcaggtgg 360
atcacctgag gtcaggagtt cgagaccagt ctggctaaca tggtgaaacc ctgtcactac 420
taaaaatacm aaaaaatcag ctactcggga ggctgaggca ggagaatcct atgaaaacgg 480
gaggcagagg ttgcagtgag ccgagatcgt gccattgcac tctagcctgg gcaatgagca 540
aaactttgtc tcaaaaaaaa aaaaaaaaaa actcgta 577

<210> SEQ ID NO 93
<211> LENGTH: 968
<212> TYPE: DNA
<213> ORGANISM: Homo sapiens
<220> FEATURE:
<221> NAME/KEY: SITE
<222> LOCATION: (904)
<223> OTHER INFORMATION: n equals a,t,g, or c
<221> NAME/KEY: SITE
<222> LOCATION: (907)
<223> OTHER INFORMATION: n equals a,t,g, or c

<400> SEQUENCE: 93
gaattcggca cgagcttact ttcactcacc gcctgtcctt cctgacacct caccatgtgt 60
acgggaaaat gtgcccgctg tgtggggctc tccctcatta ccctctgcct cgtctgcatt 120
gtggccaacg ccctcctgct ggtacctaat ggggagacct cctggaccaa caccaaccat 180
ctcagcttgc aagtctggct catgggcggc ttcattggcg ggggcctaat ggtactgtgt 240
ccagggattg cagccgttcg ggcagggggc aagggctgct gtggtgctgg gtgctgtgga 300
aaccgctgca ggatgctgcg ctcggtcttc tcctcggcgt tcggggtgct tggtgccatc 360
tactgcctct cggtgtctgg agctgggctc cgaaatggac ccagatgctt aatgaacggc 420
gagtggggct accacttcga agacaccgcg ggagcttact tgctcaaccg cactctatgg 480
gatcggtgcg aggcgccccc tcgcgtggtc ccctggaatg tgacgctctt ctcgctgctg 540
gtggccgcct cctgcctgga gatagtactg tgtgggatcc agctggtgaa cgcgaccatt 600
ggtgtcttct gcggcgattg caggaaaaaa caggacacac ctcactgagg ctccactgac 660
cgccgggtta cacctgctcc ttcctggacg ctcactccct tgctcgctag aataaactgc 720
tttgcgctct caaaaaaaaa aaaaaaaaac tcgagggggg gcccggtacc caattcgccc 780
tatagtgagt cgtattacaa ttcactggcc gtcgttttac aacgtcgtga ctgggaaaac 840
cctggcgtta cccaacttaa tcgccttgca gcacatcccc ctttcgccag ctggcgtaat 900
aacnaanaag cccgcaccga tcgcccttcc caacagttgc gcagcctgaa tggcgaatgg 960
caaattgt 968

<210> SEQ ID NO 94
<211> LENGTH: 553
<212> TYPE: DNA
<213> ORGANISM: Homo sapiens

<400> SEQUENCE: 94
gaattcggca cgagtcccta aacagttaaa atgtcacagc tgtttcttat aatgcttaca 60
ttcatatttc taaataacat gtttataatg catctaactt ccttccatgg aaaaagagta 120
tttggctttt taaaccaatc gagtcacatg catgctttcc cccttccacg ttggactaca 180
tcaatattta gtgttagtat ttttataaat agataaatat tgttcgcaaa ttttatttgc 240
tgtctattgc tgtgtaacaa attcctccaa aattattggc tttaaacaac atttattatc 300
ccatagtttc tatgagttga gaatctaagc aggcttagct gggtccacta gctcggggtc 360
tctcacaagg ccacagatca aggtgttggt cagtggtttg tgcccttagt cccagctact 420
tgggaggctg aggcaggagg atcacttgaa cccagtagtt caaggctgca gtgagcwakg 480

```
gttacaccac tgcactccar cctgggtgac agagcaagat gccatctctt aaaaaaaaaa    540

aaaaaaaact cga                                                       553


<210> SEQ ID NO 95
<211> LENGTH: 968
<212> TYPE: DNA
<213> ORGANISM: Homo sapiens

<400> SEQUENCE: 95

ggcacagcaa ccgtcactgc ctatcagaat cagcagatta ctcgcctgaa gatagatagg     60

aatccatttg ctaaaggctt ccgagactcc gggcgcaaca gaatgggttt ggaagccttg    120

gtggaatcat atgcattctg gcgaccatca ctacggactc tgacctttga agatatccct    180

ggaattccca agcaaggcaa tgcaagttcc tccaccttgc tccaagtact gggaatggcg    240

ttcctgccac tcaccctcac cttttgtctg gctcctcttg ctcctctcct gccttccatc    300

tggggcccaa caccagccag ctgtgtagtc tggcccctgc tgactattct gcctgtgccc    360

gctcaggcct caccctcaac cgatacagca catctttggc agagacctac aacaggctca    420

ccaaccaggc tggtgagacc tttgccccgc ccaggactcc ctcctatgtg ggcgtgagca    480

gcagcacctc cgtgaacatg tccatgggtg gcactgatgg ggacaccttc agctgcccam    540

agaccagctt atccatgcag atttcgggaa tgtcccccca gctccagtat atcatgccat    600

caccctccag caatgccttc gccactaacc agacccatca gggttcctat aatactttta    660

gattacacag cccctgtgca ctatatggat ataacttctc cacatcyccc aaactggctg    720

ccagtcctga gaaaattgtt tcttcccaag gaagtttctt ggggtcctca ccgagtggga    780

ccatgacgga tcggcagatg ttgccccctg tggaaggagt gcacctgctt agcatggggg    840

tcagcagagt ttctttgact ctaggaccct aggaagctta actctgtcat catctcaagt    900

atctgcacat atggtctgat gaagccttta aagttaaatg aacatttggg atctgtctaa    960

acatattt                                                             968


<210> SEQ ID NO 96
<211> LENGTH: 697
<212> TYPE: DNA
<213> ORGANISM: Homo sapiens
<220> FEATURE:
<221> NAME/KEY: SITE
<222> LOCATION: (19)
<223> OTHER INFORMATION: n equals a,t,g, or c
<221> NAME/KEY: SITE
<222> LOCATION: (50)
<223> OTHER INFORMATION: n equals a,t,g, or c
<221> NAME/KEY: SITE
<222> LOCATION: (57)
<223> OTHER INFORMATION: n equals a,t,g, or c
<221> NAME/KEY: SITE
<222> LOCATION: (662)
<223> OTHER INFORMATION: n equals a,t,g, or c
<221> NAME/KEY: SITE
<222> LOCATION: (680)
<223> OTHER INFORMATION: n equals a,t,g, or c
<221> NAME/KEY: SITE
<222> LOCATION: (690)
<223> OTHER INFORMATION: n equals a,t,g, or c

<400> SEQUENCE: 96

aagaaaatta ccctcactna aaaaaaacaa aaactaaaag ctcgcacgcn tgcaggnacg     60

acactagtgg atccaaagaa ttcggcacga ggccacatcc caccggccct tacactgtgg    120

tgtccagcag catccggctt catgggggga cttgaaccct gcagcaggct cctgctcctg    180
```

-continued

```
cctctcctgc tggctgtagg tctccgtcct gtccaggccc aggcccagag cgattgcagt    240

tgctctacgg tgagcccggg cgtgctggca gggatcgtga tgggagacct ggtgctgaca    300

gtgctcattg ccctggccgt gtacttcctg ggccggctgg tccctcgggg gcgaggggct    360

gcggaggcga cccggaaaca gcgtatcact gagaccgagt cgccttatca ggagctccag    420

ggtcagaggt cggatgtcta cagcgacctc aacacacaga ggccgtatta caaatgagcc    480

cgaatcatga cagtcagcaa catgatacct ggatccagcc attcctgaag cccaccctgc    540

acctcattcc aactcctacc gcgatacaga cccacagagt gccatccctg agagaccaga    600

ccgctcccca atactctcct aaaataaaca tgaagcacaa aaaaaaaaaa aaaaaaaact    660

cngggggggg gcccggttan ccaatttggn cctaaag                             697
```

<210> SEQ ID NO 97
<211> LENGTH: 866
<212> TYPE: DNA
<213> ORGANISM: Homo sapiens

<400> SEQUENCE: 97

```
ttttagttca ttattctctt ctattaagag aaattcactg ttaaaaaatt gtttcccatt     60

tccgtatctg aaataatgac tgtagttgag gtgatcttgc cctgggtctg aaatcatact    120

tccaaaccaa aaaggacttt gaatacaaaa cttttaagaa atcttgtatg aatacaagct    180

atatctgaaa aattgtgttt tataatattg atgcctagtt ttgccccagg ccatctgcag    240

tgtggttact atgcaaagaa tgctggtgtt gctgtttttt ttttttttctt tgttggctat    300

taacccagcg gagacaatat gtggctatgg tagtacttgg aagttctagc attacacaga    360

ctagcttcca tttctctcat agaggtcatt ttggcattta aaacacatac ttttagaaaa    420

cagatttgga tgtatgtaaa cacagggtta atccaccaca ctctggatgc tagagctgtt    480

gacaaagtca tgctttgcag attttaaaat aaacttttttg ttactcttac agcttggtat    540

tttcccctcc tatttttttt acctcctcta aataaacctc tttgttaaat aattgatgtt    600

tctggatcat agaaaatagt aagtttaaaa tacagaatat ttccaagcta actacaaatc    660

tgatgacagt tttttgagtg tgcacttttc cttttatttc ttaggtcctt tttggtcctt    720

tgcaaacata gtaagattcc atatttgtgt cccaactgtg gtaatattgc tgacttctta    780

ctggaaaaca gtcagctcta ggtagcattt cttctgtgtg gtatttaagt taaattatta    840

ccaaaaaaaa aaaaaaaagg gcggcc                                          866
```

<210> SEQ ID NO 98
<211> LENGTH: 1368
<212> TYPE: DNA
<213> ORGANISM: Homo sapiens
<220> FEATURE:
<221> NAME/KEY: SITE
<222> LOCATION: (637)
<223> OTHER INFORMATION: n equals a,t,g, or c
<221> NAME/KEY: SITE
<222> LOCATION: (1140)
<223> OTHER INFORMATION: n equals a,t,g, or c
<221> NAME/KEY: SITE
<222> LOCATION: (1170)
<223> OTHER INFORMATION: n equals a,t,g, or c
<221> NAME/KEY: SITE
<222> LOCATION: (1286)
<223> OTHER INFORMATION: n equals a,t,g, or c

<400> SEQUENCE: 98

```
ttcctgtgtg ccctgagccc gctggggcag ctgctgcagg accgctacgg ctggcggggc     60
```

-continued

```
ggcttcctca tcctgggcgg cctgctgctc aactgctgcg tgtgtgccgc actcatgagg    120
cccctggtgg tcacggccca gccgggcycg gggccgccgc gaccctcccg gcgcctgcwa    180
gacctgagcg tcttccggga ccgcggcttt gtgctttacg ccgtggccgc ctcggtcatg    240
gtgctggggc tcttcgtccc gcccgtgttc gtggtgagct acgccaagga cctgggcgtg    300
cccgacacca aggccgcctt cctgctcacc atcctgggct tcattgacat cttcgcgcgg    360
ccggccgcgg gcttcgtggc ggggcttggg aaggtgcggc cctactccgt ctacctcttc    420
agcttctcca tgttcttcaa cggcctcgcg gacctggcgg gctctacggc gggcgactac    480
ggcggcctcg tggtcttctg catcttcttt ggcatctcct acggcatggt gggggccctg    540
cagttcgagg tgctcatggc catcgtgggc acccacaagt tctccagtgc cattggcctg    600
gtgctgctga tggaggcggt ggccgtgctc gtcgggnccc cttcgggagg caaactcctg    660
gatgcgaccc acgtctacat gtacgtgttc atcctggcgg gggccgaggt gctcacctcc    720
tccctgattt tgctgctggg caacttcttc tgcattagga agaagcccaa agagccacag    780
cctgaggtgg cggccgcgga ggaggagaag ctccacaagc ctcctgcaga ctcgggggtg    840
gacttgcggg aggtggagca tttcctgaag gctgagcctg agaaaaacgg ggaggtggtt    900
cacaccccgg aaacaagtgt ctgagtggct gggcggggcc ggcagcacag gggaggaggt    960
acagaagccg gcaacgcttg ctatttattt tacaaactgg actggctcag gcagggccac   1020
ggctgggctc cagctgccgg cccagcggat cgtcgcccga tcagtgtttt gagggggaag   1080
gtggcggggt gggaaccgtg tcattccaga gtggatctgc ggtgaagcca agccgcaagn   1140
ttacaaggca tcctcaccag gggccccgcn tgctgctccc aggtggcctg cgcatggctt   1200
atgctcaagg acctggaaac ccatgcttcg agacaacgtg actttaatgg gaagggtggg   1260
tgggccgcag acaggctggc agggcnggtg ctgcgtgggg ccctctccag cccgtcctac   1320
cctgggctca catggggcct gtgcccaccc ctcttgagtg tcttgggg                1368
```

<210> SEQ ID NO 99
<211> LENGTH: 613
<212> TYPE: DNA
<213> ORGANISM: Homo sapiens
<220> FEATURE:
<221> NAME/KEY: SITE
<222> LOCATION: (25)
<223> OTHER INFORMATION: n equals a,t,g, or c

<400> SEQUENCE: 99

```
gaattcggca cgagcgggac gcggntgaag atagcctgcg gagtgtccgg gcggaacacg     60
gttgcagcac tcccagtaga ccaggagctc cgggaggcag ggccggcccc acgtcctctg    120
cgcaccaccc tgagttggat cctctgtgcg ccacccctga gttggatcca gggctagctg    180
ctgttgacct ccccactccc acgctgccct cctgcctgca gccatgacgc ccctgctcac    240
cctgatcctg gtggtcctca tgggcttacc tctggcccag gccttggact gccacgtgtg    300
tgcctacaac ggagacaact gcttcaaccc catgcgctgc ccggctatgg ttgcctactg    360
catgaccacg cgcacctact acacccccac caggatgaag gtcagtaagt cctgcgtgcc    420
ccgctgcttc gagactgtgt atgatggcta ctccaagcac gcgtccacca cctcctgctg    480
ccagtacgac ctctgcaacg gcaccggcct tgccaccccg gccaccctgg ccctggcccc    540
catcctcctg gccaccctct ggggtctcct ctaaagcccc cgaggcagac ccactcaaga    600
acaaagctct cga                                                       613
```

-continued

<210> SEQ ID NO 100
<211> LENGTH: 685
<212> TYPE: DNA
<213> ORGANISM: Homo sapiens

<400> SEQUENCE: 100
gaattcggca cgagcctcag ccacccagt agctaggact atagacacaa gctagccttt 60
ttatacttac tgttttcatc aaatgtcttt ttccaactag tttccaacct gtctttgtat 120
ttgaagtgca tctattgtag atagttcagt gttgctttta aagtgcttac tccatttgtg 180
tttagtatgt tgacatggtt ggatttagat ctactatttt gctttctgtt tttattcctg 240
tttatccttt tttacttctt acagcttaat gaattttggg gggggaatcc attttaattc 300
tctcttgggt ttttagctac atcttcttta ggattgcact agagattaca atatacattc 360
ttaacgtctc accctttgc ctggggcggt ggctcatgcc tgtaatccca gcactttggg 420
aggctgaggt gggtggattg cctgagctca ggagttccag accggcttag gcaacatggt 480
gaaaccctgt ctctatgaaa aatacagaaa cattagctgg ttgtggtggc acacacctgt 540
agtcccagct acttgggagg ctgaggtggg aggatccctt gagcctggga ggttgaggct 600
gcagtgagct gagatcatac cactgcattc tagcctgggt gacagagtga gatgctgtct 660
ccaaaaaaaa aaaaaaaaaa ctcga 685

<210> SEQ ID NO 101
<211> LENGTH: 646
<212> TYPE: DNA
<213> ORGANISM: Homo sapiens

<400> SEQUENCE: 101
tcgacccacg cgtccgataa ctttttcaag caatatcagt gagtgggtcc catcgacagg 60
gttccaggac ctggaacact ttaacagaag gaaatgccga agcagcttgc acagttgctt 120
tacagacttc caagaggctg attctggctt caagatggag ccttggagtt ggtttttttt 180
tttttttttt ttcttccctc aaagaacctg cggttgcgct ttgtgtgttt tgtttttgtt 240
ttccatttgg gggccccatg ggaaagagct tctgaactct ttcctttatg aactccccact 300 gtgttcctat aaaggccctt ttctttctta gtgttgtaag ttacattttc attatgcccc 360
atcacatctt ctttactgta aaaatattaa aaagctgttt ccaagtggga cagctaatga 420
agctctaatt attgcagaca tatttttgag atgtaaaaaa aaaaatttaa agttaaatga 480
taagtcttag aggcgagtga ggaataaaat ggatgtaaac atttacatgg gatgcattag 540
aattctgctg tgtgtactgt cttttggttg aaacaaatta tgaacagtga ctaataataa 600
aaagtcaata cccaawraaa aaaaaaaaaa aaaaaaaagg gcggcc 646

<210> SEQ ID NO 102
<211> LENGTH: 826
<212> TYPE: DNA
<213> ORGANISM: Homo sapiens
<220> FEATURE:
<221> NAME/KEY: SITE
<222> LOCATION: (726)
<223> OTHER INFORMATION: n equals a,t,g, or c

<400> SEQUENCE: 102
ggtcgaccca cgcgtccggc tccctttgtt ttggtggcag ccttcttgtg ctgtatactt 60
gttccctagg gtgtataata atatgtgcac tagagtgcta ggtaccctac cacattgctg 120
ggaccttgcc acactgctgc agccttccag taggatatgg gggaatgtca gtgaggctcc 180

-continued

```
agggatgtag atatgtaggg aatgttggac cccagggcaa catgcaatct ggtaggagtt    240

gggctctcaa aatggtgctg ctgtgtaaca gctgcttggg tcttggggta gggagtgtag    300

gacccagcat gagctccctc tttggagcag tgctgtctga gactccaggc agctccgtgt    360

attagtctca ggacctgcaa aggcctaggg gctctttttg ggtaggactg caggagtctc    420

catggtggga atgtgaacca ctggaaatct ctcatttacc atttccctgt actggagatg    480

ctttctgggc tcccagatga tactarctgg gctggttgcc tcamttcctt ctccctctgt    540

gcataaggca ttttctgtca cttctctgct gaactctagt gttctttctt agaggctgta    600

ctcaaagttt cattatccat tcagtatttt tattcttctt tgtggaggtg gcaagtgcta    660

ggtgcctcta gtcaatcatc ttgaagcccc ctgttatgtt aaagtcttta atggaaaaag    720

aagacnacat gcatgaccag gcagatactt tgagcagagt cataggaact gctaaaaaaa    780

aaaaaaaaaa aaaaaaaaaa aaaaaaaaaa aaaaaaaagg gcggcc                   826
```

```
<210> SEQ ID NO 103
<211> LENGTH: 586
<212> TYPE: DNA
<213> ORGANISM: Homo sapiens

<400> SEQUENCE: 103

gaattcggca cgaggtggct atcagatttg ggttctact ctatgagact tttaagtcat      60

tatgcaattt ctttattttw attttttga caagaagtct ggagcatgat tacattatgc    120

attttcttac tctttaaagt atttgtgggg ataatccttc attatttgat tggcaaaaat    180

atatatgttt atagtgtgta acatggtgat tggatatatg tacacattgt ggaacagcta    240

aatcaagcta ataacaaatc agttacctca catacttatt ttgtggtgaa aacatgtaaa    300

atccactctc ttagcaattt tcaagcatcc aatacattgt tawtaactgt agtcaccatg    360

ttatacaata gatctcttga acttattctt cctgtctaac taaaattttg tattccttga    420

tcaacatcta cccaatccct cactgttctc cagcctkgat aactaccatt ctactctctg    480

cttctatgaa tttgactttt ttttttttta gattccacat atgtgagatc gcgcagtatt    540

tgtctttctg tgcctggctt atttcactta atataaagtc cctcga                   586


<210> SEQ ID NO 104
<211> LENGTH: 628
<212> TYPE: DNA
<213> ORGANISM: Homo sapiens

<400> SEQUENCE: 104

tacagcagtt taaaaagcag tgtctttctt tgagagacag gaagtctagt gaagagccag     60

tattttaggg atagataatg aaagaggctg tcatttcaga cattttaatc ctctgaaaga    120

atacaaaaga aaaaaaaaag aaaacaaatc tttcagaatt gtttgaagta agaacaagac    180

aagaggaggt gattggtgtg ttactgttct acgaaaaagg agaaaaagct tcatgaaatc    240

gccattcagc aaggacagaa ctggagatgg cttctctttt acaaagaaat ctctgtccca    300

ggctttcagt ctgtttggtg ttcatacaag tgtttgtgtg ttgtgtggaa ggcgggggaa    360

ggcgggtgaa ggcggtcctg ttcagggccc cctttggtga acacagcagg caaaatactc    420

tcgtcatccc cagccaaact ggcctgcaag cgcactgact tccacatccc tagcatttag    480

gcctttgaat agaagctgac acgtagcagc cagctgaaca agtatttaat gaggagcaac    540

acaactccaa gaagggctcc ttagtgtatt gtcaagttgc tgcagccttg tgagatggaa    600
```

-continued aaaaaaaaaa aaaaaaaaaa gggcggcc 628

<210> SEQ ID NO 105
<211> LENGTH: 558
<212> TYPE: DNA
<213> ORGANISM: Homo sapiens

<400> SEQUENCE: 105
agctctaata ttactcactw tgaaggsaaa gctggatacg cctggcaggt accggttccg 60
ggrattcccg ggccccatca caccctatgg gggagagcga atgttacagg aggctttctg 120
gtgcctcgtg cacatggact gtgcatgtgg attttgccta aggtcagcct tatatgcatt 180
gtggaactag ggtatggaaa accatgaaac atgattattt tcttctagca tgcctgtcta 240
tgacttcaac tggtggtatt ctttgtactt tataatctac attatcatta atacctacat 300
cttcaagtct gtctttctgg ccatggtgta cagcaattat aggaagcatt ttcacatact 360
gtgtgtgtgt gtgtgtgtgt tttgtagtga tgaacagaac ttgttattta cccaattcta 420
ttatctatca taatagtaaa ttagctacta taatagacaa aagtatgact ctcagttaaa 480
taagagattt tttaaaaact tgttacaaaa aaaaaaaaaa aaararaaar aaaaaaaaaa 540
aaaaaaaaaa gggcggcc 558

<210> SEQ ID NO 106
<211> LENGTH: 756
<212> TYPE: DNA
<213> ORGANISM: Homo sapiens
<220> FEATURE:
<221> NAME/KEY: SITE
<222> LOCATION: (230)
<223> OTHER INFORMATION: n equals a,t,g, or c
<221> NAME/KEY: SITE
<222> LOCATION: (755)
<223> OTHER INFORMATION: n equals a,t,g, or c

<400> SEQUENCE: 106
gaattccaat gtccacaggt gatgggagag atgctgagaa agggtggcca gtgagtgagg 60
aggaaaacca gaggagtgtg tatcctgggt accctgaatg tgatgagcga caagctgtcc 120
cccagcactg tgccattgct tctcccagtt ctcttcaaag tcaccatcct gcttcagcgt 180
gtgtgcccag aagatagccc ttcctcttct gtgcttccag aatccgtagn cagggaatag 240
gaatacatgg acaagtagca tgcagtgcag tgagaatgta taacaacaga tgactctggg 300
gaccaaaatc aaatggggcc agctacaaag agggcaggaa atccccacag gtgattttac 360
tgtgaggaat tttatgaggt tcagcatcat atattgttag gagaaaatgc tgttttgata 420
agcagagata tgagaaaagt aaacgggaac tatgatttag agatctcatc tgrttacttt 480
gtcctattcy cagtttwatt actaaagagc agtaaagcca aggagaaagt agtaaagatt 540
agatgaatgg ttagcatgtg aaacctgaaa ggaaccagag tgatttccct cgaggaacaa 600
atgcacttct cttacatatg aaagatgatg tgttctgtgt tcccatagaa tctagggaaa 660
gaaaaagtga gcagatactc tgatatgagc aatataactt aggtgtaaaa aaaaaaggaa 720
ttcgatatca agcttatcga taccgtcgac ctcgna 756

<210> SEQ ID NO 107
<211> LENGTH: 1146
<212> TYPE: DNA
<213> ORGANISM: Homo sapiens

<400> SEQUENCE: 107

-continued

```
cccgtccaca atgcagcaga ctcttcccaa ggccacctag caagcaaggt tgatcggatc     60
atctaaactg gccgcctcct gaatatttca ctgaatcctg gcgttcatgt tgaagcagac    120
aaaatgagaa aggaggaggg cattgctcac ctctcaatag cttttttcgt tcaagttcta    180
tgtctttatc agctcttgcc tgtgatttta ccccaattca accttgggag tgggaagaat    240
atgaacagat aacccttggc ctaacagctc catcaaacct ccttgagagc aactacctag    300
gccaggctag tgagtgcttt gtgaggaagc tggtcagaag gttccctcaa ctccttcctg    360
gtcctcctgg acactgcaga aaagacttag ggatccccca gcagaggcca attgctctcc    420
ttccttccct gccccaccag gaaaggaata acgtccacag acttgaagca gatagtgaag    480
tagatctgtg agaggttcta ggtacttagt gtgtagactt tgacgaatat ttctcaagtt    540
gggagccctt gttaaaaatg atgtttaagg gagtggttgg ggggaagatg aaggcatgga    600
ggaggaagaa gagaaggaag cccttgccat ataaaattca tgcagactaa acagtttccc    660
tgacagaata aataaagtgg atgctacccc actccagaat caaaagcaat ttaattaaag    720
tctcttaagt tgtaaagagt tttaaatgat ccgtgttgaa ggcgaatsct gcyaaatgca    780
gtgggtctga cgtcagctgc cgggcctggg ctgggaggcc atttgctatt ctgtttaagg    840
caggctggat tgtcttattt tggaaccagc ttggtggggg gtttgctttg ctactgcttc    900
tgagccctga gcttcaaagg ctgaaattaa tggtgaacaa aattgtgcgg ctctggccat    960
cccatgcggg caagcccatt gagggttatc attaagtaaa gaaataaaga gggggaaaaa   1020
agcctgcctg ttccaaaaac ctcatcagat aatgacctca gtgattgggt tttcattacc   1080
aaacagcatc cagagattat caacccatag aagaagggag gggaaaaaaa aaaaaaaaaa   1140
aaattc                                                              1146
```

<210> SEQ ID NO 108
<211> LENGTH: 775
<212> TYPE: DNA
<213> ORGANISM: Homo sapiens

<400> SEQUENCE: 108

```
tcgacccacg cgtccgaaaa aggaaatgat acatgtcttg acatttctat tgcagtwtta     60
catcttaatt tctaagggca aaggtgatgt ttcccagttc gtaaagtctc gagagtacta    120
atgctatcaa aagtaattaa tttcaagtgt aaataagacc aaacaaaaac gatcagatgc    180
gacattgtct cataaacatg atagactatt aaatcacttt gtgtttttttg gaaacagcta    240
taactattaa tatatacagt aatctagtaa atttccttca gatatgctat tgcggataca    300
acagatcatc tattgtcaca agctaaccat tatcctaaca aaatggcgga atacagcaag    360
acataagagt aaaaagaaag aagatgagct gatattaaaa catgaacttc aattgaaaaa    420
atggaaaaat aggttaatac tcaaaagagc tgctgcagaa gaatccaatt ttcctgaacg    480
aagttcttct gaagtctttc ttgtagatga gactctaaaa tgtgacattt cactgttacc    540
kgaargrgca atattacagg tttgtatgaa ttcagtatac attatatact ataatctgcc    600
aagtgtggtg gtgcatgcct gtaatcccag ctgcttggga ggctgagaca ggagaattgc    660
ttgaacccag gaggcagagg ttgcagtgag ccgagatcac accattgcac tccagcctgg    720
gcgacaatag caaaactcca tctcaaaaaa aaaaaaaaaa aaaaaaaggg cggcc         775
```

<210> SEQ ID NO 109
<211> LENGTH: 911
<212> TYPE: DNA
<213> ORGANISM: Homo sapiens -continued

<400> SEQUENCE: 109
gaattcggca cgagacgaca atggggaacg cggtgtttcc cacctcttgt gggtagaaag 60
cagtctgctt tgaggaggcg agaaggcaaa gccagggcag ggcgttgctg tgggaagcgt 120
tcggtgaaag crggtttcga cgcttaggag ggccgaggga gaagattcca ccagcattgt 180
ccttgcttca agttttagga tgtctgaact ttcagctttc atgttttcaa ccatcatttt 240
tttaatggca caacctacat cttgttttta aaagaagtag cctcaaatta aactcctaaa 300
ctctgatgcc ctggggatga gaacaactag ctkggatctc gtgccgtgta atcaatgttt 360
cattccgctg cctccatcat gtaatagaat cgcttccaga aaggcagtta actggaagca 420
gcagaggctc ccagccgtga gaggactgct caacaatgcc ccccatcgcc gccccccccac 480
ccctcgcacc ccttgtgttt tcccctctga ggggcccaag ggttatggct ttcatgtcta 540
ggtgtgggga cagaggaggg agaggcagat ccygggccgg gagaggatgg ccctggtctg 600
aatctggagt aattaatgcc cacccaaaga aaaggccctg cccaggtcca atgttgtctt 660
agatctgatg atgctgctat ttacaaaaca ctgatcgtcc gaaagcttga atctgttcct 720
cctcgaatga ccctgtagat gcctgacctc caccgtacct ccacatcact attcatgtcc 780
ttctaggaaa atgtgcacat gcctcacgca ctatgtggga agggcgtgtt tttaaattaa 840
taaagtgtgt caccattagc catamraaaa aaaaaaaaaa aaaaaaaaaa aaaaaaaaaa 900
aaaactcgta g 911

<210> SEQ ID NO 110
<211> LENGTH: 456
<212> TYPE: DNA
<213> ORGANISM: Homo sapiens
<220> FEATURE:
<221> NAME/KEY: SITE
<222> LOCATION: (456)
<223> OTHER INFORMATION: n equals a,t,g, or c

<400> SEQUENCE: 110
gaattcggca tgagctttct ttctcctgca ggcattggaa atacagtccc agctggcaac 60
accagccagc agcacagccc ggaatcctgc tcctgacctg caccatcccc accagcccac 120
gatagaacgt ttttgtaggc attcctcctc atgggagagg atagagtaca tgcgagtttt 180
tgctctcctc ccaccctttc acaagagcac tgtgctttct tttcttctct ttttcctttc 240
ttttttttt tttaggcagg gtcttgctgt gtcasccagg ctggaatgca gtggtgcaat 300
catagctcac tgcagccttg acctcctgga ctcaagcaat cctcctgcct taacctccca 360
gctactcagg agaccgagac aggaggacca cttgagccca ggaggttgag gctgcagtga 420
gccgagattg caccactgsa mtccagcctg gggaan 456

<210> SEQ ID NO 111
<211> LENGTH: 554
<212> TYPE: DNA
<213> ORGANISM: Homo sapiens

<400> SEQUENCE: 111
gaattcggca cgagcctcca cctcccaggt tcaagagatt ctcctgcctc agcctcctga 60
gtagctggga ttacaggcgt gcaccaccac acgttgctat tttttgtact ttaagtagag 120
acggagtttt gccacattgg ccaggctggt ctcaaactcc tgacctcaag tgatccaccc 180
accttggcct cccaaggtgc tgggattaca ggcatgagcc actgtgcctg gctccattta 240

-continued

```
caactatttc tatcattata atgcaggggc tctcaaacct gagcatgcct cagaatcccc    300

cagagggctg tgcgcacaga ctgctggacc tttccccagc ttctgattcc gtccctccag    360

agtggggctc gaagattgcc tttgaggtga rgctgcgggt cgggggcacg tctgagaact    420

gctgcagagg tgartgctgt ggctctgtct gcattccccc tggaagactg argcaccagg    480

tgtgctggtg ctaacagacc acaagtccct cctggacact gcccttctct gaagggagct    540

gcctcctcac tcga                                                      554
```

<210> SEQ ID NO 112
<211> LENGTH: 722
<212> TYPE: DNA
<213> ORGANISM: Homo sapiens
<220> FEATURE:
<221> NAME/KEY: SITE
<222> LOCATION: (2)
<223> OTHER INFORMATION: n equals a,t,g, or c

<400> SEQUENCE: 112

```
gnaattcggc acgagaaaaa tttacgggta acactgaggg gtggggtgga aagttttgat     60

cataaagtgg tcaccaacaa gggcacttct gaggtgctaa tgatgttctg ttttctgatc    120

tgggtcgtgg tgacattcac atattcatta aattgtacat ttgttttaca taagtttatt    180

atatttccta attttaaaaa agttaaaagg aggaggaaaa agttggttat gaaagtgtaa    240

ccattcttcc aaaatatcaa ttaaaacaca tctgaattaa gaggtaaaat atatcaaaga    300

ttgacagaaa acaaaagctc tgaaatgata tttccagcct aagaacagtc gttgcttttg    360

ttggtttagg aagttttgtt ctcctgaact aatgttcaaa atgaaaaaaa gtcacctggg    420

ccaggagcag aggcccacac ctgtaatccc agcactttgg gaggccgarg tgggtggatc    480

acaaggtcag gagatcgaga ccatcctggt taacgtggtg aaaccccatc tctacaaaaa    540

tacaaaaaat tagctgggct tagcggtggg catctgtagc cccagctact cgggagattg    600

aggcaggaga atggcatgaa cctgggaggt agagcttgca gtgagccgag attgcgccac    660

tgtaccagcc taggtgacag agcgagactc cgtctcaaaa aaaaaaaaaa aaaaaaactc    720

ga                                                                   722
```

<210> SEQ ID NO 113
<211> LENGTH: 931
<212> TYPE: DNA
<213> ORGANISM: Homo sapiens
<220> FEATURE:
<221> NAME/KEY: SITE
<222> LOCATION: (930)
<223> OTHER INFORMATION: n equals a,t,g, or c

<400> SEQUENCE: 113

```
gaattcggca cgagaaccag atgtttttcc acacagaatg ctagttcttt aagacacagg     60

ctgggtgaca tgtttcctta gagtgacaat atttccttat agtgacattt tccttgactg    120

gctccatgca gaataggagg atatagaata ggaggagaag gtttctgctg tggcacctgg    180

agtggtactt ggtgcacgcc aggtgctaga caatgtgtgt gacaaggatg cacgtgaaat    240

gccccccccc gagtgcctca gtgactgcag taaagtggcc cttgtcatgg tcctcttcct    300

ctttctgcat cagtcttcat gctgggcggc atgaagagag aaacaaaaac cacctttctt    360

gccagggtct tagtaccatt tgctgctctt atctttcaag taagggagaa catctaagaa    420

acttatcacc gtattcattc tagactgtta gggrtttaac tcttcaccta cttccctgag    480

tggtctgggc tggargttca gagctaartg ggctgggtgt aaatcaggat tccgtccctc    540
```

-continued

```
amtagctgtg aggctgtggg taattcactt catctctctg agccttcatt ttctcacctg    600

aaaattgggc atgctaatac ttttccatct ccttcccagg gttcacagga ttaaatgaaa    660

ttattaacac aaagttcttg gcctggtagg gggcatgtac gtggccaccg tcctggtgct    720

ggacactggg gtaagagttt ggaagctatt ggctgggcaa ggtggctcac gcctgtaatc    780

ctagcacttt gggaggctga ggcaggtgga tcacgaggtc aggagattga gaccatcttg    840

gctaacacgg tgaaacaccg tctctactaa aaatacaaaa aaaaatttag ctgggcgtgg    900

tggcatgcgc ctgtagtccc atctactcgn a                                   931
```

```
<210> SEQ ID NO 114
<211> LENGTH: 588
<212> TYPE: DNA
<213> ORGANISM: Homo sapiens

<400> SEQUENCE: 114

gattcggcac gagatcaaaa tggccagttc tgtgacagta aaagaggttt gtgtcttatt     60

taatcttttg ataataataa cagctatggt gtatcacagc tttaccaagt accagacact    120

gttctaaggg ctttgcatgg ttcactcact ccttacgtca tccctcggtg gcaggtgctg    180

taattatcct tatattgcag acaaggacat tgagacagag gtcaagccac cttcccaagg    240

gcacacatgg catctgcact gctcctgacc gaccgacaga gagagctgct gtcacgatcc    300

tcaaatgagc tatgcatgtc aaaagtttaa aaataaaaaa gataaaaaca tgcacaaaat    360

ttaaaaagta aaccatttca agctggacag actaaaactg agagatggcc agagaagagt    420

atgaaagata aatctatgga cagagtaaac cctgactggc ttgaaattag ggcccttact    480

cctccacact cctgacgggt tggttcaaga ccargaawta gaagcmcmtt gtgagttcta    540

cgstgctgcc ctgggaaaca cacaggctaa acacacccac aggctcga                 588
```

```
<210> SEQ ID NO 115
<211> LENGTH: 812
<212> TYPE: DNA
<213> ORGANISM: Homo sapiens
<220> FEATURE:
<221> NAME/KEY: SITE
<222> LOCATION: (443)
<223> OTHER INFORMATION: n equals a,t,g, or c

<400> SEQUENCE: 115

gaattcggca cgagtatggc ccttctttgg cttctgggta tttaaaaaga gctcttggga     60

ctcttctgag gtcttcctgg gagcagaaca gtacacatgg tctggaattg ggttgcatgg    120

aataactttc aaggaaagcc actgaataaa gtgccctgca ttcctgtcca ttggatactg    180

ataatgctat aagatgatct ttctcttctt tattttgttt gagattattg tgactctctg    240

gctaactcct acttatcctc aggccttttc tgaactcaca attcaaatta cagctccctt    300

tggttctctt ccacagcagt tgtacttaca tatgtctatt atataattat gaattgtttc    360

atattgtcgc ccttacaggt aaactaatga atttggggct ccatctgttt gctcaccact    420

tgatcctggc agtagcacac aanggctgct caatacctat ttactgaatg agcaaakgga    480

ctggaccact tttagagact ggagtatttc cttawaccak gtgagattga wttttgagga    540

cagtttacca ctggaagctt ttgcagaact aaggtcattt ttacagtata cataacctct    600

gctgtgtttg ttgatactgt aagtttacat tttcttatga ctctttttaa gtagagcacc    660

cctgtgttta ggaaagctag agctattgtg atgcctttga gtttgcttgg ctgattgctg    720
```

-continued

```
ggacttgaac tactgagctt atctaaaagc ctcagaggcc ttgtagcctc tgtcttttag    780

agagtgtagg taaaggcttg ttttccctca aa                                  812
```

<210> SEQ ID NO 116
<211> LENGTH: 506
<212> TYPE: DNA
<213> ORGANISM: Homo sapiens
<220> FEATURE:
<221> NAME/KEY: SITE
<222> LOCATION: (13)
<223> OTHER INFORMATION: n equals a,t,g, or c

<400> SEQUENCE: 116

```
gaccatgatt acnccaagct cgaattaccc ctcactaaag ggaacaaaac tggactccaa     60

cgcgttggcg gccgctctag aactagtgga tcccccgggc tgcaggaatt cggcacgagc    120

acctcctgag gaatatggtg taggaaagcc acccgcgtgc tttctggctg ggatggctct    180

cttccttggc tgctggaggc actggagaga ggtctgataa ggatggctgt atggatcagt    240

gggtcttatt cctcattctg cagcagaagc aactgggatg ttttttctcc taatattgtg    300

ctggcttctc tgcctttctc tttccggtct gtatccaagg ctgctaaacc ctggtggctg    360

gctctccctg ctctctttcc agatggatta tggctggatt ctgccatggg gagcttgtac    420

agtcagacat ggaaagccag gaatgggaaa gaggtcaggt ggttctctcc cacacctcac    480

tgccttggtg ctatgtctca cctcga                                         506
```

<210> SEQ ID NO 117
<211> LENGTH: 751
<212> TYPE: DNA
<213> ORGANISM: Homo sapiens

<400> SEQUENCE: 117

```
gaattcggca cgagagcctc gcaggtggat tagacccacc cgaggctcgg gagaaaccac     60

ggcaccttgt tgttttgagc cactaaatgg cgggacgctt gttcacgctg ctgctatggc    120

aagagctagc gaggcggctg gtaccgggtg atgcttcacc acggctttcc agaaagcgct    180

ccgtgacccc aggcccaccc ttcccgacac tcacggttcc ctcagaaatg ctcctctcaa    240

atctctcact ctccctgcag cctttgttgt ttcttttttc tttctttctc ttttgcaaga    300

tgggatcaag gaaaggtctc agacacaaaa cgcaacattt ttcttccatg acagatcaga    360

tattgaaggg ctcagtgagg agccctgctc tgggacaact ccatgattag cgctccaaga    420

ggcagtcaca gggaagcagg tgctctgttc ccctcctggc tcagcaatcc cgcagtcctc    480

ccgtcccgct ccaggcccag ccagcctggc tgcttggatc cgagacaata gcttggtctg    540

gaggcggctc agggtgggag ggacccaggg acccgggcac cagtacagca gctgggaatt    600

caggcccagg gatagggatg gggcacagga caccaccccc atctcacaca gggagatgaa    660

ggtgggatcc agcatgggga ctggacatcc ctgagtccag ctgccccgtt acaatggggg    720

aactgagatc cggggatggg atagttctcg a                                   751
```

<210> SEQ ID NO 118
<211> LENGTH: 960
<212> TYPE: DNA
<213> ORGANISM: Homo sapiens
<220> FEATURE:
<221> NAME/KEY: SITE
<222> LOCATION: (460)
<223> OTHER INFORMATION: n equals a,t,g, or c

<400> SEQUENCE: 118

-continued

```
ttttgtctag tacatatatg taaatatatt aatgttgttt ttgtgtttgt gatgtagtaa     60

ggagatgtac atagaaattc attgaggtat atagatactc atctgtctag gcagttccca    120

attttctgaa gaatgtttta cagcaaaatt ttctattttc ttttattaaa tagtgacacg    180

tcaaacaatg tcacatccaa aacactagtt tcatcaattt ctagcagtaa taatagactt    240

gctgtaagta ttgttttctg atgccatacc cttgtcatac atattattaa atgaccaata    300

ttatgtatga agtagacaaa aaaatttact caaacttcat tcaaatccta attgtgataa    360

tttttgtttt atatttaatt ataaaccaaa atacatttgc atttttaagc taatttgtct    420

caaaattttg ctttatattt ttggatcagg ttaaagtccn gtggatcccc tgaatgttat    480

tgtccctctt gatggttttt acttctgagc tatacgtcaa aagacacata agcttcaaaa    540

gtcmagacaa acctcattgc cataaaaatc aagatataga tgttctgttc cgtaaactcc    600

ttgaaaaaca ttttaaagtc atcaatatga tctgtttccc atgaaactta agttagcttt    660

cttattggag twattycttt tctgtaagtc tgaaaagtag agattttgtt ttacgcattt    720

tagtaacctg caacaaccaa ctctaaaaaa gatttggctt gtaatgacgg tctctgcttt    780

tttgggtttg gagtacacaa ttgtaatatt tacttagtta tttgtgtttt tctttgttca    840

aggtattgac tagtttcata aattttttgm aagtttttct ttcattggtt ggaaagcaga    900

ttacattttg cactattaaa ataagtttat tactttaaaa aaaaaaaaaa aaaaactcga    960
```

<210> SEQ ID NO 119
<211> LENGTH: 1442
<212> TYPE: DNA
<213> ORGANISM: Homo sapiens
<220> FEATURE:
<221> NAME/KEY: SITE
<222> LOCATION: (1377)
<223> OTHER INFORMATION: n equals a,t,g, or c
<221> NAME/KEY: SITE
<222> LOCATION: (1419)
<223> OTHER INFORMATION: n equals a,t,g, or c

<400> SEQUENCE: 119

```
cttctatatt agatggacag atttatatac ttttccatgg aggattaagt aaactgaaac     60

ctaagacaca cgaagaaatt ctaagtggaa aggccactta ttagttagtt tacagcagta    120

tcgtaagtga caggatgata ggagtgtggt aagtgatcag gataataatc tgcttagtaa    180

gagaaacaat ttgaatttta gaaggaaatt gccttaccat ttgcaaatta aggtaattaa    240

aatacagtga atttcaaaat gcctttttaa tgacaatgtg tgaacttaat ttgttttaat    300

aaaccaaaat trttgttatt gtgttaaggc tattttacat tgaatgtgta tcttgccact    360

gatgttaact tatcccatct tacccaaggt tgtaggtaac aatatactat tgggtgacag    420

tggactaaca tctctagtga tccctttgtc agtggtcttt aacttaaaat aatttagaga    480

atatggtttc tacaacttac atttttgttt wcttgtaact acagattatt atgatggttg    540

taatgaagat tatgagtata attggagcta tatgtttctg aattctgaac aactatttat    600

aaaattttat cctacttttt tctgttgaac atatgacttc tctggtctgc taaacacata    660

cagaccttta gttttggttt acatggattt aaatatatag atatatcact gtaaaataaa    720

cttcaggtgt aacagattta tagagaaagt aatcatattt gtttatggtt gtgtacctac    780

tttgagaaga aaagaaaaat attagaatga acagataatt ttacaagtgt tgatcactta    840

ccagcaaacc agaaacttca gagattttga aagcaaatct attttctctg ctgtgtatta    900

aattcattta tctaaaatgt tattgctcct ggcttagaat catcttgtgc aaattctctt    960
```

-continued

```
tttttgttgt ttgtctgttt gcctgttgct caccatagac ataattttct tttcataaaa   1020

cattctttgt ataatcacct cagagattat gaaagtgact ttgataaaat ttaatggtgt   1080

tcacaaaata attttcacgt gagtaatttc acagtgcgtg tattgtatgt tatttagtgt   1140

attttatatt ttgtttcaat tagagaatgc tattgaatcc agtttttgtt tagttactgt   1200

tcattttact ttataaaatt gacataattg agtttattaa atttattggg ccaatttaag   1260

taaacagttg aacgtttcat aagtcatgag gtctttttgg gcatatacat gaagtaaaca   1320

aagacaatac taggctatgt aataggragg ctaccttaat taggaggtaa atattcnttt   1380

tggaaattgg gcccgtgggc ctcgggtgga aaatggggna atatccctag gtaaaaaaat   1440

gg                                                                  1442
```

<210> SEQ ID NO 120
<211> LENGTH: 845
<212> TYPE: DNA
<213> ORGANISM: Homo sapiens

<400> SEQUENCE: 120

```
gattttacac agaacatatt ctctgcatga tttcagaaaa gaaaatctaa aaaggtaata     60

cgggtatttc aaataaaatc ctttctggta tgaaaggctc cattgatttt attaagcctt    120

cctttacctt gtagtacaag gtgctttaat gggatagaac taagcatatc aatatctata    180

actgcatttt gtgctagaca attactgttc ttttctctaa aatgtatatg tcaatttaca    240

aggccaggga tagaaaacac tccataattg ctttccttga ttttgctgag gatttggtat    300

gattttagta agcaaactgt tttttggttt ttccttaatg tttttaattt tttttcctct    360

tgcaacaatg acggtgcatg ttcttataaa tataggaagg tccagatata aatagtaacc    420

taaagttctt gctgtgctta aaaaaaaaaa tcatgtggcc ctttcaatat ttgaactgct    480

aagcaatgac atctgtagtt ttatctcctt ttttatgtca tagaaattaa tatgatactt    540

taaatatgta aatataatac attaggtaat gctattattt atatctgtct taacataatt    600

taagttgtag ctgtgtcttg gaaatatttt taaggtaatc tatattcaca ttgcctgtgt    660

taatgctttt taaagtttgt atacatcaga tgtatatttt tggtttggca taagctacga    720

ttgtaatttt tcttggcttt ttgttcataa agaatttttt gaaggaatgg taacaaatgg    780

taatttacaa atggttgtga ataaacacat ttttacactt aaaggwaaaa aaaaaaaaaa    840

ctcga                                                                845
```

<210> SEQ ID NO 121
<211> LENGTH: 360
<212> TYPE: DNA
<213> ORGANISM: Homo sapiens
<220> FEATURE:
<221> NAME/KEY: SITE
<222> LOCATION: (340)
<223> OTHER INFORMATION: n equals a,t,g, or c

<400> SEQUENCE: 121

```
gaattcggca gagaatcagc atgtctatca cctcaaatac ttatttcttt ttattgggag     60

cattcaaaat cctctcttct agctattgga aaatacacac taaattactg ttaactatag    120

tccccctgca gtgctgcgga atgccacaac ttatccctcc tctccagctg tagtttagta    180

tccagtaaca tactcttttc atttcctttc tttgggcaga aggctagatg ttgcctgttt    240

ttgttttatt tttctgcttc acatatagcg cacgaaagca gagtgtattc aaaaaaggaa    300
```

-continued atgtgtttga aaaaaaaaaa aaaaaaactc gagggggggn ccggtaccca attcgcccta 360

<210> SEQ ID NO 122
<211> LENGTH: 944
<212> TYPE: DNA
<213> ORGANISM: Homo sapiens
<220> FEATURE:
<221> NAME/KEY: SITE
<222> LOCATION: (932)
<223> OTHER INFORMATION: n equals a,t,g, or c
<221> NAME/KEY: SITE
<222> LOCATION: (942)
<223> OTHER INFORMATION: n equals a,t,g, or c
<221> NAME/KEY: SITE
<222> LOCATION: (944)
<223> OTHER INFORMATION: n equals a,t,g, or c

<400> SEQUENCE: 122
tcgacccacg cgtccgccca cgcgtccgga cagacccagc ctggagctgg cccctggcct 60
gtgtgctgac ttcttggggt cctcaaacca ctgtattttt ctgttgagcc tgtacttggg 120
gagagatcag tagcatttga ggaagtaaga gaaaagaatc atggtacctc agggtttctt 180
tccctttact cgctggcagc cattgtctgt gggcacctca tgtttttcca cactctactg 240
ggccgtggag gtaacgatca cccaggccag tctcctctgc ctgggatgcg ccctctgaga 300
ggaggcctag cagggcaggc tccctctggg catccctgga tgcagcctct ggacacatgc 360
ctcctttaaa gtgtccgggt gcagctcagg ttgagtggag gtagaaggag aaacagacat 420
gtttaccacg cgttttccaa agctcctgat ctttcccaag attgtaactg aaaactgctg 480
tctcttgttt tgttcgtttt gggggtggtg gtgctggctg ggccatgctt gtgaagtgat 540
gtgtgtctct gatttaacgg attcactgtt ttctctgcta attgagagag cgttatttac 600
attatttatt tgttttgaca caagtgcttt cagtgtttta tcctagctaa tggcttctta 660
aaggtaataa aacccttcca acgtaattgg tcagataaaa cttttttttct tgtatgctta 720 aataaagcaa ttagtgaagc acttctatcc aaaatgactt ttttgtcctt ttttaaaacc 780
aatttactgt tactggaaac tttttgtaca ataawgcaat cacgcagatt aaagaaaaaa 840
aaaaaaaaaa aaaaaaaaaa aagggcggcc gctctagagg atccaagctt acgtacgcgt 900
gcatgcgacg tcatagctct tctactacgt gnaccctaac tncn 944

<210> SEQ ID NO 123
<211> LENGTH: 914
<212> TYPE: DNA
<213> ORGANISM: Homo sapiens
<220> FEATURE:
<221> NAME/KEY: SITE
<222> LOCATION: (909)
<223> OTHER INFORMATION: n equals a,t,g, or c

<400> SEQUENCE: 123
ggcagagcaa gagatgactt tagatgagtg gaaaaatctt caagaacaga ccagaccaaa 60
gcctgagttt aacatccgga aaccagaatc cactgttcct tccaaagccg tggtgattcg 120
agagtcaaaa tacagagatg atatggtaaa agatgactat gaggacgatt cccatgtttt 180
ccggaaaccc gccaatgaca tcacatccca gctggagatt aattttggta acctccctcg 240
tcctgggcgt ggagccagag gaggcacccg gggaggccgg ggaaggatca ggagggcaga 300
gaactatgga cccagagcag aagtggtgat gcaagatgtt gcccccaacc cagatgaccc 360
ggaagatttc cctgcgctgt cttgaaagag ccctgtttcc cagcaccgcg gagctgcact 420
gcacacctgt ggggagactt ttccagctgg gccaagggag tcagactcta agaacaatag 480

-continued

```
atgttgcttt tcccgtgtca tgtaaatttg ttgcactttt ttgggctgag ctgttagagg    540

ggcttctcca gaggctcgag agcaggccat ttcccaagaa gatgaagaat ggtgactgtg    600

tttttattga aggaatttca aatgaagaat aatgtttaaa atgtgtatat agagatagta    660

tagactcctc cgcggaagca tggagggaaa ggaggttgta aaatagactc catggagact    720

cttaggaagc agtagattcc cgggggctgt gcctttagcg ttagaggaaa cacatagagc    780

tggaactgtt aatggaaagc agtcacagct gagttttcgg agaccaagaa attaaaatac    840

aattgcactt acaaaaaaaa aaaaaaaaaa aaaaactcga ggggggggccc gtacccaatc    900

gccttgtgnt gcat                                                      914
```

<210> SEQ ID NO 124
<211> LENGTH: 462
<212> TYPE: DNA
<213> ORGANISM: Homo sapiens

<400> SEQUENCE: 124

```
gaattcggca cgagctgggc tcaagtgatc ctcctgccga ggcctcccaa attgctggga     60

ctgcagctgt gagccaccat gcccagcctt aacttggttt taagacctct gatttgcctt    120

gcctcaatta cctcctttct tattttcttt cctttgttga ctctcatact ctgttctcct    180

aattctcccc cttttccact ccctgcccac cctgaaagac acacacacac acaataagtg    240

ggtggagtaa gaagtcaacg gagttggata taagcattcc tgcttttctg acatctccag    300

tgtcttggag aacaaggatt ctagaatgag ggctcctcat tatgcttcct ttcaacattt    360

tttctctgtg ttacttaagc tttcacccca agcatgtttg acagagagcc agtgcattcc    420

ccttactttt tacaaaaata aaaaaaaaaa aaaaaaactc ga                       462
```

<210> SEQ ID NO 125
<211> LENGTH: 545
<212> TYPE: DNA
<213> ORGANISM: Homo sapiens
<220> FEATURE:
<221> NAME/KEY: SITE
<222> LOCATION: (7)
<223> OTHER INFORMATION: n equals a,t,g, or c
<221> NAME/KEY: SITE
<222> LOCATION: (16)
<223> OTHER INFORMATION: n equals a,t,g, or c
<221> NAME/KEY: SITE
<222> LOCATION: (41)
<223> OTHER INFORMATION: n equals a,t,g, or c
<221> NAME/KEY: SITE
<222> LOCATION: (42)
<223> OTHER INFORMATION: n equals a,t,g, or c
<221> NAME/KEY: SITE
<222> LOCATION: (87)
<223> OTHER INFORMATION: n equals a,t,g, or c

<400> SEQUENCE: 125

```
tcacttncgg ttccgntcga tgtggtgtgg attgtgagcg nntacaattt cacacaggaa     60

acagctatga ccatgattac gccaagncga aattaaccct cactaaaggg aacaaaagct    120

ggagctccac cgcggtggcg gccgctctag aactagtgga tcccccgggc tgcaggaatt    180

cggcacgaga ttcgctgcct aattccacca tgatgtttta ctatgcatgc tttatcttat    240

actcatctct ctctcctctc tctctttctc tttctccctc cctcctttct ctattataat    300

ttagtcatct tattttttga ggcatttcag aatatatcac acttgtccta aatacttcag    360

tatgaacatc attaactaga atttattctt tgttttactt ctgatgtgaa ayttatataa    420
```

-continued

```
atacaacatg ctatgaattt gttttccmaa aaaccaatca acaatttawt aagcatggka    480

acaaaaaacc tgaaggcttt atcttttaga gtagtagttt ttaaaaaaaa aaaaaaaaac    540

tcgta                                                                 545
```

<210> SEQ ID NO 126
<211> LENGTH: 912
<212> TYPE: DNA
<213> ORGANISM: Homo sapiens
<220> FEATURE:
<221> NAME/KEY: SITE
<222> LOCATION: (906)
<223> OTHER INFORMATION: n equals a,t,g, or c

<400> SEQUENCE: 126

```
gaattcggca cagagaaaca tttcatcccc agtaagattc ctcatcgtca ttcacaggtg     60

atctctgttc ccaccctagc cttggacaat tctgcatcta ctttgtagct ctataaattt    120

gccttttctg gacatttcat gtaagtcgat cacacagtat gtgttccttt gtgactggct    180

gcttttgctt agcatgacgt tcttggggct cgcaacgcag cttgtgtctg ttgttcattc    240

cttttgcagc agaatcgtat tctgttgttt ggatgggcca cctgtttgtt gtctgtttac    300

tctccagctg gtggacattt aggccgtttg cactggcggt tactgtgaat catgtcgctg    360

tgaacattgt gtgtgtgtct gcgtggactt gtgtgtcctg ttctctggga aggagttgcg    420

ggttagargg tagttttttg tttcccctgg agactctctg gtttccacat atggtagttt    480

tatgcttaac cttttgagaa attgccaaat ggctttctga agtggccacg tcattttgct    540

ccctccagcc gtttgtaatg ttcccatttc tcctatgtgt aattttaata caaagcagta    600

aaaagttgcc attatggacc tagtaaattc tgaggtaaca taagagagaa ataatgatgc    660

agccgtcatt actgtgctgg taatgtaagt ttcctttttt tttgttttta aatggagctt    720

tgcagagatc aagtcgagag aagaacactg ggccagcctg actccaaagc ctactctctt    780

aagcgctttg ctgacttgtg atgttttaaa atctagcatt attttcaaat gctgtgagag    840

cactgaagat aaaggatttg attctttttt tcaggcatcc aaggatggtt catcatcaag    900

aatcanttta at                                                        912
```

<210> SEQ ID NO 127
<211> LENGTH: 1048
<212> TYPE: DNA
<213> ORGANISM: Homo sapiens
<220> FEATURE:
<221> NAME/KEY: SITE
<222> LOCATION: (13)
<223> OTHER INFORMATION: n equals a,t,g, or c
<221> NAME/KEY: SITE
<222> LOCATION: (16)
<223> OTHER INFORMATION: n equals a,t,g, or c
<221> NAME/KEY: SITE
<222> LOCATION: (17)
<223> OTHER INFORMATION: n equals a,t,g, or c

<400> SEQUENCE: 127

```
gatcccccgg gcncgnngaa ttcggcacga gggacagagt agttccagag gcagttctca     60

ctgtgacagc ccttcgccac aagaagatgg gcagatcatg tttgatgtgg aaatgcacac    120

cagcagggac catagctctc agtcagaaga agaagttgta gaaggagaga aggaagtcga    180

ggctttgaag aaaagtgcgg actgggtatc agactggtcc agtagacccg aaaacattcc    240

acccaaggag ttccacttca gacaccctaa acgttctgtg tctttaagca tgaggaaaag    300

tggagccatg aagaaagggg gtattttctc cgcagaattt ctgaaggtgt tcattccatc    360
```

-continued

```
tctcttcctt tctcatgttt tggctttggg gctaggcatc tatattggaa agcgactgag    420

cacaccctct gccagcacct actgagggaa aggaaaagcc cctggaaatg cgtgtgacct    480

gtgaagtggt gtattgtcac agtagcttat ttgaacttga gaccattgta agcatgaccc    540

aacctaccac cctgttttta catatccaat tccagtaact ctcaaattca atattttatt    600

caaactctgt tgaggcattt tactaacctt ataccctttt tggcctgaag acattttaga    660

atttcctaac agagtttact gttgtttaga aatttgcaag ggcttctttt ccgcaaatgc    720

caccagcaga ttataatttt gtcagcaatg ctattatctc taattagtgc caccagacta    780

gacctgtatc attcatggta taaattttac tcttgcaaca taactaccat ctctctctta    840

aaacgagatc aggttagcaa atgatgtaaa agaagcttta ttgtctagtt gttttttttc    900

ccccaagaca aaggcaagtt tccctaagtt tgagttgata gttattaaaa agaaaacaaa    960

acaaaaaaaa aaggcaaggc acaacaaaaa aatatcctgg gcaataaaaa aaatatttta   1020

aaccaaaaaa aaaaaaaaaa aagggggt                                       1048
```

```
<210> SEQ ID NO 128
<211> LENGTH: 722
<212> TYPE: DNA
<213> ORGANISM: Homo sapiens
<220> FEATURE:
<221> NAME/KEY: SITE
<222> LOCATION: (251)
<223> OTHER INFORMATION: n equals a,t,g, or c

<400> SEQUENCE: 128

gaattcggca cgaggaaagt ttcaaccctc tgacatgtgg gttcagctta ttttttttctt     60

tgttcagtat ggagactctc ttacttctgc tttttttcct ttctcttcta atttttcgct    120

tcagaattct ggtttctcaa tgcataaact gaagtaattt cttccattct acttttctct    180

gccccaggct tgagatagaa ctagggagcc cagtgaggcc ttttctttcc taaattaaca    240

ggcatctgtg ncataaatgc tacctttgaa ctatgtgatt taagataatg tgcagaagta    300

cttctctggt ctttcaggtt gcytgcataa ctawgtactt ggttgaactt gtaattcttg    360

ctgacaacag tcctgctgtt ttccagtaag gttcgtgatc ctcgggccaa ttttgatcag    420

tccctacgtg tactgaaaca tgccaagaag gttcagcctg atgttatttc taaaacatct    480

ataatgttgg gtttaggcga gaatgatgag caagtatatg caacaatgaa aggtaaagaa    540

attgaaaaat gaaaaatctt tcccatgtaa tttgagtaat agccaggaac ccactcactt    600

tgaaggccct tctaagaaca aagaaaagta tatggttata gatggcagca tgaaaaggaa    660

accaacttgc acatgcaccc tcaaatctaa aatacaagtt aaaaaaaaaa aaaaaaactc    720

ga                                                                   722
```

```
<210> SEQ ID NO 129
<211> LENGTH: 477
<212> TYPE: DNA
<213> ORGANISM: Homo sapiens

<400> SEQUENCE: 129

gaattcggca cgaggtgagt atggcttttg tcttccatct tgctcagggt actttggaac     60

cgctatacat tgcaggagct tagcttctgg ttaccatggt ttgcttccag agcaacaagc    120

ctagtacttc aacatggaga caattatctt ttgtttttgt tttgttttgt ttgttttgtc    180

ttggccatgc ctttttgagt ttaccttttt atattttgtc catcattgcc atgtgtttgg    240
```

agcagtgggc gttccataac atgaactcac tgtaccatca cgaatgggaa gtaaggggaa 300
accttatcca tgtggatttt actcttccct gattccctaa attgggtttg caaaatacta 360
ctgtgcactt tcttgatgat tcgggcttat ctttatgact gtctgtkttt gtgtcagact 420
gtaaagaagt ataaaagtct ttagcttgaa aaaaaaaaaa aaaaaaaaaa aactcga 477

<210> SEQ ID NO 130
<211> LENGTH: 1296
<212> TYPE: DNA
<213> ORGANISM: Homo sapiens

<400> SEQUENCE: 130
ggcacgaggc cactggaatc tgatcctgat tgtcttccac tactaccagg ccatcaccac 60
tccgcctggg tacccacccc agggcaggaa tgatatcgcc accgtctcca tctgtragaa 120
gtgcatttac cccaagccag cccgaacaca ccactgcagc atctgcaaca ggtgtgtgct 180
gaagatggat caccactgcc cctggctaaa caattgtgtg ggccactata accatcggta 240
cttcttctct ttctgctttt tcatgactct gggctgtgtc tactgcagct atggaagttg 300
ggaccttttc cgggaggctt atgctgccat tgagaaaatg aaacagctcg acaagaacaa 360
actacaggcg gttgccaacc agacttatca ccagacccca ccacccacct tctcctttcg 420
agaaaggatg actcacaaga gtcttgtcta cctctggttc ctgtgcagtt ctgtggcact 480
tgccctgggt gccctaactg tatggcatgc tgttctcatc agtcgaggtg agactagcat 540
cgaaaggcac atcaacaaga aggagagacg tcggctacag gccaagggca gagtatttag 600
gaatccttac aactacggct gcttggacaa ctggaaggta ttcctgggtg tggatacagg 660
aaggcactgg cttactcggg tgctcttacc ttctagtcac ttgccccatg ggaatggaat 720
gagctgggag ccccctccct gggtgactgc tcactcagcc tctgtgatgg cagtgtgagc 780
tggactgtgt cagccacgac tcgagcactc attctgctcc ctatgttatt tcaagggcct 840
ccaagggcag cttttctcag aatccttgat caaaaagagc cagtgggcct gccttagggt 900
accatgcagg acaattcaag gaccagcctt tttaccactg cagaagaaag acacaatgtg 960
gagaaatctt aggactgaca tccctttact caggcaaaca gaagttccaa ccccagacta 1020
ggggtcaggc agctagctac ctaccttgcc cagtgctgac ccggacctcc tccaggatac 1080
agcactggag ttggccacca cctcttctac ttgctgtctg aaaaaacacc tgactagtac 1140
agctgagatc ttggcttctc aacagggcaa agataccagg cctgctgctg aggtcactgc 1200
cacttctcac atgctgctta agggagcaca aataaaggta ttcgattttt aaagataaaa 1260
aaaaaaaaaa aaaatttggg gggggggcc ccgtta 1296

<210> SEQ ID NO 131
<211> LENGTH: 738
<212> TYPE: DNA
<213> ORGANISM: Homo sapiens

<400> SEQUENCE: 131
gaattcggca cgagtgacaa gaaagacggt gtcagatgca cattaatctt tagcctgatg 60
tccttcatga tgtccaacct ccagtttcat ctcctgccac actcatcccc catacttcca 120
ctcttcacac tggccttact caaaatgcag attccaggac tcaggctatc tcactgcctt 180
cttacttaca attcttatac cagaacaccc ttcctcctcc cctcatctga atcttacctg 240
gtttttgaaa tttaagtcag ggccttctta ggaagatttc cctgattcag atccaagttg 300
aattatgata accctccttt ggctcccata aaatcttata acttcctaac tgtgttttat 360

-continued

```
gaatagttgt ctagtttagc actatgtcag gagctattga cagcagggct gggcacagtg    420

actcacagct gtaatcctag ccctttgaga ggacaaggtg ggaggactgt ttgaggacac    480

ctcaagccca tccagcctag gcaacagaat gagatcttgt ctgtacaaaa aaacaaaaga    540

ttaattgggc gtggtgacgt gcacctgtag tcccaactac ttgagaggct gaggcaggag    600

gattgcttga ccccaggaga tcgaggctgc agtgatccat gatggtgtca ctgcactcca    660

gtctgagcaa cagagcaaga ccccaccccc caaaaaagct attgagggta gcagtttact    720

ttcattgctc tacctcga                                                  738
```

```
<210> SEQ ID NO 132
<211> LENGTH: 442
<212> TYPE: DNA
<213> ORGANISM: Homo sapiens
<220> FEATURE:
<221> NAME/KEY: SITE
<222> LOCATION: (306)
<223> OTHER INFORMATION: n equals a,t,g, or c

<400> SEQUENCE: 132

gaattcggca cgagtgaccc agaagggtga gtcagttggt agtgtggggt gcatgagggc     60

cattgcaggt tttgataatt accctttatt ttaatttgat catacttttt tgtttataac    120

cttattctaa aaataattca aggtgaccat gcttccatta tacttcttgc aaccatacct    180

atctttggtg atatttatta tgttaaggga caattggcat cttttggccc ttacctgtag    240

ctattctatc atctggagat tatctccaga cacaaatcca tcgcccattg ctccatcgag    300

gcacantcag ctckttgtag ttgccattgc ccctctcgag ccttctccac atagccacat    360

gcaatccatt cccaaaaacc tagctcaatt ttcctcatca cagatgtttt ccctgaccct    420

ccagttggta tatatctcct cc                                             442
```

```
<210> SEQ ID NO 133
<211> LENGTH: 882
<212> TYPE: DNA
<213> ORGANISM: Homo sapiens
<220> FEATURE:
<221> NAME/KEY: SITE
<222> LOCATION: (881)
<223> OTHER INFORMATION: n equals a,t,g, or c

<400> SEQUENCE: 133

gaattcggca cgagatgttt tcttcactca aaaaatttta tattctcaaa catgtatatt     60

ctttccctgt cttgttccat tttcttttct tttttctttt ttctttttcc tttctttcgt    120

gggctgagaa aggggcaggc aaaatgaagc tggccactga aaactgtaag atggtcaaaa    180

gctgacagcc tgtgtatgtg aaaagggaat tgtaaatgga ctgcaatgta atgtacactg    240

taatttgaat acaattactg tatctaaaag gagctgctat gaagtacctt tcttatgttg    300

ctaggctact gtttctgaaa gccctggatc tctttgcacc aaaaatggtc cagatagact    360

ctttttaagg atcttggctg ctttttacta gaaggttgct tttatgagca tatttatact    420

gctgaaggat gagtgttaat tttaattaac tttgccgttt tgtagagaaa actattccac    480

aagataaatt ccaagtcttt tcacctgtca ggcatgcata ttttaatatc tgtttggata    540

gtcagaagta gaatcataaa ggtaaaatat gagttgttac tttgtttctt cgatgtcata    600

ttttatgtgt aatatatatg taaagggcca ttcttaagtt ctctccttaa acttaatgct    660

gtcaagtgtt agatgtgtgc atgtgaactt gttgcactgc agaaacatat tcagagttta    720
```

-continued

```
tctatgtaac ttattcactc tgtaaataca tttaaagttt ttgtgatgta agcttaattg    780

atattctgtt cagaactttty tttagwctaa araaagttct gaacagaata tcaattaagc    840

ttacattgat attctgttca gaactttctt tagctagaaa na                        882
```

<210> SEQ ID NO 134
<211> LENGTH: 1032
<212> TYPE: DNA
<213> ORGANISM: Homo sapiens
<220> FEATURE:
<221> NAME/KEY: SITE
<222> LOCATION: (5)
<223> OTHER INFORMATION: n equals a,t,g, or c
<221> NAME/KEY: SITE
<222> LOCATION: (593)
<223> OTHER INFORMATION: n equals a,t,g, or c

<400> SEQUENCE: 134

```
ggcanaggga accaccttct gtagaacatt caaccaggcc cagatccaga aggcttgagg      60

ccctgtggtc cccatccttg gggagaagtc agctccagca ccmatgaagg gcatcctcgt     120

tgctggtatc actgcagtgc ttgttgcagc tgtagaatyt ytgagctgcg tgcagtgtaa     180

ttcatgggaa aaatcctgtg tcaacagcat tgcctctgaa tgtccctcac atgccaacac     240

cagctgtatc agctcctcag ccagctcctc tctagagaca ccagtcagat tataccagaa     300

tatgttctgc tcagcggaga actgcagtga ggagacacac attacagcct tcactgtcca     360

cgtgtctgct gaagaacact ttcattttgt aagccagtgc tgccaaggaa aggaatgcag     420

caacaccagc gatgccctgg accctccccc tgaagaacgt gtccagcaac gcagagtgcc     480

ctgcttgtta tgaatctaat ggaactttcc tgtcatggga agccctggaa atgctatgaa     540

gaagaacagt gtgtccttcy tagttgcaga acttaagaat gacattgagt ctnaagagtc     600

tcgtgctgaa aggctgttcc caacgtcagt aacgccacct gtcagttcct gtctggtgaa     660

aacaagactc ttggaggagt catctttcga aagtttgagt gtgcaaatgt aaacagctta     720

acccccacgt ctgcaccaac cacttcccac aacgtgggct ccaaagcttc cctctacctc     780

ttggcccttg ccagcctcct tcttcgggga ctgctgccct gaggtcctgg ggctgcactt     840

tgcccagcac cccatttctg cttctctgag gtccagagca tcccctgcgg tgctgacacc     900

ctctttccct gctctgcccc gtttaactgc ccagtaagtg ggagtcacag gtctccaggc     960

aatgccgaca gctgccttgt tcttcattat taaagcactg gttcattcac tgaaaaaaaa    1020

aaaaaaaaaa aa                                                         1032
```

<210> SEQ ID NO 135
<211> LENGTH: 1766
<212> TYPE: DNA
<213> ORGANISM: Homo sapiens

<400> SEQUENCE: 135

```
gtkattcaaa gccatcacaa aacactataa gactgaccaa aatttagata acctttgaac      60

cacgattttt ttccacatct gtctgtgaga cacagcgcaa tgctactgcc cttccagaaa     120

ctgtgctaaa aagagaaagt ccaaaagact ctaaacaaaa acctcgacgc cgttgaggat     180

gtgtttcatt ctggtggtct gttttgcaag cttgataaca gaatgtccgt gccattgtaa     240

atgttgtaga gatgtgggcc gtggcccaac cgtcctatat gagatgtagc atggtacaga     300

acaaactgct tacacaggtc tcactagtta gaaacctgtg ggccatggag gtcagacatc     360

catcttgtcc atctataggc aagaagtgtt tccagatcct ttggaaaggt gggcatgggg     420
```

-continued

```
caggtgcttg gagagtggcg tttgagccag agcgacccca tttcccgtgt gaaccatagg    480

cacaacccag gaagtttccc cacttgtagg agtgtgggta ttccagagca agactgtggc    540

caccatcttc ccctcttggt gttttccgaa agtgacagtg ttggtcatcc catgaccact    600

gaagcttagt aaccagcgcc aaaaagtaga ttcatcaaac tagagacccc agctcccctt    660

ctcgccatct tctttctcaa gttgaccgtg gtgctgtttc tggaaggcat ctgcaactcc    720

aagtccatgc agaactctgg aaggccaagt tcatcgcagc atgttcacca tatcccagcc    780

tccaaatcta tcctcctacc ttccaacgca tgacctgttg gggagcagag acttaacccc    840

caactcagag gaacccttcc tccagcgtct ttggcatggt ttctagggtg agagttccca    900

atttggatag aacggccacc atattggtta ctgaatctct ctcccttgtt tttattacgt    960

ttcctttttc aaactgtcca tgggaaggct gaattgagtg actccccaga atgaagatga   1020

gaaggtgaat ataatcaatg ccaatgtaat gccagcgggg tgagatgccc gatggagrtt   1080

tcaaagatgt agctagcatt ttgaaaccat atgggcaaaa cccggcaacc agaaggggac   1140

agataaggac cgttccagaa atcccaactc tcacacccag cccaggctgc agtctccaca   1200

ccaaacagtc aacaaaacac aaaccctgaa ggaaaacctt ttccatacac ccaggctatg   1260

cattgaagag ttttccactg tatacatttt tatccagatg aaggtatttt tatattttga   1320

caataggaaa cagtgaccat tttcagagta atcaaatctg gaacaaatga aacatctttt   1380

agccaccacc accctgttgc aattaagaca accgtggggg aacacaccac tttttactgt   1440

tgaaaccaac acaacgttga aatccaggct tatacgcaga ctccgattcc ctagagaact   1500

aaatttggct ttagtgtgac gggatttgat taagcactta gtatagtctt ttgaacacgg   1560

aaatcctgtt gtacttaaag ctagcggacc cgtgaacaac tttgtcaggt tcacgtccta   1620

taacggttma aaracacaca cacacataca caaaccgttt ctatgagaga ttgatgaact   1680

ttgtttaaaa ttttaaaaaa aggaacacgt tctgtaaacg agtcgctaaa tacagaattg   1740

tataataaaa aaaaaaaaaa aaaawt                                        1766


<210> SEQ ID NO 136
<211> LENGTH: 470
<212> TYPE: DNA
<213> ORGANISM: Homo sapiens
<220> FEATURE:
<221> NAME/KEY: SITE
<222> LOCATION: (315)
<223> OTHER INFORMATION: n equals a,t,g, or c

<400> SEQUENCE: 136

ccgccgccgc cgctacagcg accctgaccg ccgtccgagc cgccagacac ccagagagac     60

gccagaggcc gcggaggggc gaagacccgg agtaactctc ccttccaccc caacccggat    120

cgccagccct cgagagctct gtgctccacg ccgaggatgc accgtctctg gattggtccg    180

gccttcttcc taatgacatc gctcagcgtc tctggagccg tcatcccgcg gaatgggggc    240

ccagggggtg tcagytcggg gccttgcctc ttgcagctac tctgtggtca ggccgggtcc    300

tccaccatca ggaanatccc atcctgagct ctgtctcctg cccctcctgc tgtgggatgc    360

tgagcacaga gcccacagcc catctgcctc ttcacctccc tgaatccgtg tccatctgca    420

ataaacgaca gcctcggctg cctcgtgctg aaaaaaaaaa aaaaaaaaaa               470


<210> SEQ ID NO 137
<211> LENGTH: 1168
<212> TYPE: DNA
<213> ORGANISM: Homo sapiens
```

-continued

<220> FEATURE:
<221> NAME/KEY: SITE
<222> LOCATION: (1163)
<223> OTHER INFORMATION: n equals a,t,g, or c

<400> SEQUENCE: 137
ctggatctat agactcttct tgccctaaag aatggcatgt ttgcactcct tcccccaaca 60
tgtacagatg cctgtcactc ttggtgactt tgctgggctt ctagtccctg cagatgttta 120
agggagcaat gaatggggag tgtggatgca aactacggcc tccttggcac tgtttcagat 180
gggggatttc ccttctctag gagaacctgt gctggaaaag gtgtggcacc cacactgaaa 240
tggggcaagc tcttcccagc tttgtggggg cccttggaaa acatccactg agatggaggc 300
agtcttcttc ctcttcttcc tcctgctcct cttgacctgg accagcaaga tagcaccaat 360
ccttttctcc tgatggcagt atctgaatga ctttcacagc tgaaggccag agaccagcct 420
acagctggga ttcaggcttc aaagctttgg tgaggatgac tccagaacca ggcaggtagt 480
ccccctccag gatgccatgg cctaaagcat ttcactcctc agtcactagg ctgtgaactc 540
attgtggctg acacttttat tcgctgctat gttttttagc aatgcccggc acacagacct 600
gcttactatg cttttgctga gtgagtgaag ggataagtcc ctttctgcct ttttgatact 660
cactttggtg ccccttgagg tcacagagac ctggatttga cttctggctc tgccacacaa 720
gagcacggat gctttgggtc agttacttca gctctgagag gctcaattgc ctcacctgtg 780
aaatgggtta gtgattccag gaatcttacc aggccccatg gacagcatgt acataaagag 840
cctagccctt ccctctcctc cctctccagg ggccaggcct gactcccctg aagccatttc 900
cttaccattt tgatccctaa gcctgttatc agatcttctt tctgatctac caccatggct 960
caaatcttgc ccttcatcct tgcctttctc aaagacaaaa acacccttcc tctgctccac 1020
tcagagtgta gcggggaggc ttatactgca gtggttaaga gcatatccct ggaattggaa 1080
ggaacagggt ctaagattat gtagatatag cacaaagcct tgctcctgct cgtgccgaat 1140
tcgatatcaa gcttatcgat acngtcga 1168

<210> SEQ ID NO 138
<211> LENGTH: 1294
<212> TYPE: DNA
<213> ORGANISM: Homo sapiens

<400> SEQUENCE: 138
gatcttgtcc aagcagtcgg ggctacttcc aagaatgtca gctcctgtta gcaaccagtg 60
gagtctggcc ttgggctcta agttgacctc tctatagctc caaatcctac caatctcaga 120
aaactgtaag aggcacagat gactccacca gctgcagagt gactctgaag agagtcttca 180
cttactgcac aggcaaagaa aggcacagga atatttccta cctctggcac gaggtgagtc 240
ccacctcccc ccacccccat ctccaggagg caggtagagc agttctgacc gagaggatag 300
actgctgttg ctgtctttcc ccagctctga actagtttta aggtagctta ggatgaaaaa 360
tggagaatga ttgggggttc caaaccactt tcttctccct tggcttatat ctcttcacca 420
tttggtggtc aactgtgggc ctaccctgga cctcatctac tcagcgagaa ttggacatga 480
agctagaggc agctgccttg gaagggaart tcaggctcac ttggacagcc caggccatgg 540
caggaagaat cccttcctct tggggtcctt gatgggcatg tgtgatgggg aaggagcagt 600
ctcccagccc tgggtctgct ccccacatct ctcctaattc cacttcacct tttgccaccc 660
cctccccacc agaggcctag cccttttgtc accgaaggcc cccagagtgt ttctgtgtga 720

-continued

```
aaccctctca tttacactgt ggcmwcaaaa atccacaaaa gatggattaa ttgcactctg    780

gttaatagca gcagcacaat gattaaaatc tatattccta tcttctctag caccctggtg    840

tggggatggg gcggaagggt gtcttgaggg gcagggagga ccccataaaa caatccctcc    900

tgcattctca ggctaaatag ggcccccagt gactacctgt tcttggctgt cccctctgaa    960

gagctctgcc ttctcacagc caccaccagt tgccccactc ccaggaaaac agcacatgtt   1020

cttcttctcc tgccttgaga ctgcgtgtta gtcttccatt cataactcat cagcagctca   1080

gtccttctta tgtctagtct cagttcattc agccaaagct catttttgtc ctatccaaag   1140

tagaaagggt tcttttagaa aacttgaaga atgtgcctcc tcttagcatc tgtttctgac   1200

tcccagttat ttttaaaata aatgatgaat aaaatgcctg ccctgaaggg ttctggagga   1260

aaaaaaaaaa aaaaaaaaaa aaaaaaaact cgta                                1294
```

<210> SEQ ID NO 139
<211> LENGTH: 1720
<212> TYPE: DNA
<213> ORGANISM: Homo sapiens

<400> SEQUENCE: 139

```
aaccagaagt ggacgtgcat gacagtggac ctagaggctg acaaacagga ctacccgcag     60

ccctcggacc tgtccacctt tgtaaacgag accaaattca gttcacccac tgaggagttg    120

gattacagaa actcctatga aattgaatat atggagaaaa ttggctcctc cttacctcag    180

gacgacgatg ccccgaagaa gcaggccttg taccttatgt ttgacacttc tcaggagagc    240

cctgtcaagt catctcccgt ccgcatgtca gagtccccga cgccgtgttc agggtcaagt    300

tttgaagaga ctgaagccct tgtgaacact gctgcgaaaa accagcatcc tgtcccacga    360

ggactggccc ctacccaaga gtcacacttg caggtgccag agaaatcctc ccagaaggag    420

ctggaggcca tgggcttggg caccccttca gaagcgattg aaattagaga ggctgctcac    480

ccaacagacg tctccatctc caaaacagcc ttgtwctccc gcatcaggac cactgaggtg    540

gagaaacctg caggccttct gttccagcag cccgaacttg gactctgccc tccagatcgc    600

cagagcagag atcataacca aggasagaga ggtctcagaa tggaaagata aatatgaaga    660

aagcaggcgg gaagtgatgg aaatgaggaa aatcagtggc cgagtatgag aagaccatcg    720

ctcagatgat agaggacgaa cagagagaga agtcagtctc ccaccagacg gtgcagcagc    780

tggttctgga gaaggagcaa gccctggccg acctgaactc cgtggagaag tctctggccg    840

acctcttcag aagatatgag aagatgaagg aggtcctaga aggcttccgc aagaatgaag    900

aggtgttgaa gagatgtgcg caggagtacc tgtcccgggt gaagaaggag gagcagaggt    960

accaggccct gaaggtgcac gcggaggaga aactggacag ggccaatgct gagattgctc   1020

aggttcgagg caaggcccag caggagcaag ccgcccacca ggccagcctg cggaaggagc   1080

agctgcgagt ggagcgccct ggaaaggacg ctggagcaga agaataaaga aatagaagaa   1140

ctcaccaaga tttgtgacga actgattgcc aaaatgggga aaagctaact ctgaaccgaa   1200

tgttttggac ttaactgttg cgtgcaatat gaccgtcggc acactgctgt tcctccagtt   1260

ccatggacag gttctgtttt cacttttttg tatgcactac tgtatttcct ttctaaataa   1320

aattgatttg attgtatgca gtactaagga gactatcaga atttcttgct attggtttgc   1380

attttcctag tataattcat agcaagttga cctcagagtt cctgtatcag ggagattgtc   1440

tgattctcta ataaaagaca cattgctgac cttggccttg ccctttgtac acaagttccc   1500

cagggtgagc agcttttgga tttaatatga acatgtacag cgtgcatagg gactcttgcc   1560
```

-continued

```
ttaaggagtg taaacttgat ctgcatttgc tgatttgttt ttaaaaaaac aagaaatgca   1620

tgtttcaaat aaaattctct attgtaaata aaattttttc tttggatctt ggcaaaaaaa   1680

aaaaaaaaaa aaaaaaaaaa aaaaaaaaaa aaaaaaattc                         1720
```

<210> SEQ ID NO 140
<211> LENGTH: 774
<212> TYPE: DNA
<213> ORGANISM: Homo sapiens
<220> FEATURE:
<221> NAME/KEY: SITE
<222> LOCATION: (697)
<223> OTHER INFORMATION: n equals a,t,g, or c
<221> NAME/KEY: SITE
<222> LOCATION: (709)
<223> OTHER INFORMATION: n equals a,t,g, or c
<221> NAME/KEY: SITE
<222> LOCATION: (716)
<223> OTHER INFORMATION: n equals a,t,g, or c
<221> NAME/KEY: SITE
<222> LOCATION: (733)
<223> OTHER INFORMATION: n equals a,t,g, or c

<400> SEQUENCE: 140

```
cggcacgagt tttgggatgc ctcttactct gccaagccgc ttagcgggag ggaacgtgtt     60

cctgatcatc tttaccccag gcttctgtcc ggggcgtgtc aatgtagaaa tcccccagcg    120

aatgttggat gaatgaatga agttgaagag agggtaggcg gggaacgagg atgaggggga    180

cggctggaga agaggtatgg gaggttcgat gtttcaggga tggcacccaa gggggggacat    240

tcgaggcagc accggtagca cttcctttgc gatgaggggc gtctctttgg acttcttgga    300

aaagaggtgg gcattggaaa ccagggtctg ggaacaaacc gtggtttgga cataacattt    360

gttaccttca cttttctggg agttggagaa gtagaggagg aagttcagac aatttcataa    420

gtgtctaaaa agagacagtt atgcgaccat tgacgaggag taaaagtcgt ctattgagca    480

tcttattcac tacaaataga agaaagaaat accagtttcc tgacaagccc caccccatgc    540

ttggccagtt cctgagtaca cttaatatat tttaggtact gtcatcaaac tcaaagctcg    600

ctgtcagcct caaaggtctg aaccctagta tagattcttg tagcttgctt gaagttacag    660

tgggtcatga tcaggaattg atgctttgtt tttgttntga aacggagtnt cgccantgca    720

ctccagcctg ggngacagag cccgagactc cttctcaaaa aaaaaaaaaa aaaa          774
```

<210> SEQ ID NO 141
<211> LENGTH: 1566
<212> TYPE: DNA
<213> ORGANISM: Homo sapiens
<220> FEATURE:
<221> NAME/KEY: SITE
<222> LOCATION: (415)
<223> OTHER INFORMATION: n equals a,t,g, or c
<221> NAME/KEY: SITE
<222> LOCATION: (718)
<223> OTHER INFORMATION: n equals a,t,g, or c
<221> NAME/KEY: SITE
<222> LOCATION: (1116)
<223> OTHER INFORMATION: n equals a,t,g, or c
<221> NAME/KEY: SITE
<222> LOCATION: (1122)
<223> OTHER INFORMATION: n equals a,t,g, or c
<221> NAME/KEY: SITE
<222> LOCATION: (1127)
<223> OTHER INFORMATION: n equals a,t,g, or c
<221> NAME/KEY: SITE
<222> LOCATION: (1312)
<223> OTHER INFORMATION: n equals a,t,g, or c
<221> NAME/KEY: SITE -continued
<222> LOCATION: (1373)
<223> OTHER INFORMATION: n equals a,t,g, or c
<221> NAME/KEY: SITE
<222> LOCATION: (1455)
<223> OTHER INFORMATION: n equals a,t,g, or c
<221> NAME/KEY: SITE
<222> LOCATION: (1456)
<223> OTHER INFORMATION: n equals a,t,g, or c
<221> NAME/KEY: SITE
<222> LOCATION: (1540)
<223> OTHER INFORMATION: n equals a,t,g, or c

<400> SEQUENCE: 141
ggcacgagac tatcctcaag gagcttacat atcagtaaat aaattattaa aggtggaaaa 60
tgtggtaaaa gagacataat gtctcggaga gagaacaaat ttctgcttta ggagtgttct 120
tagttaaggt aacattagct tctataatac gcacactccc aaatctcagt atttcaacat 180
gagtttctct cttgctcatg taaagactgg tcagggaccc aggttgacag aggctcttca 240
gtacatagct tccaagattg ctgtgggtgt gacatccagc cagaaatctg gtgaagagag 300
agcaatgatt acacaggaac ttttaatgga ccaggcctgg gacagcgtat gtcacttcca 360
ccaacatccc actcaccaga atttggtcac agggccatag ctatctgcag agaangctgg 420
gaaatggaac ttagctatgt gctcaagagg aaaagtaaaa cagttattga ataattagta 480
ataattagca agtaactacc taggggtcac agaggacctc tcaggtagaa tttagactta 540
aagatgatgg gggagtgtgt ggaagatggg tgcagaatag ggaaaggggg gattgaagga 600
agaacaagct ctagcttcac ctgcatgggt agagcccaca gtgttggtag ggacatgtta 660
gctttcaaca tcagcttctt aacagtatta ttctttcatc ggaggaaatt agtctatntc 720
tgaggaaaaa aaaatctgca atacgtagca atttacttac ttggatattg aatgttaaag 780
cagagagaga ctttgtcctc aaaaccctcc catttcagaa gtgaggagcc tggggaggtc 840
atgctctctg gatgtcacac agtgagtcac tgtcaaagcc agaatagaac ccagacctct 900
cagtttccca ttccagtgct ctttctatga ggaaagtata agtttgagca tttttaaacc 960
ttaattatgt agaaataacc atgatatttt atcgtaaatt atttcagtca tctcatttta 1020
aattttactc caaactaaag gaaaacggta ctgatttaaa acatctatca taattcaata 1080
tagcccatat ttcttcttta ggaaaaattt tttttngttt tntatcntga agacccgtgc 1140
cctcttcctg tgtctcatgt agacatttca cagtccaaat atacagagca agaatagatg 1200
aaatcaacat gtttaccatt attctatcta aattttcaaa gaaaaaggga acaaaaggtg 1260
agtgatgact gagttgcatg gctataattg agtttttgtt gcttttattt tnataatatt 1320
ttaattgaca tagatgctta aatgtatatc aaaatgcatg tcacagctct tgnacaaaga 1380
taaatttgac tctagagcac attttcttta gtgagaatga taaattatct cagagcttgt 1440
gattctctac ttttnnaaat cataaggtca gttctttaat taaaagataa agaaaagtag 1500
gcattgtcca tgtagtgaaa tcacttttat caggataatn tagtaaccaa aaaaaaaaaa 1560
aaaaaa 1566

<210> SEQ ID NO 142
<211> LENGTH: 1384
<212> TYPE: DNA
<213> ORGANISM: Homo sapiens

<400> SEQUENCE: 142
tcgacccacg cgtccggccg gactaaccag ctcctccagg cgctgggggc gggtgtggca 60
ggaggaagcc cgatcagccc caggctgtgg atgtgggaga agggcgagct caggggggcca 120

-continued

```
tcatggggtt cccccagagg caacctggcc tatcagggct gctcctcctc gtgtgggcac    180
tggcctggcc cctgccttgt atgagcttgg agctgatccc ctacacacca cagataacag    240
cttgggacct agaagggaag gtcacagcca ccacgttctc cctggagcag cctcgctgtg    300
tcctggacgg gcttgmcggc gttgccagca ccatctggct ggtggtggcc ttcagcaacg    360
cctccagaga cttccagaac ccacagacgc gagctgagat cccagccttc ccacggctgc    420
tgacggaggg gcactatatg acactgcccc tgtccctgga ccagctgccc tgtcaggacc    480
ccgcaggcgg cggcagggac gtccccttgc tgcgggtggg caatgacccc ggctgccttg    540
ctgacctcct ccagccgccc tactgcaaca gccccctccc cagccccgga ccttacaggg    600
tgaagttcct cctgatggac gccaggggct caccccaggc cgagaccagg tggtccgacc    660
ccatcgctct tcaccaaggg aagtcgccag cctccatcga cacgtggcca gggcgamgca    720
gtggtggtat gatcgtcatc acctctatcc tctcctccct ggccagcctc ctgctcctgg    780
ccttcctggc agcgtccacc scacgcttct ccagcctgtg gtggccggag gargccccgg    840
agcagctgag aattggctcc ttcatgggga agcgctacat gacccaccac atcccaccca    900
gcgaagccgc caccctgccc gtgggctgtg agcctggcyt ggaccccytc cccagcctca    960
gcccctagcc tggcccttgt ggctggggcg tgtgtggctg tggccagtgt gggggcaagg   1020
acgtggtagt tattcccagc ccctgcaccc tcctcctcac ccctgccama gtcccactga   1080
tgtaggacag atgtcagggt tctagacgtc tttggtgcaa aaagggggtt ttattcaagc   1140
acagggacag gacccatggg cagggagagc ggcaccgggg tggtgaggag tggcccgtta   1200
tatatacttt cgagttggga gggcttagag agagcgtaag tctctaagga attttggaag   1260
caaggtctcc agggtcctga gggggctagc tgttgttagg aaaaggtcat ttattactgt   1320
ttagtaaaaa ctttcacgag aaaaaaaaaa aaaaaaaaaa aaaaaaaaaa aaaaaagggc   1380
ggcc                                                                1384
```

<210> SEQ ID NO 143
<211> LENGTH: 537
<212> TYPE: DNA
<213> ORGANISM: Homo sapiens
<220> FEATURE:
<221> NAME/KEY: SITE
<222> LOCATION: (429)
<223> OTHER INFORMATION: n equals a,t,g, or c
<221> NAME/KEY: SITE
<222> LOCATION: (502)
<223> OTHER INFORMATION: n equals a,t,g, or c
<221> NAME/KEY: SITE
<222> LOCATION: (520)
<223> OTHER INFORMATION: n equals a,t,g, or c

<400> SEQUENCE: 143

```
gccccccaaa aagaaaggta attaattata gttcatttcg ttttaactaa gagttactaa     60
agcatccctg gatgctgaga ggtactctct aggaggcaga aacaggacca agcactgccc    120
acttatctcc acactatgct accaattcac ctgcagtggg catgtgcttt caggagtttt    180
ttgcttggta tagacagttc tatgttcgtc ttgtttcagc accctcgttt gaaggacaca    240
aagagctcta gggtcataga accaactctc actaactgac acagatatca ggatccaacc    300
catgcccaca gtattacccc aagtctctaa ctagctggtg taaccaataa tggaaagaaa    360
aaaagtaata ttctgttctt caacttcaac agagaataat agtgaaagaa tggtgatatt    420
tttcctaana tggactaaca agtatcctga gttgggaggt gacttccaat agtaaacaat    480
```

-continued

```
aaaataactg agaaaatgga gngaggaggg aggggagagn gagagtgggc acagaag       537
```

<210> SEQ ID NO 144
<211> LENGTH: 680
<212> TYPE: DNA
<213> ORGANISM: Homo sapiens

<400> SEQUENCE: 144

```
aatttttgt attttttagt agagacaggg tttcaccatg ttagccagga tggtctcgat      60
ctcctgacct cgtgatccac ctgccttggg ctcccaaagt gctgggatta caggcgtgag     120
cmaccacacc cggccaatca tattttttct tgttactaat tagaatcatg attctcctgg     180
cattcttcat tttgttatac ctcacttcct tttccttagc aagatctttg ccatagagta     240
tggaaaccag gttccttgcc agttaatctg tattgtgctt tgtcatgtat tgttactaaa     300
cagctcaaga tcaaggggaa gaaatgtata tgaggctcag ttcatgttca gtttttttt      360
tttcagcatt gcaacattgc cactcatcat catgagtgta gccctgtgtc aggtactgaa     420
ggtaatggaa aaggtatata aggttgatcc ctgtactctt gttgggaact tgagtggtat     480
gaatagagaa ggtgagttct tggggacaga ggctacagtt tagcaagctt tcctatgcgg     540
accttggtaa tttctttaca ttttatagac caaagaacaa tcttaacttg cccttttttc     600
taaaggcatt gtttaaaaac tgtcatcaaa tcattgcagt ttatggcaaa tggccttttt     660
ttaaaaaaaa aaaaaaaaaa                                                 680
```

<210> SEQ ID NO 145
<211> LENGTH: 1048
<212> TYPE: DNA
<213> ORGANISM: Homo sapiens
<220> FEATURE:
<221> NAME/KEY: SITE
<222> LOCATION: (79)
<223> OTHER INFORMATION: n equals a,t,g, or c
<221> NAME/KEY: SITE
<222> LOCATION: (117)
<223> OTHER INFORMATION: n equals a,t,g, or c
<221> NAME/KEY: SITE
<222> LOCATION: (138)
<223> OTHER INFORMATION: n equals a,t,g, or c
<221> NAME/KEY: SITE
<222> LOCATION: (144)
<223> OTHER INFORMATION: n equals a,t,g, or c
<221> NAME/KEY: SITE
<222> LOCATION: (147)
<223> OTHER INFORMATION: n equals a,t,g, or c
<221> NAME/KEY: SITE
<222> LOCATION: (625)
<223> OTHER INFORMATION: n equals a,t,g, or c

<400> SEQUENCE: 145

```
ggcacgagag aaagtgggcc cttaccaggc accaaatctg ccagcactct gatcttggac      60
ttccagcctc ctgaactgnt gtctgcattc aaaagaacat tctattaaag ctacctnaat     120
ttggcgctta tttttctnaa tcangtntct gacaatcata ttgtgtggaa tggttgctgc     180
tttaagtgca ataagagcta actgccatca agagccatca gtatgttctt caagctgcat     240
gcccagaaag ctggattggt tttcaaagaa agtgtttcta tttttctgat gacaccaaga     300
actggacatc aagtcagagg ttttgtgact cacaagatgc tgatcttgct caggttgaaa     360
gcttccagga actggtaaga aaatagttct ggccagaatc aaagattcag ccctacaagg     420
atatgttttc ctgtgaaatt atctaagaga atttcctgtt gagatataaa ggcccatctg     480
atcactggat tgggctgagc agagaacaag gccaaccatg gaaatggata aatggtactg     540
```

-continued

```
aatggacaag acagttagtc atgaaagaag atggtgccaa cttgtatgtt gcaaaggttt    600

cacaagttcc tcgaatgaat ccaanactgt catgggtctt actctgttac ccaggctgga    660

gtgcagtart taccatcgtg gctcactgca gccttgactt ccctggctcc aagtgagcct    720

cccatctcag gctcctgagt agctgggact acaggtttcc tatcctggga gcaggagagt    780

gtgcctattt gaatgacaaa ggtgccagta gtgccaggca ctacacagag aggaagtgga    840

tttgttccaa atcagatata catgtctaga tgttacagca aagccccaac taatctttag    900

aagcatattg gaactgataa ctccatttta aaatgagcaa agaatttatt tcttatacca    960

acaggtatat gaaaatatgc tcaatatcac taataactgg gaaaatacaa atcaaaatca   1020

tagtaaaata aaaaaaaaaa aaaaaaaa                                       1048
```

<210> SEQ ID NO 146
<211> LENGTH: 930
<212> TYPE: DNA
<213> ORGANISM: Homo sapiens

<400> SEQUENCE: 146

```
tcgagttttt tttttttttt ttttggatat ggagtctcac tctgttgccc aggctggagt     60

gctgtggtac gatttcagct caatgcaagc tctgcctcct gggtttaagc aattctcctg    120

cctcagcctc cccagtaggt gggactacgg gtgtgcaaca caacatccgg ctaatttttg    180

tatttttcgt agagacaggg tttcacatgt tggccaggct ggtcttaaac tcctgacctc    240

agttgatcca cctgcctggg cctcccaaag tgctgggatt acaggcaaaa gccactgtgc    300

ccagctgcat tgttgctgtt ttttattgtt agttaagaga gaccaaccat tagaaaaatg    360

tttaaggctt ttcaaaggaa gaatcctatg taggcagccc cactacaggt tactttctga    420

tgaatgtcca ggactattac aaaatccatg attgtggaaa ttctgtcaaa agagatgaca    480

gagaaatctt gcctttggtc acaatcctgt ctgaccccaa caaaagctaa ggaaatccta    540

atcaggtgtg actcatgata aagaaaaaca tgcatccaaa ttttggttca gaagtacaga    600

aagtgtgcaa cttctgtcaa gttaattaat gtatttgctc cataactccc cgacatataa    660

ggtaagttgg ttggagtatg tggtttgaag gctgctttca aagatttaac gtctttgatt    720

tttttagtca ccatgggtgc caggatagaa taagatctgg agactttcga ataactgctt    780

acagatgtag ataattataa attgatacta ataaagaatg aagatctcag cattccccag    840

agagggctat ttttagaaaa aggaaatagc caaaaacaaa gtaaaacaaa aaacatcatg    900

ggatatcagg acttagctcg tgccgaattc                                     930
```

<210> SEQ ID NO 147
<211> LENGTH: 830
<212> TYPE: DNA
<213> ORGANISM: Homo sapiens

<400> SEQUENCE: 147

```
ggtcgaccca cgcgtccgct gaaaggaaaa gcactgtttg gagaatgatc cacctttcaa     60

gattttactt attgttgata atgctcccac atgtcctctt ttttacgggt gatcttcatt    120

cctaatatca aagtgatatt tcttcctcca ggcaccacct ctttgatcca cacaatggat    180

caaggagtta tagcagcttt taagttctac tacctgagaa gggaggactt ttgcccagtc    240

ccatactgca gtggaggaag acactgagaa gactctgatg aaattctgaa cagcatcaag    300

aaccttgttt aggcttggat tatgtcgcta aggactgtag gaatggcacc tggaagaaga    360

cacgcaagag gtttgtcaat aacttcaaag gatttgccaa ggatgaggaa gttgcaaaaa    420
```

-continued tcaagaaggc tgtggttgag atggcaaaca actttaacct gggtgtggat gtggatgaca 480
ttgagtaatt cctagagggg gttcctgagg aattgactaa tgggttgctg ttggaactgg 540
aataggagtg catagctgaa gaagaggtaa agaaaaagaa agtgcaggag aagggaaaaa 600
agaactccca agaatactca cagtgatggg tttagcagaa gcttcttcag actccaacaa 660
gctccttaag aagtctgaaa acatggaccc caaaactgaa aggttttcac taatagagag 720
gaaagttcat ggtgcattat ctgcctacaa gcaaaaccag gattcaaaaa accctttgag 780
ctggagcttc aaagcacaaa aaaaaaaaaa aaaaaaaaaa aagggcggcc 830

<210> SEQ ID NO 148
<211> LENGTH: 865
<212> TYPE: DNA
<213> ORGANISM: Homo sapiens
<220> FEATURE:
<221> NAME/KEY: SITE
<222> LOCATION: (321)
<223> OTHER INFORMATION: n equals a,t,g, or c
<221> NAME/KEY: SITE
<222> LOCATION: (409)
<223> OTHER INFORMATION: n equals a,t,g, or c

<400> SEQUENCE: 148
ggtcgaccca cgcgtccgga gtagcagaaa tttgtcttct tacaagtagt ctatgagagt 60
agatgctgat tttctaaatg taagggaata agaaaaactt catgattaac ttttttcacg 120
tgtatttggg ctttggtggg agtaggcaag aagaatatcc gtggatttat agagtaagca 180
aaagtatgtc aggaaaaact aggaagaata gggctgaact gtggcttgat ttcaggagag 240
tttctgggat tcagacttga attaactgaa tgatgctgta atgtataagt gttggtatag 300
gtgattttat gcaaagaaga ntaaacattg gcttactttt attatcgtat acggtatggg 360
tgactactgc tgctagttca aggtctkgat tttttaaaaa tgtgtttcnt gactgtggta 420
gctgggagcc ccaggataca gacttttggt taaataacat ctgctccact ctgccttccc 480
gtgtgggcct ctctaaccct gggccaagca gttgagtctc tcctcggggt gcctggagtg 540
agggtggata cagcttgggt aattcagcat ctgtacctaa aaacttactc aaagtaggct 600
tcatgtaaag aagtcagtgg ttcttgggaa caggggtgag tgaatggagg cgaaaggtgg 660
ggccctccac aggtcagtca ggccctcagg gtgggacaag agctgtaggg ctcttggtta 720
taaacctgtg tggtggagac cagcaggtga gccaaactct tctttattat cagaacattt 780
cactaataag ggatctcaag ggtcatctgg catcagcact ttaaccaata aaaaaaaaaa 840
aaaaaaaaaa aaaaaaaggg cggcc 865

<210> SEQ ID NO 149
<211> LENGTH: 545
<212> TYPE: DNA
<213> ORGANISM: Homo sapiens

<400> SEQUENCE: 149
agccagggtt ctagtcattt aagatgyacc tgaataaaac aaagagcctt actctcctag 60
aacttgtgtt tctacctggg gagactgtca gtaaaccatc cacaaaataa atacagcaga 120
tgctgttaga agatgatggt gctatggtgt gctgtggaaa atagagaaag tagagggaag 180
tgagagggat tgcgtacact aggattgtga ctttacacag aagggtcagt ggtgccattt 240
tagcaaagat ctgagagagg taaaggaata agctttgcag aagtgtggga gacaaatgtt 300
ccaggtacag gaaatgacca acgccaagac cctagggtgg caatgtgtct gcttkgagtt 360

-continued

```
ctagagaarg ggtatattat acatcgcttt ttgtgactca ctttttggca aacattatgc    420

tctaaaatga acctgtattt tggaatawat ckgtggttca ttaattctca tctttgtaca    480

gtattctatt atataaatac accatgattt atttagtcaa ttaaaaaaaa aaaaaaaaaa    540

ctcga                                                                545
```

```
<210> SEQ ID NO 150
<211> LENGTH: 54
<212> TYPE: PRT
<213> ORGANISM: Homo sapiens
<220> FEATURE:
<221> NAME/KEY: SITE
<222> LOCATION: (54)
<223> OTHER INFORMATION: Xaa equals stop translation

<400> SEQUENCE: 150

Met Gln Leu Leu Cys Ser Pro Tyr Pro Glu Glu Lys Pro Lys Gly Ser
  1               5                  10                  15

Asn Arg Asn Phe Cys Asn Trp Phe Leu Ser Glu Arg Ser Ser Cys Leu
             20                  25                  30

Gln Met Leu Leu Lys Gly His Lys Lys Leu Glu Leu Glu Lys Ile Asp
         35                  40                  45

Glu Ser Ala Gly Val Xaa
     50


<210> SEQ ID NO 151
<211> LENGTH: 46
<212> TYPE: PRT
<213> ORGANISM: Homo sapiens
<220> FEATURE:
<221> NAME/KEY: SITE
<222> LOCATION: (46)
<223> OTHER INFORMATION: Xaa equals stop translation

<400> SEQUENCE: 151

Met Ser Asn Leu Met Val Ala Met Ile Ala Val Ile Thr Ile Ala Val
  1               5                  10                  15

Ser Ile Pro Ser Thr Arg Ala Asp Thr Glu Ile Ser Tyr Thr Tyr Trp
             20                  25                  30

Ala Tyr Leu Ser Ile Leu Ala Gly Asn Asn Ala Trp Ile Xaa
         35                  40                  45


<210> SEQ ID NO 152
<211> LENGTH: 25
<212> TYPE: PRT
<213> ORGANISM: Homo sapiens
<220> FEATURE:
<221> NAME/KEY: SITE
<222> LOCATION: (25)
<223> OTHER INFORMATION: Xaa equals stop translation

<400> SEQUENCE: 152

Met Ile Met Glu Glu Ile Phe Leu Asn Leu Ile Lys Asn Ile Tyr Lys
  1               5                  10                  15

Ser Pro Tyr Ser Gln Cys Asn Thr Xaa
             20                  25


<210> SEQ ID NO 153
<211> LENGTH: 265
<212> TYPE: PRT
<213> ORGANISM: Homo sapiens
<220> FEATURE:
<221> NAME/KEY: SITE
```

-continued

<222> LOCATION: (71)
<223> OTHER INFORMATION: Xaa equals any of the naturally occurring L-amino acids
<221> NAME/KEY: SITE
<222> LOCATION: (80)
<223> OTHER INFORMATION: Xaa equals any of the naturally occurring L-amino acids
<221> NAME/KEY: SITE
<222> LOCATION: (86)
<223> OTHER INFORMATION: Xaa equals any of the naturally occurring L-amino acids
<221> NAME/KEY: SITE
<222> LOCATION: (93)
<223> OTHER INFORMATION: Xaa equals any of the naturally occurring L-amino acids
<221> NAME/KEY: SITE
<222> LOCATION: (95)
<223> OTHER INFORMATION: Xaa equals any of the naturally occurring L-amino acids
<221> NAME/KEY: SITE
<222> LOCATION: (133)
<223> OTHER INFORMATION: Xaa equals any of the naturally occurring L-amino acids
<221> NAME/KEY: SITE
<222> LOCATION: (157)
<223> OTHER INFORMATION: Xaa equals any of the naturally occurring L-amino acids
<221> NAME/KEY: SITE
<222> LOCATION: (183)
<223> OTHER INFORMATION: Xaa equals any of the naturally occurring L-amino acids
<221> NAME/KEY: SITE
<222> LOCATION: (204)
<223> OTHER INFORMATION: Xaa equals any of the naturally occurring L-amino acids
<221> NAME/KEY: SITE
<222> LOCATION: (265)
<223> OTHER INFORMATION: Xaa equals stop translation

<400> SEQUENCE: 153

```
Met Ala Thr Pro Leu Pro Pro Pro Ser Pro Arg His Leu Arg Leu Leu
  1               5                  10                  15

Arg Leu Leu Leu Ser Gly Leu Val Leu Gly Ala Ala Leu Arg Gly Ala
             20                  25                  30

Ala Ala Gly His Pro Glu Cys Cys Arg Leu Ser Arg Glu Pro Gly Leu
         35                  40                  45

Cys Pro Glu Glu Ala Gly Lys Cys Pro Pro Gly Ala His Ala Cys Gly
     50                  55                  60

Pro Ala Phe Ser Pro Ser Xaa Arg Asn Ser Lys Gly Leu Phe Cys Xaa
 65                  70                  75                  80

Asp Ala Pro Gly Phe Xaa Arg Gly Pro Gly Pro Thr Xaa Thr Xaa Asn
                 85                  90                  95

Glu Ile Asp Ser Trp Pro Lys Gly Ala Cys Pro Glu Arg Asn Leu Asp
            100                 105                 110

Ile Asn Ser Ala Leu Thr Gln Gly Arg Thr Ala Val Pro Gly Ala Cys
        115                 120                 125

His Leu Gly Ile Xaa Gly Thr Gly Ala Gly Ala Gly Ala Gly Leu Pro
    130                 135                 140

Phe His Ser Arg Asn Pro His Ala His Ala Pro His Xaa Pro Trp Val
145                 150                 155                 160

Thr Pro Val Ser Ser Asp Pro Val His Met Ser Pro Leu Glu Pro Arg
                165                 170                 175

Gly Gly Gln Gly Asp Gly Xaa Ala Leu Val Leu Ile Leu Ala Phe Cys
            180                 185                 190

Val Ala Gly Ala Ala Ala Leu Ser Val Ala Ser Xaa Cys Trp Cys Arg
        195                 200                 205
```

-continued

```
Leu Gln Arg Glu Ile Arg Leu Thr Gln Lys Ala Glu Tyr Ala Thr Ala
    210                 215                 220

Lys Ala Leu Ala Thr Pro Ala Ala Thr Pro Asp Leu Ala Trp Gly Pro
225                 230                 235                 240

Ala Pro Gly Thr Glu Arg Gly Asp Val Pro Leu Pro Ala Pro Thr Ala
                245                 250                 255

Thr Asp Val Val Pro Gly Ala Ala Xaa
            260                 265
```

<210> SEQ ID NO 154
<211> LENGTH: 237
<212> TYPE: PRT
<213> ORGANISM: Homo sapiens
<220> FEATURE:
<221> NAME/KEY: SITE
<222> LOCATION: (137)
<223> OTHER INFORMATION: Xaa equals any of the naturally occurring L-amino acids
<221> NAME/KEY: SITE
<222> LOCATION: (151)
<223> OTHER INFORMATION: Xaa equals any of the naturally occurring L-amino acids

<400> SEQUENCE: 154

```
Met Lys Gly Ile Leu Val Ala Gly Ile Thr Ala Val Leu Val Ala Ala
  1               5                  10                  15

Val Glu Ser Leu Ser Cys Val Gln Cys Asn Ser Trp Glu Lys Ser Cys
             20                  25                  30

Val Asn Ser Ile Ala Ser Glu Cys Pro Ser His Ala Asn Thr Ser Cys
         35                  40                  45

Ile Ser Ser Ser Ala Ser Ser Ser Leu Glu Thr Pro Val Arg Leu Tyr
     50                  55                  60

Gln Asn Met Phe Cys Ser Ala Glu Asn Cys Ser Glu Glu Thr His Ile
 65                  70                  75                  80

Thr Ala Phe Thr Val His Val Ser Ala Glu Glu His Phe His Phe Val
                 85                  90                  95

Ser Gln Cys Cys Gln Gly Lys Glu Cys Ser Asn Thr Ser Asp Ala Leu
            100                 105                 110

Asp Pro Pro Leu Lys Asn Val Ser Ser Asn Ala Glu Cys Pro Ala Cys
        115                 120                 125

Tyr Glu Ser Asn Gly Thr Ser Cys Xaa Gly Lys Pro Trp Lys Cys Tyr
    130                 135                 140

Glu Glu Glu Gln Cys Val Xaa Leu Val Ala Glu Leu Lys Asn Asp Ile
145                 150                 155                 160

Glu Ser Lys Ser Leu Val Leu Lys Gly Cys Ser Asn Val Ser Asn Ala
                165                 170                 175

Thr Cys Gln Phe Leu Ser Gly Glu Asn Lys Thr Leu Gly Gly Val Ile
            180                 185                 190

Phe Arg Lys Phe Glu Cys Ala Asn Val Asn Ser Leu Thr Pro Thr Ser
        195                 200                 205

Ala Pro Thr Thr Ser His Asn Val Gly Ser Lys Ala Ser Leu Tyr Leu
    210                 215                 220

Leu Ala Leu Ala Ser Leu Leu Leu Arg Gly Leu Leu Pro
225                 230                 235
```

<210> SEQ ID NO 155
<211> LENGTH: 314
<212> TYPE: PRT

-continued

```
<213> ORGANISM: Homo sapiens
<220> FEATURE:
<221> NAME/KEY: SITE
<222> LOCATION: (49)
<223> OTHER INFORMATION: Xaa equals any of the naturally occurring L-
      amino acids
<221> NAME/KEY: SITE
<222> LOCATION: (167)
<223> OTHER INFORMATION: Xaa equals any of the naturally occurring L-
      amino acids
<221> NAME/KEY: SITE
<222> LOCATION: (314)
<223> OTHER INFORMATION: Xaa equals stop translation

<400> SEQUENCE: 155

Met Asn Gln Leu Ser Phe Leu Leu Phe Leu Ile Ala Thr Thr Arg Gly
  1               5                  10                  15

Trp Ser Thr Asp Glu Ala Asn Thr Tyr Phe Lys Glu Trp Thr Cys Ser
             20                  25                  30

Ser Ser Pro Ser Leu Pro Arg Ser Cys Lys Glu Ile Lys Asp Glu Cys
         35                  40                  45

Xaa Ser Ala Phe Asp Gly Leu Tyr Phe Leu Arg Thr Glu Asn Gly Val
     50                  55                  60

Ile Tyr Gln Thr Phe Cys Asp Met Thr Ser Gly Gly Gly Gly Trp Thr
 65                  70                  75                  80

Leu Val Ala Ser Val His Glu Asn Asp Met Arg Gly Lys Cys Thr Val
                 85                  90                  95

Gly Asp Arg Trp Ser Ser Gln Gln Gly Ser Lys Ala Asp Tyr Pro Glu
            100                 105                 110

Gly Asp Gly Asn Trp Ala Asn Tyr Asn Thr Phe Gly Ser Ala Glu Ala
        115                 120                 125

Ala Thr Ser Asp Asp Tyr Lys Asn Pro Gly Tyr Tyr Asp Ile Gln Ala
    130                 135                 140

Lys Asp Leu Gly Ile Trp His Val Pro Asn Lys Ser Pro Met Gln His
145                 150                 155                 160

Trp Arg Asn Ser Ser Leu Xaa Arg Tyr Arg Thr Asp Thr Gly Phe Leu
                165                 170                 175

Gln Thr Leu Gly His Asn Leu Phe Gly Ile Tyr Gln Lys Tyr Pro Val
            180                 185                 190

Lys Tyr Gly Glu Gly Lys Cys Trp Thr Asp Asn Gly Pro Val Ile Pro
        195                 200                 205

Val Val Tyr Asp Phe Gly Asp Ala Gln Lys Thr Ala Ser Tyr Tyr Ser
    210                 215                 220

Pro Tyr Gly Gln Arg Glu Phe Thr Ala Gly Phe Val Gln Phe Arg Val
225                 230                 235                 240

Phe Asn Asn Glu Arg Ala Ala Asn Ala Leu Cys Ala Gly Met Arg Val
                245                 250                 255

Thr Gly Cys Asn Thr Glu His His Cys Ile Gly Gly Gly Gly Tyr Phe
            260                 265                 270

Pro Glu Ala Ser Pro Gln Gln Cys Gly Asp Phe Ser Gly Phe Asp Trp
        275                 280                 285

Ser Gly Tyr Gly Thr His Val Gly Tyr Ser Ser Ser Arg Glu Ile Thr
    290                 295                 300

Glu Ala Ala Val Leu Leu Phe Tyr Arg Xaa
305                 310


<210> SEQ ID NO 156
<211> LENGTH: 99
```

-continued

```
<212> TYPE: PRT
<213> ORGANISM: Homo sapiens
<220> FEATURE:
<221> NAME/KEY: SITE
<222> LOCATION: (17)
<223> OTHER INFORMATION: Xaa equals any of the naturally occurring L-
      amino acids
<221> NAME/KEY: SITE
<222> LOCATION: (24)
<223> OTHER INFORMATION: Xaa equals any of the naturally occurring L-
      amino acids
<221> NAME/KEY: SITE
<222> LOCATION: (99)
<223> OTHER INFORMATION: Xaa equals stop translation

<400> SEQUENCE: 156

Met Leu Ala Phe Pro Val Leu Leu Glu Val Ser Trp Ser Val Leu Phe
  1               5                  10                  15

Xaa Phe Ser Phe Phe Ser Pro Xaa Pro Ser Ala Pro Gln Pro Pro Thr
             20                  25                  30

Pro Ser Arg Ser Val Leu His Ala Arg Cys Ser Asn Val Arg Ser Glu
         35                  40                  45

Met Ala Gly Thr Arg Glu Lys Leu Leu Val Ser Phe Val Ser Gly Ser
     50                  55                  60

Gly Met Ala Leu Ser Ser Leu Ala Ser Leu Phe Val Leu Phe Glu Leu
 65                  70                  75                  80

Cys Arg Ser Leu Phe Ser Gln Ala Glu Leu Pro Thr Arg Ser Ile Leu
                 85                  90                  95

Asp Gln Xaa


<210> SEQ ID NO 157
<211> LENGTH: 37
<212> TYPE: PRT
<213> ORGANISM: Homo sapiens
<220> FEATURE:
<221> NAME/KEY: SITE
<222> LOCATION: (8)
<223> OTHER INFORMATION: Xaa equals any of the naturally occurring L-
      amino acids
<221> NAME/KEY: SITE
<222> LOCATION: (19)
<223> OTHER INFORMATION: Xaa equals any of the naturally occurring L-
      amino acids
<221> NAME/KEY: SITE
<222> LOCATION: (28)
<223> OTHER INFORMATION: Xaa equals any of the naturally occurring L-
      amino acids
<221> NAME/KEY: SITE
<222> LOCATION: (37)
<223> OTHER INFORMATION: Xaa equals stop translation

<400> SEQUENCE: 157

Met Asn Pro Phe Ser Val Phe Xaa Ser Leu Cys Leu Lys Gln Phe Glu
  1               5                  10                  15

Asp Val Xaa Leu Phe Leu Gly Leu Met Phe Gly Xaa Ser Leu Asn Gly
             20                  25                  30

Gln Glu Gly Thr Xaa
         35


<210> SEQ ID NO 158
<211> LENGTH: 23
<212> TYPE: PRT
<213> ORGANISM: Homo sapiens
<220> FEATURE:
<221> NAME/KEY: SITE
<222> LOCATION: (23)
<223> OTHER INFORMATION: Xaa equals stop translation
```

-continued

<400> SEQUENCE: 158

```
Met Val Ile Phe Ile Ile Leu Leu Thr Cys Phe Gly Phe Ser Asn Gly
  1               5                  10                  15

Ser Phe Ser Phe Ser Leu Xaa
            20
```

<210> SEQ ID NO 159
<211> LENGTH: 96
<212> TYPE: PRT
<213> ORGANISM: Homo sapiens
<220> FEATURE:
<221> NAME/KEY: SITE
<222> LOCATION: (30)
<223> OTHER INFORMATION: Xaa equals any of the naturally occurring L-amino acids
<221> NAME/KEY: SITE
<222> LOCATION: (35)
<223> OTHER INFORMATION: Xaa equals any of the naturally occurring L-amino acids
<221> NAME/KEY: SITE
<222> LOCATION: (64)
<223> OTHER INFORMATION: Xaa equals any of the naturally occurring L-amino acids
<221> NAME/KEY: SITE
<222> LOCATION: (83)
<223> OTHER INFORMATION: Xaa equals any of the naturally occurring L-amino acids

<400> SEQUENCE: 159

```
Met Cys Phe Ile Leu Val Val Cys Phe Ala Ser Leu Ile Thr Glu Cys
  1               5                  10                  15

Pro Cys His Cys Lys Cys Cys Arg Asp Val Gly Arg Gly Xaa Thr Val
            20                  25                  30

Leu Tyr Xaa Cys Ser Met Val Gln Asn Lys Leu Leu Thr Gln Val Ser
        35                  40                  45

Leu Val Arg Asn Leu Trp Ala Met Glu Val Arg His Pro Ser Cys Xaa
    50                  55                  60

Ser Ile Gly Lys Lys Cys Phe Gln Ile Leu Trp Lys Gly Gly His Gly
 65                  70                  75                  80

Ala Gly Xaa Trp Arg Val Ala Phe Glu Gln Ser Asp Pro Ile Ser Val
                 85                  90                  95
```

<210> SEQ ID NO 160
<211> LENGTH: 66
<212> TYPE: PRT
<213> ORGANISM: Homo sapiens
<220> FEATURE:
<221> NAME/KEY: SITE
<222> LOCATION: (66)
<223> OTHER INFORMATION: Xaa equals stop translation

<400> SEQUENCE: 160

```
Met Val Glu Asn Trp Val Leu Glu Glu Ser Pro Gly Arg Leu Leu Ala
  1               5                  10                  15

Leu Phe Val Val Arg Arg Ala Leu Ala Gln Gly Gln Arg Glu Glu Lys
            20                  25                  30

Gly Gln Pro Ala Ala Val Glu Ser Ala Gly Trp Leu Pro Thr Arg Phe
        35                  40                  45

Leu Ser Ser Gln Asp Ser Leu Pro Leu Ser Ser Arg Ile Ser Asn Gly
    50                  55                  60

Leu Xaa
 65
```

-continued

<210> SEQ ID NO 161
<211> LENGTH: 222
<212> TYPE: PRT
<213> ORGANISM: Homo sapiens
<220> FEATURE:
<221> NAME/KEY: SITE
<222> LOCATION: (86)
<223> OTHER INFORMATION: Xaa equals any of the naturally occurring L-amino acids

<400> SEQUENCE: 161

```
Met His Phe Gln Arg Gln Lys Leu Met Ala Val Thr Glu Tyr Ile Pro
  1               5                  10                  15

Pro Lys Pro Ala Ile His Pro Ser Cys Leu Pro Ser Pro Pro Ser Pro
             20                  25                  30

Pro Gln Glu Glu Ile Gly Leu Ile Arg Leu Leu Arg Arg Glu Ile Ala
         35                  40                  45

Ala Val Phe Gln Asp Asn Arg Met Ile Ala Val Cys Gln Asn Val Ala
     50                  55                  60

Leu Ser Ala Glu Asp Lys Leu Leu Met Arg His Gln Leu Arg Lys His
 65                  70                  75                  80

Lys Ile Leu Met Lys Xaa Phe Pro Asn Gln Val Leu Lys Pro Phe Leu
                 85                  90                  95

Glu Asp Ser Lys Tyr Gln Asn Leu Leu Pro Leu Phe Val Gly His Asn
            100                 105                 110

Met Leu Leu Val Ser Glu Glu Pro Lys Val Lys Glu Met Val Arg Ile
        115                 120                 125

Leu Arg Thr Val Pro Phe Leu Pro Leu Leu Gly Gly Cys Ile Asp Asp
    130                 135                 140

Thr Ile Leu Ser Arg Gln Gly Phe Ile Asn Tyr Ser Lys Leu Pro Ser
145                 150                 155                 160

Leu Pro Leu Val Gln Gly Glu Leu Val Gly Gly Leu Thr Cys Leu Thr
                165                 170                 175

Ala Gln Thr His Ser Leu Leu Gln His Gln Pro Leu Gln Leu Thr Thr
            180                 185                 190

Leu Leu Asp Gln Tyr Ile Arg Glu Gln Arg Glu Lys Asp Ser Val Met
        195                 200                 205

Ser Ala Asn Gly Lys Pro Asp Pro Asp Thr Val Pro Asp Ser
    210                 215                 220
```

<210> SEQ ID NO 162
<211> LENGTH: 91
<212> TYPE: PRT
<213> ORGANISM: Homo sapiens
<220> FEATURE:
<221> NAME/KEY: SITE
<222> LOCATION: (53)
<223> OTHER INFORMATION: Xaa equals any of the naturally occurring L-amino acids

<400> SEQUENCE: 162

```
Met Val Val Asp Gln Lys Glu Asp Leu Ile Thr Gly Leu Gly Ile Lys
  1               5                  10                  15

Met Val Arg Lys Trp Leu Gln Gly Ser Gln Ala Trp Pro Leu Glu Arg
             20                  25                  30

Glu Glu Arg Glu Gly Leu Gly Ser Leu Cys Thr Cys Cys Pro Trp Gly
         35                  40                  45

Leu Val Arg Phe Xaa Glu Ser Leu Thr His Phe Thr Gly Glu Ala Ile
     50                  55                  60
```

-continued

Glu Pro Leu Arg Ala Glu Val Thr Asp Pro Lys His Pro Cys Ser Cys
65 70 75 80

Val Ala Glu Pro Glu Val Lys Ser Arg Ser Leu
85 90

<210> SEQ ID NO 163
<211> LENGTH: 74
<212> TYPE: PRT
<213> ORGANISM: Homo sapiens
<220> FEATURE:
<221> NAME/KEY: SITE
<222> LOCATION: (51)
<223> OTHER INFORMATION: Xaa equals any of the naturally occurring L-amino acids

<400> SEQUENCE: 163

Met Glu Asn Asp Trp Gly Phe Gln Thr Thr Phe Phe Ser Leu Gly Leu
1 5 10 15

Tyr Leu Phe Thr Ile Trp Trp Ser Thr Val Gly Leu Pro Trp Thr Ser
20 25 30

Ser Thr Gln Arg Glu Leu Asp Met Lys Leu Glu Ala Ala Ala Leu Glu
35 40 45

Gly Lys Xaa Gly Ser Leu Gly Gln Pro Arg Pro Trp Gln Glu Glu Ser
50 55 60

Leu Pro Leu Gly Val Leu Asp Gly His Val
65 70

<210> SEQ ID NO 164
<211> LENGTH: 78
<212> TYPE: PRT
<213> ORGANISM: Homo sapiens
<220> FEATURE:
<221> NAME/KEY: SITE
<222> LOCATION: (69)
<223> OTHER INFORMATION: Xaa equals any of the naturally occurring L-amino acids
<221> NAME/KEY: SITE
<222> LOCATION: (78)
<223> OTHER INFORMATION: Xaa equals stop translation

<400> SEQUENCE: 164

Met Thr Gly Gln Ile Pro Arg Leu Ser Lys Val Asn Leu Phe Thr Leu
1 5 10 15

Leu Ser Leu Trp Met Glu Leu Phe Pro Ala Glu Ala Gln Arg Gln Lys
20 25 30

Ser Gln Lys Asn Glu Glu Gly Lys His Gly Pro Leu Gly Asp Asn Glu
35 40 45

Glu Arg Thr Arg Val Ser Thr Asp Lys Arg Gln Asp Tyr Trp Glu Gln
50 55 60

Leu Arg Cys Leu Xaa Glu Arg Phe Thr Ile Thr Ala Gly Xaa
65 70 75

<210> SEQ ID NO 165
<211> LENGTH: 38
<212> TYPE: PRT
<213> ORGANISM: Homo sapiens
<220> FEATURE:
<221> NAME/KEY: SITE
<222> LOCATION: (38)
<223> OTHER INFORMATION: Xaa equals stop translation

<400> SEQUENCE: 165

Met Ala Phe Leu Leu Thr Leu Val Pro Leu Leu Pro Ser Arg Cys Leu

-continued

```
  1               5                   10                  15

Gly Leu Glu Glu Met Ala Val Pro Asn Ser Thr Cys Ile Ser Pro Phe
             20                  25                  30

Ser Cys Cys Tyr Gly Xaa
         35


<210> SEQ ID NO 166
<211> LENGTH: 45
<212> TYPE: PRT
<213> ORGANISM: Homo sapiens
<220> FEATURE:
<221> NAME/KEY: SITE
<222> LOCATION: (45)
<223> OTHER INFORMATION: Xaa equals stop translation

<400> SEQUENCE: 166

Met Phe His Val Phe Val Leu Leu Leu Thr Phe Ile Ala Leu Ser Pro
  1               5                   10                  15

Ser Gly Ile Arg Leu Leu Phe Gly Phe Ile Gln Lys Gly Leu Asn Leu
             20                  25                  30

Asn Ser Phe Met Phe Arg Leu Glu Leu Leu His Phe Xaa
         35                  40                  45


<210> SEQ ID NO 167
<211> LENGTH: 39
<212> TYPE: PRT
<213> ORGANISM: Homo sapiens
<220> FEATURE:
<221> NAME/KEY: SITE
<222> LOCATION: (39)
<223> OTHER INFORMATION: Xaa equals stop translation

<400> SEQUENCE: 167

Met Thr Ser Leu Pro Ile Leu Ala Phe Gly Ala Val Tyr Trp Pro Asp
  1               5                   10                  15

Leu Ala Ser His Ser Phe Ser Pro Ser Arg Ser Leu Ala Gln Thr Pro
             20                  25                  30

His Met Ser Val Ser Gly Xaa
         35


<210> SEQ ID NO 168
<211> LENGTH: 174
<212> TYPE: PRT
<213> ORGANISM: Homo sapiens
<220> FEATURE:
<221> NAME/KEY: SITE
<222> LOCATION: (83)
<223> OTHER INFORMATION: Xaa equals any of the naturally occurring L-
      amino acids
<221> NAME/KEY: SITE
<222> LOCATION: (110)
<223> OTHER INFORMATION: Xaa equals any of the naturally occurring L-
      amino acids
<221> NAME/KEY: SITE
<222> LOCATION: (115)
<223> OTHER INFORMATION: Xaa equals any of the naturally occurring L-
      amino acids
<221> NAME/KEY: SITE
<222> LOCATION: (118)
<223> OTHER INFORMATION: Xaa equals any of the naturally occurring L-
      amino acids
<221> NAME/KEY: SITE
<222> LOCATION: (168)
<223> OTHER INFORMATION: Xaa equals any of the naturally occurring L-
      amino acids
<221> NAME/KEY: SITE
<222> LOCATION: (174)
<223> OTHER INFORMATION: Xaa equals stop translation
```

-continued

<400> SEQUENCE: 168

Met Gln Leu Ile Pro Leu Glu Gln Leu Cys Met Leu Leu Leu Met Ser
1 5 10 15

Asp Asn Val Asp Arg Cys Phe Glu Thr Cys Pro Pro Arg Thr Phe Leu
20 25 30

Pro Ala Leu Cys Lys Ile Phe Leu Asp Glu Ser Ala Pro Asp Asn Val
35 40 45

Leu Glu Val Thr Ala Arg Ala Ile Thr Tyr Tyr Leu Asp Val Ser Ala
50 55 60

Glu Cys Thr Arg Arg Ile Val Gly Val Asp Gly Ala Ile Lys Ala Leu
65 70 75 80

Cys Asn Xaa Leu Val Val Val Glu Leu Asn Asn Arg Thr Ser Arg Asp
85 90 95

Leu Ala Glu Gln Cys Val Lys Val Leu Glu Leu Ile Cys Xaa Pro Glu
100 105 110

Ser Gly Xaa Val Phe Xaa Ala Gly Gly Leu Asn Arg Val Ala Tyr Leu
115 120 125

Pro Ser Val Asn Ser Gly His Leu Val His Lys Asp Thr Leu His Ser
130 135 140

Ala Met Ala Val Val Ser Arg Leu Cys Gly Lys Met Glu Pro Gln Asp
145 150 155 160

Ser Ser Leu Glu Ile Cys Val Xaa Ser Leu Ser Ser Leu Xaa
165 170

<210> SEQ ID NO 169
<211> LENGTH: 55
<212> TYPE: PRT
<213> ORGANISM: Homo sapiens
<220> FEATURE:
<221> NAME/KEY: SITE
<222> LOCATION: (55)
<223> OTHER INFORMATION: Xaa equals stop translation

<400> SEQUENCE: 169

Met Phe Glu Asp Thr Leu Arg Thr Leu Tyr Ile Leu Leu Phe Tyr Leu
1 5 10 15

Arg Tyr Ile Cys Leu Leu Ser Pro His Ile Ala Leu Met Thr Leu Ile
20 25 30

Leu Ile Asp Gly Phe Leu Gln Cys Tyr Tyr Cys Ala Leu His Val Pro
35 40 45

Cys Ile Ile Ala Phe Leu Xaa
50 55

<210> SEQ ID NO 170
<211> LENGTH: 344
<212> TYPE: PRT
<213> ORGANISM: Homo sapiens
<220> FEATURE:
<221> NAME/KEY: SITE
<222> LOCATION: (126)
<223> OTHER INFORMATION: Xaa equals any of the naturally occurring L-amino acids
<221> NAME/KEY: SITE
<222> LOCATION: (128)
<223> OTHER INFORMATION: Xaa equals any of the naturally occurring L-amino acids

<400> SEQUENCE: 170

Met Glu Lys Ile Gly Ser Ser Leu Pro Gln Asp Asp Asp Ala Pro Lys
1 5 10 15

-continued

```
Lys Gln Ala Leu Tyr Leu Met Phe Asp Thr Ser Gln Glu Ser Pro Val
            20                  25                  30

Lys Ser Ser Pro Val Arg Met Ser Glu Ser Pro Thr Pro Cys Ser Gly
        35                  40                  45

Ser Ser Phe Glu Glu Thr Glu Ala Leu Val Asn Thr Ala Ala Lys Asn
    50                  55                  60

Gln His Pro Val Pro Arg Gly Leu Ala Pro Asn Gln Glu Ser His Leu
65                  70                  75                  80

Gln Val Pro Glu Lys Ser Ser Gln Lys Glu Leu Glu Ala Met Gly Leu
                85                  90                  95

Gly Thr Pro Ser Glu Ala Ile Glu Ile Arg Glu Ala Ala His Pro Thr
            100                 105                 110

Asp Val Ser Ile Ser Lys Thr Ala Leu Tyr Ser Arg Ile Xaa Thr Xaa
        115                 120                 125

Glu Val Glu Lys Pro Ala Gly Leu Leu Phe Gln Gln Pro Asp Leu Asp
    130                 135                 140

Ser Ala Leu Gln Ile Ala Arg Ala Glu Ile Ile Thr Lys Glu Arg Glu
145                 150                 155                 160

Val Ser Glu Trp Lys Asp Lys Tyr Glu Glu Ser Arg Arg Glu Val Met
                165                 170                 175

Glu Met Arg Lys Ile Val Ala Glu Tyr Glu Lys Thr Ile Ala Gln Met
            180                 185                 190

Ile Glu Asp Glu Gln Arg Glu Lys Ser Val Ser His Gln Thr Val Gln
        195                 200                 205

Gln Leu Val Leu Glu Lys Glu Gln Ala Leu Ala Asp Leu Asn Ser Val
    210                 215                 220

Glu Lys Ser Leu Ala Asp Leu Phe Arg Arg Tyr Glu Lys Met Lys Glu
225                 230                 235                 240

Val Leu Glu Gly Phe Arg Lys Asn Glu Glu Val Leu Lys Arg Cys Ala
                245                 250                 255

Gln Glu Tyr Leu Ser Arg Val Lys Lys Glu Glu Gln Arg Tyr Gln Ala
            260                 265                 270

Leu Lys Val His Ala Glu Glu Lys Leu Asp Arg Ala Asn Ala Glu Ile
        275                 280                 285

Ala Gln Val Arg Gly Lys Ala Gln Gln Glu Gln Ala Ala His Gln Ala
    290                 295                 300

Ser Leu Arg Lys Glu Gln Leu Arg Val Asp Ala Leu Glu Arg Thr Leu
305                 310                 315                 320

Glu Gln Lys Asn Lys Glu Ile Glu Glu Leu Thr Lys Ile Cys Asp Glu
                325                 330                 335

Leu Ile Ala Lys Met Gly Lys Ser
            340
```

<210> SEQ ID NO 171
<211> LENGTH: 90
<212> TYPE: PRT
<213> ORGANISM: Homo sapiens
<220> FEATURE:
<221> NAME/KEY: SITE
<222> LOCATION: (90)
<223> OTHER INFORMATION: Xaa equals stop translation

<400> SEQUENCE: 171

```
Met Tyr His Tyr Ala Trp Leu Ile Phe Val Phe Leu Val Glu Met Gly
  1               5                  10                  15
```

-continued

```
Phe Cys His Val Gly Gln Ala Gly Leu Lys Leu Leu Thr Ser Ser Asp
             20                  25                  30

Pro Pro Ala Ser Ala Ser Gln Ser Ala Gly Ile Thr Gly Val Ser His
         35                  40                  45

His Ala Trp Gly Lys Arg Tyr Phe Gln Asn Ile Val Asn Asn Phe Ser
     50                  55                  60

Pro Lys Pro Arg Gln Gly Leu Ile Leu Leu Pro Arg Leu Glu Trp Gln
 65                  70                  75                  80

Gly His His Arg Ser Ser Leu Gln Pro Xaa
                 85                  90


<210> SEQ ID NO 172
<211> LENGTH: 104
<212> TYPE: PRT
<213> ORGANISM: Homo sapiens

<400> SEQUENCE: 172

Met Leu Cys Pro Asn His Gly Leu Phe Pro Asp Pro Gly Phe Gln Cys
  1               5                  10                  15

Pro Pro Leu Phe Gln Glu Val Gln Arg Asp Ala Pro His Arg Lys Gly
             20                  25                  30

Ser Ala Thr Val Leu Pro Arg Cys Pro Pro Trp Val Pro Ser Leu Lys
         35                  40                  45

His Arg Thr Ser His Thr Ser Ser Pro Ala Val Pro Leu Ile Leu Val
     50                  55                  60

Pro Arg Leu Pro Ser Leu Gln Leu His Ser Phe Ile Gln His Ser Leu
 65                  70                  75                  80

Gly Asp Phe Tyr Ile Asp Thr Pro Arg Thr Glu Ala Trp Gly Lys Asp
                 85                  90                  95

Asp Gln Glu His Val Pro Ser Arg
            100


<210> SEQ ID NO 173
<211> LENGTH: 42
<212> TYPE: PRT
<213> ORGANISM: Homo sapiens
<220> FEATURE:
<221> NAME/KEY: SITE
<222> LOCATION: (42)
<223> OTHER INFORMATION: Xaa equals stop translation

<400> SEQUENCE: 173

Met Ser Val Leu Phe Val Ala Val Ser Leu Leu Ser Ser Ile Val Pro
  1               5                  10                  15

Asp Ile Gln Tyr Arg Leu Lys Thr Tyr Leu His Ile Asp Leu Trp Lys
             20                  25                  30

Thr Asp Thr Gln Val Leu Lys Asn Lys Xaa
         35                  40


<210> SEQ ID NO 174
<211> LENGTH: 47
<212> TYPE: PRT
<213> ORGANISM: Homo sapiens
<220> FEATURE:
<221> NAME/KEY: SITE
<222> LOCATION: (47)
<223> OTHER INFORMATION: Xaa equals stop translation

<400> SEQUENCE: 174

Met Met Leu Gly Leu Phe Ser Pro Leu Cys Leu Val Thr Gly Ile Ala
  1               5                  10                  15
```

```
Glu Gly Arg Ala Glu Asp Ala Ser Leu His Asp Ile Cys Thr Thr Gln
            20                  25                  30

His Thr Leu Thr Phe Thr Pro Ser Tyr Pro Val Gly Gly Ser Xaa
        35                  40                  45


<210> SEQ ID NO 175
<211> LENGTH: 73
<212> TYPE: PRT
<213> ORGANISM: Homo sapiens
<220> FEATURE:
<221> NAME/KEY: SITE
<222> LOCATION: (44)
<223> OTHER INFORMATION: Xaa equals any of the naturally occurring L-
      amino acids
<221> NAME/KEY: SITE
<222> LOCATION: (69)
<223> OTHER INFORMATION: Xaa equals any of the naturally occurring L-
      amino acids

<400> SEQUENCE: 175

Met Ser Phe Ser Leu Ala His Val Lys Thr Gly Gln Gly Pro Arg Leu
  1               5                  10                  15

Thr Glu Ala Leu Gln Tyr Ile Ala Ser Lys Ile Ala Val Gly Val Thr
            20                  25                  30

Ser Ser Gln Lys Ser Gly Glu Glu Arg Ala Met Xaa Thr Gln Glu Leu
        35                  40                  45

Leu Met Asp Gln Ala Trp Asp Ser Val Cys His Phe His Gln His Pro
     50                  55                  60

Thr His Gln Asn Xaa Val Thr Gly Pro
 65                  70


<210> SEQ ID NO 176
<211> LENGTH: 29
<212> TYPE: PRT
<213> ORGANISM: Homo sapiens
<220> FEATURE:
<221> NAME/KEY: SITE
<222> LOCATION: (29)
<223> OTHER INFORMATION: Xaa equals stop translation

<400> SEQUENCE: 176

Met Leu Ser Leu Asp Phe Pro Leu Ile Leu Leu Gly Leu Asn Leu His
  1               5                  10                  15

Ile Ala Leu Leu Ser Leu Leu Val Pro Arg Leu Ser Xaa
            20                  25


<210> SEQ ID NO 177
<211> LENGTH: 67
<212> TYPE: PRT
<213> ORGANISM: Homo sapiens

<400> SEQUENCE: 177

Met Ile Phe Arg Asn Gly Val Arg Leu Val Phe Val Phe Val Leu Phe
  1               5                  10                  15

Tyr Thr Ser Thr Gln Ser Leu Phe Asn Ser Leu Gln Thr Ala Glu Tyr
            20                  25                  30

Val Leu Phe Cys Gln Gln Arg Leu Ser Leu Tyr Glu Pro Ser His Val
        35                  40                  45

Leu Cys Leu Cys Met Ser Pro His Arg Lys His Thr Arg Glu Ser Asp
     50                  55                  60

Thr Ser Gly
 65
```

<210> SEQ ID NO 178
<211> LENGTH: 24
<212> TYPE: PRT
<213> ORGANISM: Homo sapiens
<220> FEATURE:
<221> NAME/KEY: SITE
<222> LOCATION: (24)
<223> OTHER INFORMATION: Xaa equals stop translation

<400> SEQUENCE: 178

```
Met Asn Phe Leu Leu Leu Ile Phe Pro Tyr Phe Ser Ser Leu Leu Gly
  1               5                  10                  15

Glu Val Glu Val Val Lys Cys Xaa
             20
```

<210> SEQ ID NO 179
<211> LENGTH: 31
<212> TYPE: PRT
<213> ORGANISM: Homo sapiens
<220> FEATURE:
<221> NAME/KEY: SITE
<222> LOCATION: (31)
<223> OTHER INFORMATION: Xaa equals stop translation

<400> SEQUENCE: 179

```
Met Ser Pro Gly Arg Val Ser Val Val Ser Leu Gln Gly Ser Gln Leu
  1               5                  10                  15

Cys Leu Leu Val Ser Ile Ala Ile Met Gly Leu Leu Leu Phe Xaa
             20                  25                  30
```

<210> SEQ ID NO 180
<211> LENGTH: 11
<212> TYPE: PRT
<213> ORGANISM: Homo sapiens
<220> FEATURE:
<221> NAME/KEY: SITE
<222> LOCATION: (11)
<223> OTHER INFORMATION: Xaa equals stop translation

<400> SEQUENCE: 180

```
Met Ala Tyr Ala Phe His Arg Thr Ser Thr Xaa
  1               5                  10
```

<210> SEQ ID NO 181
<211> LENGTH: 32
<212> TYPE: PRT
<213> ORGANISM: Homo sapiens
<220> FEATURE:
<221> NAME/KEY: SITE
<222> LOCATION: (32)
<223> OTHER INFORMATION: Xaa equals stop translation

<400> SEQUENCE: 181

```
Met Ser Val Lys Val Gly Ser Leu Leu Val Leu Val Tyr Phe Thr Leu
  1               5                  10                  15

Gly Pro Val Val Ala Glu Leu Glu Val Thr Leu Pro Ser His Ser Xaa
             20                  25                  30
```

<210> SEQ ID NO 182
<211> LENGTH: 36
<212> TYPE: PRT
<213> ORGANISM: Homo sapiens
<220> FEATURE:
<221> NAME/KEY: SITE
<222> LOCATION: (36)
<223> OTHER INFORMATION: Xaa equals stop translation -continued

<400> SEQUENCE: 182

```
Met Ile Val Ile Thr Ser Ile Leu Ser Ser Leu Ala Ser Leu Leu Leu
  1               5                  10                  15

Leu Ala Phe Leu Ala Ala Ser Thr Ala Arg Leu Ser Pro Gln Ser Leu
             20                  25                  30

Pro Glu Thr Xaa
         35
```

<210> SEQ ID NO 183
<211> LENGTH: 35
<212> TYPE: PRT
<213> ORGANISM: Homo sapiens
<220> FEATURE:
<221> NAME/KEY: SITE
<222> LOCATION: (35)
<223> OTHER INFORMATION: Xaa equals stop translation

<400> SEQUENCE: 183

```
Met Ser Gly Leu Glu Ser Ala Arg Val Leu Leu Cys Ala Leu Gly Ser
  1               5                  10                  15

Phe Leu Leu Asn Ser Leu Leu Ser Thr Phe Arg Leu Asn Ser Ser Ala
             20                  25                  30

Pro Ser Xaa
         35
```

<210> SEQ ID NO 184
<211> LENGTH: 29
<212> TYPE: PRT
<213> ORGANISM: Homo sapiens
<220> FEATURE:
<221> NAME/KEY: SITE
<222> LOCATION: (29)
<223> OTHER INFORMATION: Xaa equals stop translation

<400> SEQUENCE: 184

```
Met His Ser Ile Ile Val Lys Glu Leu Ile Val Thr Phe Phe Leu Gly
  1               5                  10                  15

Ile Thr Val Leu Leu Leu Leu Met Gln Arg Ser Leu Xaa
             20                  25
```

<210> SEQ ID NO 185
<211> LENGTH: 6
<212> TYPE: PRT
<213> ORGANISM: Homo sapiens
<220> FEATURE:
<221> NAME/KEY: SITE
<222> LOCATION: (6)
<223> OTHER INFORMATION: Xaa equals stop translation

<400> SEQUENCE: 185

```
Met Gly Tyr Leu Asn Xaa
  1               5
```

<210> SEQ ID NO 186
<211> LENGTH: 58
<212> TYPE: PRT
<213> ORGANISM: Homo sapiens

<400> SEQUENCE: 186

```
Met Pro Phe Ala Trp Asn Asp Leu Thr Ser Leu Leu Phe Tyr Leu Ala
  1               5                  10                  15

Gly Cys Phe Ser Ser Cys Arg Leu Gly Gln Gly Thr Pro Gly Ser Leu
             20                  25                  30
```

```
Pro Trp Thr Ser Asn Glu Glu Gly Ile Ile Gln Gly Pro Thr Pro Met
        35                  40                  45

Phe Trp Asn Leu Thr Pro Phe Ser Gly Thr
    50                  55


<210> SEQ ID NO 187
<211> LENGTH: 406
<212> TYPE: PRT
<213> ORGANISM: Homo sapiens
<220> FEATURE:
<221> NAME/KEY: SITE
<222> LOCATION: (273)
<223> OTHER INFORMATION: Xaa equals any of the naturally occurring L-
      amino acids
<221> NAME/KEY: SITE
<222> LOCATION: (406)
<223> OTHER INFORMATION: Xaa equals stop translation

<400> SEQUENCE: 187

Met Leu Leu Leu Trp Val Ser Val Val Ala Ala Leu Ala Leu Ala Val
  1               5                  10                  15

Leu Ala Pro Gly Ala Gly Glu Gln Arg Arg Arg Ala Ala Lys Ala Pro
            20                  25                  30

Asn Val Val Leu Val Val Ser Asp Ser Tyr Asp Gly Arg Leu Thr Phe
        35                  40                  45

His Pro Gly Ser Gln Val Val Lys Leu Pro Phe Ile Asn Phe Met Lys
    50                  55                  60

Thr Arg Gly Thr Ser Phe Leu Asn Ala Tyr Thr Asn Ser Pro Ile Cys
 65                  70                  75                  80

Cys Pro Ser Arg Ala Ala Met Trp Ser Gly Leu Phe Thr His Leu Thr
                 85                  90                  95

Glu Ser Trp Asn Asn Phe Lys Gly Leu Asp Pro Asn Tyr Thr Thr Trp
            100                 105                 110

Met Asp Val Met Glu Arg His Gly Tyr Arg Thr Gln Lys Phe Gly Lys
        115                 120                 125

Leu Asp Tyr Thr Ser Gly His His Ser Ile Ser Asn Arg Val Glu Ala
    130                 135                 140

Trp Thr Arg Asp Val Ala Phe Leu Leu Arg Gln Glu Gly Arg Pro Met
145                 150                 155                 160

Val Asn Leu Ile Arg Asn Arg Thr Lys Val Arg Val Met Glu Arg Asp
                165                 170                 175

Trp Gln Asn Thr Asp Lys Ala Val Asn Trp Leu Arg Lys Glu Ala Ile
            180                 185                 190

Asn Tyr Thr Glu Pro Phe Val Ile Tyr Leu Gly Leu Asn Leu Pro His
        195                 200                 205

Pro Tyr Pro Ser Pro Ser Ser Gly Glu Asn Phe Gly Ser Ser Thr Phe
    210                 215                 220

His Thr Ser Leu Tyr Trp Leu Glu Lys Val Ser His Asp Ala Ile Lys
225                 230                 235                 240

Ile Pro Lys Trp Ser Pro Leu Ser Glu Met His Pro Val Asp Tyr Tyr
                245                 250                 255

Ser Ser Tyr Thr Lys Asn Cys Thr Gly Arg Phe Thr Lys Lys Glu Ile
            260                 265                 270

Xaa Asn Ile Arg Ala Phe Tyr Tyr Ala Met Cys Ala Glu Thr Asp Ala
        275                 280                 285

Met Leu Gly Glu Ile Ile Leu Ala Leu His Gln Leu Asp Leu Leu Gln
    290                 295                 300
```

-continued

```
Lys Thr Ile Val Ile Tyr Ser Ser Asp His Gly Glu Leu Ala Met Glu
305                 310                 315                 320

His Arg Gln Phe Tyr Lys Met Ser Met Tyr Glu Ala Ser Ala His Val
                325                 330                 335

Pro Leu Leu Met Met Gly Pro Gly Ile Lys Ala Gly Leu Gln Val Ser
            340                 345                 350

Asn Val Val Ser Leu Val Asp Ile Tyr Pro Thr Met Leu Asp Ile Ala
        355                 360                 365

Gly Ile Pro Leu Pro Gln Asn Leu Ser Gly Tyr Ser Ser Leu Pro Leu
    370                 375                 380

Ser Ser Glu Thr Phe Lys Asn Glu His Lys Val Lys Asn Leu His Pro
385                 390                 395                 400

Pro Trp Ile Thr Glu Xaa
                405


<210> SEQ ID NO 188
<211> LENGTH: 37
<212> TYPE: PRT
<213> ORGANISM: Homo sapiens
<220> FEATURE:
<221> NAME/KEY: SITE
<222> LOCATION: (37)
<223> OTHER INFORMATION: Xaa equals stop translation

<400> SEQUENCE: 188

Met Asn Gly Leu Val Arg Pro Val Glu Leu Asn Ser Leu Leu Leu Pro
  1               5                  10                  15

Val Val Arg Tyr Gln Val Ala Gln Pro Gln Lys Leu Leu Asn Val Phe
            20                  25                  30

Val Gly Gly Leu Xaa
        35


<210> SEQ ID NO 189
<211> LENGTH: 57
<212> TYPE: PRT
<213> ORGANISM: Homo sapiens
<220> FEATURE:
<221> NAME/KEY: SITE
<222> LOCATION: (51)
<223> OTHER INFORMATION: Xaa equals any of the naturally occurring L-
      amino acids

<400> SEQUENCE: 189

Met Lys Ala Leu Val Gly Asn Ser Pro Pro Val Gly Asp Ser Gly Thr
  1               5                  10                  15

Gln Pro Pro Ser Ala Leu Arg Leu Cys Leu Leu Lys Val Leu Arg Val
            20                  25                  30

Leu Ser Met Tyr Leu Ala Asn Gly Glu Arg Val Trp Arg Thr His Lys
        35                  40                  45

Arg Val Xaa His His Val Leu Arg Gly
     50                  55


<210> SEQ ID NO 190
<211> LENGTH: 128
<212> TYPE: PRT
<213> ORGANISM: Homo sapiens
<220> FEATURE:
<221> NAME/KEY: SITE
<222> LOCATION: (127)
<223> OTHER INFORMATION: Xaa equals any of the naturally occurring L-
      amino acids
<221> NAME/KEY: SITE
```

-continued

<222> LOCATION: (128)
<223> OTHER INFORMATION: Xaa equals stop translation

<400> SEQUENCE: 190

```
Met Phe Val Leu Leu Tyr Val Thr Ser Phe Ala Ile Cys Ala Ser Gly
  1               5                  10                  15

Gln Pro Arg Gly Asn Gln Leu Lys Gly Glu Asn Tyr Ser Pro Arg Tyr
             20                  25                  30

Ile Cys Ser Ile Pro Gly Leu Pro Gly Pro Pro Gly Pro Pro Gly Ala
         35                  40                  45

Asn Gly Ser Pro Gly Pro His Gly Arg Ile Gly Leu Pro Gly Arg Asp
     50                  55                  60

Gly Arg Asp Gly Arg Lys Gly Glu Lys Gly Glu Lys Gly Thr Ala Gly
 65                  70                  75                  80

Leu Arg Gly Lys Thr Gly Pro Leu Gly Leu Ala Gly Glu Lys Gly Asp
                 85                  90                  95

Gln Gly Glu Thr Gly Lys Lys Gly Pro Ile Gly Pro Glu Gly Glu Lys
            100                 105                 110

Gly Glu Val Gly Pro Ile Gly Pro Pro Gly Pro Lys Gly Asp Xaa Xaa
        115                 120                 125
```

<210> SEQ ID NO 191
<211> LENGTH: 21
<212> TYPE: PRT
<213> ORGANISM: Homo sapiens
<220> FEATURE:
<221> NAME/KEY: SITE
<222> LOCATION: (21)
<223> OTHER INFORMATION: Xaa equals stop translation

<400> SEQUENCE: 191

```
Met Lys Phe Ile Met Leu Leu Leu Leu Pro Ser Ile Phe Pro Thr Thr
  1               5                  10                  15

Val Glu Met Ile Xaa
             20
```

<210> SEQ ID NO 192
<211> LENGTH: 143
<212> TYPE: PRT
<213> ORGANISM: Homo sapiens
<220> FEATURE:
<221> NAME/KEY: SITE
<222> LOCATION: (92)
<223> OTHER INFORMATION: Xaa equals any of the naturally occurring L-amino acids
<221> NAME/KEY: SITE
<222> LOCATION: (136)
<223> OTHER INFORMATION: Xaa equals any of the naturally occurring L-amino acids
<221> NAME/KEY: SITE
<222> LOCATION: (138)
<223> OTHER INFORMATION: Xaa equals any of the naturally occurring L-amino acids
<221> NAME/KEY: SITE
<222> LOCATION: (143)
<223> OTHER INFORMATION: Xaa equals stop translation

<400> SEQUENCE: 192

```
Met Cys Ala Phe Pro Trp Leu Leu Leu Leu Leu Leu Leu Gln Glu Gly
  1               5                  10                  15

Ser Gln Arg Arg Leu Trp Arg Trp Cys Gly Ser Glu Glu Val Val Ala
             20                  25                  30

Val Leu Gln Glu Ser Ile Ser Leu Pro Leu Glu Ile Pro Pro Asp Glu
         35                  40                  45
```

-continued

Glu Val Glu Asn Ile Ile Trp Ser Ser His Lys Ser Leu Ala Thr Val
50 55 60

Val Pro Gly Lys Glu Gly His Pro Ala Thr Ile Met Val Thr Asn Pro
65 70 75 80

His Tyr Gln Gly Gln Val Ser Phe Leu Asp Pro Xaa Tyr Ser Leu His
85 90 95

Ile Ser Asn Leu Ser Trp Glu Asp Ser Gly Leu Tyr Gln Ala Gln Val
100 105 110

Asn Leu Arg Thr Ser Gln Ile Ser Thr Met Gln Gln Tyr Asn Leu Cys
115 120 125

Val Tyr Arg Trp Leu Ser Glu Xaa Pro Xaa His Cys Glu Leu Xaa
130 135 140

<210> SEQ ID NO 193
<211> LENGTH: 110
<212> TYPE: PRT
<213> ORGANISM: Homo sapiens
<220> FEATURE:
<221> NAME/KEY: SITE
<222> LOCATION: (110)
<223> OTHER INFORMATION: Xaa equals stop translation

<400> SEQUENCE: 193

Met Ile Lys Lys Asp Lys Tyr His Lys Lys Val Phe Leu Phe Gly Trp
1 5 10 15

Phe Phe Cys Leu Phe Val Phe Phe Leu Arg Leu Ser Leu Ser Leu Leu
20 25 30

Pro Lys Leu Glu Cys Asn Leu Gly Ser Leu Gln Pro Pro Pro Pro Arg
35 40 45

Phe Gln Arg Phe Ser Cys Leu Ser Leu Leu Asn Ser Trp Asp Tyr Arg
50 55 60

Arg Pro Pro Pro His Leu Ala Asn Phe Cys Val Val Ser Arg Gly Gly
65 70 75 80

Val Ser Ser Cys Trp Pro Gly Trp Ser Arg Thr Pro Asp Leu Met Ile
85 90 95

Arg Leu Pro Arg Pro Pro Arg Val Leu Gly Leu Gln Ala Xaa
100 105 110

<210> SEQ ID NO 194
<211> LENGTH: 80
<212> TYPE: PRT
<213> ORGANISM: Homo sapiens
<220> FEATURE:
<221> NAME/KEY: SITE
<222> LOCATION: (73)
<223> OTHER INFORMATION: Xaa equals any of the naturally occurring L-amino acids
<221> NAME/KEY: SITE
<222> LOCATION: (78)
<223> OTHER INFORMATION: Xaa equals any of the naturally occurring L-amino acids

<400> SEQUENCE: 194

Met Phe Leu Thr Ile Ile Val Cys Gly Met Val Ala Ala Leu Ser Ala
1 5 10 15

Ile Arg Ala Asn Cys His Gln Glu Pro Ser Val Cys Leu Gln Ala Ala
20 25 30

Cys Pro Glu Ser Trp Ile Gly Phe Gln Arg Lys Cys Phe Tyr Phe Ser
35 40 45

Asp Asp Thr Lys Asn Trp Thr Ser Ser Gln Arg Phe Cys Asp Ser Gln

```
     50                  55                  60

Asp Ala Asp Leu Ala Gln Val Glu Xaa Phe Gln Glu Leu Xaa Arg Lys
 65                  70                  75                  80


<210> SEQ ID NO 195
<211> LENGTH: 210
<212> TYPE: PRT
<213> ORGANISM: Homo sapiens
<220> FEATURE:
<221> NAME/KEY: SITE
<222> LOCATION: (210)
<223> OTHER INFORMATION: Xaa equals stop translation

<400> SEQUENCE: 195

Met Cys Pro Leu Trp Arg Leu Leu Ile Phe Leu Gly Leu Leu Ala Leu
  1               5                  10                  15

Pro Leu Ala Pro His Lys Gln Pro Trp Pro Gly Leu Ala Gln Ala His
             20                  25                  30

Arg Asp Asn Lys Ser Thr Leu Ala Arg Ile Ile Ala Gln Gly Leu Ile
         35                  40                  45

Lys His Asn Ala Glu Ser Arg Ile Gln Asn Ile His Phe Gly Asp Arg
     50                  55                  60

Leu Asn Ala Ser Ala Gln Val Ala Pro Gly Leu Val Gly Trp Leu Ile
 65                  70                  75                  80

Ser Gly Arg Lys His Gln Gln Gln Gln Glu Ser Ser Ile Asn Ile Thr
                 85                  90                  95

Asn Ile Gln Leu Asp Cys Gly Gly Ile Gln Ile Ser Phe His Lys Glu
            100                 105                 110

Trp Phe Ser Ala Asn Ile Ser Leu Glu Phe Asp Leu Glu Leu Arg Pro
        115                 120                 125

Ser Phe Asp Asn Asn Ile Ile Lys Met Cys Ala His Met Ser Ile Val
    130                 135                 140

Val Glu Phe Trp Leu Glu Lys Asp Glu Phe Gly Arg Arg Asp Leu Val
145                 150                 155                 160

Ile Gly Lys Cys Asp Ala Glu Pro Ser Ser Val His Val Ala Ile Leu
                165                 170                 175

Thr Glu Ala Ile Pro Pro Lys Met Asn Gln Phe Leu Tyr Asn Leu Lys
            180                 185                 190

Glu Asn Leu Gln Lys Val Leu Pro His Met Val Glu Ser Gln Pro Leu
        195                 200                 205

Ala Xaa
    210


<210> SEQ ID NO 196
<211> LENGTH: 149
<212> TYPE: PRT
<213> ORGANISM: Homo sapiens
<220> FEATURE:
<221> NAME/KEY: SITE
<222> LOCATION: (61)
<223> OTHER INFORMATION: Xaa equals any of the naturally occurring L-
      amino acids
<221> NAME/KEY: SITE
<222> LOCATION: (142)
<223> OTHER INFORMATION: Xaa equals any of the naturally occurring L-
      amino acids
<221> NAME/KEY: SITE
<222> LOCATION: (149)
<223> OTHER INFORMATION: Xaa equals stop translation

<400> SEQUENCE: 196
```

-continued

```
Met Arg Lys Ile Ala Gln Cys Ala Pro Gly Val Val Glu Leu Val Leu
  1               5                  10                  15

Ile Pro Leu Arg Gln Arg Leu Glu Glu Arg Gln Arg Arg Arg Lys Gln
             20                  25                  30

Gly Ala Gly Ser Leu Gln Glu Leu Ala Pro Gln Asp Gly Ser Gly Tyr
         35                  40                  45

Met Asp Val Gly Val Ser Gln Lys Ala Arg Gly Glu Xaa Val Pro Asp
     50                  55                  60

Pro Gln Gly Gly Gly Gln Leu Ser Trp Asp Arg Pro Pro Ala Pro Arg
 65                  70                  75                  80

Pro Pro Ala Tyr Asn Arg Ala Leu Gln Gly Asp Pro Ser Phe Val Leu
                 85                  90                  95

Gln Ile Ala Glu Lys Glu Gln Glu Leu Leu Ala Ser Gln Glu Thr Val
            100                 105                 110

Gln Val Leu Gln Met Lys Val Arg Arg Leu Glu His Leu Leu Gln Leu
        115                 120                 125

Lys Asn Val Arg Ile Glu Asn Leu Ser Arg Arg Leu Gln Xaa Ala Glu
    130                 135                 140

Arg Lys Gln Arg Xaa
145


<210> SEQ ID NO 197
<211> LENGTH: 36
<212> TYPE: PRT
<213> ORGANISM: Homo sapiens
<220> FEATURE:
<221> NAME/KEY: SITE
<222> LOCATION: (36)
<223> OTHER INFORMATION: Xaa equals stop translation

<400> SEQUENCE: 197

Met His Ile Thr Ser Leu Val Gly Ala Gly Thr Leu Met Val Leu Leu
  1               5                  10                  15

Leu Leu Ile Leu Leu Leu Glu Cys Phe Phe Val Ala Glu Ala Leu Val
             20                  25                  30

Met Arg Ser Xaa
         35


<210> SEQ ID NO 198
<211> LENGTH: 258
<212> TYPE: PRT
<213> ORGANISM: Homo sapiens
<220> FEATURE:
<221> NAME/KEY: SITE
<222> LOCATION: (258)
<223> OTHER INFORMATION: Xaa equals stop translation

<400> SEQUENCE: 198

Met Ala Ala Leu Thr Thr Val Val Val Ala Ala Ala Ala Thr Ala Val
  1               5                  10                  15

Ala Gly Ala Val Ala Gly Ala Gly Ala Ala Thr Gly Thr Gly Val Gly
             20                  25                  30

Ala Thr Pro Ala Pro Gln Gln Ser Asp Gly Cys Phe Ser Thr Ser Gly
         35                  40                  45

Gly Ile Arg Pro Phe His Leu Gln Asn Trp Lys Gln Lys Val Asn Gln
     50                  55                  60

Thr Lys Lys Ala Glu Phe Val Arg Thr Ala Glu Lys Phe Lys Asn Gln
 65                  70                  75                  80

Val Ile Asn Met Glu Lys Asp Lys His Ser His Phe Tyr Asn Gln Lys
```

-continued

```
                85                  90                  95

Ser Asp Phe Arg Phe Glu His Ser Met Leu Glu Glu Leu Glu Asn Lys
            100                 105                 110

Leu Ile His Ser Arg Lys Thr Glu Arg Ala Lys Phe Gln Gln Gln Leu
        115                 120                 125

Ala Lys Ile His Asn Asn Val Lys Lys Leu Gln His Gln Leu Lys Asp
    130                 135                 140

Val Lys Pro Thr Pro Asp Phe Val Glu Lys Leu Arg Glu Met Met Glu
145                 150                 155                 160

Glu Ile Glu Asn Ala Ile Asn Thr Phe Lys Glu Glu Gln Arg Leu Ile
                165                 170                 175

Tyr Glu Glu Leu Ile Lys Glu Glu Lys Thr Thr Asn Asn Glu Leu Ser
            180                 185                 190

Ala Ile Ser Arg Lys Ile Asp Thr Trp Ala Leu Gly Asn Ser Glu Thr
        195                 200                 205

Glu Lys Ala Phe Arg Ala Ile Ser Ser Lys Val Pro Val Asp Lys Val
    210                 215                 220

Thr Pro Ser Thr Leu Pro Glu Glu Val Leu Asp Phe Glu Lys Phe Leu
225                 230                 235                 240

Gln Gln Thr Gly Gly Arg Gln Gly Ala Trp Asp Val Ile Thr Arg Thr
                245                 250                 255

Leu Xaa


<210> SEQ ID NO 199
<211> LENGTH: 59
<212> TYPE: PRT
<213> ORGANISM: Homo sapiens
<220> FEATURE:
<221> NAME/KEY: SITE
<222> LOCATION: (11)
<223> OTHER INFORMATION: Xaa equals any of the naturally occurring L-
      amino acids
<221> NAME/KEY: SITE
<222> LOCATION: (59)
<223> OTHER INFORMATION: Xaa equals stop translation

<400> SEQUENCE: 199

Met Leu Cys Leu Leu Val Leu Thr Gly Leu Xaa Val Leu Ile Val Gly
  1               5                  10                  15

Ile His Ile Leu Glu Leu Leu Ile Asp Glu Ala Ala Met Pro Arg Gly
             20                  25                  30

Met Gln Gly Thr Ser Leu Gly Gln Val Ser Phe Ser Lys Leu Gly Ser
         35                  40                  45

Phe Ala Ser Ser Ala Ser Leu Ser Ala Arg Xaa
     50                  55


<210> SEQ ID NO 200
<211> LENGTH: 34
<212> TYPE: PRT
<213> ORGANISM: Homo sapiens
<220> FEATURE:
<221> NAME/KEY: SITE
<222> LOCATION: (34)
<223> OTHER INFORMATION: Xaa equals stop translation

<400> SEQUENCE: 200

Met Phe Phe Val Leu Leu Cys Phe Trp Leu Phe Pro Phe Ser Lys Asn
  1               5                  10                  15

Ser Pro Leu Trp Gly Met Leu Arg Ser Ser Phe Phe Ile Ser Ile Asn
             20                  25                  30
```

Leu Xaa

<210> SEQ ID NO 201
<211> LENGTH: 26
<212> TYPE: PRT
<213> ORGANISM: Homo sapiens
<220> FEATURE:
<221> NAME/KEY: SITE
<222> LOCATION: (26)
<223> OTHER INFORMATION: Xaa equals stop translation

<400> SEQUENCE: 201

```
Met Ser Leu Ile Leu Leu Leu Ser Val Thr Leu Leu His Leu Ser Phe
  1               5                  10                  15

Ser Val Gly Phe Phe Leu Phe Arg Leu Xaa
             20                  25
```

<210> SEQ ID NO 202
<211> LENGTH: 34
<212> TYPE: PRT
<213> ORGANISM: Homo sapiens
<220> FEATURE:
<221> NAME/KEY: SITE
<222> LOCATION: (34)
<223> OTHER INFORMATION: Xaa equals stop translation

<400> SEQUENCE: 202

```
Met Lys Ser Val Ile Phe Ile Gln Ser Val Ile Leu Phe Phe Leu Pro
  1               5                  10                  15

Met Ser Gly Asp His Gln Gly Ile Ser Gly Leu Asp Glu Leu Pro Gln
             20                  25                  30

Ala Xaa
```

<210> SEQ ID NO 203
<211> LENGTH: 58
<212> TYPE: PRT
<213> ORGANISM: Homo sapiens

<400> SEQUENCE: 203

```
Met Ser Ser Phe Leu Arg Val Ile Phe Ile Pro Asn Ile Lys Val Ile
  1               5                  10                  15

Phe Leu Pro Pro Gly Thr Thr Ser Leu Ile His Thr Met Asp Gln Gly
             20                  25                  30

Val Ile Ala Ala Phe Lys Phe Tyr Tyr Leu Arg Arg Glu Asp Phe Cys
         35                  40                  45

Pro Val Pro Tyr Cys Ser Gly Gly Arg His
     50                  55
```

<210> SEQ ID NO 204
<211> LENGTH: 75
<212> TYPE: PRT
<213> ORGANISM: Homo sapiens
<220> FEATURE:
<221> NAME/KEY: SITE
<222> LOCATION: (66)
<223> OTHER INFORMATION: Xaa equals any of the naturally occurring L-amino acids
<221> NAME/KEY: SITE
<222> LOCATION: (73)
<223> OTHER INFORMATION: Xaa equals any of the naturally occurring L-amino acids

<400> SEQUENCE: 204

```
Met Lys Pro Thr Leu Ser Lys Phe Leu Gly Thr Asp Ala Glu Leu Pro
```

-continued

```
  1               5                   10                  15

Lys Leu Tyr Pro Pro Ser Leu Gln Ala Pro Arg Gly Glu Thr Gln Leu
             20                  25                  30

Leu Gly Pro Gly Leu Glu Arg Pro Thr Arg Glu Gly Arg Val Glu Gln
         35                  40                  45

Met Leu Phe Asn Gln Lys Ser Val Ser Trp Gly Ser Gln Leu Pro Gln
     50                  55                  60

Ser Xaa Asn Thr Phe Leu Lys Asn Xaa Asp Pro
 65                  70                  75


<210> SEQ ID NO 205
<211> LENGTH: 66
<212> TYPE: PRT
<213> ORGANISM: Homo sapiens
<220> FEATURE:
<221> NAME/KEY: SITE
<222> LOCATION: (63)
<223> OTHER INFORMATION: Xaa equals any of the naturally occurring L-
      amino acids

<400> SEQUENCE: 205

Met Thr Trp Lys Gly Trp Ser Arg Thr Arg Ile Trp Lys Pro Ser Leu
  1               5                   10                  15

Pro Gln Leu Phe Thr Met Tyr Leu Leu Ala Gln Ile Arg Ala Ala Ser
             20                  25                  30

Arg Ala Ser Glu Asp Ser Cys Ser Tyr Ser Ser Asp Thr Met Trp Pro
         35                  40                  45

Gln Ser Gly Asn Ser Ser Thr Phe Ala Phe Phe Arg Pro Arg Xaa Lys
     50                  55                  60

Met Arg
 65


<210> SEQ ID NO 206
<211> LENGTH: 44
<212> TYPE: PRT
<213> ORGANISM: Homo sapiens
<220> FEATURE:
<221> NAME/KEY: SITE
<222> LOCATION: (44)
<223> OTHER INFORMATION: Xaa equals stop translation

<400> SEQUENCE: 206

Met Leu Ser Phe Val Ser Arg Cys His Trp Ser Ser Ile Ala Glu Glu
  1               5                   10                  15

Ser Glu Phe Leu Phe Leu Ile Leu Val Cys Tyr Phe Ser Ser Ser Cys
             20                  25                  30

Ser Ser Cys Ile Ile His Gln Trp Tyr Tyr Val Xaa
         35                  40


<210> SEQ ID NO 207
<211> LENGTH: 32
<212> TYPE: PRT
<213> ORGANISM: Homo sapiens
<220> FEATURE:
<221> NAME/KEY: SITE
<222> LOCATION: (32)
<223> OTHER INFORMATION: Xaa equals stop translation

<400> SEQUENCE: 207

Met Leu Gln Thr Leu Ile Leu Ile Phe Leu Leu Leu Leu Pro Cys Tyr
  1               5                   10                  15

Leu Glu Leu Leu Cys Phe Ser Leu Ile Ser Ser Ser Ala Lys Thr Xaa
```

20 25 30

<210> SEQ ID NO 208
<211> LENGTH: 48
<212> TYPE: PRT
<213> ORGANISM: Homo sapiens
<220> FEATURE:
<221> NAME/KEY: SITE
<222> LOCATION: (11)
<223> OTHER INFORMATION: Xaa equals any of the naturally occurring L-
amino acids
<221> NAME/KEY: SITE
<222> LOCATION: (48)
<223> OTHER INFORMATION: Xaa equals stop translation

<400> SEQUENCE: 208

Met Thr Pro Trp Leu Leu Ile Leu Val Ser Xaa Gly Phe Leu Lys Ser
1 5 10 15

Ile Ser Asp Pro Gln Phe Gln Glu Leu Ser Ile Asn Ile Ala Ser Cys
20 25 30

His Pro Gly Thr Val Met Pro Tyr Ser Gly Thr Ser His Leu Lys Xaa
35 40 45

<210> SEQ ID NO 209
<211> LENGTH: 37
<212> TYPE: PRT
<213> ORGANISM: Homo sapiens
<220> FEATURE:
<221> NAME/KEY: SITE
<222> LOCATION: (37)
<223> OTHER INFORMATION: Xaa equals stop translation

<400> SEQUENCE: 209

Met Thr Gly Thr Pro Ala Trp Ala His Leu Leu Leu Leu Leu Leu Leu
1 5 10 15

Gly Ser Ala Pro Gln Thr Arg Leu Trp Pro Pro Ser Gln Cys Pro Val
20 25 30

Thr Ser Pro Glu Xaa
35

<210> SEQ ID NO 210
<211> LENGTH: 74
<212> TYPE: PRT
<213> ORGANISM: Homo sapiens
<220> FEATURE:
<221> NAME/KEY: SITE
<222> LOCATION: (74)
<223> OTHER INFORMATION: Xaa equals stop translation

<400> SEQUENCE: 210

Met Gly Val Lys Leu Glu Ile Phe Arg Met Ile Ile Tyr Leu Thr Phe
1 5 10 15

Pro Val Ala Met Phe Trp Val Ser Asn Gln Ala Glu Trp Phe Glu Asp
20 25 30

Asp Val Ile Gln Arg Lys Arg Glu Leu Trp Pro Pro Glu Lys Leu Gln
35 40 45

Glu Ile Glu Glu Phe Lys Glu Arg Leu Arg Lys Arg Arg Glu Glu Lys
50 55 60

Leu Leu Arg Asp Ala Gln Gln Asn Ser Xaa
65 70

<210> SEQ ID NO 211
<211> LENGTH: 41
<212> TYPE: PRT

-continued

<213> ORGANISM: Homo sapiens
<220> FEATURE:
<221> NAME/KEY: SITE
<222> LOCATION: (41)
<223> OTHER INFORMATION: Xaa equals stop translation

<400> SEQUENCE: 211

Met Pro Phe Ser Ser Ser Val Lys Cys Leu Phe Gly Val Leu Leu Arg
1 5 10 15

Phe Cys Phe Val Val Phe Ser Val Val Val Phe Thr Phe Phe Leu Ser
20 25 30

Ile Pro Lys Arg Thr Leu Gly Tyr Xaa
35 40

<210> SEQ ID NO 212
<211> LENGTH: 54
<212> TYPE: PRT
<213> ORGANISM: Homo sapiens
<220> FEATURE:
<221> NAME/KEY: SITE
<222> LOCATION: (54)
<223> OTHER INFORMATION: Xaa equals stop translation

<400> SEQUENCE: 212

Met Trp His Leu Ser Phe His Cys Leu Leu Leu Leu Leu Pro Leu Cys
1 5 10 15

Glu Val Thr His Ser Leu Phe Ala Phe Tyr His Asn Trp Lys Leu Phe
20 25 30

Glu Ala Ser Leu Glu Thr Glu Ala Ala Met Leu Pro Val Gln Pro Ala
35 40 45

Glu Pro Arg Ala Asn Xaa
50

<210> SEQ ID NO 213
<211> LENGTH: 63
<212> TYPE: PRT
<213> ORGANISM: Homo sapiens
<220> FEATURE:
<221> NAME/KEY: SITE
<222> LOCATION: (63)
<223> OTHER INFORMATION: Xaa equals stop translation

<400> SEQUENCE: 213

Met Pro Glu Asn Leu Val Leu Ile Leu Ala Leu Leu Leu Ser Val Cys
1 5 10 15

Gly Leu Lys Gln Val Ile Phe Leu Ser Ala Ser Ile Tyr Ser Lys Met
20 25 30

Cys Thr Leu Ile Ala Thr Lys Lys Val Val Ala Lys Thr Arg Asn Asp
35 40 45

Ala Tyr Trp Tyr Leu Ile Ser Leu Lys His Ile Val Gly Phe Xaa
50 55 60

<210> SEQ ID NO 214
<211> LENGTH: 176
<212> TYPE: PRT
<213> ORGANISM: Homo sapiens
<220> FEATURE:
<221> NAME/KEY: SITE
<222> LOCATION: (142)
<223> OTHER INFORMATION: Xaa equals any of the naturally occurring L-
amino acids
<221> NAME/KEY: SITE
<222> LOCATION: (149)
<223> OTHER INFORMATION: Xaa equals any of the naturally occurring L-
amino acids -continued <221> NAME/KEY: SITE
<222> LOCATION: (155)
<223> OTHER INFORMATION: Xaa equals any of the naturally occurring L-
amino acids
<221> NAME/KEY: SITE
<222> LOCATION: (158)
<223> OTHER INFORMATION: Xaa equals any of the naturally occurring L-
amino acids
<221> NAME/KEY: SITE
<222> LOCATION: (160)
<223> OTHER INFORMATION: Xaa equals any of the naturally occurring L-
amino acids
<221> NAME/KEY: SITE
<222> LOCATION: (163)
<223> OTHER INFORMATION: Xaa equals any of the naturally occurring L-
amino acids
<221> NAME/KEY: SITE
<222> LOCATION: (176)
<223> OTHER INFORMATION: Xaa equals stop translation

<400> SEQUENCE: 214

```
Met Tyr Trp Ile Val Phe Ala Leu Tyr Thr Val Ile Glu Thr Val Ala
  1               5                  10                  15

Asp Gln Thr Val Ala Trp Phe Pro Leu Tyr Tyr Glu Leu Lys Ile Ala
             20                  25                  30

Phe Val Ile Trp Leu Leu Ser Pro Tyr Thr Lys Gly Ala Ser Leu Ile
         35                  40                  45

Tyr Arg Lys Phe Leu His Pro Leu Leu Ser Ser Lys Glu Arg Glu Ile
     50                  55                  60

Asp Asp Tyr Ile Val Gln Ala Lys Glu Arg Gly Tyr Glu Thr Met Val
 65                  70                  75                  80

Asn Phe Gly Arg Gln Gly Leu Asn Leu Ala Ala Thr Ala Ala Val Thr
                 85                  90                  95

Ala Ala Val Lys Ser Gln Gly Ala Ile Thr Glu Arg Leu Arg Ser Phe
            100                 105                 110

Ser Met His Asp Leu Thr Thr Ile Gln Gly Asp Glu Pro Val Gly Gln
        115                 120                 125

Arg Pro Tyr Gln Pro Leu Pro Glu Ala Lys Lys Lys Ser Xaa Gln Pro
    130                 135                 140

Pro Val Asn Gln Xaa Val Met Glu Phe His Xaa Lys Thr Xaa Met Xaa
145                 150                 155                 160

Lys Gln Xaa Lys Lys Gln Arg Gly His Ile Gln Ile Met Arg Cys Xaa
                165                 170                 175
```

<210> SEQ ID NO 215
<211> LENGTH: 40
<212> TYPE: PRT
<213> ORGANISM: Homo sapiens
<220> FEATURE:
<221> NAME/KEY: SITE
<222> LOCATION: (40)
<223> OTHER INFORMATION: Xaa equals stop translation

<400> SEQUENCE: 215

```
Met Arg Glu Cys Tyr Phe Leu Gly Asn Phe Leu Leu Val Phe Leu Ile
  1               5                  10                  15

Leu Ala Ser Ser Phe Ile Tyr Val Leu Val Thr Gln Val Leu Gly Gly
             20                  25                  30

Pro Ala Thr Leu Leu Ala Phe Xaa
         35                  40
```

<210> SEQ ID NO 216
<211> LENGTH: 55

<212> TYPE: PRT
<213> ORGANISM: Homo sapiens
<220> FEATURE:
<221> NAME/KEY: SITE
<222> LOCATION: (55)
<223> OTHER INFORMATION: Xaa equals stop translation

<400> SEQUENCE: 216

```
Met Val Leu Gln Asn Thr Asn Thr Leu Leu Ile Val Ser Ala Phe Leu
  1               5                  10                  15

Leu Ser Met Leu Phe Phe Lys Phe Ser Ile Ala Ile Phe Leu Val Thr
             20                  25                  30

Asn Leu Ser Phe Glu Arg Ser Asn Leu Leu Leu Gly Pro Ser Ser Asp
         35                  40                  45

Leu Phe Leu Asn Phe Lys Xaa
     50                  55
```

<210> SEQ ID NO 217
<211> LENGTH: 47
<212> TYPE: PRT
<213> ORGANISM: Homo sapiens
<220> FEATURE:
<221> NAME/KEY: SITE
<222> LOCATION: (47)
<223> OTHER INFORMATION: Xaa equals stop translation

<400> SEQUENCE: 217

```
Met Tyr Ile Phe His Phe Val Phe Leu Ile Gly Tyr Ala Met Cys Gly
  1               5                  10                  15

Ile Gln Val Thr Asn Val Thr Leu Ala Ser Gly Pro Ser Asn Leu His
             20                  25                  30

Val Tyr Leu Leu Gln Ser Tyr Leu Thr Arg Gly Pro Asn His Xaa
         35                  40                  45
```

<210> SEQ ID NO 218
<211> LENGTH: 180
<212> TYPE: PRT
<213> ORGANISM: Homo sapiens
<220> FEATURE:
<221> NAME/KEY: SITE
<222> LOCATION: (180)
<223> OTHER INFORMATION: Xaa equals stop translation

<400> SEQUENCE: 218

```
Met Leu Tyr Tyr Leu Trp Met Leu His Ser Val Thr Leu Phe Leu Asn
  1               5                  10                  15

Leu Leu Ala Cys Leu Ala Trp Phe Ser Gly Asn Ser Ser Lys Gly Val
             20                  25                  30

Asp Phe Gly Leu Ser Ile Leu Trp Phe Leu Ile Phe Thr Pro Cys Ala
         35                  40                  45

Phe Leu Cys Trp Tyr Arg Pro Ile Tyr Lys Ala Phe Arg Ser Asp Asn
     50                  55                  60

Ser Phe Ser Phe Phe Val Phe Phe Phe Val Phe Phe Cys Gln Ile Gly
 65                  70                  75                  80

Ile Tyr Ile Ile Gln Leu Val Gly Ile Pro Gly Leu Gly Asp Ser Gly
                 85                  90                  95

Trp Ile Ala Ala Leu Ser Thr Leu Asp Asn His Ser Leu Ala Ile Ser
            100                 105                 110

Val Ile Met Met Val Val Ala Gly Phe Phe Thr Leu Cys Ala Val Leu
        115                 120                 125

Ser Val Phe Leu Leu Gln Arg Val His Ser Leu Tyr Arg Arg Thr Gly
```

-continued

```
    130                 135                 140

Ala Ser Phe Gln Gln Ala Gln Glu Glu Phe Ser Gln Gly Ile Phe Ser
145                 150                 155                 160

Ser Arg Thr Phe His Arg Ala Ala Ser Ser Ala Ala Gln Gly Ala Phe
                165                 170                 175

Gln Gly Asn Xaa
            180


<210> SEQ ID NO 219
<211> LENGTH: 99
<212> TYPE: PRT
<213> ORGANISM: Homo sapiens
<220> FEATURE:
<221> NAME/KEY: SITE
<222> LOCATION: (99)
<223> OTHER INFORMATION: Xaa equals stop translation

<400> SEQUENCE: 219

Met Lys Leu Met Val Leu Val Phe Thr Ile Gly Leu Thr Leu Leu Leu
  1               5                  10                  15

Gly Val Gln Ala Met Pro Ala Asn Arg Leu Ser Cys Tyr Arg Lys Ile
             20                  25                  30

Leu Lys Asp His Asn Cys His Asn Leu Pro Glu Gly Val Ala Asp Leu
         35                  40                  45

Thr Gln Ile Asp Val Asn Val Gln Asp His Phe Trp Asp Gly Lys Gly
     50                  55                  60

Cys Glu Met Ile Cys Tyr Cys Asn Phe Ser Glu Leu Leu Cys Cys Pro
 65                  70                  75                  80

Lys Asp Val Phe Phe Gly Pro Lys Ile Ser Phe Val Ile Pro Cys Asn
                 85                  90                  95

Asn Gln Xaa


<210> SEQ ID NO 220
<211> LENGTH: 44
<212> TYPE: PRT
<213> ORGANISM: Homo sapiens
<220> FEATURE:
<221> NAME/KEY: SITE
<222> LOCATION: (44)
<223> OTHER INFORMATION: Xaa equals stop translation

<400> SEQUENCE: 220

Met Gly Gly Lys Gly Ile Asn Tyr Thr Met Pro His Ile Cys Leu Leu
  1               5                  10                  15

Leu Leu Asn Ala Leu Val Val Ser Cys Leu Leu Leu Glu Ala Ile Leu
             20                  25                  30

Leu Gln His Leu Val Leu Cys Asn Glu Leu Pro Xaa
         35                  40


<210> SEQ ID NO 221
<211> LENGTH: 42
<212> TYPE: PRT
<213> ORGANISM: Homo sapiens
<220> FEATURE:
<221> NAME/KEY: SITE
<222> LOCATION: (42)
<223> OTHER INFORMATION: Xaa equals stop translation

<400> SEQUENCE: 221

Met Phe Met Leu Cys Asn Leu Leu Leu Pro Leu Leu Glu Phe Ile Phe
  1               5                  10                  15
```

-continued

Gly Ser Thr Tyr Leu Ser Thr Asp Leu Tyr Leu His Thr Cys Met Lys
20 25 30

Asn Val Phe Leu His Ile His Ser Phe Xaa
35 40

<210> SEQ ID NO 222
<211> LENGTH: 52
<212> TYPE: PRT
<213> ORGANISM: Homo sapiens
<220> FEATURE:
<221> NAME/KEY: SITE
<222> LOCATION: (52)
<223> OTHER INFORMATION: Xaa equals stop translation

<400> SEQUENCE: 222

Met Ala Val Pro Ser Gly Cys Trp Pro Ser Trp Pro Arg Pro Ser Ser
1 5 10 15

Trp Trp Ser Thr Arg Ile Ser Pro Arg Ser Ala Thr Pro Leu Thr Ala
20 25 30

Ser Thr Trp Ser Leu Val Thr Cys Ser Ser Gln Val Ser Ala Cys Gly
35 40 45

Thr Ser Ile Xaa
50

<210> SEQ ID NO 223
<211> LENGTH: 32
<212> TYPE: PRT
<213> ORGANISM: Homo sapiens
<220> FEATURE:
<221> NAME/KEY: SITE
<222> LOCATION: (32)
<223> OTHER INFORMATION: Xaa equals stop translation

<400> SEQUENCE: 223

Met Val Ser Leu Asn Leu Ser Leu Pro Asn Asn Ile Ile Ser Leu Val
1 5 10 15

Phe Phe Phe Leu Leu Gln Pro Val Gln Lys Gly Val Ser Gly Gly Xaa
20 25 30

<210> SEQ ID NO 224
<211> LENGTH: 54
<212> TYPE: PRT
<213> ORGANISM: Homo sapiens
<220> FEATURE:
<221> NAME/KEY: SITE
<222> LOCATION: (54)
<223> OTHER INFORMATION: Xaa equals stop translation

<400> SEQUENCE: 224

Met Leu Val Leu Met Thr Thr Cys Ile Leu Ala Ala Val Cys Val His
1 5 10 15

Thr Ala Gln Cys Ala Pro Asp Ser Arg Met Asp Asn Asp Cys Pro Ser
20 25 30

His Gln Ala Gln Ile His Phe Arg Ala Ser Glu Val Arg Arg Gly Trp
35 40 45

Thr Phe Asn His Asp Xaa
50

<210> SEQ ID NO 225
<211> LENGTH: 41
<212> TYPE: PRT
<213> ORGANISM: Homo sapiens
<220> FEATURE:
<221> NAME/KEY: SITE -continued
<222> LOCATION: (41)
<223> OTHER INFORMATION: Xaa equals stop translation

<400> SEQUENCE: 225

Met Gly Pro Ser Gln Arg Glu Val Thr Val Gln Trp His Arg Ala Leu
1 5 10 15

Phe Leu Leu Pro Leu Leu Leu Leu Ser Thr Arg Thr Glu Thr Lys Asn
20 25 30

Phe Gly Phe Lys Trp Leu Lys Asp Xaa
35 40

<210> SEQ ID NO 226
<211> LENGTH: 31
<212> TYPE: PRT
<213> ORGANISM: Homo sapiens
<220> FEATURE:
<221> NAME/KEY: SITE
<222> LOCATION: (31)
<223> OTHER INFORMATION: Xaa equals stop translation

<400> SEQUENCE: 226

Met Gln Leu Ser Lys Phe Leu Leu Phe Leu Phe Val Tyr Thr Arg Glu
1 5 10 15

Asn Pro Thr Ser Ala Cys Val Trp Gly Glu Lys Ser Thr Val Xaa
20 25 30

<210> SEQ ID NO 227
<211> LENGTH: 60
<212> TYPE: PRT
<213> ORGANISM: Homo sapiens
<220> FEATURE:
<221> NAME/KEY: SITE
<222> LOCATION: (60)
<223> OTHER INFORMATION: Xaa equals stop translation

<400> SEQUENCE: 227

Met Val Val Val Ser Thr Asn Gly Phe Leu Leu Leu Leu Leu Phe Leu
1 5 10 15

Asn Arg Lys Ser Gly Leu Cys Ser Tyr Arg Lys Ala Val His Arg Leu
20 25 30

Ser Ser Cys Pro Ser Arg His Gln Ala Gly Pro Arg Ile Lys Cys Asp
35 40 45

Phe Lys Trp Gly Lys Leu Cys Tyr Ser Cys Ala Xaa
50 55 60

<210> SEQ ID NO 228
<211> LENGTH: 35
<212> TYPE: PRT
<213> ORGANISM: Homo sapiens
<220> FEATURE:
<221> NAME/KEY: SITE
<222> LOCATION: (35)
<223> OTHER INFORMATION: Xaa equals stop translation

<400> SEQUENCE: 228

Met Gly Trp Gly Lys Glu Val Val Ser Leu Ile Val Leu Leu Val Asn
1 5 10 15

Leu Phe Leu Cys Pro Trp Ala Leu Gly Leu Cys Leu Leu Ser Val Ser
20 25 30

Ser Leu Xaa
35

<210> SEQ ID NO 229

-continued

```
<211> LENGTH: 39
<212> TYPE: PRT
<213> ORGANISM: Homo sapiens
<220> FEATURE:
<221> NAME/KEY: SITE
<222> LOCATION: (39)
<223> OTHER INFORMATION: Xaa equals stop translation

<400> SEQUENCE: 229

Met Met Asn Ile Leu Leu Leu Lys Tyr Ile Leu Glu Ile Leu Ile Leu
  1               5                  10                  15

Ser Glu Asn Leu Asn Leu Phe Asn Ile Thr Tyr Gly Lys Tyr Asn Leu
             20                  25                  30

Phe Phe Leu Tyr Arg Tyr Xaa
         35


<210> SEQ ID NO 230
<211> LENGTH: 39
<212> TYPE: PRT
<213> ORGANISM: Homo sapiens
<220> FEATURE:
<221> NAME/KEY: SITE
<222> LOCATION: (39)
<223> OTHER INFORMATION: Xaa equals stop translation

<400> SEQUENCE: 230

Met Tyr Ile Phe Tyr Leu Tyr Lys Ile Tyr Ile Tyr Thr His Ile Cys
  1               5                  10                  15

Ile Tyr Ile Pro Leu Phe Leu Cys Leu Leu Ile Leu Ala Ile Lys Glu
             20                  25                  30

Gly Ala Ala Phe Asn Val Xaa
         35


<210> SEQ ID NO 231
<211> LENGTH: 62
<212> TYPE: PRT
<213> ORGANISM: Homo sapiens
<220> FEATURE:
<221> NAME/KEY: SITE
<222> LOCATION: (62)
<223> OTHER INFORMATION: Xaa equals stop translation

<400> SEQUENCE: 231

Met Asn Glu Ser Val Tyr Asp Asp Ser Thr Ser Ser Tyr Thr Pro Ser
  1               5                  10                  15

Leu His Ile Leu Gly Cys Leu Leu Leu Leu Phe Leu Gly Val Glu Arg
             20                  25                  30

Ala Leu Glu Pro Phe Ser Gly Leu Cys Ala Ser Leu His Asp Val Arg
         35                  40                  45

Pro Ile Val Asn Pro Leu Thr Ser Phe Ser Leu Ile Tyr Xaa
     50                  55                  60


<210> SEQ ID NO 232
<211> LENGTH: 198
<212> TYPE: PRT
<213> ORGANISM: Homo sapiens
<220> FEATURE:
<221> NAME/KEY: SITE
<222> LOCATION: (198)
<223> OTHER INFORMATION: Xaa equals stop translation

<400> SEQUENCE: 232

Met Cys Thr Gly Lys Cys Ala Arg Cys Val Gly Leu Ser Leu Ile Thr
  1               5                  10                  15
```

-continued

```
Leu Cys Leu Val Cys Ile Val Ala Asn Ala Leu Leu Leu Val Pro Asn
            20                  25                  30

Gly Glu Thr Ser Trp Thr Asn Thr Asn His Leu Ser Leu Gln Val Trp
        35                  40                  45

Leu Met Gly Gly Phe Ile Gly Gly Gly Leu Met Val Leu Cys Pro Gly
    50                  55                  60

Ile Ala Ala Val Arg Ala Gly Gly Lys Gly Cys Cys Gly Ala Gly Cys
65                  70                  75                  80

Cys Gly Asn Arg Cys Arg Met Leu Arg Ser Val Phe Ser Ser Ala Phe
                85                  90                  95

Gly Val Leu Gly Ala Ile Tyr Cys Leu Ser Val Ser Gly Ala Gly Leu
            100                 105                 110

Arg Asn Gly Pro Arg Cys Leu Met Asn Gly Glu Trp Gly Tyr His Phe
        115                 120                 125

Glu Asp Thr Ala Gly Ala Tyr Leu Leu Asn Arg Thr Leu Trp Asp Arg
    130                 135                 140

Cys Glu Ala Pro Pro Arg Val Val Pro Trp Asn Val Thr Leu Phe Ser
145                 150                 155                 160

Leu Leu Val Ala Ala Ser Cys Leu Glu Ile Val Leu Cys Gly Ile Gln
                165                 170                 175

Leu Val Asn Ala Thr Ile Gly Val Phe Cys Gly Asp Cys Arg Lys Lys
            180                 185                 190

Gln Asp Thr Pro His Xaa
        195


<210> SEQ ID NO 233
<211> LENGTH: 62
<212> TYPE: PRT
<213> ORGANISM: Homo sapiens
<220> FEATURE:
<221> NAME/KEY: SITE
<222> LOCATION: (62)
<223> OTHER INFORMATION: Xaa equals stop translation

<400> SEQUENCE: 233

Met Ser Gln Leu Phe Leu Ile Met Leu Thr Phe Ile Phe Leu Asn Asn
  1               5                  10                  15

Met Phe Ile Met His Leu Thr Ser Phe His Gly Lys Arg Val Phe Gly
            20                  25                  30

Phe Leu Asn Gln Ser Ser His Met His Ala Phe Pro Leu Pro Arg Trp
        35                  40                  45

Thr Thr Ser Ile Phe Ser Val Ser Ile Phe Ile Asn Arg Xaa
    50                  55                  60


<210> SEQ ID NO 234
<211> LENGTH: 81
<212> TYPE: PRT
<213> ORGANISM: Homo sapiens
<220> FEATURE:
<221> NAME/KEY: SITE
<222> LOCATION: (81)
<223> OTHER INFORMATION: Xaa equals stop translation

<400> SEQUENCE: 234

Met Ala Phe Leu Pro Leu Thr Leu Thr Phe Cys Leu Ala Pro Leu Ala
  1               5                  10                  15

Pro Leu Leu Pro Ser Ile Trp Gly Pro Thr Pro Ala Ser Cys Val Val
            20                  25                  30

Trp Pro Leu Leu Thr Ile Leu Pro Val Pro Ala Gln Ala Ser Pro Ser
```

35 40 45

Thr Asp Thr Ala His Leu Trp Gln Arg Pro Thr Thr Gly Ser Pro Thr
50 55 60

Arg Leu Val Arg Pro Leu Pro Arg Pro Gly Leu Pro Pro Met Trp Ala
65 70 75 80

Xaa

<210> SEQ ID NO 235
<211> LENGTH: 111
<212> TYPE: PRT
<213> ORGANISM: Homo sapiens

<400> SEQUENCE: 235

Met Gly Gly Leu Glu Pro Cys Ser Arg Leu Leu Leu Leu Pro Leu Leu
1 5 10 15

Leu Ala Val Gly Leu Arg Pro Val Gln Ala Gln Ala Gln Ser Asp Cys
20 25 30

Ser Cys Ser Thr Val Ser Pro Gly Val Leu Ala Gly Ile Val Met Gly
35 40 45

Asp Leu Val Leu Thr Val Leu Ile Ala Leu Ala Val Tyr Phe Leu Gly
50 55 60

Arg Leu Val Pro Arg Gly Arg Gly Ala Ala Glu Ala Thr Arg Lys Gln
65 70 75 80

Arg Ile Thr Glu Thr Glu Ser Pro Tyr Gln Glu Leu Gln Gly Gln Arg
85 90 95

Ser Asp Val Tyr Ser Asp Leu Asn Thr Gln Arg Pro Tyr Tyr Lys
100 105 110

<210> SEQ ID NO 236
<211> LENGTH: 33
<212> TYPE: PRT
<213> ORGANISM: Homo sapiens
<220> FEATURE:
<221> NAME/KEY: SITE
<222> LOCATION: (33)
<223> OTHER INFORMATION: Xaa equals stop translation

<400> SEQUENCE: 236

Met Gln Arg Met Leu Val Leu Leu Phe Phe Phe Phe Ser Leu Leu Ala
1 5 10 15

Ile Asn Pro Ala Glu Thr Ile Cys Gly Tyr Gly Ser Thr Trp Lys Phe
20 25 30

Xaa

<210> SEQ ID NO 237
<211> LENGTH: 229
<212> TYPE: PRT
<213> ORGANISM: Homo sapiens
<220> FEATURE:
<221> NAME/KEY: SITE
<222> LOCATION: (134)
<223> OTHER INFORMATION: Xaa equals any of the naturally occurring L-
amino acids
<221> NAME/KEY: SITE
<222> LOCATION: (229)
<223> OTHER INFORMATION: Xaa equals stop translation

<400> SEQUENCE: 237

Met Val Leu Gly Leu Phe Val Pro Pro Val Phe Val Val Ser Tyr Ala
1 5 10 15

Lys Asp Leu Gly Val Pro Asp Thr Lys Ala Ala Phe Leu Leu Thr Ile

-continued

```
            20                  25                  30

Leu Gly Phe Ile Asp Ile Phe Ala Arg Pro Ala Ala Gly Phe Val Ala
        35                  40                  45

Gly Leu Gly Lys Val Arg Pro Tyr Ser Val Tyr Leu Phe Ser Phe Ser
    50                  55                  60

Met Phe Phe Asn Gly Leu Ala Asp Leu Ala Gly Ser Thr Ala Gly Asp
 65                 70                  75                  80

Tyr Gly Gly Leu Val Val Phe Cys Ile Phe Phe Gly Ile Ser Tyr Gly
                85                  90                  95

Met Val Gly Ala Leu Gln Phe Glu Val Leu Met Ala Ile Val Gly Thr
            100                 105                 110

His Lys Phe Ser Ser Ala Ile Gly Leu Val Leu Leu Met Glu Ala Val
        115                 120                 125

Ala Val Leu Val Gly Xaa Pro Ser Gly Gly Lys Leu Leu Asp Ala Thr
    130                 135                 140

His Val Tyr Met Tyr Val Phe Ile Leu Ala Gly Ala Glu Val Leu Thr
145                 150                 155                 160

Ser Ser Leu Ile Leu Leu Leu Gly Asn Phe Phe Cys Ile Arg Lys Lys
                165                 170                 175

Pro Lys Glu Pro Gln Pro Glu Val Ala Ala Ala Glu Glu Glu Lys Leu
            180                 185                 190

His Lys Pro Pro Ala Asp Ser Gly Val Asp Leu Arg Glu Val Glu His
        195                 200                 205

Phe Leu Lys Ala Glu Pro Glu Lys Asn Gly Glu Val Val His Thr Pro
    210                 215                 220

Glu Thr Ser Val Xaa
225


<210> SEQ ID NO 238
<211> LENGTH: 117
<212> TYPE: PRT
<213> ORGANISM: Homo sapiens
<220> FEATURE:
<221> NAME/KEY: SITE
<222> LOCATION: (117)
<223> OTHER INFORMATION: Xaa equals stop translation

<400> SEQUENCE: 238

Met Thr Pro Leu Leu Thr Leu Ile Leu Val Val Leu Met Gly Leu Pro
  1               5                  10                  15

Leu Ala Gln Ala Leu Asp Cys His Val Cys Ala Tyr Asn Gly Asp Asn
            20                  25                  30

Cys Phe Asn Pro Met Arg Cys Pro Ala Met Val Ala Tyr Cys Met Thr
        35                  40                  45

Thr Arg Thr Tyr Tyr Thr Pro Thr Arg Met Lys Val Ser Lys Ser Cys
    50                  55                  60

Val Pro Arg Cys Phe Glu Thr Val Tyr Asp Gly Tyr Ser Lys His Ala
 65                 70                  75                  80

Ser Thr Thr Ser Cys Cys Gln Tyr Asp Leu Cys Asn Gly Thr Gly Leu
                85                  90                  95

Ala Thr Pro Ala Thr Leu Ala Leu Ala Pro Ile Leu Leu Ala Thr Leu
            100                 105                 110

Trp Gly Leu Leu Xaa
        115


<210> SEQ ID NO 239
```

-continued

<211> LENGTH: 37
<212> TYPE: PRT
<213> ORGANISM: Homo sapiens
<220> FEATURE:
<221> NAME/KEY: SITE
<222> LOCATION: (37)
<223> OTHER INFORMATION: Xaa equals stop translation

<400> SEQUENCE: 239

Met Leu Thr Trp Leu Asp Leu Asp Leu Leu Phe Cys Phe Leu Phe Leu
1 5 10 15

Phe Leu Phe Ile Leu Phe Tyr Phe Leu Gln Leu Asn Glu Phe Trp Gly
20 25 30

Gly Asn Pro Phe Xaa
35

<210> SEQ ID NO 240
<211> LENGTH: 58
<212> TYPE: PRT
<213> ORGANISM: Homo sapiens

<400> SEQUENCE: 240

Met Glu Pro Trp Ser Trp Phe Phe Phe Phe Phe Phe Phe Phe Pro Gln
1 5 10 15

Arg Thr Cys Gly Cys Ala Leu Cys Val Leu Phe Leu Phe Ser Ile Trp
20 25 30

Gly Pro His Gly Lys Glu Leu Leu Asn Ser Phe Leu Tyr Glu Leu Pro
35 40 45

Leu Cys Ser Tyr Lys Gly Pro Phe Leu Ser
50 55

<210> SEQ ID NO 241
<211> LENGTH: 48
<212> TYPE: PRT
<213> ORGANISM: Homo sapiens
<220> FEATURE:
<221> NAME/KEY: SITE
<222> LOCATION: (48)
<223> OTHER INFORMATION: Xaa equals stop translation

<400> SEQUENCE: 241

Met Gln Ser Gly Arg Ser Trp Ala Leu Lys Met Val Leu Leu Cys Asn
1 5 10 15

Ser Cys Leu Gly Leu Gly Val Gly Ser Val Gly Pro Ser Met Ser Ser
20 25 30

Leu Phe Gly Ala Val Leu Ser Glu Thr Pro Gly Ser Ser Val Tyr Xaa
35 40 45

<210> SEQ ID NO 242
<211> LENGTH: 32
<212> TYPE: PRT
<213> ORGANISM: Homo sapiens
<220> FEATURE:
<221> NAME/KEY: SITE
<222> LOCATION: (32)
<223> OTHER INFORMATION: Xaa equals stop translation

<400> SEQUENCE: 242

Met Ile Thr Leu Cys Ile Phe Leu Leu Phe Lys Val Phe Val Gly Ile
1 5 10 15

Ile Leu His Tyr Leu Ile Gly Lys Asn Ile Tyr Val Tyr Ser Val Xaa
20 25 30

-continued

<210> SEQ ID NO 243
<211> LENGTH: 64
<212> TYPE: PRT
<213> ORGANISM: Homo sapiens
<220> FEATURE:
<221> NAME/KEY: SITE
<222> LOCATION: (64)
<223> OTHER INFORMATION: Xaa equals stop translation

<400> SEQUENCE: 243

```
Met Ala Ser Leu Leu Gln Arg Asn Leu Cys Pro Arg Leu Ser Val Cys
  1               5                  10                  15

Leu Val Phe Ile Gln Val Phe Val Cys Cys Val Glu Gly Gly Gly Arg
             20                  25                  30

Arg Val Lys Ala Val Leu Phe Arg Ala Pro Phe Gly Glu His Ser Arg
         35                  40                  45

Gln Asn Thr Leu Val Ile Pro Ser Gln Thr Gly Leu Gln Ala His Xaa
     50                  55                  60
```

<210> SEQ ID NO 244
<211> LENGTH: 68
<212> TYPE: PRT
<213> ORGANISM: Homo sapiens
<220> FEATURE:
<221> NAME/KEY: SITE
<222> LOCATION: (68)
<223> OTHER INFORMATION: Xaa equals stop translation

<400> SEQUENCE: 244

```
Met Pro Val Tyr Asp Phe Asn Trp Trp Tyr Ser Leu Tyr Phe Ile Ile
  1               5                  10                  15

Tyr Ile Ile Ile Asn Thr Tyr Ile Phe Lys Ser Val Phe Leu Ala Met
             20                  25                  30

Val Tyr Ser Asn Tyr Arg Lys His Phe His Ile Leu Cys Val Cys Val
         35                  40                  45

Cys Val Phe Cys Ser Asp Glu Gln Asn Leu Leu Phe Thr Gln Phe Tyr
     50                  55                  60

Tyr Leu Ser Xaa
 65
```

<210> SEQ ID NO 245
<211> LENGTH: 46
<212> TYPE: PRT
<213> ORGANISM: Homo sapiens
<220> FEATURE:
<221> NAME/KEY: SITE
<222> LOCATION: (43)
<223> OTHER INFORMATION: Xaa equals any of the naturally occurring L-
      amino acids
<221> NAME/KEY: SITE
<222> LOCATION: (46)
<223> OTHER INFORMATION: Xaa equals stop translation

<400> SEQUENCE: 245

```
Met Ser Asp Lys Leu Ser Pro Ser Thr Val Pro Leu Leu Leu Pro Val
  1               5                  10                  15

Leu Phe Lys Val Thr Ile Leu Leu Gln Arg Val Cys Pro Glu Asp Ser
             20                  25                  30

Pro Ser Ser Ser Val Leu Pro Glu Ser Val Xaa Arg Glu Xaa
         35                  40                  45
```

<210> SEQ ID NO 246
<211> LENGTH: 43
<212> TYPE: PRT

-continued

<213> ORGANISM: Homo sapiens
<220> FEATURE:
<221> NAME/KEY: SITE
<222> LOCATION: (43)
<223> OTHER INFORMATION: Xaa equals stop translation

<400> SEQUENCE: 246

```
Met Arg Lys Glu Glu Gly Ile Ala His Leu Ser Ile Ala Phe Phe Val
  1               5                  10                  15

Gln Val Leu Cys Leu Tyr Gln Leu Leu Pro Val Ile Leu Pro Gln Phe
             20                  25                  30

Asn Leu Gly Ser Gly Lys Asn Met Asn Arg Xaa
         35                  40
```

<210> SEQ ID NO 247
<211> LENGTH: 32
<212> TYPE: PRT
<213> ORGANISM: Homo sapiens
<220> FEATURE:
<221> NAME/KEY: SITE
<222> LOCATION: (11)
<223> OTHER INFORMATION: Xaa equals any of the naturally occurring L-
      amino acids
<221> NAME/KEY: SITE
<222> LOCATION: (32)
<223> OTHER INFORMATION: Xaa equals stop translation

<400> SEQUENCE: 247

```
Met Ile His Val Leu Thr Phe Leu Leu Gln Xaa Tyr Ile Leu Ile Ser
  1               5                  10                  15

Lys Gly Lys Gly Asp Val Ser Gln Phe Val Lys Ser Arg Glu Tyr Xaa
             20                  25                  30
```

<210> SEQ ID NO 248
<211> LENGTH: 24
<212> TYPE: PRT
<213> ORGANISM: Homo sapiens
<220> FEATURE:
<221> NAME/KEY: SITE
<222> LOCATION: (24)
<223> OTHER INFORMATION: Xaa equals stop translation

<400> SEQUENCE: 248

```
Met Ser Glu Leu Ser Ala Phe Met Phe Ser Thr Ile Ile Phe Leu Met
  1               5                  10                  15

Ala Gln Pro Thr Ser Cys Phe Xaa
             20
```

<210> SEQ ID NO 249
<211> LENGTH: 80
<212> TYPE: PRT
<213> ORGANISM: Homo sapiens
<220> FEATURE:
<221> NAME/KEY: SITE
<222> LOCATION: (36)
<223> OTHER INFORMATION: Xaa equals any of the naturally occurring L-
      amino acids
<221> NAME/KEY: SITE
<222> LOCATION: (80)
<223> OTHER INFORMATION: Xaa equals stop translation

<400> SEQUENCE: 249

```
Met Arg Val Phe Ala Leu Leu Pro Pro Phe His Lys Ser Thr Val Leu
  1               5                  10                  15

Ser Phe Leu Leu Phe Phe Leu Ser Phe Phe Phe Phe Arg Gln Gly Leu
             20                  25                  30
```

-continued

```
Ala Val Ser Xaa Arg Leu Glu Cys Ser Gly Ala Ile Ile Ala His Cys
         35                  40                  45

Ser Leu Asp Leu Leu Asp Ser Ser Asn Pro Pro Ala Leu Thr Ser Gln
     50                  55                  60

Leu Leu Arg Arg Pro Arg Gln Glu Asp His Leu Ser Pro Gly Gly Xaa
 65                  70                  75                  80


<210> SEQ ID NO 250
<211> LENGTH: 16
<212> TYPE: PRT
<213> ORGANISM: Homo sapiens
<220> FEATURE:
<221> NAME/KEY: SITE
<222> LOCATION: (16)
<223> OTHER INFORMATION: Xaa equals stop translation

<400> SEQUENCE: 250

Met Ser His Cys Ala Trp Leu His Leu Gln Leu Phe Leu Ser Leu Xaa
  1               5                  10                  15


<210> SEQ ID NO 251
<211> LENGTH: 47
<212> TYPE: PRT
<213> ORGANISM: Homo sapiens
<220> FEATURE:
<221> NAME/KEY: SITE
<222> LOCATION: (47)
<223> OTHER INFORMATION: Xaa equals stop translation

<400> SEQUENCE: 251

Met Met Phe Cys Phe Leu Ile Trp Val Val Val Thr Phe Thr Tyr Ser
  1               5                  10                  15

Leu Asn Cys Thr Phe Val Leu His Lys Phe Ile Ile Phe Pro Asn Phe
             20                  25                  30

Lys Lys Val Lys Arg Arg Arg Lys Lys Leu Val Met Lys Val Xaa
         35                  40                  45


<210> SEQ ID NO 252
<211> LENGTH: 32
<212> TYPE: PRT
<213> ORGANISM: Homo sapiens
<220> FEATURE:
<221> NAME/KEY: SITE
<222> LOCATION: (32)
<223> OTHER INFORMATION: Xaa equals stop translation

<400> SEQUENCE: 252

Met Pro Pro Pro Glu Cys Leu Ser Asp Cys Ser Lys Val Ala Leu Val
  1               5                  10                  15

Met Val Leu Phe Leu Phe Leu His Gln Ser Ser Cys Trp Ala Ala Xaa
             20                  25                  30


<210> SEQ ID NO 253
<211> LENGTH: 36
<212> TYPE: PRT
<213> ORGANISM: Homo sapiens
<220> FEATURE:
<221> NAME/KEY: SITE
<222> LOCATION: (36)
<223> OTHER INFORMATION: Xaa equals stop translation

<400> SEQUENCE: 253

Met Ala Ser Ser Val Thr Val Lys Glu Val Cys Val Leu Phe Asn Leu
  1               5                  10                  15

Leu Ile Ile Ile Thr Ala Met Val Tyr His Ser Phe Thr Lys Tyr Gln
```

-continued

```
            20                  25                  30

Thr Leu Phe Xaa
        35


<210> SEQ ID NO 254
<211> LENGTH: 51
<212> TYPE: PRT
<213> ORGANISM: Homo sapiens
<220> FEATURE:
<221> NAME/KEY: SITE
<222> LOCATION: (51)
<223> OTHER INFORMATION: Xaa equals stop translation

<400> SEQUENCE: 254

Met Ile Phe Leu Phe Phe Ile Leu Phe Glu Ile Ile Val Thr Leu Trp
  1               5                  10                  15

Leu Thr Pro Thr Tyr Pro Gln Ala Phe Ser Glu Leu Thr Ile Gln Ile
            20                  25                  30

Thr Ala Pro Phe Gly Ser Leu Pro Gln Gln Leu Tyr Leu His Met Ser
        35                  40                  45

Ile Ile Xaa
    50


<210> SEQ ID NO 255
<211> LENGTH: 76
<212> TYPE: PRT
<213> ORGANISM: Homo sapiens

<400> SEQUENCE: 255

Met Phe Phe Leu Leu Ile Leu Cys Trp Leu Leu Cys Leu Ser Leu Ser
  1               5                  10                  15

Gly Leu Tyr Pro Arg Leu Leu Asn Pro Gly Gly Trp Leu Ser Leu Leu
            20                  25                  30

Ser Phe Gln Met Asp Tyr Gly Trp Ile Leu Pro Trp Gly Ala Cys Thr
        35                  40                  45

Val Arg His Gly Lys Pro Gly Met Gly Lys Arg Ser Gly Gly Ser Leu
    50                  55                  60

Pro His Leu Thr Ala Leu Val Leu Cys Leu Thr Ser
 65                  70                  75


<210> SEQ ID NO 256
<211> LENGTH: 61
<212> TYPE: PRT
<213> ORGANISM: Homo sapiens
<220> FEATURE:
<221> NAME/KEY: SITE
<222> LOCATION: (61)
<223> OTHER INFORMATION: Xaa equals stop translation

<400> SEQUENCE: 256

Met Leu Leu Ser Asn Leu Ser Leu Ser Leu Gln Pro Leu Leu Phe Leu
  1               5                  10                  15

Phe Ser Phe Phe Leu Phe Cys Lys Met Gly Ser Arg Lys Gly Leu Arg
            20                  25                  30

His Lys Thr Gln His Phe Ser Ser Met Thr Asp Gln Ile Leu Lys Gly
        35                  40                  45

Ser Val Arg Ser Pro Ala Leu Gly Gln Leu His Asp Xaa
    50                  55                  60


<210> SEQ ID NO 257
<211> LENGTH: 37
```

-continued

<212> TYPE: PRT
<213> ORGANISM: Homo sapiens
<220> FEATURE:
<221> NAME/KEY: SITE
<222> LOCATION: (37)
<223> OTHER INFORMATION: Xaa equals stop translation

<400> SEQUENCE: 257

```
Met Tyr Glu Val Asp Lys Lys Ile Tyr Ser Asn Phe Ile Gln Ile Leu
  1               5                  10                  15

Ile Val Ile Ile Phe Val Leu Tyr Leu Ile Ile Asn Gln Asn Thr Phe
             20                  25                  30

Ala Phe Leu Ser Xaa
         35
```

<210> SEQ ID NO 258
<211> LENGTH: 43
<212> TYPE: PRT
<213> ORGANISM: Homo sapiens
<220> FEATURE:
<221> NAME/KEY: SITE
<222> LOCATION: (43)
<223> OTHER INFORMATION: Xaa equals stop translation

<400> SEQUENCE: 258

```
Met Cys Ile Leu Pro Leu Met Leu Thr Tyr Pro Ile Leu Pro Lys Val
  1               5                  10                  15

Val Gly Asn Asn Ile Leu Leu Gly Asp Ser Gly Leu Thr Ser Leu Val
             20                  25                  30

Ile Pro Leu Ser Val Val Phe Asn Leu Lys Xaa
         35                  40
```

<210> SEQ ID NO 259
<211> LENGTH: 39
<212> TYPE: PRT
<213> ORGANISM: Homo sapiens
<220> FEATURE:
<221> NAME/KEY: SITE
<222> LOCATION: (39)
<223> OTHER INFORMATION: Xaa equals stop translation

<400> SEQUENCE: 259

```
Met Ile Leu Val Ser Lys Leu Phe Phe Gly Phe Ser Leu Met Phe Leu
  1               5                  10                  15

Ile Phe Phe Pro Leu Ala Thr Met Thr Val His Val Leu Ile Asn Ile
             20                  25                  30

Gly Arg Ser Arg Tyr Lys Xaa
         35
```

<210> SEQ ID NO 260
<211> LENGTH: 51
<212> TYPE: PRT
<213> ORGANISM: Homo sapiens
<220> FEATURE:
<221> NAME/KEY: SITE
<222> LOCATION: (51)
<223> OTHER INFORMATION: Xaa equals stop translation

<400> SEQUENCE: 260

```
Met Ser Ile Thr Ser Asn Thr Tyr Phe Phe Leu Leu Gly Ala Phe Lys
  1               5                  10                  15

Ile Leu Ser Ser Ser Tyr Trp Lys Ile His Thr Lys Leu Leu Leu Thr
             20                  25                  30

Ile Val Pro Leu Gln Cys Cys Gly Met Pro Gln Leu Ile Pro Pro Leu
```

-continued 35 40 45

Gln Leu Xaa
50

<210> SEQ ID NO 261
<211> LENGTH: 76
<212> TYPE: PRT
<213> ORGANISM: Homo sapiens
<220> FEATURE:
<221> NAME/KEY: SITE
<222> LOCATION: (76)
<223> OTHER INFORMATION: Xaa equals stop translation

<400> SEQUENCE: 261

Met Phe Thr Thr Arg Phe Pro Lys Leu Leu Ile Phe Pro Lys Ile Val
1 5 10 15

Thr Glu Asn Cys Cys Leu Leu Phe Cys Ser Phe Trp Gly Trp Trp Cys
20 25 30

Trp Leu Gly His Ala Cys Glu Val Met Cys Val Ser Asp Leu Thr Asp
35 40 45

Ser Leu Phe Ser Leu Leu Ile Glu Arg Ala Leu Phe Thr Leu Phe Ile
50 55 60

Cys Phe Asp Thr Ser Ala Phe Ser Val Leu Ser Xaa
65 70 75

<210> SEQ ID NO 262
<211> LENGTH: 45
<212> TYPE: PRT
<213> ORGANISM: Homo sapiens
<220> FEATURE:
<221> NAME/KEY: SITE
<222> LOCATION: (45)
<223> OTHER INFORMATION: Xaa equals stop translation

<400> SEQUENCE: 262

Met Thr Ser His Pro Ser Trp Arg Leu Ile Leu Val Thr Ser Leu Val
1 5 10 15

Leu Gly Val Glu Pro Glu Glu Ala Pro Gly Glu Ala Gly Glu Gly Ser
20 25 30

Gly Gly Gln Arg Thr Met Asp Pro Glu Gln Lys Trp Xaa
35 40 45

<210> SEQ ID NO 263
<211> LENGTH: 53
<212> TYPE: PRT
<213> ORGANISM: Homo sapiens
<220> FEATURE:
<221> NAME/KEY: SITE
<222> LOCATION: (53)
<223> OTHER INFORMATION: Xaa equals stop translation

<400> SEQUENCE: 263

Met Pro Ser Leu Asn Leu Val Leu Arg Pro Leu Ile Cys Leu Ala Ser
1 5 10 15

Ile Thr Ser Phe Leu Ile Phe Phe Pro Leu Leu Thr Leu Ile Leu Cys
20 25 30

Ser Pro Asn Ser Pro Pro Phe Pro Leu Pro Ala His Pro Glu Arg His
35 40 45

Thr His Thr Gln Xaa
50

<210> SEQ ID NO 264

-continued

<211> LENGTH: 43
<212> TYPE: PRT
<213> ORGANISM: Homo sapiens
<220> FEATURE:
<221> NAME/KEY: SITE
<222> LOCATION: (43)
<223> OTHER INFORMATION: Xaa equals stop translation

<400> SEQUENCE: 264

```
Met His Ala Leu Ser Tyr Thr His Leu Ser Leu Leu Ser Leu Phe Leu
  1               5                  10                  15

Phe Leu Pro Pro Ser Phe Leu Tyr Tyr Asn Leu Val Ile Leu Phe Phe
             20                  25                  30

Glu Ala Phe Gln Asn Ile Ser His Leu Ser Xaa
         35                  40
```

<210> SEQ ID NO 265
<211> LENGTH: 74
<212> TYPE: PRT
<213> ORGANISM: Homo sapiens

<400> SEQUENCE: 265

```
Met Gly His Leu Phe Val Val Cys Leu Leu Ser Ser Trp Trp Thr Phe
  1               5                  10                  15

Arg Pro Phe Ala Leu Ala Val Thr Val Asn His Val Ala Val Asn Ile
             20                  25                  30

Val Cys Val Ser Ala Trp Thr Cys Val Ser Cys Ser Leu Gly Arg Ser
         35                  40                  45

Cys Gly Leu Glu Gly Ser Phe Leu Phe Pro Leu Glu Thr Leu Trp Phe
     50                  55                  60

Pro His Met Val Val Leu Cys Leu Thr Phe
 65                  70
```

<210> SEQ ID NO 266
<211> LENGTH: 52
<212> TYPE: PRT
<213> ORGANISM: Homo sapiens
<220> FEATURE:
<221> NAME/KEY: SITE
<222> LOCATION: (52)
<223> OTHER INFORMATION: Xaa equals stop translation

<400> SEQUENCE: 266

```
Met Arg Lys Ser Gly Ala Met Lys Lys Gly Gly Ile Phe Ser Ala Glu
  1               5                  10                  15

Phe Leu Lys Val Phe Ile Pro Ser Leu Phe Leu Ser His Val Leu Ala
             20                  25                  30

Leu Gly Leu Gly Ile Tyr Ile Gly Lys Arg Leu Ser Thr Pro Ser Ala
         35                  40                  45

Ser Thr Tyr Xaa
     50
```

<210> SEQ ID NO 267
<211> LENGTH: 41
<212> TYPE: PRT
<213> ORGANISM: Homo sapiens
<220> FEATURE:
<221> NAME/KEY: SITE
<222> LOCATION: (41)
<223> OTHER INFORMATION: Xaa equals stop translation

<400> SEQUENCE: 267

```
Met Trp Val Gln Leu Ile Phe Phe Phe Val Gln Tyr Gly Asp Ser Leu
```

-continued

```
  1               5                  10                  15

Thr Ser Ala Phe Phe Pro Phe Ser Ser Asn Phe Ser Leu Gln Asn Ser
            20                  25                  30

Gly Phe Ser Met His Lys Leu Lys Xaa
        35                  40
```

<210> SEQ ID NO 268
<211> LENGTH: 79
<212> TYPE: PRT
<213> ORGANISM: Homo sapiens
<220> FEATURE:
<221> NAME/KEY: SITE
<222> LOCATION: (79)
<223> OTHER INFORMATION: Xaa equals stop translation

<400> SEQUENCE: 268

```
Met Val Cys Phe Gln Ser Asn Lys Pro Ser Thr Ser Thr Trp Arg Gln
  1               5                  10                  15

Leu Ser Phe Val Phe Val Leu Phe Cys Leu Phe Cys Leu Gly His Ala
            20                  25                  30

Phe Leu Ser Leu Pro Phe Tyr Ile Leu Ser Ile Ile Ala Met Cys Leu
        35                  40                  45

Glu Gln Trp Ala Phe His Asn Met Asn Ser Leu Tyr His His Glu Trp
     50                  55                  60

Glu Val Arg Gly Asn Leu Ile His Val Asp Phe Thr Leu Pro Xaa
 65                  70                  75
```

<210> SEQ ID NO 269
<211> LENGTH: 117
<212> TYPE: PRT
<213> ORGANISM: Homo sapiens
<220> FEATURE:
<221> NAME/KEY: SITE
<222> LOCATION: (117)
<223> OTHER INFORMATION: Xaa equals stop translation

<400> SEQUENCE: 269

```
Met Thr His Lys Ser Leu Val Tyr Leu Trp Phe Leu Cys Ser Ser Val
  1               5                  10                  15

Ala Leu Ala Leu Gly Ala Leu Thr Val Trp His Ala Val Leu Ile Ser
            20                  25                  30

Arg Gly Glu Thr Ser Ile Glu Arg His Ile Asn Lys Lys Glu Arg Arg
        35                  40                  45

Arg Leu Gln Ala Lys Gly Arg Val Phe Arg Asn Pro Tyr Asn Tyr Gly
     50                  55                  60

Cys Leu Asp Asn Trp Lys Val Phe Leu Gly Val Asp Thr Gly Arg His
 65                  70                  75                  80

Trp Leu Thr Arg Val Leu Leu Pro Ser Ser His Leu Pro His Gly Asn
                 85                  90                  95

Gly Met Ser Trp Glu Pro Pro Pro Trp Val Thr Ala His Ser Ala Ser
            100                 105                 110

Val Met Ala Val Xaa
        115
```

<210> SEQ ID NO 270
<211> LENGTH: 62
<212> TYPE: PRT
<213> ORGANISM: Homo sapiens
<220> FEATURE:
<221> NAME/KEY: SITE
<222> LOCATION: (62)

-continued

```
<223> OTHER INFORMATION: Xaa equals stop translation

<400> SEQUENCE: 270

Met Ser Asn Leu Gln Phe His Leu Leu Pro His Ser Ser Pro Ile Leu
  1               5                  10                  15

Pro Leu Phe Thr Leu Ala Leu Leu Lys Met Gln Ile Pro Gly Leu Arg
             20                  25                  30

Leu Ser His Cys Leu Leu Thr Tyr Asn Ser Tyr Thr Arg Thr Pro Phe
         35                  40                  45

Leu Leu Pro Ser Ser Glu Ser Tyr Leu Val Phe Glu Ile Xaa
     50                  55                  60


<210> SEQ ID NO 271
<211> LENGTH: 98
<212> TYPE: PRT
<213> ORGANISM: Homo sapiens
<220> FEATURE:
<221> NAME/KEY: SITE
<222> LOCATION: (53)
<223> OTHER INFORMATION: Xaa equals any of the naturally occurring L-
      amino acids
<221> NAME/KEY: SITE
<222> LOCATION: (56)
<223> OTHER INFORMATION: Xaa equals any of the naturally occurring L-
      amino acids

<400> SEQUENCE: 271

Met Leu Pro Leu Tyr Phe Leu Gln Pro Tyr Leu Ser Leu Val Ile Phe
  1               5                  10                  15

Ile Met Leu Arg Asp Asn Trp His Leu Leu Ala Leu Thr Cys Ser Tyr
             20                  25                  30

Ser Ile Ile Trp Arg Leu Ser Pro Asp Thr Asn Pro Ser Pro Ile Ala
         35                  40                  45

Pro Ser Arg His Xaa Gln Leu Xaa Val Val Ala Ile Ala Pro Leu Glu
     50                  55                  60

Pro Ser Pro His Ser His Met Gln Ser Ile Pro Lys Asn Leu Ala Gln
 65                  70                  75                  80

Phe Ser Ser Ser Gln Met Phe Ser Leu Thr Leu Gln Leu Val Tyr Ile
                 85                  90                  95
Ser Ser


<210> SEQ ID NO 272
<211> LENGTH: 32
<212> TYPE: PRT
<213> ORGANISM: Homo sapiens
<220> FEATURE:
<221> NAME/KEY: SITE
<222> LOCATION: (32)
<223> OTHER INFORMATION: Xaa equals stop translation

<400> SEQUENCE: 272

Met Tyr Ile Leu Ser Leu Ser Cys Ser Ile Phe Phe Ser Phe Phe Phe
  1               5                  10                  15

Phe Leu Phe Pro Phe Phe Arg Gly Leu Arg Lys Gly Gln Ala Lys Xaa
             20                  25                  30


<210> SEQ ID NO 273
<211> LENGTH: 15
<212> TYPE: PRT
<213> ORGANISM: Homo sapiens
<220> FEATURE:
<221> NAME/KEY: SITE
<222> LOCATION: (15)
<223> OTHER INFORMATION: Xaa equals stop translation
```

<400> SEQUENCE: 273

Ala Ser Ser Leu Leu Val Ser Leu Gln Cys Leu Leu Gln Leu Xaa
1 5 10 15

<210> SEQ ID NO 274
<211> LENGTH: 37
<212> TYPE: PRT
<213> ORGANISM: Homo sapiens
<220> FEATURE:
<221> NAME/KEY: SITE
<222> LOCATION: (37)
<223> OTHER INFORMATION: Xaa equals stop translation

<400> SEQUENCE: 274

Met Cys Phe Ile Leu Val Val Cys Phe Ala Ser Leu Ile Thr Glu Cys
1 5 10 15

Pro Cys His Cys Lys Cys Cys Arg Asp Val Gly Arg Gly Pro Thr Val
20 25 30

Leu Tyr Glu Met Xaa
35

<210> SEQ ID NO 275
<211> LENGTH: 57
<212> TYPE: PRT
<213> ORGANISM: Homo sapiens
<220> FEATURE:
<221> NAME/KEY: SITE
<222> LOCATION: (53)
<223> OTHER INFORMATION: Xaa equals any of the naturally occurring L-amino acids
<221> NAME/KEY: SITE
<222> LOCATION: (57)
<223> OTHER INFORMATION: Xaa equals stop translation

<400> SEQUENCE: 275

Met His Arg Leu Trp Ile Gly Pro Ala Phe Phe Leu Met Thr Ser Leu
1 5 10 15

Ser Val Ser Gly Ala Val Ile Pro Arg Asn Gly Gly Pro Gly Gly Val
20 25 30

Ser Ser Gly Pro Cys Leu Leu Gln Leu Leu Cys Gly Gln Ala Gly Ser
35 40 45

Ser Thr Ile Arg Xaa Ile Pro Ser Xaa
50 55

<210> SEQ ID NO 276
<211> LENGTH: 27
<212> TYPE: PRT
<213> ORGANISM: Homo sapiens
<220> FEATURE:
<221> NAME/KEY: SITE
<222> LOCATION: (27)
<223> OTHER INFORMATION: Xaa equals stop translation

<400> SEQUENCE: 276

Met Glu Ala Val Phe Phe Leu Phe Phe Leu Leu Leu Leu Leu Thr Trp
1 5 10 15

Thr Ser Lys Ile Ala Pro Ile Leu Phe Ser Xaa
20 25

<210> SEQ ID NO 277
<211> LENGTH: 68
<212> TYPE: PRT
<213> ORGANISM: Homo sapiens
<220> FEATURE:

-continued

<221> NAME/KEY: SITE
<222> LOCATION: (68)
<223> OTHER INFORMATION: Xaa equals stop translation

<400> SEQUENCE: 277

Asp Trp Gly Phe Gln Thr Thr Phe Phe Ser Leu Gly Leu Tyr Leu Phe
1 5 10 15

Thr Ile Trp Trp Ser Thr Val Gly Leu Pro Trp Thr Ser Ser Thr Gln
20 25 30

Arg Glu Leu Asp Met Lys Leu Glu Ala Ala Ala Leu Glu Gly Lys Phe
35 40 45

Arg Leu Thr Trp Thr Ala Gln Ala Met Ala Gly Arg Ile Pro Ser Ser
50 55 60

Trp Gly Pro Xaa
65

<210> SEQ ID NO 278
<211> LENGTH: 46
<212> TYPE: PRT
<213> ORGANISM: Homo sapiens
<220> FEATURE:
<221> NAME/KEY: SITE
<222> LOCATION: (46)
<223> OTHER INFORMATION: Xaa equals stop translation

<400> SEQUENCE: 278

Met Pro Arg Arg Ser Arg Pro Cys Thr Leu Cys Leu Thr Leu Leu Arg
1 5 10 15

Arg Ala Leu Ser Ser His Leu Pro Ser Ala Cys Gln Ser Pro Arg Arg
20 25 30

Arg Val Gln Gly Gln Val Leu Lys Arg Leu Lys Pro Leu Xaa
35 40 45

<210> SEQ ID NO 279
<211> LENGTH: 40
<212> TYPE: PRT
<213> ORGANISM: Homo sapiens
<220> FEATURE:
<221> NAME/KEY: SITE
<222> LOCATION: (40)
<223> OTHER INFORMATION: Xaa equals stop translation

<400> SEQUENCE: 279

Met Pro Leu Thr Leu Pro Ser Arg Leu Ala Gly Gly Asn Val Phe Leu
1 5 10 15

Ile Ile Phe Thr Pro Gly Phe Cys Pro Gly Arg Val Asn Val Glu Ile
20 25 30

Pro Gln Arg Met Leu Asp Glu Xaa
35 40

<210> SEQ ID NO 280
<211> LENGTH: 11
<212> TYPE: PRT
<213> ORGANISM: Homo sapiens
<220> FEATURE:
<221> NAME/KEY: SITE
<222> LOCATION: (11)
<223> OTHER INFORMATION: Xaa equals stop translation

<400> SEQUENCE: 280

Met Ser Arg Arg Glu Asn Lys Phe Leu Leu Xaa
1 5 10

-continued

<210> SEQ ID NO 281
<211> LENGTH: 11
<212> TYPE: PRT
<213> ORGANISM: Homo sapiens
<220> FEATURE:
<221> NAME/KEY: SITE
<222> LOCATION: (11)
<223> OTHER INFORMATION: Xaa equals stop translation

<400> SEQUENCE: 281

```
Met Ser Arg Arg Glu Asn Lys Phe Leu Leu Xaa
  1               5                  10
```

<210> SEQ ID NO 282
<211> LENGTH: 47
<212> TYPE: PRT
<213> ORGANISM: Homo sapiens

<400> SEQUENCE: 282

```
Met Leu Pro Ile His Leu Gln Trp Ala Cys Ala Phe Arg Ser Phe Leu
  1               5                  10                  15

Leu Gly Ile Asp Ser Ser Met Phe Val Leu Phe Gln His Pro Arg Leu
             20                  25                  30

Lys Asp Thr Lys Ser Ser Arg Val Ile Glu Pro Thr Leu Thr Asn
         35                  40                  45
```

<210> SEQ ID NO 283
<211> LENGTH: 23
<212> TYPE: PRT
<213> ORGANISM: Homo sapiens
<220> FEATURE:
<221> NAME/KEY: SITE
<222> LOCATION: (23)
<223> OTHER INFORMATION: Xaa equals stop translation

<400> SEQUENCE: 283

```
Met Ile Leu Leu Ala Phe Phe Ile Leu Leu Tyr Leu Thr Ser Phe Ser
  1               5                  10                  15

Leu Ala Arg Ser Leu Pro Xaa
             20
```

<210> SEQ ID NO 284
<211> LENGTH: 21
<212> TYPE: PRT
<213> ORGANISM: Homo sapiens
<220> FEATURE:
<221> NAME/KEY: SITE
<222> LOCATION: (21)
<223> OTHER INFORMATION: Xaa equals stop translation

<400> SEQUENCE: 284

```
Ser Ser Ser Cys Met Pro Arg Lys Leu Asp Trp Phe Ser Lys Lys Val
  1               5                  10                  15

Phe Leu Phe Phe Xaa
             20
```

<210> SEQ ID NO 285
<211> LENGTH: 122
<212> TYPE: PRT
<213> ORGANISM: Homo sapiens

<400> SEQUENCE: 285

```
Met Gln Ala Leu Pro Pro Gly Phe Lys Gln Phe Ser Cys Leu Ser Leu
  1               5                  10                  15

Pro Ser Arg Trp Asp Tyr Gly Cys Ala Thr Gln His Pro Ala Asn Phe
```

-continued

```
            20                  25                  30

Cys Ile Phe Arg Arg Asp Arg Val Ser His Val Gly Gln Ala Gly Leu
        35                  40                  45

Lys Leu Leu Thr Ser Val Asp Pro Pro Ala Trp Ala Ser Gln Ser Ala
    50                  55                  60

Gly Ile Thr Gly Lys Ser His Cys Ala Gln Leu His Cys Cys Cys Phe
65                  70                  75                  80

Leu Leu Leu Val Lys Arg Asp Gln Pro Leu Glu Lys Cys Leu Arg Leu
                85                  90                  95

Phe Lys Gly Arg Ile Leu Cys Arg Gln Pro His Tyr Arg Leu Leu Ser
            100                 105                 110

Asp Glu Cys Pro Gly Leu Leu Gln Asn Pro
        115                 120


<210> SEQ ID NO 286
<211> LENGTH: 27
<212> TYPE: PRT
<213> ORGANISM: Homo sapiens
<220> FEATURE:
<221> NAME/KEY: SITE
<222> LOCATION: (27)
<223> OTHER INFORMATION: Xaa equals stop translation

<400> SEQUENCE: 286

Met Ile His Leu Ser Arg Phe Tyr Leu Leu Leu Ile Met Leu Pro His
  1               5                  10                  15

Val Leu Phe Phe Thr Gly Asp Leu His Ser Xaa
            20                  25


<210> SEQ ID NO 287
<211> LENGTH: 8
<212> TYPE: PRT
<213> ORGANISM: Homo sapiens
<220> FEATURE:
<221> NAME/KEY: SITE
<222> LOCATION: (8)
<223> OTHER INFORMATION: Xaa equals stop translation

<400> SEQUENCE: 287

Met Tyr Lys Cys Trp Tyr Arg Xaa
  1               5


<210> SEQ ID NO 288
<211> LENGTH: 29
<212> TYPE: PRT
<213> ORGANISM: Homo sapiens
<220> FEATURE:
<221> NAME/KEY: SITE
<222> LOCATION: (2)
<223> OTHER INFORMATION: Xaa equals any of the naturally occurring L-
      amino acids
<221> NAME/KEY: SITE
<222> LOCATION: (29)
<223> OTHER INFORMATION: Xaa equals stop translation

<400> SEQUENCE: 288

Met Xaa Leu Asn Lys Thr Lys Ser Leu Thr Leu Leu Glu Leu Val Phe
  1               5                  10                  15

Leu Pro Gly Glu Thr Val Ser Lys Pro Ser Thr Lys Xaa
            20                  25


<210> SEQ ID NO 289
<211> LENGTH: 65
<212> TYPE: PRT
```

-continued

<213> ORGANISM: Homo sapiens

<400> SEQUENCE: 289

```
Val Asp Pro Arg Val Arg Arg Phe Trp Glu Asp Pro Glu Tyr Pro Pro
  1               5                  10                  15

Val Ala Val Met Ser Arg Leu Met Leu Arg Arg Ile Pro Thr Val Met
             20                  25                  30

Ser Asn Thr His Arg Thr Gln Pro Ser Thr Trp Glu Gln Ile Lys Lys
         35                  40                  45

Leu Ser Gln Met Val Gly Glu Asn Leu Arg Lys Ala Gly Gln Pro Val
     50                  55                  60

Thr
 65
```

<210> SEQ ID NO 290
<211> LENGTH: 25
<212> TYPE: PRT
<213> ORGANISM: Homo sapiens

<400> SEQUENCE: 290

```
Val Arg Arg Phe Trp Glu Asp Pro Glu Tyr Pro Pro Val Ala Val Met
  1               5                  10                  15

Ser Arg Leu Met Leu Arg Arg Ile Pro
             20                  25
```

<210> SEQ ID NO 291
<211> LENGTH: 27
<212> TYPE: PRT
<213> ORGANISM: Homo sapiens

<400> SEQUENCE: 291

```
Ser Asn Thr His Arg Thr Gln Pro Ser Thr Trp Glu Gln Ile Lys Lys
  1               5                  10                  15

Leu Ser Gln Met Val Gly Glu Asn Leu Arg Lys
             20                  25
```

<210> SEQ ID NO 292
<211> LENGTH: 116
<212> TYPE: PRT
<213> ORGANISM: Homo sapiens

<400> SEQUENCE: 292

```
Ser Ala Cys His Ser His Thr Val Phe Asn Trp Ser Glu Gln Asn Gly
  1               5                  10                  15

Gln Met Val Gln Met Val Arg Arg Met Ala Arg Val Pro Ile Ile Trp
             20                  25                  30

Asn His Gly Ser Ile Gly Ala Pro Gln Pro Gln Met Ile Trp Pro Ile
         35                  40                  45

Val Gly Ala Lys His Lys Asp Leu Trp Gln Leu Leu Ile Ala Leu Asn
     50                  55                  60

Lys Ile Lys Ile Trp Glu Arg Ile Lys Lys His Leu Glu Gly His Ser
 65                  70                  75                  80

Ala Asn Leu Ser Leu Asp Ile Ala Lys Tyr Ile Tyr Ile Phe Lys Ala
                 85                  90                  95

Ser Gln Ala His Leu Thr Leu Met Pro Glu Leu Glu Cys Ser Lys Glu
            100                 105                 110

Leu Gln Thr Asp
        115
```

-continued

<210> SEQ ID NO 293
<211> LENGTH: 25
<212> TYPE: PRT
<213> ORGANISM: Homo sapiens

<400> SEQUENCE: 293

Met Ala Arg Val Pro Ile Ile Trp Asn His Gly Ser Ile Gly Ala Pro
1 5 10 15

Gln Pro Gln Met Ile Trp Pro Ile Val
20 25

<210> SEQ ID NO 294
<211> LENGTH: 32
<212> TYPE: PRT
<213> ORGANISM: Homo sapiens

<400> SEQUENCE: 294

Arg Ile Lys Lys His Leu Glu Gly His Ser Ala Asn Leu Ser Leu Asp
1 5 10 15

Ile Ala Lys Tyr Ile Tyr Ile Phe Lys Ala Ser Gln Ala His Leu Thr
20 25 30

<210> SEQ ID NO 295
<211> LENGTH: 66
<212> TYPE: PRT
<213> ORGANISM: Homo sapiens

<400> SEQUENCE: 295

Val Phe Leu Gln Gln Gly Leu Thr Gln Arg Ser Val Ile Leu Ile Gly
1 5 10 15

His Ile Cys Gln Phe Trp Leu Ala Ile Met Pro Gly Tyr Asn His Phe
20 25 30

Met Thr Gln Leu His Met Leu Ser Gly Leu Asn Ile Tyr His Asn Lys
35 40 45

Ser Ala Pro Ile Ile Glu Ala Tyr His Pro Gln Lys Ser Ile Cys Lys
50 55 60

Gln Asn
65

<210> SEQ ID NO 296
<211> LENGTH: 28
<212> TYPE: PRT
<213> ORGANISM: Homo sapiens

<400> SEQUENCE: 296

Ile Gly His Ile Cys Gln Phe Trp Leu Ala Ile Met Pro Gly Tyr Asn
1 5 10 15

His Phe Met Thr Gln Leu His Met Leu Ser Gly Leu
20 25

<210> SEQ ID NO 297
<211> LENGTH: 58
<212> TYPE: PRT
<213> ORGANISM: Homo sapiens

<400> SEQUENCE: 297

Ser Ile Pro Gly Thr Pro Asp Leu Asn Ala Arg Thr Gly Val Leu Glu
1 5 10 15

Gly Ala Ala Asp Arg Leu Ala Ala Ser Asn Pro Leu Lys Trp Ile Lys
20 25 30

-continued

```
Thr Leu Arg Ser Ser Val Ile Ser Met Met Ile Val Leu Leu Ile Cys
         35                  40                  45

Val Val Cys Leu Tyr Ile Val Cys Arg Cys
     50                  55


<210> SEQ ID NO 298
<211> LENGTH: 27
<212> TYPE: PRT
<213> ORGANISM: Homo sapiens

<400> SEQUENCE: 298

Val Leu Glu Gly Ala Ala Asp Arg Leu Ala Ala Ser Asn Pro Leu Lys
  1               5                  10                  15

Trp Ile Lys Thr Leu Arg Ser Ser Val Ile Ser
             20                  25


<210> SEQ ID NO 299
<211> LENGTH: 75
<212> TYPE: PRT
<213> ORGANISM: Homo sapiens

<400> SEQUENCE: 299

Leu Thr Val Thr Lys Leu Pro Trp Leu Phe Ile Ala Leu Gln Asn Lys
  1               5                  10                  15

Arg Met Gly Thr Ser Trp Glu Gln Ala Pro Lys Ser Gly His Lys Leu
             20                  25                  30

Ala Pro Lys Leu Val Ile Asn Lys Ile Ser Ala Ala Leu Ser His Ala
         35                  40                  45

Cys Asp Ser Leu Thr Pro Thr Leu Glu Gly Cys Arg Phe Thr Gly Met
     50                  55                  60

Arg Ala Arg Asn Asn Trp Pro Thr Gln Gly Gly
 65                  70                  75


<210> SEQ ID NO 300
<211> LENGTH: 29
<212> TYPE: PRT
<213> ORGANISM: Homo sapiens

<400> SEQUENCE: 300

Met Gly Thr Ser Trp Glu Gln Ala Pro Lys Ser Gly His Lys Leu Ala
  1               5                  10                  15

Pro Lys Leu Val Ile Asn Lys Ile Ser Ala Ala Leu Ser
             20                  25


<210> SEQ ID NO 301
<211> LENGTH: 52
<212> TYPE: PRT
<213> ORGANISM: Homo sapiens

<400> SEQUENCE: 301

Ser Thr His Ala Ser Val Gln Lys Lys Asp Leu Thr Lys Phe Ser Ala
  1               5                  10                  15

His Ser Trp Leu Lys Lys Lys Lys Thr Phe Arg Lys Met Ile Met Glu
             20                  25                  30

Glu Ile Phe Leu Asn Leu Ile Lys Asn Ile Tyr Lys Ser Pro Tyr Ser
         35                  40                  45

Gln Cys Asn Thr
     50


<210> SEQ ID NO 302
```

-continued

<211> LENGTH: 17
<212> TYPE: PRT
<213> ORGANISM: Homo sapiens

<400> SEQUENCE: 302

Val Arg Ser Glu Lys Gly Phe Asp Lys Ile Gln Cys Pro Phe Met Val
1 5 10 15

Lys

<210> SEQ ID NO 303
<211> LENGTH: 46
<212> TYPE: PRT
<213> ORGANISM: Homo sapiens

<400> SEQUENCE: 303

Phe Ser Lys Pro Ser Ser Tyr Lys Thr Tyr Ile Pro Lys Ile Asn Leu
1 5 10 15

His Phe Tyr Ile Leu Leu Met Asn Ile Trp Glu Thr Ile Lys Ile Val
20 25 30

Pro Leu Asn Asn Cys Phe Thr Lys Met Asn Tyr Leu Gly Ile
35 40 45

<210> SEQ ID NO 304
<211> LENGTH: 14
<212> TYPE: PRT
<213> ORGANISM: Homo sapiens

<400> SEQUENCE: 304

Lys Lys Glu Thr Lys Leu Ser Leu Phe Ala Asn Asp Met Ile
1 5 10

<210> SEQ ID NO 305
<211> LENGTH: 23
<212> TYPE: PRT
<213> ORGANISM: Homo sapiens

<400> SEQUENCE: 305

Ser Pro Leu Leu Phe Asn Ile Leu Leu Glu Val Leu Ser Ser Ala Val
1 5 10 15

Arg Lys Glu Lys Glu Leu Lys
20

<210> SEQ ID NO 306
<211> LENGTH: 122
<212> TYPE: PRT
<213> ORGANISM: Homo sapiens

<400> SEQUENCE: 306

Leu Arg Arg Pro Ser Thr Pro Leu Arg Arg Pro Trp Leu His Leu Gln
1 5 10 15

Leu Pro Arg Ile Ser Leu Gly Asp Gln Arg Leu Ala Gln Ser Ala Glu
20 25 30

Met Tyr His Tyr Gln His Gln Arg Gln Gln Met Leu Ser Leu Glu Arg
35 40 45

His Lys Glu Pro Pro Lys Glu Leu Asp Thr Ala Leu Arg Met Arg Arg
50 55 60

Met Arg Thr Glu Thr Ser Arg Cys Thr Ser Ala Arg Ala Trp Pro Arg
65 70 75 80

Pro Gly Lys Trp Arg Cys Ala Thr Ile Cys Ser Thr Thr Pro His Cys
85 90 95

-continued

```
Pro Arg Pro Cys Arg Pro Pro Ala His Arg Leu His Cys His Asp Leu
            100                 105                 110

Glu Ala Asp Arg Arg Pro Leu Ala Pro Arg
        115                 120


<210> SEQ ID NO 307
<211> LENGTH: 60
<212> TYPE: PRT
<213> ORGANISM: Homo sapiens

<400> SEQUENCE: 307

Arg Ala Thr Gln Gly Ala Gly His Gly Ser Ser Asp Glu Glu Asn Glu
  1               5                  10                  15

Asp Gly Asp Phe Thr Val Tyr Glu Cys Pro Gly Met Ala Pro Thr Gly
             20                  25                  30

Glu Met Glu Val Arg Asn His Leu Phe Asp His Ala Ala Leu Ser Ala
         35                  40                  45

Pro Leu Pro Ala Pro Ser Ser Pro Leu Ala Leu Pro
     50                  55                  60


<210> SEQ ID NO 308
<211> LENGTH: 47
<212> TYPE: PRT
<213> ORGANISM: Homo sapiens

<400> SEQUENCE: 308

Lys Ala Glu Tyr Ala Thr Ala Lys Ala Leu Ala Thr Pro Ala Ala Thr
  1               5                  10                  15

Pro Asp Leu Ala Trp Gly Pro Ala Pro Gly Thr Glu Arg Gly Asp Val
             20                  25                  30

Pro Leu Pro Ala Pro Thr Ala Thr Asp Val Val Pro Gly Ala Ala
         35                  40                  45


<210> SEQ ID NO 309
<211> LENGTH: 15
<212> TYPE: PRT
<213> ORGANISM: Homo sapiens

<400> SEQUENCE: 309

Ser Ala Glu Met Tyr His Tyr Gln His Gln Arg Gln Gln Met Leu
  1               5                  10                  15


<210> SEQ ID NO 310
<211> LENGTH: 11
<212> TYPE: PRT
<213> ORGANISM: Homo sapiens

<400> SEQUENCE: 310

Leu Glu Arg His Lys Glu Pro Pro Lys Glu Leu
  1               5                  10


<210> SEQ ID NO 311
<211> LENGTH: 12
<212> TYPE: PRT
<213> ORGANISM: Homo sapiens

<400> SEQUENCE: 311

Ala Lys Cys Pro Pro Gly Ala His Ala Cys Gly Pro
  1               5                  10


<210> SEQ ID NO 312
<211> LENGTH: 9
```

-continued

<212> TYPE: PRT
<213> ORGANISM: Homo sapiens

<400> SEQUENCE: 312

Pro Val His Met Ser Pro Leu Glu Pro
1 5

<210> SEQ ID NO 313
<211> LENGTH: 12
<212> TYPE: PRT
<213> ORGANISM: Homo sapiens

<400> SEQUENCE: 313

Trp Cys Arg Leu Gln Arg Glu Ile Arg Leu Thr Gln
1 5 10

<210> SEQ ID NO 314
<211> LENGTH: 18
<212> TYPE: PRT
<213> ORGANISM: Homo sapiens

<400> SEQUENCE: 314

Ser Ser Asp Glu Glu Asn Glu Asp Gly Asp Phe Thr Val Tyr Glu Cys
1 5 10 15

Pro Gly

<210> SEQ ID NO 315
<211> LENGTH: 10
<212> TYPE: PRT
<213> ORGANISM: Homo sapiens

<400> SEQUENCE: 315

Ala Pro Thr Gly Glu Met Glu Val Arg Asn
1 5 10

<210> SEQ ID NO 316
<211> LENGTH: 10
<212> TYPE: PRT
<213> ORGANISM: Homo sapiens

<400> SEQUENCE: 316

Cys Pro Gly Ser Leu Asp Cys Ala Leu Lys
1 5 10

<210> SEQ ID NO 317
<211> LENGTH: 60
<212> TYPE: PRT
<213> ORGANISM: Homo sapiens

<400> SEQUENCE: 317

Arg Ala Thr Gln Gly Ala Gly His Gly Ser Ser Asp Glu Glu Asn Glu
1 5 10 15

Asp Gly Asp Phe Thr Val Tyr Glu Cys Pro Gly Met Ala Pro Thr Gly
20 25 30

Glu Met Glu Val Arg Asn His Leu Phe Asp His Ala Ala Leu Ser Ala
35 40 45

Pro Leu Pro Ala Pro Ser Ser Pro Leu Ala Leu Pro
50 55 60

<210> SEQ ID NO 318
<211> LENGTH: 22
<212> TYPE: PRT
<213> ORGANISM: Homo sapiens -continued

<400> SEQUENCE: 318

```
Asn Glu Asp Gly Asp Phe Thr Val Tyr Glu Cys Pro Gly Met Ala Pro
  1               5                  10                  15

Thr Gly Glu Met Glu Val
             20
```

<210> SEQ ID NO 319
<211> LENGTH: 159
<212> TYPE: PRT
<213> ORGANISM: Homo sapiens
<220> FEATURE:
<221> NAME/KEY: SITE
<222> LOCATION: (114)
<223> OTHER INFORMATION: Xaa equals any of the naturally occurring L-amino acids
<221> NAME/KEY: SITE
<222> LOCATION: (123)
<223> OTHER INFORMATION: Xaa equals any of the naturally occurring L-amino acids
<221> NAME/KEY: SITE
<222> LOCATION: (129)
<223> OTHER INFORMATION: Xaa equals any of the naturally occurring L-amino acids
<221> NAME/KEY: SITE
<222> LOCATION: (136)
<223> OTHER INFORMATION: Xaa equals any of the naturally occurring L-amino acids

<400> SEQUENCE: 319

```
Arg Pro Thr Arg Pro Ser Ser Ser Cys Val Leu Pro Arg Cys Leu Arg
  1               5                  10                  15

Cys Ser Arg Arg Gly Ala Arg Ser Pro Arg Arg Ala Pro Gly Leu Ala
             20                  25                  30

Val Pro Cys Cys Pro Gly Gly Gly Ala Glu Gly Trp Arg Arg Arg Cys
         35                  40                  45

Leu Arg Pro Pro Arg Gly Thr Cys Gly Cys Cys Gly Cys Cys Ser Pro
     50                  55                  60

Ala Ser Ser Ser Ala Pro Pro Cys Val Glu Pro Pro Pro Ala Thr Arg
 65                  70                  75                  80

Asn Val Ala Ala Cys Pro Gly Ser Leu Asp Cys Ala Leu Lys Lys Arg
                 85                  90                  95

Ala Ser Val Leu Leu Val His Met Pro Val Gly Leu Pro Ser Ala Leu
            100                 105                 110

Pro Xaa Gly Thr Ala Lys Ala Cys Phe Ala Xaa Met Arg Arg Ala Ser
        115                 120                 125

Xaa Gly Gly Arg Ala Gln Pro Xaa Leu Glu Met Arg Leu Ile Pro Gly
    130                 135                 140

Pro Arg Glu Leu Ala Arg Lys Gly Ile Trp Thr Ser Ile Pro Pro
145                 150                 155
```

<210> SEQ ID NO 320
<211> LENGTH: 25
<212> TYPE: PRT
<213> ORGANISM: Homo sapiens

<400> SEQUENCE: 320

```
Arg Cys Leu Arg Cys Ser Arg Arg Gly Ala Arg Ser Pro Arg Arg Ala
  1               5                  10                  15

Pro Gly Leu Ala Val Pro Cys Cys Pro
             20                  25
```

<210> SEQ ID NO 321
<211> LENGTH: 34
<212> TYPE: PRT
<213> ORGANISM: Homo sapiens
<220> FEATURE:
<221> NAME/KEY: SITE
<222> LOCATION: (28)
<223> OTHER INFORMATION: Xaa equals any of the naturally occurring L-
amino acids

<400> SEQUENCE: 321

Gly Ser Leu Asp Cys Ala Leu Lys Lys Arg Ala Ser Val Leu Leu Val
1 5 10 15

His Met Pro Val Gly Leu Pro Ser Ala Leu Pro Xaa Gly Thr Ala Lys
20 25 30

Ala Cys

<210> SEQ ID NO 322
<211> LENGTH: 25
<212> TYPE: PRT
<213> ORGANISM: Homo sapiens

<400> SEQUENCE: 322

Asp Ser His Gln Ala Arg Ser Arg Arg Leu Glu Ala Leu Trp Ser Pro
1 5 10 15

Ser Leu Gly Glu Val Ser Ser Ser Thr
20 25

<210> SEQ ID NO 323
<211> LENGTH: 8
<212> TYPE: PRT
<213> ORGANISM: Homo sapiens

<400> SEQUENCE: 323

Arg Ser Cys Lys Glu Ile Lys Asp
1 5

<210> SEQ ID NO 324
<211> LENGTH: 13
<212> TYPE: PRT
<213> ORGANISM: Homo sapiens

<400> SEQUENCE: 324

Gly Gly Gly Trp Thr Leu Val Ala Ser Val His Glu Asn
1 5 10

<210> SEQ ID NO 325
<211> LENGTH: 19
<212> TYPE: PRT
<213> ORGANISM: Homo sapiens

<400> SEQUENCE: 325

Ala Asp Tyr Pro Glu Gly Asp Gly Asn Trp Ala Asn Tyr Asn Thr Phe
1 5 10 15

Gly Ser Ala

<210> SEQ ID NO 326
<211> LENGTH: 14
<212> TYPE: PRT
<213> ORGANISM: Homo sapiens

<400> SEQUENCE: 326

Ala Thr Ser Asp Asp Tyr Lys Asn Pro Gly Tyr Tyr Asp Ile

-continued 1 5 10

<210> SEQ ID NO 327
<211> LENGTH: 11
<212> TYPE: PRT
<213> ORGANISM: Homo sapiens

<400> SEQUENCE: 327

Cys Ile Gly Gly Gly Gly Tyr Phe Pro Glu Ala
1 5 10

<210> SEQ ID NO 328
<211> LENGTH: 11
<212> TYPE: PRT
<213> ORGANISM: Homo sapiens

<400> SEQUENCE: 328

Glu Ile Thr Glu Ala Ala Val Leu Leu Phe Tyr
1 5 10

<210> SEQ ID NO 329
<211> LENGTH: 6
<212> TYPE: PRT
<213> ORGANISM: Homo sapiens

<400> SEQUENCE: 329

Asp Ser Asp Lys Ile Thr
1 5

<210> SEQ ID NO 330
<211> LENGTH: 8
<212> TYPE: PRT
<213> ORGANISM: Homo sapiens

<400> SEQUENCE: 330

Tyr Gln Thr Phe Cys Asp Met Thr
1 5

<210> SEQ ID NO 331
<211> LENGTH: 154
<212> TYPE: PRT
<213> ORGANISM: Homo sapiens

<400> SEQUENCE: 331

Met Gly Lys Arg Ala His Glu Val Arg Arg Pro Pro His Ser Arg Pro
1 5 10 15

Leu His Gly Thr Pro Ala Gly Trp Val Leu Asp Pro Ser Gly Tyr Lys
20 25 30

Asp Val Thr Gln Asp Ala Glu Val Met Glu Val Leu Gln Asn Leu Tyr
35 40 45

Arg Thr Lys Ser Phe Leu Phe Val Gly Cys Gly Glu Thr Leu Arg Asp
50 55 60

Gln Ile Phe Gln Ala Leu Phe Leu Tyr Ser Val Pro Asn Lys Val Asp
65 70 75 80

Leu Glu His Tyr Met Leu Val Leu Lys Glu Asn Glu Asp His Phe Phe
85 90 95

Lys His Gln Ala Asp Met Leu Leu His Gly Ile Lys Val Val Ser Tyr
100 105 110

Gly Asp Cys Phe Asp His Phe Pro Gly Tyr Val Gln Asp Leu Ala Thr
115 120 125

Gln Ile Cys Lys Gln Gln Ser Pro Gly His Leu Tyr Ser Asn Ser Trp

-continued

```
130                 135                 140

Ser Ala Thr Pro Asp Gly Arg Gly Gly Pro
145                 150


<210> SEQ ID NO 332
<211> LENGTH: 26
<212> TYPE: PRT
<213> ORGANISM: Homo sapiens

<400> SEQUENCE: 332

Val Leu Asp Pro Ser Gly Tyr Lys Asp Val Thr Gln Asp Ala Glu Val
  1               5                  10                  15

Met Glu Val Leu Gln Asn Leu Tyr Arg Thr
             20                  25


<210> SEQ ID NO 333
<211> LENGTH: 26
<212> TYPE: PRT
<213> ORGANISM: Homo sapiens

<400> SEQUENCE: 333

Tyr Ser Val Pro Asn Lys Val Asp Leu Glu His Tyr Met Leu Val Leu
  1               5                  10                  15

Lys Glu Asn Glu Asp His Phe Phe Lys His
             20                  25


<210> SEQ ID NO 334
<211> LENGTH: 25
<212> TYPE: PRT
<213> ORGANISM: Homo sapiens

<400> SEQUENCE: 334

Asp Leu Ala Thr Gln Ile Cys Lys Gln Gln Ser Pro Gly His Leu Tyr
  1               5                  10                  15

Ser Asn Ser Trp Ser Ala Thr Pro Asp
             20                  25


<210> SEQ ID NO 335
<211> LENGTH: 121
<212> TYPE: PRT
<213> ORGANISM: Homo sapiens

<400> SEQUENCE: 335

Arg Arg Met Lys Thr Ile Ser Leu Ser Ile Arg Gln Ile Cys Phe Cys
  1               5                  10                  15

Thr Glu Ser Lys Leu Tyr Pro Thr Gly Thr Val Leu Thr Thr Phe Gln
             20                  25                  30

Asp Met Cys Lys Thr Leu Pro Leu Arg Ser Ala Asn Ser Lys Ala Gln
         35                  40                  45

Asp Ile Cys Thr Arg Ile His Gly Val Pro Leu Leu Met Gly Glu Glu
     50                  55                  60

Ala His Asp Ser Asp Ser His Ala Ser Asp Arg Gly His His Thr Met
 65                  70                  75                  80

Leu Pro Leu Pro Ala Gly Ser Phe Ser Glu Ser Ser His Gln Ala Trp
                 85                  90                  95

Glu Val Glu Met Leu Ile Ala Trp Thr Ala Pro His Tyr Trp Val Met
            100                 105                 110

His Ala Arg Thr Val Gln Arg Gly Ser
        115                 120
```

<210> SEQ ID NO 336
<211> LENGTH: 27
<212> TYPE: PRT
<213> ORGANISM: Homo sapiens

<400> SEQUENCE: 336

```
Thr Glu Ser Lys Leu Tyr Pro Thr Gly Thr Val Leu Thr Thr Phe Gln
  1               5                  10                  15

Asp Met Cys Lys Thr Leu Pro Leu Arg Ser Ala
             20                  25
```

<210> SEQ ID NO 337
<211> LENGTH: 27
<212> TYPE: PRT
<213> ORGANISM: Homo sapiens

<400> SEQUENCE: 337

```
Leu Met Gly Glu Glu Ala His Asp Ser Asp Ser His Ala Ser Asp Arg
  1               5                  10                  15

Gly His His Thr Met Leu Pro Leu Pro Ala Gly
             20                  25
```

<210> SEQ ID NO 338
<211> LENGTH: 86
<212> TYPE: PRT
<213> ORGANISM: Homo sapiens

<400> SEQUENCE: 338

```
Leu Cys Ala Val Glu Lys Thr Arg Thr Phe Thr Arg Gly Asp Cys Gly
  1               5                  10                  15

Pro Asn Arg His His Lys His Val Leu Lys Ala Lys Asp Asn Asn His
             20                  25                  30

Ile Gln Arg His Gln Phe Ser Ser Thr Leu Glu Phe Ser Ser Asn Ser
         35                  40                  45

Thr Asp Gly Leu Lys Tyr Ile Cys Val Tyr Leu Tyr Val Cys Thr His
     50                  55                  60

Pro Cys Ile Tyr Ile Tyr Leu Ser Ala His Thr Leu His Met Tyr Thr
 65                  70                  75                  80

His Tyr Leu Cys Lys Ile
                 85
```

<210> SEQ ID NO 339
<211> LENGTH: 30
<212> TYPE: PRT
<213> ORGANISM: Homo sapiens

<400> SEQUENCE: 339

```
Ser Ser Thr Leu Glu Phe Ser Ser Asn Ser Thr Asp Gly Leu Lys Tyr
  1               5                  10                  15

Ile Cys Val Tyr Leu Tyr Val Cys Thr His Pro Cys Ile Tyr
             20                  25                  30
```

<210> SEQ ID NO 340
<211> LENGTH: 69
<212> TYPE: PRT
<213> ORGANISM: Homo sapiens

<400> SEQUENCE: 340

```
Ser Thr Ser Val Cys Ile Cys Thr Cys Ala His Thr His Val Tyr Ile
  1               5                  10                  15
```

-continued

```
Phe Ile Tyr Leu His Thr His Tyr Ile Cys Ile His Thr Ile Tyr Val
            20                  25                  30

Lys Tyr Asn Ile Cys Ile Met His Ile Asn Ser Asn Lys Cys Ile Cys
        35                  40                  45

Val Ile Phe Lys Ile Glu Gln Leu Tyr Leu Glu Val Val Asn Ala Glu
    50                  55                  60

Asn Trp Phe Tyr Cys
65


<210> SEQ ID NO 341
<211> LENGTH: 31
<212> TYPE: PRT
<213> ORGANISM: Homo sapiens

<400> SEQUENCE: 341

Ile His Thr Ile Tyr Val Lys Tyr Asn Ile Cys Ile Met His Ile Asn
  1               5                  10                  15

Ser Asn Lys Cys Ile Cys Val Ile Phe Lys Ile Glu Gln Leu Tyr
            20                  25                  30


<210> SEQ ID NO 342
<211> LENGTH: 9
<212> TYPE: PRT
<213> ORGANISM: Homo sapiens

<400> SEQUENCE: 342

Asn Ser Ala Val Thr Val Gln Met Ala
  1               5


<210> SEQ ID NO 343
<211> LENGTH: 8
<212> TYPE: PRT
<213> ORGANISM: Homo sapiens

<400> SEQUENCE: 343

Thr Lys Thr Ser Thr Pro Leu Arg
  1               5


<210> SEQ ID NO 344
<211> LENGTH: 14
<212> TYPE: PRT
<213> ORGANISM: Homo sapiens

<400> SEQUENCE: 344

Val Cys Ile Pro Gly Ala Ala Gly Leu Ser Val Leu Leu Gly
  1               5                  10


<210> SEQ ID NO 345
<211> LENGTH: 45
<212> TYPE: PRT
<213> ORGANISM: Homo sapiens

<400> SEQUENCE: 345

Ser Ile Leu Pro Val Glu Met Ala Ala Ala Val Ala Gly Met Leu Arg
  1               5                  10                  15

Gly Gly Leu Leu Pro Gln Ala Gly Arg Leu Pro Thr Leu Gln Thr Val
            20                  25                  30

Arg Tyr Gly Ser Lys Ala Val Thr Arg His Arg Arg Val
        35                  40                  45


<210> SEQ ID NO 346
<211> LENGTH: 26
```

-continued

<212> TYPE: PRT
<213> ORGANISM: Homo sapiens

<400> SEQUENCE: 346

Ala Gly Met Leu Arg Gly Gly Leu Leu Pro Gln Ala Gly Arg Leu Pro
1 5 10 15

Thr Leu Gln Thr Val Arg Tyr Gly Ser Lys
20 25

<210> SEQ ID NO 347
<211> LENGTH: 24
<212> TYPE: PRT
<213> ORGANISM: Homo sapiens

<400> SEQUENCE: 347

Ala Arg Ala Gly Gln Met Gln Asn Leu Glu Ser Ala Arg Ala Gly Arg
1 5 10 15

Ser Val Ser Thr Gln Thr Gly Ser
20

<210> SEQ ID NO 348
<211> LENGTH: 300
<212> TYPE: PRT
<213> ORGANISM: Homo sapiens
<220> FEATURE:
<221> NAME/KEY: SITE
<222> LOCATION: (4)
<223> OTHER INFORMATION: Xaa equals any of the naturally occurring L-amino acids
<221> NAME/KEY: SITE
<222> LOCATION: (62)
<223> OTHER INFORMATION: Xaa equals any of the naturally occurring L-amino acids

<400> SEQUENCE: 348

Lys His Glu Xaa His Gln Val Ser Asp Gly Ala Leu Arg Cys Phe Ala
1 5 10 15

Ser Leu Ala Asp Arg Phe Thr Arg Arg Gly Val Asp Pro Ala Pro Leu
20 25 30

Ala Lys His Gly Leu Thr Glu Glu Leu Leu Ser Arg Met Ala Ala Ala
35 40 45

Gly Gly Thr Val Ser Gly Pro Ser Ser Ala Cys Lys Pro Xaa Arg Ser
50 55 60

Thr Thr Gly Ala Pro Ser Thr Thr Ala Asp Ser Lys Leu Ser Asn Gln
65 70 75 80

Val Ser Thr Ile Val Ser Leu Leu Ser Thr Leu Cys Arg Gly Ser Pro
85 90 95

Val Val Thr His Asp Leu Leu Arg Ser Glu Leu Pro Asp Ser Ile Glu
100 105 110

Ser Ala Leu Gln Gly Asp Glu Arg Cys Val Leu Asp Thr Met Arg Leu
115 120 125

Val Asp Phe Leu Leu Val Leu Leu Phe Glu Gly Arg Lys Ala Leu Pro
130 135 140

Lys Ser Ser Ala Gly Ser Thr Gly Arg Ile Pro Gly Leu Arg Arg Leu
145 150 155 160

Asp Ser Ser Gly Glu Arg Ser His Arg Gln Leu Ile Asp Cys Ile Arg
165 170 175

Ser Lys Asp Thr Asp Ala Leu Ile Asp Ala Ile Asp Thr Gly Ala Phe
180 185 190

Glu Val Asn Phe Met Asp Asp Val Gly Gln Thr Leu Leu Asn Trp Ala

-continued

```
        195                 200                 205

Ser Ala Phe Gly Thr Gln Glu Met Val Glu Phe Leu Cys Glu Arg Gly
    210                 215                 220

Ala Asp Val Asn Arg Gly Gln Arg Ser Ser Ser Leu His Tyr Ala Ala
225                 230                 235                 240

Cys Phe Gly Arg Pro Gln Val Ala Lys Thr Leu Leu Arg His Gly Ala
                245                 250                 255

Asn Pro Asp Leu Arg Asp Glu Asp Gly Lys Thr Pro Leu Asp Lys Ala
            260                 265                 270

Arg Glu Arg Gly His Ser Glu Val Val Ala Ile Leu Gln Ser Pro Gly
        275                 280                 285

Asp Trp Met Cys Pro Val Asn Lys Gly Asp Asp Lys
    290                 295                 300


<210> SEQ ID NO 349
<211> LENGTH: 17
<212> TYPE: PRT
<213> ORGANISM: Homo sapiens

<400> SEQUENCE: 349

Pro Leu Asp Lys Ala Arg Glu Arg Gly His Ser Glu Val Val Ala Ile
  1               5                  10                  15

Leu


<210> SEQ ID NO 350
<211> LENGTH: 15
<212> TYPE: PRT
<213> ORGANISM: Homo sapiens

<400> SEQUENCE: 350

Ala Lys Thr Leu Leu Arg His Gly Ala Asn Pro Asp Leu Arg Asp
  1               5                  10                  15


<210> SEQ ID NO 351
<211> LENGTH: 54
<212> TYPE: PRT
<213> ORGANISM: Homo sapiens
<220> FEATURE:
<221> NAME/KEY: SITE
<222> LOCATION: (49)
<223> OTHER INFORMATION: Xaa equals any of the naturally occurring L-
      amino acids
<221> NAME/KEY: SITE
<222> LOCATION: (50)
<223> OTHER INFORMATION: Xaa equals any of the naturally occurring L-
      amino acids
<221> NAME/KEY: SITE
<222> LOCATION: (52)
<223> OTHER INFORMATION: Xaa equals any of the naturally occurring L-
      amino acids

<400> SEQUENCE: 351

Gly Arg Gly Arg Ala Trp Leu Cys Arg Arg Pro Val Gly Ser Trp Ile
  1               5                  10                  15

Gly Ala Val Trp Asn Asp Lys Pro Asp Lys Glu Thr Phe Lys Lys Pro
             20                  25                  30

Trp Gln Met Trp Thr Gln Ile His Cys Trp Asn Gly Tyr Arg Trp Asp
         35                  40                  45

Xaa Xaa Asp Xaa Lys Asp
     50


<210> SEQ ID NO 352
```

-continued

```
<211> LENGTH: 23
<212> TYPE: PRT
<213> ORGANISM: Homo sapiens

<400> SEQUENCE: 352

Ser Trp Ile Gly Ala Val Trp Asn Asp Lys Pro Asp Lys Glu Thr Phe
  1               5                  10                  15

Lys Lys Pro Trp Gln Met Trp
             20


<210> SEQ ID NO 353
<211> LENGTH: 30
<212> TYPE: PRT
<213> ORGANISM: Homo sapiens
<220> FEATURE:
<221> NAME/KEY: SITE
<222> LOCATION: (19)
<223> OTHER INFORMATION: Xaa equals any of the naturally occurring L-
      amino acids
<221> NAME/KEY: SITE
<222> LOCATION: (22)
<223> OTHER INFORMATION: Xaa equals any of the naturally occurring L-
      amino acids

<400> SEQUENCE: 353

Lys Thr Met Ala Asp Val Asp Pro Asp Thr Leu Leu Glu Trp Leu Gln
  1               5                  10                  15

Met Gly Xaa Gly Arg Xaa Lys Gly His Ala Thr Asn Thr Pro
             20                  25                  30


<210> SEQ ID NO 354
<211> LENGTH: 34
<212> TYPE: PRT
<213> ORGANISM: Homo sapiens

<400> SEQUENCE: 354

Arg Gly Val Asp Pro Ala Pro Leu Ala Lys His Gly Leu Thr Glu Glu
  1               5                  10                  15

Leu Leu Ser Arg Met Ala Ala Ala Gly Gly Thr Val Ser Gly Pro Ser
             20                  25                  30

Ser Ala


<210> SEQ ID NO 355
<211> LENGTH: 31
<212> TYPE: PRT
<213> ORGANISM: Homo sapiens

<400> SEQUENCE: 355

Arg Ser Thr Thr Gly Ala Pro Ser Thr Thr Ala Asp Ser Lys Leu Ser
  1               5                  10                  15

Asn Gln Val Ser Thr Ile Val Ser Leu Leu Ser Thr Leu Cys Arg
             20                  25                  30


<210> SEQ ID NO 356
<211> LENGTH: 34
<212> TYPE: PRT
<213> ORGANISM: Homo sapiens

<400> SEQUENCE: 356

Phe Glu Val Asn Phe Met Asp Asp Val Gly Gln Thr Leu Leu Asn Trp
  1               5                  10                  15

Ala Ser Ala Phe Gly Thr Gln Glu Met Val Glu Phe Leu Cys Glu Arg
             20                  25                  30
```

-continued

Gly Ala

<210> SEQ ID NO 357
<211> LENGTH: 28
<212> TYPE: PRT
<213> ORGANISM: Homo sapiens

<400> SEQUENCE: 357

Glu Asp Gly Lys Thr Pro Leu Asp Lys Ala Arg Glu Arg Gly His Ser
1 5 10 15

Glu Val Val Ala Ile Leu Gln Ser Pro Gly Asp Trp
20 25

<210> SEQ ID NO 358
<211> LENGTH: 15
<212> TYPE: PRT
<213> ORGANISM: Homo sapiens

<400> SEQUENCE: 358

Thr Arg Pro Thr Met Pro Asn Phe Leu Trp Phe Pro Lys Cys Ala
1 5 10 15

<210> SEQ ID NO 359
<211> LENGTH: 44
<212> TYPE: PRT
<213> ORGANISM: Homo sapiens

<400> SEQUENCE: 359

Leu Pro Pro Cys Leu Ala Gln Ile Phe Pro Phe Phe Ser Ser Gly Thr
1 5 10 15

Asn Leu Thr Phe Cys Phe Phe Val Phe Val Phe Val Phe Val Phe Ala
20 25 30

Glu Leu Asp Tyr Arg Asn Ser Tyr Glu Ile Glu Tyr
35 40

<210> SEQ ID NO 360
<211> LENGTH: 9
<212> TYPE: PRT
<213> ORGANISM: Homo sapiens

<400> SEQUENCE: 360

Leu Lys Cys Thr Ile Tyr Gly Gly Ala
1 5

<210> SEQ ID NO 361
<211> LENGTH: 56
<212> TYPE: PRT
<213> ORGANISM: Homo sapiens

<400> SEQUENCE: 361

His Val Leu Trp Ser Leu Leu Ser Ala Cys Trp Thr Gln Phe Leu Val
1 5 10 15

Tyr Phe Cys Cys Leu Met Ile Leu Gln Arg Thr Phe Pro Pro Arg Ala
20 25 30

Leu Arg Thr Ser Pro Trp Leu Ser Asn Pro Met Gly Val Lys Gly Lys
35 40 45

Lys Lys Lys Gly Thr Phe Met Glu
50 55

<210> SEQ ID NO 362
<211> LENGTH: 30
<212> TYPE: PRT

-continued

<213> ORGANISM: Homo sapiens

<400> SEQUENCE: 362

Phe Leu Val Tyr Phe Cys Cys Leu Met Ile Leu Gln Arg Thr Phe Pro
1 5 10 15

Pro Arg Ala Leu Arg Thr Ser Pro Trp Leu Ser Asn Pro Met
20 25 30

<210> SEQ ID NO 363
<211> LENGTH: 52
<212> TYPE: PRT
<213> ORGANISM: Homo sapiens
<220> FEATURE:
<221> NAME/KEY: SITE
<222> LOCATION: (26)
<223> OTHER INFORMATION: Xaa equals any of the naturally occurring L-amino acids
<221> NAME/KEY: SITE
<222> LOCATION: (29)
<223> OTHER INFORMATION: Xaa equals any of the naturally occurring L-amino acids

<400> SEQUENCE: 363

Asp Cys Asn Arg Asp Tyr His Lys Ala Phe Gly Asn Leu Arg Ser Pro
1 5 10 15

Gly Trp Pro Asp Asn Tyr Asp Asn Asp Xaa Asp Cys Xaa Val Thr Leu
20 25 30

Thr Ala Pro Gln Asn His His Ser Gly Ile Val Glu Asn Ala Glu Thr
35 40 45

Ile Ser Trp Arg
50

<210> SEQ ID NO 364
<211> LENGTH: 15
<212> TYPE: PRT
<213> ORGANISM: Homo sapiens

<400> SEQUENCE: 364

Phe Gly Asn Leu Arg Ser Pro Gly Trp Pro Asp Asn Tyr Asp Asn
1 5 10 15

<210> SEQ ID NO 365
<211> LENGTH: 16
<212> TYPE: PRT
<213> ORGANISM: Homo sapiens
<220> FEATURE:
<221> NAME/KEY: SITE
<222> LOCATION: (6)
<223> OTHER INFORMATION: Xaa equals any of the naturally occurring L-amino acids

<400> SEQUENCE: 365

Ala Pro Gln Asn His Xaa Leu Lys Cys Arg Asn Asp Phe Leu Glu Val
1 5 10 15

<210> SEQ ID NO 366
<211> LENGTH: 7
<212> TYPE: PRT
<213> ORGANISM: Homo sapiens

<400> SEQUENCE: 366

Ala Ser Phe Tyr Arg Thr Ser
1 5

<210> SEQ ID NO 367

-continued

<211> LENGTH: 26
<212> TYPE: PRT
<213> ORGANISM: Homo sapiens

<400> SEQUENCE: 367

```
Lys Ala Asp Val Lys Trp His Met Cys Leu Gln Ser Pro Leu Cys Gly
  1               5                  10                  15

Leu Phe Cys Ser Ile Glu Gly Val Leu Lys
             20                  25
```

<210> SEQ ID NO 368
<211> LENGTH: 218
<212> TYPE: PRT
<213> ORGANISM: Homo sapiens
<220> FEATURE:
<221> NAME/KEY: SITE
<222> LOCATION: (59)
<223> OTHER INFORMATION: Xaa equals any of the naturally occurring L-amino acids
<221> NAME/KEY: SITE
<222> LOCATION: (99)
<223> OTHER INFORMATION: Xaa equals any of the naturally occurring L-amino acids
<221> NAME/KEY: SITE
<222> LOCATION: (101)
<223> OTHER INFORMATION: Xaa equals any of the naturally occurring L-amino acids

<400> SEQUENCE: 368

```
Ala Cys Met Asn Pro Ala Met Cys Phe Val Cys Ala Cys Pro His Thr
  1               5                  10                  15

Gly Ser Thr Pro Glu Lys Ala Ile Leu Gln Gly Arg Leu Ile Ser Leu
             20                  25                  30

Gly Thr Ser Leu Ser Pro Ala Ser Asn Gly Ser Gly Gln Gln Ser Phe
         35                  40                  45

Ser Ile Cys Met Ile Asn Pro Ser Leu Pro Xaa Ser Thr Ser Ser His
     50                  55                  60

His Leu Phe Ser Val Leu Thr Gly Asp Leu Asp Ser Tyr Ser Gln Arg
 65                  70                  75                  80

Lys Leu Lys Pro Thr Ser Arg Lys Ser Phe Leu Leu Pro Lys Thr Gln
                 85                  90                  95

Thr Tyr Xaa Val Xaa His Pro Ser Ser Pro Pro Leu Val Leu Val Gln
            100                 105                 110

His Arg Ser Pro Leu Ser Thr Tyr Pro Lys Pro Val Pro Ser Cys Cys
        115                 120                 125

Ala Leu Asp Leu Ile Ser Val Ile Ala Leu Glu Thr Phe Leu Val Tyr
    130                 135                 140

Ile His Leu Phe Pro Ser Ile Asp Leu Ser Tyr Trp Ile Leu Ser Met
145                 150                 155                 160

Leu Gln Pro Leu Leu Leu Ile Lys Gln Gln Ser Thr Lys Thr Leu Ser
                165                 170                 175

Leu Asn Cys Met Leu Tyr Ser Ser Tyr Tyr Leu Ile Ser Phe Leu Ser
            180                 185                 190

Phe Lys Ala Lys Val Leu Arg Arg Gly Gly Asn Ile Leu His His Phe
        195                 200                 205

Phe Thr Ser Tyr Ser Phe Phe Asn Thr Tyr
    210                 215
```

<210> SEQ ID NO 369
<211> LENGTH: 28
<212> TYPE: PRT

-continued

<213> ORGANISM: Homo sapiens

<400> SEQUENCE: 369

Cys Pro His Thr Gly Ser Thr Pro Glu Lys Ala Ile Leu Gln Gly Arg
1 5 10 15

Leu Ile Ser Leu Gly Thr Ser Leu Ser Pro Ala Ser
20 25

<210> SEQ ID NO 370
<211> LENGTH: 24
<212> TYPE: PRT
<213> ORGANISM: Homo sapiens

<400> SEQUENCE: 370

Gln His Arg Ser Pro Leu Ser Thr Tyr Pro Lys Pro Val Pro Ser Cys
1 5 10 15

Cys Ala Leu Asp Leu Ile Ser Val
20

<210> SEQ ID NO 371
<211> LENGTH: 29
<212> TYPE: PRT
<213> ORGANISM: Homo sapiens

<400> SEQUENCE: 371

Ile Lys Gln Gln Ser Thr Lys Thr Leu Ser Leu Asn Cys Met Leu Tyr
1 5 10 15

Ser Ser Tyr Tyr Leu Ile Ser Phe Leu Ser Phe Lys Ala
20 25

<210> SEQ ID NO 372
<211> LENGTH: 24
<212> TYPE: PRT
<213> ORGANISM: Homo sapiens

<400> SEQUENCE: 372

Lys Tyr Leu Val Ser Ser Val Leu Pro Thr Ile Ser Met Ala Arg Ser
1 5 10 15

Leu Ile Ser Ala Leu Arg Ser Gly
20

<210> SEQ ID NO 373
<211> LENGTH: 27
<212> TYPE: PRT
<213> ORGANISM: Homo sapiens

<400> SEQUENCE: 373

Met Arg Thr Leu Phe Gly Ala Val Arg Ala Pro Phe Ser Ser Leu Thr
1 5 10 15

Leu Leu Leu Ile Thr Pro Ser Pro Ser Pro Leu
20 25

<210> SEQ ID NO 374
<211> LENGTH: 10
<212> TYPE: PRT
<213> ORGANISM: Homo sapiens

<400> SEQUENCE: 374

Met Ala Tyr Ala Phe His Arg Thr Ser Thr
1 5 10

<210> SEQ ID NO 375

<211> LENGTH: 22
<212> TYPE: PRT
<213> ORGANISM: Homo sapiens

<400> SEQUENCE: 375

Leu Lys Ser Thr Tyr Thr Leu Leu Ser Ile Leu Trp Phe Leu Val Leu
1 5 10 15

Ile Pro Val Glu Gly Asn
20

<210> SEQ ID NO 376
<211> LENGTH: 18
<212> TYPE: PRT
<213> ORGANISM: Homo sapiens

<400> SEQUENCE: 376

Gly Pro Leu Leu Ala Ser His Ala Thr Leu Cys Phe Ser Leu Gly Ser
1 5 10 15

Lys Phe

<210> SEQ ID NO 377
<211> LENGTH: 10
<212> TYPE: PRT
<213> ORGANISM: Homo sapiens

<400> SEQUENCE: 377

Thr Val Trp Gly Ile Leu Pro Arg Lys Arg
1 5 10

<210> SEQ ID NO 378
<211> LENGTH: 20
<212> TYPE: PRT
<213> ORGANISM: Homo sapiens

<400> SEQUENCE: 378

Ala Ser Ile Asp Thr Trp Pro Gly Arg Arg Ser Gly Gly Met Ile Val
1 5 10 15

Ile Thr Ser Ile
20

<210> SEQ ID NO 379
<211> LENGTH: 41
<212> TYPE: PRT
<213> ORGANISM: Homo sapiens

<400> SEQUENCE: 379

Gly Ser Pro Gln Ala Glu Thr Arg Trp Ser Asp Pro Ile Ala Leu His
1 5 10 15

Gln Gly Lys Ser Pro Ala Ser Ile Asp Thr Trp Pro Gly Arg Arg Ser
20 25 30

Gly Gly Met Ile Val Ile Thr Ser Ile
35 40

<210> SEQ ID NO 380
<211> LENGTH: 43
<212> TYPE: PRT
<213> ORGANISM: Homo sapiens
<220> FEATURE:
<221> NAME/KEY: SITE
<222> LOCATION: (2)
<223> OTHER INFORMATION: Xaa equals any of the naturally occurring L-
amino acids

<400> SEQUENCE: 380

```
Val Xaa Asp Ile Thr Phe Asp Pro Asp Thr Ala His Lys Tyr Leu Arg
  1               5                  10                  15

Leu Gln Glu Glu Asn Arg Lys Val Thr Asn Thr Thr Pro Trp Glu His
             20                  25                  30

Pro Tyr Pro Asp Leu Pro Ser Arg Phe Leu His
         35                  40


<210> SEQ ID NO 381
<211> LENGTH: 19
<212> TYPE: PRT
<213> ORGANISM: Homo sapiens

<400> SEQUENCE: 381

Leu Tyr Leu His Arg Tyr Tyr Phe Glu Val Glu Ile Phe Gly Ala Gly
  1               5                  10                  15

Thr Tyr Val


<210> SEQ ID NO 382
<211> LENGTH: 22
<212> TYPE: PRT
<213> ORGANISM: Homo sapiens

<400> SEQUENCE: 382

Ser Cys Ile Ser Gly Asn Asn Phe Ser Trp Ser Leu Gln Trp Asn Gly
  1               5                  10                  15

Lys Glu Phe Thr Ala Trp
             20


<210> SEQ ID NO 383
<211> LENGTH: 17
<212> TYPE: PRT
<213> ORGANISM: Homo sapiens

<400> SEQUENCE: 383

Thr Pro Leu Lys Ala Gly Pro Phe Trp Ser Ser Gly Ser Ile Leu Thr
  1               5                  10                  15

Ser


<210> SEQ ID NO 384
<211> LENGTH: 39
<212> TYPE: PRT
<213> ORGANISM: Homo sapiens
<220> FEATURE:
<221> NAME/KEY: SITE
<222> LOCATION: (32)
<223> OTHER INFORMATION: Xaa equals any of the naturally occurring L-
      amino acids

<400> SEQUENCE: 384

Ser Val Ser Glu Val Lys Ala Val Ala Glu Met Gln Phe Gly Glu Leu
  1               5                  10                  15

Leu Ala Ala Val Arg Lys Ala Gln Ala Asn Val Met Leu Phe Leu Xaa
             20                  25                  30

Glu Lys Glu Gln Ala Ala Leu
         35


<210> SEQ ID NO 385
<211> LENGTH: 43
<212> TYPE: PRT
<213> ORGANISM: Homo sapiens

<400> SEQUENCE: 385
```

-continued

Glu Lys Ser Lys Gln Glu Leu Glu Thr Met Ala Ala Ile Ser Asn Thr
1 5 10 15

Val Gln Phe Leu Glu Glu Tyr Cys Lys Phe Lys Asn Thr Glu Asp Ile
20 25 30

Thr Phe Pro Ser Val Tyr Ile Gly Leu Lys Asp
35 40

<210> SEQ ID NO 386
<211> LENGTH: 29
<212> TYPE: PRT
<213> ORGANISM: Homo sapiens
<220> FEATURE:
<221> NAME/KEY: SITE
<222> LOCATION: (26)
<223> OTHER INFORMATION: Xaa equals any of the naturally occurring L-amino acids

<400> SEQUENCE: 386

Leu Glu Asn Tyr Lys Lys Lys Leu Gln Glu Phe Ser Lys Glu Glu Glu
1 5 10 15

Tyr Asp Ile Arg Thr Gln Val Ser Ala Xaa Val Gln Arg
20 25

<210> SEQ ID NO 387
<211> LENGTH: 38
<212> TYPE: PRT
<213> ORGANISM: Homo sapiens

<400> SEQUENCE: 387

Gly Val Tyr Ile Asp Phe Pro Gly Gly Ile Leu Ser Phe Tyr Gly Val
1 5 10 15

Glu Tyr Asp Ser Met Thr Leu Val His Lys Phe Ala Cys Lys Phe Ser
20 25 30

Glu Pro Val Tyr Ala Ala
35

<210> SEQ ID NO 388
<211> LENGTH: 10
<212> TYPE: PRT
<213> ORGANISM: Homo sapiens

<400> SEQUENCE: 388

Gly Thr Val Ser Arg Glu Arg Arg Ala Gly
1 5 10

<210> SEQ ID NO 389
<211> LENGTH: 82
<212> TYPE: PRT
<213> ORGANISM: Homo sapiens

<400> SEQUENCE: 389

His Gly Asp Pro Thr Gln Ser Trp Pro Phe Leu Glu Leu Gly Val Tyr
1 5 10 15

Ile Asp Phe Pro Gly Gly Ile Leu Ser Phe Tyr Gly Val Glu Tyr Asp
20 25 30

Ser Met Thr Leu Val His Lys Phe Ala Cys Lys Phe Ser Glu Pro Val
35 40 45

Tyr Ala Ala Phe Trp Leu Ser Lys Lys Glu Asn Ala Ile Arg Ile Val
50 55 60

Asp Leu Gly Glu Glu Pro Glu Lys Pro Ala Pro Ser Leu Val Gly Thr
65 70 75 80

-continued

Ala Pro

<210> SEQ ID NO 390
<211> LENGTH: 30
<212> TYPE: PRT
<213> ORGANISM: Homo sapiens

<400> SEQUENCE: 390

Ser Phe Tyr Gly Val Glu Tyr Asp Ser Met Thr Leu Val His Lys Phe
1 5 10 15

Ala Cys Lys Phe Ser Glu Pro Val Tyr Ala Ala Phe Trp Leu
20 25 30

<210> SEQ ID NO 391
<211> LENGTH: 337
<212> TYPE: PRT
<213> ORGANISM: Homo sapiens
<220> FEATURE:
<221> NAME/KEY: SITE
<222> LOCATION: (65)
<223> OTHER INFORMATION: Xaa equals any of the naturally occurring L-amino acids
<221> NAME/KEY: SITE
<222> LOCATION: (150)
<223> OTHER INFORMATION: Xaa equals any of the naturally occurring L-amino acids
<221> NAME/KEY: SITE
<222> LOCATION: (151)
<223> OTHER INFORMATION: Xaa equals any of the naturally occurring L-amino acids
<221> NAME/KEY: SITE
<222> LOCATION: (177)
<223> OTHER INFORMATION: Xaa equals any of the naturally occurring L-amino acids
<221> NAME/KEY: SITE
<222> LOCATION: (200)
<223> OTHER INFORMATION: Xaa equals any of the naturally occurring L-amino acids
<221> NAME/KEY: SITE
<222> LOCATION: (278)
<223> OTHER INFORMATION: Xaa equals any of the naturally occurring L-amino acids
<221> NAME/KEY: SITE
<222> LOCATION: (284)
<223> OTHER INFORMATION: Xaa equals any of the naturally occurring L-amino acids

<400> SEQUENCE: 391

Ala Glu Leu Gln Cys Thr Gln Leu Asp Leu Glu Arg Lys Leu Lys Leu
1 5 10 15

Asn Glu Asn Ala Ile Ser Arg Leu Gln Ala Asn Gln Lys Ser Val Leu
20 25 30

Val Ser Val Ser Glu Val Lys Ala Val Ala Glu Met Gln Phe Gly Glu
35 40 45

Leu Leu Ala Ala Val Arg Lys Ala Gln Ala Asn Val Met Leu Phe Leu
50 55 60

Xaa Glu Lys Glu Gln Ala Ala Leu Ser Gln Ala Asn Gly Ile Lys Ala
65 70 75 80

His Leu Glu Tyr Lys Ser Ala Glu Met Glu Lys Ser Lys Gln Glu Leu
85 90 95

Glu Thr Met Ala Ala Ile Ser Asn Thr Val Gln Phe Leu Glu Glu Tyr
100 105 110

Cys Lys Phe Lys Asn Thr Glu Asp Ile Thr Phe Pro Ser Val Tyr Ile
115 120 125

Gly Leu Lys Asp Lys Leu Ser Gly Ile Arg Lys Val Ile Thr Glu Ser

-continued

```
    130                 135                 140

Thr Val His Leu Ile Xaa Xaa Leu Glu Asn Tyr Lys Lys Lys Leu Gln
145                 150                 155                 160

Glu Phe Ser Lys Glu Glu Glu Tyr Asp Ile Arg Thr Gln Val Ser Ala
                165                 170                 175

Xaa Val Gln Arg Lys Tyr Trp Thr Ser Lys Pro Glu Pro Ser Thr Arg
            180                 185                 190

Glu Gln Phe Leu Gln Tyr Val Xaa Asp Ile Thr Phe Asp Pro Asp Thr
        195                 200                 205

Ala His Lys Tyr Leu Arg Leu Gln Glu Glu Asn Arg Lys Val Thr Asn
    210                 215                 220

Thr Thr Pro Trp Glu His Pro Tyr Pro Asp Leu Pro Ser Arg Phe Leu
225                 230                 235                 240

His Trp Arg Gln Val Leu Ser Gln Gln Ser Leu Tyr Leu His Arg Tyr
                245                 250                 255

Tyr Phe Glu Val Glu Ile Phe Gly Ala Gly Thr Tyr Val Gly Leu Thr
            260                 265                 270

Cys Lys Gly Ile Asp Xaa Lys Gly Glu Glu Arg Xaa Ser Cys Ile Ser
        275                 280                 285

Gly Asn Asn Phe Ser Trp Ser Leu Gln Trp Asn Gly Lys Glu Phe Thr
    290                 295                 300

Ala Trp Tyr Ser Asp Met Glu Thr Pro Leu Lys Ala Gly Pro Phe Trp
305                 310                 315                 320

Ser Ser Gly Ser Ile Leu Thr Ser Gln Glu Gly Ser Phe Pro Ser Met
                325                 330                 335

Ala


<210> SEQ ID NO 392
<211> LENGTH: 301
<212> TYPE: PRT
<213> ORGANISM: Homo sapiens
<220> FEATURE:
<221> NAME/KEY: SITE
<222> LOCATION: (166)
<223> OTHER INFORMATION: Xaa equals any of the naturally occurring L-
      amino acids
<221> NAME/KEY: SITE
<222> LOCATION: (172)
<223> OTHER INFORMATION: Xaa equals any of the naturally occurring L-
      amino acids
<221> NAME/KEY: SITE
<222> LOCATION: (250)
<223> OTHER INFORMATION: Xaa equals any of the naturally occurring L-
      amino acids
<221> NAME/KEY: SITE
<222> LOCATION: (299)
<223> OTHER INFORMATION: Xaa equals any of the naturally occurring L-
      amino acids
<221> NAME/KEY: SITE
<222> LOCATION: (300)
<223> OTHER INFORMATION: Xaa equals any of the naturally occurring L-
      amino acids

<400> SEQUENCE: 392

Arg Thr Ala Pro Tyr Gly Ala Lys Glu Ser Ser Trp Arg Met Phe Ser
  1               5                  10                  15

Phe Arg Asp Pro Ile Gly Phe Gln Lys Pro Ala Thr Ile Ser Ser Tyr
             20                  25                  30

Phe Cys Pro Gln Ile Thr Leu Lys Cys Lys Ser His His Cys Ser Trp
         35                  40                  45

Gln Arg Ser Gly Ile Trp Leu Leu Glu Ser Arg Glu Gln Ser Pro Pro
```

-continued

```
    50                  55                  60

Arg Thr Val Leu Ala Ser Arg Val Pro Leu Pro Asp Leu Gln Ser Gly
 65                 70                  75                  80

Trp Arg Phe Pro Ser Trp Lys Ala Arg Arg Gln His Arg Leu Val Leu
                85                  90                  95

Lys Thr Cys Arg Gln Thr Cys Glu Pro Glu Ser Trp Asn His Thr Leu
            100                 105                 110

Arg His Arg Arg Lys Gly Ser Leu Leu Gly Ser Gln Tyr Arg Pro Arg
        115                 120                 125

Ala Pro Glu Arg Ala Ser Phe Glu Trp Gly Leu His Val Thr Val Pro
    130                 135                 140

Gly Arg Glu Leu Leu Pro Val Pro Leu Glu Ala Pro Gly Glu Val Val
145                 150                 155                 160

Ser Gly Asn Ala Thr Xaa Ala Leu Leu Pro Phe Xaa Val Asp Ala Phe
                165                 170                 175

Ala Gly Gln Ala Asn Ile Gly Ala Cys Pro Glu Asp Leu His Leu Lys
            180                 185                 190

Ile Val Pro Val Gln Val Gln Thr Leu Leu Gly Gln His Leu Pro Pro
        195                 200                 205

Val Gln Glu Pro Ala Gly Glu Val Arg Val Gly Met Leu Pro Gly Arg
    210                 215                 220

Gly Val Gly Asp Leu Ala Val Leu Leu Leu Gln Pro Glu Ile Leu Val
225                 230                 235                 240

Cys Cys Val Arg Val Glu Arg Asp Val Xaa His Ile Leu Glu Glu Leu
                245                 250                 255

Phe Pro Gly Ala Gly Leu Arg Phe Gly Ser Pro Ile Phe Ala Leu Asn
            260                 265                 270

Asn Gly Arg His Leu Ser Ser Asp Val Ile Leu Leu Phe Leu Gly Lys
        275                 280                 285

Leu Leu Glu Leu Phe Leu Ile Val Leu Gln Xaa Xaa Asp
    290                 295                 300


<210> SEQ ID NO 393
<211> LENGTH: 196
<212> TYPE: PRT
<213> ORGANISM: Homo sapiens

<400> SEQUENCE: 393

Ser Lys Ile Lys Tyr Asp Trp Tyr Gln Thr Glu Ser Gln Val Val Ile
  1               5                  10                  15

Thr Leu Met Ile Lys Asn Val Gln Lys Asn Asp Val Asn Val Glu Phe
            20                  25                  30

Ser Glu Lys Glu Leu Ser Ala Leu Val Lys Leu Pro Ser Gly Glu Asp
         35                  40                  45

Tyr Asn Leu Lys Leu Glu Leu Leu His Pro Ile Ile Pro Glu Gln Ser
     50                  55                  60

Thr Phe Lys Val Leu Ser Thr Lys Ile Glu Ile Lys Leu Lys Lys Pro
 65                  70                  75                  80

Glu Ala Val Arg Trp Glu Lys Leu Glu Gly Gln Gly Asp Val Pro Thr
                 85                  90                  95

Pro Lys Gln Phe Val Ala Asp Val Lys Asn Leu Tyr Pro Ser Ser Ser
            100                 105                 110

Pro Tyr Thr Arg Asn Trp Asp Lys Leu Val Gly Glu Ile Lys Glu Glu
        115                 120                 125
```

-continued

```
Glu Lys Asn Glu Lys Leu Glu Gly Asp Ala Ala Leu Asn Arg Leu Phe
    130                 135                 140

Gln Gln Ile Tyr Ser Asp Gly Ser Asp Glu Val Lys Arg Ala Met Asn
145                 150                 155                 160

Lys Ser Phe Met Glu Ser Gly Gly Thr Val Leu Ser Thr Asn Trp Ser
                165                 170                 175

Asp Val Gly Lys Arg Lys Val Glu Ile Asn Pro Pro Asp Asp Met Glu
            180                 185                 190

Trp Lys Lys Tyr
        195


<210> SEQ ID NO 394
<211> LENGTH: 39
<212> TYPE: PRT
<213> ORGANISM: Homo sapiens

<400> SEQUENCE: 394

Gly Asp Ala Ala Leu Asn Arg Leu Phe Gln Gln Ile Tyr Ser Asp Gly
  1               5                  10                  15

Ser Asp Glu Val Lys Arg Ala Met Asn Lys Ser Phe Met Glu Ser Gly
             20                  25                  30

Gly Thr Val Leu Ser Thr Asn
         35


<210> SEQ ID NO 395
<211> LENGTH: 23
<212> TYPE: PRT
<213> ORGANISM: Homo sapiens

<400> SEQUENCE: 395

Asp Trp Tyr Gln Thr Glu Ser Gln Val Val Ile Thr Leu Met Ile Lys
  1               5                  10                  15

Asn Val Gln Lys Asn Asp Val
             20


<210> SEQ ID NO 396
<211> LENGTH: 146
<212> TYPE: PRT
<213> ORGANISM: Homo sapiens
<220> FEATURE:
<221> NAME/KEY: SITE
<222> LOCATION: (9)
<223> OTHER INFORMATION: Xaa equals any of the naturally occurring L-
      amino acids
<221> NAME/KEY: SITE
<222> LOCATION: (10)
<223> OTHER INFORMATION: Xaa equals any of the naturally occurring L-
      amino acids

<400> SEQUENCE: 396

Met Ala Ala Ala Ala Ala Gly Thr Xaa Xaa Ser Gln Arg Phe Phe Gln
  1               5                  10                  15

Ser Phe Ser Asp Ala Leu Ile Asp Glu Asp Pro Gln Ala Ala Leu Glu
             20                  25                  30

Glu Leu Thr Lys Ala Leu Glu Gln Lys Pro Asp Asp Ala Gln Tyr Tyr
         35                  40                  45

Cys Gln Arg Ala Tyr Cys His Ile Leu Leu Gly Asn Tyr Cys Val Ala
     50                  55                  60

Val Ala Asp Ala Lys Lys Ser Leu Glu Leu Asn Pro Asn Asn Ser Thr
 65                  70                  75                  80

Ala Met Leu Arg Lys Gly Ile Cys Glu Tyr His Glu Lys Asn Tyr Ala
```

-continued

```
                85                  90                  95

Ala Ala Leu Glu Thr Phe Thr Glu Gly Gln Lys Leu Asp Ser Ala Asp
            100                 105                 110

Ala Asn Phe Ser Val Trp Ile Lys Arg Cys Gln Glu Ala Gln Asn Gly
        115                 120                 125

Ser Glu Ser Glu Val Val Ser Pro Lys Phe Ser Phe Phe Met Phe Leu
    130                 135                 140

Leu Phe
145


<210> SEQ ID NO 397
<211> LENGTH: 38
<212> TYPE: PRT
<213> ORGANISM: Homo sapiens

<400> SEQUENCE: 397

Leu Glu Glu Leu Thr Lys Ala Leu Glu Gln Lys Pro Asp Asp Ala Gln
  1               5                  10                  15

Tyr Tyr Cys Gln Arg Ala Tyr Cys His Ile Leu Leu Gly Asn Tyr Cys
             20                  25                  30

Val Ala Val Ala Asp Ala
         35


<210> SEQ ID NO 398
<211> LENGTH: 31
<212> TYPE: PRT
<213> ORGANISM: Homo sapiens

<400> SEQUENCE: 398

Ala Met Leu Arg Lys Gly Ile Cys Glu Tyr His Glu Lys Asn Tyr Ala
  1               5                  10                  15

Ala Ala Leu Glu Thr Phe Thr Glu Gly Gln Lys Leu Asp Ser Ala
             20                  25                  30


<210> SEQ ID NO 399
<211> LENGTH: 37
<212> TYPE: PRT
<213> ORGANISM: Homo sapiens

<400> SEQUENCE: 399

Leu Arg Leu Trp Asn Arg Asn Gln Met Met His Ser Ile Ile Val Lys
  1               5                  10                  15

Glu Leu Ile Val Thr Phe Phe Leu Gly Ile Thr Val Leu Leu Leu Leu
             20                  25                  30

Met Gln Arg Ser Leu
         35


<210> SEQ ID NO 400
<211> LENGTH: 10
<212> TYPE: PRT
<213> ORGANISM: Homo sapiens

<400> SEQUENCE: 400

Asn Ser Ile Gln Ile Ile Pro Leu Leu Cys
  1               5                  10


<210> SEQ ID NO 401
<211> LENGTH: 228
<212> TYPE: PRT
<213> ORGANISM: Homo sapiens
```

-continued

<400> SEQUENCE: 401

```
Tyr Met His Phe Asn Asn Thr Val Ala Lys Leu Thr Cys Lys Asn Leu
  1               5                  10                  15

Ser Leu Ser Thr Tyr Gln Asn Gln Ser Ala Ser Gln Trp Thr His Gln
             20                  25                  30

Ser Lys Ile Lys Tyr Asp Trp Tyr Gln Thr Glu Ser Gln Val Val Ile
         35                  40                  45

Thr Leu Met Ile Lys Asn Val Gln Lys Asn Asp Val Asn Val Glu Phe
     50                  55                  60

Ser Glu Lys Glu Leu Ser Ala Leu Val Lys Leu Pro Ser Gly Glu Asp
 65                  70                  75                  80

Tyr Asn Leu Lys Leu Glu Leu Leu His Pro Ile Ile Pro Glu Gln Ser
                 85                  90                  95

Thr Phe Lys Val Leu Ser Thr Lys Ile Glu Ile Lys Leu Lys Lys Pro
            100                 105                 110

Glu Ala Val Arg Trp Glu Lys Leu Glu Gly Gln Gly Asp Val Pro Thr
        115                 120                 125

Pro Lys Gln Phe Val Ala Asp Val Lys Asn Leu Tyr Pro Ser Ser Ser
    130                 135                 140

Pro Tyr Thr Arg Asn Trp Asp Lys Leu Val Gly Glu Ile Lys Glu Glu
145                 150                 155                 160

Glu Lys Asn Glu Lys Leu Glu Gly Asp Ala Ala Leu Asn Arg Leu Phe
                165                 170                 175

Gln Gln Ile Tyr Ser Asp Gly Ser Asp Glu Val Lys Arg Ala Met Asn
            180                 185                 190

Lys Ser Phe Met Glu Ser Gly Gly Thr Val Leu Ser Thr Asn Trp Ser
        195                 200                 205

Asp Val Gly Lys Arg Lys Val Glu Ile Asn Pro Pro Asp Asp Met Glu
    210                 215                 220

Trp Lys Lys Tyr
225
```

<210> SEQ ID NO 402
<211> LENGTH: 29
<212> TYPE: PRT
<213> ORGANISM: Homo sapiens

<400> SEQUENCE: 402

```
Thr Cys Lys Asn Leu Ser Leu Ser Thr Tyr Gln Asn Gln Ser Ala Ser
  1               5                  10                  15

Gln Trp Thr His Gln Ser Lys Ile Lys Tyr Asp Trp Tyr
             20                  25
```

<210> SEQ ID NO 403
<211> LENGTH: 24
<212> TYPE: PRT
<213> ORGANISM: Homo sapiens

<400> SEQUENCE: 403

```
Glu Lys Glu Leu Ser Ala Leu Val Lys Leu Pro Ser Gly Glu Asp Tyr
  1               5                  10                  15

Asn Leu Lys Leu Glu Leu Leu His
             20
```

<210> SEQ ID NO 404
<211> LENGTH: 29
<212> TYPE: PRT

-continued

<213> ORGANISM: Homo sapiens

<400> SEQUENCE: 404

Leu His Pro Ile Ile Pro Glu Gln Ser Thr Phe Lys Val Leu Ser Thr
1 5 10 15

Lys Ile Glu Ile Lys Leu Lys Lys Pro Glu Ala Val Arg
20 25

<210> SEQ ID NO 405
<211> LENGTH: 24
<212> TYPE: PRT
<213> ORGANISM: Homo sapiens

<400> SEQUENCE: 405

Lys Gln Phe Val Ala Asp Val Lys Asn Leu Tyr Pro Ser Ser Ser Pro
1 5 10 15

Tyr Thr Arg Asn Trp Asp Lys Leu
20

<210> SEQ ID NO 406
<211> LENGTH: 17
<212> TYPE: PRT
<213> ORGANISM: Homo sapiens

<400> SEQUENCE: 406

Gly Ser Lys Gly Gln Glu Arg Lys Trp Arg Val Arg Met Gly Tyr Leu
1 5 10 15

Asn

<210> SEQ ID NO 407
<211> LENGTH: 55
<212> TYPE: PRT
<213> ORGANISM: Homo sapiens

<400> SEQUENCE: 407

Gln Arg Tyr Arg Leu Leu Pro Leu Phe Cys Tyr Val Cys Ser Arg Lys
1 5 10 15

Ile Lys Leu Asn Glu Asn Leu Phe Val Phe Ser Ala Tyr Ser Leu Ala
20 25 30

Thr Leu Pro His Thr Tyr Leu Phe Ser Ile Val Glu Cys Ser Ser Phe
35 40 45

Cys Leu Ser Gly Thr Arg Asn
50 55

<210> SEQ ID NO 408
<211> LENGTH: 27
<212> TYPE: PRT
<213> ORGANISM: Homo sapiens

<400> SEQUENCE: 408

Phe Ser Ala Tyr Ser Leu Ala Thr Leu Pro His Thr Tyr Leu Phe Ser
1 5 10 15

Ile Val Glu Cys Ser Ser Phe Cys Leu Ser Gly
20 25

<210> SEQ ID NO 409
<211> LENGTH: 35
<212> TYPE: PRT
<213> ORGANISM: Homo sapiens

<400> SEQUENCE: 409

-continued

```
Ala Ser Phe Gly Ser Cys Ser Leu Ser Leu Pro Cys Ser Ala Arg Glu
  1               5                  10                  15

Arg Thr Pro Glu Gly Gly Gly Trp Pro Gly Gly Arg Leu Ser Glu Pro
             20                  25                  30

Leu Pro Ala
         35
```

<210> SEQ ID NO 410
<211> LENGTH: 7
<212> TYPE: PRT
<213> ORGANISM: Homo sapiens

<400> SEQUENCE: 410

```
Ala Pro Asn Val Val Leu Val
  1               5
```

<210> SEQ ID NO 411
<211> LENGTH: 6
<212> TYPE: PRT
<213> ORGANISM: Homo sapiens

<400> SEQUENCE: 411

```
Asp Gly Arg Leu Thr Phe
  1               5
```

<210> SEQ ID NO 412
<211> LENGTH: 14
<212> TYPE: PRT
<213> ORGANISM: Homo sapiens

<400> SEQUENCE: 412

```
Pro Gly Ser Gln Val Val Lys Leu Pro Phe Ile Asn Phe Met
  1               5                  10
```

<210> SEQ ID NO 413
<211> LENGTH: 9
<212> TYPE: PRT
<213> ORGANISM: Homo sapiens

<400> SEQUENCE: 413

```
Phe Leu Asn Ala Tyr Thr Asn Ser Pro
  1               5
```

<210> SEQ ID NO 414
<211> LENGTH: 36
<212> TYPE: PRT
<213> ORGANISM: Homo sapiens

<400> SEQUENCE: 414

```
Ile Cys Cys Pro Ser Arg Ala Ala Met Trp Ser Gly Leu Phe Thr His
  1               5                  10                  15

Leu Thr Glu Ser Trp Asn Asn Phe Lys Gly Leu Asp Pro Asn Tyr Thr
             20                  25                  30

Thr Trp Met Asp
         35
```

<210> SEQ ID NO 415
<211> LENGTH: 6
<212> TYPE: PRT
<213> ORGANISM: Homo sapiens

<400> SEQUENCE: 415

```
Thr Gln Lys Phe Gly Lys
```

-continued 1 5

<210> SEQ ID NO 416
<211> LENGTH: 9
<212> TYPE: PRT
<213> ORGANISM: Homo sapiens

<400> SEQUENCE: 416

Asp Tyr Thr Ser Gly His His Ser Ile
1 5

<210> SEQ ID NO 417
<211> LENGTH: 21
<212> TYPE: PRT
<213> ORGANISM: Homo sapiens

<400> SEQUENCE: 417

Ser Asn Arg Val Glu Ala Trp Thr Arg Asp Val Ala Phe Leu Leu Arg
1 5 10 15

Gln Glu Gly Arg Pro
20

<210> SEQ ID NO 418
<211> LENGTH: 8
<212> TYPE: PRT
<213> ORGANISM: Homo sapiens

<400> SEQUENCE: 418

Asp Trp Gln Asn Thr Asp Lys Ala
1 5

<210> SEQ ID NO 419
<211> LENGTH: 34
<212> TYPE: PRT
<213> ORGANISM: Homo sapiens

<400> SEQUENCE: 419

Tyr Leu Gly Leu Asn Leu Pro His Pro Tyr Pro Ser Pro Ser Ser Gly
1 5 10 15

Glu Asn Phe Gly Ser Ser Thr Phe His Thr Ser Leu Tyr Trp Leu Glu
20 25 30

Lys Val

<210> SEQ ID NO 420
<211> LENGTH: 8
<212> TYPE: PRT
<213> ORGANISM: Homo sapiens

<400> SEQUENCE: 420

Asp Ala Ile Lys Ile Pro Lys Trp
1 5

<210> SEQ ID NO 421
<211> LENGTH: 7
<212> TYPE: PRT
<213> ORGANISM: Homo sapiens

<400> SEQUENCE: 421

Tyr Thr Lys Asn Cys Thr Gly
1 5

<210> SEQ ID NO 422
<211> LENGTH: 25

-continued

<212> TYPE: PRT
<213> ORGANISM: Homo sapiens

<400> SEQUENCE: 422

Asn Ile Arg Ala Phe Tyr Tyr Ala Met Cys Ala Glu Thr Asp Ala Met
1               5                   10                  15

Leu Gly Glu Ile Ile Leu Ala Leu His
            20                  25

<210> SEQ ID NO 423
<211> LENGTH: 11
<212> TYPE: PRT
<213> ORGANISM: Homo sapiens

<400> SEQUENCE: 423

Leu Asp Leu Leu Gln Lys Thr Ile Val Ile Tyr
1               5                   10

<210> SEQ ID NO 424
<211> LENGTH: 15
<212> TYPE: PRT
<213> ORGANISM: Homo sapiens

<400> SEQUENCE: 424

Met Glu His Arg Gln Phe Tyr Lys Met Ser Met Tyr Glu Ala Ser
1               5                   10                  15

<210> SEQ ID NO 425
<211> LENGTH: 13
<212> TYPE: PRT
<213> ORGANISM: Homo sapiens

<400> SEQUENCE: 425

His Val Pro Leu Leu Met Met Gly Pro Gly Ile Lys Ala
1               5                   10

<210> SEQ ID NO 426
<211> LENGTH: 17
<212> TYPE: PRT
<213> ORGANISM: Homo sapiens

<400> SEQUENCE: 426

Val Val Ser Leu Val Asp Ile Tyr Pro Thr Met Leu Asp Ile Ala Gly
1               5                   10                  15

Ile

<210> SEQ ID NO 427
<211> LENGTH: 7
<212> TYPE: PRT
<213> ORGANISM: Homo sapiens

<400> SEQUENCE: 427

Asp Pro Asp Glu Leu Thr Asn
1               5

<210> SEQ ID NO 428
<211> LENGTH: 6
<212> TYPE: PRT
<213> ORGANISM: Homo sapiens

<400> SEQUENCE: 428

Trp Lys Tyr Ile Ala Tyr
1               5

-continued

<210> SEQ ID NO 429
<211> LENGTH: 82
<212> TYPE: PRT
<213> ORGANISM: Homo sapiens

<400> SEQUENCE: 429

Asn Phe Pro Glu Ile Thr Tyr Ser Leu Asp Gln Lys Leu His Ser Ile
1 5 10 15

Ile Asn Tyr Pro Lys Val Ser Ala Ser Val His Gln Tyr Asn Lys Glu
20 25 30

Gln Phe Ile Lys Trp Lys Gln Ser Ile Gly Gln Asn Tyr Ser Asn Val
35 40 45

Ile Ala Asn Phe Arg Trp His Gln Asp Trp Gln Lys Glu Pro Arg Lys
50 55 60

Tyr Glu Asn Ala Ile Asp Gln Trp Leu Lys Thr His Met Asn Pro Arg
65 70 75 80

Ala Val

<210> SEQ ID NO 430
<211> LENGTH: 12
<212> TYPE: PRT
<213> ORGANISM: Homo sapiens

<400> SEQUENCE: 430

Phe Pro Glu Ile Thr Tyr Ser Leu Asp Gln Lys Leu
1 5 10

<210> SEQ ID NO 431
<211> LENGTH: 18
<212> TYPE: PRT
<213> ORGANISM: Homo sapiens

<400> SEQUENCE: 431

Asn Tyr Pro Lys Val Ser Ala Ser Val His Gln Tyr Asn Lys Glu Gln
1 5 10 15

Phe Ile

<210> SEQ ID NO 432
<211> LENGTH: 9
<212> TYPE: PRT
<213> ORGANISM: Homo sapiens

<400> SEQUENCE: 432

Gly Gln Asn Tyr Ser Asn Val Ile Ala
1 5

<210> SEQ ID NO 433
<211> LENGTH: 7
<212> TYPE: PRT
<213> ORGANISM: Homo sapiens

<400> SEQUENCE: 433

Arg Trp His Gln Asp Trp Gln
1 5

<210> SEQ ID NO 434
<211> LENGTH: 8
<212> TYPE: PRT
<213> ORGANISM: Homo sapiens

<400> SEQUENCE: 434

-continued

```
Pro Arg Lys Tyr Glu Asn Ala Ile
  1               5


<210> SEQ ID NO 435
<211> LENGTH: 35
<212> TYPE: PRT
<213> ORGANISM: Homo sapiens

<400> SEQUENCE: 435

Arg Asn Ser Leu His Cys Tyr Asn Glu Gln Pro Pro Asn Ala Ser Gly
  1               5                  10                  15

Leu Ile Gln Trp Ser Ser Asp Leu Ile Pro Ile Ser Leu Gln Cys Gly
             20                  25                  30

Cys Ser Trp
         35


<210> SEQ ID NO 436
<211> LENGTH: 162
<212> TYPE: PRT
<213> ORGANISM: Homo sapiens
<220> FEATURE:
<221> NAME/KEY: SITE
<222> LOCATION: (1)
<223> OTHER INFORMATION: Xaa equals any of the naturally occurring L-
      amino acids
<221> NAME/KEY: SITE
<222> LOCATION: (33)
<223> OTHER INFORMATION: Xaa equals any of the naturally occurring L-
      amino acids
<221> NAME/KEY: SITE
<222> LOCATION: (48)
<223> OTHER INFORMATION: Xaa equals any of the naturally occurring L-
      amino acids

<400> SEQUENCE: 436

Xaa Leu Trp Asp Pro Gly Leu Pro Gly Val Cys Arg Cys Gly Ser Ile
  1               5                  10                  15

Val Leu Lys Ser Ala Phe Ser Val Gly Ile Thr Thr Ser Tyr Pro Glu
             20                  25                  30

Xaa Arg Leu Pro Ile Ile Phe Asn Lys Val Leu Leu Pro Arg Gly Xaa
         35                  40                  45

Ala Leu Gln Pro Cys His Arg Gly Ser Ser Ser Val Leu Ser Gln Gly
     50                  55                  60

Ile Tyr Tyr Phe Ser Tyr Asp Ile Thr Leu Ala Asn Lys His Leu Ala
 65                  70                  75                  80

Ile Gly Leu Val His Asn Gly Gln Tyr Arg Ile Lys Thr Phe Asp Ala
                 85                  90                  95

Asn Thr Gly Asn His Asp Val Ala Ser Gly Ser Thr Val Ile Tyr Leu
            100                 105                 110

Gln Pro Glu Asp Glu Val Trp Leu Glu Ile Phe Phe Thr Asp Gln Asn
        115                 120                 125

Gly Leu Phe Ser Asp Pro Gly Trp Ala Asp Ser Leu Phe Ser Gly Phe
    130                 135                 140

Leu Leu Tyr Val Asp Thr Asp Tyr Leu Asp Ser Ile Ser Glu Asp Asp
145                 150                 155                 160

Glu Leu


<210> SEQ ID NO 437
<211> LENGTH: 15
<212> TYPE: PRT
<213> ORGANISM: Homo sapiens
```

-continued

<400> SEQUENCE: 437

Gly Ser Ile Val Leu Lys Ser Ala Phe Ser Val Gly Ile Thr Thr
1 5 10 15

<210> SEQ ID NO 438
<211> LENGTH: 14
<212> TYPE: PRT
<213> ORGANISM: Homo sapiens

<400> SEQUENCE: 438

Gly Ile Tyr Tyr Phe Ser Tyr Asp Ile Thr Leu Ala Asn Lys
1 5 10

<210> SEQ ID NO 439
<211> LENGTH: 13
<212> TYPE: PRT
<213> ORGANISM: Homo sapiens

<400> SEQUENCE: 439

Asp Ser Leu Phe Ser Gly Phe Leu Leu Tyr Val Asp Thr
1 5 10

<210> SEQ ID NO 440
<211> LENGTH: 13
<212> TYPE: PRT
<213> ORGANISM: Homo sapiens

<400> SEQUENCE: 440

Asn His Asp Val Ala Ser Gly Ser Thr Val Ile Tyr Leu
1 5 10

<210> SEQ ID NO 441
<211> LENGTH: 14
<212> TYPE: PRT
<213> ORGANISM: Homo sapiens

<400> SEQUENCE: 441

Ser Asn Ser His Thr His Thr His Val Lys Ser Phe Leu Arg
1 5 10

<210> SEQ ID NO 442
<211> LENGTH: 10
<212> TYPE: PRT
<213> ORGANISM: Homo sapiens

<400> SEQUENCE: 442

Ile Thr Pro Leu Gly Leu Gly Ala Ala Asp
1 5 10

<210> SEQ ID NO 443
<211> LENGTH: 149
<212> TYPE: PRT
<213> ORGANISM: Homo sapiens

<400> SEQUENCE: 443

Thr Leu Arg Val Leu Gly Lys Val Pro Ala Val Cys Pro Trp Cys Ala
1 5 10 15

Leu Trp Arg Lys Ala Gly Met Asp Met Thr Tyr Ser Trp Leu Ser Arg
20 25 30

Gly Asp Ser Thr Tyr Thr Phe His Glu Gly Pro Val Leu Ser Thr Ser
35 40 45

Trp Arg Pro Gly Asp Ser Ala Leu Ser Tyr Thr Cys Arg Ala Asn Asn
50 55 60

```
Pro Ile Ser Asn Val Ser Ser Cys Pro Ile Pro Asp Gly Pro Phe Tyr
 65                  70                  75                  80

Ala Asp Pro Asn Tyr Ala Ser Glu Lys Pro Ser Thr Ala Phe Cys Leu
                 85                  90                  95

Leu Ala Lys Gly Leu Leu Ile Phe Leu Leu Leu Val Ile Leu Ala Met
            100                 105                 110

Gly Leu Trp Val Ile Arg Val Gln Lys Arg His Lys Met Pro Arg Met
        115                 120                 125

Lys Lys Leu Met Arg Asn Arg Met Lys Leu Arg Lys Glu Ala Lys Pro
    130                 135                 140

Gly Ser Ser Pro Ala
145


<210> SEQ ID NO 444
<211> LENGTH: 21
<212> TYPE: PRT
<213> ORGANISM: Homo sapiens

<400> SEQUENCE: 444

Ala Val Cys Pro Trp Cys Ala Leu Trp Arg Lys Ala Gly Met Asp Met
  1               5                  10                  15

Thr Tyr Ser Trp Leu
             20


<210> SEQ ID NO 445
<211> LENGTH: 24
<212> TYPE: PRT
<213> ORGANISM: Homo sapiens

<400> SEQUENCE: 445

Pro Gly Asp Ser Ala Leu Ser Tyr Thr Cys Arg Ala Asn Asn Pro Ile
  1               5                  10                  15

Ser Asn Val Ser Ser Cys Pro Ile
             20


<210> SEQ ID NO 446
<211> LENGTH: 24
<212> TYPE: PRT
<213> ORGANISM: Homo sapiens

<400> SEQUENCE: 446

Tyr Ala Ser Glu Lys Pro Ser Thr Ala Phe Cys Leu Leu Ala Lys Gly
  1               5                  10                  15

Leu Leu Ile Phe Leu Leu Leu Val
             20


<210> SEQ ID NO 447
<211> LENGTH: 26
<212> TYPE: PRT
<213> ORGANISM: Homo sapiens

<400> SEQUENCE: 447

Gln Lys Arg His Lys Met Pro Arg Met Lys Lys Leu Met Arg Asn Arg
  1               5                  10                  15

Met Lys Leu Arg Lys Glu Ala Lys Pro Gly
             20                  25


<210> SEQ ID NO 448
<211> LENGTH: 23
<212> TYPE: PRT
```

-continued

```
<213> ORGANISM: Homo sapiens

<400> SEQUENCE: 448

Ile Ala Trp Ser Gly Asn Ile Pro Ser Leu Leu Cys Leu Phe Glu His
  1               5                  10                  15

Asp Met Ser Phe Gln Asp Glu
             20


<210> SEQ ID NO 449
<211> LENGTH: 89
<212> TYPE: PRT
<213> ORGANISM: Homo sapiens
<220> FEATURE:
<221> NAME/KEY: SITE
<222> LOCATION: (60)
<223> OTHER INFORMATION: Xaa equals any of the naturally occurring L-
      amino acids
<221> NAME/KEY: SITE
<222> LOCATION: (75)
<223> OTHER INFORMATION: Xaa equals any of the naturally occurring L-
      amino acids

<400> SEQUENCE: 449

Glu Asn Phe Leu Leu Arg Tyr Lys Gly Pro Ser Asp His Trp Ile Gly
  1               5                  10                  15

Leu Ser Arg Glu Gln Gly Gln Pro Trp Lys Trp Ile Asn Gly Thr Glu
             20                  25                  30

Trp Thr Arg Gln Leu Val Met Lys Glu Asp Gly Ala Asn Leu Tyr Val
         35                  40                  45

Ala Lys Val Ser Gln Val Pro Arg Met Asn Pro Xaa Leu Ser Trp Val
     50                  55                  60

Leu Leu Cys Tyr Pro Gly Trp Ser Ala Val Xaa Thr Ile Val Ala His
 65                  70                  75                  80

Cys Ser Leu Asp Phe Pro Gly Ser Lys
                 85


<210> SEQ ID NO 450
<211> LENGTH: 63
<212> TYPE: PRT
<213> ORGANISM: Homo sapiens

<400> SEQUENCE: 450

Glu Leu Thr Ala Ile Lys Ser His Gln Tyr Val Leu Gln Ala Ala Cys
  1               5                  10                  15

Pro Glu Ser Trp Ile Gly Phe Gln Arg Lys Cys Phe Tyr Phe Ser Asp
             20                  25                  30

Asp Thr Lys Asn Trp Thr Ser Ser Gln Arg Phe Cys Asp Ser Gln Asp
         35                  40                  45

Ala Asp Leu Ala Gln Val Glu Ser Phe Gln Glu Leu Val Arg Lys
     50                  55                  60


<210> SEQ ID NO 451
<211> LENGTH: 17
<212> TYPE: PRT
<213> ORGANISM: Homo sapiens

<400> SEQUENCE: 451

Trp Ile Gly Leu Ser Arg Glu Gln Gly Gln Pro Trp Lys Trp Ile Asn
  1               5                  10                  15

Gly
```

-continued

<210> SEQ ID NO 452
<211> LENGTH: 12
<212> TYPE: PRT
<213> ORGANISM: Homo sapiens

<400> SEQUENCE: 452

Cys Pro Glu Ser Trp Ile Gly Phe Gln Arg Lys Cys
1 5 10

<210> SEQ ID NO 453
<211> LENGTH: 16
<212> TYPE: PRT
<213> ORGANISM: Homo sapiens

<400> SEQUENCE: 453

Asn Phe Leu Leu Arg Tyr Lys Gly Pro Ser Asp His Trp Ile Gly Leu
1 5 10 15

<210> SEQ ID NO 454
<211> LENGTH: 50
<212> TYPE: PRT
<213> ORGANISM: Homo sapiens

<400> SEQUENCE: 454

Ala Ser His Leu Arg Leu Leu Ser Ser Trp Asp Tyr Arg Phe Pro Ile
1 5 10 15

Leu Gly Ala Gly Glu Cys Ala Tyr Leu Asn Asp Lys Gly Ala Ser Ser
20 25 30

Ala Arg His Tyr Thr Glu Arg Lys Trp Ile Cys Ser Lys Ser Asp Ile
35 40 45

His Val
50

<210> SEQ ID NO 455
<211> LENGTH: 89
<212> TYPE: PRT
<213> ORGANISM: Homo sapiens
<220> FEATURE:
<221> NAME/KEY: SITE
<222> LOCATION: (60)
<223> OTHER INFORMATION: Xaa equals any of the naturally occurring L-amino acids
<221> NAME/KEY: SITE
<222> LOCATION: (75)
<223> OTHER INFORMATION: Xaa equals any of the naturally occurring L-amino acids

<400> SEQUENCE: 455

Glu Asn Phe Leu Leu Arg Tyr Lys Gly Pro Ser Asp His Trp Ile Gly
1 5 10 15

Leu Ser Arg Glu Gln Gly Gln Pro Trp Lys Trp Ile Asn Gly Thr Glu
20 25 30

Trp Thr Arg Gln Leu Val Met Lys Glu Asp Gly Ala Asn Leu Tyr Val
35 40 45

Ala Lys Val Ser Gln Val Pro Arg Met Asn Pro Xaa Leu Ser Trp Val
50 55 60

Leu Leu Cys Tyr Pro Gly Trp Ser Ala Val Xaa Thr Ile Val Ala His
65 70 75 80

Cys Ser Leu Asp Phe Pro Gly Ser Lys
85

<210> SEQ ID NO 456
<211> LENGTH: 76

-continued

<212> TYPE: PRT
<213> ORGANISM: Homo sapiens
<220> FEATURE:
<221> NAME/KEY: SITE
<222> LOCATION: (9)
<223> OTHER INFORMATION: Xaa equals any of the naturally occurring L-amino acids
<221> NAME/KEY: SITE
<222> LOCATION: (22)
<223> OTHER INFORMATION: Xaa equals any of the naturally occurring L-amino acids
<221> NAME/KEY: SITE
<222> LOCATION: (29)
<223> OTHER INFORMATION: Xaa equals any of the naturally occurring L-amino acids

<400> SEQUENCE: 456

```
Ser Trp Thr Ser Ser Leu Leu Asn Xaa Cys Leu His Ser Lys Glu His
  1               5                  10                  15

Ser Ile Lys Ala Thr Xaa Ile Trp Arg Leu Phe Phe Xaa Ile Leu Thr
             20                  25                  30

Ile Ile Leu Cys Gly Met Val Ala Ala Leu Ser Ala Ile Arg Ala Asn
         35                  40                  45

Cys His Gln Glu Pro Ser Val Cys Ser Ser Ser Cys Met Pro Arg Lys
     50                  55                  60

Leu Asp Trp Phe Ser Lys Lys Val Phe Leu Phe Phe
 65                  70                  75
```

<210> SEQ ID NO 457
<211> LENGTH: 39
<212> TYPE: PRT
<213> ORGANISM: Homo sapiens

<400> SEQUENCE: 457

```
Glu Gln Leu Glu Glu Leu Glu Leu Lys Lys Lys Asp Phe Ile Lys Ile
  1               5                  10                  15

Leu Glu Ser Val Gln Gly Asn Trp Arg Gln Asn Glu Asp Ser Gly Lys
             20                  25                  30

Gly Pro Gln Arg Ser Cys Leu
         35
```

<210> SEQ ID NO 458
<211> LENGTH: 19
<212> TYPE: PRT
<213> ORGANISM: Homo sapiens

<400> SEQUENCE: 458

```
Phe Trp Pro Glu Ser Lys Ile Gln Pro Tyr Lys Asp Met Phe Ser Cys
  1               5                  10                  15

Glu Ile Ile
```

<210> SEQ ID NO 459
<211> LENGTH: 58
<212> TYPE: PRT
<213> ORGANISM: Homo sapiens

<400> SEQUENCE: 459

```
Glu Gln Leu Glu Glu Leu Glu Leu Lys Lys Lys Asp Phe Ile Lys Ile
  1               5                  10                  15

Leu Glu Ser Val Gln Gly Asn Trp Arg Gln Asn Glu Asp Ser Gly Lys
             20                  25                  30

Gly Pro Gln Arg Ser Cys Leu His Ser Lys Glu His Ser Ile Lys Ala
         35                  40                  45
```

-continued

```
Thr Leu Ile Trp Arg Leu Phe Phe Leu Ile
     50                  55


<210> SEQ ID NO 460
<211> LENGTH: 36
<212> TYPE: PRT
<213> ORGANISM: Homo sapiens
<220> FEATURE:
<221> NAME/KEY: SITE
<222> LOCATION: (18)
<223> OTHER INFORMATION: Xaa equals any of the naturally occurring L-
      amino acids
<221> NAME/KEY: SITE
<222> LOCATION: (19)
<223> OTHER INFORMATION: Xaa equals any of the naturally occurring L-
      amino acids

<400> SEQUENCE: 460

Glu Asn Phe Leu Leu Arg Tyr Lys Gly Pro Ser Asp His Trp Ile Gly
  1               5                  10                  15

Leu Xaa Xaa Glu Gln Gly Gln Pro Trp Lys Trp Ile Asn Gly Thr Glu
             20                  25                  30

Trp Thr Arg Gln
         35


<210> SEQ ID NO 461
<211> LENGTH: 7
<212> TYPE: PRT
<213> ORGANISM: Homo sapiens

<400> SEQUENCE: 461

Arg His Glu Pro Asp Pro Met
  1               5


<210> SEQ ID NO 462
<211> LENGTH: 109
<212> TYPE: PRT
<213> ORGANISM: Homo sapiens
<220> FEATURE:
<221> NAME/KEY: SITE
<222> LOCATION: (24)
<223> OTHER INFORMATION: Xaa equals any of the naturally occurring L-
      amino acids
<221> NAME/KEY: SITE
<222> LOCATION: (25)
<223> OTHER INFORMATION: Xaa equals any of the naturally occurring L-
      amino acids
<221> NAME/KEY: SITE
<222> LOCATION: (31)
<223> OTHER INFORMATION: Xaa equals any of the naturally occurring L-
      amino acids

<400> SEQUENCE: 462

Leu Lys Gly Arg Glu Ala Gly Ala Gly Pro Gly Thr Ala Gly Ala Pro
  1               5                  10                  15

Gly Arg Glu Asp Ala Asn Gly Xaa Xaa Arg Gly Arg Gly Gly Xaa His
             20                  25                  30

Gln Leu Tyr Leu Trp Val Asp Asn Ile Pro Leu Ser Arg Pro Lys Arg
         35                  40                  45

Asn Leu Ser Arg Asp Phe Ser Asp Gly Val Leu Val Ala Glu Val Ile
     50                  55                  60

Lys Phe Tyr Phe Pro Lys Met Val Glu Met His Asn Tyr Val Gly Thr
 65                  70                  75                  80

Ser Ser Leu Gln Gln Lys Leu Ser Asn Trp Gly His Leu Asn Arg Lys
                 85                  90                  95
```

Val Leu Lys Arg Leu Asn Phe Ser Val Pro Asp Asp Val
100 105

<210> SEQ ID NO 463
<211> LENGTH: 25
<212> TYPE: PRT
<213> ORGANISM: Homo sapiens

<400> SEQUENCE: 463

Trp Val Asp Asn Ile Pro Leu Ser Arg Pro Lys Arg Asn Leu Ser Arg
1 5 10 15

Asp Phe Ser Asp Gly Val Leu Val Ala
20 25

<210> SEQ ID NO 464
<211> LENGTH: 25
<212> TYPE: PRT
<213> ORGANISM: Homo sapiens

<400> SEQUENCE: 464

Tyr Val Gly Thr Ser Ser Leu Gln Gln Lys Leu Ser Asn Trp Gly His
1 5 10 15

Leu Asn Arg Lys Val Leu Lys Arg Leu
20 25

<210> SEQ ID NO 465
<211> LENGTH: 97
<212> TYPE: PRT
<213> ORGANISM: Homo sapiens

<400> SEQUENCE: 465

Gly Ser Ala Trp Arg Arg Gly Arg Gly Ala Gly Ser Arg Ala Pro Ala
1 5 10 15

Pro Tyr Arg Ser Trp Leu Pro Arg Met Ala Val Ala Thr Trp Met Trp
20 25 30

Val Tyr Pro Arg Arg Pro Glu Val Lys Val Ser Arg Thr Pro Arg Glu
35 40 45

Gly Val Ser Ser Ala Gly Thr Gly Arg Arg Arg Leu Gly Leu Gln Arg
50 55 60

Ile Thr Gly Arg Cys Arg Ala Thr Pro Ala Ser Ser Ser Arg Ser Leu
65 70 75 80

Lys Arg Ser Arg Ser Cys Trp Pro Leu Lys Arg Pro Cys Arg Ser Cys
85 90 95

Arg

<210> SEQ ID NO 466
<211> LENGTH: 21
<212> TYPE: PRT
<213> ORGANISM: Homo sapiens

<400> SEQUENCE: 466

Trp Leu Pro Arg Met Ala Val Ala Thr Trp Met Trp Val Tyr Pro Arg
1 5 10 15

Arg Pro Glu Val Lys
20

<210> SEQ ID NO 467
<211> LENGTH: 23
<212> TYPE: PRT
<213> ORGANISM: Homo sapiens -continued

<400> SEQUENCE: 467

Cys Arg Ala Thr Pro Ala Ser Ser Ser Arg Ser Leu Lys Arg Ser Arg
1 5 10 15

Ser Cys Trp Pro Leu Lys Arg
20

<210> SEQ ID NO 468
<211> LENGTH: 347
<212> TYPE: PRT
<213> ORGANISM: Homo sapiens
<220> FEATURE:
<221> NAME/KEY: SITE
<222> LOCATION: (241)
<223> OTHER INFORMATION: Xaa equals any of the naturally occurring L-amino acids
<221> NAME/KEY: SITE
<222> LOCATION: (243)
<223> OTHER INFORMATION: Xaa equals any of the naturally occurring L-amino acids

<400> SEQUENCE: 468

Glu His Asn Thr Asp Phe Asn Gly Ala Ala Leu Ser Arg Asn Leu Gln
1 5 10 15

Thr Phe Arg Leu Ser Thr Pro Cys Ala Arg Arg Glu Gly Arg Leu Leu
20 25 30

Arg Ala His Arg Arg Cys Pro Pro Tyr Ser Trp Arg Ser His Ala Ser
35 40 45

Pro Leu Pro Leu Gln Leu Leu Arg Ser Pro Ser Pro Arg Trp Val Pro
50 55 60

Gly Lys Leu Pro Gly Gly Ala Gly Glu Pro Leu Ser Gly Pro Gly Gln
65 70 75 80

Ile Pro Pro Trp Leu Arg Ala Trp Gly Thr Ser Leu Asp Gly Asp Ala
85 90 95

Ala Val Leu Gly Ala Gly Arg Gly Pro Asp Ser Gly Gly Val Asp Arg
100 105 110

Ala Lys Gly Pro Pro Pro Lys Ala Gln Arg Arg Glu Met Gln Gly Arg
115 120 125

Ala Gln Gly Val Gly His Cys Phe Gly Gly Gln Ala Arg Ser Leu His
130 135 140

Val Ala Ser Gly Leu Trp Lys Ala Val His Ser Pro Asp Pro Asp Leu
145 150 155 160

Arg Ser Gly Arg Arg Arg Leu Ser Pro Gly Pro Ala Leu Leu Glu Phe
165 170 175

Leu Ser His Leu Leu His Ala His Pro Ser Gln Gly Arg Arg Ala Leu
180 185 190

Gly Pro Gln Gln Ala Arg Glu Ser Ser Gly Leu Arg Pro Pro Asn Gly
195 200 205

Leu Ser Ile Gly Gly Trp Val Arg Arg Gly Val Gly Ala Leu Ala Gly
210 215 220

Thr Arg Ala Ser Pro Arg Gly Pro Gly Arg Arg Ser Pro Leu Leu Thr
225 230 235 240

Xaa Arg Xaa Leu Glu Pro Pro Gly Glu Val Phe Asp Pro His Ile Leu
245 250 255

Glu Leu Glu Gln Val Leu Gln Ala Pro Tyr Leu His Leu Gln Asp Leu
260 265 270

His Gly Leu Leu Arg Gly Gln Gln Leu Leu Leu Leu Phe Ser Asp Leu
275 280 285

-continued

```
Glu Asp Glu Ala Gly Val Ala Leu Gln Arg Pro Val Ile Arg Trp Arg
    290                 295                 300

Pro Arg Arg Arg Arg Pro Val Pro Ala Glu Leu Thr Pro Ser Leu Gly
305                 310                 315                 320

Val Arg Asp Thr Phe Thr Ser Gly Leu Leu Gly Tyr Thr His Ile His
                325                 330                 335

Val Ala Thr Ala Ile Leu Gly Ser Gln Leu Leu
            340                 345


<210> SEQ ID NO 469
<211> LENGTH: 26
<212> TYPE: PRT
<213> ORGANISM: Homo sapiens

<400> SEQUENCE: 469

Thr Asp Phe Asn Gly Ala Ala Leu Ser Arg Asn Leu Gln Thr Phe Arg
  1               5                  10                  15

Leu Ser Thr Pro Cys Ala Arg Arg Glu Gly
             20                  25


<210> SEQ ID NO 470
<211> LENGTH: 25
<212> TYPE: PRT
<213> ORGANISM: Homo sapiens

<400> SEQUENCE: 470

Arg Cys Pro Pro Tyr Ser Trp Arg Ser His Ala Ser Pro Leu Pro Leu
  1               5                  10                  15

Gln Leu Leu Arg Ser Pro Ser Pro Arg
             20                  25


<210> SEQ ID NO 471
<211> LENGTH: 24
<212> TYPE: PRT
<213> ORGANISM: Homo sapiens

<400> SEQUENCE: 471

Gly Ala Gly Glu Pro Leu Ser Gly Pro Gly Gln Ile Pro Pro Trp Leu
  1               5                  10                  15

Arg Ala Trp Gly Thr Ser Leu Asp
             20


<210> SEQ ID NO 472
<211> LENGTH: 30
<212> TYPE: PRT
<213> ORGANISM: Homo sapiens

<400> SEQUENCE: 472

Leu Gly Ala Gly Arg Gly Pro Asp Ser Gly Gly Val Asp Arg Ala Lys
  1               5                  10                  15

Gly Pro Pro Pro Lys Ala Gln Arg Arg Glu Met Gln Gly Arg
             20                  25                  30


<210> SEQ ID NO 473
<211> LENGTH: 23
<212> TYPE: PRT
<213> ORGANISM: Homo sapiens

<400> SEQUENCE: 473

Gln Ala Arg Ser Leu His Val Ala Ser Gly Leu Trp Lys Ala Val His
  1               5                  10                  15
```

-continued

```
Ser Pro Asp Pro Asp Leu Arg
            20


<210> SEQ ID NO 474
<211> LENGTH: 20
<212> TYPE: PRT
<213> ORGANISM: Homo sapiens

<400> SEQUENCE: 474

His Pro Ser Gln Gly Arg Arg Ala Leu Gly Pro Gln Gln Ala Arg Glu
  1               5                  10                  15

Ser Ser Gly Leu
            20


<210> SEQ ID NO 475
<211> LENGTH: 27
<212> TYPE: PRT
<213> ORGANISM: Homo sapiens

<400> SEQUENCE: 475

Ile Gly Gly Trp Val Arg Arg Gly Val Gly Ala Leu Ala Gly Thr Arg
  1               5                  10                  15

Ala Ser Pro Arg Gly Pro Gly Arg Arg Ser Pro
            20                  25


<210> SEQ ID NO 476
<211> LENGTH: 25
<212> TYPE: PRT
<213> ORGANISM: Homo sapiens

<400> SEQUENCE: 476

Glu Pro Pro Gly Glu Val Phe Asp Pro His Ile Leu Glu Leu Glu Gln
  1               5                  10                  15

Val Leu Gln Ala Pro Tyr Leu His Leu
            20                  25


<210> SEQ ID NO 477
<211> LENGTH: 28
<212> TYPE: PRT
<213> ORGANISM: Homo sapiens

<400> SEQUENCE: 477

Val Pro Ala Glu Leu Thr Pro Ser Leu Gly Val Arg Asp Thr Phe Thr
  1               5                  10                  15

Ser Gly Leu Leu Gly Tyr Thr His Ile His Val Ala
            20                  25


<210> SEQ ID NO 478
<211> LENGTH: 187
<212> TYPE: PRT
<213> ORGANISM: Homo sapiens

<400> SEQUENCE: 478

Ala Lys Asn Ser Gln Lys Glu Glu Asn Pro Glu His Val Glu Ile Gln
  1               5                  10                  15

Lys Met Met Asp Ser Leu Phe Leu Lys Leu Asp Ala Leu Ser Asn Phe
            20                  25                  30

His Phe Ile Pro Lys Pro Pro Val Pro Glu Ile Lys Val Val Ser Asn
        35                  40                  45

Leu Pro Ala Ile Thr Met Glu Glu Val Ala Pro Val Ser Val Ser Asp
    50                  55                  60
```

-continued

```
Ala Ala Leu Leu Ala Pro Glu Glu Ile Lys Glu Lys Asn Lys Ala Gly
 65                  70                  75                  80

Asp Ile Lys Thr Ala Ala Glu Lys Thr Ala Thr Asp Lys Lys Arg Glu
                 85                  90                  95

Arg Arg Lys Lys Lys Tyr Gln Lys Arg Met Lys Ile Lys Glu Lys Glu
            100                 105                 110

Lys Arg Arg Lys Leu Leu Glu Lys Ser Ser Val Asp Gln Ala Gly Lys
        115                 120                 125

Tyr Ser Lys Thr Val Ala Ser Glu Lys Leu Lys Gln Leu Thr Lys Thr
    130                 135                 140

Gly Lys Ala Ser Phe Ile Lys Val Arg Thr Arg Glu Arg Lys Leu Leu
145                 150                 155                 160

Lys Gly Thr Phe Val Gly Glu Val Asp Ser Lys Cys Trp Val Thr Gly
                165                 170                 175

Met Ser Glu Pro Ala Asp Ser Pro Pro Val Gly
            180                 185


<210> SEQ ID NO 479
<211> LENGTH: 51
<212> TYPE: PRT
<213> ORGANISM: Homo sapiens

<400> SEQUENCE: 479

Leu Gln Asp Glu Gly Lys Asp Lys Ala Leu Lys Ser Ser Gln Ala Phe
  1               5                  10                  15

Phe Ser Lys Leu Gln Asp Gln Val Lys Met Gln Ile Asn Asp Ala Lys
             20                  25                  30

Lys Thr Glu Lys Lys Lys Lys Lys Arg Gln Asp Ile Ser Val His Lys
         35                  40                  45

Leu Lys Leu
     50


<210> SEQ ID NO 480
<211> LENGTH: 29
<212> TYPE: PRT
<213> ORGANISM: Homo sapiens

<400> SEQUENCE: 480

Asp Glu Gly Lys Asp Lys Ala Leu Lys Ser Ser Gln Ala Phe Phe Ser
  1               5                  10                  15

Lys Leu Gln Asp Gln Val Lys Met Gln Ile Asn Asp Ala
             20                  25


<210> SEQ ID NO 481
<211> LENGTH: 28
<212> TYPE: PRT
<213> ORGANISM: Homo sapiens

<400> SEQUENCE: 481

Glu Glu Asn Pro Glu His Val Glu Ile Gln Lys Met Met Asp Ser Leu
  1               5                  10                  15

Phe Leu Lys Leu Asp Ala Leu Ser Asn Phe His Phe
             20                  25


<210> SEQ ID NO 482
<211> LENGTH: 13
<212> TYPE: PRT
<213> ORGANISM: Homo sapiens
```

-continued

<400> SEQUENCE: 482

```
Ser Asn Leu Pro Ala Ile Thr Met Glu Glu Val Ala Pro
  1               5                  10
```

<210> SEQ ID NO 483
<211> LENGTH: 31
<212> TYPE: PRT
<213> ORGANISM: Homo sapiens

<400> SEQUENCE: 483

```
Ser Ser Val Asp Gln Ala Gly Lys Tyr Ser Lys Thr Val Ala Ser Glu
  1               5                  10                  15

Lys Leu Lys Gln Leu Thr Lys Thr Gly Lys Ala Ser Phe Ile Lys
             20                  25                  30
```

<210> SEQ ID NO 484
<211> LENGTH: 23
<212> TYPE: PRT
<213> ORGANISM: Homo sapiens

<400> SEQUENCE: 484

```
Val Ser Val Ser Asp Ala Ala Leu Leu Ala Pro Glu Glu Ile Lys Glu
  1               5                  10                  15

Lys Asn Lys Ala Gly Asp Ile
             20
```

<210> SEQ ID NO 485
<211> LENGTH: 11
<212> TYPE: PRT
<213> ORGANISM: Homo sapiens

<400> SEQUENCE: 485

```
Val Leu Glu Val Met Val Thr Val Ala Pro Lys
  1               5                  10
```

<210> SEQ ID NO 486
<211> LENGTH: 35
<212> TYPE: PRT
<213> ORGANISM: Homo sapiens

<400> SEQUENCE: 486

```
Leu Gln Asp Glu Gly Lys Asp Lys Ala Leu Lys Ser Ser Gln Ala Phe
  1               5                  10                  15

Phe Ser Lys Leu Gln Asp Gln Val Lys Met Gln Ile Asn Asp Ala Lys
             20                  25                  30

Lys Thr Glu
         35
```

<210> SEQ ID NO 487
<211> LENGTH: 34
<212> TYPE: PRT
<213> ORGANISM: Homo sapiens

<400> SEQUENCE: 487

```
His Glu Ala Ala Gln Gly Ala Val Cys Arg Gly Gln Gly Ala Pro Ala
  1               5                  10                  15

Thr Asn Pro Gln Ala Pro Val Ala Ala Ala Ala Arg Val Ala Arg Arg
             20                  25                  30

Val Asn
```

<210> SEQ ID NO 488

-continued

<211> LENGTH: 255
<212> TYPE: PRT
<213> ORGANISM: Homo sapiens

<400> SEQUENCE: 488

```
Lys Ile Pro Ser Ala Asn Arg Arg Ala Thr Arg Cys Leu Gly Cys Asp
  1               5                  10                  15

His Gln Asn Phe Val Lys Val Arg Asn Lys His Lys Gly Lys Pro Thr
             20                  25                  30

Phe Met Glu Glu Val Leu Glu His Leu Pro Gly Lys Thr Gln Asp Glu
         35                  40                  45

Val Gln Gln His Glu Lys Trp Tyr Gln Lys Phe Leu Ala Leu Glu Glu
     50                  55                  60

Arg Lys Lys Glu Ser Ile Gln Ile Trp Lys Thr Lys Lys Gln Gln Lys
 65                  70                  75                  80

Arg Glu Glu Ile Phe Lys Leu Lys Glu Lys Ala Asp Asn Thr Pro Val
                 85                  90                  95

Leu Phe His Asn Lys Gln Glu Asp Asn Gln Lys Gln Lys Glu Glu Gln
            100                 105                 110

Arg Lys Lys Gln Lys Leu Ala Val Glu Ala Trp Lys Lys Gln Lys Ser
        115                 120                 125

Ile Glu Met Ser Met Lys Cys Ala Ser Gln Leu Lys Lys Lys Lys Lys
    130                 135                 140

Lys Lys Lys Lys Asn Gln Lys Glu Arg Gln Arg Gln Phe Lys Leu Lys
145                 150                 155                 160

Leu Leu Leu Glu Ser Tyr Thr Gln Gln Lys Lys Glu Gln Glu Glu Phe
                165                 170                 175

Leu Arg Leu Glu Lys Glu Ile Arg Glu Lys Ala Glu Lys Ala Glu Lys
            180                 185                 190

Arg Lys Asn Ala Ala Asp Glu Ile Ser Arg Phe Gln Glu Arg Asp Leu
        195                 200                 205

His Lys Leu Glu Leu Lys Ile Leu Asp Arg Gln Ala Lys Glu Asp Glu
    210                 215                 220

Lys Ser Gln Lys Gln Arg Arg Leu Ala Lys Leu Lys Glu Lys Val Glu
225                 230                 235                 240

Asn Asn Val Ser Arg Asp Pro Ser Arg Leu Tyr Lys Pro Thr Lys
                245                 250                 255
```

<210> SEQ ID NO 489
<211> LENGTH: 24
<212> TYPE: PRT
<213> ORGANISM: Homo sapiens

<400> SEQUENCE: 489

```
Val Lys Val Arg Asn Lys His Lys Gly Lys Pro Thr Phe Met Glu Glu
  1               5                  10                  15

Val Leu Glu His Leu Pro Gly Lys
             20
```

<210> SEQ ID NO 490
<211> LENGTH: 23
<212> TYPE: PRT
<213> ORGANISM: Homo sapiens

<400> SEQUENCE: 490

```
Gln His Glu Lys Trp Tyr Gln Lys Phe Leu Ala Leu Glu Glu Arg Lys
  1               5                  10                  15
```

-continued

Lys Glu Ser Ile Gln Ile Trp
20

<210> SEQ ID NO 491
<211> LENGTH: 31
<212> TYPE: PRT
<213> ORGANISM: Homo sapiens

<400> SEQUENCE: 491

Phe Lys Leu Lys Glu Lys Ala Asp Asn Thr Pro Val Leu Phe His Asn
1 5 10 15

Lys Gln Glu Asp Asn Gln Lys Gln Lys Glu Glu Gln Arg Lys Lys
20 25 30

<210> SEQ ID NO 492
<211> LENGTH: 36
<212> TYPE: PRT
<213> ORGANISM: Homo sapiens

<400> SEQUENCE: 492

Phe Leu Arg Leu Glu Lys Glu Ile Arg Glu Lys Ala Glu Lys Ala Glu
1 5 10 15

Lys Arg Lys Asn Ala Ala Asp Glu Ile Ser Arg Phe Gln Glu Arg Asp
20 25 30

Leu His Lys Leu
35

<210> SEQ ID NO 493
<211> LENGTH: 24
<212> TYPE: PRT
<213> ORGANISM: Homo sapiens

<400> SEQUENCE: 493

Lys Gln Arg Arg Leu Ala Lys Leu Lys Glu Lys Val Glu Asn Asn Val
1 5 10 15

Ser Arg Asp Pro Ser Arg Leu Tyr
20

<210> SEQ ID NO 494
<211> LENGTH: 18
<212> TYPE: PRT
<213> ORGANISM: Homo sapiens

<400> SEQUENCE: 494

Val Lys Pro Pro Asp Gln Ser Cys Asn His Trp Arg Asp Glu Gln Cys
1 5 10 15

Leu Val

<210> SEQ ID NO 495
<211> LENGTH: 20
<212> TYPE: PRT
<213> ORGANISM: Homo sapiens

<400> SEQUENCE: 495

Met Ala Ile Pro Ala Phe Ser Ser Cys Gln Gln Ile Ser Ser Ala Ala
1 5 10 15

Ala Leu Gln Ile
20

<210> SEQ ID NO 496
<211> LENGTH: 14
<212> TYPE: PRT

<213> ORGANISM: Homo sapiens

<400> SEQUENCE: 496

Cys Asn Gly Pro Phe Lys His Phe Ser Phe Thr Val Ser Thr
1 5 10

<210> SEQ ID NO 497
<211> LENGTH: 18
<212> TYPE: PRT
<213> ORGANISM: Homo sapiens

<400> SEQUENCE: 497

Ile Arg His Glu Arg Leu Trp Ala Glu Leu Ala Leu Leu Thr Gly Arg
1 5 10 15

Asn Glu

<210> SEQ ID NO 498
<211> LENGTH: 59
<212> TYPE: PRT
<213> ORGANISM: Homo sapiens

<400> SEQUENCE: 498

Gly Thr Glu Ser Pro Met Val Met Cys Cys Arg Glu Val Ser Gln Ser
1 5 10 15

Glu Asn Cys Leu Phe Leu Asp Thr Thr Phe Arg Phe Ile Phe Gly Lys
20 25 30

Thr Phe Thr Asn His Asp Tyr Ile Ser Ile His Phe Tyr Phe Leu Lys
35 40 45

Ala Phe Leu Phe Ser Phe Phe Tyr Ser Asn Val
50 55

<210> SEQ ID NO 499
<211> LENGTH: 15
<212> TYPE: PRT
<213> ORGANISM: Homo sapiens

<400> SEQUENCE: 499

Ile Arg His Glu Glu Lys Gly Gly Lys Ala Gln Arg Trp Ala Glu
1 5 10 15

<210> SEQ ID NO 500
<211> LENGTH: 11
<212> TYPE: PRT
<213> ORGANISM: Homo sapiens

<400> SEQUENCE: 500

Cys Arg Trp Arg Pro Glu Ser Ala Ala Pro Cys
1 5 10

<210> SEQ ID NO 501
<211> LENGTH: 12
<212> TYPE: PRT
<213> ORGANISM: Homo sapiens

<400> SEQUENCE: 501

Thr Arg Pro Gly Arg Gly Ala Gln Ala Pro Val Lys
1 5 10

<210> SEQ ID NO 502
<211> LENGTH: 21
<212> TYPE: PRT
<213> ORGANISM: Homo sapiens -continued

<400> SEQUENCE: 502

Met Val Ser Trp Met Ile Ser Arg Ala Val Val Leu Val Phe Gly Met
1 5 10 15

Leu Tyr Pro Ala Tyr
20

<210> SEQ ID NO 503
<211> LENGTH: 17
<212> TYPE: PRT
<213> ORGANISM: Homo sapiens

<400> SEQUENCE: 503

Gly Met Leu Tyr Pro Ala Tyr Tyr Ser Tyr Lys Ala Val Lys Thr Lys
1 5 10 15

Asn

<210> SEQ ID NO 504
<211> LENGTH: 17
<212> TYPE: PRT
<213> ORGANISM: Homo sapiens

<400> SEQUENCE: 504

Glu Tyr Val Arg Trp Met Met Tyr Trp Ile Val Phe Ala Leu Tyr Thr
1 5 10 15

Val

<210> SEQ ID NO 505
<211> LENGTH: 17
<212> TYPE: PRT
<213> ORGANISM: Homo sapiens

<400> SEQUENCE: 505

Tyr Pro Ala Tyr Tyr Ser Tyr Lys Ala Val Lys Thr Lys Asn Val Lys
1 5 10 15

Glu

<210> SEQ ID NO 506
<211> LENGTH: 13
<212> TYPE: PRT
<213> ORGANISM: Homo sapiens

<400> SEQUENCE: 506

Val Ala Trp Phe Pro Leu Tyr Tyr Glu Leu Lys Ile Ala
1 5 10

<210> SEQ ID NO 507
<211> LENGTH: 186
<212> TYPE: PRT
<213> ORGANISM: Homo sapiens
<220> FEATURE:
<221> NAME/KEY: SITE
<222> LOCATION: (181)
<223> OTHER INFORMATION: Xaa equals any of the naturally occurring L-
amino acids

<400> SEQUENCE: 507

Met Val Ser Trp Met Ile Ser Arg Ala Val Val Leu Val Phe Gly Met
1 5 10 15

Leu Tyr Pro Ala Tyr Tyr Ser Tyr Lys Ala Val Lys Thr Lys Asn Val
20 25 30

Lys Glu Tyr Val Arg Trp Met Met Tyr Trp Ile Val Phe Ala Leu Tyr
35 40 45

-continued

```
Thr Val Ile Glu Thr Val Ala Asp Gln Thr Val Ala Trp Phe Pro Leu
     50                  55                  60

Tyr Tyr Glu Leu Lys Ile Ala Phe Val Ile Trp Leu Leu Ser Pro Tyr
 65                  70                  75                  80

Thr Lys Gly Ala Ser Leu Ile Tyr Arg Lys Phe Leu His Pro Leu Leu
                 85                  90                  95

Ser Ser Lys Glu Arg Glu Ile Asp Asp Tyr Ile Val Gln Ala Lys Glu
            100                 105                 110

Arg Gly Tyr Glu Thr Met Val Asn Phe Gly Arg Gln Gly Leu Asn Leu
        115                 120                 125

Ala Ala Thr Ala Ala Val Thr Ala Ala Val Lys Ser Gln Gly Ala Ile
    130                 135                 140

Thr Glu Arg Leu Arg Ser Phe Ser Met His Asp Leu Thr Thr Ile Gln
145                 150                 155                 160

Gly Asp Glu Pro Val Gly Gln Arg Pro Tyr Gln Pro Leu Pro Glu Ala
                165                 170                 175

Lys Lys Lys Ser Xaa Gln Pro Pro Val Asn
            180                 185
```

<210> SEQ ID NO 508
<211> LENGTH: 15
<212> TYPE: PRT
<213> ORGANISM: Homo sapiens

<400> SEQUENCE: 508

```
Gln Pro Tyr Gln Val Leu Pro Ser Arg Gln Val Phe Ala Leu Ile
  1               5                  10                  15
```

<210> SEQ ID NO 509
<211> LENGTH: 24
<212> TYPE: PRT
<213> ORGANISM: Homo sapiens

<400> SEQUENCE: 509

```
Val Phe Ser Cys Ile Tyr Gly Glu Gly Tyr Ser Asn Ala His Glu Ser
  1               5                  10                  15

Lys Gln Met Tyr Cys Val Phe Asn
             20
```

<210> SEQ ID NO 510
<211> LENGTH: 18
<212> TYPE: PRT
<213> ORGANISM: Homo sapiens

<400> SEQUENCE: 510

```
Arg Asn Glu Asp Ala Cys Arg Tyr Gly Ser Ala Ile Gly Val Leu Ala
  1               5                  10                  15

Phe Leu
```

<210> SEQ ID NO 511
<211> LENGTH: 17
<212> TYPE: PRT
<213> ORGANISM: Homo sapiens

<400> SEQUENCE: 511

```
Leu Val Val Asp Ala Tyr Phe Pro Gln Ile Ser Asn Ala Thr Asp Arg
  1               5                  10                  15

Lys
```

-continued

<210> SEQ ID NO 512
<211> LENGTH: 25
<212> TYPE: PRT
<213> ORGANISM: Homo sapiens

<400> SEQUENCE: 512

Ser Ala Leu Trp Thr Phe Leu Trp Phe Val Gly Phe Cys Phe Leu Thr
1 5 10 15

Asn Gln Trp Ala Val Thr Asn Pro Lys
20 25

<210> SEQ ID NO 513
<211> LENGTH: 82
<212> TYPE: PRT
<213> ORGANISM: Homo sapiens

<400> SEQUENCE: 513

Leu Asn Ile Asp Ser Phe Asp Tyr Gly Lys Phe Glu Ser Leu Leu Ala
1 5 10 15

Lys Gln His Tyr Lys Phe Ser Phe Leu Leu Pro Leu Ala Ala Gly Thr
20 25 30

Glu Arg Cys Lys Trp Trp Leu Lys Ile Glu Glu Ala Ser Ser Asp Gln
35 40 45

Cys Gly Cys Trp Phe Leu Val Lys Cys Val Pro Lys Pro Pro Ser Pro
50 55 60

Cys Arg Gln Pro Pro Thr Gln Val Ser Lys Ile Gly His Ala Pro Phe
65 70 75 80

Phe Leu

<210> SEQ ID NO 514
<211> LENGTH: 13
<212> TYPE: PRT
<213> ORGANISM: Homo sapiens

<400> SEQUENCE: 514

Ser Leu Gln Tyr Arg Ile Arg Ile Pro Gly Arg Pro Thr
1 5 10

<210> SEQ ID NO 515
<211> LENGTH: 22
<212> TYPE: PRT
<213> ORGANISM: Homo sapiens

<400> SEQUENCE: 515

Asp Leu Val Thr Tyr Thr Ser Ser Leu Gln Tyr Arg Ile Arg Ile Pro
1 5 10 15

Gly Arg Pro Thr Arg Pro
20

<210> SEQ ID NO 516
<211> LENGTH: 36
<212> TYPE: PRT
<213> ORGANISM: Homo sapiens

<400> SEQUENCE: 516

Leu Gly Asn Lys Lys Tyr Ile Asn Ile Arg Cys Leu Glu Met Gln Val
1 5 10 15

Thr Leu Lys Ile Leu Cys Glu Ile Glu Lys Lys Glu Arg Arg Gly Thr
20 25 30

His Cys Leu Val

35

<210> SEQ ID NO 517
<211> LENGTH: 22
<212> TYPE: PRT
<213> ORGANISM: Homo sapiens

<400> SEQUENCE: 517

Val Lys Thr Ala Glu Cys Tyr Ser Ile Pro Leu Gly Ser Cys Pro Val
1 5 10 15

Asn Ile Gln Arg Val Arg
20

<210> SEQ ID NO 518
<211> LENGTH: 60
<212> TYPE: PRT
<213> ORGANISM: Homo sapiens

<400> SEQUENCE: 518

Leu Phe Tyr Leu Leu Thr Cys Ser Cys Ala Pro Gly His Leu Ala Phe
1 5 10 15

Val Cys Ser Gln Cys Leu Pro Phe Asp Met Gly Lys Glu Leu Trp Pro
20 25 30

Lys Ser Pro Ser Ser Cys Thr Ser Thr Ser Val Ala Gln Gly Trp Gly
35 40 45

Gly Arg Gly Arg Pro Ser Pro Tyr Ile Cys Val Val
50 55 60

<210> SEQ ID NO 519
<211> LENGTH: 61
<212> TYPE: PRT
<213> ORGANISM: Homo sapiens

<400> SEQUENCE: 519

Ile Gln Gly Ser Arg Leu Pro Pro Leu Pro Ala Pro Leu His Pro Leu
1 5 10 15

Pro Leu Ile Tyr Leu Leu Leu Gly Ser Pro Ala Gln Ser Trp Leu Leu
20 25 30

Val Pro Ser Trp Gly His Pro Ser Thr Leu Thr Leu Thr Met Ala Ala
35 40 45

Glu His Gln Ala Trp Pro Ser Gly Phe His Gly Asp His
50 55 60

<210> SEQ ID NO 520
<211> LENGTH: 23
<212> TYPE: PRT
<213> ORGANISM: Homo sapiens

<400> SEQUENCE: 520

Val Asp Pro Pro Gly Cys Arg Asn Ser Ala Arg Gly Cys Thr Arg Leu
1 5 10 15

Leu Arg Gly Ser Ser Lys Ile
20

<210> SEQ ID NO 521
<211> LENGTH: 12
<212> TYPE: PRT
<213> ORGANISM: Homo sapiens

<400> SEQUENCE: 521

Ile Thr Leu Cys Leu Val Cys Ile Val Ala Asn Ala

-continued 1 5 10

<210> SEQ ID NO 522
<211> LENGTH: 24
<212> TYPE: PRT
<213> ORGANISM: Homo sapiens

<400> SEQUENCE: 522

Val Thr Ala Tyr Gln Asn Gln Gln Ile Thr Arg Leu Lys Ile Asp Arg
1 5 10 15

Asn Pro Phe Ala Lys Gly Phe Arg
20

<210> SEQ ID NO 523
<211> LENGTH: 16
<212> TYPE: PRT
<213> ORGANISM: Homo sapiens

<400> SEQUENCE: 523

Gly Thr Ala Thr Val Thr Ala Tyr Gln Asn Gln Gln Ile Thr Arg Leu
1 5 10 15

<210> SEQ ID NO 524
<211> LENGTH: 24
<212> TYPE: PRT
<213> ORGANISM: Homo sapiens

<400> SEQUENCE: 524

Lys Ile Asp Arg Asn Pro Phe Ala Lys Gly Phe Arg Asp Ser Gly Arg
1 5 10 15

Asn Arg Met Gly Leu Glu Ala Leu
20

<210> SEQ ID NO 525
<211> LENGTH: 21
<212> TYPE: PRT
<213> ORGANISM: Homo sapiens

<400> SEQUENCE: 525

Ser Thr Leu Leu Gln Val Leu Gly Met Ala Phe Leu Pro Leu Thr Leu
1 5 10 15

Thr Phe Cys Leu Ala
20

<210> SEQ ID NO 526
<211> LENGTH: 30
<212> TYPE: PRT
<213> ORGANISM: Homo sapiens

<400> SEQUENCE: 526

Val Glu Ser Tyr Ala Phe Trp Arg Pro Ser Leu Arg Thr Leu Thr Phe
1 5 10 15

Glu Asp Ile Pro Gly Ile Pro Lys Gln Gly Asn Ala Ser Ser
20 25 30

<210> SEQ ID NO 527
<211> LENGTH: 14
<212> TYPE: PRT
<213> ORGANISM: Homo sapiens

<400> SEQUENCE: 527

Gln Ala Gln Ser Asp Cys Ser Cys Ser Thr Val Ser Pro Gly
1 5 10

<210> SEQ ID NO 528
<211> LENGTH: 24
<212> TYPE: PRT
<213> ORGANISM: Homo sapiens

<400> SEQUENCE: 528

Val Leu Ala Gly Ile Val Met Gly Asp Leu Val Leu Thr Val Leu Ile
1 5 10 15

Ala Leu Ala Val Tyr Phe Leu Gly
20

<210> SEQ ID NO 529
<211> LENGTH: 37
<212> TYPE: PRT
<213> ORGANISM: Homo sapiens

<400> SEQUENCE: 529

Val Pro Arg Gly Arg Gly Ala Ala Glu Ala Thr Arg Lys Gln Arg Ile
1 5 10 15

Thr Glu Thr Glu Ser Pro Tyr Gln Glu Leu Gln Gly Gln Arg Ser Asp
20 25 30

Val Tyr Ser Asp Leu
35

<210> SEQ ID NO 530
<211> LENGTH: 22
<212> TYPE: PRT
<213> ORGANISM: Homo sapiens

<400> SEQUENCE: 530

Glu Thr Glu Ser Pro Tyr Gln Glu Leu Gln Gly Gln Arg Ser Asp Val
1 5 10 15

Tyr Ser Asp Leu Asn Thr
20

<210> SEQ ID NO 531
<211> LENGTH: 28
<212> TYPE: PRT
<213> ORGANISM: Homo sapiens

<400> SEQUENCE: 531

Phe Leu Cys Ala Leu Ser Pro Leu Gly Gln Leu Leu Gln Asp Arg Tyr
1 5 10 15

Gly Trp Arg Gly Gly Phe Leu Ile Leu Gly Gly Leu
20 25

<210> SEQ ID NO 532
<211> LENGTH: 27
<212> TYPE: PRT
<213> ORGANISM: Homo sapiens
<220> FEATURE:
<221> NAME/KEY: SITE
<222> LOCATION: (22)
<223> OTHER INFORMATION: Xaa equals any of the naturally occurring L-amino acids

<400> SEQUENCE: 532

Leu Leu Asn Cys Cys Val Cys Ala Ala Leu Met Arg Pro Leu Val Val
1 5 10 15

Thr Ala Gln Pro Gly Xaa Gly Pro Pro Arg Pro
20 25

-continued

<210> SEQ ID NO 533
<211> LENGTH: 25
<212> TYPE: PRT
<213> ORGANISM: Homo sapiens
<220> FEATURE:
<221> NAME/KEY: SITE
<222> LOCATION: (5)
<223> OTHER INFORMATION: Xaa equals any of the naturally occurring L-
amino acids

<400> SEQUENCE: 533

```
Ser Arg Arg Leu Xaa Asp Leu Ser Val Phe Arg Asp Arg Gly Phe Val
  1               5                  10                  15

Leu Tyr Ala Val Ala Ala Ser Val Met
             20                  25
```

<210> SEQ ID NO 534
<211> LENGTH: 57
<212> TYPE: PRT
<213> ORGANISM: Homo sapiens

<400> SEQUENCE: 534

```
Met Met Ala Thr Pro Ser Thr Arg Pro Pro Pro Pro Ala Ala Ser Thr
  1               5                  10                  15

Thr Ser Ala Thr Ala Pro Ala Leu Pro Pro Arg Pro Pro Trp Pro Trp
             20                  25                  30

Pro Pro Ser Ser Trp Pro Pro Ser Gly Val Ser Ser Lys Ala Pro Glu
         35                  40                  45

Ala Asp Pro Leu Lys Asn Lys Ala Leu
     50                  55
```

<210> SEQ ID NO 535
<211> LENGTH: 76
<212> TYPE: PRT
<213> ORGANISM: Homo sapiens

<400> SEQUENCE: 535

```
Leu Leu Leu Thr Ser Pro Leu Pro Arg Cys Pro Pro Ala Cys Ser His
  1               5                  10                  15

Asp Ala Pro Ala His Pro Asp Pro Gly Gly Pro His Gly Leu Thr Ser
             20                  25                  30

Gly Pro Gly Leu Gly Leu Pro Arg Val Cys Leu Gln Arg Arg Gln Leu
         35                  40                  45

Leu Gln Pro His Ala Leu Pro Gly Tyr Gly Cys Leu Leu His Asp His
     50                  55                  60

Ala His Leu Leu His Pro His Gln Asp Glu Gly Gln
 65                  70                  75
```

<210> SEQ ID NO 536
<211> LENGTH: 56
<212> TYPE: PRT
<213> ORGANISM: Homo sapiens

<400> SEQUENCE: 536

```
Trp Leu Leu Gln Ala Arg Val His His Leu Leu Leu Pro Val Arg Pro
  1               5                  10                  15

Leu Gln Arg His Arg Pro Cys His Pro Gly His Pro Gly Pro Gly Pro
             20                  25                  30

His Pro Pro Gly His Pro Leu Gly Ser Pro Leu Lys Pro Pro Arg Gln
         35                  40                  45
```

-continued

```
Thr His Ser Arg Thr Lys Leu Ser
     50                  55


<210> SEQ ID NO 537
<211> LENGTH: 52
<212> TYPE: PRT
<213> ORGANISM: Homo sapiens

<400> SEQUENCE: 537

Gln Glu Phe Gln Thr Gly Leu Gly Asn Met Val Lys Pro Cys Leu Tyr
  1               5                  10                  15

Glu Lys Tyr Arg Asn Ile Ser Trp Leu Trp Trp His Thr Pro Val Val
             20                  25                  30

Pro Ala Thr Trp Glu Ala Glu Val Gly Gly Ser Leu Glu Pro Gly Arg
         35                  40                  45

Leu Arg Leu Gln
     50


<210> SEQ ID NO 538
<211> LENGTH: 65
<212> TYPE: PRT
<213> ORGANISM: Homo sapiens

<400> SEQUENCE: 538

Ile Leu Gly Gly Glu Ser Ile Leu Ile Leu Ser Trp Val Phe Ser Tyr
  1               5                  10                  15

Ile Phe Phe Arg Ile Ala Leu Glu Ile Thr Ile Tyr Ile Leu Asn Val
             20                  25                  30

Ser Pro Phe Cys Leu Gly Arg Trp Leu Met Pro Val Ile Pro Ala Leu
         35                  40                  45

Trp Glu Ala Glu Val Gly Gly Leu Pro Glu Leu Arg Ser Ser Arg Pro
     50                  55                  60

Ala
 65


<210> SEQ ID NO 539
<211> LENGTH: 15
<212> TYPE: PRT
<213> ORGANISM: Homo sapiens

<400> SEQUENCE: 539

Met Pro Lys Gln Leu Ala Gln Leu Leu Tyr Arg Leu Pro Arg Gly
  1               5                  10                  15


<210> SEQ ID NO 540
<211> LENGTH: 46
<212> TYPE: PRT
<213> ORGANISM: Homo sapiens

<400> SEQUENCE: 540

Leu Phe Gln Ala Ile Ser Val Ser Gly Ser His Arg Gln Gly Ser Arg
  1               5                  10                  15

Thr Trp Asn Thr Leu Thr Glu Gly Asn Ala Glu Ala Ala Cys Thr Val
             20                  25                  30

Ala Leu Gln Thr Ser Lys Arg Leu Ile Leu Ala Ser Arg Trp
         35                  40                  45


<210> SEQ ID NO 541
<211> LENGTH: 50
<212> TYPE: PRT
<213> ORGANISM: Homo sapiens
```

-continued

<400> SEQUENCE: 541

Thr Leu Ser Phe Met Asn Ser His Cys Val Pro Ile Lys Ala Leu Phe
1 5 10 15

Phe Leu Ser Val Val Ser Tyr Ile Phe Ile Met Pro His His Ile Phe
20 25 30

Phe Thr Val Lys Ile Leu Lys Ser Cys Phe Gln Val Gly Gln Leu Met
35 40 45

Lys Leu
50

<210> SEQ ID NO 542
<211> LENGTH: 109
<212> TYPE: PRT
<213> ORGANISM: Homo sapiens

<400> SEQUENCE: 542

Arg Pro Thr Arg Pro Ile Thr Phe Ser Ser Asn Ile Ser Glu Trp Val
1 5 10 15

Pro Ser Thr Gly Phe Gln Asp Leu Glu His Phe Asn Arg Arg Lys Cys
20 25 30

Arg Ser Ser Leu His Ser Cys Phe Thr Asp Phe Gln Glu Ala Asp Ser
35 40 45

Gly Phe Lys Met Glu Pro Trp Ser Trp Phe Phe Phe Phe Phe Phe Phe
50 55 60

Phe Pro Gln Arg Thr Cys Gly Cys Ala Leu Cys Val Leu Phe Leu Phe
65 70 75 80

Ser Ile Trp Gly Pro His Gly Lys Glu Leu Leu Asn Ser Phe Leu Tyr
85 90 95

Glu Leu Pro Leu Cys Ser Tyr Lys Gly Pro Phe Leu Ser
100 105

<210> SEQ ID NO 543
<211> LENGTH: 62
<212> TYPE: PRT
<213> ORGANISM: Homo sapiens

<400> SEQUENCE: 543

Val Asp Pro Arg Val Arg Leu Pro Leu Phe Trp Trp Gln Pro Ser Cys
1 5 10 15

Ala Val Tyr Leu Phe Pro Arg Val Tyr Asn Asn Met Cys Thr Arg Val
20 25 30

Leu Gly Thr Leu Pro His Cys Trp Asp Leu Ala Thr Leu Leu Gln Pro
35 40 45

Ser Ser Arg Ile Trp Gly Asn Val Ser Glu Ala Pro Gly Met
50 55 60

<210> SEQ ID NO 544
<211> LENGTH: 87
<212> TYPE: PRT
<213> ORGANISM: Homo sapiens

<400> SEQUENCE: 544

Val Pro Tyr His Ile Ala Gly Thr Leu Pro His Cys Cys Ser Leu Pro
1 5 10 15

Val Gly Tyr Gly Gly Met Ser Val Arg Leu Gln Gly Cys Arg Tyr Val
20 25 30

Gly Asn Val Gly Pro Gln Gly Asn Met Gln Ser Gly Arg Ser Trp Ala

-continued

```
        35                  40                  45

Leu Lys Met Val Leu Leu Cys Asn Ser Cys Leu Gly Leu Gly Val Gly
     50                  55                  60

Ser Val Gly Pro Ser Met Ser Ser Leu Phe Gly Ala Val Leu Ser Glu
 65                  70                  75                  80

Thr Pro Gly Ser Ser Val Tyr
                 85
```

<210> SEQ ID NO 545
<211> LENGTH: 29
<212> TYPE: PRT
<213> ORGANISM: Homo sapiens

<400> SEQUENCE: 545

```
Met Leu Asp Pro Arg Ala Thr Cys Asn Leu Val Gly Val Gly Leu Ser
  1               5                  10                  15

Lys Trp Cys Cys Cys Val Thr Ala Ala Trp Val Leu Gly
             20                  25
```

<210> SEQ ID NO 546
<211> LENGTH: 65
<212> TYPE: PRT
<213> ORGANISM: Homo sapiens
<220> FEATURE:
<221> NAME/KEY: SITE
<222> LOCATION: (48)
<223> OTHER INFORMATION: Xaa equals any of the naturally occurring L-
      amino acids

<400> SEQUENCE: 546

```
His Gly Asp Trp Ile Tyr Val His Ile Val Glu Gln Leu Asn Gln Ala
  1               5                  10                  15

Asn Asn Lys Ser Val Thr Ser His Thr Tyr Phe Val Val Lys Thr Cys
             20                  25                  30

Lys Ile His Ser Leu Ser Asn Phe Gln Ala Ser Asn Thr Leu Leu Xaa
        35                  40                  45

Thr Val Val Thr Met Leu Tyr Asn Arg Ser Leu Glu Leu Ile Leu Pro
     50                  55                  60

Val
 65
```

<210> SEQ ID NO 547
<211> LENGTH: 68
<212> TYPE: PRT
<213> ORGANISM: Homo sapiens
<220> FEATURE:
<221> NAME/KEY: SITE
<222> LOCATION: (26)
<223> OTHER INFORMATION: Xaa equals any of the naturally occurring L-
      amino acids

<400> SEQUENCE: 547

```
Thr Tyr Ser Ser Cys Leu Thr Lys Ile Leu Tyr Ser Leu Ile Asn Ile
  1               5                  10                  15

Tyr Pro Ile Pro His Cys Ser Pro Ala Xaa Ile Thr Thr Ile Leu Leu
             20                  25                  30

Ser Ala Ser Met Asn Leu Thr Phe Phe Phe Phe Arg Phe His Ile Cys
        35                  40                  45

Glu Ile Ala Gln Tyr Leu Ser Phe Cys Ala Trp Leu Ile Ser Leu Asn
     50                  55                  60

Ile Lys Ser Leu
```

-continued

65

<210> SEQ ID NO 548
<211> LENGTH: 33
<212> TYPE: PRT
<213> ORGANISM: Homo sapiens

<400> SEQUENCE: 548

Met Asn Leu Thr Phe Phe Phe Phe Arg Phe His Ile Cys Glu Ile Ala
1 5 10 15

Gln Tyr Leu Ser Phe Cys Ala Trp Leu Ile Ser Leu Asn Ile Lys Ser
20 25 30

Leu

<210> SEQ ID NO 549
<211> LENGTH: 58
<212> TYPE: PRT
<213> ORGANISM: Homo sapiens

<400> SEQUENCE: 549

Leu Val Cys Tyr Cys Ser Thr Lys Lys Glu Lys Lys Leu His Glu Ile
1 5 10 15

Ala Ile Gln Gln Gly Gln Asn Trp Arg Trp Leu Leu Phe Tyr Lys Glu
20 25 30

Ile Ser Val Pro Gly Phe Gln Ser Val Trp Cys Ser Tyr Lys Cys Leu
35 40 45

Cys Val Val Trp Lys Ala Gly Glu Gly Gly
50 55

<210> SEQ ID NO 550
<211> LENGTH: 36
<212> TYPE: PRT
<213> ORGANISM: Homo sapiens

<400> SEQUENCE: 550

Arg Arg Ser Cys Ser Gly Pro Pro Leu Val Asn Thr Ala Gly Lys Ile
1 5 10 15

Leu Ser Ser Ser Pro Ala Lys Leu Ala Cys Lys Arg Thr Asp Phe His
20 25 30

Ile Pro Ser Ile
35

<210> SEQ ID NO 551
<211> LENGTH: 37
<212> TYPE: PRT
<213> ORGANISM: Homo sapiens

<400> SEQUENCE: 551

Arg Ala Ser Ile Leu Gly Ile Asp Asn Glu Arg Gly Cys His Phe Arg
1 5 10 15

His Phe Asn Pro Leu Lys Glu Tyr Lys Arg Lys Lys Lys Glu Asn Lys
20 25 30

Ser Phe Arg Ile Val
35

<210> SEQ ID NO 552
<211> LENGTH: 77
<212> TYPE: PRT
<213> ORGANISM: Homo sapiens

<400> SEQUENCE: 552

```
Ser Lys Asn Lys Thr Arg Gly Gly Asp Trp Cys Val Thr Val Leu Arg
  1               5                  10                  15

Lys Arg Arg Lys Ser Phe Met Lys Ser Pro Phe Ser Lys Asp Arg Thr
             20                  25                  30

Gly Asp Gly Phe Ser Phe Thr Lys Lys Ser Leu Ser Gln Ala Phe Ser
         35                  40                  45

Leu Phe Gly Val His Thr Ser Val Cys Val Leu Cys Gly Arg Arg Gly
     50                  55                  60

Lys Ala Gly Glu Gly Gly Pro Val Gln Gly Pro Leu Trp
 65                  70                  75


<210> SEQ ID NO 553
<211> LENGTH: 55
<212> TYPE: PRT
<213> ORGANISM: Homo sapiens

<400> SEQUENCE: 553

Met Lys Ser Pro Phe Ser Lys Asp Arg Thr Gly Asp Gly Phe Ser Phe
  1               5                  10                  15

Thr Lys Lys Ser Leu Ser Gln Ala Phe Ser Leu Phe Gly Val His Thr
             20                  25                  30

Ser Val Cys Val Leu Cys Gly Arg Arg Gly Lys Ala Gly Glu Gly Gly
         35                  40                  45

Pro Val Gln Gly Pro Leu Trp
     50                  55


<210> SEQ ID NO 554
<211> LENGTH: 24
<212> TYPE: PRT
<213> ORGANISM: Homo sapiens

<400> SEQUENCE: 554

Met Gly Glu Ser Glu Cys Tyr Arg Arg Leu Ser Gly Ala Ser Cys Thr
  1               5                  10                  15

Trp Thr Val His Val Asp Phe Ala
             20


<210> SEQ ID NO 555
<211> LENGTH: 33
<212> TYPE: PRT
<213> ORGANISM: Homo sapiens

<400> SEQUENCE: 555

Met His Cys Gly Thr Arg Val Trp Lys Thr Met Lys His Asp Tyr Phe
  1               5                  10                  15

Leu Leu Ala Cys Leu Ser Met Thr Ser Thr Gly Gly Ile Leu Cys Thr
             20                  25                  30

Leu


<210> SEQ ID NO 556
<211> LENGTH: 67
<212> TYPE: PRT
<213> ORGANISM: Homo sapiens

<400> SEQUENCE: 556

Ser Thr Leu Ser Leu Ile Pro Thr Ser Ser Ser Leu Ser Phe Trp Pro
  1               5                  10                  15

Trp Cys Thr Ala Ile Ile Gly Ser Ile Phe Thr Tyr Cys Val Cys Val
             20                  25                  30
```

```
Cys Val Cys Phe Val Val Met Asn Arg Thr Cys Tyr Leu Pro Asn Ser
         35                  40                  45

Ile Ile Tyr His Asn Ser Lys Leu Ala Thr Ile Ile Asp Lys Ser Met
     50                  55                  60

Thr Leu Ser
 65


<210> SEQ ID NO 557
<211> LENGTH: 20
<212> TYPE: PRT
<213> ORGANISM: Homo sapiens

<400> SEQUENCE: 557

Met Trp Ile Leu Pro Lys Val Ser Leu Ile Cys Ile Val Glu Leu Gly
  1               5                  10                  15

Tyr Gly Lys Pro
             20


<210> SEQ ID NO 558
<211> LENGTH: 62
<212> TYPE: PRT
<213> ORGANISM: Homo sapiens

<400> SEQUENCE: 558

Met Ser Thr Gly Asp Gly Arg Asp Ala Glu Lys Gly Trp Pro Val Ser
  1               5                  10                  15

Glu Glu Glu Asn Gln Arg Ser Val Tyr Pro Gly Tyr Pro Glu Cys Asp
             20                  25                  30

Glu Arg Gln Ala Val Pro Gln His Cys Ala Ile Ala Ser Pro Ser Ser
         35                  40                  45

Leu Gln Ser His His Pro Ala Ser Ala Cys Val Pro Arg Arg
     50                  55                  60


<210> SEQ ID NO 559
<211> LENGTH: 38
<212> TYPE: PRT
<213> ORGANISM: Homo sapiens

<400> SEQUENCE: 559

Gln Gln Met Thr Leu Gly Thr Lys Ile Lys Trp Gly Gln Leu Gln Arg
  1               5                  10                  15

Gly Gln Glu Ile Pro Thr Gly Asp Phe Thr Val Arg Asn Phe Met Arg
             20                  25                  30

Phe Ser Ile Ile Tyr Cys
         35


<210> SEQ ID NO 560
<211> LENGTH: 31
<212> TYPE: PRT
<213> ORGANISM: Homo sapiens
<220> FEATURE:
<221> NAME/KEY: SITE
<222> LOCATION: (11)
<223> OTHER INFORMATION: Xaa equals any of the naturally occurring L-
      amino acids

<400> SEQUENCE: 560

Pro Phe Leu Phe Cys Ala Ser Arg Ile Arg Xaa Gln Gly Ile Gly Ile
  1               5                  10                  15

His Gly Gln Val Ala Cys Ser Ala Val Arg Met Tyr Asn Asn Arg
             20                  25                  30
```

-continued

<210> SEQ ID NO 561
<211> LENGTH: 45
<212> TYPE: PRT
<213> ORGANISM: Homo sapiens

<400> SEQUENCE: 561

Val Leu Cys Glu Glu Ala Gly Gln Lys Val Pro Ser Thr Pro Ser Trp
1 5 10 15

Ser Ser Trp Thr Leu Gln Lys Arg Leu Arg Gly Ser Pro Ala Glu Ala
20 25 30

Asn Cys Ser Pro Ser Phe Pro Ala Pro Pro Gly Lys Glu
35 40 45

<210> SEQ ID NO 562
<211> LENGTH: 103
<212> TYPE: PRT
<213> ORGANISM: Homo sapiens

<400> SEQUENCE: 562

Met Ser Leu Ser Ala Leu Ala Cys Asp Phe Thr Pro Ile Gln Pro Trp
1 5 10 15

Glu Trp Glu Glu Tyr Glu Gln Ile Thr Leu Gly Leu Thr Ala Pro Ser
20 25 30

Asn Leu Leu Glu Ser Asn Tyr Leu Gly Gln Ala Ser Glu Cys Phe Val
35 40 45

Arg Lys Leu Val Arg Arg Phe Pro Gln Leu Leu Pro Gly Pro Pro Gly
50 55 60

His Cys Arg Lys Asp Leu Gly Asp Pro Gln Gln Arg Pro Ile Ala Leu
65 70 75 80

Leu Pro Ser Leu Pro His Gln Glu Arg Asn Asn Val His Arg Leu Glu
85 90 95

Ala Asp Ser Glu Val Asp Leu
100

<210> SEQ ID NO 563
<211> LENGTH: 46
<212> TYPE: PRT
<213> ORGANISM: Homo sapiens

<400> SEQUENCE: 563

Cys Val Asp Phe Asp Glu Tyr Phe Ser Ser Trp Glu Pro Leu Leu Lys
1 5 10 15

Met Met Phe Lys Gly Val Val Gly Gly Lys Met Lys Ala Trp Arg Arg
20 25 30

Lys Lys Arg Arg Lys Pro Leu Pro Tyr Lys Ile His Ala Asp
35 40 45

<210> SEQ ID NO 564
<211> LENGTH: 30
<212> TYPE: PRT
<213> ORGANISM: Homo sapiens

<400> SEQUENCE: 564

Met Met Phe Lys Gly Val Val Gly Gly Lys Met Lys Ala Trp Arg Arg
1 5 10 15

Lys Lys Arg Arg Lys Pro Leu Pro Tyr Lys Ile His Ala Asp
20 25 30

-continued

<210> SEQ ID NO 565
<211> LENGTH: 37
<212> TYPE: PRT
<213> ORGANISM: Homo sapiens

<400> SEQUENCE: 565

Leu Ile Ser Ser Val Asn Lys Thr Lys Gln Lys Arg Ser Asp Ala Thr
1 5 10 15

Leu Ser His Lys His Asp Arg Leu Leu Asn His Phe Val Phe Phe Gly
20 25 30

Asn Ser Tyr Asn Tyr
35

<210> SEQ ID NO 566
<211> LENGTH: 127
<212> TYPE: PRT
<213> ORGANISM: Homo sapiens
<220> FEATURE:
<221> NAME/KEY: SITE
<222> LOCATION: (95)
<223> OTHER INFORMATION: Xaa equals any of the naturally occurring L-
amino acids

<400> SEQUENCE: 566

Ser Ser Lys Phe Pro Ser Asp Met Leu Leu Arg Ile Gln Gln Ile Ile
1 5 10 15

Tyr Cys His Lys Leu Thr Ile Ile Leu Thr Lys Trp Arg Asn Thr Ala
20 25 30

Arg His Lys Ser Lys Lys Lys Glu Asp Glu Leu Ile Leu Lys His Glu
35 40 45

Leu Gln Leu Lys Lys Trp Lys Asn Arg Leu Ile Leu Lys Arg Ala Ala
50 55 60

Ala Glu Glu Ser Asn Phe Pro Glu Arg Ser Ser Ser Glu Val Phe Leu
65 70 75 80

Val Asp Glu Thr Leu Lys Cys Asp Ile Ser Leu Leu Pro Glu Xaa Ala
85 90 95

Ile Leu Gln Val Cys Met Asn Ser Val Tyr Ile Ile Tyr Tyr Asn Leu
100 105 110

Pro Ser Val Val Val His Ala Cys Asn Pro Ser Cys Leu Gly Gly
115 120 125

<210> SEQ ID NO 567
<211> LENGTH: 11
<212> TYPE: PRT
<213> ORGANISM: Homo sapiens

<400> SEQUENCE: 567

Ser Leu Glu Ser Thr Asn Ala Ile Lys Ser Asn
1 5 10

<210> SEQ ID NO 568
<211> LENGTH: 19
<212> TYPE: PRT
<213> ORGANISM: Homo sapiens

<400> SEQUENCE: 568

Ile Arg Pro Asn Lys Asn Asp Gln Met Arg His Cys Leu Ile Asn Met
1 5 10 15

Ile Asp Tyr

<210> SEQ ID NO 569

<211> LENGTH: 37
<212> TYPE: PRT
<213> ORGANISM: Homo sapiens

<400> SEQUENCE: 569

Ile Thr Leu Cys Phe Leu Glu Thr Ala Ile Thr Ile Asn Ile Tyr Ser
1 5 10 15

Asn Leu Val Asn Phe Leu Gln Ile Cys Tyr Cys Gly Tyr Asn Arg Ser
20 25 30

Ser Ile Val Thr Ser
35

<210> SEQ ID NO 570
<211> LENGTH: 31
<212> TYPE: PRT
<213> ORGANISM: Homo sapiens

<400> SEQUENCE: 570

Ile Ser Phe Arg Tyr Ala Ile Ala Asp Thr Thr Asp His Leu Leu Ser
1 5 10 15

Gln Ala Asn His Tyr Pro Asn Lys Met Ala Glu Tyr Ser Lys Thr
20 25 30

<210> SEQ ID NO 571
<211> LENGTH: 86
<212> TYPE: PRT
<213> ORGANISM: Homo sapiens
<220> FEATURE:
<221> NAME/KEY: SITE
<222> LOCATION: (18)
<223> OTHER INFORMATION: Xaa equals any of the naturally occurring L-
amino acids

<400> SEQUENCE: 571

Pro Gln Ile Lys Leu Leu Asn Ser Asp Ala Leu Gly Met Arg Thr Thr
1 5 10 15

Ser Xaa Asp Leu Val Pro Cys Asn Gln Cys Phe Ile Pro Leu Pro Pro
20 25 30

Ser Cys Asn Arg Ile Ala Ser Arg Lys Ala Val Asn Trp Lys Gln Gln
35 40 45

Arg Leu Pro Ala Val Arg Gly Leu Leu Asn Asn Ala Pro His Arg Arg
50 55 60

Pro Pro Thr Pro Arg Thr Pro Cys Val Phe Pro Ser Glu Gly Pro Lys
65 70 75 80

Gly Tyr Gly Phe His Val
85

<210> SEQ ID NO 572
<211> LENGTH: 39
<212> TYPE: PRT
<213> ORGANISM: Homo sapiens
<220> FEATURE:
<221> NAME/KEY: SITE
<222> LOCATION: (5)
<223> OTHER INFORMATION: Xaa equals any of the naturally occurring L-
amino acids

<400> SEQUENCE: 572

Glu Gln Leu Ala Xaa Ile Ser Cys Arg Val Ile Asn Val Ser Phe Arg
1 5 10 15

Cys Leu His His Val Ile Glu Ser Leu Pro Glu Arg Gln Leu Thr Gly
20 25 30

Ser Ser Arg Gly Ser Gln Pro
35

<210> SEQ ID NO 573
<211> LENGTH: 73
<212> TYPE: PRT
<213> ORGANISM: Homo sapiens
<220> FEATURE:
<221> NAME/KEY: SITE
<222> LOCATION: (45)
<223> OTHER INFORMATION: Xaa equals any of the naturally occurring L-amino acids

<400> SEQUENCE: 573

Glu Asp Cys Ser Thr Met Pro Pro Ile Ala Ala Pro Pro Pro Leu Ala
1 5 10 15

Pro Leu Val Phe Ser Pro Leu Arg Gly Pro Arg Val Met Ala Phe Met
20 25 30

Ser Arg Cys Gly Asp Arg Gly Gly Arg Gly Arg Ser Xaa Ala Gly Arg
35 40 45

Gly Trp Pro Trp Ser Glu Ser Gly Val Ile Asn Ala His Pro Lys Lys
50 55 60

Arg Pro Cys Pro Gly Pro Met Leu Ser
65 70

<210> SEQ ID NO 574
<211> LENGTH: 48
<212> TYPE: PRT
<213> ORGANISM: Homo sapiens

<400> SEQUENCE: 574

Glu Phe Gly Thr Arg Arg Gln Trp Gly Thr Arg Cys Phe Pro Pro Leu
1 5 10 15

Val Gly Arg Lys Gln Ser Ala Leu Arg Arg Arg Glu Gly Lys Ala Arg
20 25 30

Ala Gly Arg Cys Cys Gly Lys Arg Ser Val Lys Ala Gly Phe Asp Ala
35 40 45

<210> SEQ ID NO 575
<211> LENGTH: 52
<212> TYPE: PRT
<213> ORGANISM: Homo sapiens

<400> SEQUENCE: 575

Ala Phe Phe Leu Leu Gln Ala Leu Glu Ile Gln Ser Gln Leu Ala Thr
1 5 10 15

Pro Ala Ser Ser Thr Ala Arg Asn Pro Ala Pro Asp Leu His His Pro
20 25 30

His Gln Pro Thr Ile Glu Arg Phe Cys Arg His Ser Ser Ser Trp Glu
35 40 45

Arg Ile Glu Tyr
50

<210> SEQ ID NO 576
<211> LENGTH: 42
<212> TYPE: PRT
<213> ORGANISM: Homo sapiens

<400> SEQUENCE: 576

Ala Thr Val Pro Gly Ser Ile Tyr Asn Tyr Phe Tyr His Tyr Asn Ala
1 5 10 15

-continued

```
Gly Ala Leu Lys Pro Glu His Ala Ser Glu Ser Pro Arg Gly Leu Cys
            20                  25                  30

Ala Gln Thr Ala Gly Pro Phe Pro Ser Phe
        35                  40


<210> SEQ ID NO 577
<211> LENGTH: 56
<212> TYPE: PRT
<213> ORGANISM: Homo sapiens

<400> SEQUENCE: 577

Ile Arg His Glu Pro Pro Pro Pro Arg Phe Lys Arg Phe Ser Cys Leu
  1               5                  10                  15

Ser Leu Leu Ser Ser Trp Asp Tyr Arg Arg Ala Pro Pro His Val Ala
            20                  25                  30

Ile Phe Cys Thr Leu Ser Arg Asp Gly Val Leu Pro His Trp Pro Gly
        35                  40                  45

Trp Ser Gln Thr Pro Asp Leu Lys
    50                  55


<210> SEQ ID NO 578
<211> LENGTH: 72
<212> TYPE: PRT
<213> ORGANISM: Homo sapiens

<400> SEQUENCE: 578

Ser Thr His Leu Gly Leu Pro Arg Cys Trp Asp Tyr Arg His Glu Pro
  1               5                  10                  15

Leu Cys Leu Ala Pro Phe Thr Thr Ile Ser Ile Ile Ile Met Gln Gly
            20                  25                  30

Leu Ser Asn Leu Ser Met Pro Gln Asn Pro Pro Glu Gly Cys Ala His
        35                  40                  45

Arg Leu Leu Asp Leu Ser Pro Ala Ser Asp Ser Val Pro Pro Glu Trp
    50                  55                  60

Gly Ser Lys Ile Ala Phe Glu Val
 65                  70


<210> SEQ ID NO 579
<211> LENGTH: 26
<212> TYPE: PRT
<213> ORGANISM: Homo sapiens

<400> SEQUENCE: 579

Leu Arg Val Gly Gly Thr Ser Glu Asn Cys Cys Arg Gly Glu Cys Cys
  1               5                  10                  15

Gly Ser Val Cys Ile Pro Pro Gly Arg Leu
            20                  25


<210> SEQ ID NO 580
<211> LENGTH: 40
<212> TYPE: PRT
<213> ORGANISM: Homo sapiens

<400> SEQUENCE: 580

Met Cys Val Thr Arg Met His Val Lys Cys Pro Pro Pro Ser Ala Ser
  1               5                  10                  15

Val Thr Ala Val Lys Trp Pro Leu Ser Trp Ser Ser Ser Ser Phe Cys
            20                  25                  30

Ile Ser Leu His Ala Gly Arg His
        35                  40
```

-continued

<210> SEQ ID NO 581
<211> LENGTH: 36
<212> TYPE: PRT
<213> ORGANISM: Homo sapiens

<400> SEQUENCE: 581

```
Glu Glu Arg Asn Lys Asn His Leu Ser Cys Gln Gly Leu Ser Thr Ile
  1               5                  10                  15

Cys Cys Ser Tyr Leu Ser Ser Lys Gly Glu His Leu Arg Asn Leu Ser
             20                  25                  30

Pro Tyr Ser Phe
         35
```

<210> SEQ ID NO 582
<211> LENGTH: 46
<212> TYPE: PRT
<213> ORGANISM: Homo sapiens

<400> SEQUENCE: 582

```
Gly Leu Cys Met Val His Ser Leu Leu Thr Ser Ser Leu Gly Gly Arg
  1               5                  10                  15

Cys Cys Asn Tyr Pro Tyr Ile Ala Asp Lys Asp Ile Glu Thr Glu Val
             20                  25                  30

Lys Pro Pro Ser Gln Gly His Thr Trp His Leu His Cys Ser
         35                  40                  45
```

<210> SEQ ID NO 583
<211> LENGTH: 75
<212> TYPE: PRT
<213> ORGANISM: Homo sapiens

<400> SEQUENCE: 583

```
Gln Leu Trp Cys Ile Thr Ala Leu Pro Ser Thr Arg His Cys Ser Lys
  1               5                  10                  15

Gly Phe Ala Trp Phe Thr His Ser Leu Arg His Pro Ser Val Ala Gly
             20                  25                  30

Ala Val Ile Ile Leu Ile Leu Gln Thr Arg Thr Leu Arg Gln Arg Ser
         35                  40                  45

Ser His Leu Pro Lys Gly Thr His Gly Ile Cys Thr Ala Pro Asp Arg
     50                  55                  60

Pro Thr Glu Arg Ala Ala Val Thr Ile Leu Lys
 65                  70                  75
```

<210> SEQ ID NO 584
<211> LENGTH: 39
<212> TYPE: PRT
<213> ORGANISM: Homo sapiens

<400> SEQUENCE: 584

```
Ser Phe Asp Asn Asn Asn Ser Tyr Gly Val Ser Gln Leu Tyr Gln Val
  1               5                  10                  15

Pro Asp Thr Val Leu Arg Ala Leu His Gly Ser Leu Thr Pro Tyr Val
             20                  25                  30

Ile Pro Arg Trp Gln Val Leu
         35
```

<210> SEQ ID NO 585
<211> LENGTH: 38
<212> TYPE: PRT

-continued

<213> ORGANISM: Homo sapiens

<400> SEQUENCE: 585

```
Asp Arg Gly Gln Ala Thr Phe Pro Arg Ala His Met Ala Ser Ala Leu
  1               5                  10                  15

Leu Leu Thr Asp Arg Gln Arg Glu Leu Leu Ser Arg Ser Ser Asn Glu
             20                  25                  30

Leu Cys Met Ser Lys Val
         35
```

<210> SEQ ID NO 586
<211> LENGTH: 73
<212> TYPE: PRT
<213> ORGANISM: Homo sapiens
<220> FEATURE:
<221> NAME/KEY: SITE
<222> LOCATION: (66)
<223> OTHER INFORMATION: Xaa equals any of the naturally occurring L-
amino acids

<400> SEQUENCE: 586

```
Leu Leu Leu Ile Leu Arg Pro Phe Leu Asn Ser Gln Phe Lys Leu Gln
  1               5                  10                  15

Leu Pro Leu Val Leu Phe His Ser Ser Cys Thr Tyr Ile Cys Leu Leu
             20                  25                  30

Tyr Asn Tyr Glu Leu Phe His Ile Val Ala Leu Thr Gly Lys Leu Met
         35                  40                  45

Asn Leu Gly Leu His Leu Phe Ala His His Leu Ile Leu Ala Val Ala
     50                  55                  60

His Xaa Gly Cys Ser Ile Pro Ile Tyr
 65                  70
```

<210> SEQ ID NO 587
<211> LENGTH: 37
<212> TYPE: PRT
<213> ORGANISM: Homo sapiens

<400> SEQUENCE: 587

```
Thr His Asn Ser Asn Tyr Ser Ser Leu Trp Phe Ser Ser Thr Ala Val
  1               5                  10                  15

Val Leu Thr Tyr Val Tyr Tyr Ile Ile Met Asn Cys Phe Ile Leu Ser
             20                  25                  30

Pro Leu Gln Val Asn
         35
```

<210> SEQ ID NO 588
<211> LENGTH: 53
<212> TYPE: PRT
<213> ORGANISM: Homo sapiens

<400> SEQUENCE: 588

```
Thr Leu Val Ala Gly Ser Pro Cys Ser Leu Ser Arg Trp Ile Met Ala
  1               5                  10                  15

Gly Phe Cys His Gly Glu Leu Val Gln Ser Asp Met Glu Ser Gln Glu
             20                  25                  30

Trp Glu Arg Gly Gln Val Val Leu Ser His Thr Ser Leu Pro Trp Cys
         35                  40                  45

Tyr Val Ser Pro Arg
     50
```

-continued

<210> SEQ ID NO 589
<211> LENGTH: 39
<212> TYPE: PRT
<213> ORGANISM: Homo sapiens

<400> SEQUENCE: 589

```
Met Ala Gly Phe Cys His Gly Glu Leu Val Gln Ser Asp Met Glu Ser
  1               5                  10                  15

Gln Glu Trp Glu Arg Gly Gln Val Val Leu Ser His Thr Ser Leu Pro
             20                  25                  30

Trp Cys Tyr Val Ser Pro Arg
         35
```

<210> SEQ ID NO 590
<211> LENGTH: 94
<212> TYPE: PRT
<213> ORGANISM: Homo sapiens

<400> SEQUENCE: 590

```
Met Ala Val Trp Ile Ser Gly Ser Tyr Ser Ser Phe Cys Ser Arg Ser
  1               5                  10                  15

Asn Trp Asp Val Phe Ser Pro Asn Ile Val Leu Ala Ser Leu Pro Phe
             20                  25                  30

Ser Phe Arg Ser Val Ser Lys Ala Ala Lys Pro Trp Trp Leu Ala Leu
         35                  40                  45

Pro Ala Leu Phe Pro Asp Gly Leu Trp Leu Asp Ser Ala Met Gly Ser
     50                  55                  60

Leu Tyr Ser Gln Thr Trp Lys Ala Arg Asn Gly Lys Glu Val Arg Trp
 65                  70                  75                  80

Phe Ser Pro Thr Pro His Cys Leu Gly Ala Met Ser His Leu
                 85                  90
```

<210> SEQ ID NO 591
<211> LENGTH: 19
<212> TYPE: PRT
<213> ORGANISM: Homo sapiens

<400> SEQUENCE: 591

```
Gly Trp Leu Tyr Gly Ser Val Gly Leu Ile Pro His Ser Ala Ala Glu
  1               5                  10                  15

Ala Thr Gly
```

<210> SEQ ID NO 592
<211> LENGTH: 82
<212> TYPE: PRT
<213> ORGANISM: Homo sapiens

<400> SEQUENCE: 592

```
Arg Ser Lys Arg Gln Ser Gln Gly Ser Arg Cys Ser Val Pro Leu Leu
  1               5                  10                  15

Ala Gln Gln Ser Arg Ser Pro Pro Val Pro Leu Gln Ala Gln Pro Ala
             20                  25                  30

Trp Leu Leu Gly Ser Glu Thr Ile Ala Trp Ser Gly Gly Gly Ser Gly
         35                  40                  45

Trp Glu Gly Pro Arg Asp Pro Gly Thr Ser Thr Ala Ala Gly Asn Ser
     50                  55                  60

Gly Pro Gly Ile Gly Met Gly His Arg Thr Pro Pro Pro Ser His Thr
 65                  70                  75                  80

Gly Arg
```

-continued

<210> SEQ ID NO 593
<211> LENGTH: 30
<212> TYPE: PRT
<213> ORGANISM: Homo sapiens

<400> SEQUENCE: 593

Arg Trp Asp Pro Ala Trp Gly Leu Asp Ile Pro Glu Ser Ser Cys Pro
1 5 10 15

Val Thr Met Gly Glu Leu Arg Ser Gly Asp Gly Ile Val Leu
20 25 30

<210> SEQ ID NO 594
<211> LENGTH: 50
<212> TYPE: PRT
<213> ORGANISM: Homo sapiens

<400> SEQUENCE: 594

Gly Ala Leu Leu Trp Asp Asn Ser Met Ile Ser Ala Pro Arg Gly Ser
1 5 10 15

His Arg Glu Ala Gly Ala Leu Phe Pro Ser Trp Leu Ser Asn Pro Ala
20 25 30

Val Leu Pro Ser Arg Ser Arg Pro Ser Gln Pro Gly Cys Leu Asp Pro
35 40 45

Arg Gln
50

<210> SEQ ID NO 595
<211> LENGTH: 49
<212> TYPE: PRT
<213> ORGANISM: Homo sapiens

<400> SEQUENCE: 595

Asn Ser Ala Arg Glu Pro Arg Arg Trp Ile Arg Pro Thr Arg Gly Ser
1 5 10 15

Gly Glu Thr Thr Ala Pro Cys Cys Phe Glu Pro Leu Asn Gly Gly Thr
20 25 30

Leu Val His Ala Ala Ala Met Ala Arg Ala Ser Glu Ala Ala Gly Thr
35 40 45

Gly

<210> SEQ ID NO 596
<211> LENGTH: 11
<212> TYPE: PRT
<213> ORGANISM: Homo sapiens

<400> SEQUENCE: 596

Met Ala Arg Ala Ser Glu Ala Ala Gly Thr Gly
1 5 10

<210> SEQ ID NO 597
<211> LENGTH: 84
<212> TYPE: PRT
<213> ORGANISM: Homo sapiens

<400> SEQUENCE: 597

Cys Phe Thr Thr Ala Phe Gln Lys Ala Leu Arg Asp Pro Arg Pro Thr
1 5 10 15

Leu Pro Asp Thr His Gly Ser Leu Arg Asn Ala Pro Leu Lys Ser Leu
20 25 30

-continued

```
Thr Leu Pro Ala Ala Phe Val Val Ser Phe Phe Phe Leu Ser Leu Leu
        35                  40                  45

Gln Asp Gly Ile Lys Glu Arg Ser Gln Thr Gln Asn Ala Thr Phe Phe
    50                  55                  60

Phe His Asp Arg Ser Asp Ile Glu Gly Leu Ser Glu Glu Pro Cys Ser
65                  70                  75                  80

Gly Thr Thr Pro


<210> SEQ ID NO 598
<211> LENGTH: 95
<212> TYPE: PRT
<213> ORGANISM: Homo sapiens

<400> SEQUENCE: 598

Leu Ala Leu Gln Glu Ala Val Thr Gly Lys Gln Val Leu Cys Ser Pro
  1               5                  10                  15

Pro Gly Ser Ala Ile Pro Gln Ser Ser Arg Pro Ala Pro Gly Pro Ala
            20                  25                  30

Ser Leu Ala Ala Trp Ile Arg Asp Asn Ser Leu Val Trp Arg Arg Leu
        35                  40                  45

Arg Val Gly Gly Thr Gln Gly Pro Gly His Gln Tyr Ser Ser Trp Glu
    50                  55                  60

Phe Arg Pro Arg Asp Arg Asp Gly Ala Gln Asp Thr Thr Pro Ile Ser
65                  70                  75                  80

His Arg Glu Met Lys Val Gly Ser Ser Met Gly Thr Gly His Pro
                85                  90                  95


<210> SEQ ID NO 599
<211> LENGTH: 47
<212> TYPE: PRT
<213> ORGANISM: Homo sapiens

<400> SEQUENCE: 599

Met Ala Gly Arg Leu Phe Thr Leu Leu Leu Trp Gln Glu Leu Ala Arg
  1               5                  10                  15

Arg Leu Val Pro Gly Asp Ala Ser Pro Arg Leu Ser Arg Lys Arg Ser
            20                  25                  30

Val Thr Pro Gly Pro Pro Phe Pro Thr Leu Thr Val Pro Ser Glu
        35                  40                  45


<210> SEQ ID NO 600
<211> LENGTH: 42
<212> TYPE: PRT
<213> ORGANISM: Homo sapiens

<400> SEQUENCE: 600

Met Phe Tyr Ser Lys Ile Phe Tyr Phe Leu Leu Leu Asn Ser Asp Thr
  1               5                  10                  15

Ser Asn Asn Val Thr Ser Lys Thr Leu Val Ser Ser Ile Ser Ser Ser
            20                  25                  30

Asn Asn Arg Leu Ala Val Ser Ile Val Phe
        35                  40


<210> SEQ ID NO 601
<211> LENGTH: 47
<212> TYPE: PRT
<213> ORGANISM: Homo sapiens

<400> SEQUENCE: 601
```

-continued

```
Ser Arg Gln Lys Asn Leu Leu Lys Leu His Ser Asn Pro Asn Cys Asp
  1               5                  10                  15

Asn Phe Cys Phe Ile Phe Asn Tyr Lys Pro Lys Tyr Ile Cys Ile Phe
             20                  25                  30

Lys Leu Ile Cys Leu Lys Ile Leu Leu Tyr Ile Phe Gly Ser Gly
         35                  40                  45


<210> SEQ ID NO 602
<211> LENGTH: 56
<212> TYPE: PRT
<213> ORGANISM: Homo sapiens
<220> FEATURE:
<221> NAME/KEY: SITE
<222> LOCATION: (24)
<223> OTHER INFORMATION: Xaa equals any of the naturally occurring L-
      amino acids

<400> SEQUENCE: 602

Met Leu Leu Ser Leu Leu Met Val Phe Thr Ser Glu Leu Tyr Val Lys
  1               5                  10                  15

Arg His Ile Ser Phe Lys Ser Xaa Asp Lys Pro His Cys His Lys Asn
             20                  25                  30

Gln Asp Ile Asp Val Leu Phe Arg Lys Leu Leu Glu Lys His Phe Lys
         35                  40                  45

Val Ile Asn Met Ile Cys Phe Pro
     50                  55


<210> SEQ ID NO 603
<211> LENGTH: 12
<212> TYPE: PRT
<213> ORGANISM: Homo sapiens

<400> SEQUENCE: 603

Phe Arg Glu Tyr Gly Phe Tyr Asn Leu His Phe Cys
  1               5                  10


<210> SEQ ID NO 604
<211> LENGTH: 38
<212> TYPE: PRT
<213> ORGANISM: Homo sapiens

<400> SEQUENCE: 604

Leu Val Thr Thr Asp Tyr Tyr Asp Gly Cys Asn Glu Asp Tyr Glu Tyr
  1               5                  10                  15

Asn Trp Ser Tyr Met Phe Leu Asn Ser Glu Gln Leu Phe Ile Lys Phe
             20                  25                  30

Tyr Pro Thr Phe Phe Cys
         35


<210> SEQ ID NO 605
<211> LENGTH: 52
<212> TYPE: PRT
<213> ORGANISM: Homo sapiens

<400> SEQUENCE: 605

Asn Val Ile Ala Pro Gly Leu Glu Ser Ser Cys Ala Asn Ser Leu Phe
  1               5                  10                  15

Leu Leu Phe Val Cys Leu Pro Val Ala His His Arg His Asn Phe Leu
             20                  25                  30

Phe Ile Lys His Ser Leu Tyr Asn His Leu Arg Asp Tyr Glu Ser Asp
         35                  40                  45
```

-continued

```
Phe Asp Lys Ile
     50


<210> SEQ ID NO 606
<211> LENGTH: 34
<212> TYPE: PRT
<213> ORGANISM: Homo sapiens

<400> SEQUENCE: 606

Pro Lys Val Leu Ala Val Leu Lys Lys Lys Asn His Val Ala Leu Ser
  1               5                  10                  15

Ile Phe Glu Leu Leu Ser Asn Asp Ile Cys Ser Phe Ile Ser Phe Phe
             20                  25                  30

Met Ser


<210> SEQ ID NO 607
<211> LENGTH: 28
<212> TYPE: PRT
<213> ORGANISM: Homo sapiens

<400> SEQUENCE: 607

Glu Gly Pro Asp Ile Asn Ser Asn Leu Lys Phe Leu Leu Cys Leu Lys
  1               5                  10                  15

Lys Lys Ile Met Trp Pro Phe Gln Tyr Leu Asn Cys
             20                  25


<210> SEQ ID NO 608
<211> LENGTH: 47
<212> TYPE: PRT
<213> ORGANISM: Homo sapiens

<400> SEQUENCE: 608

Leu Leu Ser Leu Ile Leu Leu Arg Ile Trp Tyr Asp Phe Ser Lys Gln
  1               5                  10                  15

Thr Val Phe Trp Phe Phe Leu Asn Val Phe Asn Phe Phe Ser Ser Cys
             20                  25                  30

Asn Asn Asp Gly Ala Cys Ser Tyr Lys Tyr Arg Lys Val Gln Ile
         35                  40                  45


<210> SEQ ID NO 609
<211> LENGTH: 12
<212> TYPE: PRT
<213> ORGANISM: Homo sapiens

<400> SEQUENCE: 609

His Thr Leu Phe Ile Ser Phe Leu Trp Ala Glu Gly
  1               5                  10


<210> SEQ ID NO 610
<211> LENGTH: 28
<212> TYPE: PRT
<213> ORGANISM: Homo sapiens

<400> SEQUENCE: 610

Met Leu Pro Val Phe Val Leu Phe Phe Cys Phe Thr Tyr Ser Ala Arg
  1               5                  10                  15

Lys Gln Ser Val Phe Lys Lys Gly Asn Val Phe Glu
             20                  25


<210> SEQ ID NO 611
<211> LENGTH: 63
<212> TYPE: PRT
```

-continued

<213> ORGANISM: Homo sapiens

<400> SEQUENCE: 611

Ser Pro Cys Ser Ala Ala Glu Cys His Asn Leu Ser Leu Leu Ser Ser
1 5 10 15

Cys Ser Leu Val Ser Ser Asn Ile Leu Phe Ser Phe Pro Phe Phe Gly
20 25 30

Gln Lys Ala Arg Cys Cys Leu Phe Leu Phe Tyr Phe Ser Ala Ser His
35 40 45

Ile Ala His Glu Ser Arg Val Tyr Ser Lys Lys Glu Met Cys Leu
50 55 60

<210> SEQ ID NO 612
<211> LENGTH: 65
<212> TYPE: PRT
<213> ORGANISM: Homo sapiens

<400> SEQUENCE: 612

His Lys Cys Phe Gln Cys Phe Ile Leu Ala Asn Gly Phe Leu Lys Val
1 5 10 15

Ile Lys Pro Phe Gln Arg Asn Trp Ser Asp Lys Thr Phe Phe Leu Val
20 25 30

Cys Leu Asn Lys Ala Ile Ser Glu Ala Leu Leu Ser Lys Met Thr Phe
35 40 45

Leu Ser Phe Phe Lys Thr Asn Leu Leu Leu Leu Glu Thr Phe Cys Thr
50 55 60

Ile
65

<210> SEQ ID NO 613
<211> LENGTH: 99
<212> TYPE: PRT
<213> ORGANISM: Homo sapiens

<400> SEQUENCE: 613

Leu Leu Gly Val Leu Lys Pro Leu Tyr Phe Ser Val Glu Pro Val Leu
1 5 10 15

Gly Glu Arg Ser Val Ala Phe Glu Glu Val Arg Glu Lys Asn His Gly
20 25 30

Thr Ser Gly Phe Leu Ser Leu Tyr Ser Leu Ala Ala Ile Val Cys Gly
35 40 45

His Leu Met Phe Phe His Thr Leu Leu Gly Arg Gly Gly Asn Asp His
50 55 60

Pro Gly Gln Ser Pro Leu Pro Gly Met Arg Pro Leu Arg Gly Gly Leu
65 70 75 80

Ala Gly Gln Ala Pro Ser Gly His Pro Trp Met Gln Pro Leu Asp Thr
85 90 95

Cys Leu Leu

<210> SEQ ID NO 614
<211> LENGTH: 43
<212> TYPE: PRT
<213> ORGANISM: Homo sapiens

<400> SEQUENCE: 614

Arg Pro Thr Arg Pro Pro Thr Arg Pro Asp Arg Pro Ser Leu Glu Leu
1 5 10 15

Ala Pro Gly Leu Cys Ala Asp Phe Leu Gly Ser Ser Asn His Cys Ile

-continued

```
            20                  25                  30

Phe Leu Leu Ser Leu Tyr Leu Gly Arg Asp Gln
        35                  40


<210> SEQ ID NO 615
<211> LENGTH: 49
<212> TYPE: PRT
<213> ORGANISM: Homo sapiens

<400> SEQUENCE: 615

Glu Lys Arg Ile Met Val Pro Gln Gly Phe Phe Pro Phe Thr Arg Trp
  1               5                  10                  15

Gln Pro Leu Ser Val Gly Thr Ser Cys Phe Ser Thr Leu Tyr Trp Ala
            20                  25                  30

Val Glu Val Thr Ile Thr Gln Ala Ser Leu Leu Cys Leu Gly Cys Ala
        35                  40                  45

Leu


<210> SEQ ID NO 616
<211> LENGTH: 123
<212> TYPE: PRT
<213> ORGANISM: Homo sapiens

<400> SEQUENCE: 616

Met Thr Leu Asp Glu Trp Lys Asn Leu Gln Glu Gln Thr Arg Pro Lys
  1               5                  10                  15

Pro Glu Phe Asn Ile Arg Lys Pro Glu Ser Thr Val Pro Ser Lys Ala
            20                  25                  30

Val Val Ile Arg Glu Ser Lys Tyr Arg Asp Asp Met Val Lys Asp Asp
        35                  40                  45

Tyr Glu Asp Asp Ser His Val Phe Arg Lys Pro Ala Asn Asp Ile Thr
     50                  55                  60

Ser Gln Leu Glu Ile Asn Phe Gly Asn Leu Pro Arg Pro Gly Arg Gly
 65                  70                  75                  80

Ala Arg Gly Gly Thr Arg Gly Gly Arg Gly Arg Ile Arg Arg Ala Glu
                 85                  90                  95

Asn Tyr Gly Pro Arg Ala Glu Val Val Met Gln Asp Val Ala Pro Asn
            100                 105                 110

Pro Asp Asp Pro Glu Asp Phe Pro Ala Leu Ser
        115                 120


<210> SEQ ID NO 617
<211> LENGTH: 100
<212> TYPE: PRT
<213> ORGANISM: Homo sapiens

<400> SEQUENCE: 617

Cys Lys Met Leu Pro Pro Thr Gln Met Thr Arg Lys Ile Ser Leu Arg
  1               5                  10                  15

Cys Leu Glu Arg Ala Leu Phe Pro Ser Thr Ala Glu Leu His Cys Thr
            20                  25                  30

Pro Val Gly Arg Leu Phe Gln Leu Gly Gln Gly Ser Gln Thr Leu Arg
        35                  40                  45

Thr Ile Asp Val Ala Phe Pro Val Ser Cys Lys Phe Val Ala Leu Phe
     50                  55                  60

Trp Ala Glu Leu Leu Glu Gly Leu Leu Gln Arg Leu Glu Ser Arg Pro
 65                  70                  75                  80
```

-continued

```
Phe Pro Lys Lys Met Lys Asn Gly Asp Cys Val Phe Ile Glu Gly Ile
                85                  90                  95

Ser Asn Glu Glu
            100


<210> SEQ ID NO 618
<211> LENGTH: 41
<212> TYPE: PRT
<213> ORGANISM: Homo sapiens

<400> SEQUENCE: 618

Pro Pro Ser Ser Trp Ala Trp Ser Gln Arg Arg His Pro Gly Arg Pro
  1               5                  10                  15

Gly Lys Asp Gln Glu Gly Arg Glu Leu Trp Thr Gln Ser Arg Ser Gly
             20                  25                  30

Asp Ala Arg Cys Cys Pro Gln Pro Arg
         35                  40


<210> SEQ ID NO 619
<211> LENGTH: 22
<212> TYPE: PRT
<213> ORGANISM: Homo sapiens

<400> SEQUENCE: 619

Cys Leu Lys Cys Val Tyr Arg Asp Ser Ile Asp Ser Ser Ala Glu Ala
  1               5                  10                  15

Trp Arg Glu Arg Arg Leu
             20


<210> SEQ ID NO 620
<211> LENGTH: 29
<212> TYPE: PRT
<213> ORGANISM: Homo sapiens

<400> SEQUENCE: 620

Leu Ser Tyr Ser Val Leu Leu Ile Leu Pro Leu Phe His Ser Leu Pro
  1               5                  10                  15

Thr Leu Lys Asp Thr His Thr His Asn Lys Trp Val Glu
             20                  25


<210> SEQ ID NO 621
<211> LENGTH: 61
<212> TYPE: PRT
<213> ORGANISM: Homo sapiens

<400> SEQUENCE: 621

Glu Val Asn Gly Val Gly Tyr Lys His Ser Cys Phe Ser Asp Ile Ser
  1               5                  10                  15

Ser Val Leu Glu Asn Lys Asp Ser Arg Met Arg Ala Pro His Tyr Ala
             20                  25                  30

Ser Phe Gln His Phe Phe Ser Val Leu Leu Lys Leu Ser Pro Gln Ala
         35                  40                  45

Cys Leu Thr Glu Ser Gln Cys Ile Pro Leu Thr Phe Tyr
     50                  55                  60


<210> SEQ ID NO 622
<211> LENGTH: 37
<212> TYPE: PRT
<213> ORGANISM: Homo sapiens

<400> SEQUENCE: 622
```

-continued

```
Lys Thr His Thr His Thr Ile Ser Gly Trp Ser Lys Lys Ser Thr Glu
  1               5                  10                  15

Leu Asp Ile Ser Ile Pro Ala Phe Leu Thr Ser Pro Val Ser Trp Arg
             20                  25                  30

Thr Arg Ile Leu Glu
         35


<210> SEQ ID NO 623
<211> LENGTH: 29
<212> TYPE: PRT
<213> ORGANISM: Homo sapiens

<400> SEQUENCE: 623

Ile Arg His Glu Leu Gly Ser Ser Asp Pro Pro Ala Glu Ala Ser Gln
  1               5                  10                  15

Ile Ala Gly Thr Ala Ala Val Ser His His Ala Gln Pro
             20                  25


<210> SEQ ID NO 624
<211> LENGTH: 25
<212> TYPE: PRT
<213> ORGANISM: Homo sapiens

<400> SEQUENCE: 624

Met Leu Tyr Leu Ile Leu Ile Ser Leu Ser Ser Leu Ser Phe Ser Phe
  1               5                  10                  15

Ser Leu Pro Pro Phe Ser Ile Ile Ile
             20                  25


<210> SEQ ID NO 625
<211> LENGTH: 24
<212> TYPE: PRT
<213> ORGANISM: Homo sapiens

<400> SEQUENCE: 625

Ser Ser Tyr Phe Leu Arg His Phe Arg Ile Tyr His Thr Cys Pro Lys
  1               5                  10                  15

Tyr Phe Ser Met Asn Ile Ile Asn
             20


<210> SEQ ID NO 626
<211> LENGTH: 69
<212> TYPE: PRT
<213> ORGANISM: Homo sapiens

<400> SEQUENCE: 626

Lys Leu Thr Leu Thr Lys Gly Asn Lys Ser Trp Ser Ser Thr Ala Val
  1               5                  10                  15

Ala Ala Ala Leu Glu Leu Val Asp Pro Pro Gly Cys Arg Asn Ser Ala
             20                  25                  30

Arg Asp Ser Leu Pro Asn Ser Thr Met Met Phe Tyr Tyr Ala Cys Phe
         35                  40                  45

Ile Leu Tyr Ser Ser Leu Ser Pro Leu Ser Leu Ser Leu Ser Pro Ser
     50                  55                  60

Leu Leu Ser Leu Leu
 65


<210> SEQ ID NO 627
<211> LENGTH: 14
<212> TYPE: PRT
<213> ORGANISM: Homo sapiens
```

<400> SEQUENCE: 627

Gln Phe His Thr Gly Asn Ser Tyr Asp His Asp Tyr Ala Lys
1 5 10

<210> SEQ ID NO 628
<211> LENGTH: 35
<212> TYPE: PRT
<213> ORGANISM: Homo sapiens

<400> SEQUENCE: 628

Ala Val Cys Thr Gly Gly Tyr Cys Glu Ser Cys Arg Cys Glu His Cys
1 5 10 15

Val Cys Val Cys Val Asp Leu Cys Val Leu Phe Ser Gly Lys Glu Leu
20 25 30

Arg Val Arg
35

<210> SEQ ID NO 629
<211> LENGTH: 72
<212> TYPE: PRT
<213> ORGANISM: Homo sapiens

<400> SEQUENCE: 629

Val Ser Phe Phe Phe Val Phe Lys Trp Ser Phe Ala Glu Ile Lys Ser
1 5 10 15

Arg Glu Glu His Trp Ala Ser Leu Thr Pro Lys Pro Thr Leu Leu Ser
20 25 30

Ala Leu Leu Thr Cys Asp Val Leu Lys Ser Ser Ile Ile Phe Lys Cys
35 40 45

Cys Glu Ser Thr Glu Asp Lys Gly Phe Asp Ser Phe Phe Gln Ala Ser
50 55 60

Lys Asp Gly Ser Ser Ser Arg Ile
65 70

<210> SEQ ID NO 630
<211> LENGTH: 99
<212> TYPE: PRT
<213> ORGANISM: Homo sapiens

<400> SEQUENCE: 630

Arg Ser Trp Gly Ser Gln Arg Ser Leu Cys Leu Leu Phe Ile Pro Phe
1 5 10 15

Ala Ala Glu Ser Tyr Ser Val Val Trp Met Gly His Leu Phe Val Val
20 25 30

Cys Leu Leu Ser Ser Trp Trp Thr Phe Arg Pro Phe Ala Leu Ala Val
35 40 45

Thr Val Asn His Val Ala Val Asn Ile Val Cys Val Ser Ala Trp Thr
50 55 60

Cys Val Ser Cys Ser Leu Gly Arg Ser Cys Gly Leu Glu Gly Ser Phe
65 70 75 80

Leu Phe Pro Leu Glu Thr Leu Trp Phe Pro His Met Val Val Leu Cys
85 90 95

Leu Thr Phe

<210> SEQ ID NO 631
<211> LENGTH: 74
<212> TYPE: PRT
<213> ORGANISM: Homo sapiens -continued

<400> SEQUENCE: 631

```
Met Gly His Leu Phe Val Val Cys Leu Leu Ser Ser Trp Trp Thr Phe
  1               5                  10                  15

Arg Pro Phe Ala Leu Ala Val Thr Val Asn His Val Ala Val Asn Ile
             20                  25                  30

Val Cys Val Ser Ala Trp Thr Cys Val Ser Cys Ser Leu Gly Arg Ser
         35                  40                  45

Cys Gly Leu Glu Gly Ser Phe Leu Phe Pro Leu Glu Thr Leu Trp Phe
     50                  55                  60

Pro His Met Val Val Leu Cys Leu Thr Phe
 65                  70
```

<210> SEQ ID NO 632
<211> LENGTH: 51
<212> TYPE: PRT
<213> ORGANISM: Homo sapiens

<400> SEQUENCE: 632

```
His Asp Val Leu Gly Ala Arg Asn Ala Ala Cys Val Cys Cys Ser Phe
  1               5                  10                  15

Leu Leu Gln Gln Asn Arg Ile Leu Leu Phe Gly Trp Ala Thr Cys Leu
             20                  25                  30

Leu Ser Val Tyr Ser Pro Ala Gly Gly His Leu Gly Arg Leu His Trp
         35                  40                  45

Arg Leu Leu
     50
```

<210> SEQ ID NO 633
<211> LENGTH: 130
<212> TYPE: PRT
<213> ORGANISM: Homo sapiens

<400> SEQUENCE: 633

```
Met Leu Asp Phe Lys Thr Ser Gln Val Ser Lys Ala Leu Lys Arg Val
  1               5                  10                  15

Gly Phe Gly Val Arg Leu Ala Gln Cys Ser Ser Leu Asp Leu Ile Ser
             20                  25                  30

Ala Lys Leu His Leu Lys Thr Lys Lys Lys Glu Thr Tyr Ile Thr Ser
         35                  40                  45

Thr Val Met Thr Ala Ala Ser Leu Phe Leu Ser Tyr Val Thr Ser Glu
     50                  55                  60

Phe Thr Arg Ser Ile Met Ala Thr Phe Tyr Cys Phe Val Leu Lys Leu
 65                  70                  75                  80

His Ile Gly Glu Met Gly Thr Leu Gln Thr Ala Gly Gly Ser Lys Met
                 85                  90                  95

Thr Trp Pro Leu Gln Lys Ala Ile Trp Gln Phe Leu Lys Arg Leu Ser
            100                 105                 110

Ile Lys Leu Pro Tyr Val Glu Thr Arg Glu Ser Pro Gly Glu Thr Lys
        115                 120                 125

Asn Tyr
    130
```

<210> SEQ ID NO 634
<211> LENGTH: 28
<212> TYPE: PRT
<213> ORGANISM: Homo sapiens -continued

<400> SEQUENCE: 634

Leu Thr Arg Asn Ser Phe Pro Glu Asn Arg Thr His Lys Ser Thr Gln
1 5 10 15

Thr His Thr Gln Cys Ser Gln Arg His Asp Ser Gln
20 25

<210> SEQ ID NO 635
<211> LENGTH: 90
<212> TYPE: PRT
<213> ORGANISM: Homo sapiens

<400> SEQUENCE: 635

Ile Arg His Glu Gly Gln Ser Ser Ser Arg Gly Ser Ser His Cys Asp
1 5 10 15

Ser Pro Ser Pro Gln Glu Asp Gly Gln Ile Met Phe Asp Val Glu Met
20 25 30

His Thr Ser Arg Asp His Ser Ser Gln Ser Glu Glu Glu Val Val Glu
35 40 45

Gly Glu Lys Glu Val Glu Ala Leu Lys Lys Ser Ala Asp Trp Val Ser
50 55 60

Asp Trp Ser Ser Arg Pro Glu Asn Ile Pro Pro Lys Glu Phe His Phe
65 70 75 80

Arg His Pro Lys Arg Ser Val Ser Leu Ser
85 90

<210> SEQ ID NO 636
<211> LENGTH: 40
<212> TYPE: PRT
<213> ORGANISM: Homo sapiens

<400> SEQUENCE: 636

Gly Ile Leu Leu Thr Leu Tyr Pro Phe Trp Pro Glu Asp Ile Leu Glu
1 5 10 15

Phe Pro Asn Arg Val Tyr Cys Cys Leu Glu Ile Cys Lys Gly Phe Phe
20 25 30

Ser Ala Asn Ala Thr Ser Arg Leu
35 40

<210> SEQ ID NO 637
<211> LENGTH: 47
<212> TYPE: PRT
<213> ORGANISM: Homo sapiens

<400> SEQUENCE: 637

Glu Phe Gly Thr Arg Asp Arg Val Val Pro Glu Ala Val Leu Thr Val
1 5 10 15

Thr Ala Leu Arg His Lys Lys Met Gly Arg Ser Cys Leu Met Trp Lys
20 25 30

Cys Thr Pro Ala Gly Thr Ile Ala Leu Ser Gln Lys Lys Lys Leu
35 40 45

<210> SEQ ID NO 638
<211> LENGTH: 52
<212> TYPE: PRT
<213> ORGANISM: Homo sapiens

<400> SEQUENCE: 638

Ala His Pro Leu Pro Ala Pro Thr Glu Gly Lys Glu Lys Pro Leu Glu
1 5 10 15

-continued

```
Met Arg Val Thr Cys Glu Val Val Tyr Cys His Ser Ser Leu Phe Glu
             20                  25                  30

Leu Glu Thr Ile Val Ser Met Thr Gln Pro Thr Thr Leu Phe Leu His
        35                  40                  45

Ile Gln Phe Gln
     50


<210> SEQ ID NO 639
<211> LENGTH: 68
<212> TYPE: PRT
<213> ORGANISM: Homo sapiens

<400> SEQUENCE: 639

Thr Phe Cys Val Phe Lys His Glu Glu Lys Trp Ser His Glu Glu Arg
  1               5                  10                  15

Gly Tyr Phe Leu Arg Arg Ile Ser Glu Gly Val His Ser Ile Ser Leu
             20                  25                  30

Pro Phe Ser Cys Phe Gly Phe Gly Ala Arg His Leu Tyr Trp Lys Ala
        35                  40                  45

Thr Glu His Thr Leu Cys Gln His Leu Leu Arg Glu Arg Lys Ser Pro
     50                  55                  60

Trp Lys Cys Val
 65


<210> SEQ ID NO 640
<211> LENGTH: 64
<212> TYPE: PRT
<213> ORGANISM: Homo sapiens

<400> SEQUENCE: 640

Gln Ser Leu Leu Leu Phe Arg Asn Leu Gln Gly Leu Leu Phe Arg Lys
  1               5                  10                  15

Cys His Gln Gln Ile Ile Ile Leu Ser Ala Met Leu Leu Ser Leu Ile
             20                  25                  30

Ser Ala Thr Arg Leu Asp Leu Tyr His Ser Trp Tyr Lys Phe Tyr Ser
        35                  40                  45

Cys Asn Ile Thr Thr Ile Ser Leu Leu Lys Arg Asp Gln Val Ser Lys
     50                  55                  60


<210> SEQ ID NO 641
<211> LENGTH: 22
<212> TYPE: PRT
<213> ORGANISM: Homo sapiens

<400> SEQUENCE: 641

Ile Arg His Glu Glu Ser Phe Asn Pro Leu Thr Cys Gly Phe Ser Leu
  1               5                  10                  15

Phe Phe Ser Leu Phe Ser
             20


<210> SEQ ID NO 642
<211> LENGTH: 27
<212> TYPE: PRT
<213> ORGANISM: Homo sapiens

<400> SEQUENCE: 642

Met Glu Thr Leu Leu Leu Leu Leu Phe Phe Leu Ser Leu Leu Ile Phe
  1               5                  10                  15

Arg Phe Arg Ile Leu Val Ser Gln Cys Ile Asn
             20                  25
```

-continued

<210> SEQ ID NO 643
<211> LENGTH: 65
<212> TYPE: PRT
<213> ORGANISM: Homo sapiens

<400> SEQUENCE: 643

```
Phe Leu Leu Thr Thr Val Leu Leu Phe Ser Ser Lys Val Arg Asp Pro
  1               5                  10                  15

Arg Ala Asn Phe Asp Gln Ser Leu Arg Val Leu Lys His Ala Lys Lys
             20                  25                  30

Val Gln Pro Asp Val Ile Ser Lys Thr Ser Ile Met Leu Gly Leu Gly
         35                  40                  45

Glu Asn Asp Glu Gln Val Tyr Ala Thr Met Lys Gly Lys Glu Ile Glu
     50                  55                  60

Lys
 65
```

<210> SEQ ID NO 644
<211> LENGTH: 23
<212> TYPE: PRT
<213> ORGANISM: Homo sapiens

<400> SEQUENCE: 644

```
Gln Gln Ser Cys Cys Phe Pro Val Arg Phe Val Ile Leu Gly Pro Ile
  1               5                  10                  15

Leu Ile Ser Pro Tyr Val Tyr
             20
```

<210> SEQ ID NO 645
<211> LENGTH: 59
<212> TYPE: PRT
<213> ORGANISM: Homo sapiens

<400> SEQUENCE: 645

```
Val Trp Leu Leu Ser Ser Ile Leu Leu Arg Val Leu Trp Asn Arg Tyr
  1               5                  10                  15

Thr Leu Gln Glu Leu Ser Phe Trp Leu Pro Trp Phe Ala Ser Arg Ala
             20                  25                  30

Thr Ser Leu Val Leu Gln His Gly Asp Asn Tyr Leu Leu Phe Leu Phe
         35                  40                  45

Cys Phe Val Cys Phe Val Leu Ala Met Pro Phe
     50                  55
```

<210> SEQ ID NO 646
<211> LENGTH: 26
<212> TYPE: PRT
<213> ORGANISM: Homo sapiens

<400> SEQUENCE: 646

```
Ile Arg His Glu Val Ser Met Ala Phe Val Phe His Leu Ala Gln Gly
  1               5                  10                  15

Thr Leu Glu Pro Leu Tyr Ile Ala Gly Ala
             20                  25
```

<210> SEQ ID NO 647
<211> LENGTH: 40
<212> TYPE: PRT
<213> ORGANISM: Homo sapiens

<400> SEQUENCE: 647

-continued

```
Asn Ser Ala Arg Gly Glu Tyr Gly Phe Cys Leu Pro Ser Cys Ser Gly
  1               5                  10                  15

Tyr Phe Gly Thr Ala Ile His Cys Arg Ser Leu Ala Ser Gly Tyr His
             20                  25                  30

Gly Leu Leu Pro Glu Gln Gln Ala
         35                  40


<210> SEQ ID NO 648
<211> LENGTH: 26
<212> TYPE: PRT
<213> ORGANISM: Homo sapiens

<400> SEQUENCE: 648

His Glu Leu Thr Val Pro Ser Arg Met Gly Ser Lys Gly Lys Pro Tyr
  1               5                  10                  15

Pro Cys Gly Phe Tyr Ser Ser Leu Ile Pro
             20                  25


<210> SEQ ID NO 649
<211> LENGTH: 103
<212> TYPE: PRT
<213> ORGANISM: Homo sapiens

<400> SEQUENCE: 649

Lys Cys Ile Tyr Pro Lys Pro Ala Arg Thr His His Cys Ser Ile Cys
  1               5                  10                  15

Asn Arg Cys Val Leu Lys Met Asp His His Cys Pro Trp Leu Asn Asn
             20                  25                  30

Cys Val Gly His Tyr Asn His Arg Tyr Phe Phe Ser Phe Cys Phe Phe
         35                  40                  45

Met Thr Leu Gly Cys Val Tyr Cys Ser Tyr Gly Ser Trp Asp Leu Phe
     50                  55                  60

Arg Glu Ala Tyr Ala Ala Ile Glu Lys Met Lys Gln Leu Asp Lys Asn
 65                  70                  75                  80

Lys Leu Gln Ala Val Ala Asn Gln Thr Tyr His Gln Thr Pro Pro Pro
                 85                  90                  95

Thr Phe Ser Phe Arg Glu Arg
            100


<210> SEQ ID NO 650
<211> LENGTH: 38
<212> TYPE: PRT
<213> ORGANISM: Homo sapiens

<400> SEQUENCE: 650

Ala Arg Gly His Trp Asn Leu Ile Leu Ile Val Phe His Tyr Tyr Gln
  1               5                  10                  15

Ala Ile Thr Thr Pro Pro Gly Tyr Pro Pro Gln Gly Arg Asn Asp Ile
             20                  25                  30

Ala Thr Val Ser Ile Cys
         35


<210> SEQ ID NO 651
<211> LENGTH: 33
<212> TYPE: PRT
<213> ORGANISM: Homo sapiens

<400> SEQUENCE: 651

Trp Gln Cys Glu Leu Asp Cys Val Ser His Asp Ser Ser Thr His Ser
```

-continued

```
  1               5                   10                  15

Ala Pro Tyr Val Ile Ser Arg Ala Ser Lys Gly Ser Phe Ser Gln Asn
             20                  25                  30

Pro


<210> SEQ ID NO 652
<211> LENGTH: 83
<212> TYPE: PRT
<213> ORGANISM: Homo sapiens

<400> SEQUENCE: 652

Ser Lys Arg Ala Ser Gly Pro Ala Leu Gly Tyr His Ala Gly Gln Phe
  1               5                   10                  15

Lys Asp Gln Pro Phe Tyr His Cys Arg Arg Lys Thr Gln Cys Gly Glu
             20                  25                  30

Ile Leu Gly Leu Thr Ser Leu Tyr Ser Gly Lys Gln Lys Phe Gln Pro
         35                  40                  45

Gln Thr Arg Gly Gln Ala Ala Ser Tyr Leu Pro Cys Pro Val Leu Thr
     50                  55                  60

Arg Thr Ser Ser Arg Ile Gln His Trp Ser Trp Pro Pro Pro Leu Leu
 65                  70                  75                  80

Leu Ala Val


<210> SEQ ID NO 653
<211> LENGTH: 31
<212> TYPE: PRT
<213> ORGANISM: Homo sapiens

<400> SEQUENCE: 653

Glu Ser Leu Gln Leu Arg Leu Leu Gly Gln Leu Glu Gly Ile Pro Gly
  1               5                   10                  15

Cys Gly Tyr Arg Lys Ala Leu Ala Tyr Ser Gly Ala Leu Thr Phe
             20                  25                  30


<210> SEQ ID NO 654
<211> LENGTH: 66
<212> TYPE: PRT
<213> ORGANISM: Homo sapiens

<400> SEQUENCE: 654

Ser Leu Ala Pro Trp Glu Trp Asn Glu Leu Gly Ala Pro Ser Leu Gly
  1               5                   10                  15

Asp Cys Ser Leu Ser Leu Cys Asp Gly Ser Val Ser Trp Thr Val Ser
             20                  25                  30

Ala Thr Thr Arg Ala Leu Ile Leu Leu Pro Met Leu Phe Gln Gly Pro
         35                  40                  45

Pro Arg Ala Ala Phe Leu Arg Ile Leu Asp Gln Lys Glu Pro Val Gly
     50                  55                  60

Leu Pro
 65


<210> SEQ ID NO 655
<211> LENGTH: 72
<212> TYPE: PRT
<213> ORGANISM: Homo sapiens

<400> SEQUENCE: 655

Thr Ala Thr Leu Asn Ser Phe Phe Gly Gly Trp Gly Leu Ala Leu Leu
  1               5                   10                  15
```

-continued

```
Leu Arg Leu Glu Cys Ser Asp Thr Ile Met Asp His Cys Ser Leu Asp
            20                  25                  30

Leu Leu Gly Ser Ser Asn Pro Pro Ala Ser Ala Ser Gln Val Val Gly
        35                  40                  45

Thr Thr Gly Ala Arg His His Ala Gln Leu Ile Phe Cys Phe Phe Val
    50                  55                  60

Gln Thr Arg Ser His Ser Val Ala
65                  70


<210> SEQ ID NO 656
<211> LENGTH: 47
<212> TYPE: PRT
<213> ORGANISM: Homo sapiens

<400> SEQUENCE: 656

Met Asp His Cys Ser Leu Asp Leu Leu Gly Ser Ser Asn Pro Pro Ala
  1               5                  10                  15

Ser Ala Ser Gln Val Val Gly Thr Thr Gly Ala Arg His His Ala Gln
            20                  25                  30

Leu Ile Phe Cys Phe Phe Val Gln Thr Arg Ser His Ser Val Ala
        35                  40                  45


<210> SEQ ID NO 657
<211> LENGTH: 14
<212> TYPE: PRT
<213> ORGANISM: Homo sapiens

<400> SEQUENCE: 657

Gly Val Leu Lys Gln Ser Ser His Leu Val Leu Ser Lys Gly
  1               5                  10


<210> SEQ ID NO 658
<211> LENGTH: 21
<212> TYPE: PRT
<213> ORGANISM: Homo sapiens

<400> SEQUENCE: 658

Asp Tyr Ser Cys Glu Ser Leu Cys Pro Ala Leu Leu Ser Ile Ala Pro
  1               5                  10                  15

Asp Ile Val Leu Asn
            20


<210> SEQ ID NO 659
<211> LENGTH: 27
<212> TYPE: PRT
<213> ORGANISM: Homo sapiens

<400> SEQUENCE: 659

Thr Thr Ile His Lys Thr Gln Leu Gly Ser Tyr Lys Ile Leu Trp Glu
  1               5                  10                  15

Pro Lys Glu Gly Tyr His Asn Ser Thr Trp Ile
            20                  25


<210> SEQ ID NO 660
<211> LENGTH: 9
<212> TYPE: PRT
<213> ORGANISM: Homo sapiens

<400> SEQUENCE: 660

Ile Arg Glu Ile Phe Leu Arg Arg Pro
  1               5
```

-continued

<210> SEQ ID NO 661
<211> LENGTH: 24
<212> TYPE: PRT
<213> ORGANISM: Homo sapiens

<400> SEQUENCE: 661

Leu Lys Phe Gln Lys Pro Gly Lys Ile Gln Met Arg Gly Gly Gly Arg
1 5 10 15

Val Phe Trp Tyr Lys Asn Cys Lys
20

<210> SEQ ID NO 662
<211> LENGTH: 30
<212> TYPE: PRT
<213> ORGANISM: Homo sapiens

<400> SEQUENCE: 662

Asn Ser Ala Arg Val Thr Gln Lys Gly Glu Ser Val Gly Ser Val Gly
1 5 10 15

Cys Met Arg Ala Ile Ala Gly Phe Asp Asn Tyr Pro Leu Phe
20 25 30

<210> SEQ ID NO 663
<211> LENGTH: 33
<212> TYPE: PRT
<213> ORGANISM: Homo sapiens

<400> SEQUENCE: 663

Gly Thr Ile Gly Ile Phe Trp Pro Leu Pro Val Ala Ile Leu Ser Ser
1 5 10 15

Gly Asp Tyr Leu Gln Thr Gln Ile His Arg Pro Leu Leu His Arg Gly
20 25 30

Thr

<210> SEQ ID NO 664
<211> LENGTH: 20
<212> TYPE: PRT
<213> ORGANISM: Homo sapiens

<400> SEQUENCE: 664

Leu Pro Leu Pro Leu Ser Ser Leu Leu His Ile Ala Thr Cys Asn Pro
1 5 10 15

Phe Pro Lys Thr
20

<210> SEQ ID NO 665
<211> LENGTH: 46
<212> TYPE: PRT
<213> ORGANISM: Homo sapiens

<400> SEQUENCE: 665

Ser Tyr Phe Phe Val Tyr Asn Leu Ile Leu Lys Ile Ile Gln Gly Asp
1 5 10 15

His Ala Ser Ile Ile Leu Leu Ala Thr Ile Pro Ile Phe Gly Asp Ile
20 25 30

Tyr Tyr Val Lys Gly Gln Leu Ala Ser Phe Gly Pro Tyr Leu
35 40 45

<210> SEQ ID NO 666
<211> LENGTH: 21

-continued

<212> TYPE: PRT
<213> ORGANISM: Homo sapiens

<400> SEQUENCE: 666

Leu Phe Tyr His Leu Glu Ile Ile Ser Arg His Lys Ser Ile Ala His
1 5 10 15

Cys Ser Ile Glu Ala
20

<210> SEQ ID NO 667
<211> LENGTH: 12
<212> TYPE: PRT
<213> ORGANISM: Homo sapiens

<400> SEQUENCE: 667

Cys Ser Cys His Cys Pro Ser Arg Ala Phe Ser Thr
1 5 10

<210> SEQ ID NO 668
<211> LENGTH: 29
<212> TYPE: PRT
<213> ORGANISM: Homo sapiens

<400> SEQUENCE: 668

Pro His Ala Ile His Ser Gln Lys Pro Ser Ser Ile Phe Leu Ile Thr
1 5 10 15

Asp Val Phe Pro Asp Pro Pro Val Gly Ile Tyr Leu Leu
20 25

<210> SEQ ID NO 669
<211> LENGTH: 48
<212> TYPE: PRT
<213> ORGANISM: Homo sapiens

<400> SEQUENCE: 669

Arg Lys Leu Phe His Lys Ile Asn Ser Lys Ser Phe His Leu Ser Gly
1 5 10 15

Met His Ile Leu Ile Ser Val Trp Ile Val Arg Ser Arg Ile Ile Lys
20 25 30

Val Lys Tyr Glu Leu Leu Leu Cys Phe Phe Asp Val Ile Phe Tyr Val
35 40 45

<210> SEQ ID NO 670
<211> LENGTH: 41
<212> TYPE: PRT
<213> ORGANISM: Homo sapiens

<400> SEQUENCE: 670

Asn Ser Ala Arg Asp Val Phe Phe Thr Gln Lys Ile Leu Tyr Ser Gln
1 5 10 15

Thr Cys Ile Phe Phe Pro Cys Leu Val Pro Phe Ser Phe Leu Phe Ser
20 25 30

Phe Phe Phe Phe Leu Ser Phe Val Gly
35 40

<210> SEQ ID NO 671
<211> LENGTH: 56
<212> TYPE: PRT
<213> ORGANISM: Homo sapiens

<400> SEQUENCE: 671

Met Phe Ser Ser Leu Lys Lys Phe Tyr Ile Leu Lys His Val Tyr Ser

-continued

```
  1               5                  10                  15

Phe Pro Val Leu Phe His Phe Leu Phe Phe Phe Leu Phe Ser Phe Ser
            20                  25                  30

Phe Leu Ser Trp Ala Glu Lys Gly Ala Gly Lys Met Lys Leu Ala Thr
        35                  40                  45

Glu Asn Cys Lys Met Val Lys Ser
    50                  55


<210> SEQ ID NO 672
<211> LENGTH: 39
<212> TYPE: PRT
<213> ORGANISM: Homo sapiens

<400> SEQUENCE: 672

Ile Gln Leu Leu Tyr Leu Lys Gly Ala Ala Met Lys Tyr Leu Ser Tyr
  1               5                  10                  15

Val Ala Arg Leu Leu Phe Leu Lys Ala Leu Asp Leu Phe Ala Pro Lys
            20                  25                  30

Met Val Gln Ile Asp Ser Phe
        35
```